United States Patent [19]

Bodor

[11] Patent Number: 4,900,837

[45] **Date of Patent: * Feb. 13, 1990**

[54] BRAIN-SPECIFIC DRUG DELIVERY OF STEROID SEX HORMONES CLEAVED FROM PYRIDINIUM CARBOXYLATES AND DIHYDRO-PYRIDINE CARBOXYLATE PRECURSORS

[75] Inventor: Nicholas S. Bodor, Gainesville, Fla.

[73] Assignee: University of Florida, Gainesville, Fla.

[*] Notice: The portion of the term of this patent subsequent to Sep. 10, 2002 has been disclaimed.

[21] Appl. No.: 76,191

[22] Filed: Jul. 21, 1987

Related U.S. Application Data

[60] Division of Ser. No. 665,940, Oct. 29, 1984, Pat. No. 4,824,850, which is a continuation-in-part of Ser. No. 379,316, May 18, 1982, Pat. No. 4,479,932, and a continuation-in-part of Ser. No. 461,543, Jan. 27, 1983, abandoned, and a continuation-in-part of Ser. No. 475,493, Mar. 15, 1983, Pat. No. 4,622,218, and a continuation-in-part of Ser. No. 516,382, Jul. 22, 1983, Pat. No. 4,540,564.

[30] Foreign Application Priority Data

| | | | |
|---|---|---|---|
| Jun. 14, 1982 | [JP] | Japan | 57-101940 |
| May 16, 1983 | [CA] | Canada | 428192 |
| May 17, 1983 | [IE] | Ireland | 1149/83 |
| May 17, 1983 | [ZA] | South Africa | 83/3521 |
| May 17, 1983 | [ES] | Spain | 522489 |
| May 18, 1983 | [IT] | Italy | 48327 A/83 |

[51] Int. Cl.[4] .......... C07D 213/55

[52] U.S. Cl. .......... 546/285; 546/146; 546/165; 546/316; 546/318; 546/323

[58] Field of Search .......... 546/318, 285

[56] References Cited

U.S. PATENT DOCUMENTS

| | | | |
|---|---|---|---|
| 3,338,969 | 8/1967 | Muller et al. | 568/369 |
| 3,413,314 | 11/1968 | Amiard et al. | 549/280 |
| 3,962,447 | 6/1976 | Higuchi et al. . | |
| 4,035,507 | 7/1977 | Bodor et al. . | |
| 4,057,561 | 11/1977 | Fürst et al. | 549/421 |
| 4,065,566 | 12/1977 | Bodor et al. . | |
| 4,479,932 | 10/1984 | Bodor | 424/9 |
| 4,540,564 | 9/1985 | Bodor | 424/9 |

OTHER PUBLICATIONS

Bodor et al., *Science* 190, 155–156 (1975).
Shek et al., *J. Med. Chem.* 19, 113–117 (1976).
Bodor et al., in *Design of Biopharmaceutical Properties through Prodrugs and Analogs*, ed. Edward B. Roche, American Pharmaceutical Association, Washington, D.C. 98–135 (1977).
Bodor et al. *J. Pharm. Sci.* 67, 685–687 (1978).
Bodor et al., *Science* 214, 1370–1372 (1981).
Brewster III, *Dis. Abst. Int. B.*, vol. 43, #9, p. 2910 B (1983).
Bodor et al., *J. Med. Chem.* 26, 313–318 (1983).
Bodor et al., *J. Med. Chem.* 26, 528–534 (1983).
Bodor et al., *Pharmac. Ther.* 19, 337–386 (1983).
Bodor et al., *J. Pharm. Sci.* 73, 385–389 (1984).
Bodor et al., *Science* 221, 65–67 (1983).
*Chemical and Engineering News*, Dec. 21, 1981, 24–25.
*Science News*, Jan. 2, 1982, vol. 121, No. 1, p. 7.

*Primary Examiner*—Alan R. Rotman
*Attorney, Agent, or Firm*—Mary Katherine Baumeister; Dennis P. Clarke

[57] ABSTRACT

The subject compounds, which are adapted for the site-specific/sustained delivery of centrally acting drug species to the brain, are:
(a) compounds of the formula $$[D—DHC] \qquad (I)$$

wherein [D] is a centrally acting drug species, and [DHC] is the reduced, biooxidizable, blood-brain barrier penetrating lipoidal form of a dihydropyridine⇄pyridinium salt redox carrier, with the proviso that when [DHC] is (Abstract continued on next page.)

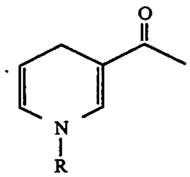

wherein R is lower alkyl or benzyl and [D] is a drug species containing a single $NH_2$ or OH functional group, the single OH group when present being a primary or secondary OH group, said drug species being linked directly through said $NH_2$ or OH function group to the carbonyl function of [DHC], then [D] must be other than a sympathetic stimulant, steroid sex hormone or long chain alkanol; and (b) non-toxic pharmaceutically acceptable salts of compounds of formula (I) wherein [D] is a centrally acting drug species and [DHC] is the reduced, biooxidizable, blood-brain barrier penetrating lipoidal form of a dihydropyridine⇄pyridinium salt redox carrier. The corresponding ionic pyridinium salt type drug/carrier entitles $[D—QC]^+X^-$ are also disclosed.

41 Claims, 8 Drawing Sheets

BRAIN-SPECIFIC DRUG DELIVERY OF STEROID SEX HORMONES CLEAVED FROM PYRIDINIUM CARBOXYLATES AND DIHYDRO-PYRIDINE CARBOXYLATE PRECURSORS

CROSS-REFERENCE TO RELATED APPLICATIONS

This application is a continuation-in-part of my earlier copending applications Ser. No. 379,316, filed May 18, 1982, now U.S. Pat. No. 4,449,932, filed Jan. 27, 1983, abandoned in favor of Ser. No. 733,463, filed May 13, 1985; Ser. No. 475,493, filed Mar. 15, 1983, now U.S. Pat. No. 4,622,218 and Ser. No. 516,382, filed July 22, 1983, now U.S. Pat. No. 4,540,564. Each of said earlier copending applications is hereby expressly incorporated by reference herein in its entirety and relied upon.

FIELD OF THE INVENTION

The present invention relates to a dihydropyridine/-pyridinium salt type or redox system for the site-specific or sustained delivery (or both) of a wide variety of drug species to the the brain. More especially, this invention relates to the discovery that a biologically active compound coupled to a lipoidal carrier moiety comprising a dihydropyridine nucleus readily and easily penetrates the blood-brain barrier ("BBB") and attains increased levels of concentration in the brain; oxidation of the dihydropyridine carrier moiety in vivo to the ionic pyridinium salts prevents its elimination from the brain, while elimination from the general circulation is accelerated, resulting in significant and prolongedly sustained brain-specific drug activity, whether ascribable to the cleavage of the [D—QC]+ entity and sustained release of the drug in the brain and/or to [D—QC]+ itself.

BACKGROUND OF THE INVENTION

The delivery of drug species to the brain is ofttimes seriously limited by transport and metabolism factors and, more specifically, by the functional barrier of the endothelial brain capillary wall deemed the blood-brain barrier, BBB. Site-specific delivery and sustained delivery of drugs to the brain are even more difficult, and to date (i.e. prior to the dates of applicant's earlier copending applications) no useful simple or generic techniques to achieve such phenomena are known to the art.

Indeed, the barriers separating plasma from the brain and cerebrospinal fluid (CSF) are complex systems involving passive and active transport and subserve a number of important functions. The boundary between plasma and the central nervous system (CNS) is much less permeable than that between plasma and other tissue cells to a variety of water soluble substances, such as organic electrolytes, organic acids and bases, as well as to large molecules such as proteins. Such a barrier also provides a path for clearance from the brain of the breakdown products of cellular metabolism. The CNS and its fluids can be considered basically a three-compartment system: the blood or the plasma, CSF and brain tissue. There is a diffusion-controlled exchange between CSF and the extracellular fluid (CF) of the brain. It has also been suggested that the permeabilities of blood-CSF and blood-brain barriers are practically identical with respect to drugs and other foreign substances. Mayer et al, *J. Pharmacol. and Exp. Therap.*, 125, 185 (1959).

The BBB is, moreover, basically the result of the fact that the endothelial cells in the brain capillaries are joined by continuous, tight intercellular junctions, such that material has to pass through the cells rather than between them in order to move from blood to brain. It is interesting that there are areas within the brain, such as the subfornical body and the postremia, in which the capillary cells are not closely linked so that they lack the characteristics of the BBB. They provide the entry of small amounts of compounds which would not ordinarily enter the barriers. Hoffman and Olszewzki, *Neurology (Minneap.)*, 11, 1081 (1961).

Foreign compounds which enter organs other than the central nervous system with ease, may penetrate the CNS slowly or hardly at all. A number of theories concerning the nature of the barrier have been proposed. The widely accepted concept describes the boundary as a fat-like layer interspersed with small pores, although the BBB is not a simple, anatomically well-defined unitary physical entity. Shuttleworth, *Prog. Exp. Tumor Res.*, 17, 279 (1972). Penetration of such a barrier may occur by several processes: lipid soluble substances may passively penetrate into the cells, while small molecules such as water and urea may pass through the pores. In addition to these simple physical processes, carrier-mediated and active transport processes govern the movement of many molecules through the BBB. Thus, it is generally accepted that lipid solubility, degree of ionic dissociation or protonation and the ability of temporary combination with membrane constituents affect delivery through the BBB. It has been shown, for example, that in the class of barbiturates, a quantitative correlation could be established between their ease to pass into the brain (as reflected by the different times of onset of anesthetic action) and their lipid/water partition coefficient. Mark et al, *J. Pharmacol. and Exp. Therap.*, 123, 79 (1957). The role of lipid solubility in drug penetration through the BBB is also exemplified by the better absorption of the sparingly water-soluble thiamine propyl disulfide (TPD) as compared to the water-soluble thiamine hydrochloride (THCl). Thomson et al, *Ann. Int. Med.*, 74,Z 529 (1971). Some materials such as glucose and amino acids are transported by active mechanism, characterized by saturation, bidirectional molecular specificity, bidirectional competitive inhibition and bidirectional countertransport. Fishman, *Am. J. Physiol.*, 206, 836 (1964).

Changes in permeability of the BBB can be caused by several pathological and toxicological processes. Pardridge, Connor and Crawford, *CRC Crit. Rev. Toxicol.*, 179 (1975). A general increase in the barrier permeability, such as a nonspecific breakdown of the barrier has, however, severe consequences, including cerebral edema.

It too is well documented that the BBB is relatively impermeable to the ionized forms of drugs and other molecules. Drugs which are weak organic electrolytes appear to pass from blood to CSF to reach a steady state ratio characteristic of each molecule according to its $pK_a$ and the existence of a normal pH gradient between blood and CSF. It is clear that it is the most difficult for quaternary pyridinium or ammonium salt to penetrate the BBB.

And removal of substances from the brain and CSF is obviously a significant factor in regulating drug concentrations in the CNS. There are several efflux processes: bulk flow via the arachnoid villi, diffusion of lipid soluble substances into brain and blood, active transport and metabolism by adjacent meninges. Once a drug or metabolite enters the CSF from blood or brain by simple diffusion, it may rapidly be removed, either by nonselective bulk flow or by active transport mechanism associated with the choroid plexus or other nondefined structures in the CSF compartment. It is generally accepted that highly lipid-soluble drugs leave the CSF more rapidly than poorly lipid-soluble ones, but the barrier to passage of compounds from CSF has only superficial similarity to the blood-CSF barrier.

Drug elimination processes from the brain are significantly directly related to drug accumulation in the brain. It is generally assumed that efflux in the opposite direction involves almost the same processes as for entry, except that the role of the bulk flow and the metabolic processes in the brain are not to be overlooked.

The two elimination processes studied in the earlier literature and which can be said to have a certain bearing on the present invention involve elimination from the brain of ionic species. Thus, it is found that non-metabolized ionic species, such as the acetate ion, have a three times slower elimination rate from the CSF than from the blood. Freundt, *Arz., Forsch.*, 23, 949 (1973). An even more dramatic change in the elimination rate was found in the case of a quaternary piperidinium salt. The quaternary salt, formed in situ after delivery of a haloalkylamine, which undergoes cyclization to the quaternary salt, in the brain, as well, was found to have an at least ten times slower elimination rate from the brain than from the rest of the body. It was concluded by the authors [Ross and Froden, *Eur. J. Pharmacol.*, 13, 46 (1970)] that the outflow rate of the quaternary salt corresponded to the inflow rate. Similar results were obtained for the erythrocytes: the efflux of the quaternary salt was very slow. Ross, *J. Pharm. Pharmacol.*, 27, 322(1975).

And while it too has been suggested to deliver a drug species, specifically N-methylpyridinium-2-carbaldoxime chloride (2-PAM), into the brain, the active nucleus of which in and of itself constitutes a quaternary pyridinium salt, by way of the dihydropyridine latentiated prodrug form thereof, such approach was conspicuously delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. Hence, no "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, *J. Pharm. Sci.*, 67, No. 5, pp. 685–687 (1978); Bodor et al, *Science*, Vol. 190 (1975), pp. 155–156; Shek, Higuchi and Bodor, *J. Med. Chem.*, Vol. 19 (1976), pp. 113–117. A more recent extension of this approach is described by Brewster, *Dissertation Abstracts International*, Vol. 43, No. 09, March 1983, p. 2910B. It has also been speculated to deliver, e.g., an antitumor agent, into the brain by utilizing a dihydropyridine/pyridinium redox carrier moiety therefor, but this particular hypothesis necessarily entails derivatizing the dihydropyridine/pyridinium carrier with a substituent itself critically designed to control the release rate of the active drug species from the quaternary derivative thereof, as well as being critically functionally coordinated with the particular chemical and therapeutic activity/nature of the anti-tumor drug species itself; Bodor et al, *J. Pharm. Sci.*, supra. See also Bodor, "Novel Approaches for the Design of Membrane Transport Properties of Drugs", in *Design of Biopharmaceutical Properties Through Prodrugs and Analogs*, Roche, E. B. (ed.), APhA Academy of Pharmaceutical Sciences, Washington, D.C., pp. 98–135 (1976). Moreover, the hypothesis does not include any indication of what chemical transformations would be needed to link any specific antitumor agent (or indeed any specific drug) to an appropriate carrier moiety.

Accordingly, acutely serious need exists in this art for a truly effective generaic but nonetheless flexible method for the site-specific, or sustained delivery, or both, of drug species to the brain, while at the same time avoiding the aforesaid noted and notable disadvantages and drawbacks associated with penetration of the blood-brain barrier, with dihydropyridine latentiated prodrug forms of drug species themselves comprising a pyridinium salt active nucleus, and with the necessity for introducing critically coordinated and designed, release rate-controlling substituents onto any particular drug carrier moiety. This need has been addressed by applicant's earlier copending applications referred to hereinabove, and especially by the Serial Nos. 379,316 and 516,382, and is also addressed by the present application.

It is also known to this art that Parkinsonism, a striatal dopamine deficiency syndrome [H. Ehringer and O. Hornykiewicz, *Klin. Wsch.*, 38, 1236 (1960)], cannot be treated directly with dopamine, for dopamine and related catecholamines also do not cross the blood-brain barrier ([B. E. Roos and G. Steg, *Life Sci.*, 3, 351 (1964)]. L-Dopa, considered as a prodrug for dopamine, was first discovered to be useful in the treatment of Parkinsonism more than twenty years ago [A. Barbeau, *Excepta Medica, Int. Congr. Ser.*, 38, 152 (1961); W. Birkmayer and O. Hornykiewicz, *Wien. Klin. Wochenschr.*, 73, 787 (1961)]. Indeed, L-Dopa is considered to be the best available treatment for Parkinsonism, but, unfortunately, at the expense of a wide variety of undesirable side effects [A. Barbeau, TIPS, 2, (11), 297 (1981]. The peripheral side effects of L-Dopa, which range from nausea and vomiting to cardiac arrythmias and hypotension, appear to be due to one or more of the metabolic products thereof, rather than L-Dopa per se. L-Aromatic amino acid decarboxylase enzyme is responsible for the major metabolism of L-Dopa, whether prior, during or after absorption. Concurrent administration of L-Dopa with an inhibitor of aromatic amino acid decarboxylase, which should not be able to penetrate the BBB, reduces the decarboxylation of L-Dopa in peripheral tissues. Such reduction allows higher proportions of L-Dopa to reach the CNS and at the same time diminishes the peripheral side effects considerably, particularly vomiting and cardiac arrythmias, but a number of serious side effects still persist [A. Barbeau, TIPS, supra; A. Barbeau ad M. Roy, *Neurology*, 26, 399 [(1976)]. Attempts have also been made to alleviate the well-known dissolution, absorption and metabolism problems of L-Dopa [H. Ninterberger, *Biochem. Med.*, 5, 412 (1971); H. Shindo, T. Komai, K. Tanaka, E. Nakajima and N. Miyakoshi, *Chem. Pharm. Bull.*, 21, 826 (1973); C. O. Rutledge and M. M. Hoehn, *Nature (London)*, 244, 447 (1973); R. L. Bronaugh, R. J. McMurty, M. M. Hoehn and C. O. Rutledge, *Biochem. Pharmacol.*, 24, 1317 (1975)], employing prodrug approaches [N. Bodor, K. B. Sloan, T. Higuchi and K. Sasahara, *J. Med. Chem.*, 20, 1435 (1977); A. M. Felix, D. P. Winter, S. S. Wang, I. D. Kulesha, W. R. Pool, D. L. Hane and H. Sheppard, *J. Med. Chem.*, 17, 422 (1974)].

Additional, dopamine agonists, which are used in the treatment of hyperproclactinemia associated with pituitary adenomas or amenorrhea [R. F. Spark and G. Dickenstein, *Ann. Int. Med.*, 90, 949 (1979)], also induce unwanted side effects.

Thus, especially acutely serious need exists in this art to deliver a dopaminergic agent directly and specifically to the brain, in a sustained manner, and there elicit the desired dopaminergic response, e.g., for the treatment of the Parkinsonism or hyperprolactinemia. This need has been addressed by applicant's earlier copending applications referred to above, and especially by the Ser. No. 461,543, and is also addressed by the present application.

SUMMARY AND OBJECTS OF THE INVENTION

Accordingly, a major object of the present invention is the provision of a generic method for the specific and/or target enhanced delivery to the brain of a wide variety of drug species and to achieve brain-specific drug delivery by effecting the bidirectional transport of the drug species into and out of the brain employing dihydropyridine⇄pyridinium salt carrier type redpox systems.

Another object of the invention is to provide for brain specific drug delivery utilizing a dihydropyridine⇄pyridinium salt carrier type redox system, shich drug/carrier system is characterized by enhanced drug efficacy and decreased toxicity. Indeed, consistent herewith systemic toxicity is significantly reduced by accelerating the elimination of the drug/quaternary carrier system, and even central toxicity is reduced by providing a low level, sustained release of the active drug species in the brain.

Yet another object of this invention is the provision of a chemical delivery system for the site-specific and sustained release of drug species to the brain, and one in which a special pro-prodrug reduced form of an active drug species is actually delivered to the body of a patient, not a prodrug as such and not a drug/carrier entity necessarily comprised of critically tailored release rate-controlling substituent(s).

Yet another object of this invention is to provide enhanced delivery to the brain of a wide variety of centrally acting agents which are not themselves able to penetrate the blood-brain barrier to any considerable extent.

Briefly, the present invention features a dihydropyridine⇄pyridinium salt carrier redox system for the specific and sustained delivery of drug species to the brain according to the following Scheme 1:

Scheme 1: BBB, blood-brain barrier.

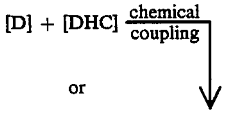

-continued

Scheme 1: BBB, blood-brain barrier.

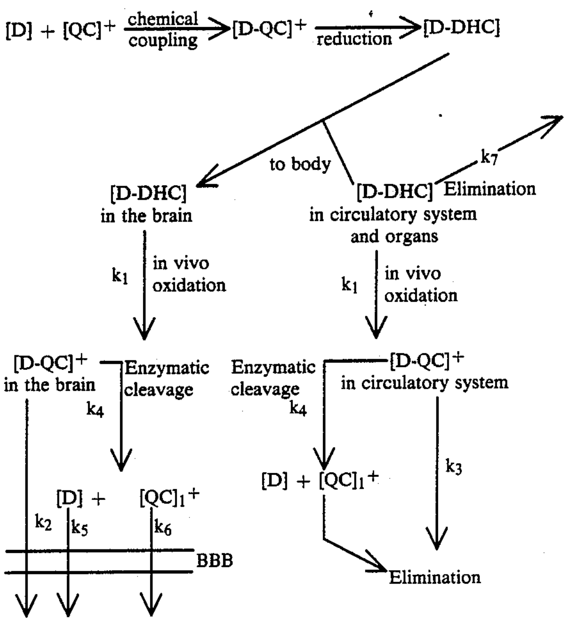

Consistent with the foregoing Scheme 1, any drug species [D] is coupled to a quaternary pyridinium salt carrier [QC]+ and the prodrug ([D—QC+ which results is then reduced chemically to the lipoidal dihydro pro-prodrug form [D—DHC]. Alternatively, the drug species [D] can be directly coupled to the dihydro carrier [DHC] in certain instances to yield said pro-prodrug form [D—DHC]. After administration of the [D—DHC] in vivo, it is rapidly distributed throughout the body, including the brain . The dihydro form [D—DHC] is then in situ oxidized (rate constant, $k_1$) (by the NAD⇄NADH system) to the ideally inactive original [D—QC]+ quaternary salt prodrug, which, because of its ionic, hydrophilic character, is rapidly eliminated from the general circulation of the body, while the blood-brain barrier prevents its elimination from the brain ($k_3>>k_2$; $k_3>>k_7$). Enzymatic cleavage of the [D—QC] that is "locked" in the brain effects a sustained delivery of the drug species [D], followed by its normal elimination ($k_5$), metabolism. A properly selected carrier [QC]+ will also be rapidly eliminated from the brain ($k_6>>k_2$). Because of the facile elimination of [D—QC+ from the general circualtion, only minor amounts of drug are released in the body ($k_3>>k_4$); [D] is released primarily in the brain ($k_4>k_2$). The overall result is a brain-specific, sustained release of the target drug species. Cf. Bodor et al, *Science*, Vol. 214, Dec. 18, 1981, pp. 1370–1372; *The Friday Evening Post*, Aug. 14, 1981, Health Center Communications, University of Florida, Gainesville, Fla; *Chemical & Engineering News*, Dec. 21, 1981, pp. 24–25; *Science News*, Jan. 2, 1982, Vol. 121, No. 1, page 7. See also Bodor et al, *J. Med. Chem.*, Vol. 26, March 1983, pp. 313–317; Bodor et al, *J. Med. Chem.*, Vol. 26, April 1983, pp. 528–534; Bodor et al, *Pharmacology and Therapeutics*, Vol. 19, No. 3, pp. 337–386 (April 1983); Bodor et al, *Science*, Vol. 221, July 1983, pp. 65–67; and Bodor et al, *J. Pharm. Sci.*, Vol. 73, No. 3, March 1984, pp. 385–388.

In accord with the foregoing, the present invention provides compounds adapted for the site-specific/sustained delivery of a centrally acting drug species to the brain, said compounds being:

(a) compounds of the formula

[D—DHC] (I)

wherein [D] is centrally acting drug species, and [DHC] is the reduced, biooxidizable, blood-brain barrier penetrating lipoidal form of a dihydropyridine⇄pyridinium salt redox carrier, with the proviso that when [DHC] is

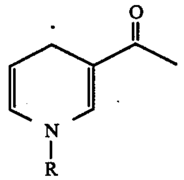

wherein R is lower alkyl or benzyl and [D] is a drug species containing a single $NH_2$ or OH functional group, the single OH group when present being a primary or secondary OH group, said drug species being linked directly through said $NH_2$ or OH functional group to the carbonyl function of [DHC], then [D] must be other than a sympathetic stimulant, steroid sex hormone or long chain alkanol; or (b) non-toxic pharmaceutically acceptable salts of compounds of formula (I) wherein [D] is a centrally acting drug species and [DHC] is the reduced, biooxidizable, blood-brain barrier penetrating lipoidal form of a dihydropyridine⇄pyridinium salt redox carrier.

In another aspect, the present invention provides compounds having the formula $[D—QC]^+X^-$ (II)

wherein $X^-$ is the anion of a non-toxic pharmaceutically acceptable acid, [D] is a centrally acting drug species and $[QC]^+$ is the hydrophilic, ionic pyridinium salt form of a dihydropyridine⇄pyridinium salt redox carrier, with the proviso that when $[QC]^+$ is

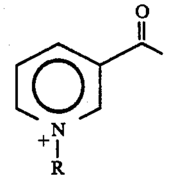

wherein R is lower alkyl or benzyl and [D] is a drug species containing a single $NH_2$ or OH functional group, the single OH group when present being a primary or secondary OH group, said drug species being linked directly through said $NH_2$ or OH functional group to the carbonyl function of $[QC]^+$, then [D] must be other than a sympathetic stimulant, steroid sex hormone or long chain alkanol.

The present invention further provides a generic method for specific and/or target enhanced delivery to the brain of a wide variety of centrally acting drug species, such brain-specific drug delivery being effected via the bidirectional transport of the drug species into and out of the brain by means of dihydropyridine⇄pyridinium salt carrier type redox systems.

In yet another aspect, the present invention provides, as an effective dopaminergic chemical delivery system, compounds having the formula

[D—DHC] (I)

and non-toxic pharmaceutically acceptable salts thereof, wherein [D] is a dopamine having the structural formula

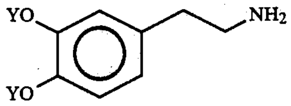

in which each Y is independently hydrogen or a hydrolytically or metabolically cleavable hydroxyl protective group, and [DHC] is the reduced, biooxidizable, blood-brain barrier penetrating, lipoidal form of a dihydropyridine⇄pyridinium salt redox carrier.

In still another aspect, the present invention provides compounds having the formula $[D—QC]^+X^-$ (II)

wherein $X^-$ is defined above and [D] is a dopamine having the structural formula

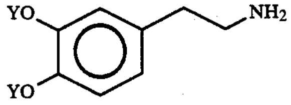

in which each Y is independently hydrogen or a hydrolytically or metabolically cleavable hydroxy protective group, and $[QC]^+$ is the hydrophilic, ionic pyridinium salt form of a dihydropyridine⇄pyridinium salt redox carrier.

Briefly, one presently preferred chemical delivery system for dopamine according to this invention has the structure (2) in the following Scheme 2, wherein the amino function of dopamine is appropriately linked to the dihydropyridine-type carrier system, while the catechol function is advantageously protected, for example, as a corresponding ester function, e.g., the dipivalyl ester illustrated. The brain-specific delivery of dopamine, or the otherwise eliciting of a dopaminergic response, requires a succession of processes, including oxidation of the dihydropyridine ring to the corresponding pyridinium salt (for example, structure 3), which provides the basis for "locking-in" in the brain the molecule, hydrolysis of the, e.g., pivalyl esters (see structure 4) likely via the 3- and/or 4-monopivalyl esters and, finally, the release of dopamine (1) from 4, which can be either a hydrolysis or a reductive process [a possible reductive release of dopamine was very recently suggested by a model for a presynaptic terminal, L. L. Miller, A. N. K. Lau and E. K. Miller, *J. Am. Chem. Soc.*, 104, 5242 (1982)].

Scheme 2:

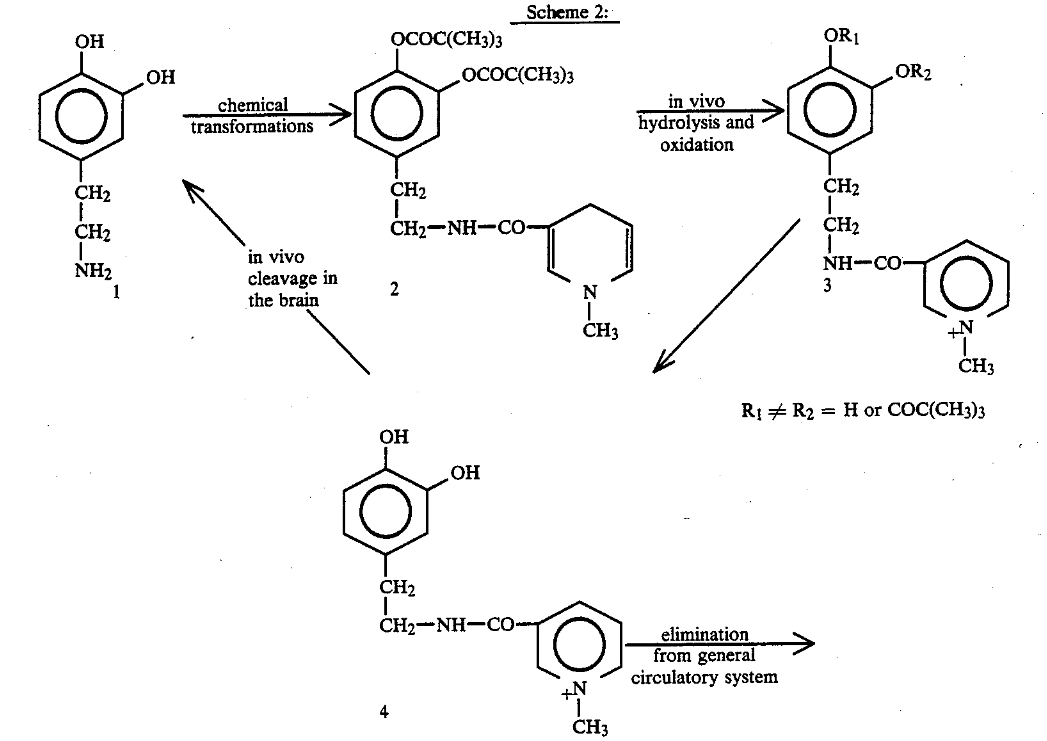

1 2 3 4

$R_1 \neq R_2$ = H or $COC(CH_3)_3$

As per the above Scheme 2, for the brain specific delivery of dopamine (1), structure 2 is one chemical delivery system consistent herewith, and 4 is one precursor locked in the brain and eliminated rapidly from the rest of the body. Structures 3 depict intermediates formed during the stepwise hydrolysis and oxidation processes.

DETAILED DESCRIPTION OF THE INVENTION

Figure 1:
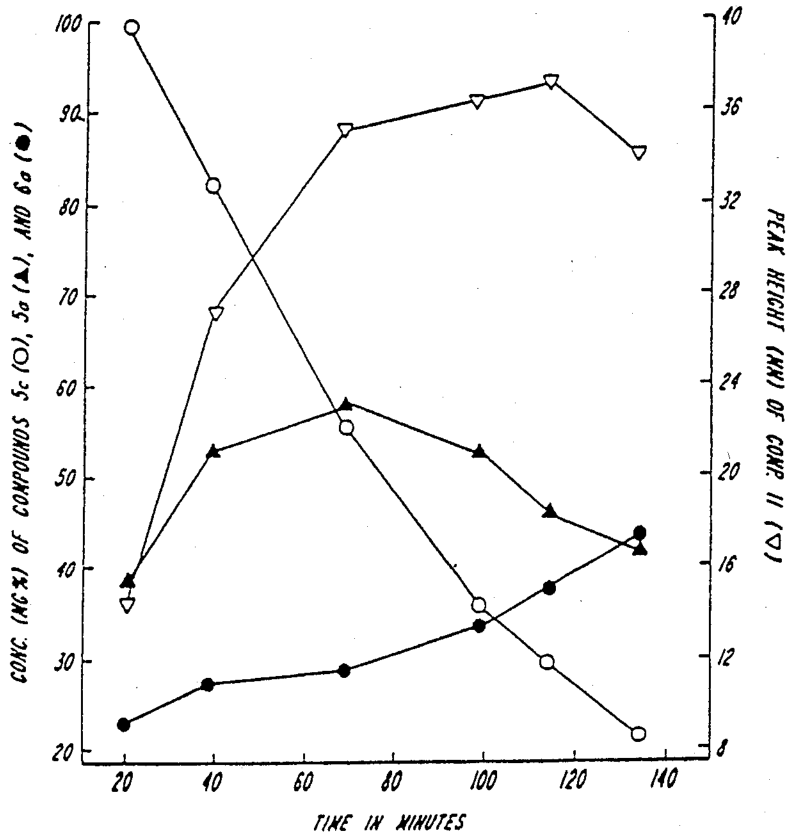
FIG. 1 is a graph plotting the time course of 1-methyl-3-{N-[β-(3,4-dipivalyloxphenyl)ethyl]}carbamoyl-1,4-dihydropyridine 5c (O) and its products, the monopivalyl-dihydro derivative 11 (▽), the dihydrodopamine derivative 5a (▲) and the quaternary dopamine precursor 6c (●) in plasma.
Figure 2:
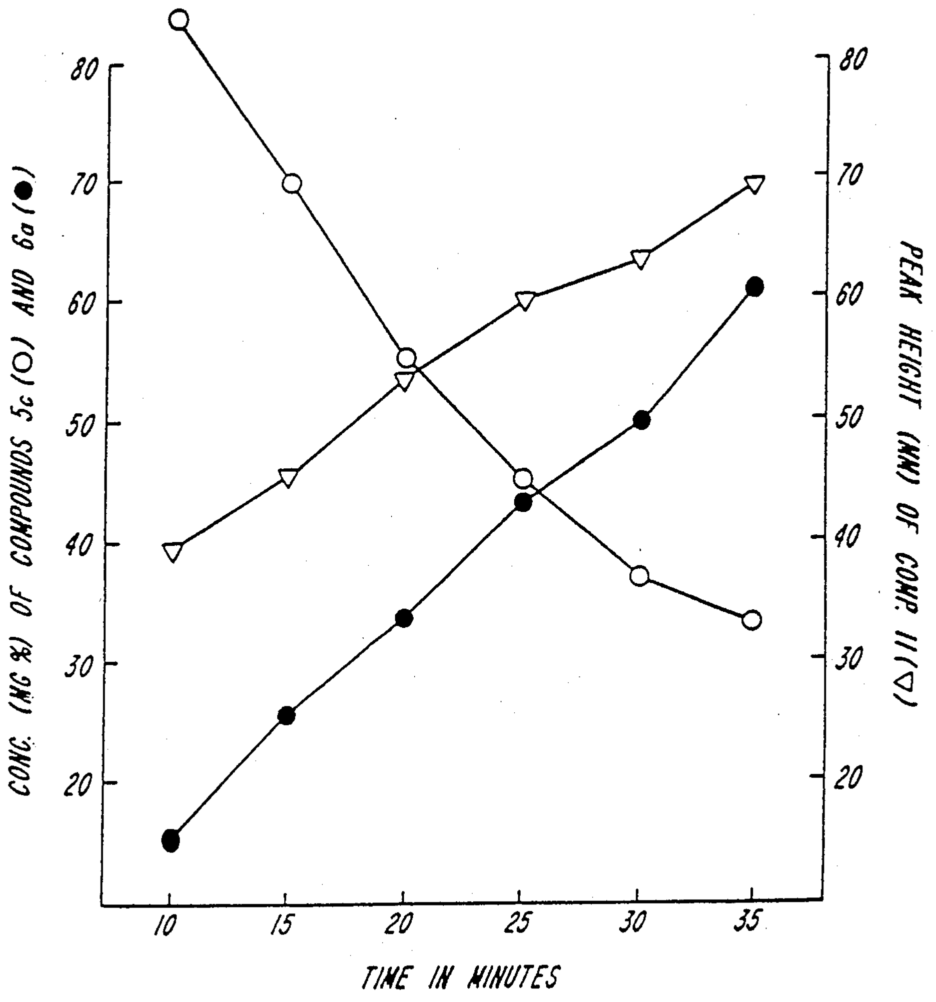
FIG. 2 is a graph plotting the time course of 1-methyl-3-{N-[β-(3,4-dipivalyloxyphenyl)ethyl]}carbamoyl-1,4-dihydropyridine 5c (O) and its products, the monopivalyl-dihydro drivative 11 (▽) and the quaternary dopamine precursor 6a (●) in whole blood.
Figure 3:
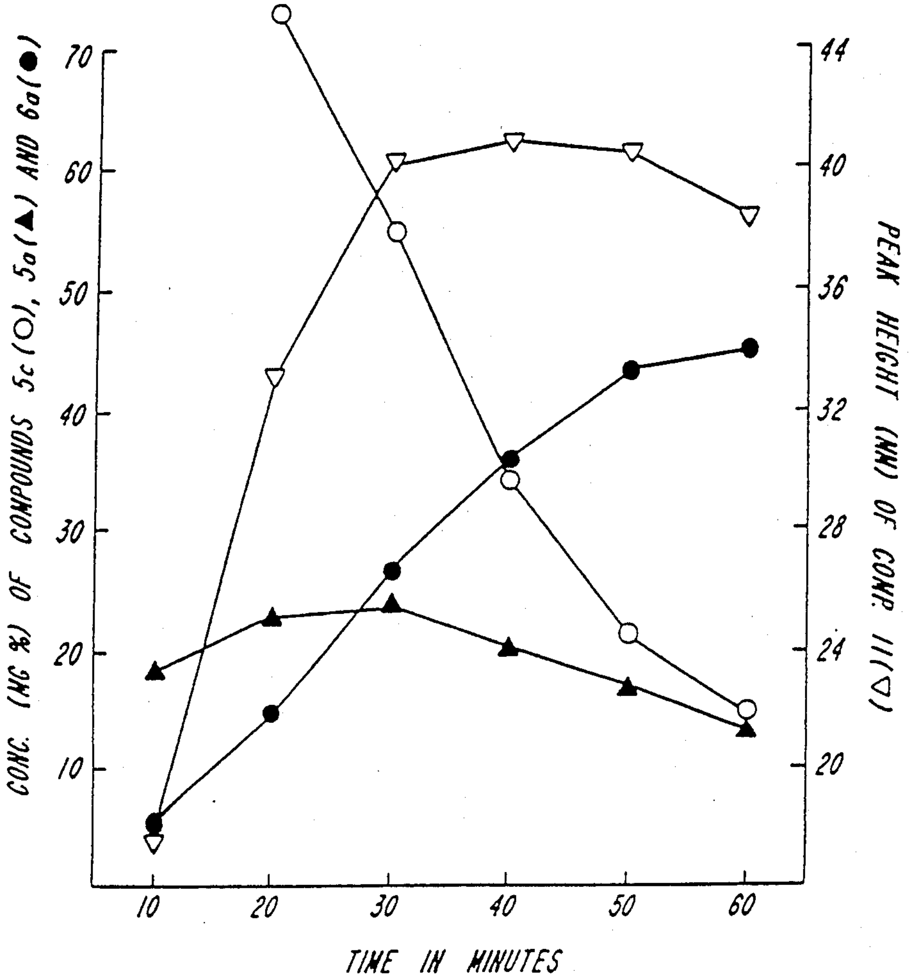
FIG. 3 is a graph plotting the time course of 1-methyl-3-{N-[β-(3,4-dipivalyloxyphenyl)ethyl]}carbamoyl-1,4-dihydropyridine 5c (O) and its products, the monopivalyl-dihydro derivative 11 (▽), the dihydrodopamine derivative 5a (▲) and the quaternary dopamine precursor 6a (●) in 20% brain homogenate.
Figure 4:
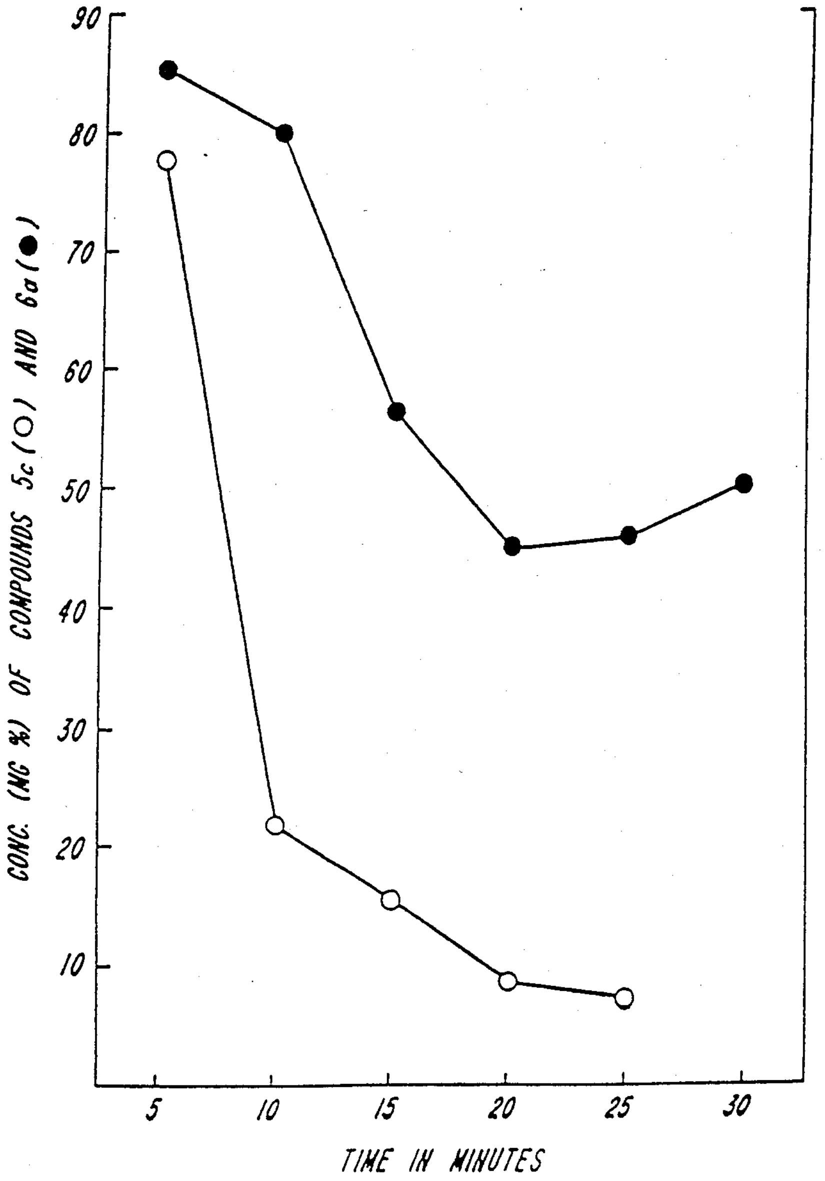
FIG. 4 is a graph plotting the time course of 1-methyl-3-{N-[β-(3,4-dipivalyloxyphenyl)ethyl]}carbamoyl-1,4-dihydroxypridine 5c (O) and its product, the quaternary dopamine precursor 6a (●) in 20% liver homogenate.

More particularly in accord with the present invention, the following definitions are applicable:

The term "lipoidal" as used herein is intended to designate a carrier moiety which is lipid-soluble or lipophilic.

The expression "hydroxyl protective group" is intended to designate a group which is inserted in place of the hydrogen atom(s) of an OH group or groups in order to prevent premature metabolism of said OH group or groups prior to the compound's reaching the desired site in the body. Typical hydroxyl protective groups contemplated by the present invention (e.g., for Y in the case of the dopamine derivatives) are acyl groups and carbonates.

When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

$$\text{cycloalkyl-}C_rH_{2r}-\overset{\overset{\displaystyle O}{\|}}{C}-$$

wherein the cycloalkyl portion contains 3 to 7 ring atoms and r is zero, one, two or three; phenoxyacetyl; pyridinecarbonyl; and $$\text{phenyl-}C_rH_{2r}-\overset{\overset{\displaystyle O}{\|}}{C}-$$

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is $$\text{cycloalkyl-}C_rH_{2r}-\overset{\overset{\displaystyle O}{\|}}{C}-$$

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is $$\text{phenyl-}C_rH_{2r}-\overset{\overset{\displaystyle O}{\|}}{C}-$$

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, p-n-butoxybenzoyl, 2,4,6-triethoxybenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(p-trifluoromethylphenyl)propionyl, 2-methyl-4-methoxybenzoyl, 3-chloro-4-ethoxybenzoyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl and p-acetamidophenylpropionyl.

When the hydroxyl protective group is a carbonate grouping, it has the structural formula $$Y'-O-\overset{\overset{\displaystyle O}{\|}}{C}-$$

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

$$\text{cycloalkyl}-C_rH_{2r}-$$

wherein the cycloalkyl portion contains 3 to 7 ring atoms and r is zero, one, two or three; phenoxy; 2-, 3- or 4-pyridyl; or $$\text{phenyl}-C_rH_{2r}-$$

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$–$C_7$ alkyl, particularly ethyl or isopropyl.

Similarly, the expression "carboxyl protective group" is intended to designate a group which is inserted in place of the hydrogen atom(s) of a COOH group or groups in order to prevent premature metabolism of said COOH group or groups prior to the compound's reaching the desired site in the body. Typical carboxyl protecting groups are the groups encompassed by Y' above, especially $C_1$–$C_7$ alkyl, particularly ethyl, isopropyl and t-butyl. While such simple alkyl esters and the like are often useful, other carboxyl protecting groups may be selected in order to achieve greater control over the rate of in vivo hydrolysis of the ester back to the acid and thus enhance drug delivery. To that end, carboxyl protecting groups such as the following may be used to replace the hydrogen of the —COOH group:

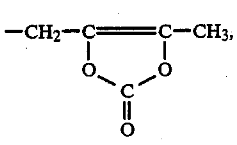, $-\text{alk-O}\overset{\overset{\displaystyle O}{\|}}{C}-\text{alkyl}$, -continued

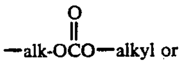 or —alk-O—alkyl, wherein alk is $C_1$–$C_6$ straight or branched alkylene and the alkyl radical is straight or branched and contains 1 to 7 carbon atoms (e.g.

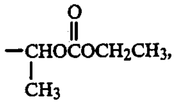

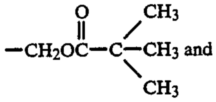 and —$CH_2OCH_3$).

The expression "amino protective group" as used herein is intended to designate a group which is inserted in place of the hydrogen atom(s) of an amino group or groups in order to prevent unwanted reaction of the amino function(s) during chemical synthesis. Such protective groups are well-known in the art and include t-butoxycarbonyl and carbobenzoxy (i.e. benzyloxycarbonyl). Other appropriate amino protective groups will be apparent to those skilled in the art. Unlike the instant hydroxyl and carboxyl protective groups described above, which not only prevent unwanted chemical reaction but also protect those hydroxyl and carboxyl functions from premature metabolism in vivo, the amino protective groups are primarily intended for use during synthesis and are typically removed by well-known procedures at an appropriate stage of the synthetic pathway after they have achieved their protective function and are no longer needed. Occasionally, however, an amino protective function will be retained in the compound of formula (I) to also protect the amino group in vivo.

The term "drug" as used herein means any substance intended for use in the diagnosis, cure, mitigation, treatment or prevention of disease or in the enhancement of desirable physical or mental development and conditions in man or animal.

By "centrally acting" drug species, active agent or compound as utilized herein, there is of course intended any drug species or the like, a significant (usually, principal) pharmacological activity of which is CNS and a result of direct action in the brain.

Exemplary such centrally acting drug species are the CNS-amines and other nervous system agents, whether sympathetic or parasympathetic, e.g., phenylethylamine (a stimulant), dopamine (a neurotransmitter and dopaminergic agent used, e.g., in the treatment of Parkinsonism or hyperprolactinemia), tyramine (a stimulant), L-DOPA (a dopamine precursor used, for example, in the treatment of Parkinsonism); muscle relaxants, tranquilizers and antidepressants, e.g., benzodiazepine tranquilizers such as diazepam and oxazepam and phenothiazine tranquilizers such as carphenazine, fluphenazine and the like; mild and strong analgesics and narcotics; sedatives and hypnotics; narcotic antagonists; vascular agents; stimulants; anesthetics; small peptides, such as the di-, tri-, tetra and pentapeptides, and other small 2–20 amino acid unit containing peptides, e.g. the enkephalins (for example, Tyr-Gly-Gly-Phe-Leu), which, besides being analgesics, initiate epileptic activity in the brain at doses that are about tenfold lower than for effecting analgesic activity; larger peptides, such as pituitary hormones and related agents; growth-promoting substances; antiepileptic and anticonvulsant drugs generally, including hydantoins such as phenytoin and ethotoin, barbituates such as phenobarbital; hormones, such as the steroid hormones, e.g., estradiol, testosterone, 17 $\alpha$-ethylnyl testosterone (ethisterone), and the like (recent studies on histological mapping of hormone-sensitive and specific steroid binding cells in the brain have underscored the importance of the steroid action in the brain on sexual behavior); amphetamine-like drugs; anticancer and anti-Parkinsonism agents; antihypertensives; agents to enhance learning cpacity and the memory processes, including treatment of dementias, such as Alzheimer's disease; antibacterials; centrally acting hypotensive agents; centally acting prostaglandins, such as $PGD_2$; diagonstic agents, such as radio-pharmaceuticals; monoamine oxidase (MAO) inhibitor drugs; CNS or brain important/essential amino acids, such as tryptophan (which is an antidepressant as well as a nutrient); and any like centrally acting compounds. For the purposes of this invention, dopa or L-DOPA is not classified as an amino acid but rather as a CNS amine and dopaminergic agent used, e.g. in the treatment of Parkinsonism.

Other illustrative ultimate species of centrally acting drug entities are: amphetamine, dextroamphetamine, levamphetamine, aletamine, cypenamine, fencamfamin, fenozolone, zylofuramine, methamphetamine, phenmetrazine and phentermine, which are sympathomimetic amines/cerebral stimulants and appetite suppressants; etryptamine, a cerebral stimulant; codeine, oxycodone, pentazocine, anileridine, hydromorphone, morphine and oxymorphone, which are narcotic analgesics; desipramine, nortriptyline, octriptyline, maprotiline, opipramol and protriptyline, which are cerebral stimulants/tricylic antidepressants of the dibenzazepine type used, e.g., in endogenous depressions; clonidine and methyldopa, which are sympatholytic agents used, e.g., in hypertension; biperiden, cycrimine and procyclidine, which are centrally acting anticholinergics; tranylcypromine, a sympathomimetic cerebral stimulant/MAO inhibitor and antidepressant; acetophenazine, carphenazine, fluphenazine, perphenazine and piperacetazine, which are phenothiazine-type tranquilizers; benzoctamine, a sedative/muscle relaxant which structurally is an analogue of the phenothiazine tranquilizers; chlordiazepoxide, clorazepate, nitrazepam and temazepam, which are benzodiazepine-type tranquilizers; noracymethadol, a narcotic analgesic of the methadone type; piminodine, a narcotic analgesic of the meperidine type; tracazolate, a sedative/hypotensive; prizidilol, a centrally acting hypotensive; sulpiride, an antidepressant/psychotropic; haloperidol and clopenthixol, which are tranquilizers; norepinephrine, a sympathetic stimulant/adrenergic agent; nalorphine and naloxone, narcotic antagonists; hydralazine, a hypotensive; ethotoin, phenobarbital and aminoglutethimide, anticonvulsants; epinephrine, an adrenergic agent; ethamivan, a medullary stimulant; bemegride, a barbiturate antagonist; amiphenazole, a stimulant; iopydol, iodopyracet, idouppurate (o-iodohippuric acid), iodamide and iopanoic acid, which are radiodiagnostics; ephedrine, pseudoephedrine, oxymetazoline and phenylephrine, which are sympathomimetic amines and decongestants; estradiol, estrone and estriol, the natural estrogens; amoxicillin, oxacillin, carbenicillin, benzylpenicillin, phenoxymethylpenicillin, methicillin, nafcillin, ticarcillin, bacampicillin, epicillin, hetacillin, pivampacillin, the methoxymethyl ester of hetacillin, and ampicillin, which are penicillin-type antibiotics; amobarbital; a sedative; trihexyphenidyl, a centrally acting antichloinergic; hydroxyzine, a tranquilizer; chlortetracycline, demeclocycline, minocycline, doxycycline, oxytertracycline, tetracycline and methacycline, which are tetracycline-type antibiotics; flurazepam, bromazepam, demoxepam and lorazepam, benzodiazepine tranquilizers; phenytoin, an anticonvulsant; glutethimide, a mild hypnotic/-sedative; clindamycin, lincomycin, nalidixic acid, oxolinic acid and phenazopyridine, antibacterials/antibiotics; bethanidine and guanethidine, hypotensives/sympatholytics; captopril, a hypotensive; methyprylon, a mild hypnotic; amedalin, bupropion, cartazolate, daledalin, difluanine, fluoxetine and nisoxetine, which are cerebral stimulants; propranolol, a $\beta$-blocker antihypertensive; dicloxacillin, a penicillin-type antibacterial; butalbital, a barbiturate sedative; GABA, $\gamma$-vinyl GABA, $\gamma$-acetylenic GABA, neurotransmitters for possible use in epilepsy; valproic acid and its metabolites such as 5-hydroxy-2-n-propyl-pentanoic acid, 4-hydroxy-2-n-propylpentanoic acid, 3-hydroxy-2-n-propylpentanoic acid, for use as anticonvulsants; valpromide, a valproic acid derivative for use as an anticonvulsant; apomorphine, a narcotic depressant/emetic which has been used in the treatment of photosensitive epilepsy; pholcodine, a narcotic antitussive; methotrexate, mitoxantrone, podophyllotoxin derivatives (etopside, teniposide), doxorubicin, daunamycin and cyclophosphamide, anticancer/antitumor agents; methylphenidate, a stimulant; thiopental, an anesthetic; ethinyl estradiol and mestranol, estrogens; meptazinol, cyclazocine, phenazocine, profadol, metopon, drocode and myfadol, which are narcotic analgesics; buprenorphine, nalbuphine, butorphanol, levallorphan, naltrexone, alazocine, oxilorphan and nalmexone, which are narcotic antagonists or agonist-antagonists; norgestrel and norethindrone, progestins; cephalothin, cephalexin, cefazolin, cefoxitin, moxalactam, ceforanide, cefroxadine and cephapirin, cephalosporin antibiotics; atenolol, nadolol, timolol and metoprolol, $\beta$-blockers/hypotensives; ACTH (corticotropin), a hormone which stimulates glucocorticoid production; LHRH, a neurotransmitter which stimulates secretion of the pituitary hormones, LH and FSH, and has been used to induce ovulation as well as for fertility control/contraception; sulfadiazine and other sulfonamide antibiotics; ribavarin and acyclovir, antiviral agents; chlorambucil and melphalan, nitrogen mustard-type anticancer/antitumor agents; methotrexate and aminopterin, which are folic acid antagonist-type anticancer/antitumor agents; platinum coordination complexes, i.e. cisplatin analogue-type anticancer/antitumor agents; dactinomycin and mitomycin C, used in cancer chemotherapy; thioguanine, a purine/pyrimidine antagonist used in cancer treatment; vincristine and vinblastine, anticancer alkaloids; hydroxyurea and DON, anticancer urea derivatives; FSH, HCG and HCS, pituitary and nonpituitary gonadotropins, used, for example, in certain reproductive disorders; N,N'-bis(dichloracetyl)-1,8-octamethylenediamine (fertilysin), an agent for male fertility inhibition; levorphanol, a narcotic analgesic; benzestrol and diethylstilbestrol, synthetic estrogens; ethyl $\beta$-carboline-3-carboxylate, a benzodiazepine antagonist; furosemide, a diuretic/antihypertensive; dipyridamole and nifedipine, coronary vasodilators; and progabide, a GABA-agonist and prodrug of GABA. Yet other ultimate species include nonsteroidal antiinflammatory agents/non-narcotic analgesics, e.g. propionic acid derivatives, acetic acid derivatives, fenamic acid derivatives and biphenylcarboxylic acid derivatives. Specific NSAID's/non-narcotic analgesics contemplated for use herein include ibuprofen, naproxen, flurbiprofen, zomepirac, sulindac, indomethacin, fenbufen, fenoprofen, indoproxen, ketoprofen, fluprofen, bucloxic acid, tolmethin, alclofenac, fenclozic acid, ibufenac, flufenisal, pirprofen, flufenamic acid, mefenamic acid, clonixeril, clonixin, meclofenamic acid, flunixin, diclofenac, carprofen, etodolac, endosal, prodolic acid, sermetacin, indoxle, tetrydamine, diflunisal, naproxol, piroxicam, metazamide, flutiazin and tesicam.

Preferred classes of centrally acting drugs for use herein are the central neurotransmitters, steroids, anticancer and antitumor agents, antiviral agents, tranquilizers, memory enhancers, hypotensives, sedatives, antipsychotics and cerebral stimulants (especially tricyclic antidepressants). Among the neurotransmitters, there can be mentioned amino acids, such as GABA, GABA derivatives and other omega-amino acids, as well as glycine, glutamic acid, tyrosine, aspartic acid and other natural amino acids; catecholamines, such as dopamine, norepinephrine and epinephrine; serotonin, histamine and tryptamine; and peptides such as neurotensin, luteinizing hormone-releasing hormone (LHRH), somatostatin, enkephalins such as met$^5$-enkephalin and leu$^5$-enkephalin, endorphins such as $\gamma$-, $\alpha$- and $\beta$-endorphins, oxytocin M and vasopressin. Synthetic and semi-synthetic analogues, e.g. analogues of LHRH in which one or more amino acid(s) has/have been eliminated and/or replaced with one or more different amino acid(s), and which may be agonists or antagonists, are also contemplated, e.g. the primary and secondary amine LHRH analogues disclosed in U.S. Pat. Nos. 4,377,574, 3,917,825, 4,034,082 and 4,338,305. Among the steroids, there can be mentioned anti-inflammatory adrenal cortical steroids such as hydrocortisone, betamethaxone, cortisone, dexamethaxone, flumethasone, fluprednisolone, meprednisone, methyl prednisolone, prednisolone, prednisone, triamcinolone, cortodoxone, fluroroctisone, flurandrenolone acetonide (flurandrenolide), paramethasone and the like; male sex hormones (androgens), such as testosterone and its close analogues, e.g. methyl testosterone (17-methyltestosterone); and female sex hormones, both estrogens and progestins, e.g. progestins such as norgestrel, norethindrone, norethynodrel, ethisterone, dimethisterone, allylestrenol, cingestol, ethynerone, lynestrenol, norgesterone, norvinisterone, ethynodiol, oxogestone and tigestol, and estrogens such as ethinyl estradiol, mestranol, estradiol, estriol, estrone and quinestrol and the like. Among the anticancer and antitumor agents, there can be mentioned Ara-AC, pentostatin (2'-deoxycoformycin), Ara-C (cytarabine), 3-deazaguanine, dihydro-5-azacytidine, tiazofurin, sangivamycin, Ara-A (vitarabine), 6-MMPR, PCNU, spiromustine, bisbenzimidazole, L-alanosine (6-diazo-5-oxo-L-norleucine), DON, L-ICRF, trimethyl, TMM, 5-methyltetrahydrohomofolic acid, glyoxylic acid sulfonylhydrazone, DACH, SR-2555, SR-2508, desmethylmisonidazole, mitoxantrone, menogarol, aclacinomycin A, phyllanthoside, bactobolin, aphidocolin, homoharringtonine, levonatradol, acivicin, streptozotocin, hydroxyurea, chlorambucil, cyclophosphamide, uracil mustard, melphalan, 5-FUDR (floxuridine), vincristine, vinblastine, cytosine arabinoside, 6-mercaptopurine, thioguanine, 5-azacytidine, methotrexate, adriamycin (doxorubicin), daunomycin (daunorubicin), largomycine polypeptide, aminopterin, dactinomycin, mitomycin C, and podophyllotoxin derivatives, such as etoposide (VP-16) and teniposide. Among the antiviral agents, there can be mentioned ribavarin; acyclovir (ACV); amantadine (also of possible value as an anti-Parkinsonism agent); diarylamidines such as 5-amidino-2-(5-amidino-2-benzofuranyl)indole and 4',6-diimidazolino-2-phenylbenzo(b)thiophene; 2-aminooxazoles such as 2-guanidino-4,5-di-n-propyloxazole and 2-guanidino-4,5-diphenyloxazole; benzimidazole analogues such as the syn and anti isomer of 6[[(hydroxyimino)phenyl]methyl]-1-[(1-methylethyl)sulfonyl]-1H-benzimidazol-2-amine; bridgehead C-nucleosides such as 5,7-dimethyl-2-β-D-ribofuranosyl-s-triazole(1,5-a)pyrimidine; glycosides such as 2-deoxy-D-glucose, glucosamine, 2-deoxy-2-fluoro-D-mannose and 6-amino-6-deoxy-D-glucose; phenyl glucoside derivatives such as phenyl-6-chloro-6-deoxy-β-D-glucopyranoside; (S)-9-(2,3-dihydroxypropyl)adenine; 6-azauridine; idoxuridine; trifluridine; BDVU (bisdihydroxyvinyluridine); and 5,6-dichloro-1-β-D-ribofuranosylbenzimidazole. Among the tranquilizers, there can be mentioned benzodiazepine tranquilizers, such as diazepam, oxazepam, lorazepam, chloridazepoxide, flurazepam, bromazepam, chlorazepate, nitrazepam and temazepam; hydantoin-type tranquilizers/anticonvulsants such as phenytoin, ethotoin, mephenytoin; phenothiazine-type tranquilizers such as acetophenazine, carphenazine, fluphenazine, perphenazine and piperacetazine; and others. Among the hypotensives, there can be mentioned clonidine, methyldopa, bethanidine, debrisoquin, hydralazine, and guanethidine and its analogues. Among the sedatives, tranquilizers and antipsychotics, there can be mentioned the many specific compounds of this type disclosed above, especially the phenothiazines and benzodiazepines and their analogues. Among the cerebral stimulants, there also can be mentioned the many specific compounds set forth hereinabove, particularly the sympathomimetic amine-type cerebral stimulants and the tricyclic antidepressants, especially preferred tricyclics being the dibenzazepines and their analogues.

Also illustrative of the centrally acting drug species contemplated by this invention are centrally active metabolites of centrally acting drugs. Such metaolites are typified by hydroxylated metabolites of tricyclic antidepressants, such as the E- and Z-isomers of 10-hydroxynortriptyline, 2-hydroxyimipramine, 2-hydroxydesipramine and 8-hydroxychlorimpramine; hydroxylated metabolites of phenothiazine tranquilizers, e.g. 7-hydroxychlorpromazine; and desmethyl metabolites of N-methyl benzodiazepine tranquilizers, e.g. desmethyldiazepam. Other CNS active metabolites for use herein will be apparent to those skilled in the art, e.g. SL 75102, which is an active metabolite of progabide, a GABA agonist. Typically, these CNS active metabolites have been identified as such in the scientific literature but have not been administered as drugs themselves. In many cases, the active metabolites are believed to be comparable in CNS activity to their parent drugs; frequently, however, the metabolites have not been administered per se because they are not themselves able to penetrate the blood-brain barrier.

As indicated hereinabove, diagnostic agents, including radiopharmaceuticals, are encompassed by the expression "centrally acting drug" or the like as used herein. Any diagnostic agent which can be derivatized to afford a compound of formula (I) which will penetrate the BBB and concentrate in the brain in its quaternary form (II) and can be detected therein is encompassed by this invention. The diagnostic may be "cold" and be detected by X-ray (e.g. radiopaque agents) or other means such as mass spectrophotometry, NMR or other non-invasive techniques (e.g. when the compound includes stable isotopes such as C13, N15, O18, S33 and S34). The diagnostic alternatively may be "hot", i.e. radiolabeled, such as with radioactive iodine (I 123, I 125, I 131) and detected/imaged by radiation detection/imaging means. Typical "cold" diagnostics for derivation herein include p-iodohippuric acid, iothalamic acid, iopydol, iodamide and iopanoic aicd. Typical radiolabeled diagnostics include diohippuric acid (I 125, I 131), diotyrosine (I 125, I 131), o-iodohippuric acid (I 131), iothalamic acid (I 125, I 131), thyroxine (I 125, I 131), iotyrosine (I 131) and iodometaraminol (I 123), which has the structural formula

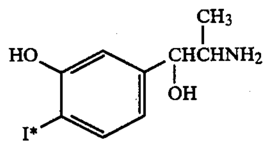

In the case of diagnostics, unlike the case of drugs which are for the treatment of disease, the "locked in" quaternary form will be the form that is imaged or otherwise detected, not the original diagnostic itself. Moreover, any of the centrally acting drugs encompassed by this invention which are intended for the treatment or prevention of medical disorders but which can be radiolabeled, e.g. with a radioisotope such as iodine, or labeled with a stable isotope, can thus be converted to a diagnostic for use herein. Put another way, any compound of formula (I) of this invention which can have incorporated into its structure such a radioactive or stable isotope [either directly or through incorporation of the isotope into the structure of the corresponding compound of formula (II)] can be used for diagnostic purposes.

It will be apparent from the known structures of the many drug species exemplified above, that in many cases the selected drug will possess more than one reactive functional group, and, in particular, that the drug may contain hydroxyl or carboxyl or amino or other functional groups in addition to the groups to which the carrer will be linked, and that these additional groups will at times benefit from being protected during synthesis and/or during administration. The nature of such protection is described in more detail below. Obviously, such protected drug species are encompassed by the definition of "drug" set forth hereinabove.

It too will be appreciated that by "dihydropyridine carrier" or "[DHC]", there is intended any nontoxic carrier moiety comprising, containing or including the dihydropyridine nucleus, whether or not a part of any larger basic nucleus, and whether substituted or unsubstituted, the only criterion therefor being capacity for BBB penetration and in vivo oxidation thereof to the corresponding quaternary pyridinium salt carrier [QC]+. As aforesaid, the ionic pyridinium salt drug/carrier prodrug entity [D—OC]+ which results from such in vivo oxidation is prevented from efflux from the brain, while elimination from the general circulation is accelerated. Subsequently, the covalent or equivalent bond coupling the drug species [D] to the quaternary carrier [QC]+ is metabolically cleaved, which results in sustained delivery of the drug [D] in the brain and facile elimination of the carrier moiety [QC]+. Such "covalent or equivalent bond" between the drug and the quaternary carrier can be a simple direct chemical bond, e.g., an amide, an ester, or any other like bond, or same can even be comprised of a linking group or function, e.g., a thiazolidine bridge or a peptide linkage, typically necessitated when the drug species is not susceptible to direct chemical coupling to either the dihydropyridine carrier or the quaternary carrier. Nonetheless, the bond in the formulae [D—QC]+ and [D—DHC] is intended to be, and is hereby defined as inclusive of all such alternatives. And the cleavage of the [D—QC]+ prodrug to sustainedly delivery the drug species [D] in the brain with concomitant facile elimination of the carrier moiety [QC]+ is characteristically enzymatic cleavage, e.g., by esterase, amidase, cholinesterase, hydrolytic enzyme, or peptidase, albeit any type of in brain cleavage which might result, whether enzymatic, metabolic or otherwise, of course remains within the ambit of this invention. Thus, the drug release rate controlling parameter of the subject pro-prodrugs is imparted simply via the cleavable bonding between drug and carrier, and not by any release rate controlling substituent(s).

The expression "non-toxic pharmaceutically acceptable salts" as used herein generally includes the non-toxic salts of compounds of formula (I), wherein [D] is a centrally acting drug species and [DHC] is the reduced, biooxidizable, blood-brain barrier penetrating form of a dihydropyridine⇄pyridinium salt redox carrier, formed with nontoxic, pharmaceutically acceptable inorganic or organic acids XH. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like. The expression "anion of a non-toxic pharmaceutically acceptable acid" as used herein, e.g. in connection with structure (II), is intended to include anions of such inorganic or organic acids HX.

In one embodiment according to this invention, simple nontoxic carrier systems [D—QC]+⇄[D—DHC] are envisaged, utilizing a wide variety of models for D, such as those above outlined. Representative such carrier systems and models are:

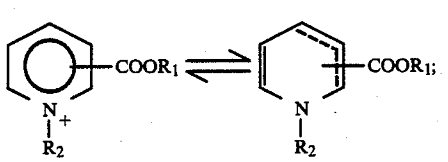

$R_1O$— or $R_1NH$— = D

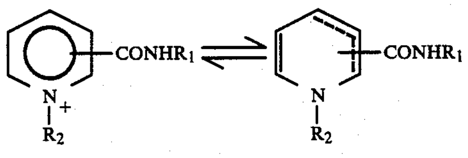

wherein $R_2$ is simply alkyl, e.g., $CH_3$, or benzyl, albient virtually any other effective substituent is intended. (As depicted above, the isomeric dihydropyridine structure depends on the position of the substituent relative to the pyridine nitrogen.) Exemplary of such simple carrier systems are N-alkyl nicotinamide and nicotinate ester derivatives, tethered to such drug species as dopamine, melphalan and testosterone. The trigonelline (N-methylnicotinic acid) system is quite effective as a carrier; it also is readily eliminated from the circulation and is virtually non-toxic.

Indeed, the present invention provides a flexible arsenal of dihydropyridine⇄pyridinium salt redox carriers for the site-specific/sustained delivery of virtually any centrally acting drug species to the brain. Moreover, any dihydropyridine/pyridinium salt redox carrier entity is contemplated and intended hereby generically, and any such carrier moiety need not be, and is not, derivatized with a drug release rate controlling substituent critically tailored to meet, or be coordinated with, the chemical nature and deliveery requirements of the particular drug species sought to be preferentially administered to the brain. As utilized herein, the term "carrier" is to be understood as connoting just such a non-derivatized, non-drug/carrier coordinated entity, for consistent herewith it is the "carrier" entity itself and not the nature of any activity or release rate controlling/modifying substituent which is responsible for providing the desired brain-specific result.

Additional examples of such redox carriers include the quaternary pyridinium alcohols (1), the analog isoquinoline acid and alcohol systems (2), and multicharged delivery forms, exemplified by structure 3 (D represents drug, Z a colvant link) and obviously the corresponding dihydro forms.

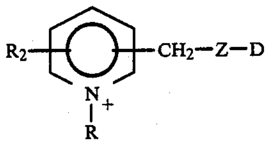

1

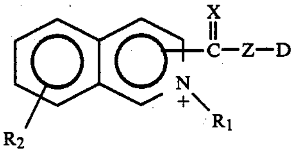

2

X = $H_2$ or O

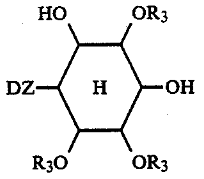

3

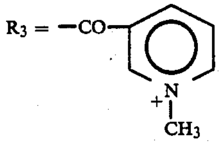

Yet other redox carriers include those comprising an acidic chain directly linked to the heterocyclic nitrogen, in quaternary or tertiary amine form. Also the hydroxide type carriers, e.g., the glucosamine analog indicated below. Representative are:

(a)

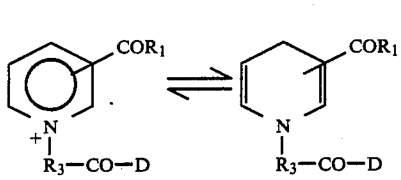

$R_1$ = $NH_2$; $OR_2$; and the like
$R_2$ = alcohol residue
$R_3$ = $(CH_2)_n$ n = 1-10
or $C_1$-$C_{12}$ branched alkyl,
aryl-alkyl, and the like
D = drug-$NH_2$ or —OH;

Preparation:

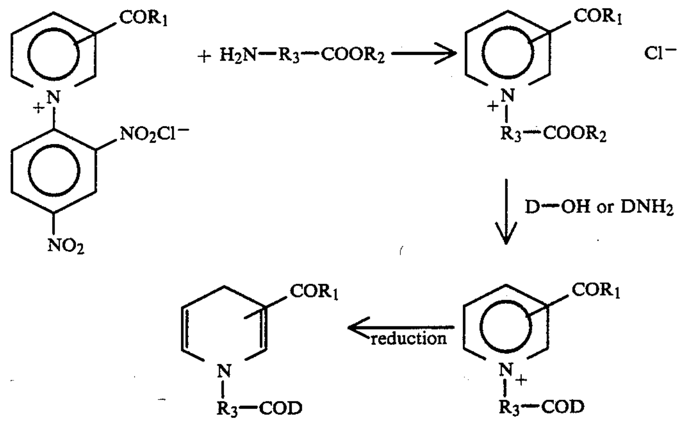

Method of: H. Lattre et al., *Annalen,* 579, 123 (1953).

(b)

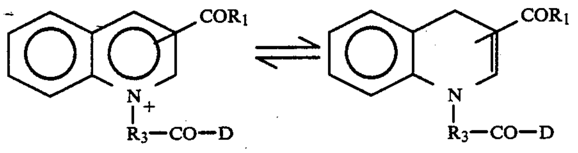

(c)

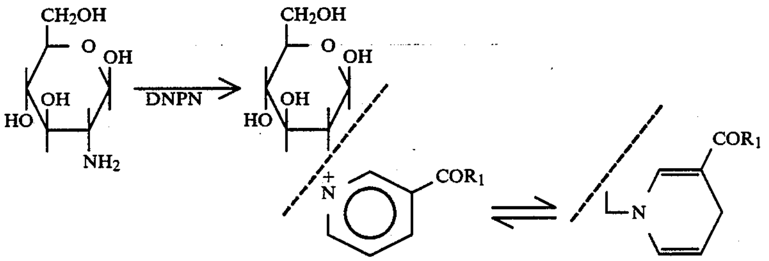

Generally preferred dihydropyridine⇄pyridinium salt redox carriers for use in the present invention include the following (where D represents the drug), and obviously the corresponding dihydro forms:

(a) the pyridinium systems (i)

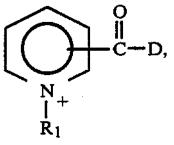

-continued (ii)

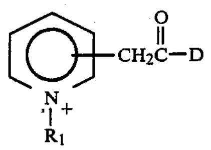

and (iii)

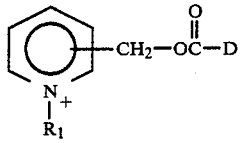

in which the depicted substituent is in the 2-, 3- or 4-position, and $R_1$ is $C_1$–$C_7$ alkyl or $C_7$–$C_{10}$ aralkyl, preferably methyl or benzyl;

(b) the pyridinium system (iv)

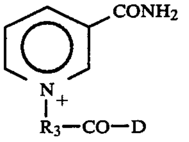

in which $R_3$ is $C_1$ to $C_3$ alkylene, i.e., $(CH_2)_n$ where n=1–3;

(c) the isoquinolinium and quinolinium systems (v)

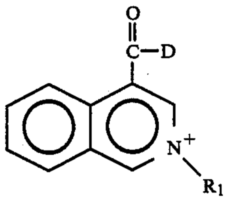

and (vi)

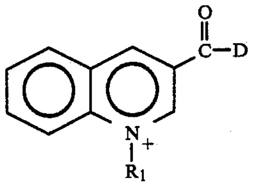

in which $R_1$ is defined as above; and (d) the quinolinium andisoquinolinium systems (vii)

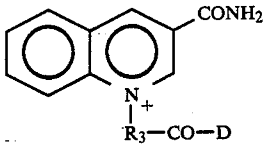

and (viii)

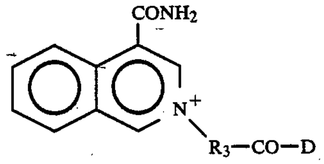

in which $R_3$ is defined as above. The corresponding dihydro forms of the foregoing preferred pyridinium salts are depicted below, wherein the position and identity of the structural variables are as indicated above:

(i)

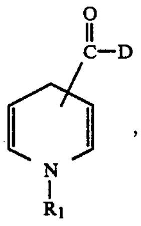

, (ii)

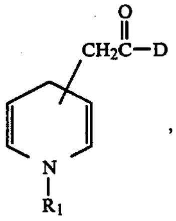

,

-continued (iii)

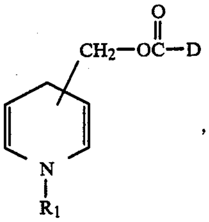

, (iv)

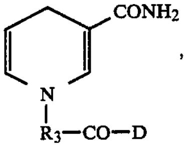

, (v)

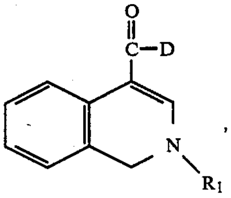

, (vi)

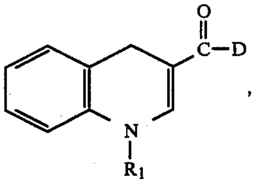

, (vii)

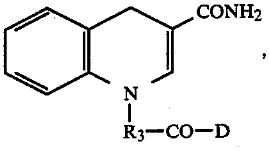

, (viii)

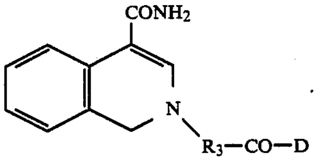

In accord with the present invention, the sustained delivery of a drug to the brain in sufficient concentrations to achieve the desired pharmacological effect can be accomplished with much lower concentrations in the peripheral circulation and other tissues. The present invention of course will allow such treatment of any other organs or glands in which sufficient drug accumulates. Thus, for example, it is expected that the quaternary form (II) which is locked in the brain will be locked in the tests as well. See applicant's earlier copending Application Ser. No. 475,493.

The novel chemical delivery system of this invention begins with the preparation of the novel quaternary intermediates of formula (II). The preparation of those intermediates will be tailored to the particular drug portion and carrier portion to be combined, and especially to the nature of the chemical bond between them, e.g. whether the linkage is an ester or amide linkage, as well as to the presence or absence of other reactive functional groups (amino, mercapto, carboxyl, hydroxyl, hydroxy) in either the drug or carrier portion.

Typicaly, if such other reactive groups are present, they are found in the drug portion. In any event, when such groups are present and it is desired to protect them, a step that introduces appropriate protecting groups can be incorporated at a suitable stage of the synthetic pathway. Typical protective groups are well known in the art and have been defined hereinabove. When carbonate protecting groups for hydroxy radicals are desired, the step of introducing the protecting groups will involve reacting the alcohol with a halocarbonate of the type ROCOCl or ROCOBr (formed by reaction of ROH with $COCl_2$ or $COBr_2$, R typically being lower akyl). For acyl protecting groups, the alcoholic hydroxyl is reacted with an acyl halides RCl or RBr, R being e.g., $—COCH_3$ or $—COC(CH_3)_3$. Yet other reaction schemes and reactants will be readily apparent to those skilled in the art, as well the appropriate means for removing such protective groups after they have achieved their function and are no longer needed. As already explained above, carboxyl and hydroxyl protecting groups are typically retained in the compounds of formulas (I) and (II) rather than being removed, so that they can perform their protective function in vivo as well.

In forming the intermediates of formula (II), at least one amino, hydroxyl, mercapto, carboxyl, amide or imide group in a drug will be bonded to [QC+], the hydrophilic, ionic pyridinium salt form of a dihydropyridine⇄pyridinium salt redox carrier.

In a preferred embodiment of the present invention, sustained delivery of drug to the brain in pharmacologically effective concentrations has now been demonstrated, paralleled with much lower concentrations in the peripheral circulation and other tissues, utilizing dopamine as the target drug species and a trigonelline-type carrier system, with the catechol moiety thereof in certain instances being acylated, e.g., acetylated or pivalylated. According to Scheme 3 which follows, one specific delivery system for dopamine, compound 5, on administratio (e.g., by injection) is distributed throughout the body and by reason of its lipophilic character facilely penetrates the blood-brain barrier and enters the CNS. Following oxidation both in the brain and in the other tissues, the corresponding hydrophilic quaternary salt (6) is formed. The quaternary salt 6 is essentially "locked in" the brain and its concentration is considered to increase with time until reaching a maximum, which depends primarily on the relative rates of entrance of the dihydro compound (5) to the brain ($K_1$) as compared to $K_2$ to the other tissues, the rate of oxidation of the dihydro form to the quaternary ($K_3$ and $K_7$) and the rates of its disappearance from the brain ($K_4+K_5$). At the same time, the very water soluble quaternary forms) 6 is/are excreted readily via the kidney and the liver ($K_8>>K_4$). Derivatives 6 are considered to be essentially inactive forms ($K_8>>K_9$), and thus systemic activity/toxicity is minimized. Hence, the concentration of 5 and 6 in the blood rapidly increases. The ratio of the quateernary salt 6 in the brain relative to the blood increases to the point where 6, or metabolites thereof, can only be found in the brain. The quaternary 6, whether in the brain, blood or other tissues, is deemed to release dopamine and the non-toxic compound, trigeonelline, depending upon the rates of site-specific conversion of the precursor 6 to the drug at each of these sites. The concentration of any released dopamine at any time is much higher in the brain than in the blood or other tissues. Also, as the enzymatic transformation of the quaternary precursor 6 to the drug (dopamine) is relatively slow, same permits a sustained release of dopamine. Too, the simultaneous protection/lipophilic derivatization of the catechol system in dopamine has also now been demonstrated.

It will be appreciated that a compound of formula (I), suc as compound 5, may be administered as the free base, e.g. as depicted in Scheme 3, or in the form of a non-toxic pharmaceutically acceptable salt thereof, i.e., a salt which can be represented generally by the formula

[D—DHC].HX and more specifically with respect to Scheme 3 by the formula

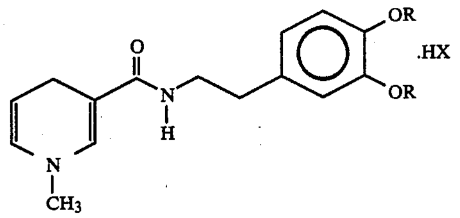

(R is defined as in Scheme 3)

wherein HX is as defined befoe; and that, regardless of the actual form in which the compound is administered, it will be converted in vivo to a quaternary salt of formula (II), i.e. a salt of the compound 6 type, the anion $X^-$ being an anion present in vivo. It is not necessary that the anion be introduced as part of the compound administered. And even when the compound of formula I (e.g. compound 5) is used in its salt form, the anion of the formula (II) compound (e.g. of compound 6) is not necessarily the same as that present in the formula (I) compound. In any event, the exact identity of the anionic portion of the compound of formula (II), is immaterial to the in vivo transformation of (I) to (II), e.g. the depicted enzymatic transformation.

Scheme 3:
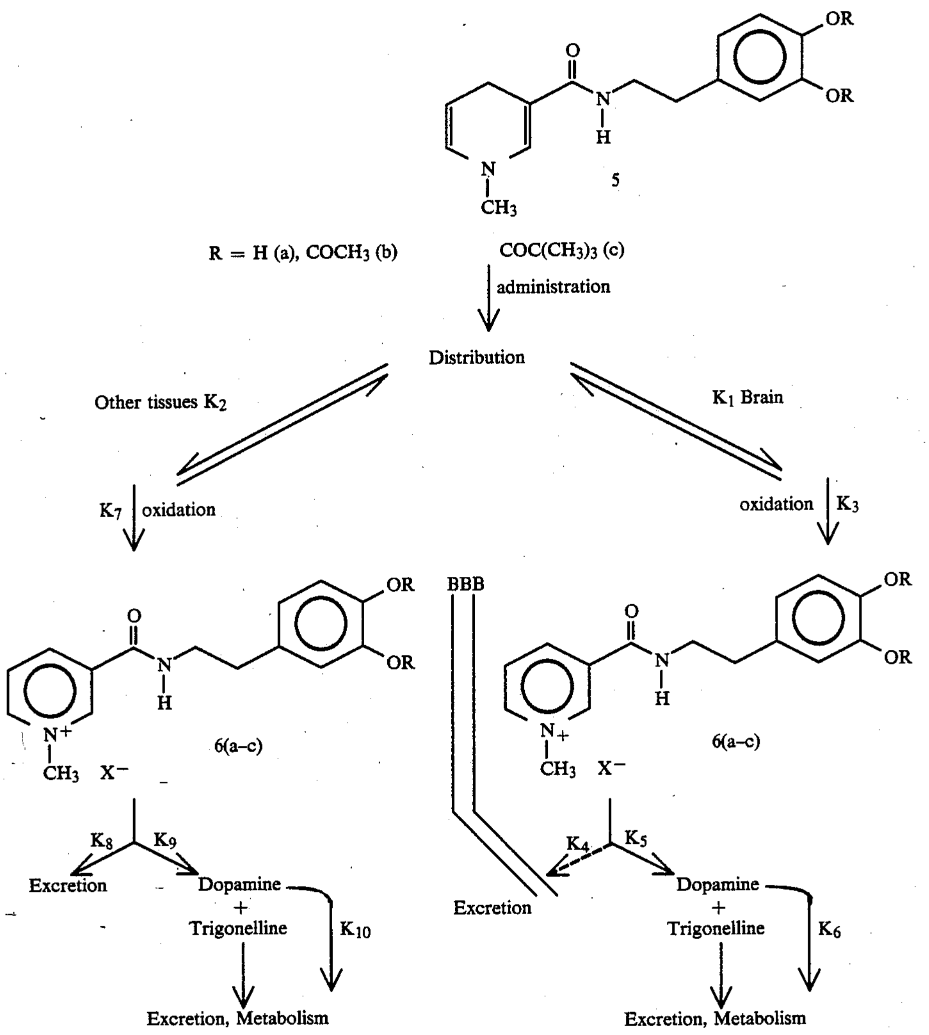
With specific reference to the immediately above, the 1,4-dihydropyridine derivatives (5) were prepared as in the following Scheme 4:
Scheme 4:
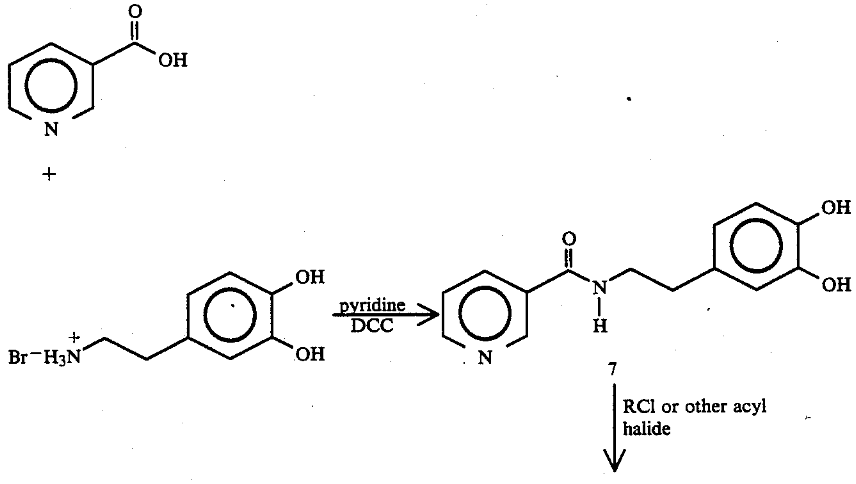

-continued

Scheme 4:

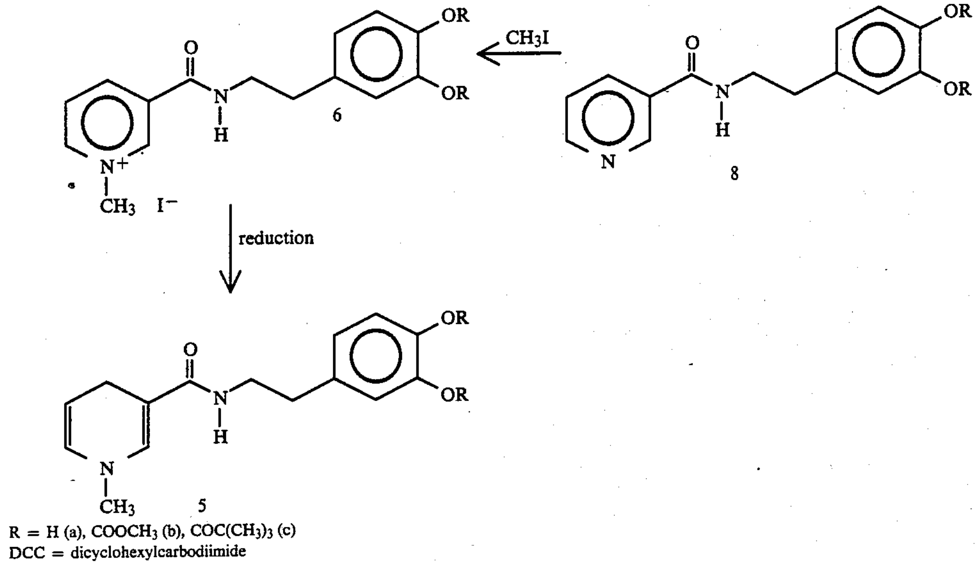

R = H (a), $COOCH_3$ (b), $COC(CH_3)_3$ (c)
DCC = dicyclohexylcarbodiimide

Similar schemes can be shown for the preparation of the other dopamine derivatives of the invention. The step which introduces the protecting groups is of course only required when it is desired to protect the catechol hydroxyl groups. Moreover, when carbonate rather than acyl protecting groups are desired, the step of introducing the protecting groups will involve reacting the catechol with a halocarbonate of the type Y'OCOCl or Y'OCOBr (formed by reaction of Y'OH with $COCl_2$ or $COBr_2$), rather than with an acyl halide YCl or YBr, Y and Y' being as generically defined hereinabove. Also, the order of steps shown in Scheme 4 may be altered; quaternization, followed by reduction, need not be in the final two steps but may be carried out earlier in the reaction sequence. Yet other reaction schemes and reactants (e.g., using an anhydride rather than an acyl halide to convert 7 to 8) will be readily apparent to those skilled in the art, Scheme 4 being simply a preferred approach for the specific compounds there depicted. Variations of this approach are likewise applicable to preparing derivatives of other hydroxy-containing amines.

In an attempt to ascertain whether any biotransformation of the free catechol is taking place by COMT (catechol-O-methyltransferase) either before or after oxiation, the possible O-methyl metabolites (9 and 10) were synthesized separately following Scheme 4 with 3-methoxytyramine hydrochloride as the starting material.

9

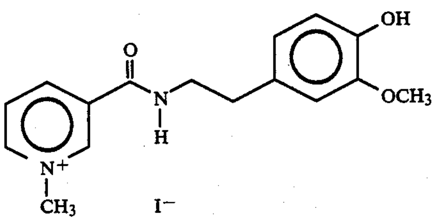

-continued

10

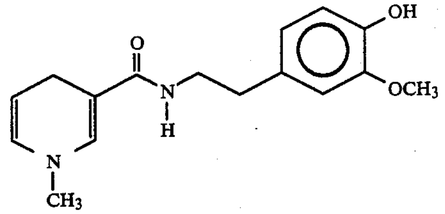

The stability of the 1,4-dihydropyridine derivatives (5) was determined in the presence of the oxidizing agents, alcoholic $AgNO_3$ and hydrogen peroxide. The in vitro rates of oxidation of the 1,4-dihydropyridine derivative (5c) in 80% plasma, 20% brain homogenate, 20% liver homogenate and in whole blood were determined.

The dihydropyridine derivative (5c) was then selected for the in vivo study. A solution in DMSO (dimethylsulfoxide) was injected through the jugular vein to a group of male Sprague-Dawley rats which were then sacrificed at various time intervals; their blood and brains were analyzed for the quaternary percursor of dopamine (6a). The in vivo dopaminergic activities of the selected compounds 5c vs. 6a were then determined.

Consistent with the above, it was found that N-nicotinoyldopamine (7) could be obtained in good yields by coupling dopamine hydrobromide with nicotinic acid in pyridine as a solvent and with dicyclohexylcarbodiimide as the coupling agent. Attempts to prepare 7 by using dopamine free base were largely unsuccessful. As for the catechol protecting groups, the acetyl and pivalyl moieties were selected due to their rather different steric and partitioning parameters. Acylation could be accomplished with the acyl chlorides by using conventional methods. Reduction of the quaternaries (6a–c and 9) was accomplished by using sodium dithionite in mildly basic aqueous solution, ($NaHCO_3$). It was observed that the dihydro compound obtained in the case of the quaternary 6b gave a faint green color with ferric ions, indicating partial hydrolysis of at least one of the acetyl moieties during reduction, even in the cold, weakly basic solution used as a medium. The dihydropyridine derivatives isolated (5a–c and 10) were determined to have the expected 1,4-dihydropyridine structure, based on their NMR and UV spectra. Attempts to prepare the β-protonated enamine salts of the isolated dihydro derivatives were also largely unsuccessful, due to acid catalyzed addition reactions. The 1,4-dihydropyridine derivatives (5a–c) were found to be relatively stable towards oxidation. Compound 5c was quantitatively oxidized to the corresponding quaternary salt 6c by $H_2O_2$ or alcoholic $AgNO_3$ solution.

The diacetyl derivatives (5b and 6b) appeared to be labile to hydrolysis and therefore were not pursued in vitro. The dipivalyldihydro derivative (5c) was thoroughly investigated for its in vitro rates of disappearance and metabolic degradation in various biological fluids. It is evident that 5c represents a rather complex case, as besides oxidation, a two-step hydrolysis will also take place. Scheme 5 illustrates the interconversion of the possible components.

Scheme 5:

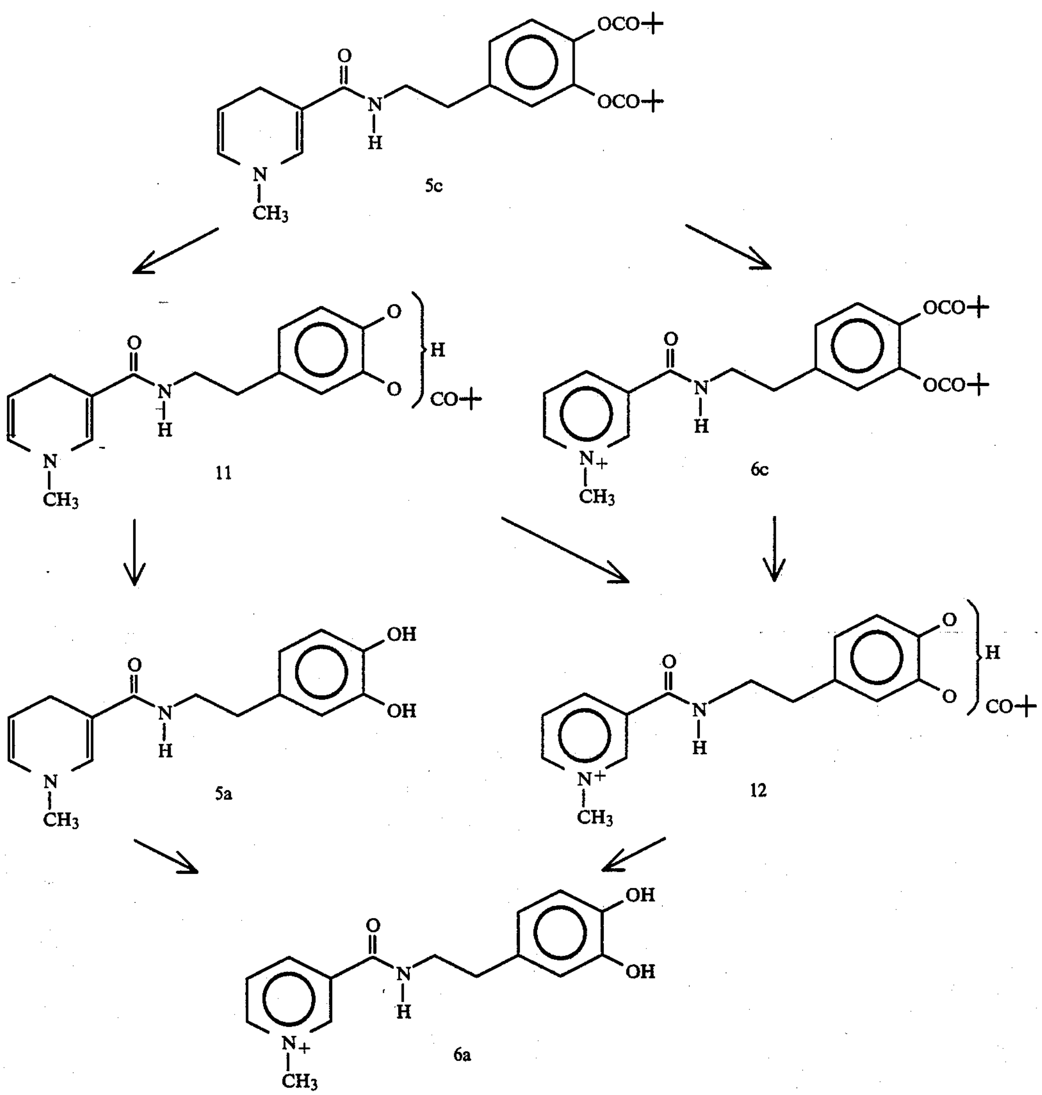

5c 11 6c 5a 12 6a

Figure 5:
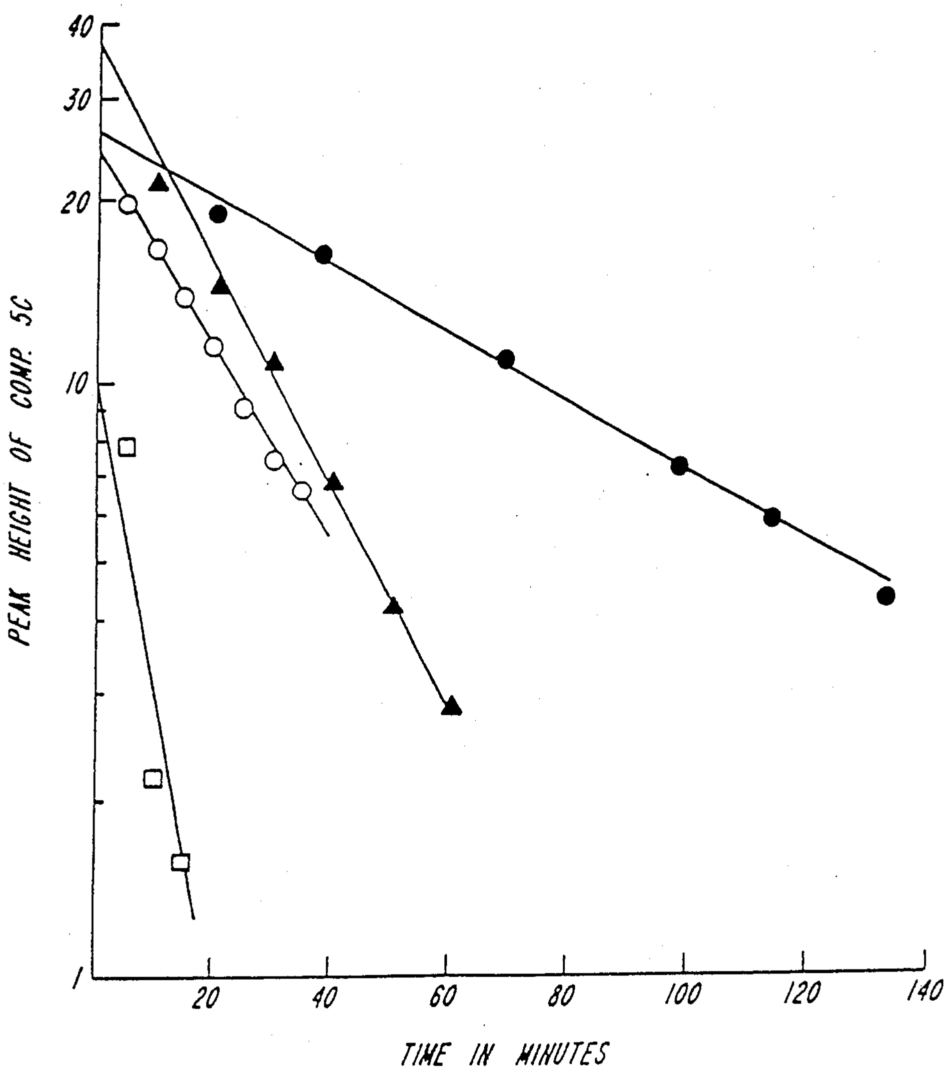
FIG. 5 is a semilog plot of peak heights of 1-methyl-3-{N-[β-(3,4-dipivalyloxyphenyl)ethyl]}carbamoyl-1,4-dihydropyridine 5c against time in plasma (●), brain homogenate (▲), whole blood (O) and liver homogenate (□)

FIGS. 1-4 illustrate the results of such an investigation. The apparent half-lives for the disappearance of 5c in biological fluids at 37° C. were calculated. Although the process does not truly follow first order kinetics, the data fit very closely a pseudo first order process (FIG. 5). The obtained values, 51 min (80% plasma), 17 min (20% brain homogenate), 18 min (whole citrated blood) and 6 min (20% liver homogenate), reflect an acceptable stability of the dihydro derivative 5c. The disappearance of 5c is accompanied by formation of some monoester (11) and dihydroxy dihydro form (5a) in all the media except the liver homogenate. The rate of hydrolysis of the first ester moiety is faster than the second and a reasonable amount of monoester 11 builds up with time. The monohydroxy quaternary 12 could not be detected except in the blood as a very small peak which does not change significantly with time. A steady increase in the concentration of the dihydroxy quaternary 6a was observed in all media except liver homogenate. Thus, it is established that this derivative, 6a, is forming as the main product of the various interconversion routes and it is the direct precursor thus concluded to be locked in the brain in the in vivo experiment. No formation of the methoxy derivatives 9 and 10 could be detected in any of the biological fluids studied; 5a and 6a do not appear to be good substrates for COMT.

Figure 6:
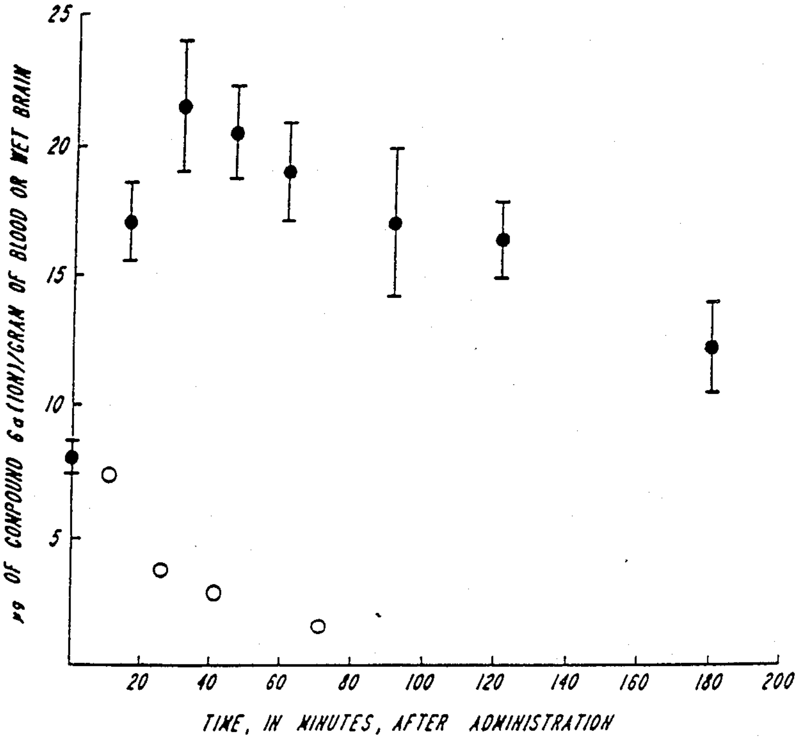
FIG. 6 is a graph plotting concentrations against time of 1-methyl-3-{N-[β-(3,4-dihydroxyphenyl)ethyl]}carbamoyl pyridinium cation (6a) in brain (●) and in blood (O) following administration of 1-methyl-3-{N-[β-(3,4-dipivalyloxyphenyl)-ethyl]}carbamoyl-1,4-dihydropyridine (5c), with the error bars indicating SEM.

The first objective of the in vivo studies was to trace the appearance and disappearance of 6a in blood and brain following administration of 5c. FIG. 6 summarizes such results, and is consistent with the mechanism shown in Scheme 3. After one single injection of the 1,4-dihydropyridine derivative 5c to the rat, the dihydroxy quaternary 6a (ion), which is the only detectable derivative, could be seen to appear and then to disappear quickly from the blood, with a half-life of 27 min. On the contrary, the concentration of 6a (ion) is increasing in the brain steadily, reaching a maximum at about 30 min following administration. The descending portion indicates a half-life of disappearance from the brain of about 3.2 h. No formation of O-methyl metabolites (9, 10) could be detected in the brain. This confirms the in vitro results that 6a (or 5a) is not a good substrate for COMT.

To determine whether dopamine itself was finally released in the brain upon completion of the aforesaid complex delivery process, 5c was administered intrajugularly and changes in brain-dopamine concentrations following that administration were studied. Some of the rats showed up to threefold increase in the dopamine concentrations, others practically none. Since it is possible (and even desired) that the intrinsic brain metabolism of the dopamine does not permit significant build-up of its concentration, specific pharmacologic activity was investigated, using change in the in vivo prolactin secretion. It is known that dopamine and its agonists decrease prolactin secretion following their binding to stereospecific receptors located on lactophors in the anterior pituitary (AP) gland [G. P. Mueller, J. W. Simpkins, J. Meites and K. E. Moore, *Neuroendocrinology,* 20, 121 (1976); W. Wuttke, E. Cassell and J. Meites, *Endocrinology,* 88, 737 (1971); J. A. Clemens, E. B. Smalstig and C. J. Shaar, *Acta Endocrinol.,* 79, 230 (1975)]. This effect is dose-dependent and it can also be observed in vitro, incubating anterior pituitaries with dopamine or its agonists [R. M. MacLeod in "Frontiers in Neuroendocrinology", Ed. L. Martini and W. F. Ganong, Raven Press].

Figure 7:
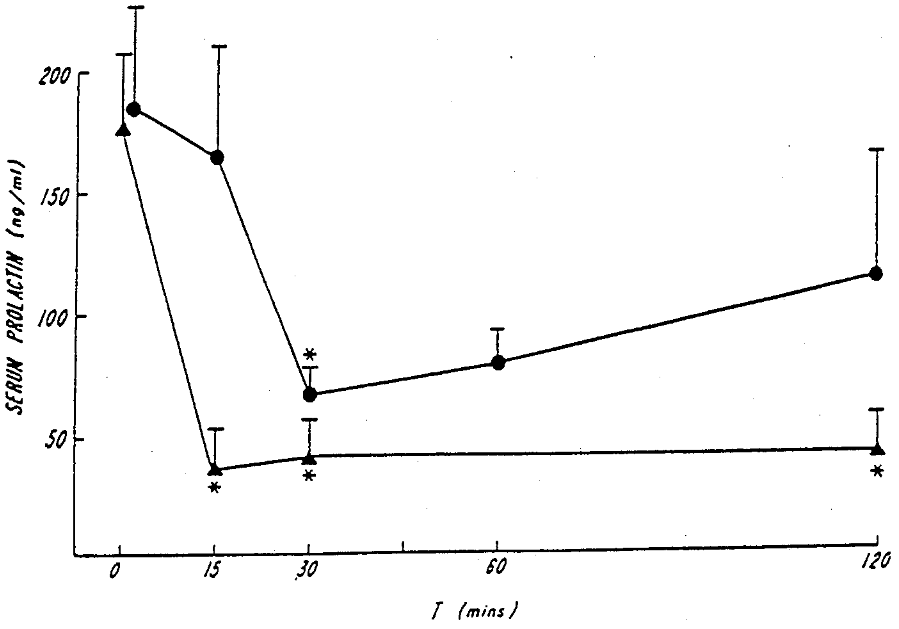
FIG. 7 is a graph plotting the effects of compounds 5c (▲) and 6a (●) administered I.V. at 1 mg/kg dose level, on the serum prolactin levels in rats.

It was then determined that exposure of male rats to 17-$\beta$-estradiol for two days elevated serum prolactin levels to greater than 150 ng/ml. Intravenous administration of 5c caused a 79% decrease in serum prolactin concentrations and this dramatic reduction was maintained through 120 min after treatment. In contrast, 6a had no significant effect on the serum prolactin concentrations by 15 min, and caused a 67% reduction by 30 min. Thereafter, serum prolactin levels increased progressively to levels which are not significantly different from vehicle injected controls, by 60 and 120 min. These results are summarized in FIG. 7. The rapid onset and prolonged inhibitory effects of 5c on prolactin secretion is consistent with the time course of the appearance of 6a in the brain following administration of 5c. The "trapping" of 6a in the brain subsequent to I.V. injection of 5c provides a constant source of a potent dopaminergic agent, either dopamine or 6a itself. The significantly lower effect of 6a when administered I.V. does not unequivocally clarify which alternative is the more responsible. This was resolved by in vitro comparison of the relative activities of dopamine versus 6a.

Fresh anterior pituitaries obtained from female rats were incubated with various concentrations of dopamine (DA) and 6a, repsectively, and their effects on the rate of release of prolactin were measured. It was found that at $2\times10^{-8}$M concentrations, neither DA nor 6a had any effect, but at $2\times10^{-7}$ M, DA caused a 57% reduction of the prolactin rate secretion, while 6a had no effect. These results are summarized in the following Table I.

TABLE I

Comparative in vitro activity of 6a vs. dopamine[a]

Prolactin ng/mg./h[b]

| Dopamine (DA)[c] | | | | 6a[d] | | | |
|---|---|---|---|---|---|---|---|
| Control | DA $2\times10^{-8}$ M | Control | DA $2\times10^{-7}$ M | Control | 6a $2\times10^{-8}$ M | Control | 6a $2\times10^{-7}$ M |
| 344 ± 50 | 355 ± 67 | 282 ± 34 | 121 ± 38* | 342 ± 38 | 386 ± 29 | 250 ± 30 | 277 ± 32 |

[a]On freshly obtained anterior pituitary (AP) at 37° C. All values are average of 9 separate AP-S.
[b]Prolactin release rate of the incubated AP-S.
[c]Weight of the AP-S: Control 4.6 ± 0.2 mg. DA treated 4.5 ± 0.3 mg.
[d]Weight of the AP-S: Control 4.6 ± 0.3 6a treated 4.7 ± 0.4
*$P < 0.05$ These results indicate that if 6a has any activity, it must be significantly less than that of DA. Based on the delayed onset of the activity when 6a was adminitered I.V. and considering the in vitro results, it logically follows that the high and prolonged activity of the 6a locked in the brain following administration of 5c is due to the fact that 6a is slowly releasing the active DA in the brain.

Accordingly, provided hereby is a potent, brain-specific dopaminergic agent comprising a lipophilic dihydropyridine carrier-type chemical delivery system of dopamine ["pro-prodrug" or "pro-pro-prodrug" in the case of the catechol protectiv group(s)], which penetrates the BBB passive transport. The rapid oxidation in the brain of the carrier moiety to the corresponding quaternary pyridinium salt results in an activated amide of dopamine. The oxidation process is much faster than amide cleavage of the beginning compound 5 or of 6. Moreover, the ionic nature of the activated quaternary salt results in a significant slowdown of the efflux of this specific form through the BBB, resulting in a selective concentration enhancement of the precursor 6a in the brain. Too, brain-specific dopaminergic activity is assured, logically as dopamine is released from this activated form upon hydrolytic, enzymatic or metabolic cleavage, as is facile excretion of the carrier moiety from the brain.

In yet another embodiment of the invention, like synthesis of the analogous tyramine system has been carried out, and the corresponding determinations made. Such tyramine system is represented as follows:

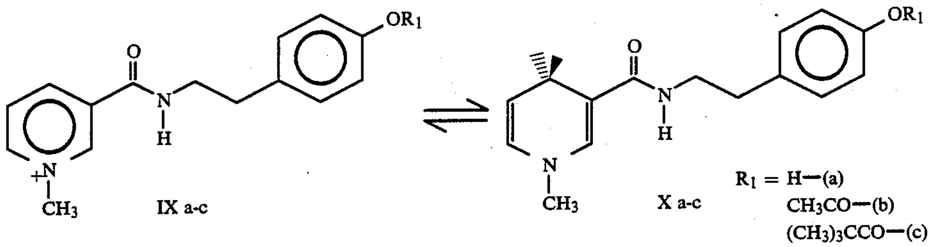

IX a-c X a-c $R_1$ = H—(a) $CH_3CO$—(b) $(CH_3)_3CCO$—(c)

Naturally, selection of the particular dihydropyridine ⇄ pyridinium salt redox carrier to be used will depend on the chemical structure of the specific drug involved. And not only should the nature of the functional group which is to be linked to the carrier system be considered in selecting the carrier, but the manner in which the ultimate compound is prepared should be tailored to the presence of any other reactive groups in the molecule. The following examples of specific drug/carrier combinations and their manner of synthesis are set forth for the purpose of illustration only and are not to be considered limitative in any way whatsoever.

Thus, in one specific illustration, the selected drug is testosterone and the selected carrier system is trigonelline ⇄dihydrotrigonelline; according to this embodiment, testosterone is reacted with nicotinoyl chloride, the resultant ester is then quaternized with methyl iodide, and the quaternary iodide is then reduced with $Na_2S_2O_4$ to afford the testosterone-CDS (chemical delivery system)

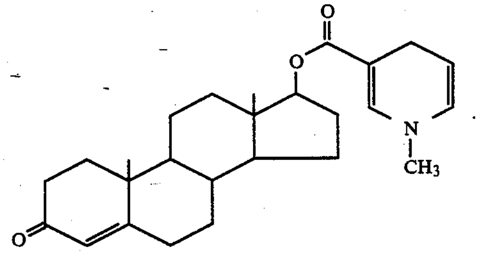

Other steroids can be similarly derivatized, e.g., 17α-ethynyltestosterone, estradiol and the like.

Another specific illustration involves selecting melphalan and the same type of carrier system as above, but forming an amide rather than an ester linkage. Thus, melphalan is converted to its hydrobromide, which is reacted with nicotinic acid to afford the amide having the formula

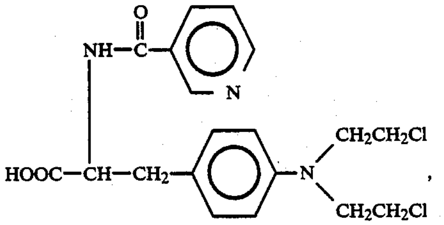

which can be esterified, if desired (to increase lipoidal characteristics), followed by, when the ethyl ester is prepared, quaternizing same with methyl iodide to form

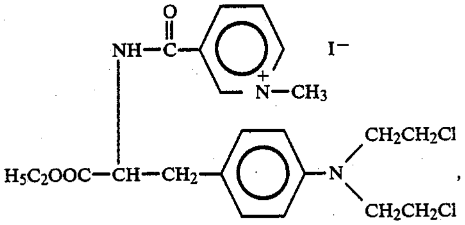

which can then be reduced to afford the melphalan-CDS

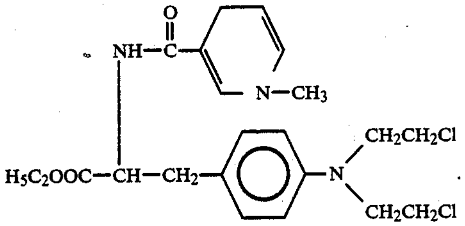

As one of several alternative schemes, melphalan can be derivatized by first esterifying it, e.g., to convert the carboxy function to the ethyl ester, then reacting the resultant melphalan ethyl ester with nicotinoyl chloride to form the amide of the formula

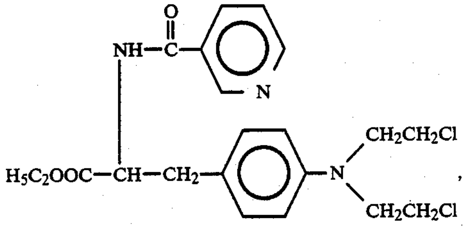

which can then be quaternized and the quarternary salt subsequently reduced as indicated above to afford to same melphalan-CDS as depicted above.

Yet another specific illustration utilizes chlorambucil as the target drug, in which case the desired nicotinic acid carrier system is linked to the drug via a bridging group. Thus, nicotinic acid can be reacted with an appropriate di- or polyhydroxy compound such as ethylene glycol, propylene glycol or inositol and the resultant intermediate is linked via its free hydroxy group(s) to the carboxylic acid function of chlorambucil. That intermediate is then quaternized and the quaternary salt is reduced to afford the chlorambucil-CDS. In the case of nicotinic acid and ethylene glycol starting materials, the chlorambucil-CDS has the formula

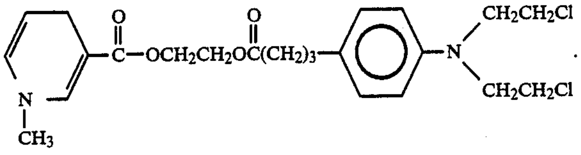

On the other hand, when a polyhydroxy compound is reacted with nicotinic acid in the first step, a variety of products are possible. Thus, for example, when inositol is used, the final product may contain anywhere from 1 carrier/5 drug residues to 5 carrier/1 drug residue. In the case of the inositol trinicotinate intermediate

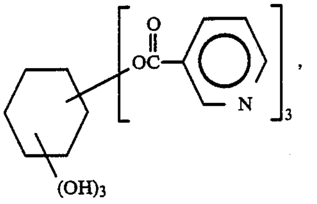

conditions for reacting same with chlorambucil can be selected so that one, two or three of the hydroxy functions react with the acid. When all three hydroxys react, the ultimate chlorambucil-CDS has the formula

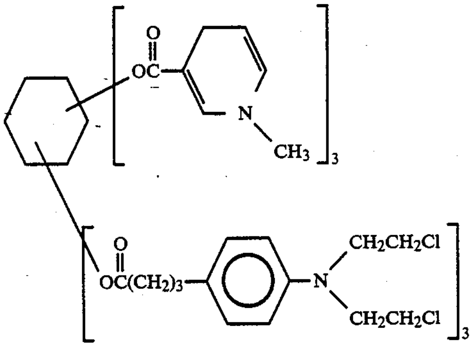

and contain 3 drug residues and 3 carrier groupings.

As another example, methotrexate, which has the structural formula

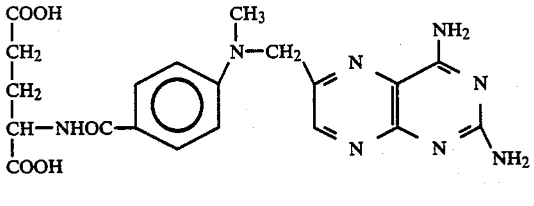

can be derivatized similarly to chlorambucil via its carboxy function(s), e.g., utilizing the inositol trigonellinates or a glucosamine analogue.

As a further example, podophyllotoxin and its derivatives can be linked to a carrier system of this invention. These drugs can be represented by the structural formula

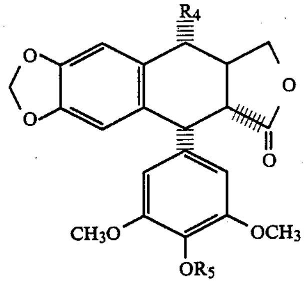

$R_5$ = H or $CH_3$
$R_4$ = OH—podophyllotoxin

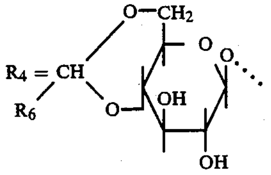

$R_4$($R_6$ = $CH_3$—etoposide

= 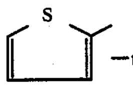 —teniposide)

and can be derivatized by reacting the hydroxy group in podophyllotoxin ($R_4$=OH) or the hydroxy groups in the glycosidic portions in $R_4$ with acidic type redox carriers, e.g., in a manner analogous to the testosterone-CDS depicted above. Known cisplatin analogues, in which typically the amino groups have been replaced with organic radicals, can be similarly derivatized according to the invention, the method of choice depending on the nature of the functional groups in the organic radicals.

Similarly, syntheses and like determinations as regards the redox carrier-linked enkephalins can be carried out. First synthesized is the known leucine enkephalin XI. The quaternary pyridinium analog XII, the corresponding O-benzyl ether XIII and the amide XIV are next synthesized.

Tyr—Gly—Gly—Phe—Leu XI

-continued

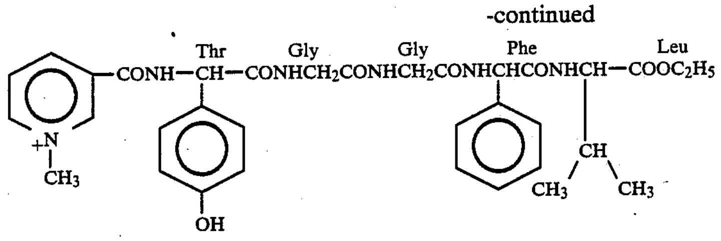

XII

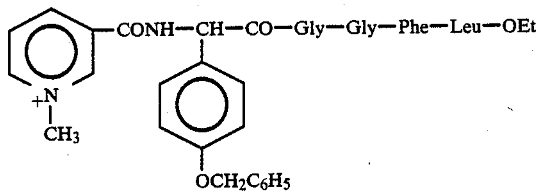

XIII

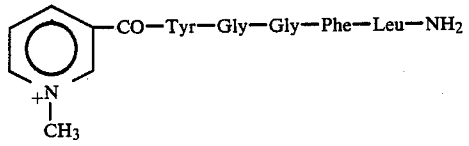

XIV

The O-benzyl pentapeptide ethyl ester derivative of XI is synthesized sequentially and then coupled with nicotinic acid, followed by methylation. Alternate methods involve introduction of carrier at an earlier stage in the synthesis. The reduction of XII and XIII results in a mixture of products due to the base sensitivity of the ester. Likewise prepared are the corresponding leucinol trigonelline ester XV and its dihydro derivative XVI.

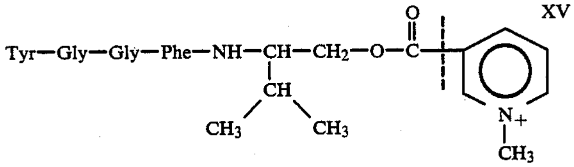

XV

-continued

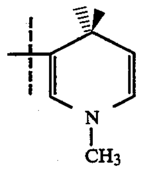

XVI

Thus, the site-specific brain delivery of the enkephalins for the treatment of epilepsy is established consistent with the Scheme 1, as is their analgesic activity.

Similarly, as regards the benzodiazepine tranquilizers, e.g.:

1. Oxazepam:

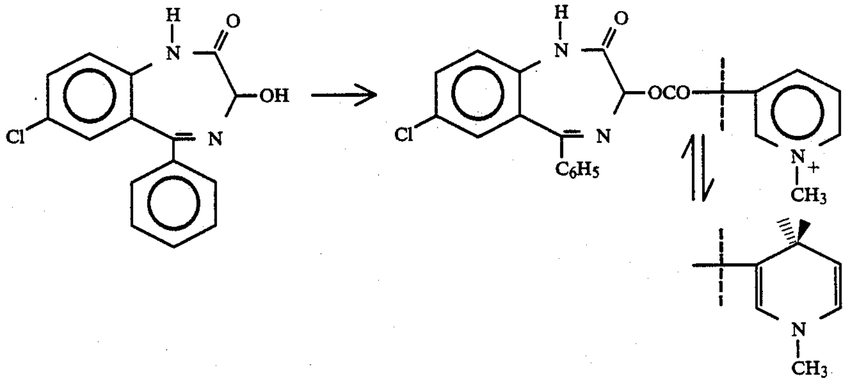

2. Diazepam:

-continued

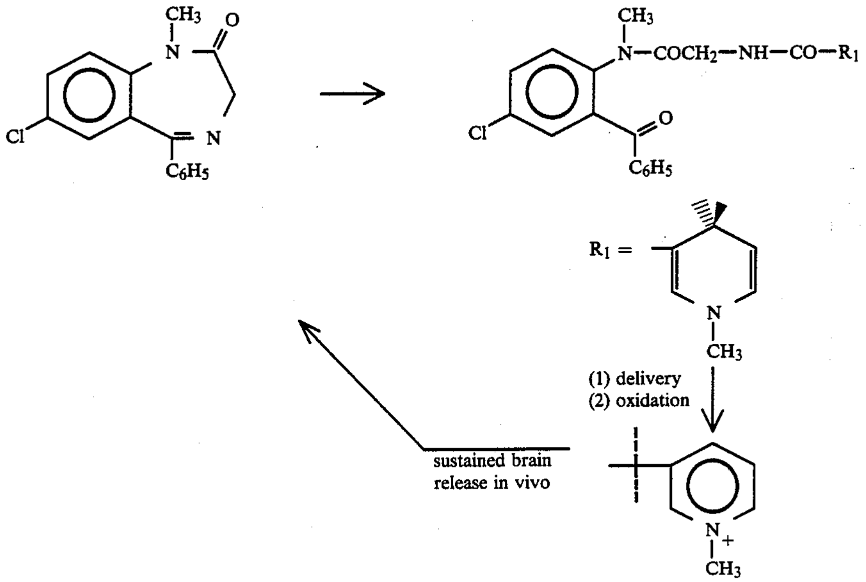

This reaction scheme utilizes conventional opening of the 7-member ring, accompanied by coupling of the drug to the carrier. The following drugs can be similarly derivatized to the corresponding dihydro derivatives:

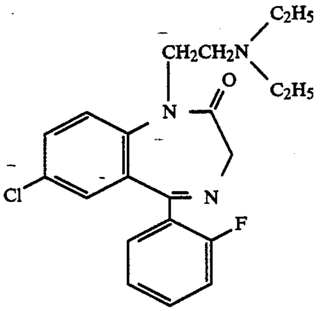

flurazepam

-continued

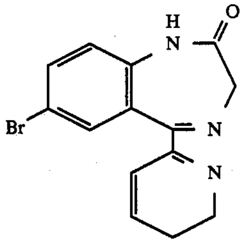

bromazepam

Yet another example of tailoring chemical synthesis to the particular drug involved is shown in Scheme 6 below, which depicts synthesis of a radio-diagnostic, I 123 labeled metaraminol, carrier system. Note that in the case of radiolabeled compounds, the method of choice generally involved introducing the radioactive element toward the end of the reaction sequence, rather than using the radiolabeled parent drug itself as the starting material.

Scheme 6

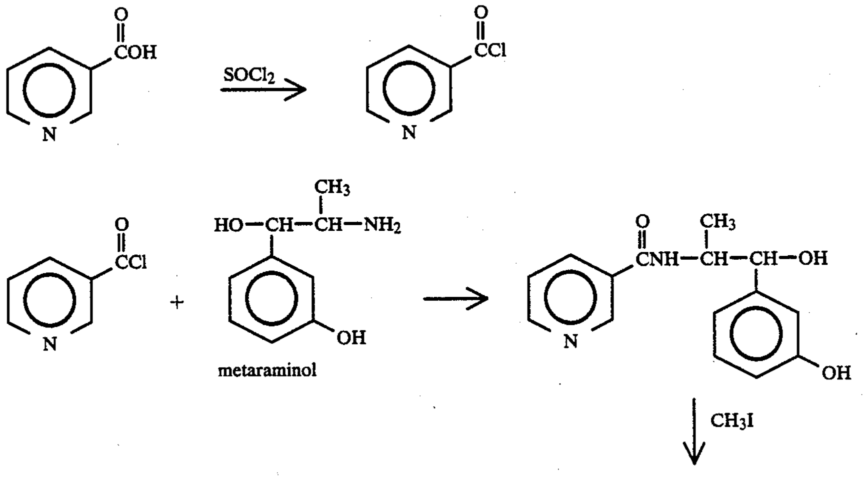

metaraminol

-continued

Scheme 6

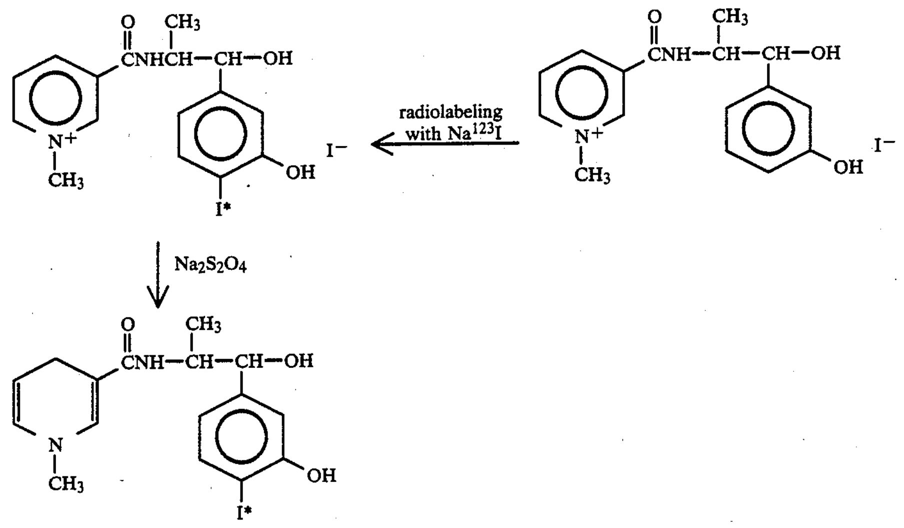

And in another preferred embodiment of the invention, there is provided the effective, selective and nontoxic treatment of epilepsy, based upon the mechanism illustrated in Scheme 1. Indeed, commencing from the "GABA-hypothesis" of epilepsy, the brain-specific, enhanced and sustained release of GABA (γ-aminobutyric acid) itself, and various other compounds either directly or indirectly affecting the concentrations of GABA in the brain, is circumscribed consistent herewith. Model compounds include carboxylic acids, most specifically valproic acid, as well as some of the GABA analogs which inhibit irreversibly the GABA-T, such as γ-vinyl and/or γ-acetylenic GABA. Using the aforesaid trigonelline (N-methylnicotinic acid)⇌dihydrotrigonelline system, for example, the selected compounds can be effectively delivered per Scheme 1.

Thus, representative target compounds are the dihydropyridine carrier-drug combinations 1 and the corresponding pyridinium carrier-drug species, for example, GABA and its esters:

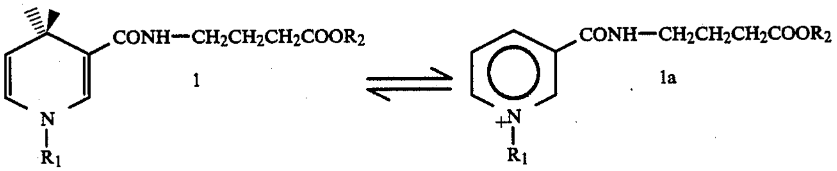

1 1a $R_1 = CH_3, C_3H_7$ or $CH_2C_6H_5$
$R_2 = H, C_2H_5, CH(CH_3)_2$, etc.

Related derivatives for γ-vinyl and γ-acetylenic GABA are:

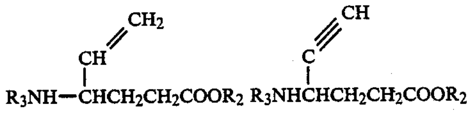

2 and 2a 3 and 3a $R_3$ =

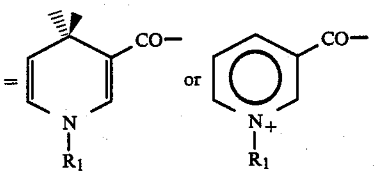

or

In the case of valproic acid, other alternatives are:

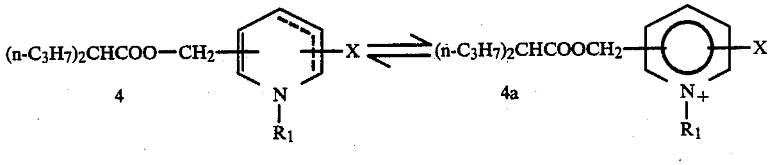

4 4a

X = H, $CONH_2$, $CHNOR_2$, etc.

In another embodiment of like delivery system, applicable for both the GABA and related compounds and for the carboxylic acids, or for any other drug species to be linked to such a carrier, either directly or indirectly, i.e., mediated by a carboxylic acid, e.g., succinic acid, or other linkage, provided is a mono- or poly-substituted nontoxic polyol (such as inositol or sugars) having the trigonelline⇌dihydrotrigonelline system and the compounds to be delivered linked to the same molecule as exemplified by the GABA case (5⇌5a) and valproic acid (6⇌6a):

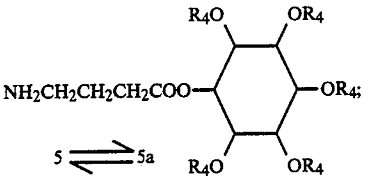

5 5a

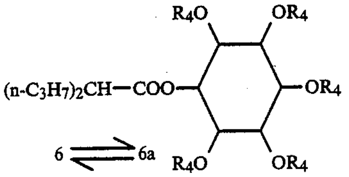

6 6a $R_4$=H, GABA or valproic acid, but at least one of $R_4$ is:

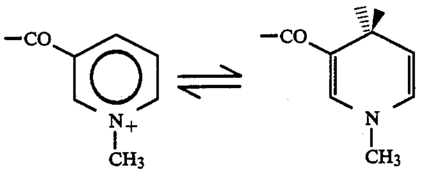

(in 5a and 6a) (in 5 and 6)

$R_4$ can be partically replaced by additional GABA or valproic acid, changing the carrier/drug ratio as necessary. Some of the valproic acid metabolites can be coupled with carriers of the redox type, via the various hydroxy groups formed during the oxidative degradation:

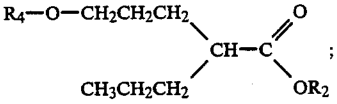

;

7 and 7a

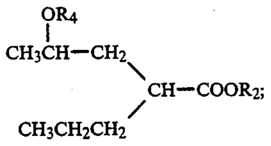

;

8 and 8a

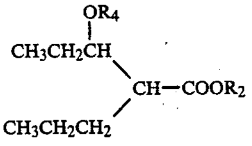

9 and 9a

Illustrative examples are the corresponding derivatives of the 5-, 4-, and 3-hydroxy-2-n-propyl pentanoic acid derivatives. Additional carrier systems, such as the isoquinoline⇌dihydroisoquinoline system, can also be developed consistent herewith.

Moreover, based upon the observation that NADH content is significantly reduced in epileptic and like seizures, the use of the subject redox system (in reduced form) will bias the NAD⇌NADH balance towards NADH during the dihydro carrier→quaternary transformation. Also, the brain-specific delivery of small peptides consistent herewith, e.g, the enkephalins, which have been found to initiate epileptic, seizures, has led to the design of a variety of long lasting potent antagonists.

And the subject chemical delivery system is also useful for the delivery of other anticonvulsants in a sustained, brain-specific fashion, e.g., the benzodiazepines and hydrantoins, and those compounds, like apomorphine, which are useful in the treatment of photosensitive epilepsy.

It will of course be appreciated in the immediately above regard that the drug treatment of epilepsy has always posed formidable problems. There are many different anticonvulsants available, some more specific for different types of seizures. Indeed, there exist a wide variety of opinions as to which is the most suitable drug for any particular type of seizure, and drug mixtures are typically employed. An inevitable result of the traditional therapy is the development of chronic toxicity, but such result is conspicuously avoided according to the present invention.

It too will be appreciated that the desired therapeutic effects of all antiepileptic agents investigated, as well as their undesired toxic effects, reflect a statistically significant correlation with the drug levels in plasma. This correlation is based upon a close relationship between the drug concentrations in plasma and brain tissue. Hence, a primary attribute of this invention is to enable attainment of high and sustained brain levels of the selected active agents, essentially against the plasma-brain concentration gradient and independent of the drug concentration in the blood.

GABA and related compounds are logical candidates. It has been shown that GABA neuron function is impaired in at least certain types of human epilepsy. Animal studies also showed that seizures are induced by reduction of GABA mneuron function to a critical degree by (1) inhibition of GABA synthesis, (2) blockade of GABA receptors or (3) inhibition of GABA-receptor mediated ionic events. In addition, enhancement of GABA synaptic activity (by direct receptor stimulation or by increasing GABA levels in the synapase) has a potent and wide spectrum anticonvulsant effect. These findings foreshadowed that an enhanced and sustained GABA brain delivery or a brain-specific delivery in a sustained manner of a good GABA-agonist would be efficacious in different forms of epilepsy. It is well known that GABA itself, when administered systemically, does not penetrate the normal blood-brain barrier to any significant extent. Among the potential sites at which drugs may act to influence GABA-mediated synaptic function, the first target is to effect the BBB transfer of GABA via redox delivery system. The second main target is to effect the catabolism of GABA. This invention, accordingly, specifically provides for the efficacious delivery of the GABA-T inhibitors, γ-vinyl and γ-acetylene-GABA, but the delivery of vaproic acid, specifically to the brain and without requiring high circulating blood levels, is also envisaged. In order to achieve the required activity, sodium valproate must have a relatively high, 50–100 μg/ml, level in the blood. The value of valproic acid is well established in most types of epilepsy. It is evident that valproic acid produces significant increases in both brain and synaptosomal GABA concentrations. Valproic acid itself undergoes extensive metabolism.

In capsule summary, the present invention provides for the significantly improved treatment of epilepsy, and concomitant reduction in toxicity of a number of antiepileptic drug species currently in use. And made available to the brain is a variety of important compounds, such as GABA and a wealth of GABA-ergic agents.

Processes similar to those described hereinabove can be shown for the preparation of the other compounds of this invention. The acylation steps which introduce hydroxyl protecting groups are of course only needed when there are hydroxyl groups which it is desired to protect. Moreover, carbonate rather than acyl protecting groups could be introduced instead, as already discused hereinabove. Also, the order of steps may be altered; quaternization, followed by reduction, need not always constitute the final two steps but may be carried out earlier in the reaction sequence. Yet other reaction schemes, reactants, solvents, reaction conditions, etc. (e.g. using an anhydride rather than an acyl halide for the acylation step, or preparing a different acyl derivative e.g. the acetyl rather than the pivalyl derivative) will be readily apparent to those skilled in the art. Also, insofar as concerns the quaternary compounds, when an anion different from the one obtained is desired, the anion in the quaternary salt may be subjected to anion exchange via an anion exchange resin or, more conveniently, by use of the method of Kaminski et al, *Tetrahedron,* Vol. 34, pp. 2857–2859 (1978). According to the Kaminski et al method, a methanolic solution of an HX acid will react with a quaternary ammonium halide to produce the methyl halide and the corresponding quaternary.X salt. Moreover, the manner in which the ultimate compound is prepared should be tailored to the presence of any other reactive groups in the molecule. For example, when the parent drug contains an —OH or —$NH_2$ group to be derivatized as well as carboxy functions, such COOH functions will typically be esterified, e.g. converted to the corresponding ethyl ester, or otherwise suitably protected, usually prior to formation of the quaternary compound. Thus, a wide variety of synthetic approaches can be utilized, depending on the desired structure of the final product. And compounds containing more than one category of reactive functional groups may be derivatized in a variety of ways; for example, a compound containing reactive hydroxyl and carboxyl groups may have the hydroxyl group(s) protected and the carboxyl group(s) linked to the carrier, or the hydroxyl(s) may be linked to the carrier and the carboxyl(s) protected.

Various illustrative synthetic schemes as applied to specific centrally acting drugs in accord with this invention are set forth below in the section entitled "Illustrative Synthetic Methods". While the sequence of reaction steps can be varied in many cases, in general, the final step (except in the case of optional salt formation or possibly in the case of radiolabeling) will be reduction of a quaternary compound of formula (II) to the corresponding dihydro compound of formula (I). The reduction is usually conducted at a temperature from about −10° C. to room temperature, for a period of time from about 10 minutes to 2 hours, conveniently at atmospheric pressure. Typically, a large excess of reducing agent is employed, e.g., a 1:5 molar ratio of reducing agent to starting [D—QC]+ compound. The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product [D-DHC] is usually insoluble in water and thus can be readily separated from the reaction medium. In the case of sodium borohydride reduction, an organic reaction medium is employed, e.g., a lower alkanol such as methanol, an aqueous alkanol or other protic solvent.

In a presently preferred embodiment of the present invention, the centrally acting drug of which D is the residue is dopamine or L-DOPA or a protected counterpart thereof, and the instant redox system is thus designed to elicit a sustained and brainspecific dopaminergic (e.g. anti-Parkinsonism or anti-hyperprolactinemia) response in the animal to which the formula (I) derivative is administered. In an analogous fashion, the instant redox carrier system I→II in which D is the residue of any other centrally acting drug as defined herein is designed to elicit the kind of pharmacological response which would be obtained by delivery of the drug itself to the brain, i.e., when the centrally acting parent drug is an antitumor/anticancer agent, the instant redox system is employed to elicit an antitumor/anticancer response; when the parent drug is a sympathetic stimulant, the instant redox system is used to elicit a sympathetic stimulant or amphetamine-like response; when the parent drug is an anticonvulsant compound, the instant redox system is used to elicit an anticonvulsant response; when the parent drug is a tranquilizer, the instant system is used to elicit a tranquilizing response; when the parent drug is an antidepressant, the instant system is used to elicit an antidepressant response; and so forth.

Suitable nontoxic pharmaceutically acceptable carriers for use with the topic compounds [D—DHC], e.g., those less toxic than the target drug species themselves, will be apparent to those skilled in this art. Compare, for example, *Remington's Pharmaceutical Sciences,* 4th Edition (1970). Obviously, the choice of suitable carriers will depend upon the exact nature of the particular dosage form selected, as well as upon the identity of the active drug species [D] and the compound to be administered. The therapeutic dosage ranges for administration of the compounds according to this invention will generally be the same as, or less than, those which would characteristically be used in this art for administration of the known drug species [D], per se. Naturally, such therapeutic dosage ranges will vary with the size of the patient, the condition for which the [D—DHC] compound is administered, the particular dosage form employed, and the like. The quantity of given dosage form needed to deliver the desired dose of [D] will of course depend upon the concentration of [D—DHC] in any given pharmaceutical composition/dosage form thereof. Obviously, in the case of diagnostic agents, the dosage of formula (I) compound used will be a quantity sufficient to deliver to the target body area a quantity sufficient to deliver an amount of radioisotope, stable isotope or the like which can be effectively detected by radioimaging or other detection means. The amount of radioisotope, stable isotope or the like present in the dosage form will be within or below the ranges conventionally used for diagnostic purposes.

The ability of the topic compounds to cross the BBB and to be "locked into " the brain allows administration of the drug in a site-specific manner. A combination of the present dihydropyridine⇄pyridinium salt redox system with a sustained release system will further enhance this site-specificity. Thus, a preferred embodiment of the invention comprises formulating the [D—DHC] compound or the salt of the [D—DHC]

compound utilizing a sustained release carrier system and/or route of administration capable of slowly releasing the chemical, e.g. sustained release tablets and capsules for oral administration; subcutaneous injection, or implantation of drugs in solid pellet form (for example, distributed in a biodegradable polymer); intramuscular injection of the compound in solution in oil or suspended in a repository vehicle; a transdermal delivery device or form such as an ointment to be applied locally to the desired site (when the drug is susceptible of delivery through the skin), slow intravenous infusion and the like. The rate of release of compound from the sustained release system should be comparable to the rate of in vivo oxidation of the dihydro form of the redox system in order to achieve the greatest degree of enhancement of specificity.

In applicant's copending application Ser. No. 632,314, filed July 19, 1984 (itself a continuation-in-part of applicant's earlier Ser. Nos. 379,316, 461,543, 475,493 and 516,382), the concept of applicant's redox carrier system was expanded to provide novel carrier-containing chelating agents, precursors thereto and radiopharmaceuticals derived therefrom, utilizing the dihydropyridine⇄pyridinium salt type carriers disclosed herein and in the four earlier applications. The present application discloses several specific groups of carrier moieties only generically disclosed in its parent applications. The teachings of Ser. No. 632,314, which is incorporated by reference herein in its entirety and relied upon, can be readily combined with the teachings of the present application to expand the classes of chelating agents, precursors and radiopharmaceuticals defined therein to specifically include the new dihydropyridine⇄pyridinium salt redox carriers disclosed in the present application.

ILLUSTRATIVE SYNTHETIC METHODS

I.

Methods for Derivatizing $-NH_2$ or $-NH-$ Functions in Drugs

Method A

The drug is reacted with nicotinoyl chloride, with nicotinic anhydride, or with nicotinic acid in the presence of a suitable coupling agent such as dicyclohexylcarbodiimide, in an appropriate organic solvent, to afford the corresponding nicotinamide. The nicotinamide is then quaternized, typically by treatment with methyl iodide in a suitable organic solvent, to afford the quaternary derivative of formula (II), which is then reduced by treatment with sodium dithionite or sodium borohydride as generally described hereinabove to afford the desired compound of formula (I). The representative drugs depicted below may be derivatized in this manner to the corresponding compounds of formulas (II) and (I). Compounds such as bupropion, difluamine, propranolol, ethyl β-carboline-3-carboxylate, prizidilol, pseudoephedrine, 5-amidino-2-(5-amidino-2-benzofuranyl)indole, 4',6-diimidazolino-2-phenylbenzo(b)-thiophene, 2-guanidino-4,5-di-n-propyloxazole, 2-guanidino-4,5-diphenyloxazole, glucosamine, 6-amino-6-deoxy-D-glucose, somatostatin, vasopressin and 6[[(hydroxyimino)phenyl]methyl]-1-[(methylethyl)sulfonyl-1H-benzimidazol-2-amine may be similarly derivatized.

The foregoing procedure may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this method to the corresponding picolinamides and isonicotinamides and then to the corresponding compounds of formulas (II) and (I).

Alternatively, the drug may be reacted with an activated ester of nicotinic acid, picolinic acid or isonicotinic acid, e.g. a succinimidyl ester such as

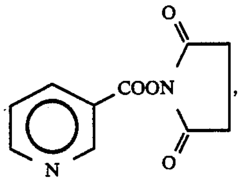
, and the procedure described above repeated to afford the identical products. As yet another alternative, the activated ester, e.g. the succinimidyl ester depicted above, may be quaternized (e.g. by treatment with methyl iodide) and the quaternized activated ester then reacted with the drug. The quaternary compound of formula (II) thus obtained may then be reduced as described in the first paragraph of this method to give the corresponding compound of formula (I).

| Starting Material | ¹[D—QC]⁺* | [D—DHC] |
| --- | --- | --- |
| 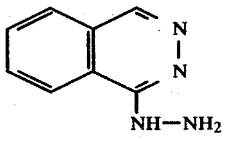 hydralazine | 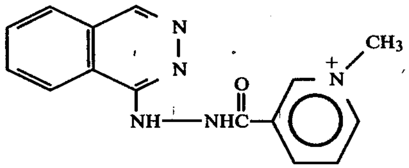 | 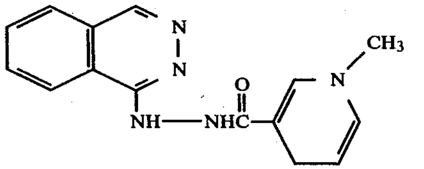 |
| 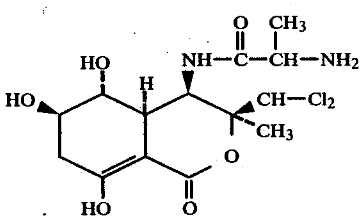 bactobolin | 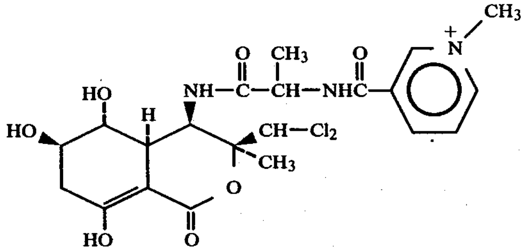 | 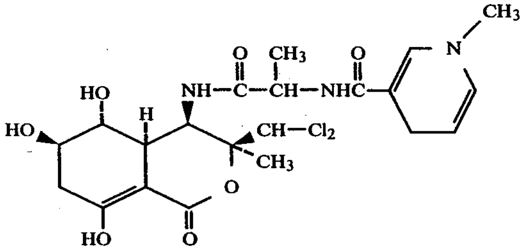 |
| 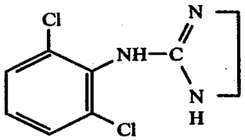 clonidine | 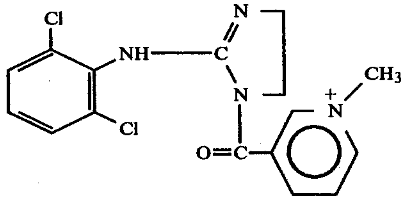 | 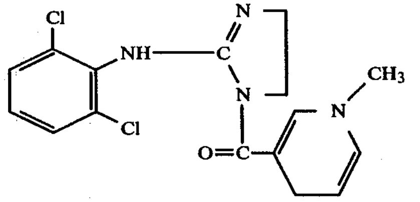 |
| 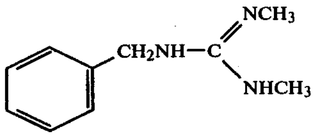 bethanidine | 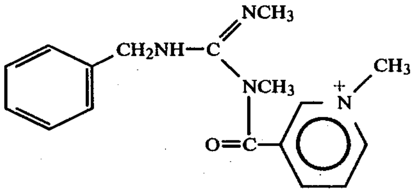 | 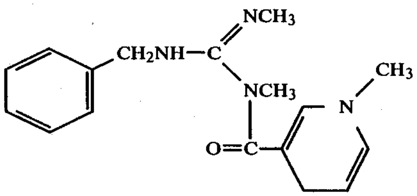 |

-continued
| Starting Material | [D—QC]+* | [D—DHC] |
|---|---|---|
| 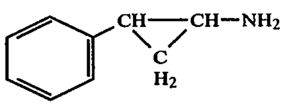 tranylcypromine | 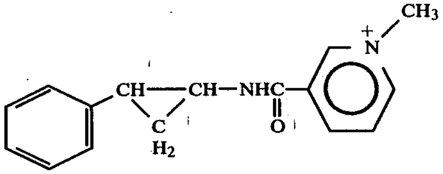 | 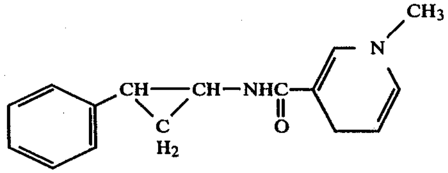 |
| 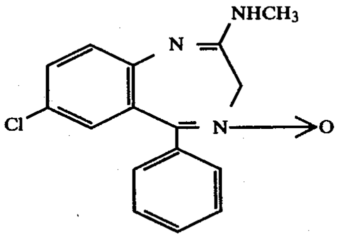 chlordiazepoxide | 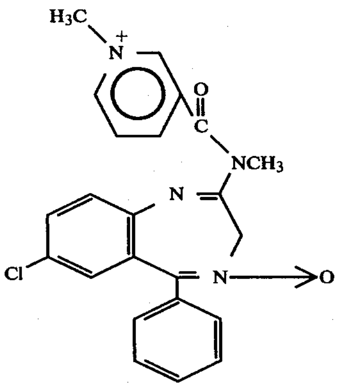 | 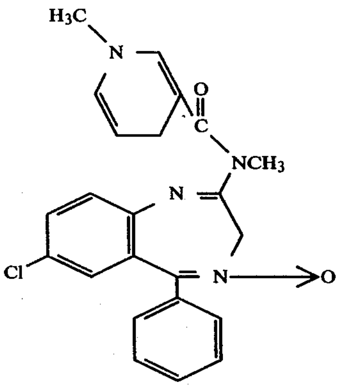 |
| 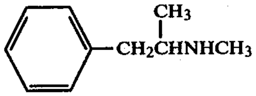 methamphetamine | 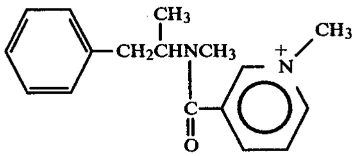 | 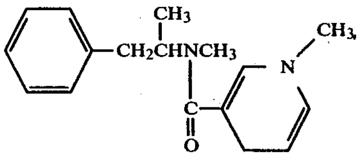 |
| 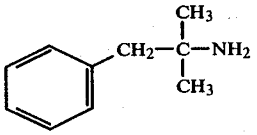 phentermine | 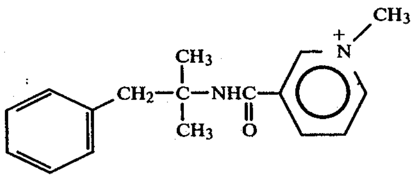 | 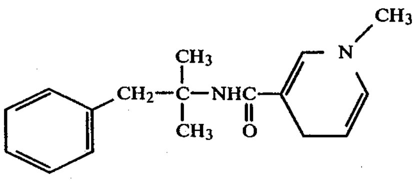 |

-continued
| Starting Material | [D—QC]+* | [D—DHC] |
| --- | --- | --- |
| 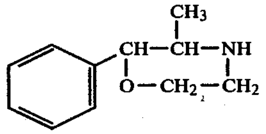 phenmetrazine | 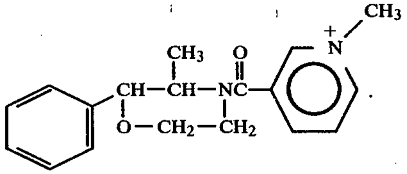 | 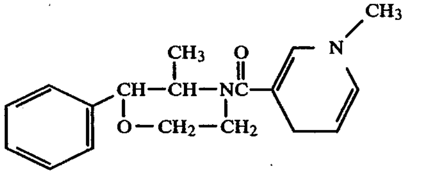 |
| 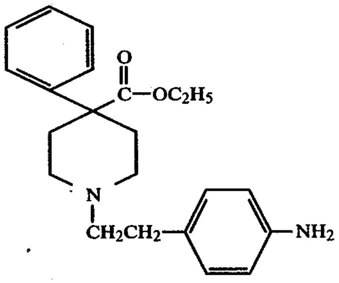 anileridine | 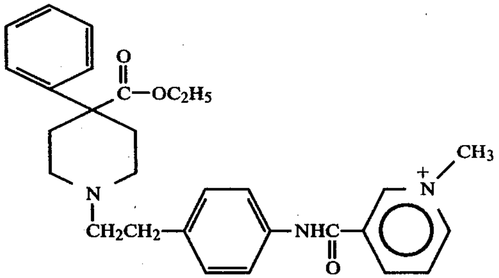 | 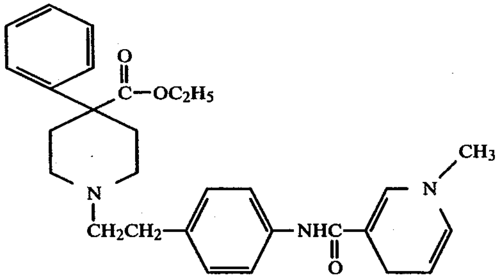 |
| 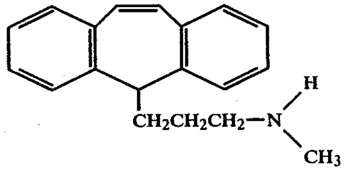 protriptyline | 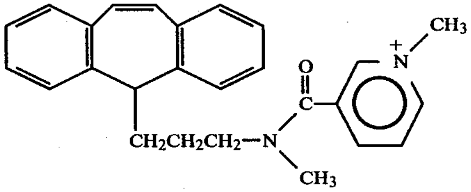 | 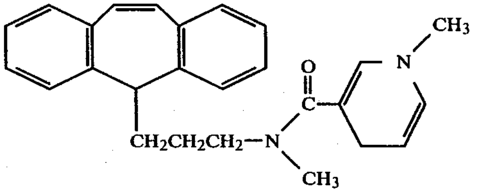 |

-continued
| Starting Material | [D—QC]+* | [D—DHC] |
| --- | --- | --- |
| 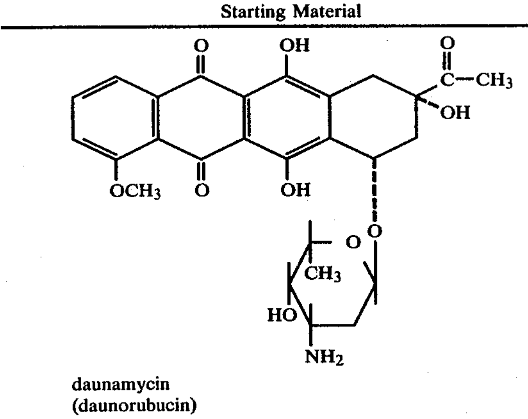 daunamycin (daunorubucin) | 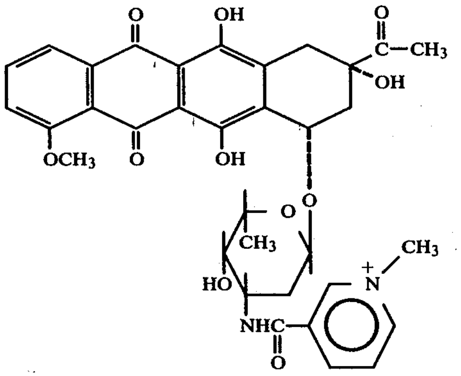 | 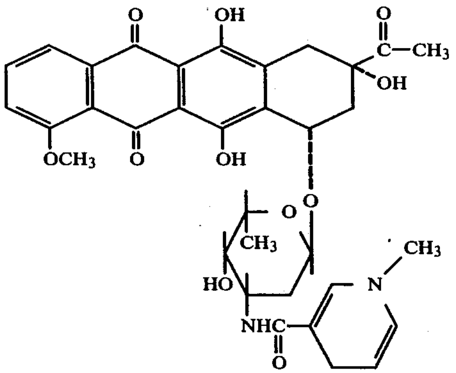 |
| 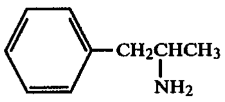 d-isomer dextroamphetamine | 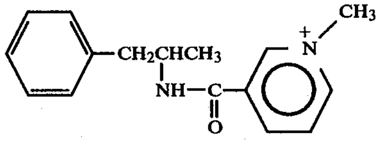 d-isomer | 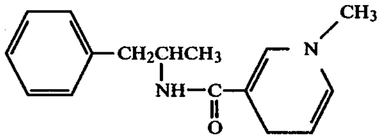 d-isomer |
| 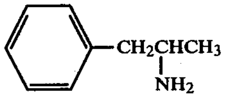 l-isomer levamphetamine | 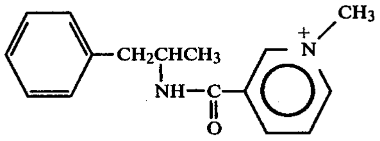 l-isomer | 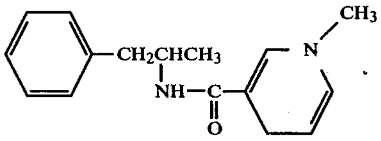 l-isomer |
| 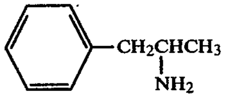 amphetamine | 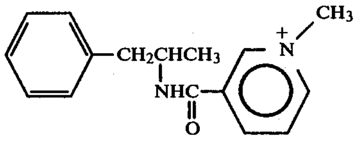 | 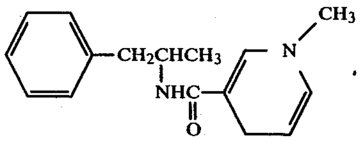 |

-continued
| Starting Material | [D—QC]+* | [D—DHC] |
|---|---|---|
| 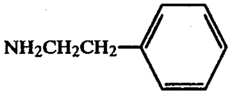 phenylethylamine (phenethylamine) | 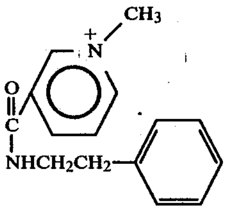 | 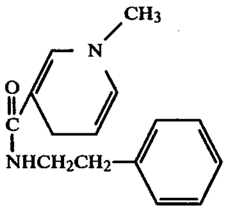 |
| 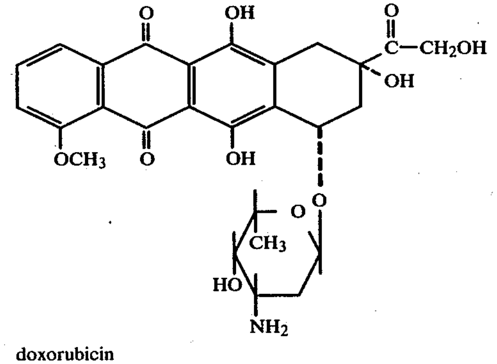 doxorubicin (adriamycin) | 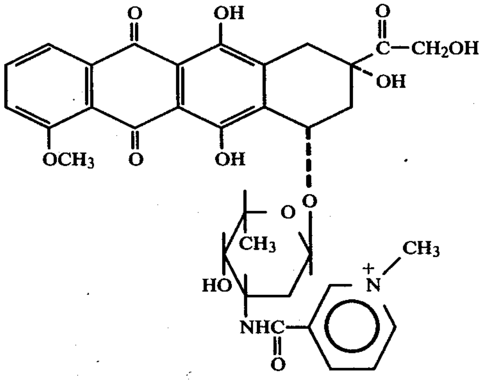 | 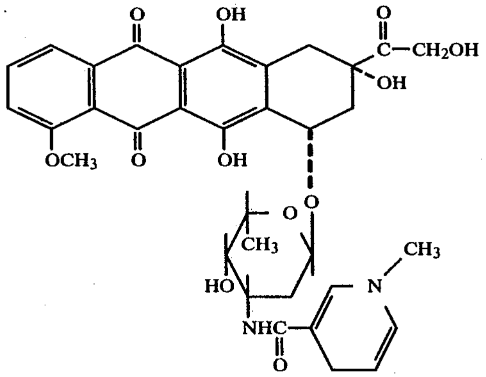 |
| 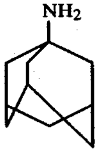 amantadine | 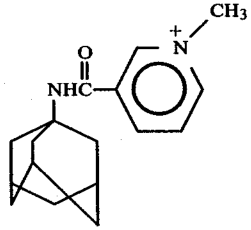 | 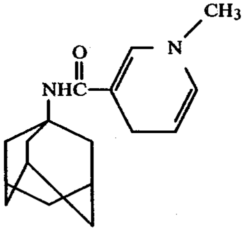 |

-continued
| Starting Material | [D—QC]+* | [D—DHC] |
|---|---|---|
| 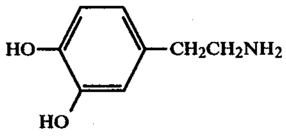 dopamine | 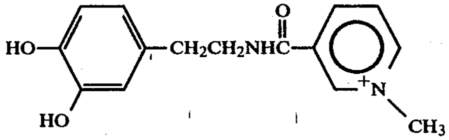 | 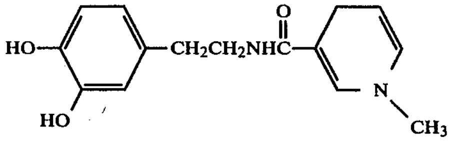 |
| 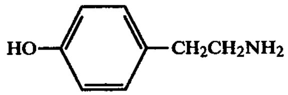 tyramine | 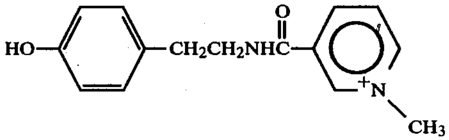 | 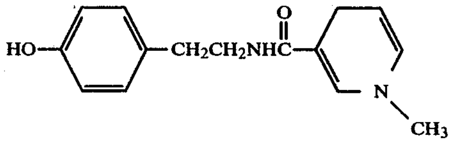 |
| 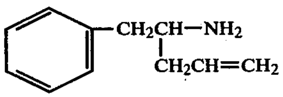 aletamine | 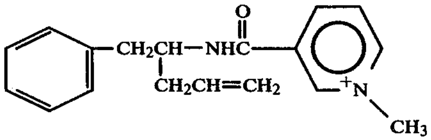 | 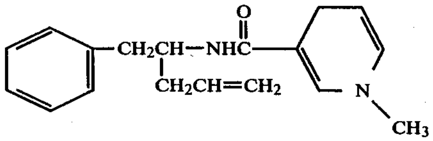 |
| 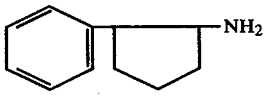 cypenamine | 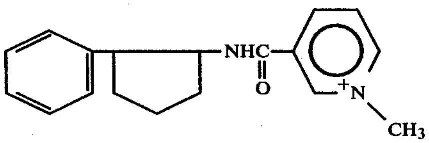 | 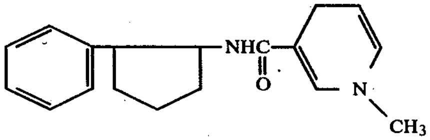 |
| 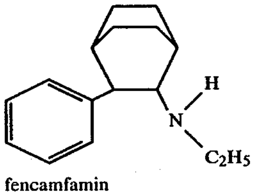 fencamfamin | 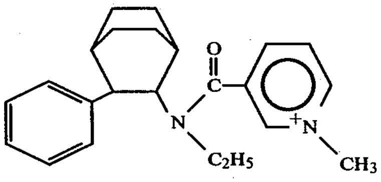 | 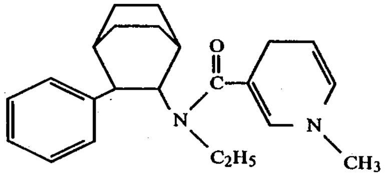 |

-continued
| Starting Material | [D—QC]+* | [D—DHC] |
|---|---|---|
| 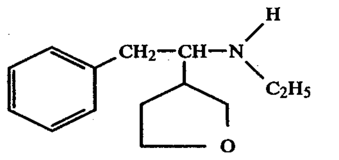 zylofuramine | 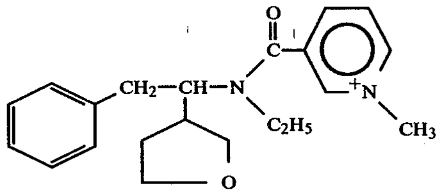 | 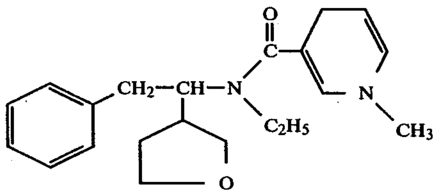 |
| 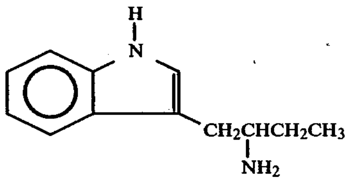 etryptamine | 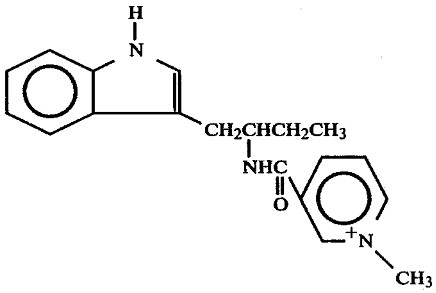 | 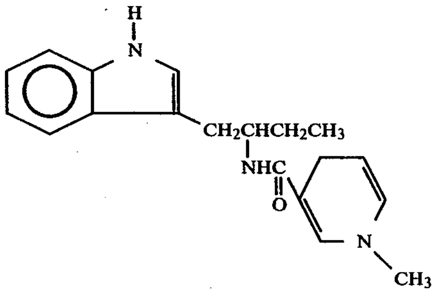 |
| 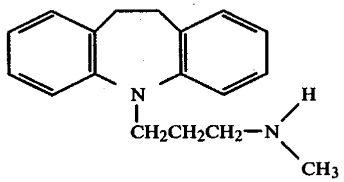 desipramine | 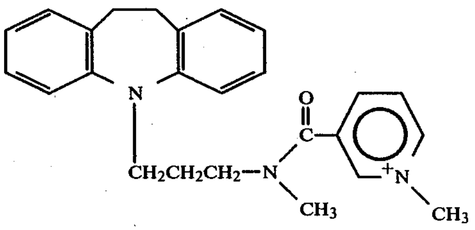 | 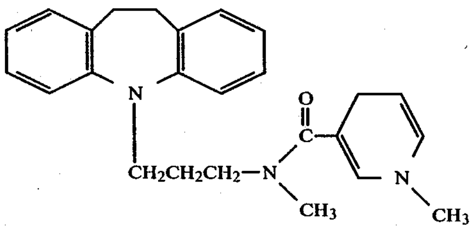 |

-continued
| Starting Material | [D—QC]+* | [D—DHC] |
|---|---|---|
| 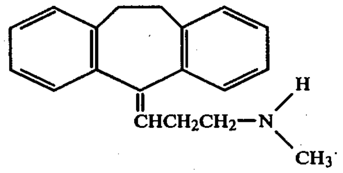 nortriptyline | 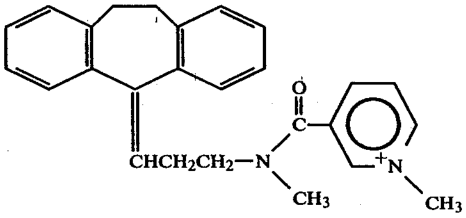 | 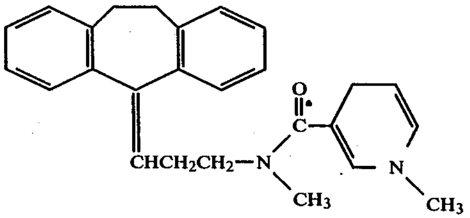 |
| 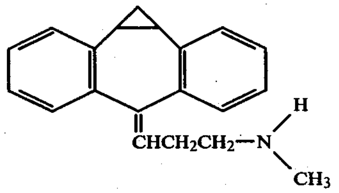 octriptyline | 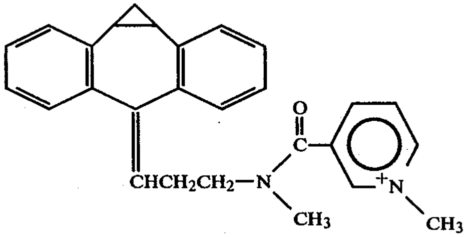 | 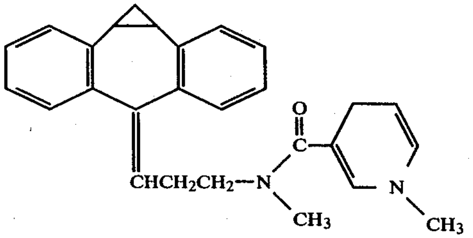 |
| 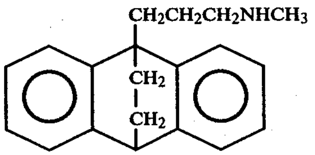 maprotiline | 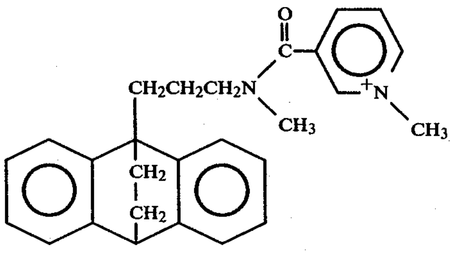 | 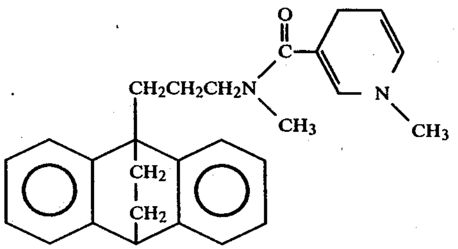 |

-continued
| Starting Material | [D—QC]+* | [D—DHC] |
|---|---|---|
| 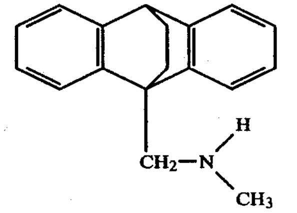 benzoctamine | 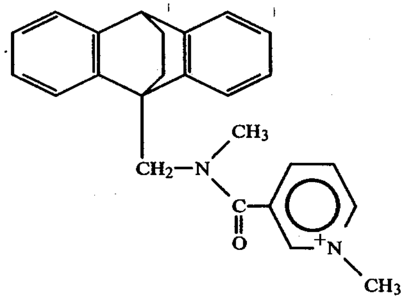 | 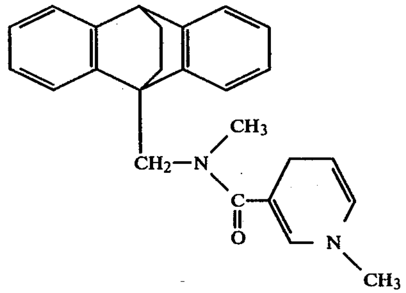 |
| 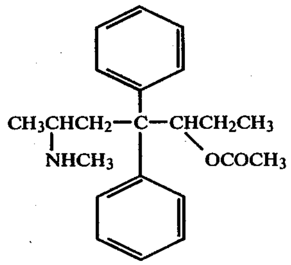 noracymethadol | 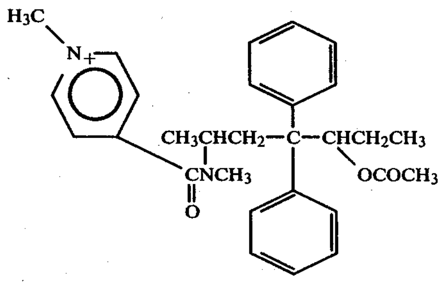 | 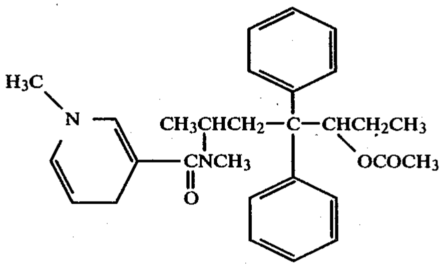 |

-continued
| Starting Material | [D—QC]+* | [D—DHC] |
|---|---|---|
| 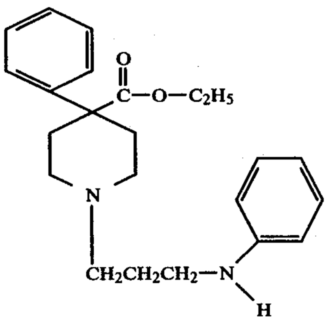 piminodine | 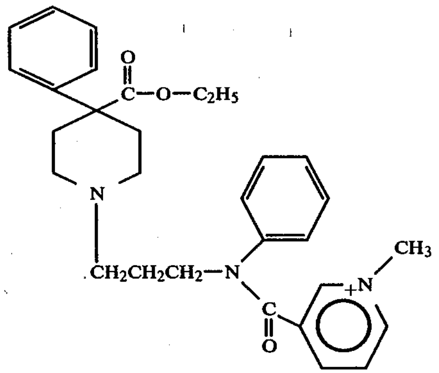 | 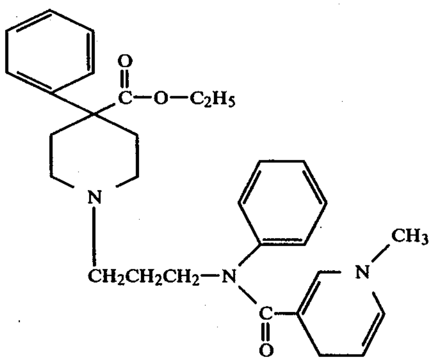 |
| 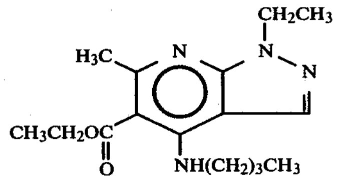 tracazolate | 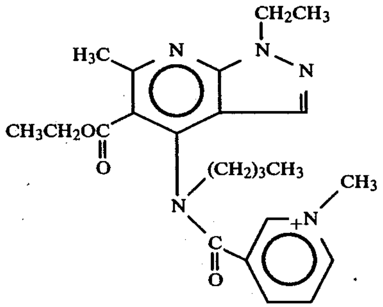 | 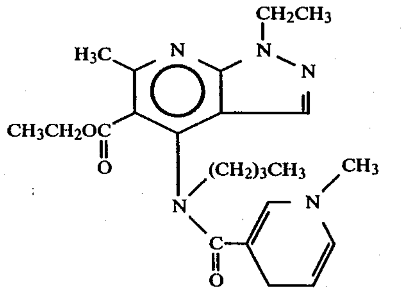 |

-continued
| Starting Material | [D—QC]+* | [D—DHC] |
|---|---|---|
| 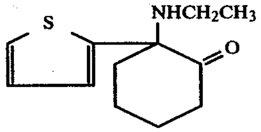 tiletamine | 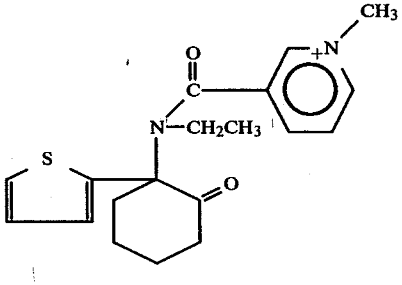 | 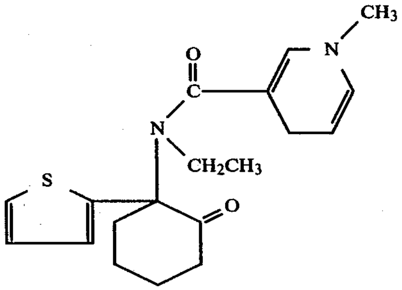 |
| 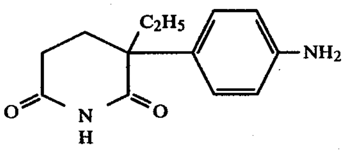 aminoglutethimide | 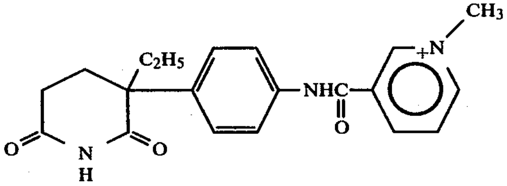 | 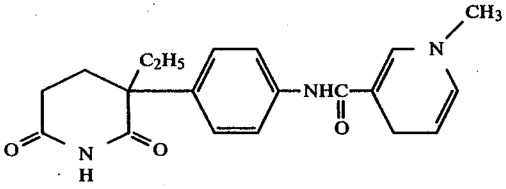 |
| 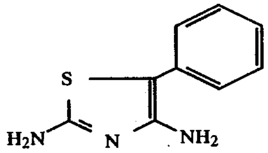 amiphenazole | 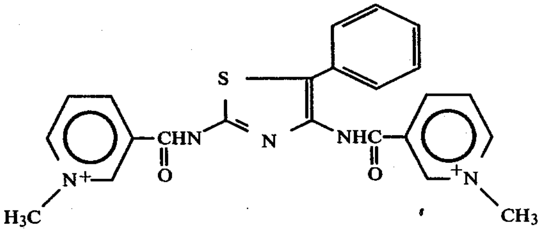 | 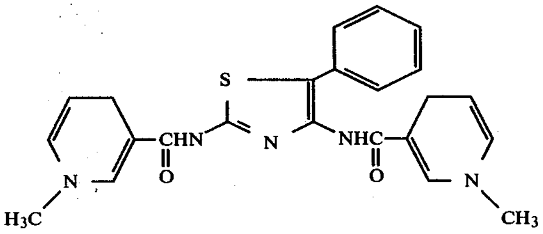 |
| 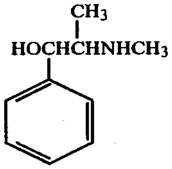 ephedrine | 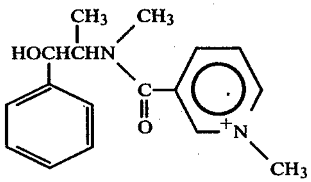 | 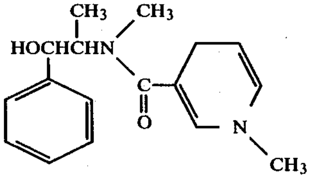 |

-continued
| Starting Material | [D—QC]+* | [D—DHC] |
| --- | --- | --- |
| 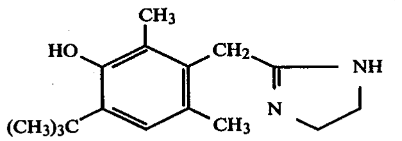 oxymetazoline | 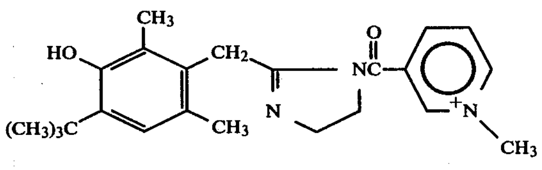 | 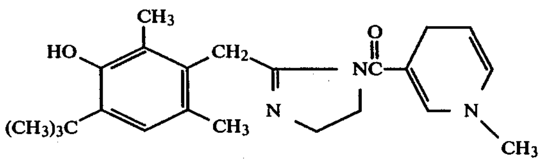 |
| 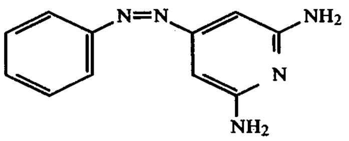 phenazopyridine | 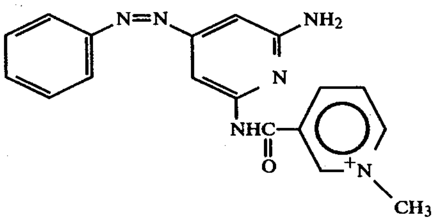 | 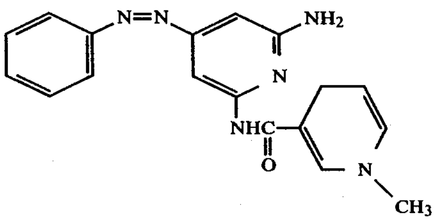 |
| 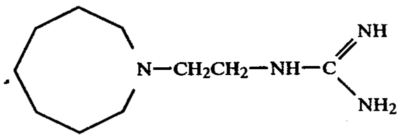 guanethidine | 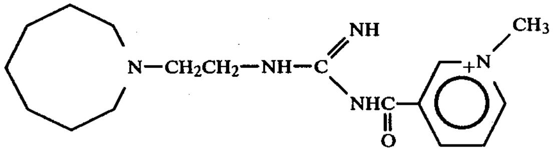 | 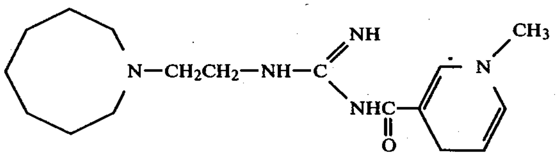 |

-continued
| Starting Material | [D—QC]+* | [D—DHC] |
|---|---|---|
| 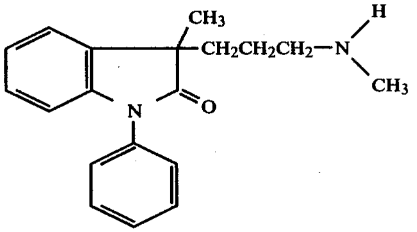 amedalin | 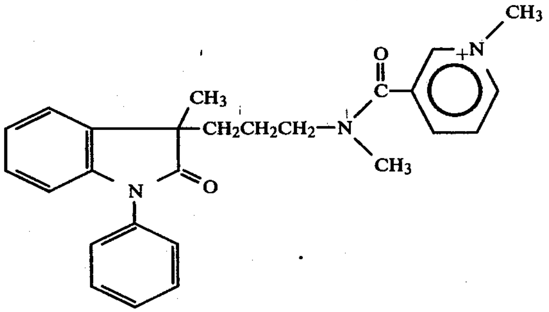 | 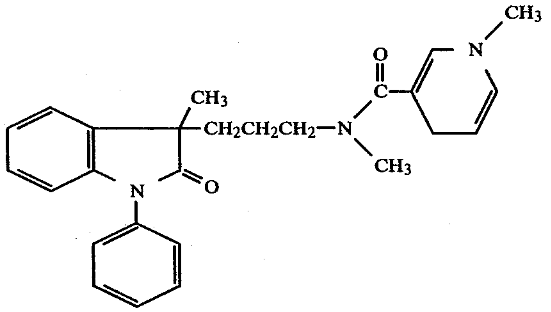 |
| 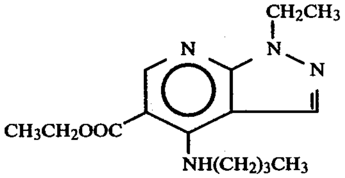 cartazolate | 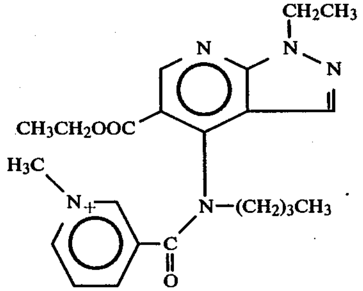 | 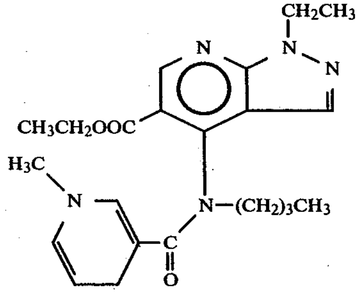 |
| 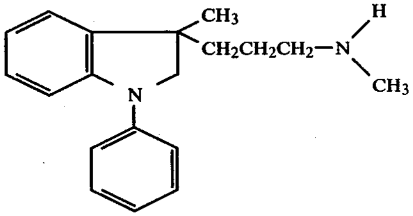 daledalin | 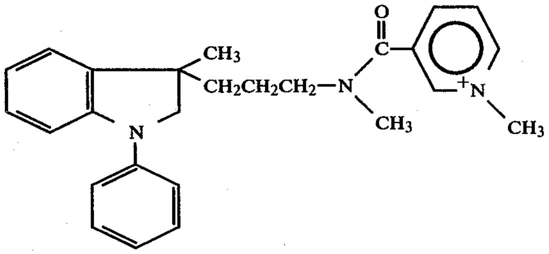 | 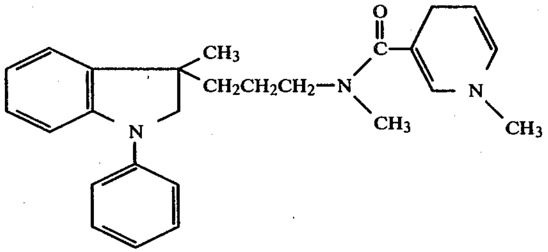 |

-continued
| Starting Material | [D—QC]+* | [D—DHC] |
| --- | --- | --- |
| 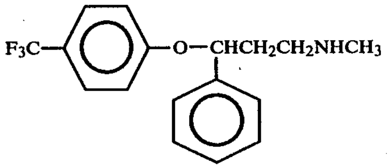 fluoxetine | 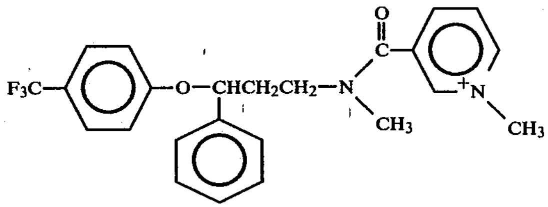 | 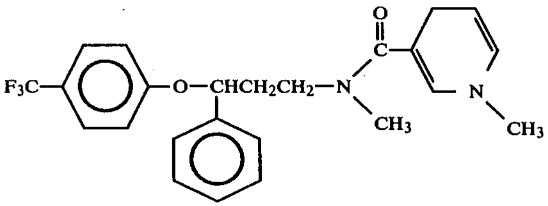 |
| 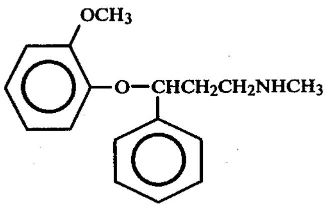 nisoxetine | 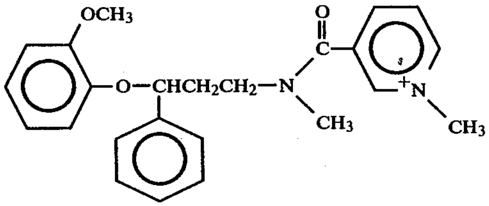 | 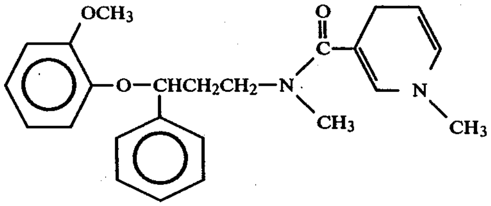 |
| 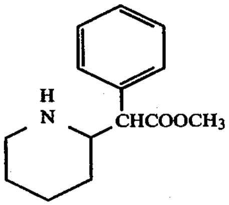 methylphenidate | 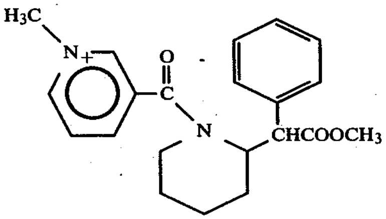 | 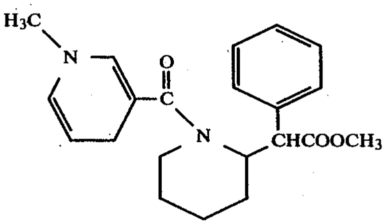 |
| 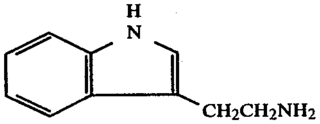 tryptamine | 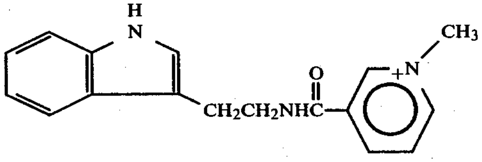 | 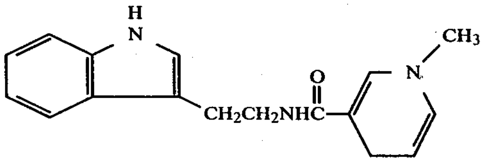 |

-continued
| Starting Material | [D—QC]+* | [D—DHC] |
|---|---|---|
| 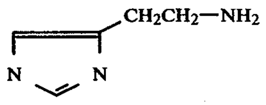 histamine | 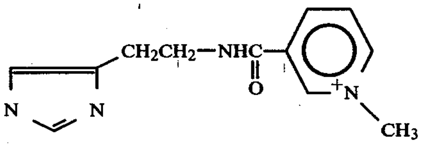 | 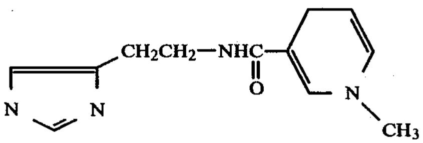 |
| 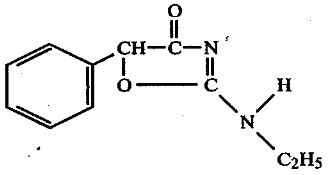 fenozolone | 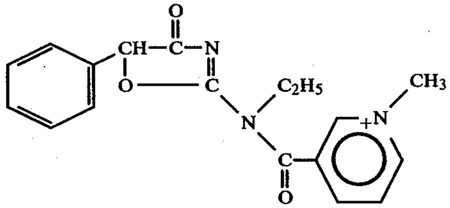 | 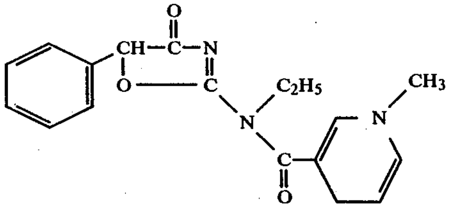 |
| 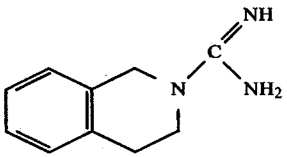 debrisoquin | 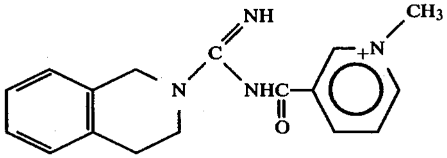 | 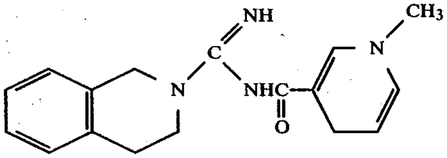 |
| 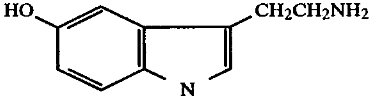 serotonin | 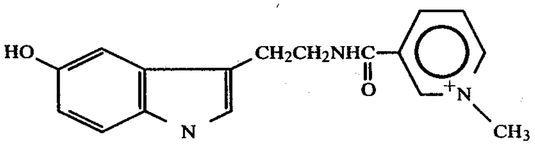 | 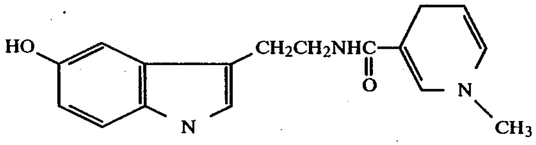 |

-continued
| Starting Material | [D—QC]$^{+}$* | [D—DHC] |
| --- | --- | --- |
| 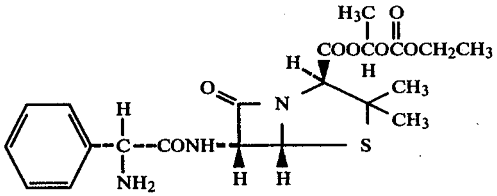 bacampicillin | 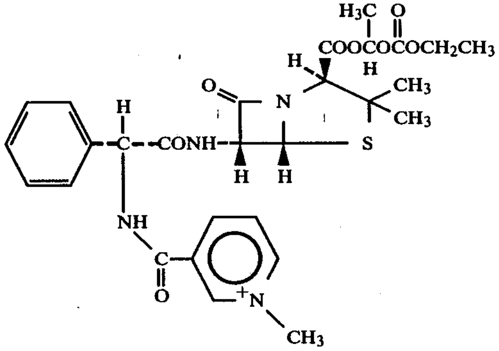 | 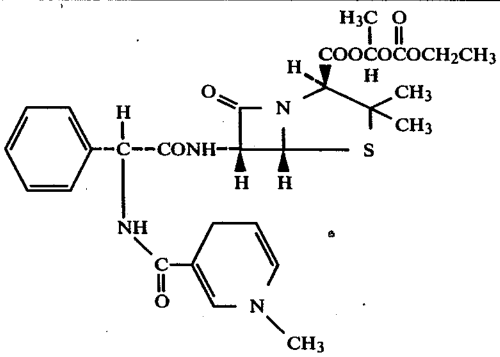 |
| 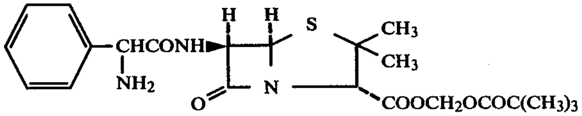 pivampicillin | 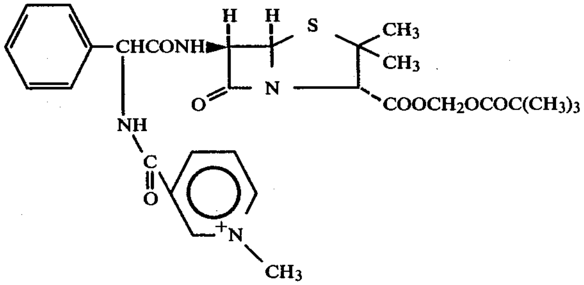 | 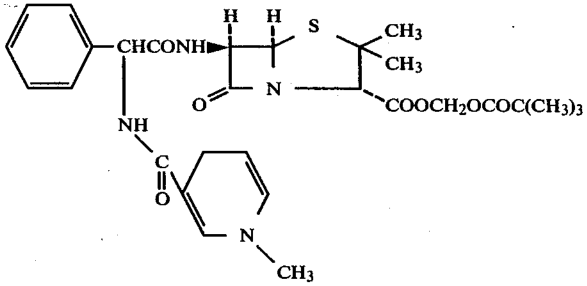 |

-continued
| Starting Material | [D—QC]+* | [D—DHC] |
|---|---|---|
| 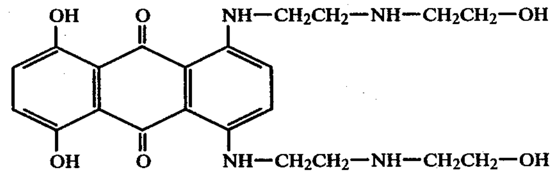 mitoxantrone | 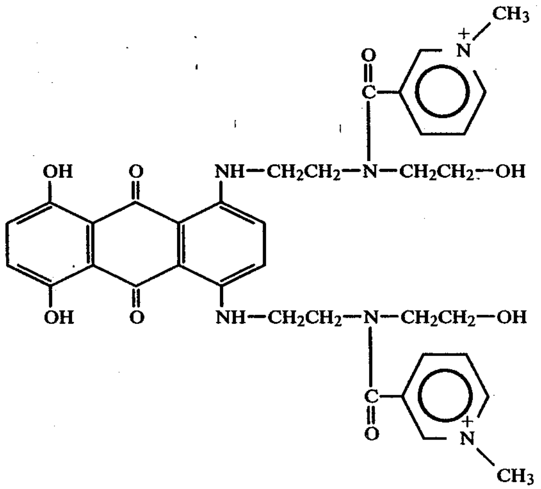 | 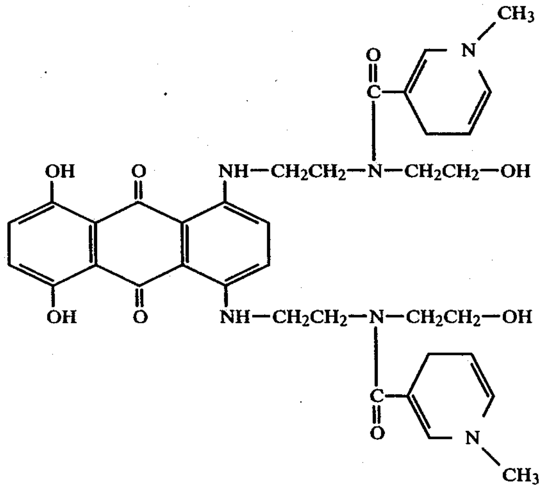 |
*cation only depicted in this column throughout Illustrative Synthetic Methods Method B This is a variation of Method A used when the drug contains at least one —COOH function which is to be protected.

The drug is first converted to the corresponding ethyl or t-butyl ester by conventional esterification techniques. That ester is then used as the starting material and Method A is repeated.

Obviously, other esters may be similarly prepared in the first step by use of other esterifying agents.

The representative drugs depicted below may be derivatized in this manner to the corresponding compounds of formulas (II) and (I). Omega amino acids other than GABA, other natural amino acids such as glycine, tyrosine, aspartic acid and glutamic acid, small peptides (2–20 amino acids, e.g. met$^5$-enkephalin and leu$^5$-enkephalin), ceforanide, furosemide and the like may be similarly derivatized.

The picolinamide and isonicotinamide quaternary and dihydro derivatives of the drugs specifically mentioned for derivatizing according to this method may be similarly prepared. See Method A.

| Starting Material | [D—QC]+ | [D—DHC] |
| --- | --- | --- |
| 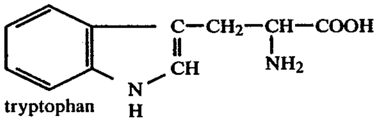 tryptophan | 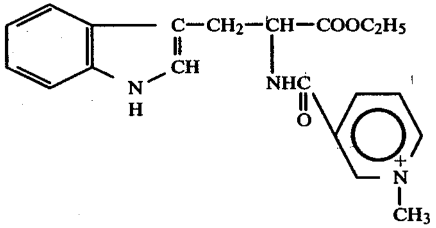 | 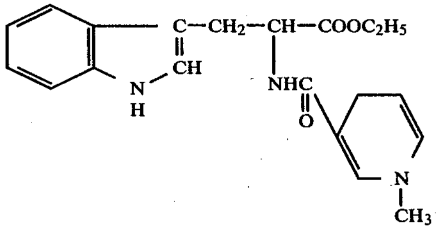 |
| 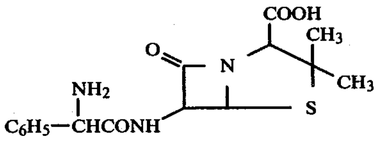 ampicillin | 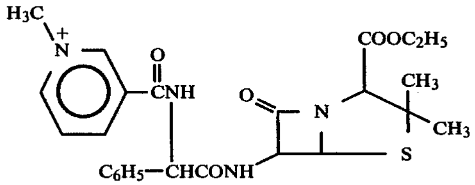 | 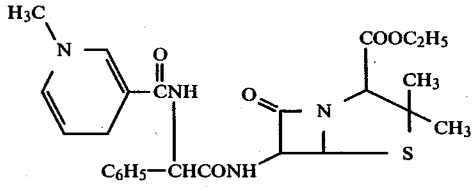 |
| 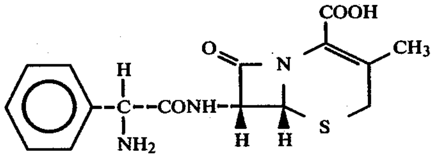 cephalexin | 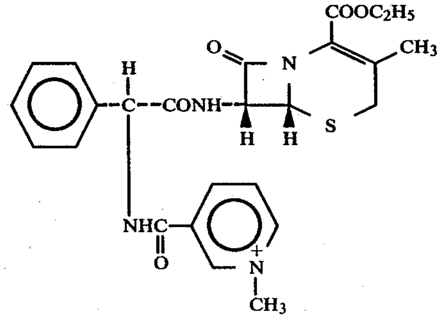 | 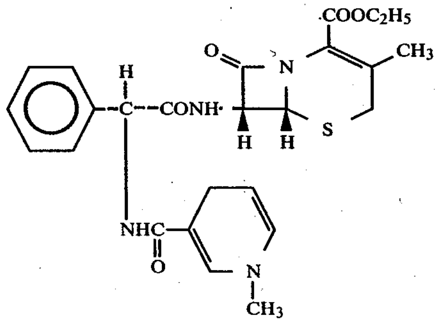 |

-continued
| Starting Material | [D—QC]+ | [D—DHC] |
|---|---|---|
| 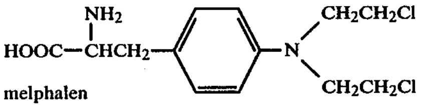 melphalen | 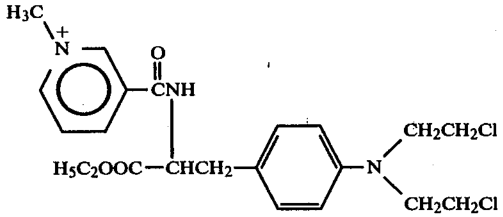 | 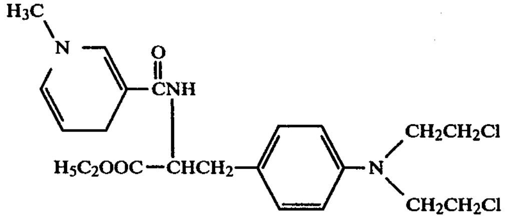 |
| 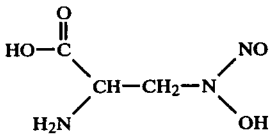 L—alanosine | 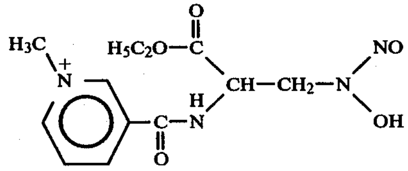 | 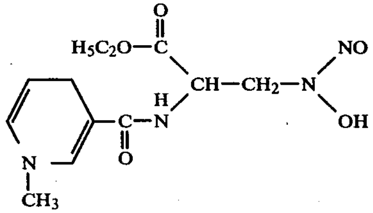 |
| 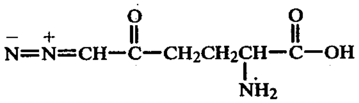 DON | 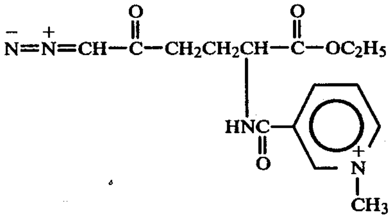 | 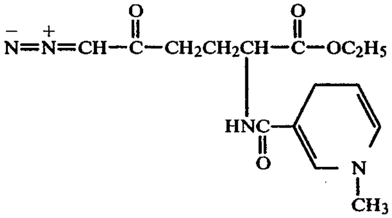 |
| 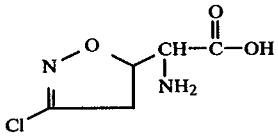 acivicin | 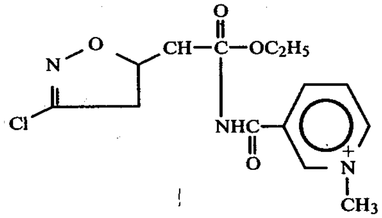 | 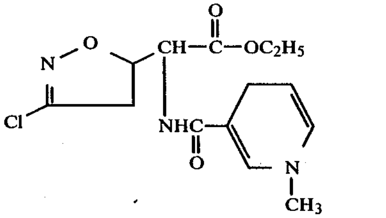 |

-continued
| Starting Material | [D—QC]$^+$ | [D—DHC] |
|---|---|---|
| $NH_2—CH_2CH_2CH_2COOH$<br>GABA | 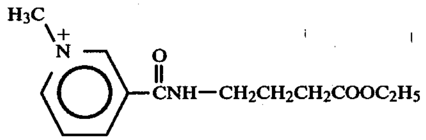 | 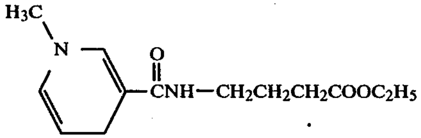 |
| 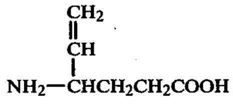<br>γ-vinyl GABA | 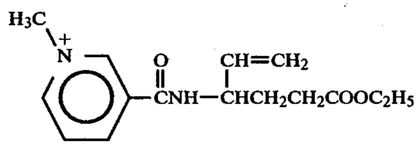 | 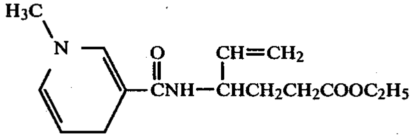 |
| 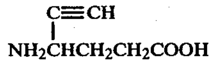<br>γ-acetylenic GABA | 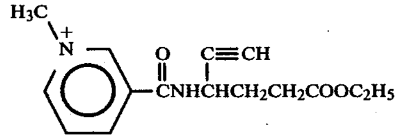 | 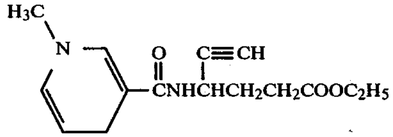 |
| 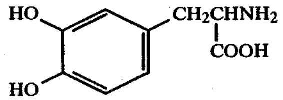<br>L—DOPA | 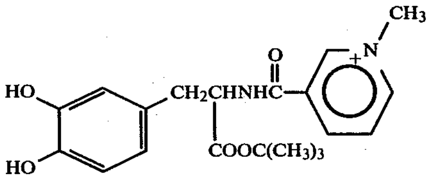 | 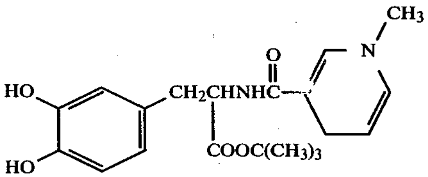 |

-continued
| Starting Material | [D—QC]+ | [D—DHC] |
| --- | --- | --- |
| 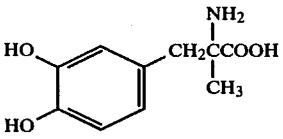 methyldope | 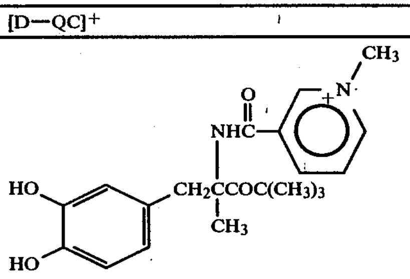 | 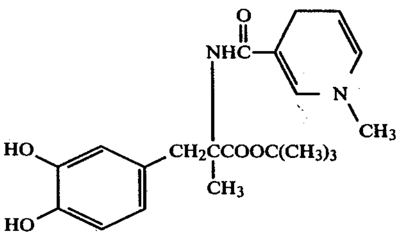 |
| 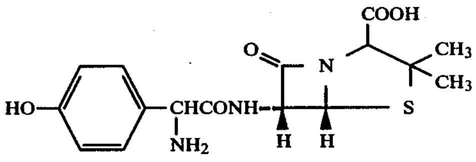 amoxicillin | 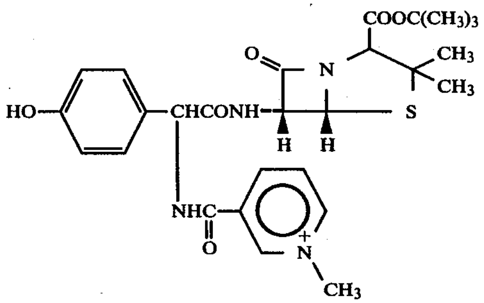 | 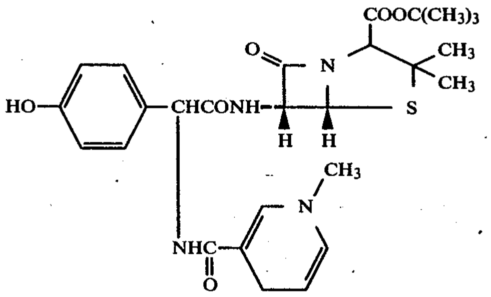 |
| 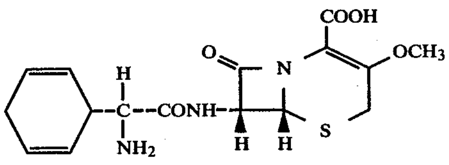 cefroxodine | 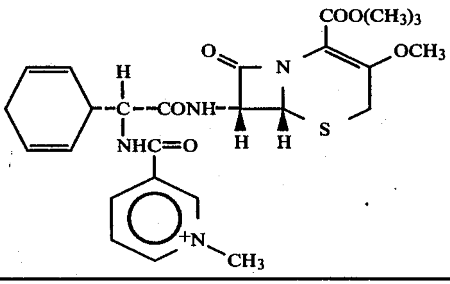 | 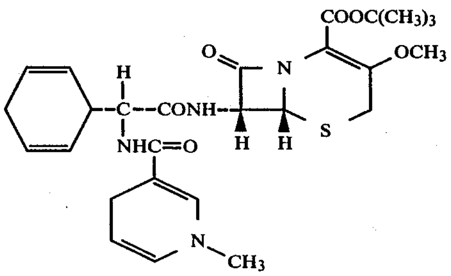 |

Method C

This is a variation of Method A used when the drug contains one or more OH functions which are to be protected.

The drug is first reacted with excess trimethylacetyl chloride to convert the hydroxy group(s) to pivalyloxy group(s). (This process is generally conducted in the presence of a base; however, strongly acid conditions are used if an amine function is present.) That protected derivative is then used as the starting material and subjected to Method A. Alternatively, the first two steps may be reversed, i.e. the drug may be first converted to the nicotinamide, which may then be reacted with trimethylacetyl chloride to form the protected nicotinamide.

Various other hydroxy protecting groups may be introduced in similar fashion.

The representative drugs depicted below may be derivatized in this manner to the corresponding compounds of formulas (II) and (I). The corresponding picolinamide and isonicotinamide quaternary and dihydro derivatives may be similarly prepared. See Method A. Moreover, drugs such as atenolol, metoprolol, pentostatin (2′-deoxycoformycin), glucosamine, 6-amino-6-deoxy-D-glucose and pseudoephedrine may be similarly derivatized.

| Starting Material | [D—QC]+ | [D—DHC] |
|---|---|---|
| 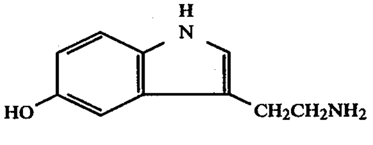 serotonin | 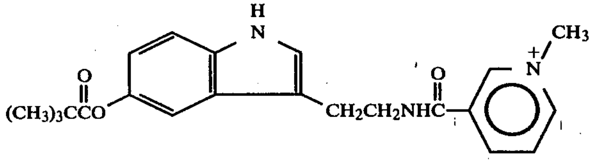 | 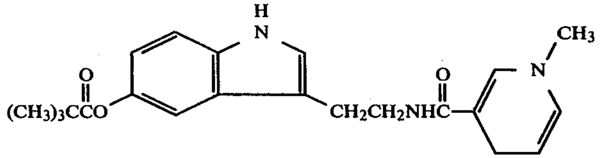 |
| 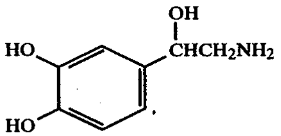 norepinephrine | 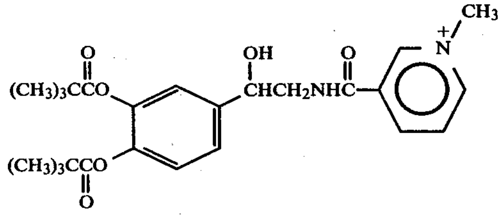 | 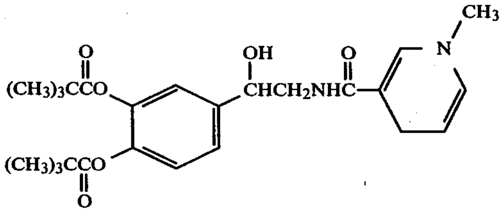 |
| 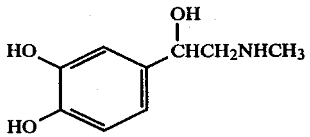 epinephrine | 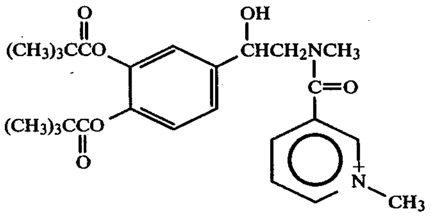 | 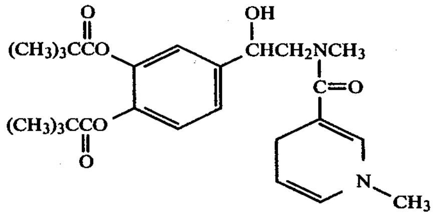 |
| 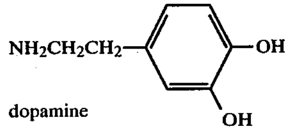 dopamine | 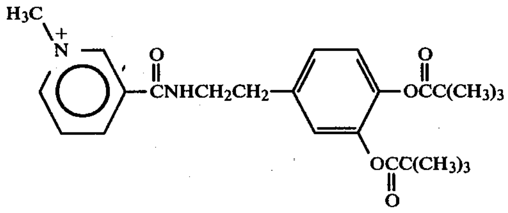 | 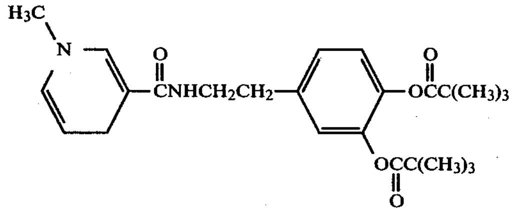 |

-continued
| Starting Material | [D—QC]+ | [D—DHC] |
|---|---|---|
| 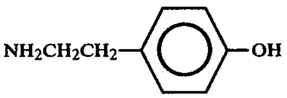<br>tyramine | 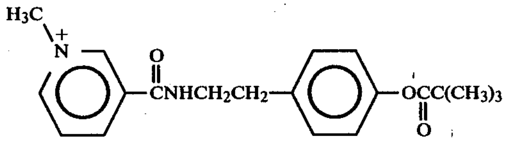 | 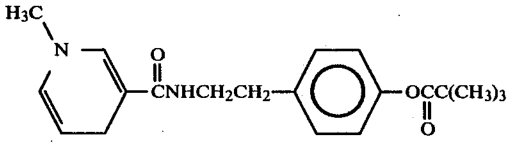 |
| 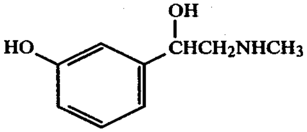<br>phenylephrine | 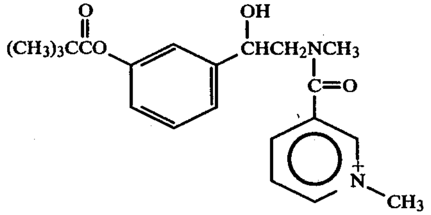 | 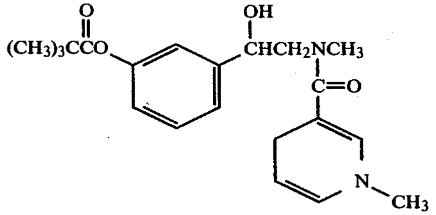 |
| 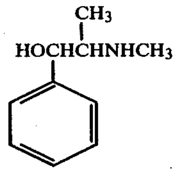<br>ephedrine | 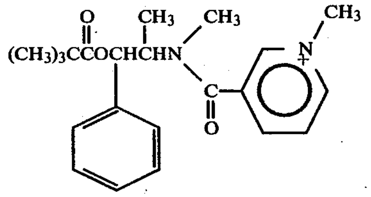 | 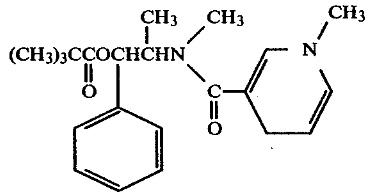 |

Method D

This variation of Method A can be used when the drug contains one or more OH and COOH functions which are to be protected. The protecting groups, typically the ethyl or t-butyl ester and pivalyloxy groups, are introduced as described in Methods B and C, in the sequence considered most convenient. Obviously, other protecting groups can be introduced instead. The amine function is derivatized according to Method A.

The representative drugs depicted below may be derivatized in this manner to the corresponding compounds of formulas (II) and (I). The corresponding picolinamide and isonicotinamide quaternary and dihydro derivatives may be similarly prepared. See Method A.

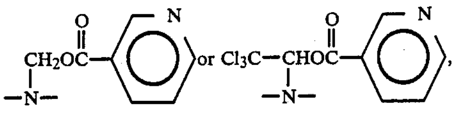

respectively. The resultant intermediate is then quaternized and reduced as in Method A. The alternative process utilizing an activated ester or quaternary derivative thereof which is described in Method A may be utilized here as well.

The representative starting drugs depicted below may be derivatized in this manner to the corresponding compounds of formulas (II) and (I). Drugs such as minocycline, doxycycline, oxytetracycline, tetracycline, methacycline, atenolol, sulfadiazine, dactinomy-

| Starting Material | [D—QC]+ | [D—DHC] |
|---|---|---|
| 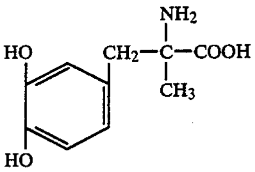 methyldopa | 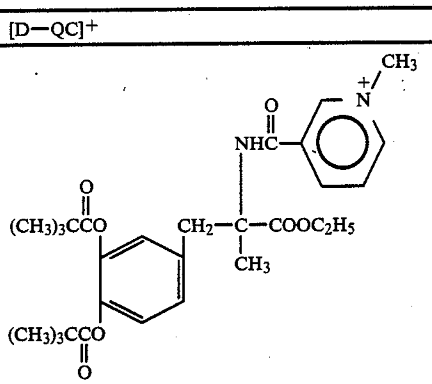 | 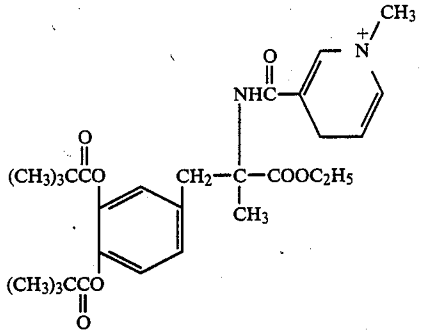 |
| 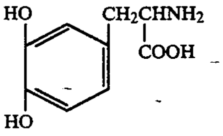 levodopa (L—DOPA) | 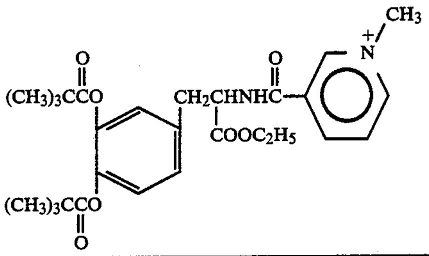 | 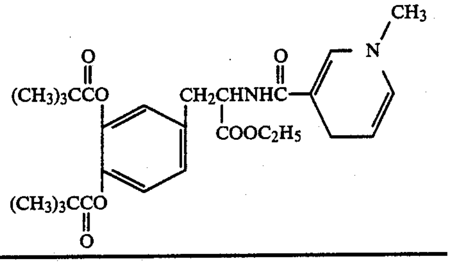 |

Method E

This method is of particular use when the —NH— function is part of an amide or imide or a very low pKa primary or secondary amine.

The drug is first reacted with an aldehyde [e.g. formaldehyde, benzaldehyde, acetaldehyde or chloral ($Cl_3CCHO$)]; for example, in the case of formaldehyde or chloral, one converts the —NH— function to a

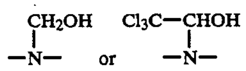

function, respectively, and thus forms a suitable bridging group. The resultant compound can then be derivatized in the same manner as any drug containing a reactive —OH group; for example, it is then reacted with nicotinic acid in the presence of a suitable coupling agent, or with nicotinoyl chloride or nicotinic anhydride, to form the corresonding nicotinic acid ester of the partial formula cin, mitomycin, methylphenidate, ethyl β-carboline 3-carboxylate, nifedipine, 3-deazaguanine, 6-mercaptopurine, cyclophosphamide and progabide may be similarly derivatized.

The foregoing procedure may be repeated using picolinic acid or its acid chloride or anhydride or activated ester, or isonicotinic acid or its acid chloride or anhydride or activated ester, in place of nicotinic acid or its acid chloride or anhydride, or activated ester, respectively, to convert drugs such as those specifically mentioned for derivatizing according to this method to the corresponding picolinic acid esters and isonicotinic acid esters and then to the corresponding compounds of formulas (II) and (I).

As yet another alternative, the intermediate compound containing the

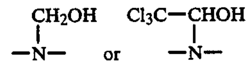

group or the like may be reacted with thionyl chloride to afford the corresponding compound containing a

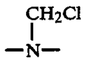
or
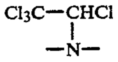

or similar group. That derivative may then be reacted with a metallic salt (especially a silver or thallous salt) of nicotinic acid or the like (formed, e.g. by reacting nicotinic acid or the like with fresh silver hydroxide or oxide or with thallous ethoxide). The resultant nicotinic acid ester of the partial formula

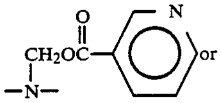
or
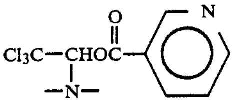

or like derivative is then quaternized and subsequently reduced as in Method A.

| Starting Material | [D—QC]+ | [D—DHC] |
| --- | --- | --- |
| 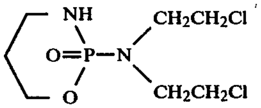<br>cyclophosphamide | 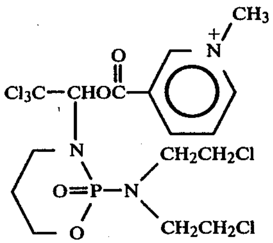 | 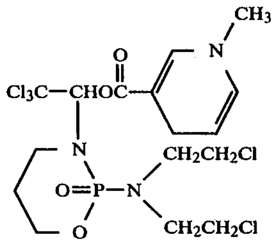 |
| 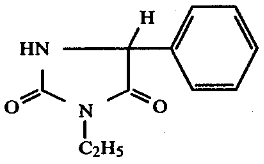<br>ethotoin | 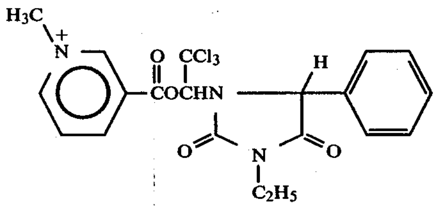 | 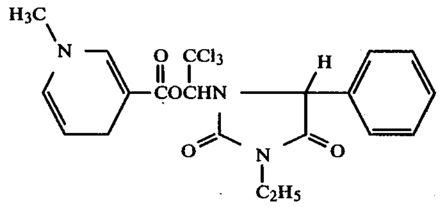 |
| 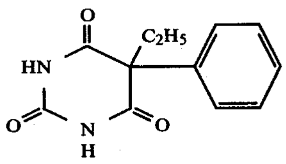<br>phenobarbital | 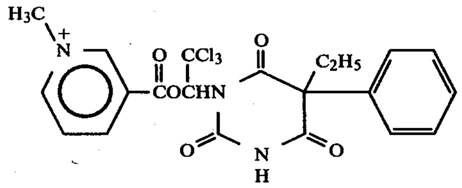 | 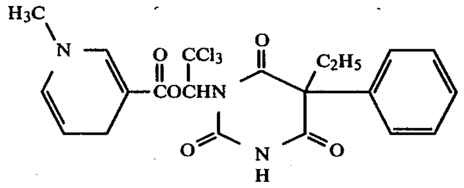 |
| 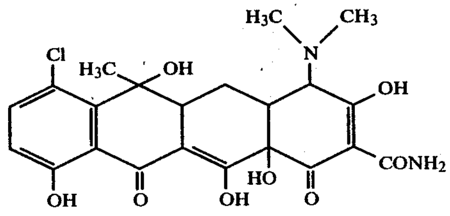<br>chlortetracycline | 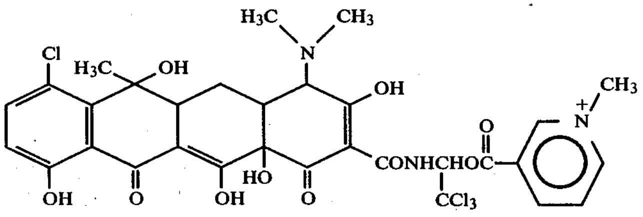 | 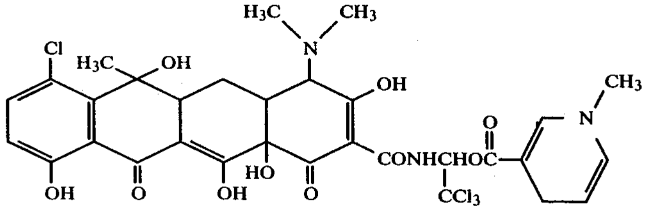 |

-continued
| Starting Material | [D—QC]+ | [D—DHC] |
|---|---|---|
| 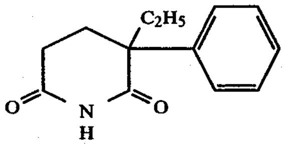 glutethimide | 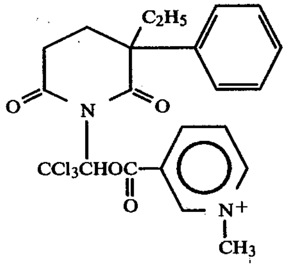 | 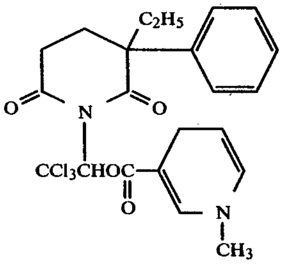 |
| 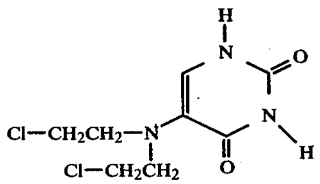 uracil mustard | 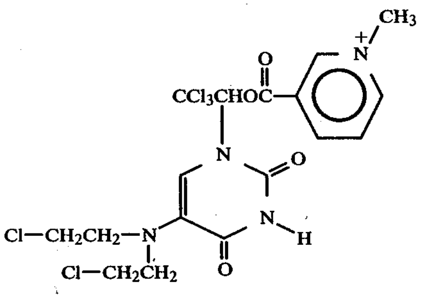 | 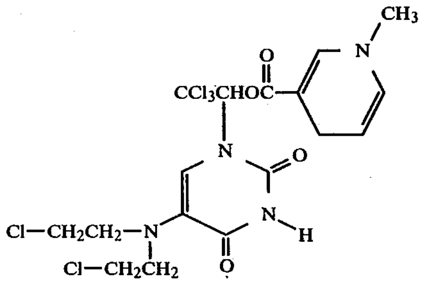 |
| 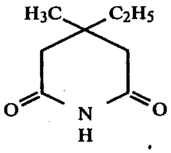 bemegride | 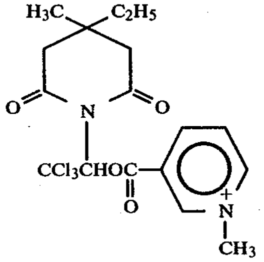 | 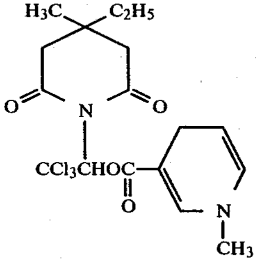 |

-continued
| Starting Material | [D—QC]+ | [D—DHC] |
|---|---|---|
| 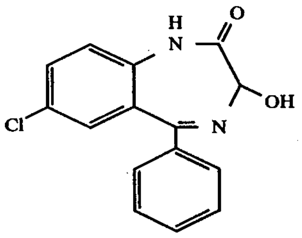 oxazepam | 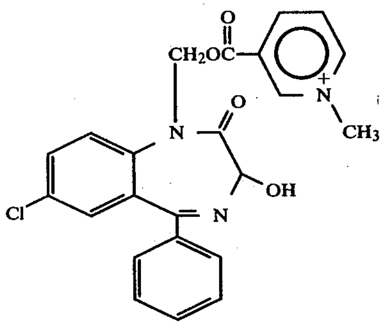 | 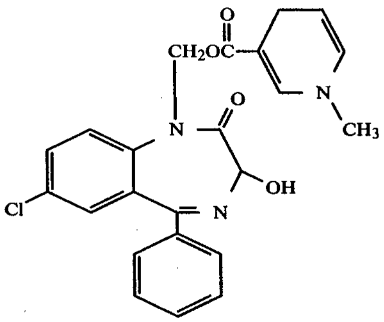 |
| 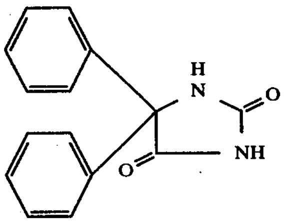 phenytoin | 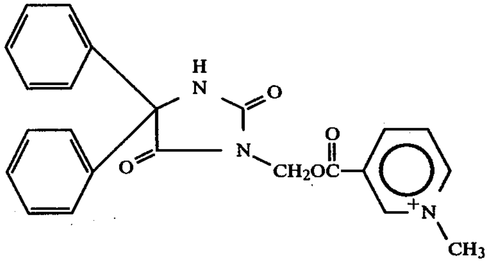 | 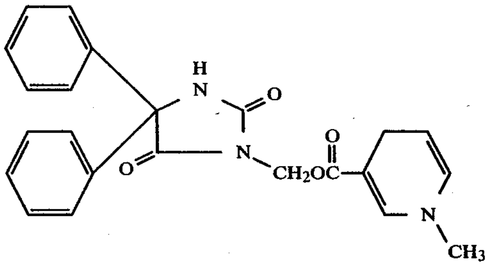 |
| 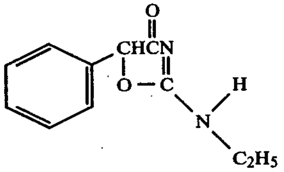 fenozolone | 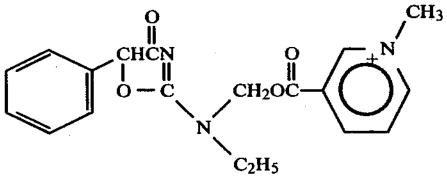 | 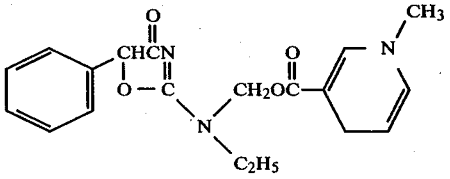 |

-continued
| Starting Material | [D—QC]+ | [D—DHC] |
|---|---|---|
| 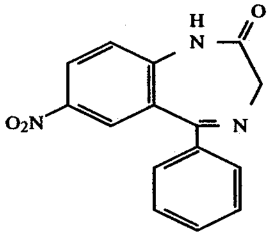<br>nitrazepam | 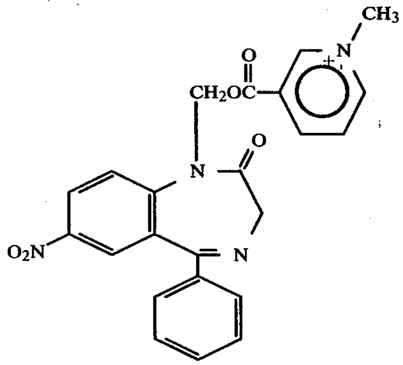 | 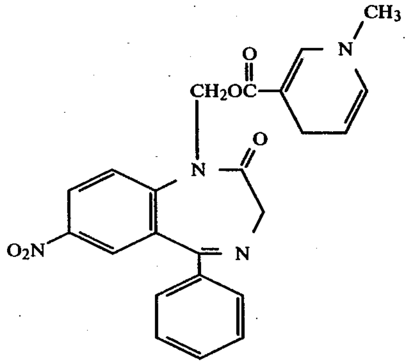 |
| 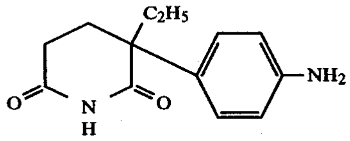<br>aminoglutethimide | 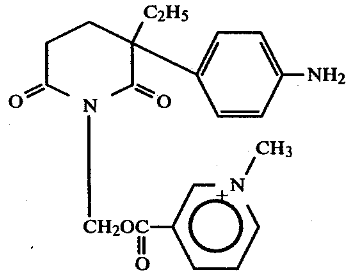 | 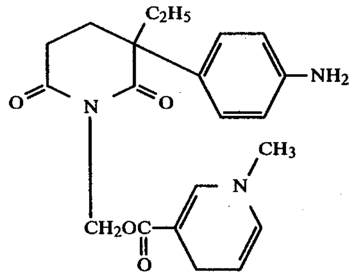 |
| 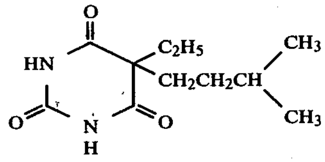<br>amobarbital | 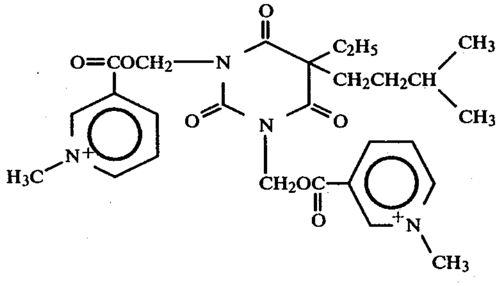 | 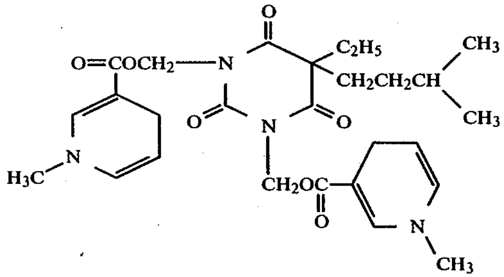 |

-continued
| Starting Material | [D—QC]+ | [D—DHC] |
|---|---|---|
| 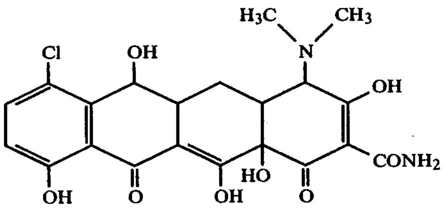 demeclocycline | 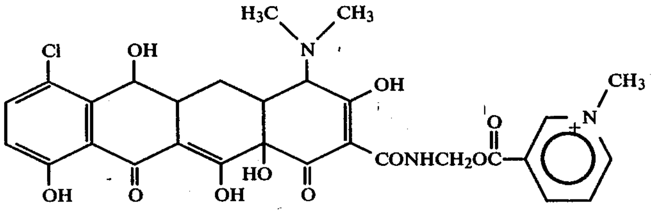 | 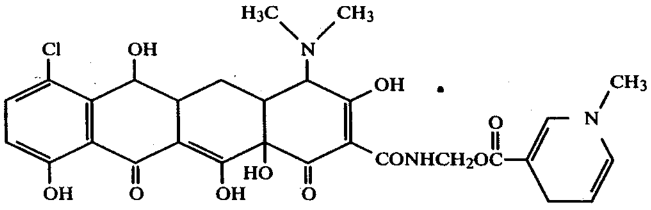 |
| 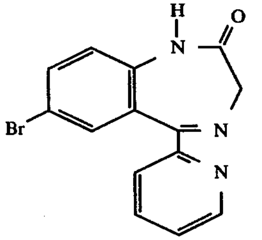 bromazepam | 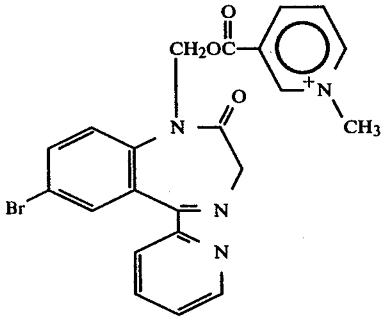 | 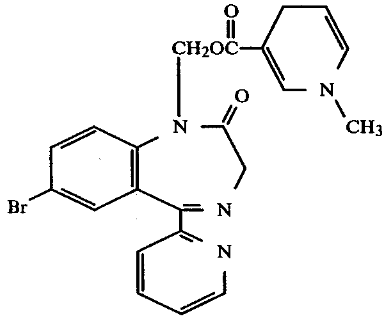 |
| 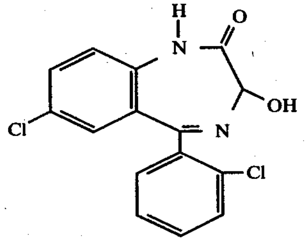 lorazepam | 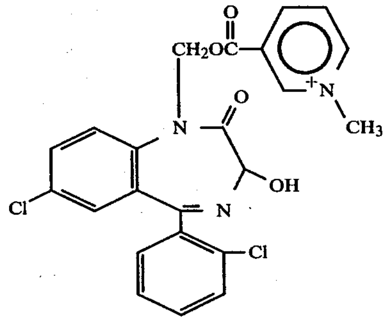 | 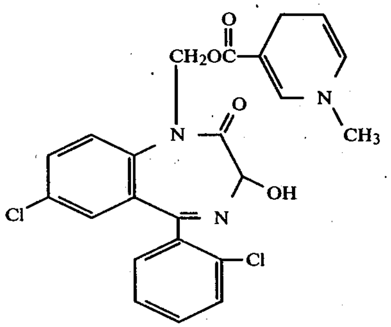 |

-continued
| Starting Material | [D—QC]+ | [D—DHC] |
| --- | --- | --- |
| 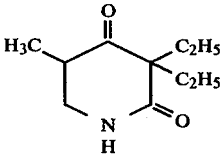 methyprylon | 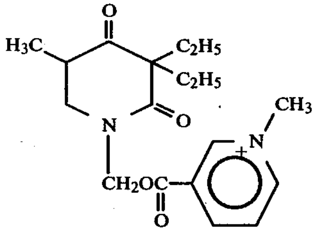 | 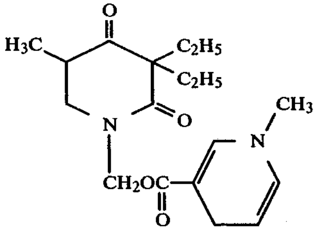 |
| 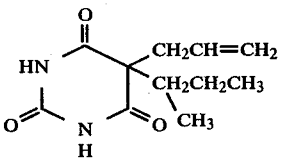 butalbital | 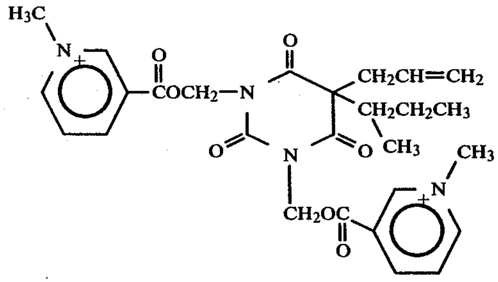 | 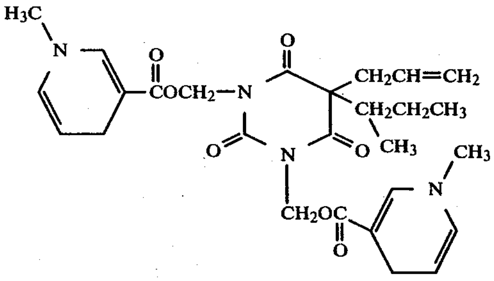 |
| 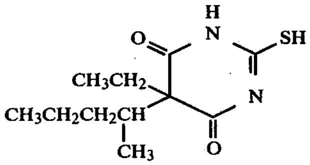 thiopental | 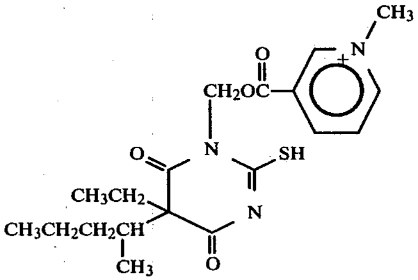 | 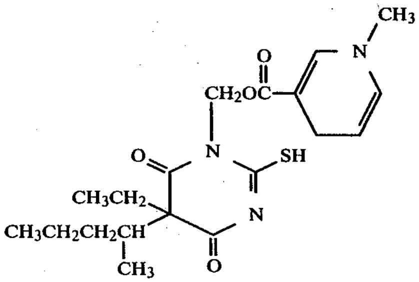 |

-continued
| Starting Material | [D—QC]+ | [D—DHC] |
| --- | --- | --- |
| 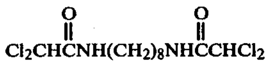 fertilysin | 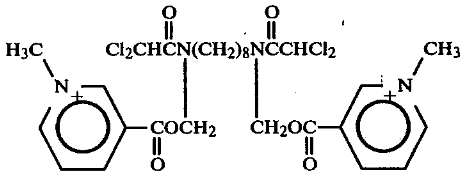 | 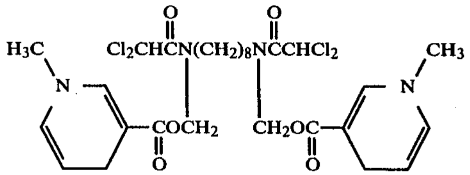 |
| 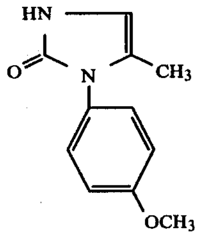 metazamide | 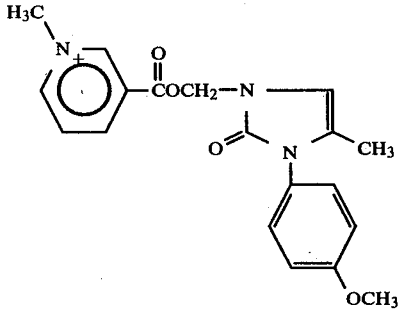 | 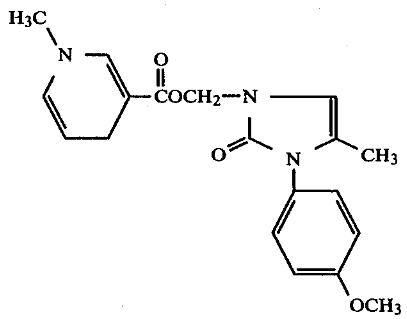 |
| 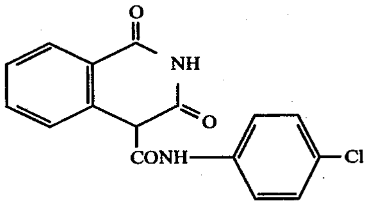 tesicam | 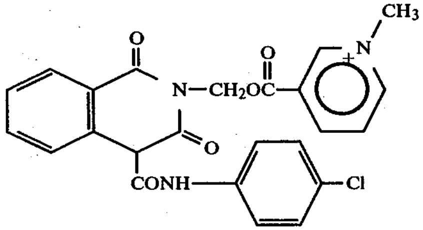 | 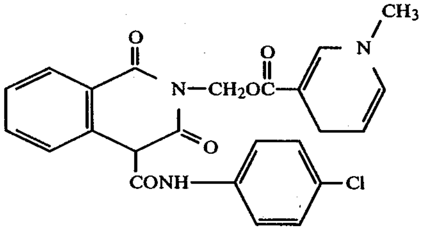 |

-continued
| Starting Material | [D—QC]+ | [D—DHC] |
| --- | --- | --- |
| 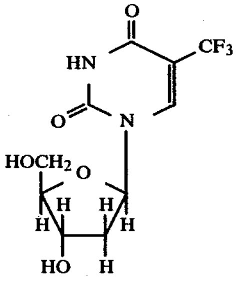 trifluridine | 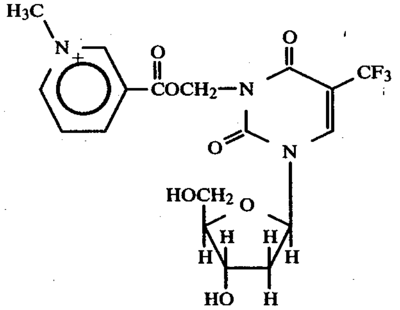 | 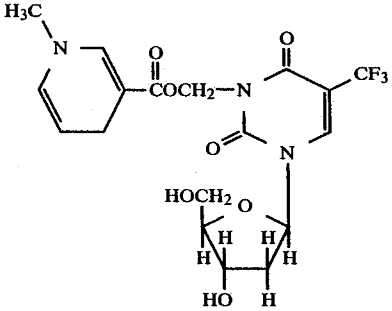 |
| 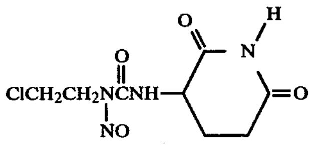 PCNU | 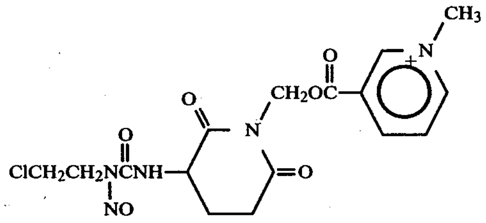 | 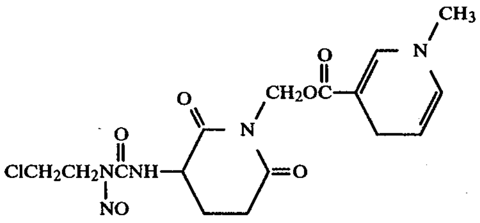 |
| 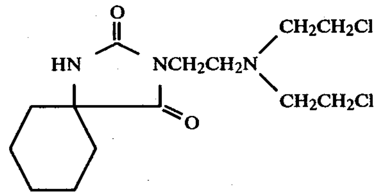 spiromustine | 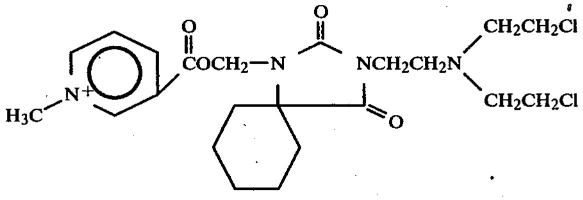 | 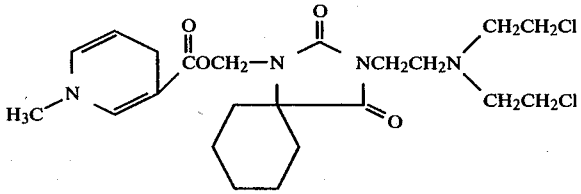 |

-continued
| Starting Material | [D—QC]+ | [D—DHC] |
| --- | --- | --- |
| 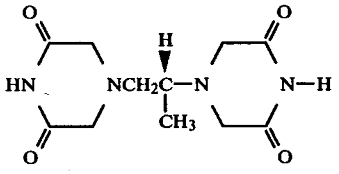<br>L-ICRF | 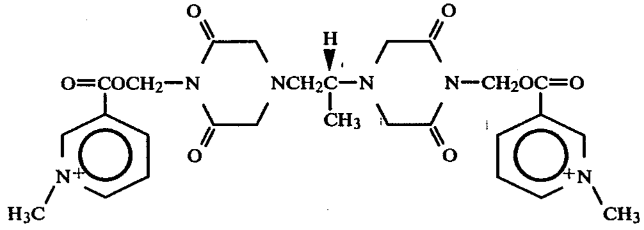 | 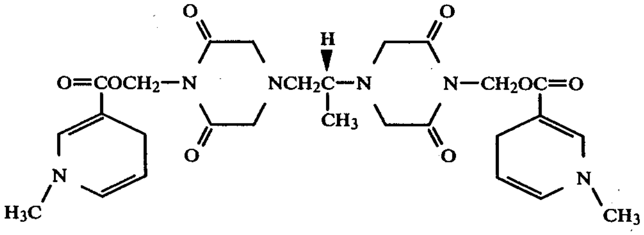 |
| 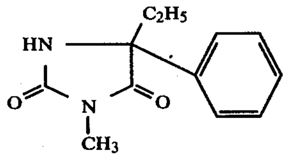<br>mephenytoin | 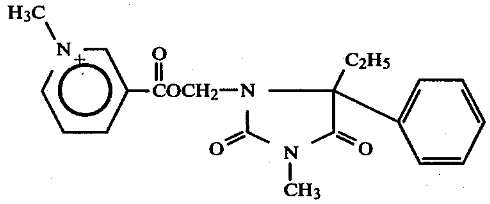 | 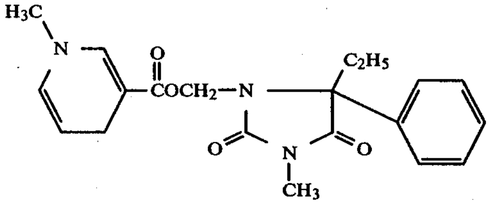 |
| 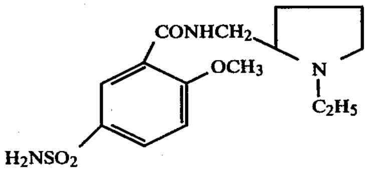<br>sulpiride | 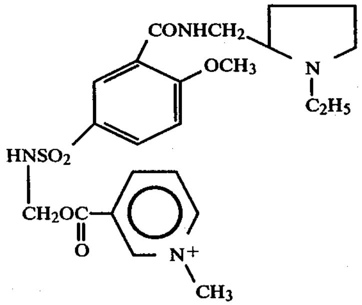 | 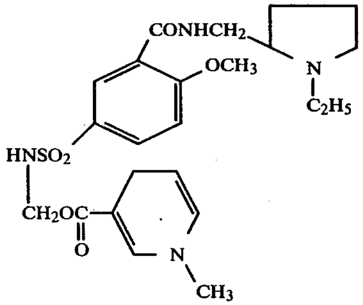 |
| 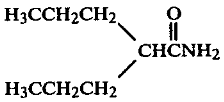<br>valpromide | 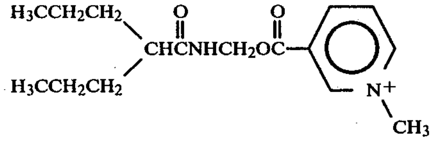 | 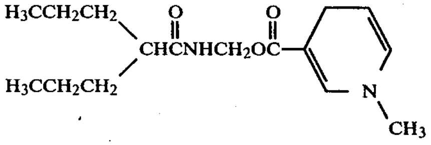 |

-continued
| Starting Material | [D—QC]+ | [D—DHC] |
|---|---|---|
| 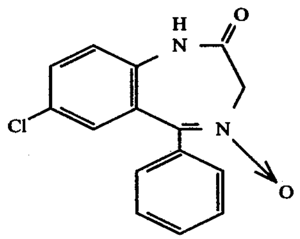 demoxepam | 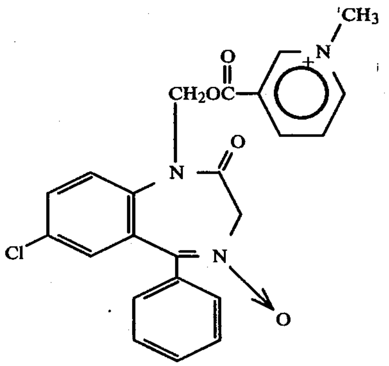 | 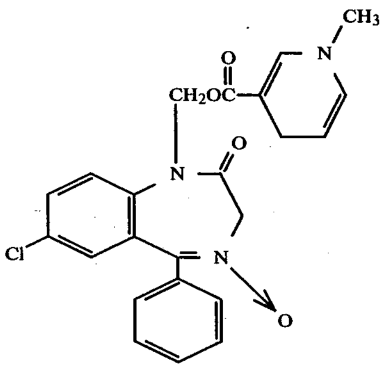 |
| 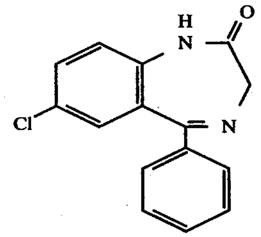 desmethyldiazepam | 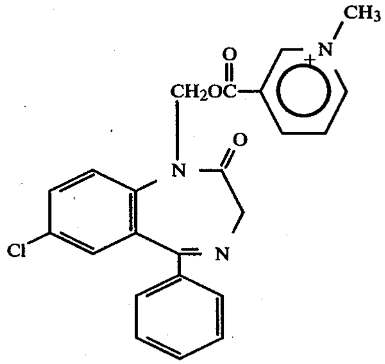 | 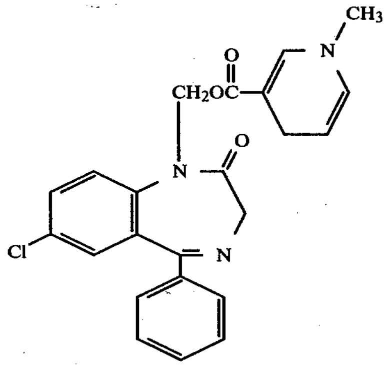 |

Method F

This method is a variation of Method E which can be used when the —NH— function is part of an amide or imide or low pKa primary or secondary amine and the drug contains one or more —COOH functions which is/are to be protected. Typically, the carboxyl group or groups is/are first converted to the corresponding pivaloyloxymethyl ester by known esterification techniques. Obviously, other esters may be similarly prepared. The ester is then used as the starting material and Method E is repeated.

The representative starting drugs depicted below may be derivatized in this manner to the corresponding compounds of formulas (II) and (I). Drugs such as carbenicillin, phenoxymethylpenicillin, methicillin, nafcillin, ticarcillin, dicloxacillin, cefazolin, cefoxitin, moxalactam, aminopterin, furosemide, and 5-methyltetrahydrohomofolic acid may be similarly derivatized.

The alternative procedures described in Method E may be used in Method F also.

| STARTING MATERIAL | $[D-QC]^+$ | [D—DHC] |
|---|---|---|
| 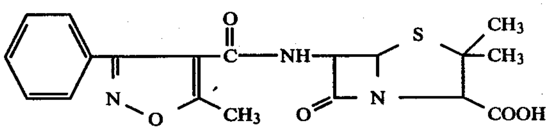<br>oxacillin | 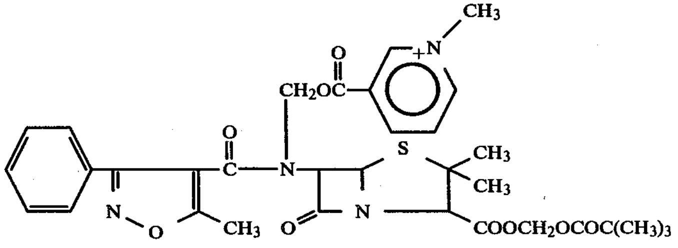 | 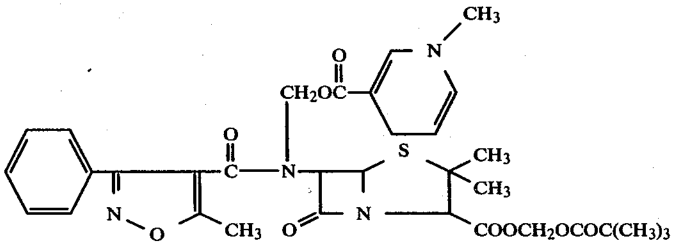 |
| 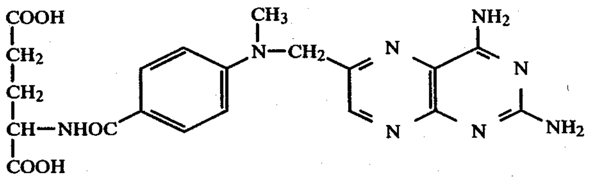<br>methotrexate | | 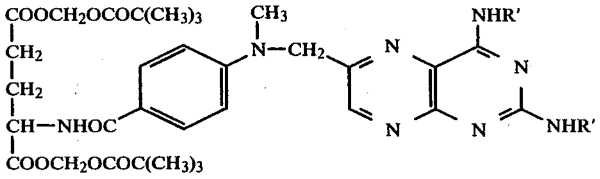<br>One R' is 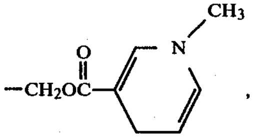,<br>the other R' is H or 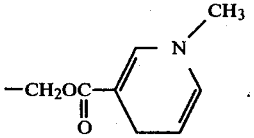. |

-continued
| STARTING MATERIAL | [D—QC]+ | [D—DHC] |
|---|---|---|
| | 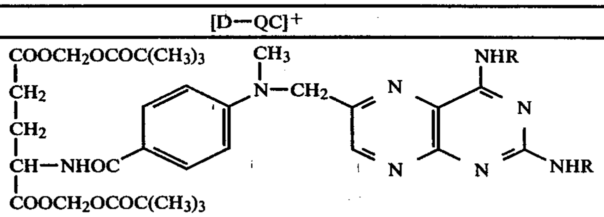 One R is 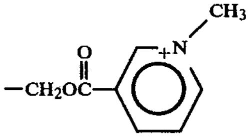 the other R is H or 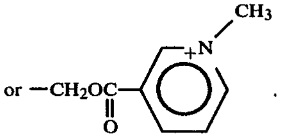 | |
| 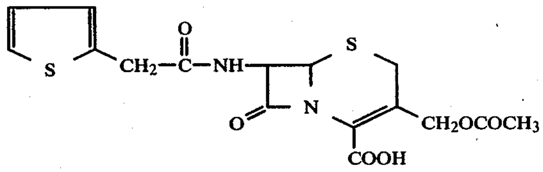 cephalothin | 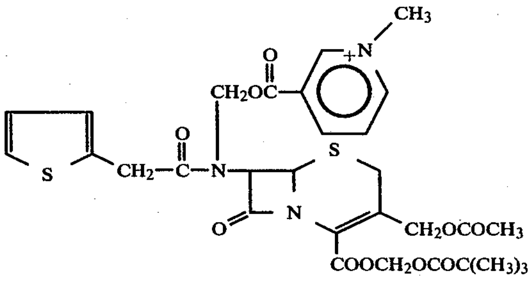 | 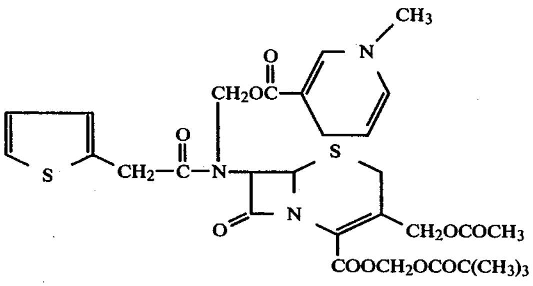 |
| 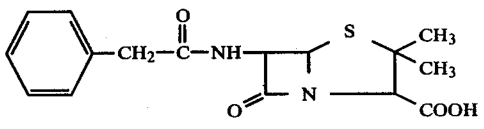 benzylpenicillin | 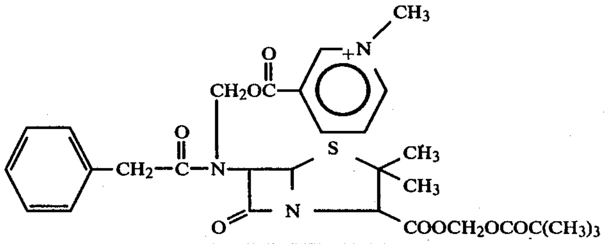 | 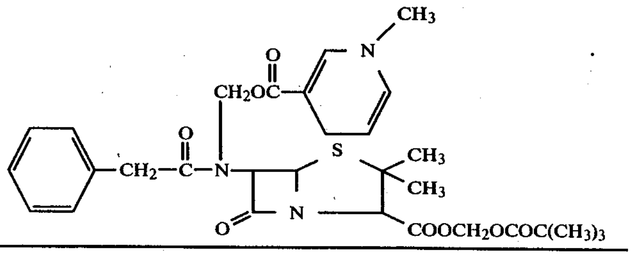 |

Method G

This is a variation of Method E used when the drug also contains one or more hydroxy functions which are to be protected. Typically, the drug is first reacted with excess trimethylacetyl chloride to convert the hydroxy group(s) to pivalyloxy group(s). That protected derivative is then used as the starting material and subjected to Method E.

Other hydroxy protecting groups may be introduced in similar fashion.

The representative drugs depicted below may be derivatized in this manner to the corresponding compounds of formulas (II) and (I).

The alternative procedures described in Method E may be used in Method G also.

| STARTING MATERIAL | $[D-QC]^+$ | [D—DHC] |
|---|---|---|
| 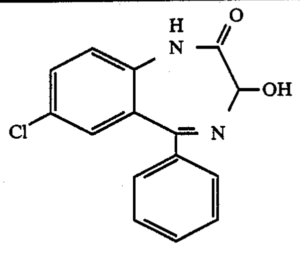 oxazepam | 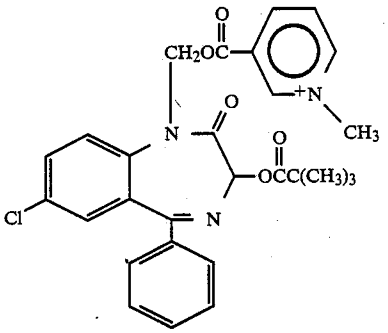 | 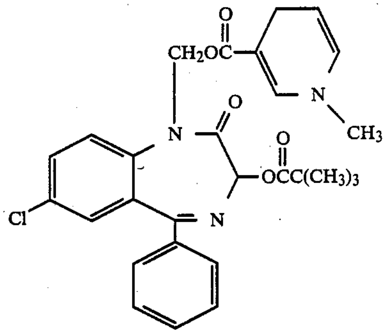 |
| 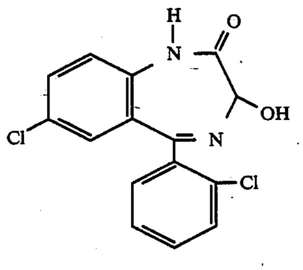 lorazepam | 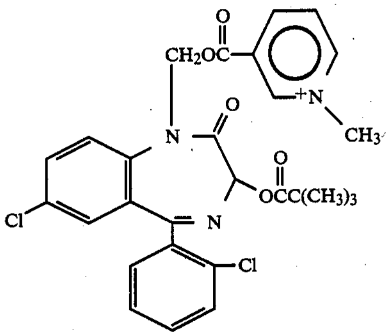 | 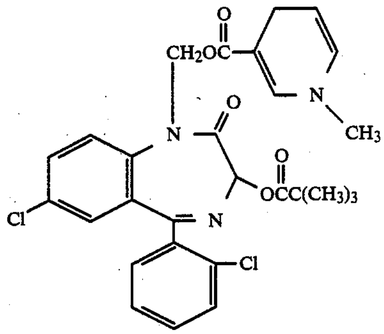 |
| 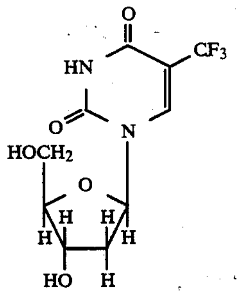 trifluridine | 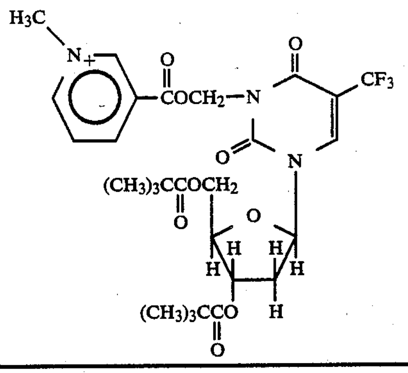 | 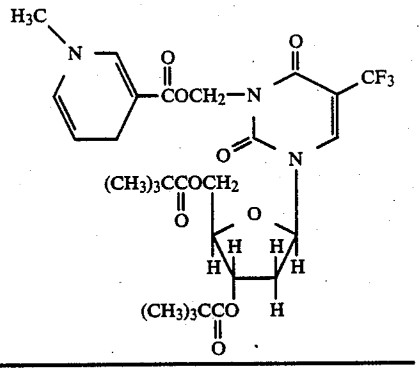 |

Method H

Method A is followed, except that in the first step, the drug is reacted with 3-quinolinecarboxylic acid or its acid chloride or anhydride or activated ester instead of nicotinic acid or its acid chloride or anhydride or activated ester.

The representative drugs depicted below may be derivatized in this manner to the corresponding compounds of formulas (II) and (I), as may the remaining drugs mentioned with Method A.

Similarly, Method H may be combined with Methods B, C, D, E, F or G to afford the corresponding derivatives, e.g., of the drugs listed with those methods.

The foregoing procedure can be repeated using 4-isoquinolinecarboxylic acid or its acid chloride or anhydride or activated ester in place of 3-quinolinecarboxylic acid or its acid chloride or anhydride or activated ester to convert drugs such as those mentioned with Methods A, B, C, D, E, F or G to the corresponding derivatives.

The general procedures described above may be utilized to provide the 1,2-dihydro derivatives as well as the depicted 1,4-dihydros.

| Starting Material | [D—QC]+ | [D—DHC] |
| --- | --- | --- |
| 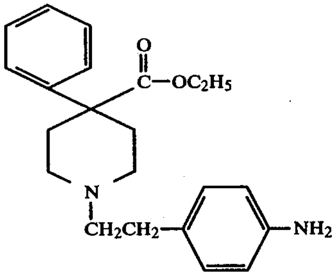 anileridine | 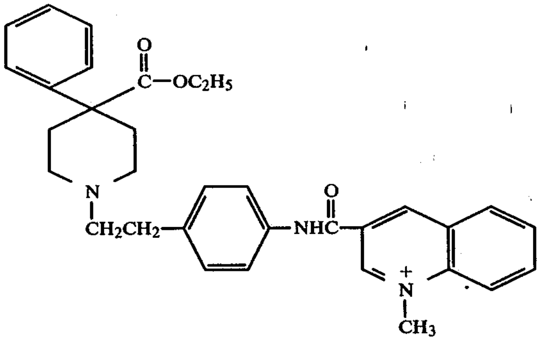 | 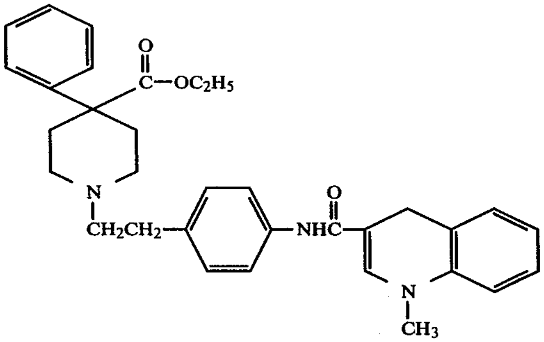 |
| 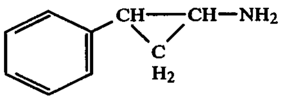 tranylcypromine | 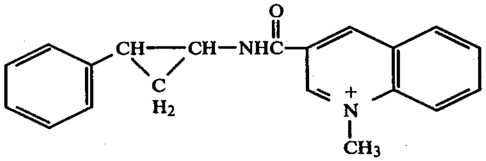 | 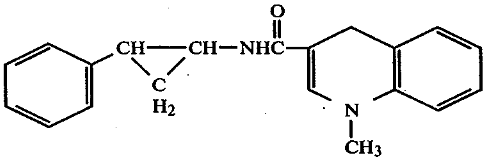 |
| 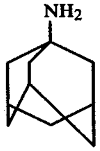 amantadine | 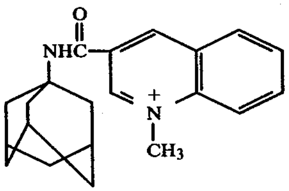 | 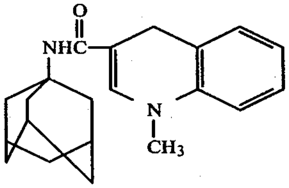 |
| 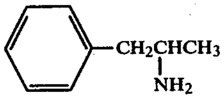 amphetamine | 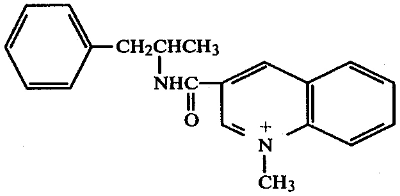 | 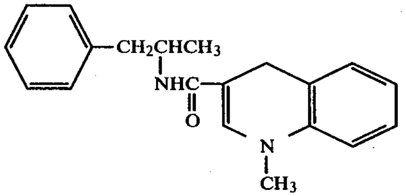 |

-continued
| Starting Material | [D—QC]+ | [D—DHC] |
|---|---|---|
| 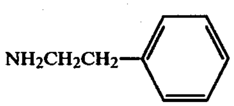 phenylethylamine | 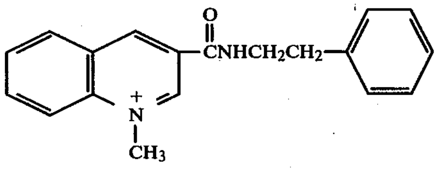 | 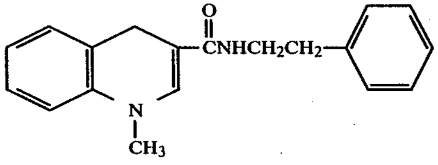 |
| 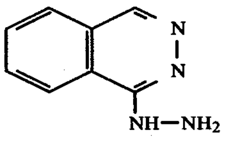 hydralazine | 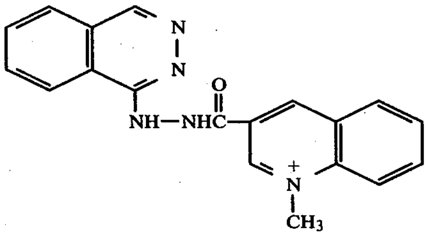 | 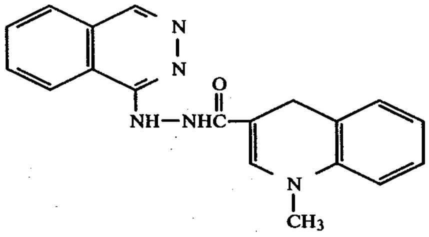 |
| 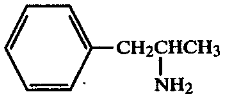 d-isomer dextroamphetamine | 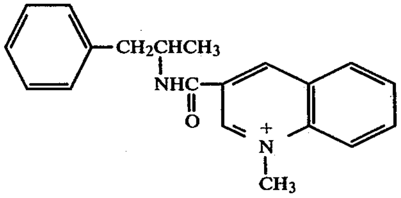 d-isomer | 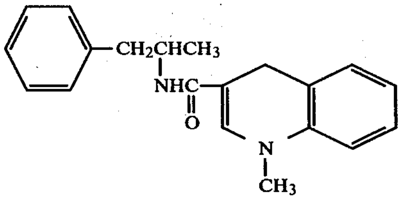 d-isomer |

-continued
| Starting Material | [D—QC]+· | [D—DHC] |
|---|---|---|
| 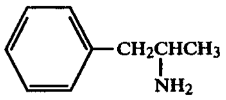 l-isomer levamphetamine | 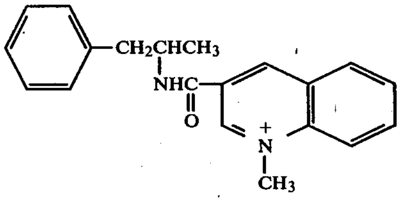 l-isomer | 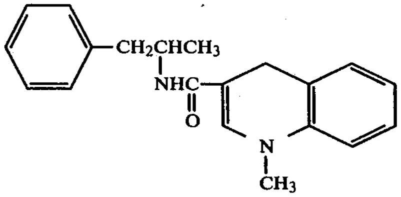 l-isomer |
| 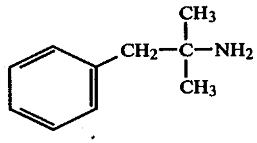 phentermine | 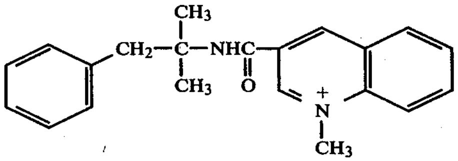 | 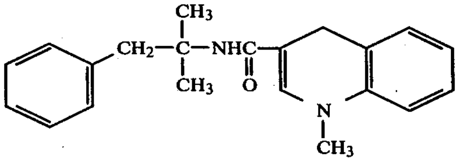 |
| 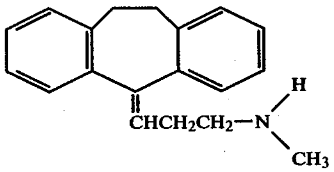 nortriptyline | 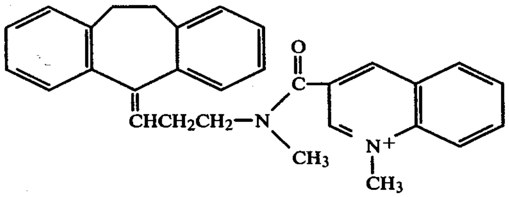 | 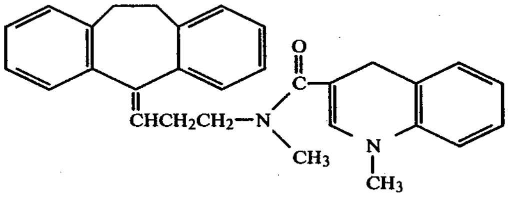 |
| 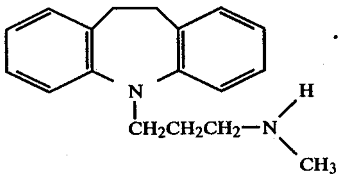 desipramine | 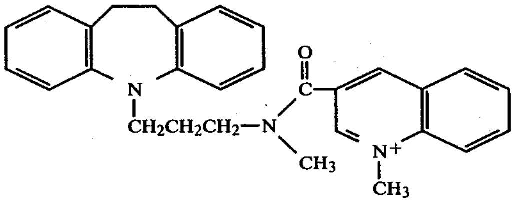 | 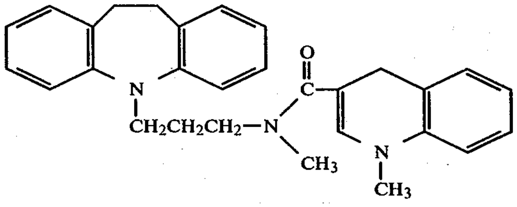 |

-continued
| Starting Material | [D—QC]+ | [D—DHC] |
|---|---|---|
| 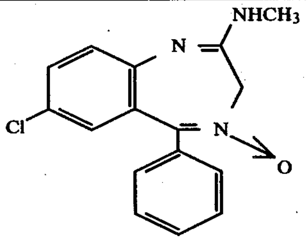 chlordiazepoxide | 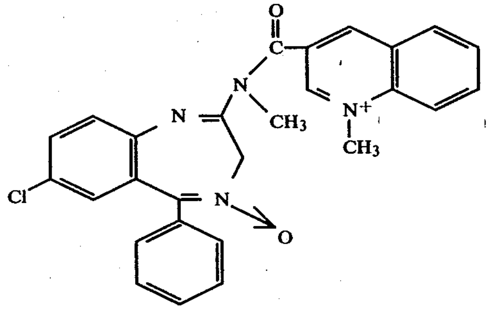 | 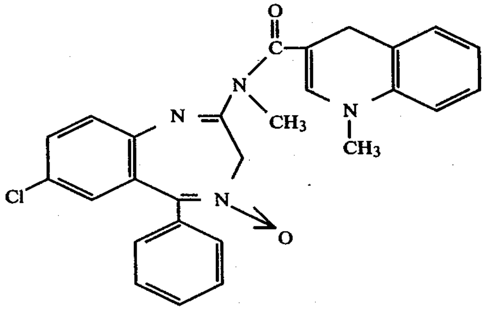 |

Method I

Method A is followed, except that in the first step, a reactant of the formula

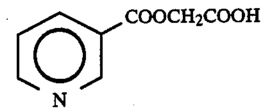

is used in place of nicotinic acid. (That starting material may be prepared by reacting nicotinic anhydride, nicotinoyl chloride or nicotinic acid with glycolic acid.)

The representative drugs depicted below may be derivatized in this manner to the corresponding compounds of formulas (II) and (I), as may the remaining drugs mentioned with Method A.

Similarly, Method I may be combined with Methods B, C, D, E, F or G to afford the corresponding derivatives, e.g. of the drugs mentioned with those methods.

The foregoing procedure can be repeated using picolinic acid or its acid chloride or anhydride, or isonicotinic acid or its acid chloride or anhydride, in place of nicotinic acid or its acid chloride or anhydride, respectively, in the preparation of the reactant depicted above. This variation affords a reactant of the formula

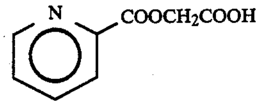

or

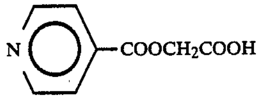

which can then be used in place of nicotinic acid to prepare derivatives of drugs such as those mentioned with Methods A, B, C, D, E, F or G.

| Starting Material | [D—QC]$^+$ | [D—DHC] |
|---|---|---|
| 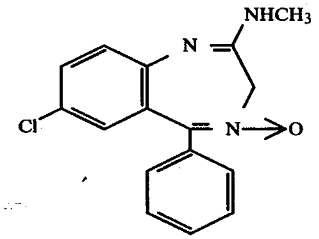 chlordiazepoxide | 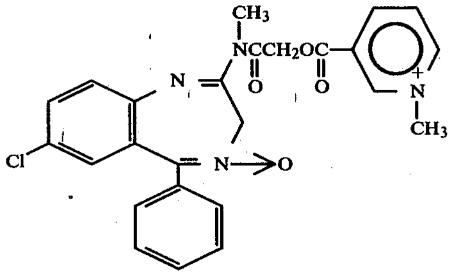 | 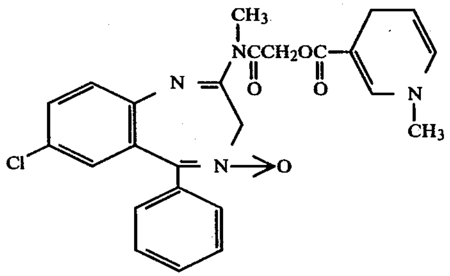 |
| 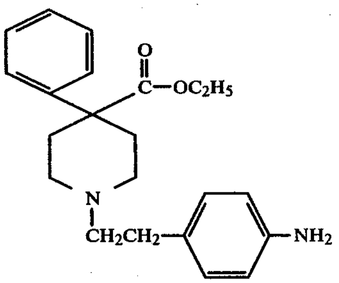 anileridine | 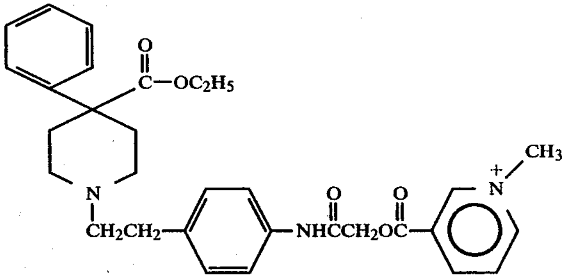 | 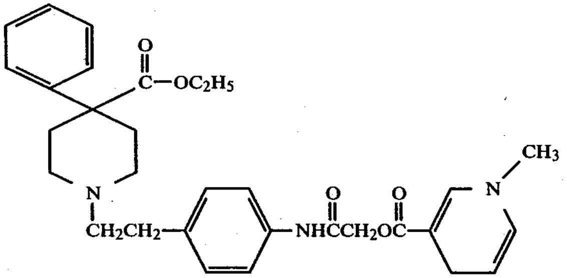 |
| 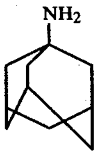 amantadine | 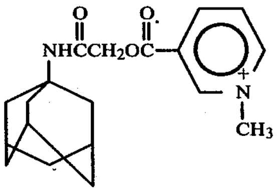 | 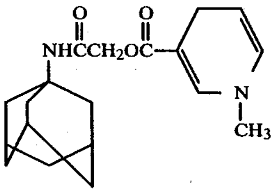 |

-continued
| Starting Material | [D—QC]+ | [D—DHC] |
| --- | --- | --- |
| 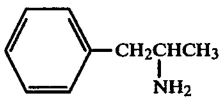 amphetamine | 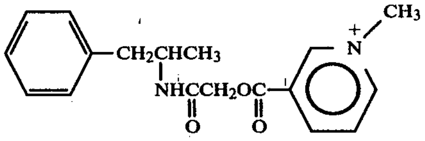 | 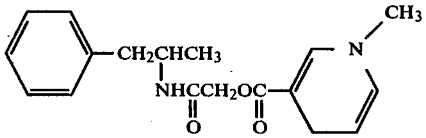 |
| 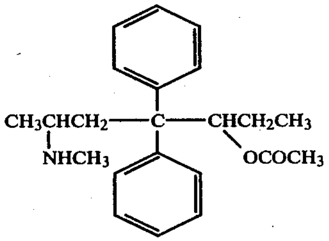 noracymethadol | 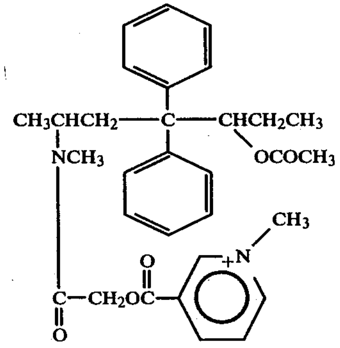 | 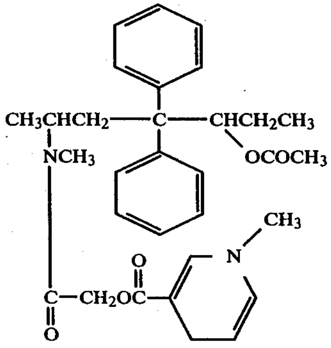 |
| 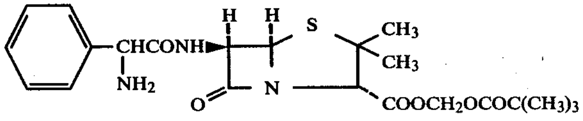 pivampicillin | | 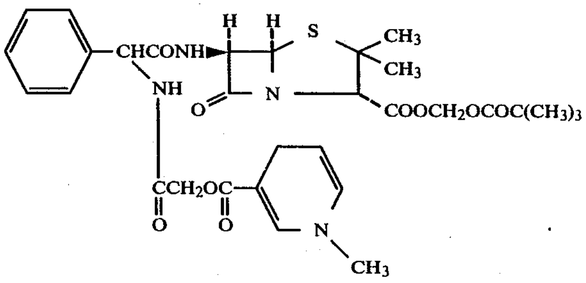 |

-continued
| Starting Material | [D—QC]$^+$ | [D—DHC] |
|---|---|---|
| | 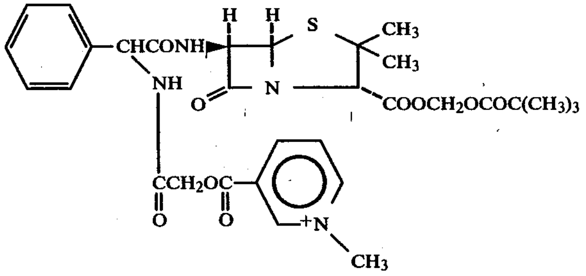 | |
| 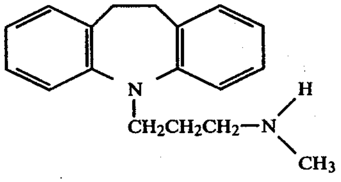 desipramine | 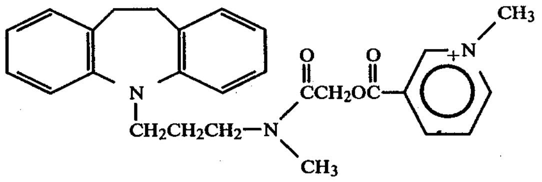 | 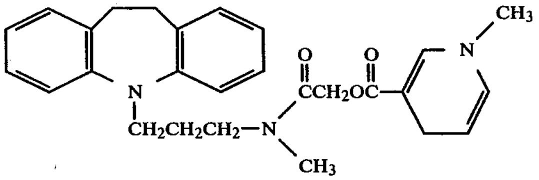 |

Method J

Method A is followed, except that in the first step, a reactant of the formula

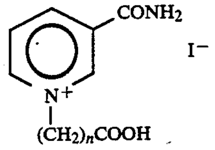

wherein n=1–3, preferably 2, is used in place of nicotinic acid. (That starting material may be prepared from nicotinamide, e.g. when n=2, by reacting 3-liodopropionic acid with nicotinamide.) The quaternary salt of formula (II) thus obtained may then be reduced as described in Method A.

The drugs depicted below may be derivatized in this manner to the corresponding compounds of formulas (II) and (I), as may the remaining drugs mentioned with Method A.

Similarly, Mehtod J may be combined with Methods B, C, D, E, F or G to afford the corresponding derivatives, e.g. of the drugs mentioned with those methods.

The foregoing procedure can be repeated using picolinamide or isonicotinamide in place of nicotinamide in the preparation of the starting material. This variation affords a reactant of the formula

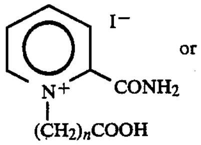

or

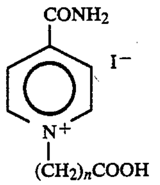

which can then be used in place of nicotinic acid in the procedure of this method, to afford the corresponding derivatives, e.g. of the drugs mentioned with Methods A, B, C, D, E, F or G.

| STARTING MATERIAL | [D—QC]+ | [D—DHC] |
| --- | --- | --- |
| 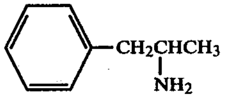<br>amphetamine | 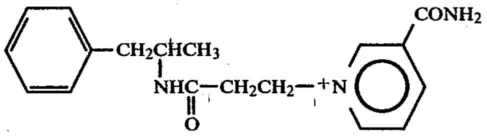 | 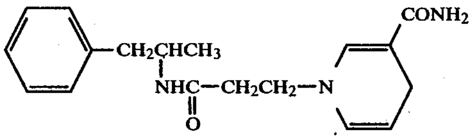 |
| 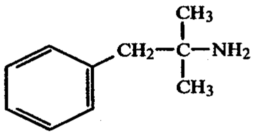<br>phentermine | 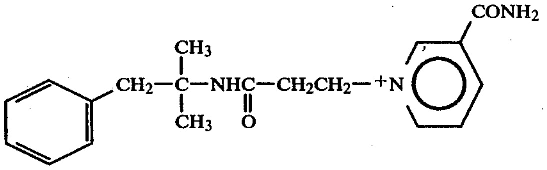 | 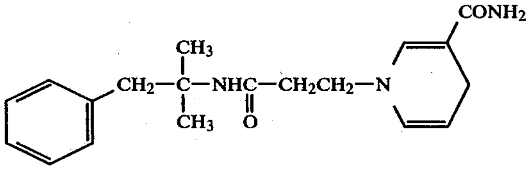 |
| 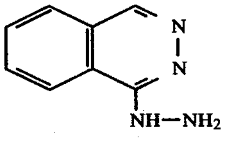<br>hydralazine | 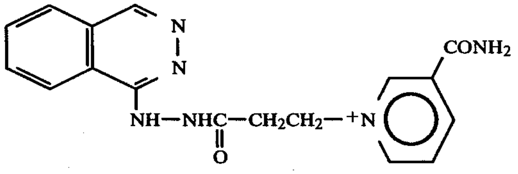 | 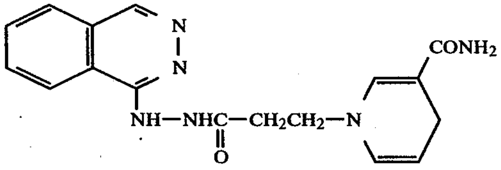 |
| 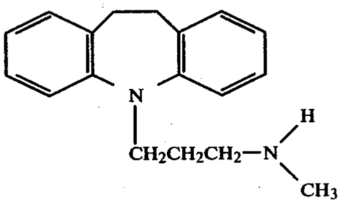<br>desipromine | 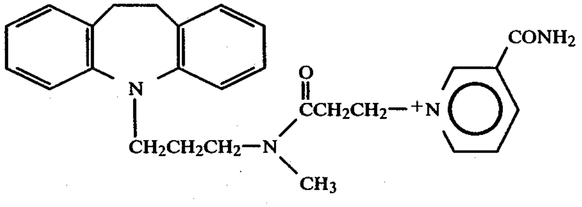 | 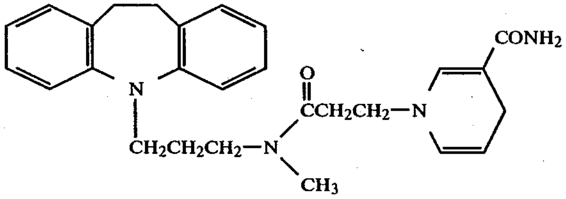 |

-continued
| STARTING MATERIAL | [D—QC]+ | [D—DHC] |
|---|---|---|
| 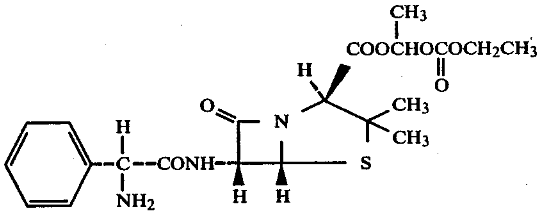 bacompicillin | 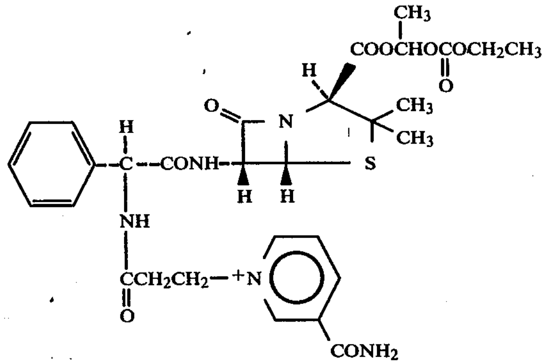 | 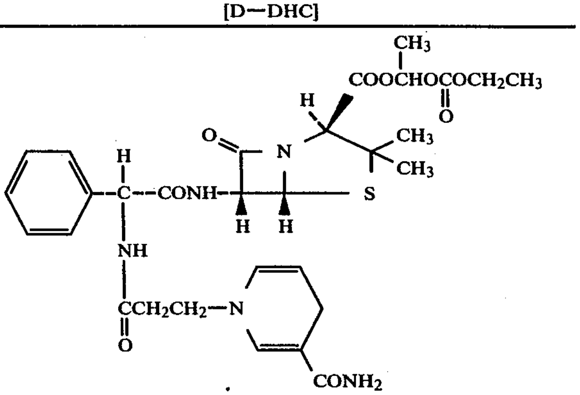 |

II.

Methods for Derivatizing —OH and —SH Functions in Drugs

Method K

The drug is reacted with nicotinoyl chloride, with nicotinic anhydride, or with nicotinic acid in the presence of a suitable coupling agent such as dicyclohexylcarbodiimide, in an appropriate organic solvent, to afford the corresponding nicotinate. The nicotinate is then quaternized and subsequently reduced as described above in Method A. When the drug contains more than one reactive hydroxyl or thiol function, reaction conditions may be varied so that more than one hydroxyl or thiol function will be converted to nicotinate groupings. The alternative process utilizing an activated ester or quaternary derivative thereof which is described in Method A may be utilized here as well.

The representative drugs depicted below may be derivatized in this manner to the corresponding compounds of formulas (II) and (I). 2-Deoxy-D-glucose, 2-deoxy-2-fluoro-D-mannose, bisdihydroxyvinyluridine (BDVU), meptazinol, cyclazocine, phenazocine, metopon, myfadol, thioguanine, naltrexone, alazocine, oxilorphan, nalmexone and estriol may be similarly derivatized.

The foregoing procedure may be repeated using picolinic acid or its acid chloride or anhydride or activated ester, or isonicotinic acid or its acid chloride or anhydride or activated ester, in place of nicotinic acid or its acid chloride or anhydride or activated ester, respectively, to convert drugs such as those specifically mentioned for derivatizing by this method to the corresponding picolinic acid esters or isonicotinic acid esters and then to the corresponding compounds of formulas (II) and (I).

| Starting Material | [D—QC]+ | [D—DHC] |
|---|---|---|
| 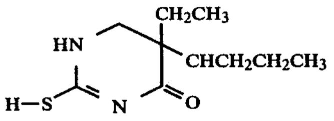 thiopental | 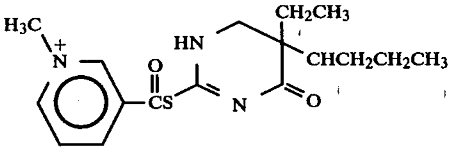 | 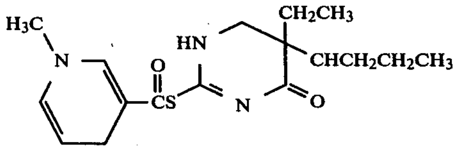 |
| 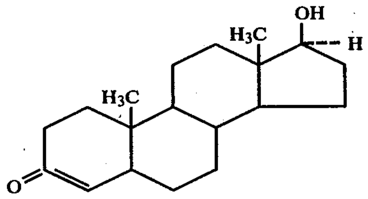 testosterone | 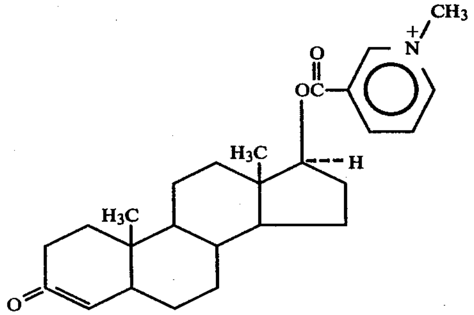 | 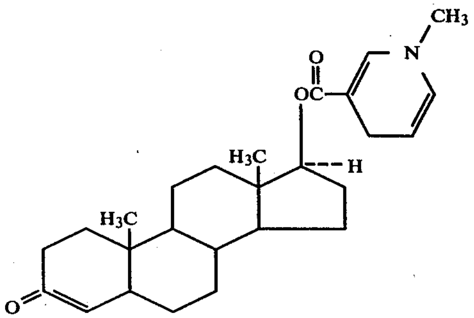 |
| 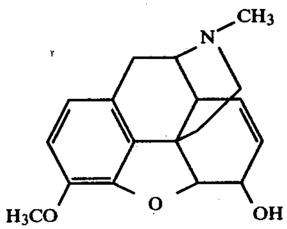 codeine | 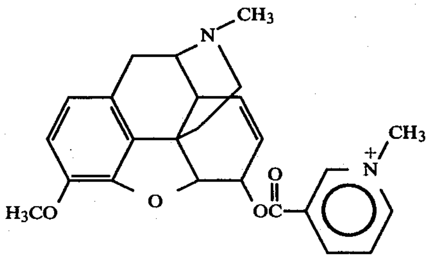 | 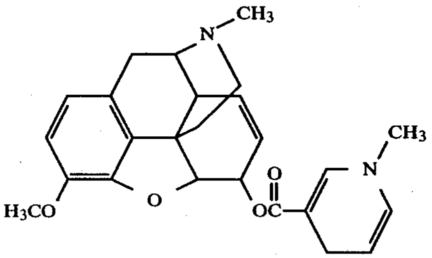 |

-continued
| Starting Material | [D—QC]+ | [D—DHC] |
| --- | --- | --- |
| 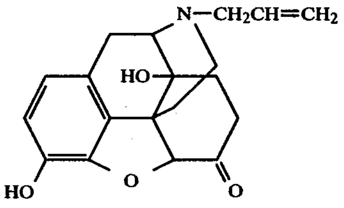 naloxone | 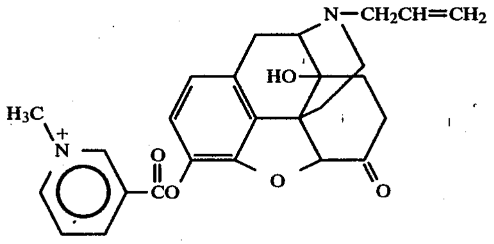 | 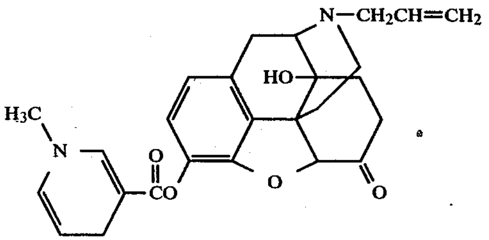 |
| 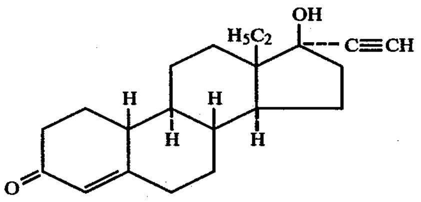 norgestrel | 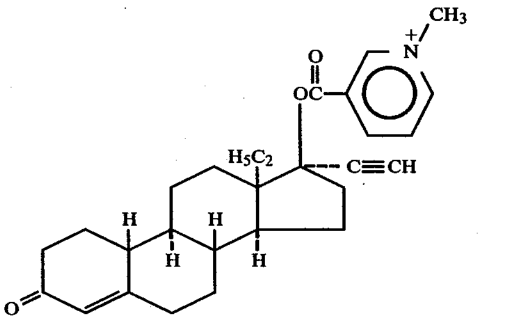 | 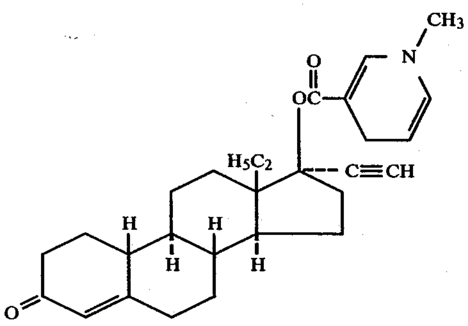 |
| 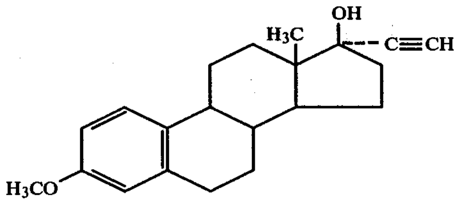 mestranol | 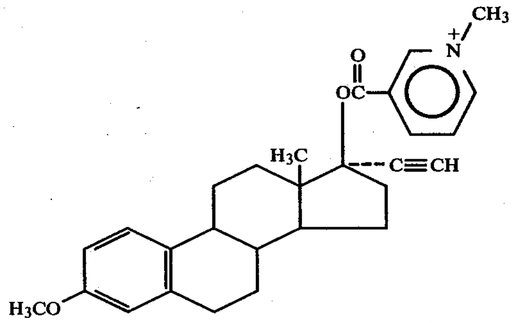 | 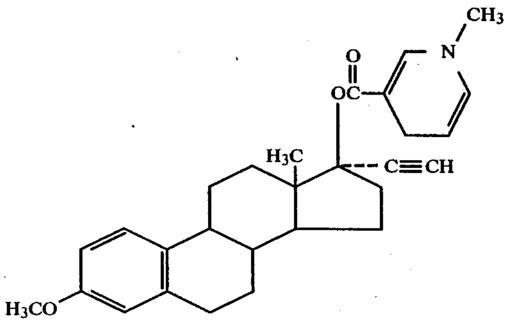 |

-continued
| Starting Material | [D—QC]+ | [D—DHC] |
|---|---|---|
| 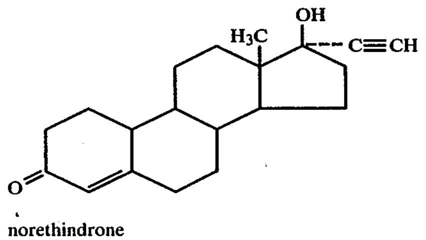 norethindrone | 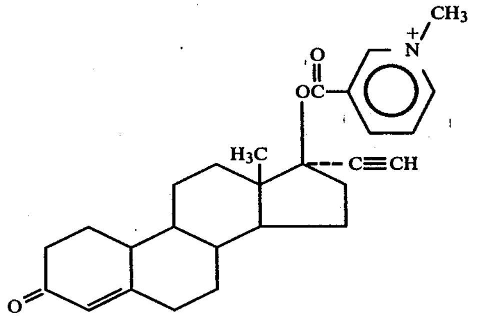 | 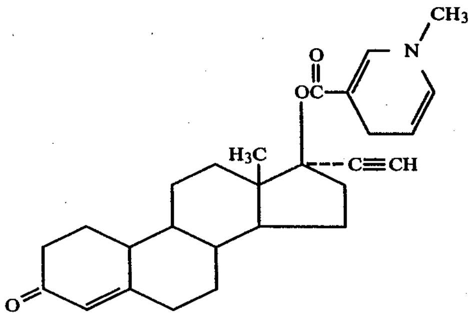 |
| 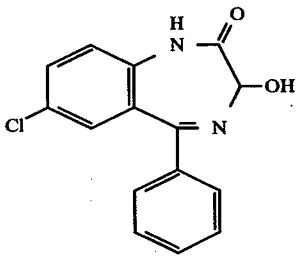 oxazepam | 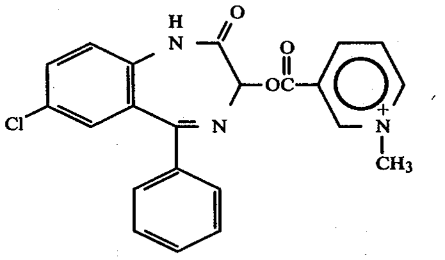 | 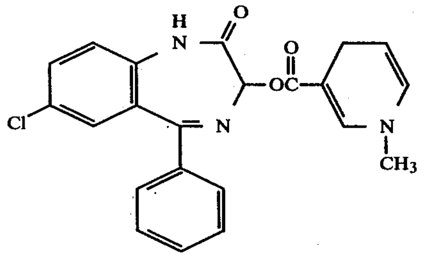 |
| 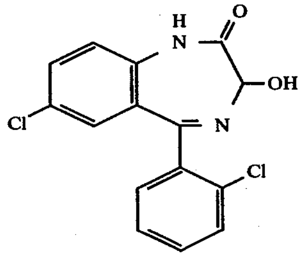 lorazepam | 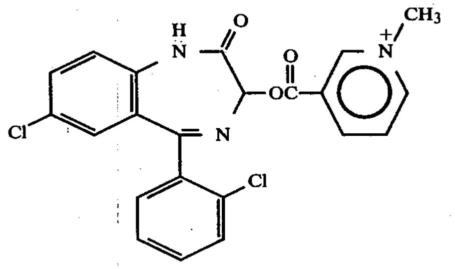 | 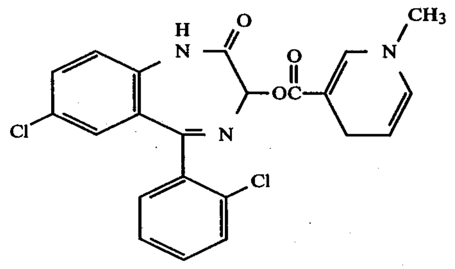 |

-continued
| Starting Material | [D—QC]+ | [D—DHC] |
| --- | --- | --- |
| 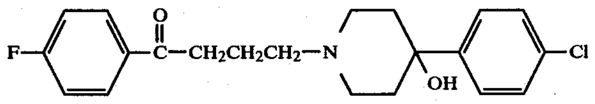 haloperidol | 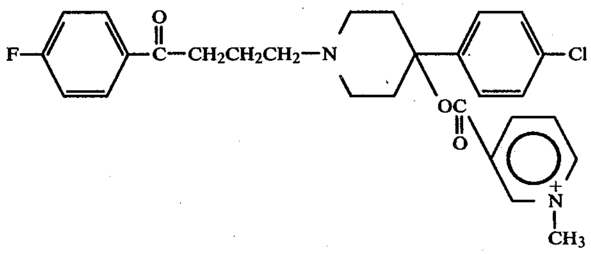 | 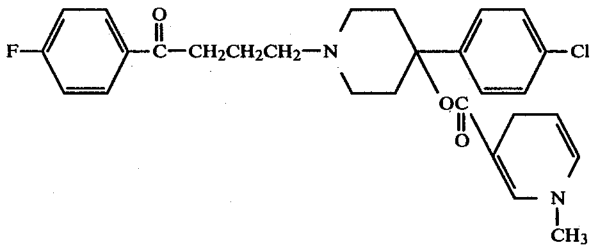 |
| 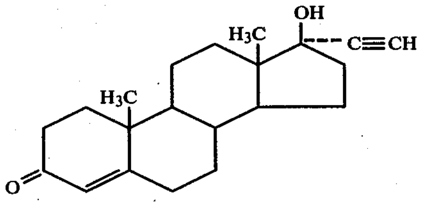 ethisterone | 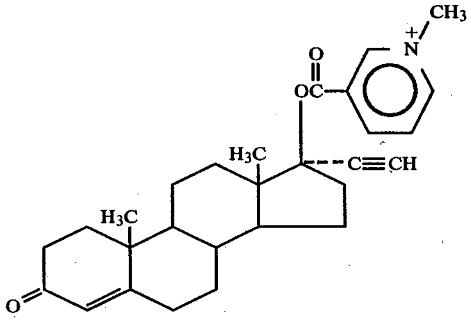 | 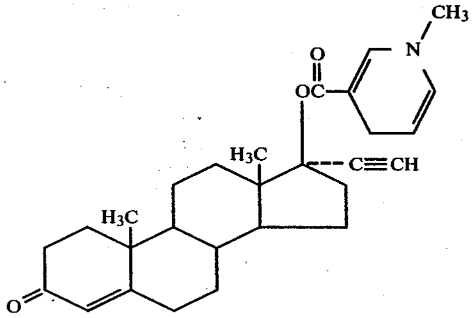 |

-continued
| Starting Material | [D—QC]+ | [D—DHC] |
|---|---|---|
| 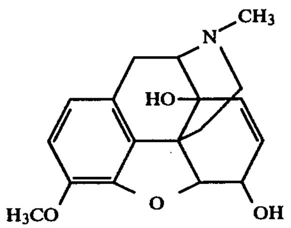 oxycodone | 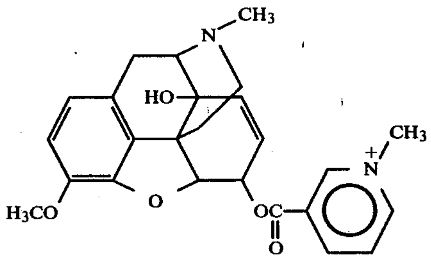 | 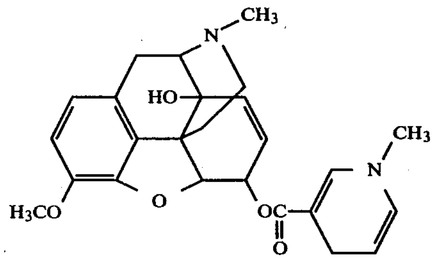 |
| 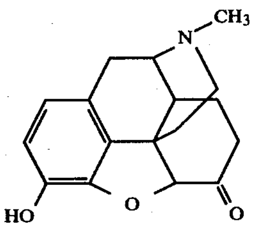 hydromorphone | 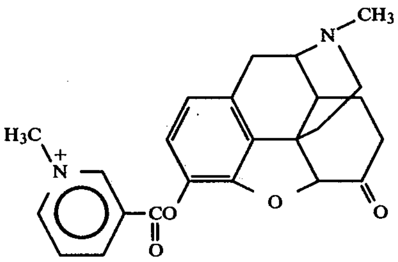 | 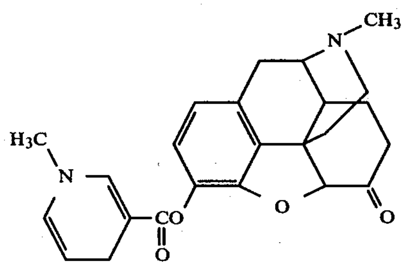 |
| 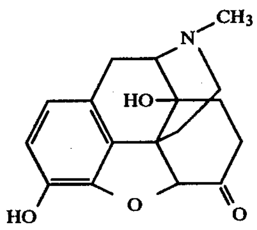 oxymorphone | 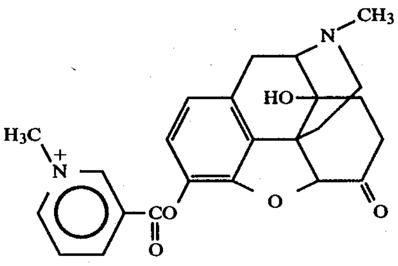 | 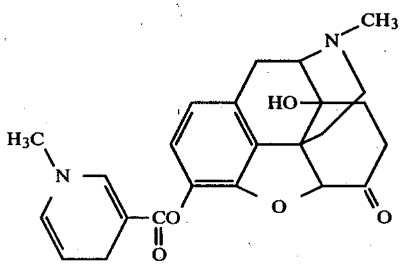 |

-continued
| Starting Material | [D—QC]+ | [D—DHC] |
|---|---|---|
| 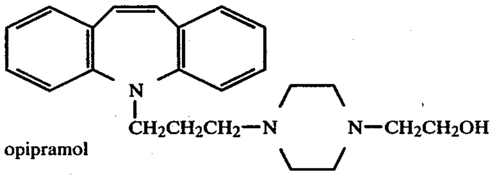 opipramol | 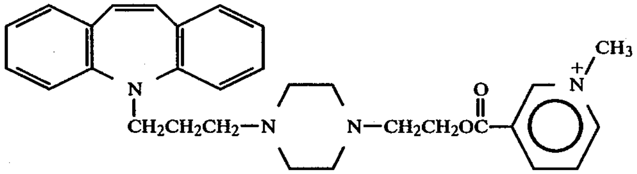 | 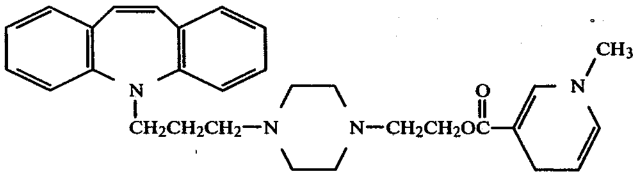 |
| 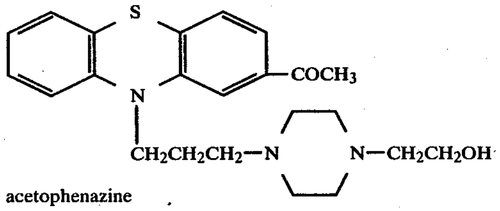 acetophenazine | 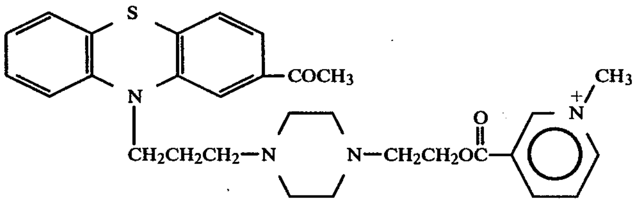 | 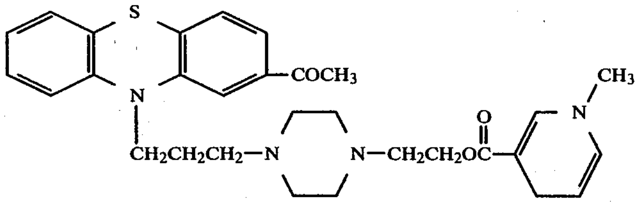 |

-continued
| Starting Material | [D—QC]+ | [D—DHC] |
| --- | --- | --- |
| 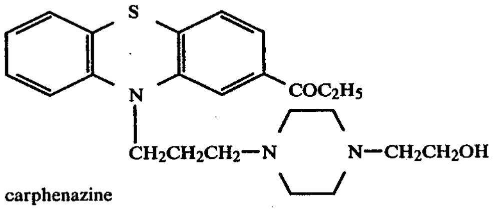 carphenazine | 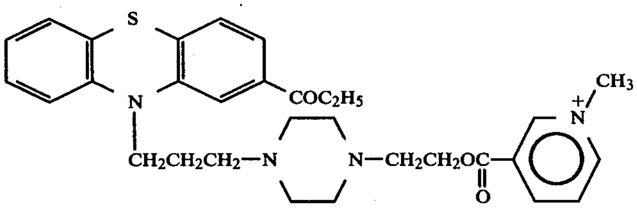 | 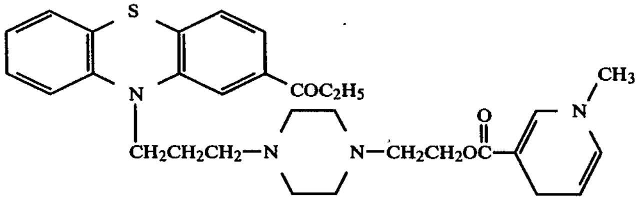 |
| 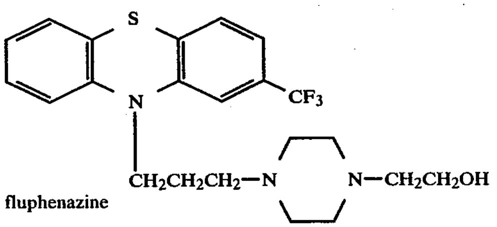 fluphenazine | 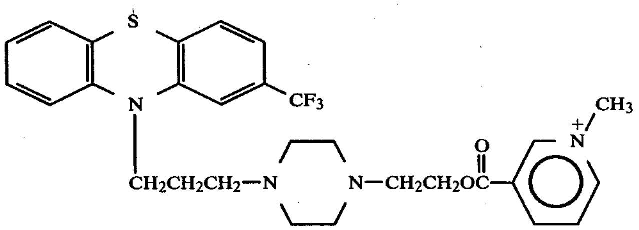 | 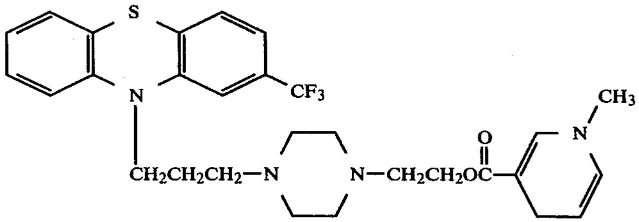 |

-continued
| Starting Material | [D—QC]+ | [D—DHC] |
| --- | --- | --- |
| 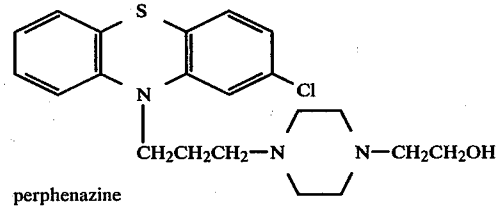 perphenazine | 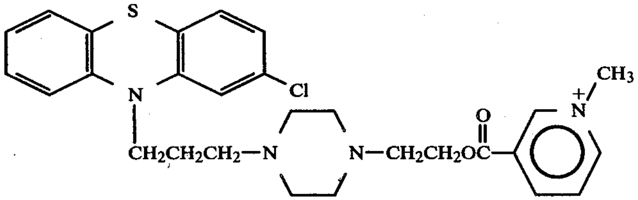 | 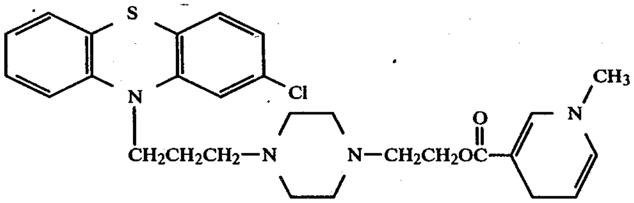 |
| 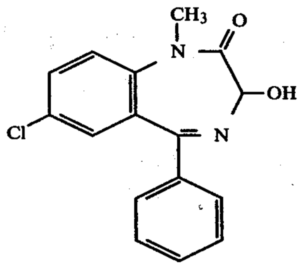 temazepam | 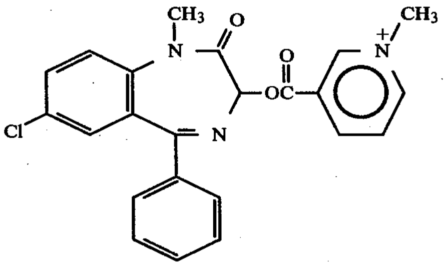 | 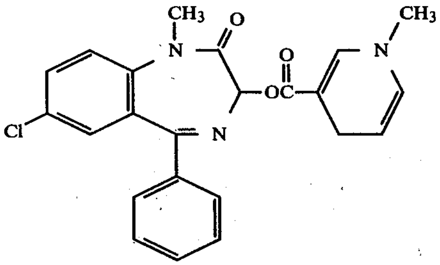 |
| 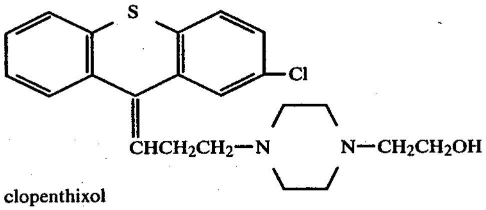 clopenthixol | 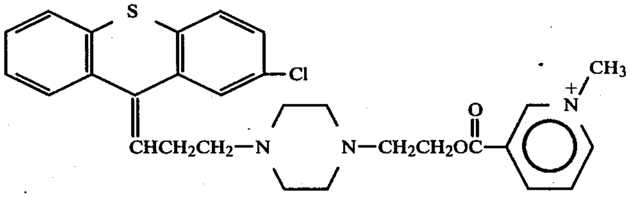 | 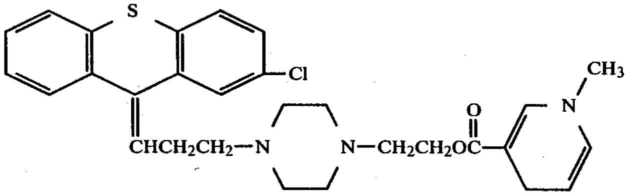 |

-continued
| Starting Material | [D—QC]+ | [D—DHC] |
|---|---|---|
| 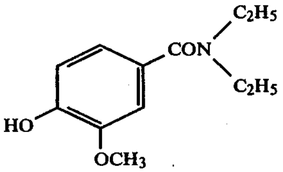 ethamivan | 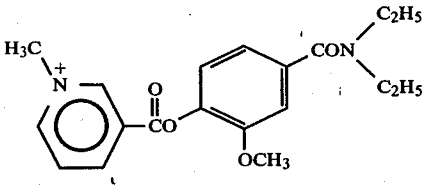 | 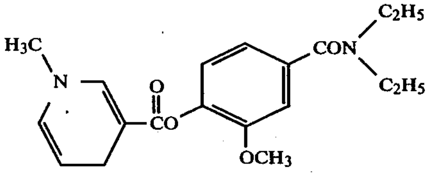 |
| 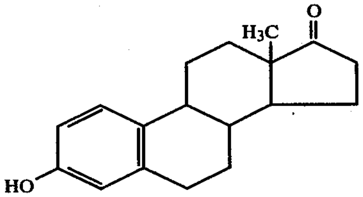 estrone | 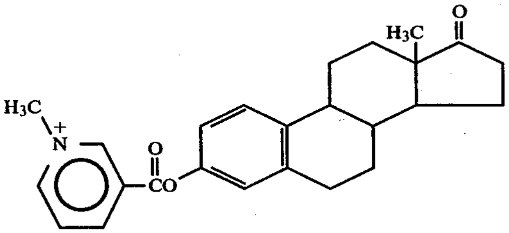 | 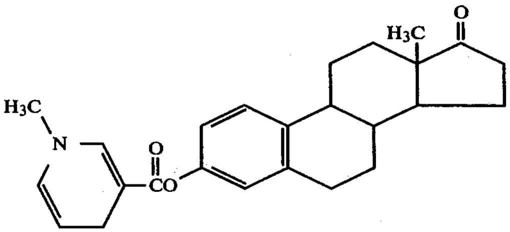 |
| 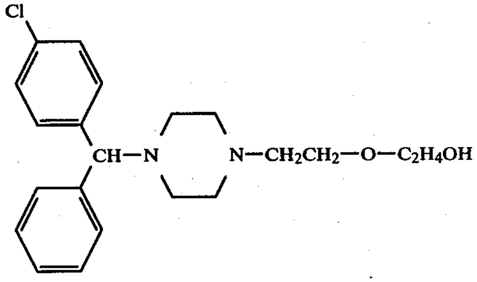 hydroxyzine | 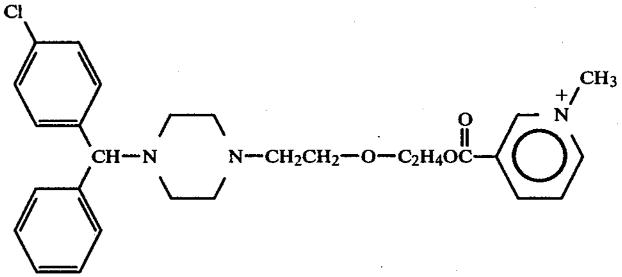 | 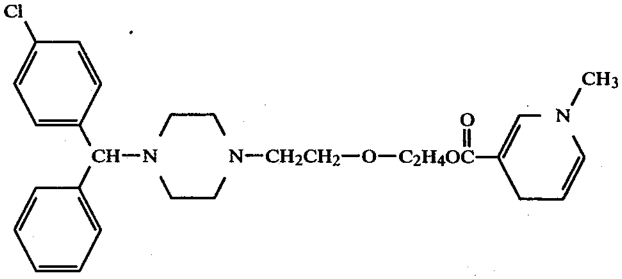 |

-continued
| Starting Material | [D—QC]+ | [D—DHC] |
| --- | --- | --- |
| 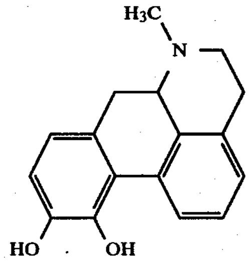 apomorphine | 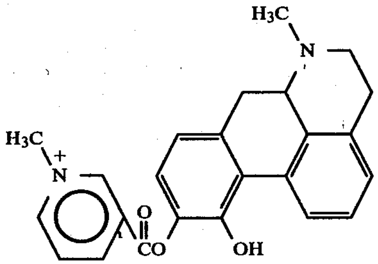 | 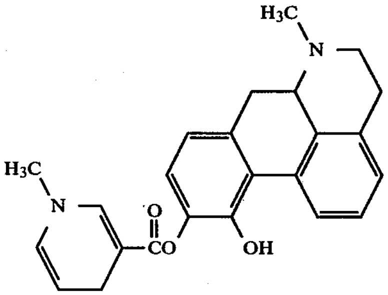 |
| 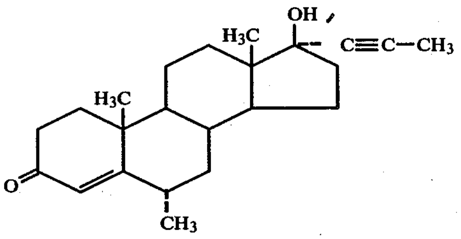 dimethisterone | 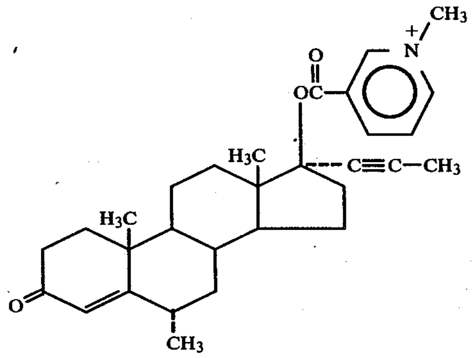 | 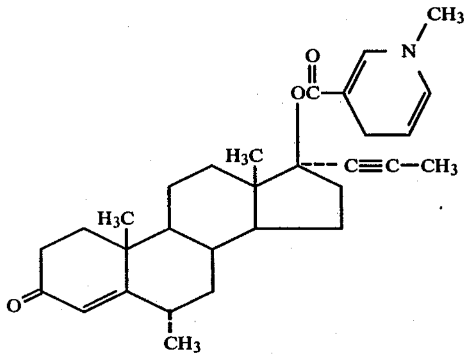 |
| 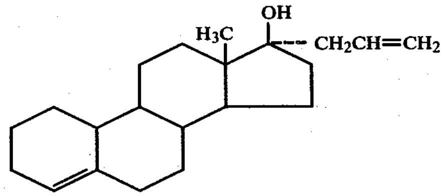 allylestrenol | 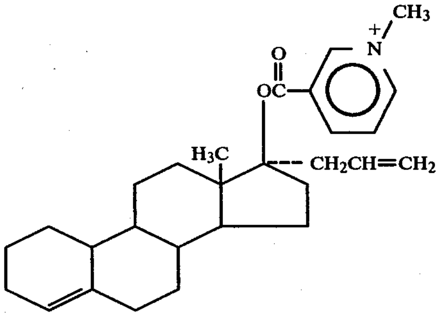 | 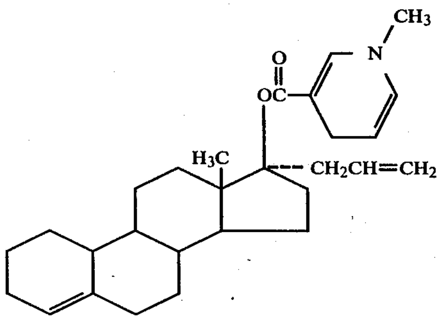 |

-continued
| Starting Material | [D—QC]+ | [D—DHC] |
| --- | --- | --- |
| 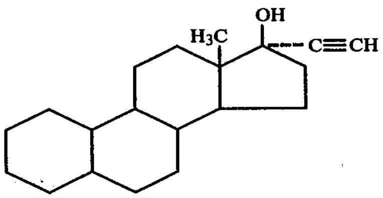 cingestol | 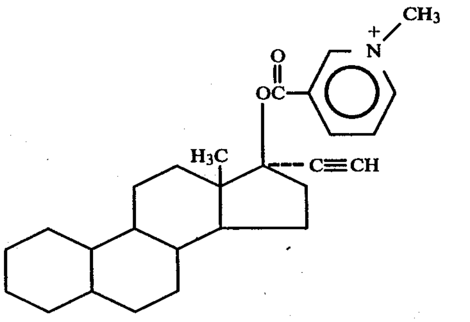 | 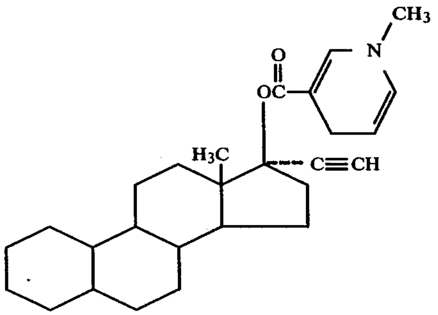 |
| 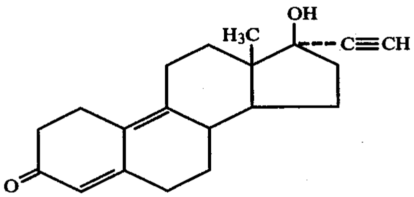 ethynerone | 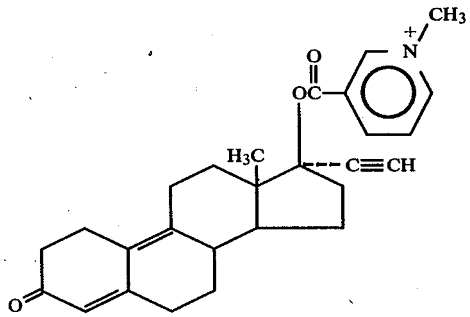 | 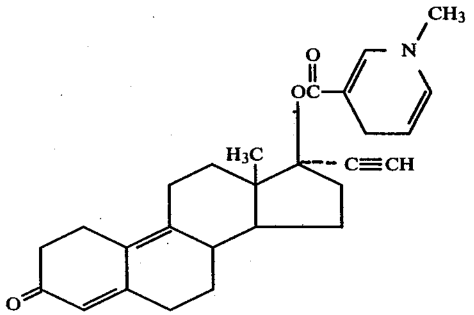 |

-continued
| Starting Material | [D—QC]+ | [D—DHC] |
| --- | --- | --- |
| 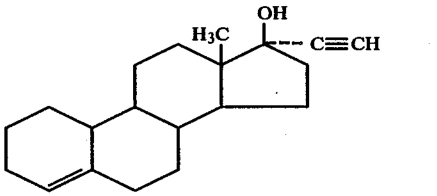 lynestrenol | 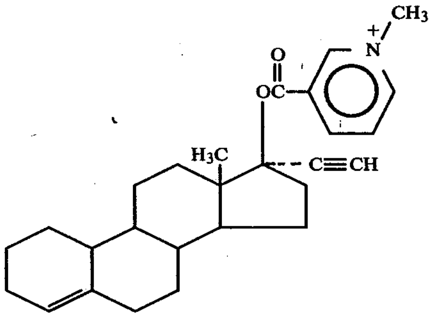 | 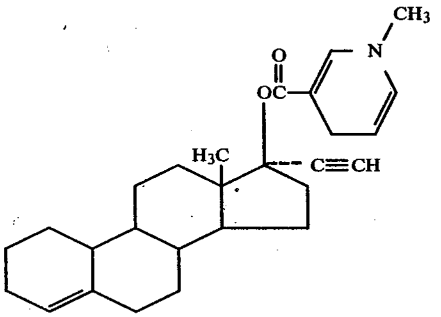 |
| 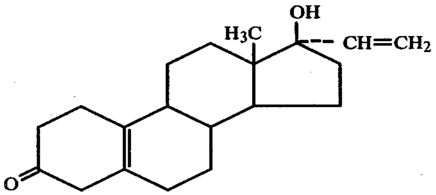 norgesterone | 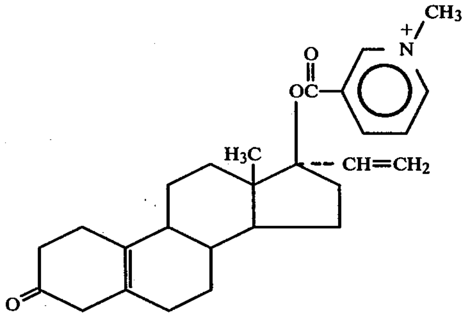 | 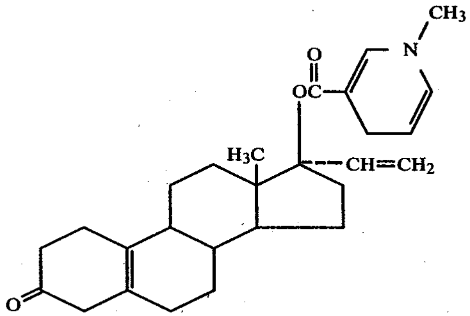 |
| 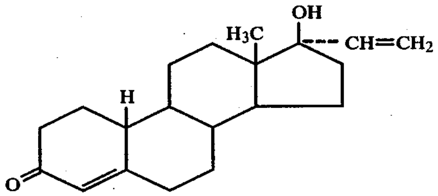 norvinisterone | 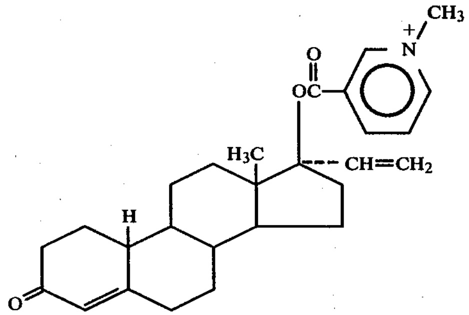 | 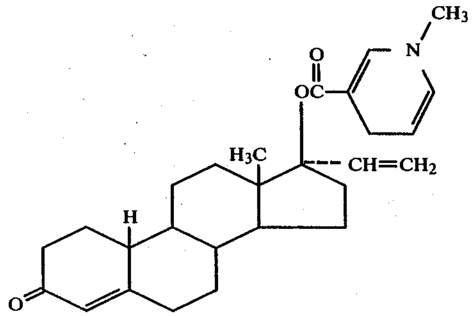 |

-continued
| Starting Material | [D—QC]$^+$ | [D—DHC] |
|---|---|---|
| 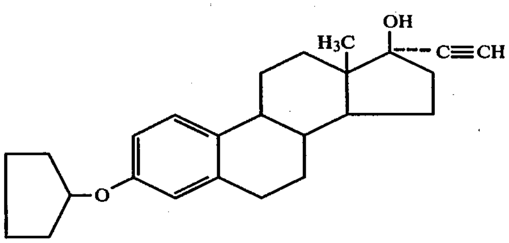 quinestrol | 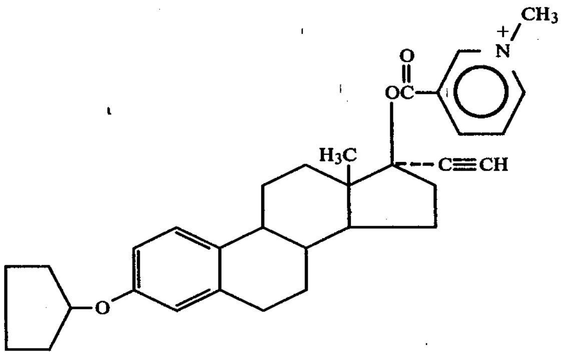 | 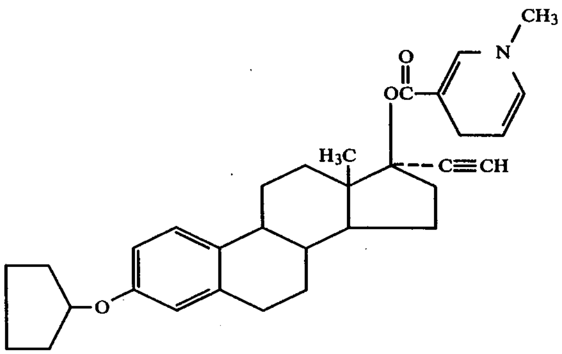 |
| 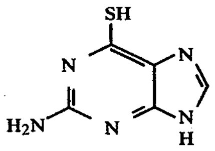 thioguanine | 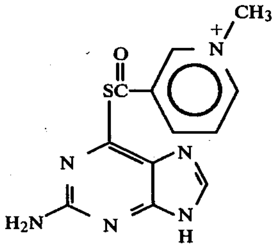 | 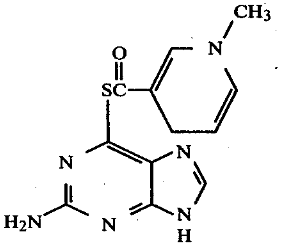 |
| 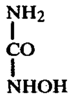 hydroxyurea | 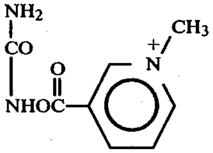 | 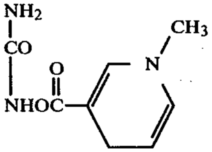 |

| Starting Material | [D—QC]+ | [D—DHC] |
|---|---|---|
| 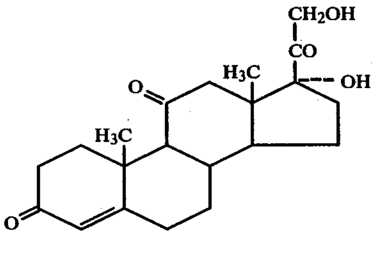 cortisone | 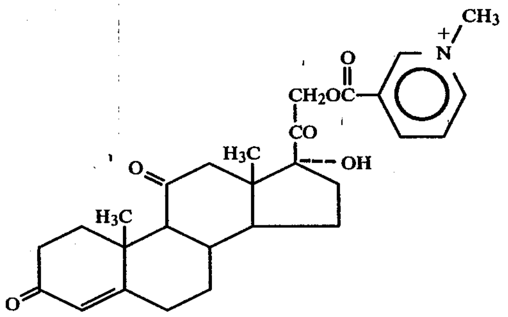 | 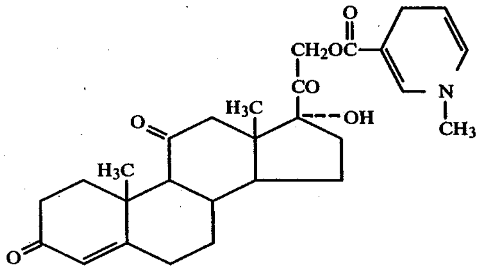 |
| 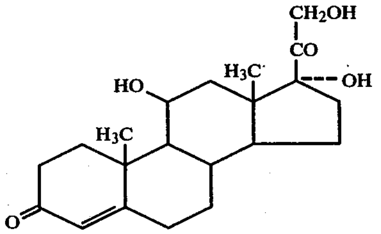 hydrocortisone | 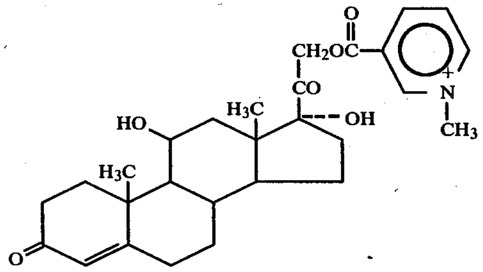 | 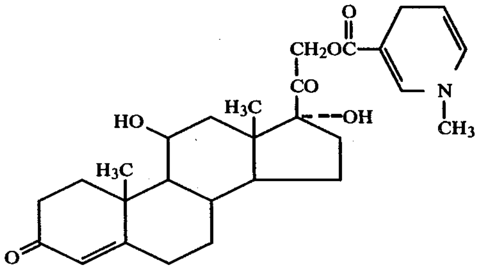 |
| 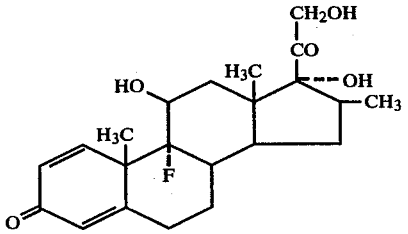 betamethasone | 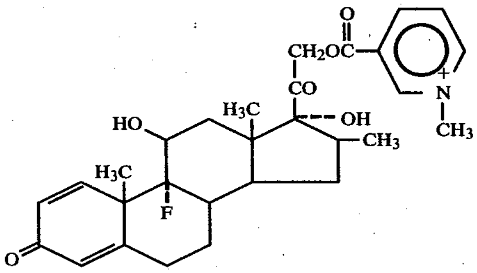 | 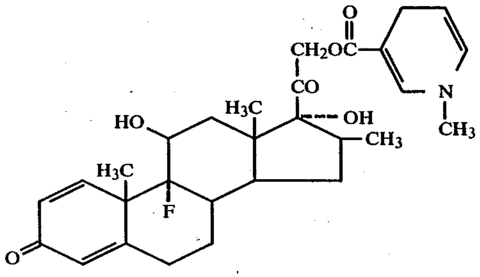 |

-continued
| Starting Material | [D—QC]+ | [D—DHC] |
| --- | --- | --- |
| 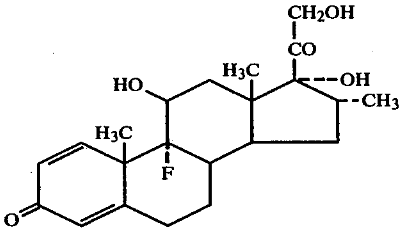 dexamethasone | 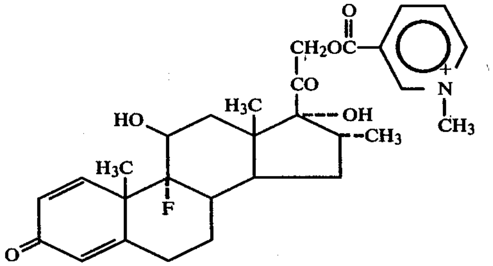 | 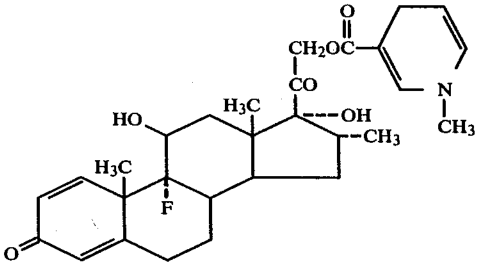 |
| 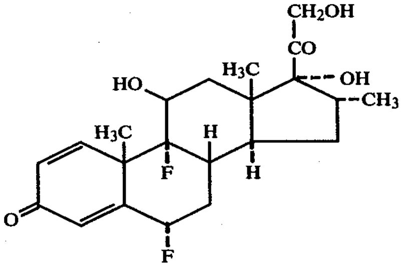 flumethasone | 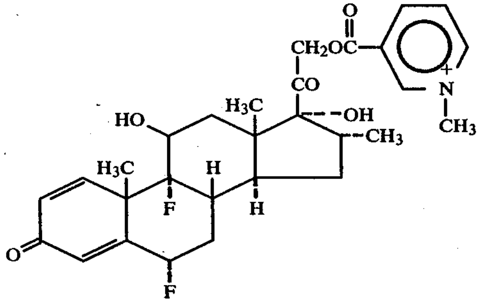 | 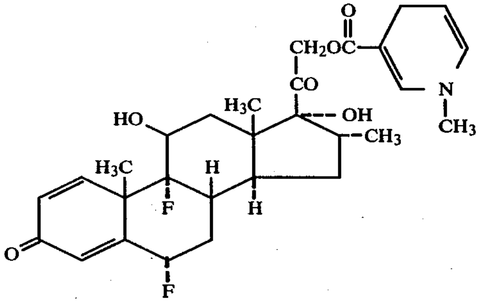 |
| 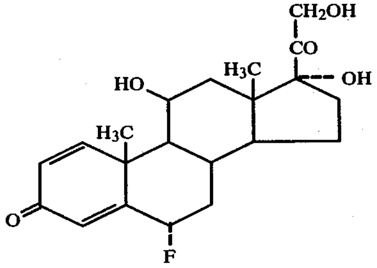 fluprednisolone | 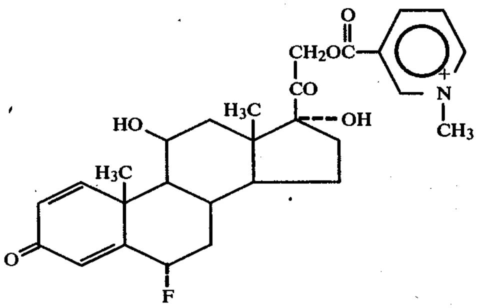 | 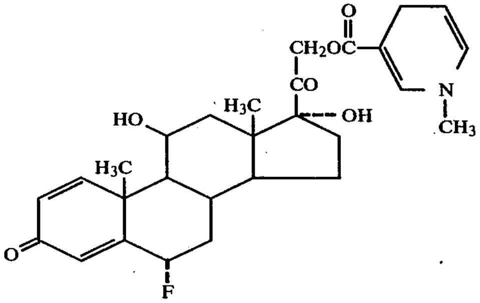 |

-continued
| Starting Material | [D—QC]+ | [D—DHC] |
| --- | --- | --- |
| 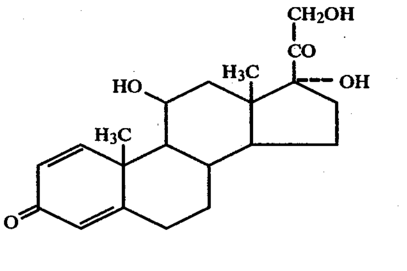 methyl prednisolone | 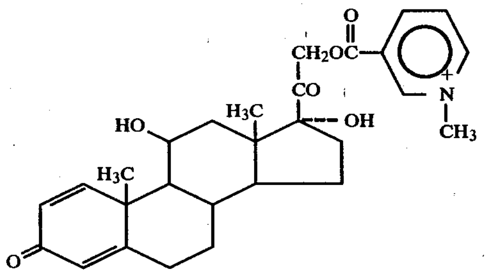 | 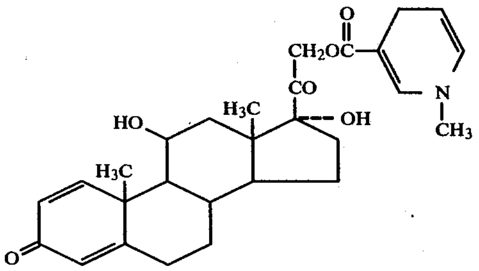 |
| 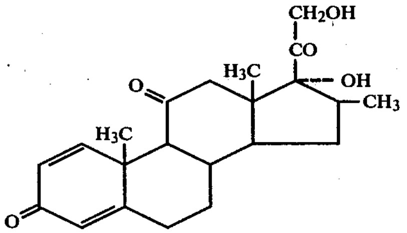 meprednisone | 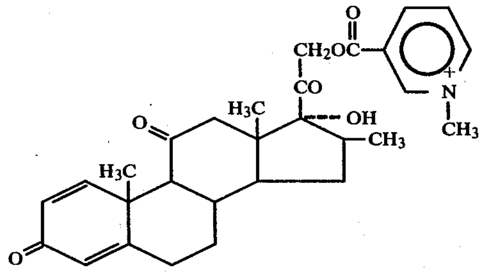 | 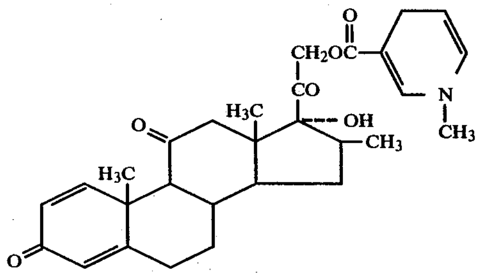 |
| 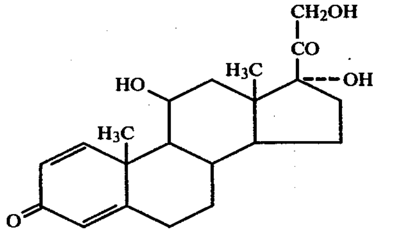 prednisolone | 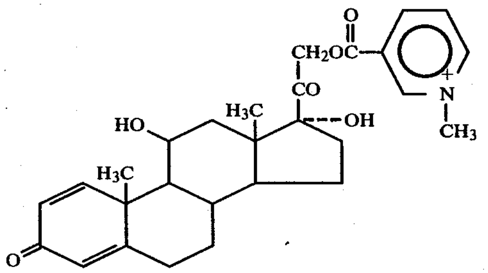 | 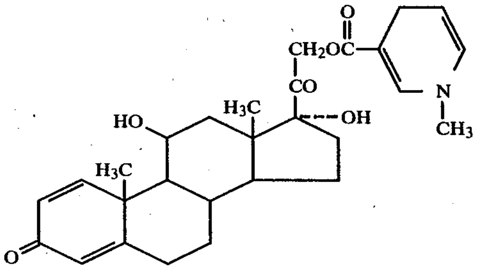 |

-continued
| Starting Material | [D—QC]+ | [D—DHC] |
| --- | --- | --- |
| 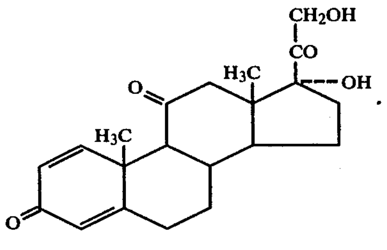 prednisone | 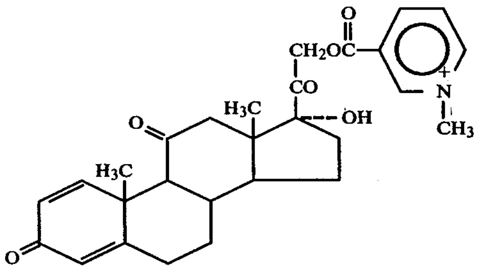 | 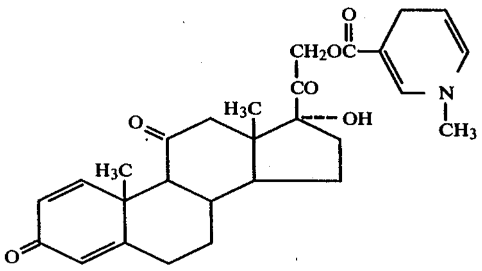 |
| 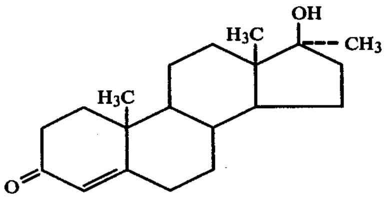 methyl testosterone | 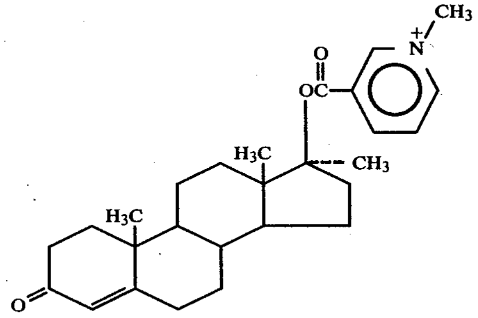 | 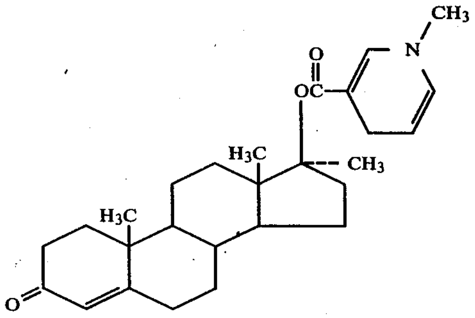 |
| 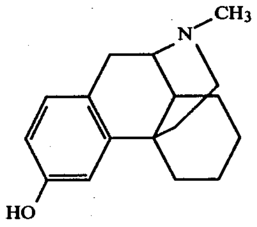 levorphanol | 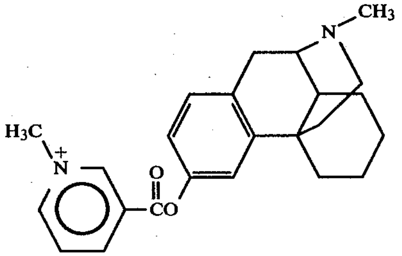 | 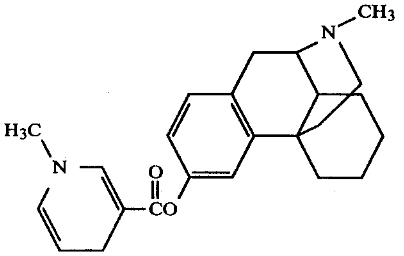 |

-continued
| Starting Material | [D—QC]+ | [D—DHC] |
|---|---|---|
| 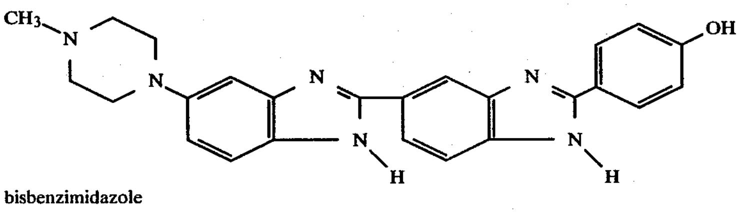<br>bisbenzimidazole | | 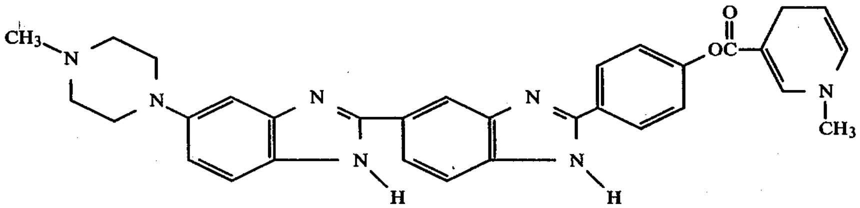 |
| | 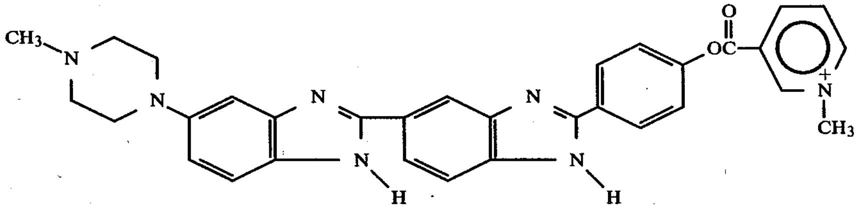 | |
| 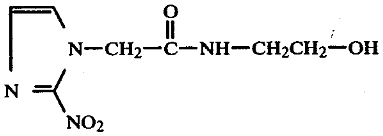<br>SR-2508 | 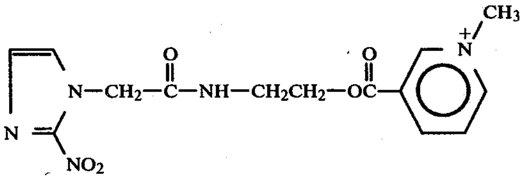 | 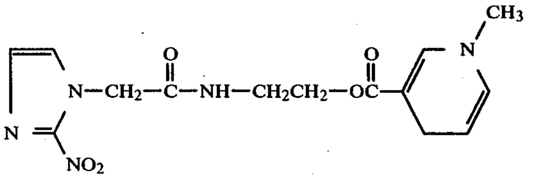 |

-continued
| Starting Material | [D—QC]+ | [D—DHC] |
|---|---|---|
| 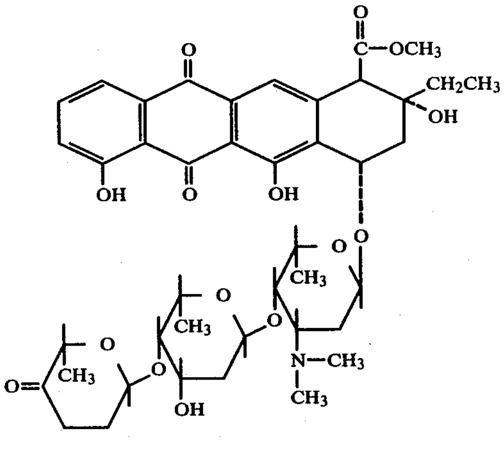 aclacinomycin A | 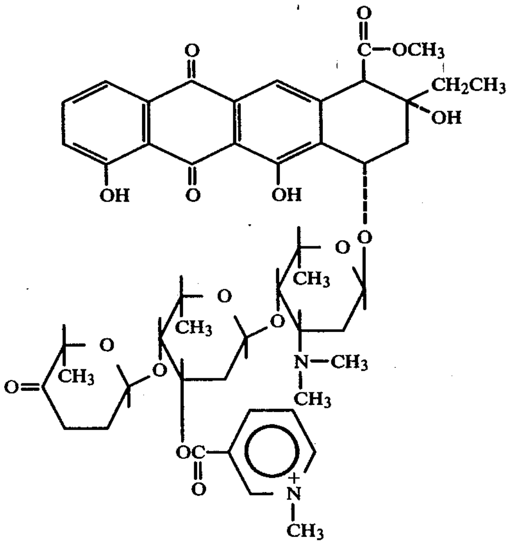 | 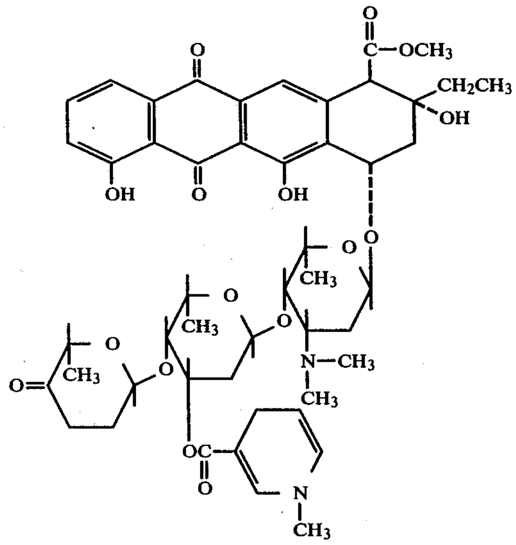 |
| 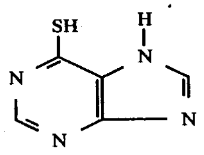 6-mercaptopurine | 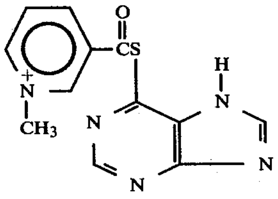 | 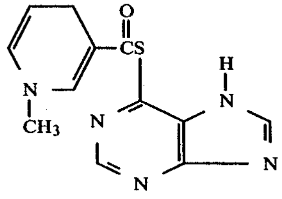 |

-continued
| Starting Material | [D—QC]+ | [D—DHC] |
| --- | --- | --- |
| 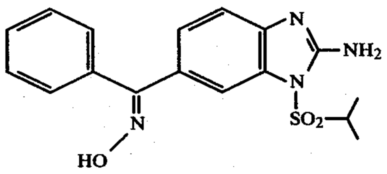 anti-6-[[(hydroxyimino)-phenyl]methyl]-1-[(1-methylethyl)sulfonyl]-1H—benzimidazol-2-amine | 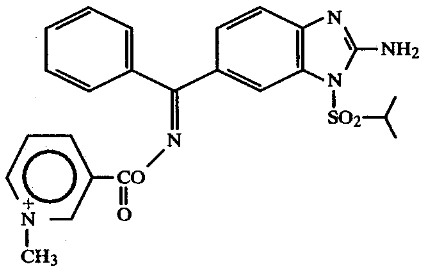 | 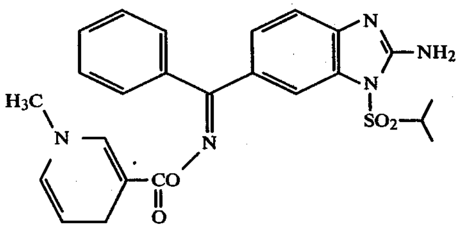 |
| 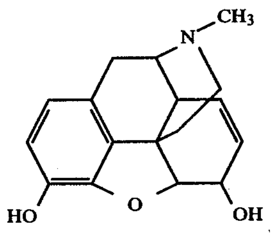 morphine | 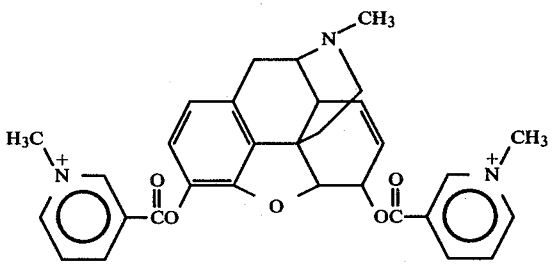 | 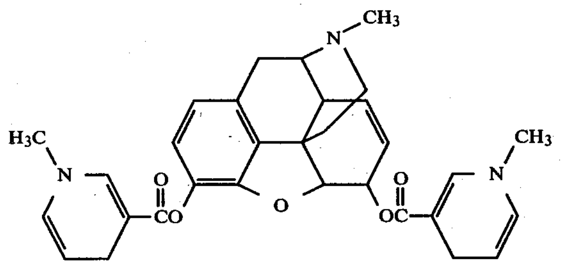 |
| 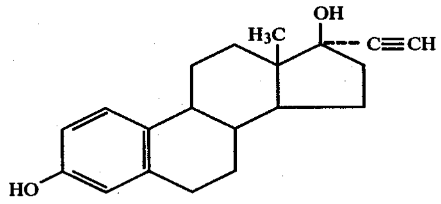 ethinyl estradiol | 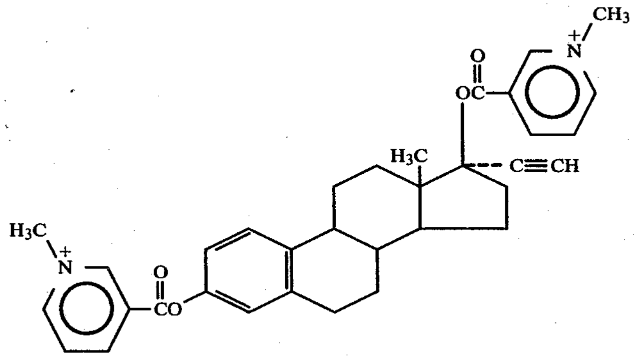 | 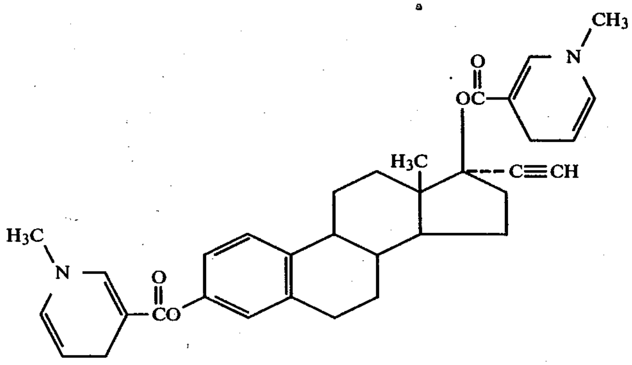 |

-continued
| Starting Material | [D—QC]+ | [D—DHC] |
|---|---|---|
| 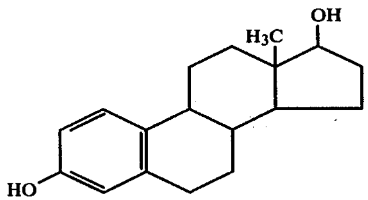 estradiol | 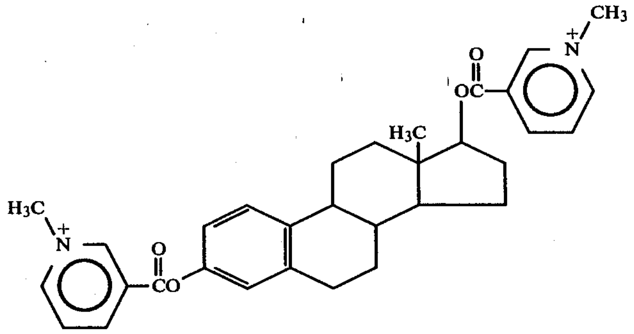 This compound can be selectively hydrolyzed by known methods to the corresponding 17-monoester, which can be reduced to give the preferred 17-monoester of formula (I). | 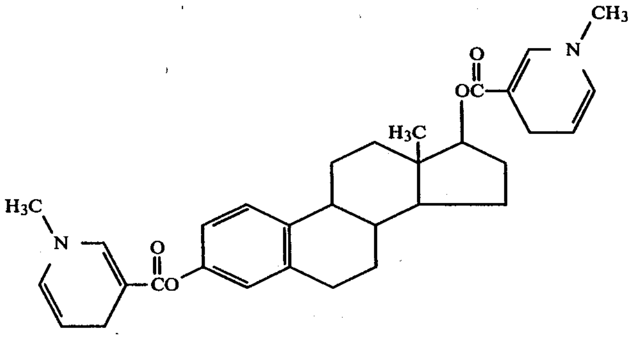 |
| 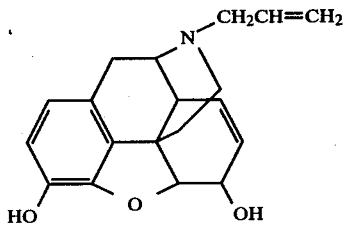 nalorphine | 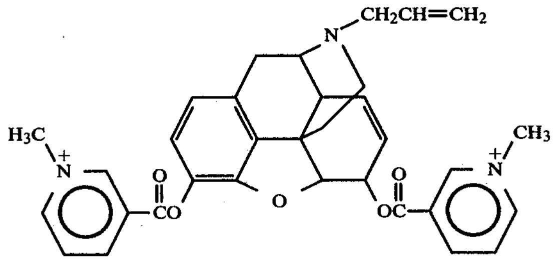 | 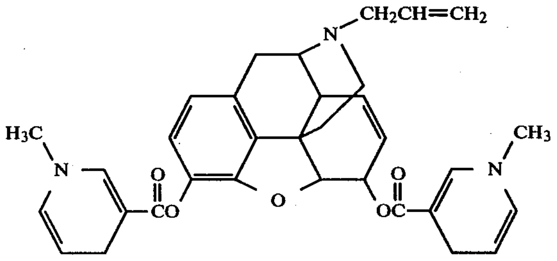 |

-continued
| Starting Material | [D—QC]+ | [D—DHC] |
|---|---|---|
| 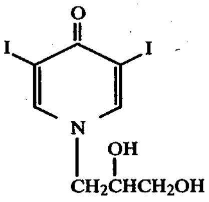 iopydol | 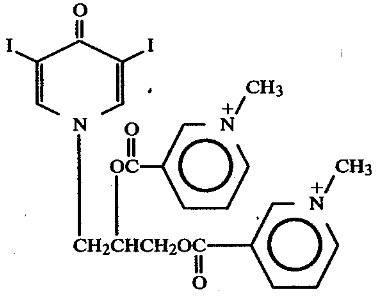 | 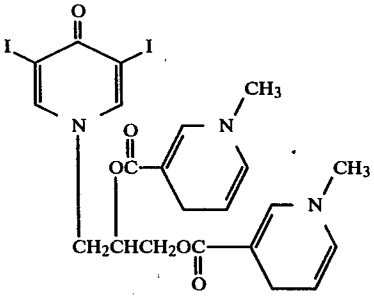 |
| 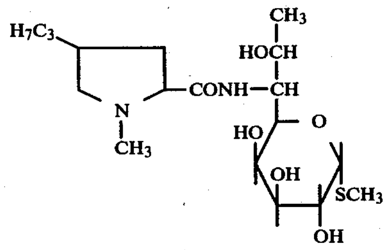 lincomycin | 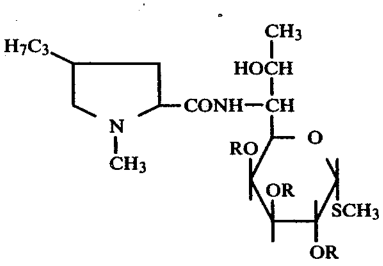 | 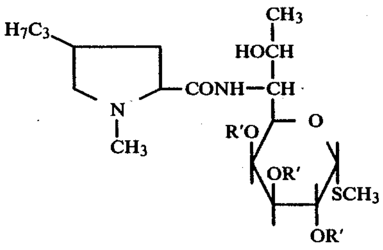 |
| | R = 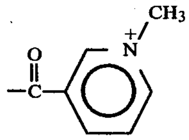 | R′ = 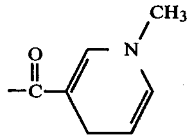 |

-continued
| Starting Material | $[D-QC]^+$ | $[D-DHC]$ |
| --- | --- | --- |
| 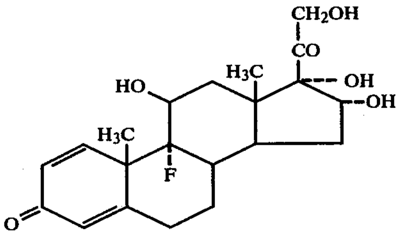 triamcinolone | 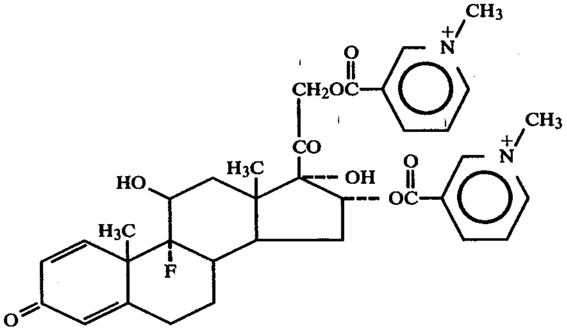 | 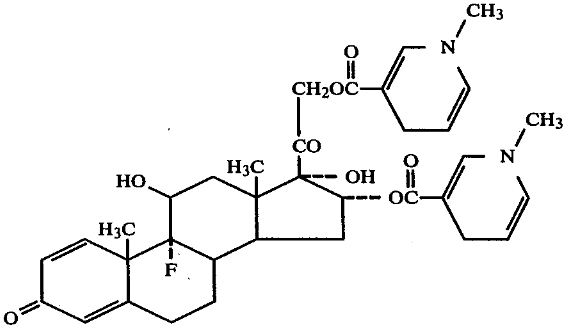 |
| 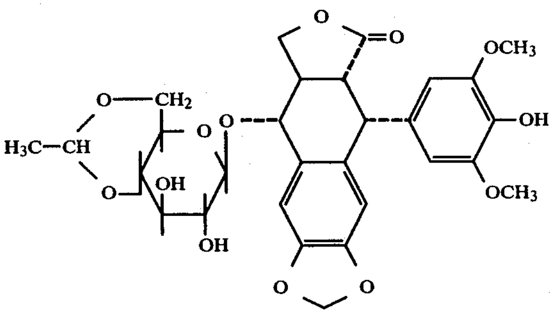 etoposide | 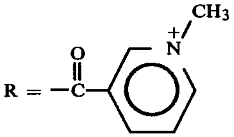 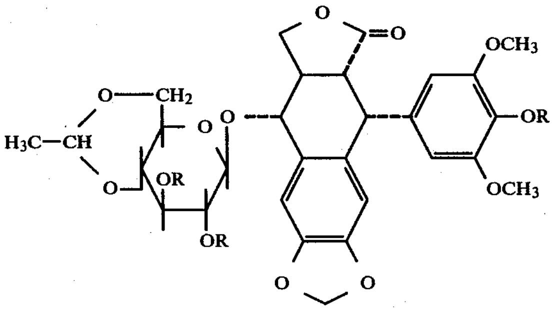 | 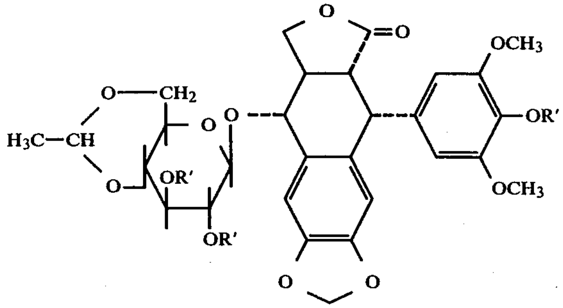 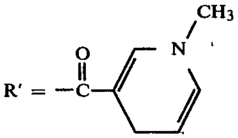 |

-continued
| Starting Material | [D—QC]+ | [D—DHC] |
|---|---|---|
| 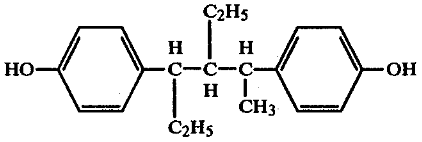 benzestrol | 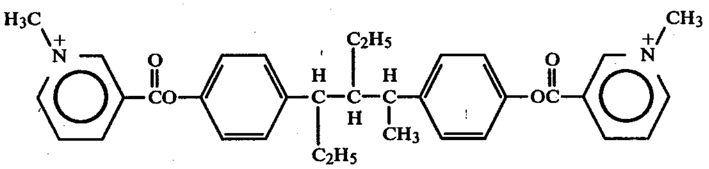 | 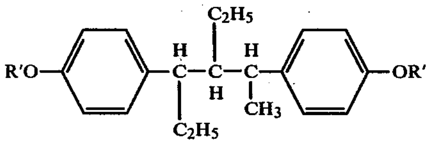 |
| 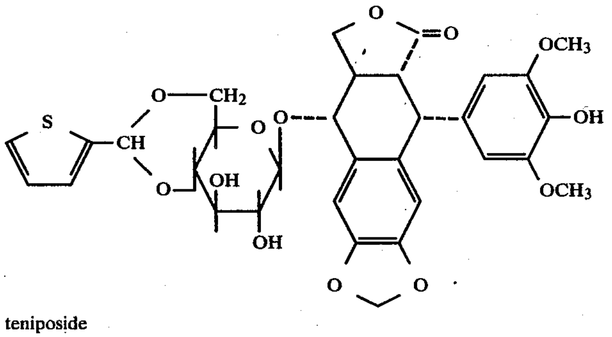 teniposide | 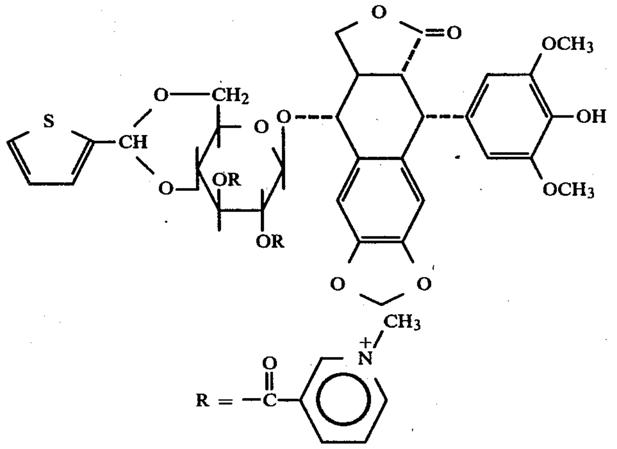 | 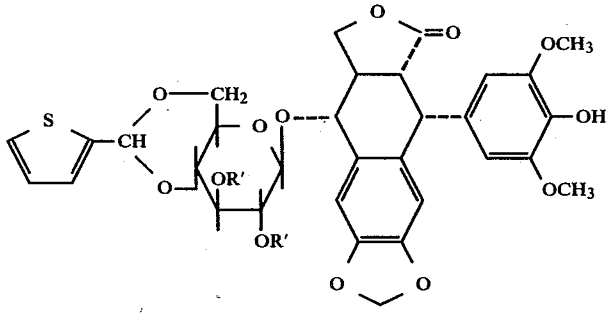 |

-continued
| Starting Material | [D—QC]+ | [D—DHC] |
|---|---|---|
| 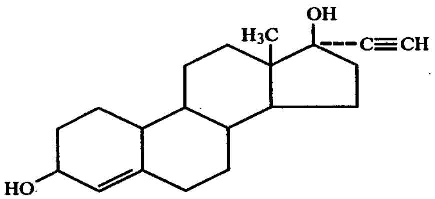 ethynodiol | 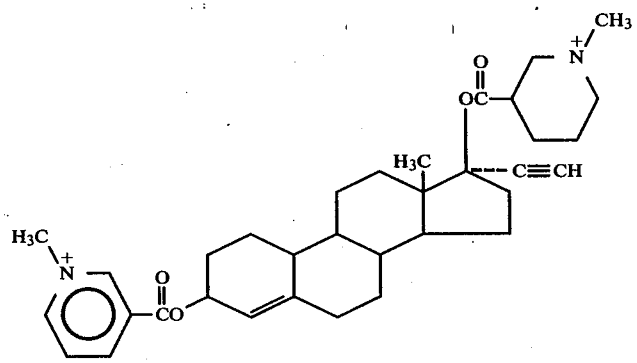 | 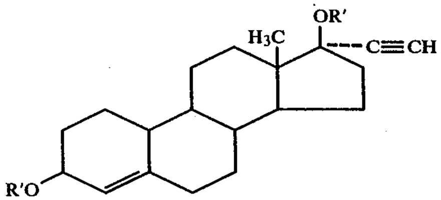 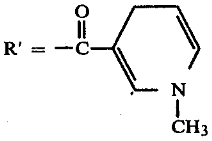 |
| 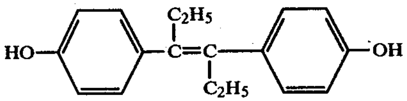 diethylstilbestrol | 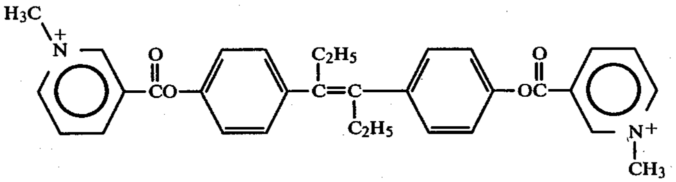 | 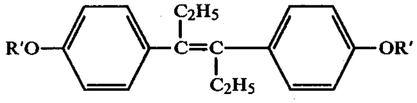 |

-continued
| Starting Material | $[D-QC]^+$ | [D—DHC] |
|---|---|---|
| 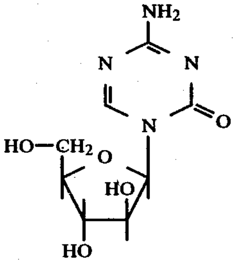 Ara-AC | 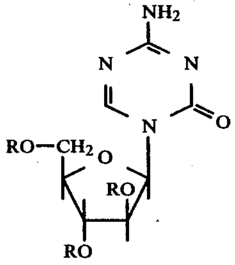 One R is 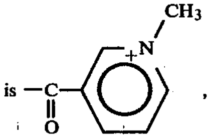 , each remaining R is H or 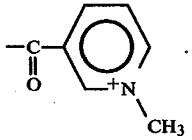 . | 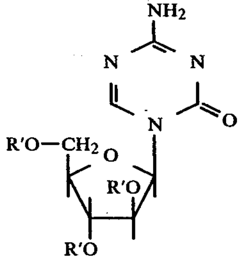 One R' is 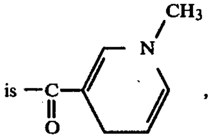 , each remaining R' is H or 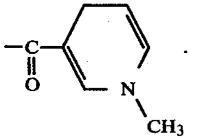 . |
| 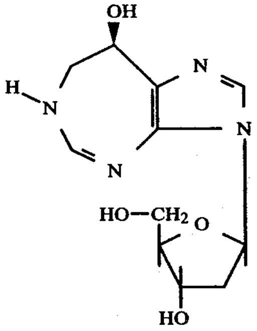 pentostatin (2'-deoxycoformycin) | 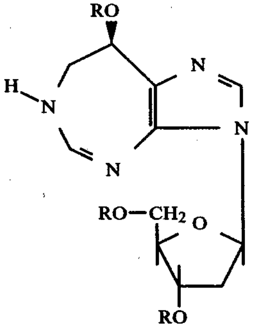 One R is 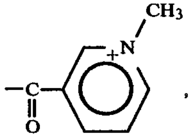 , each remaining R is H or 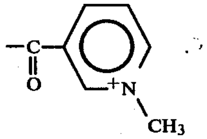 . | 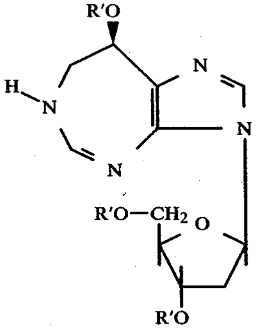 One R' is 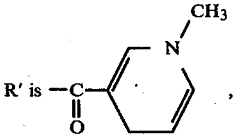 , each remaining R' is H or 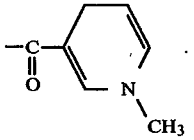 . |

| Starting Material | [D—QC]+ | [D—DHC] |
|---|---|---|
| 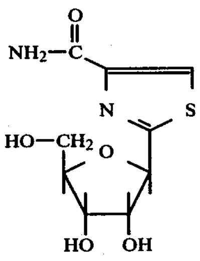 tiazofurin | 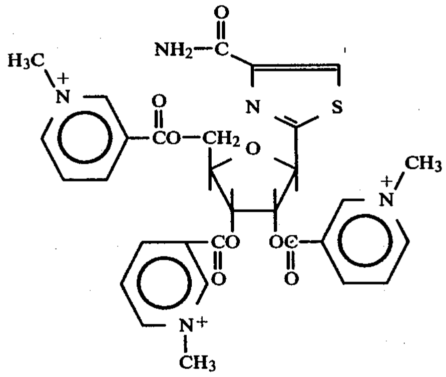 | 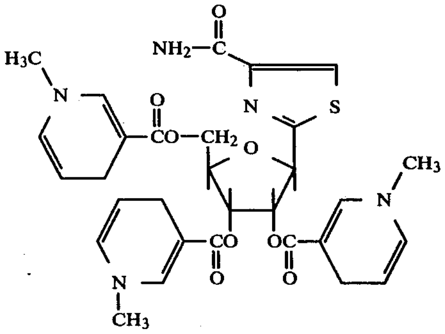 |
| 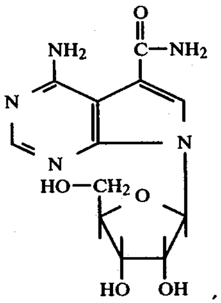 , sangivamycin | 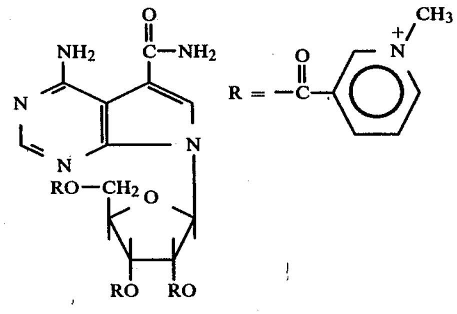 | 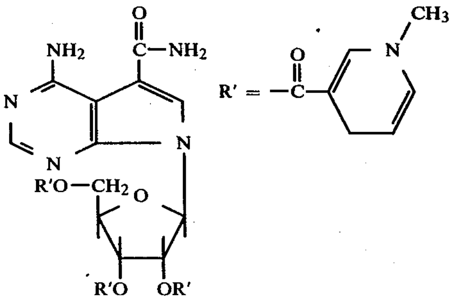 |

-continued
| Starting Material | [D—QC]+ | [D—DHC] |
|---|---|---|
| 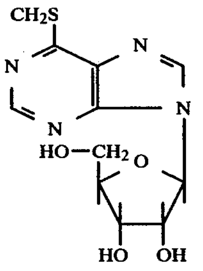 6-MMPR | 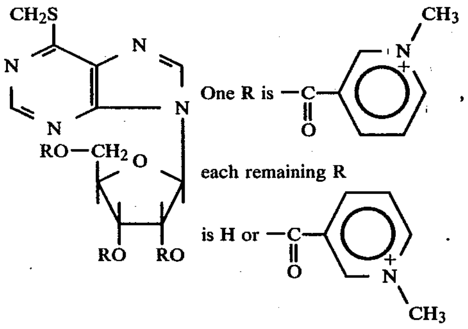 | 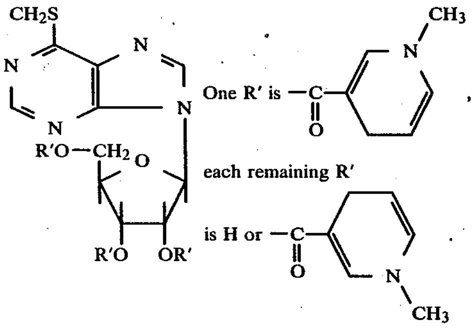 |
| 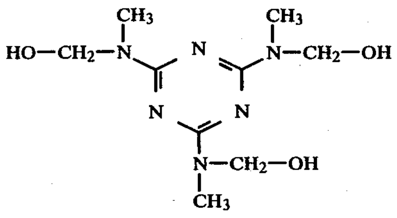 trimethyl TMM | 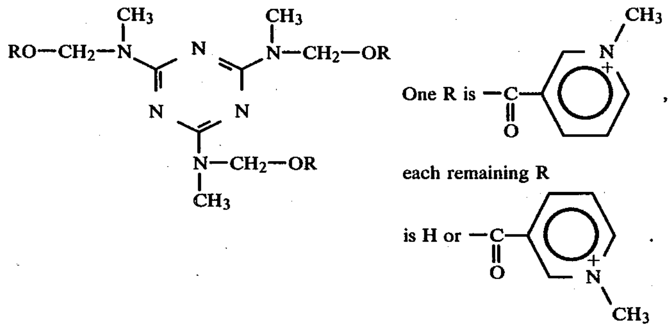 | 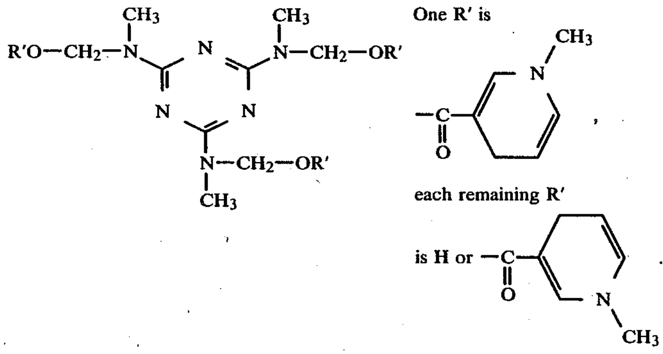 |
| 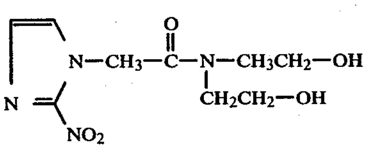 SR-2555 | 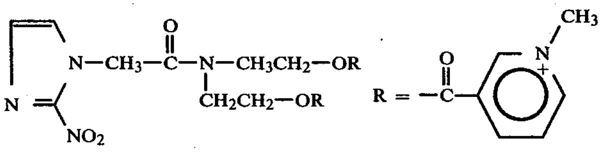 | 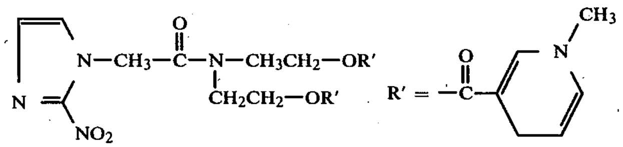 |

-continued
| Starting Material | [D—QC]+ | [D—DHC] |
| --- | --- | --- |
| 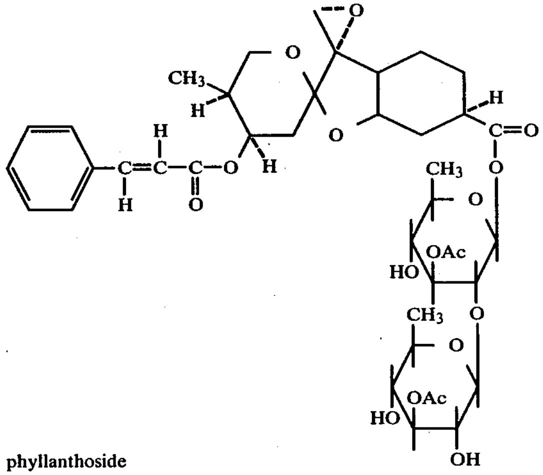 phyllanthoside | 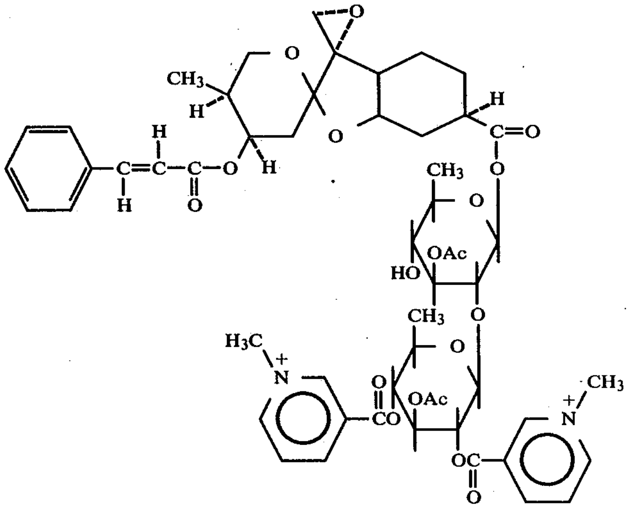 | 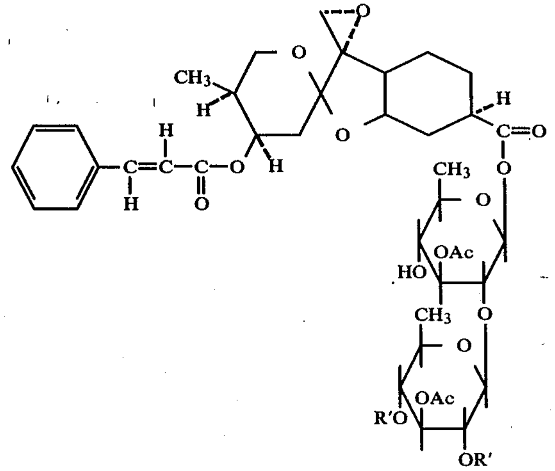 R' = 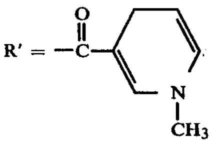 |

-continued
| Starting Material | [D—QC]+ | [D—DHC] |
|---|---|---|
| 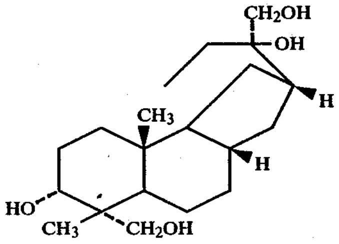 aphidicolin | 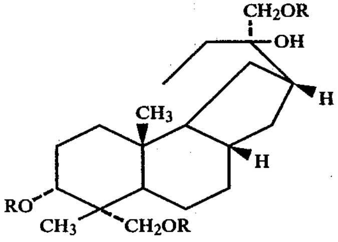 One R is 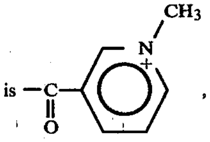, each remaining R is H or 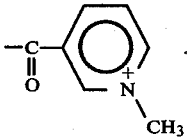. | 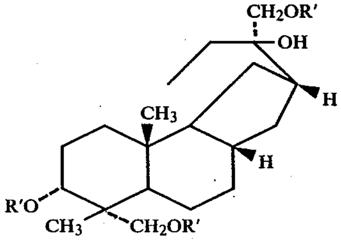 One R' is 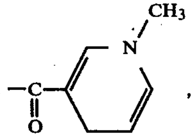, each remaining R' is H or 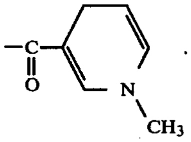. |
| 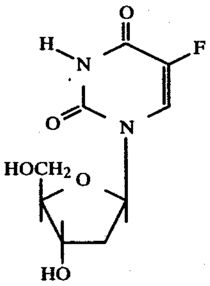 5-FUDR | 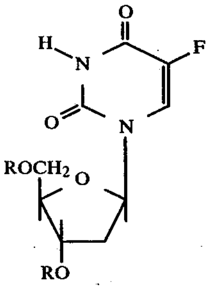 One R is 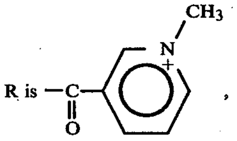, each remaining R is H or 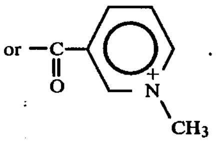. | 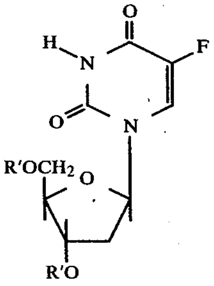 One R' is 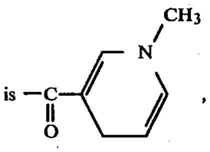, each remaining R' is H or 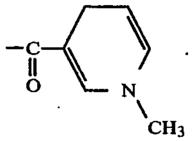. |
| 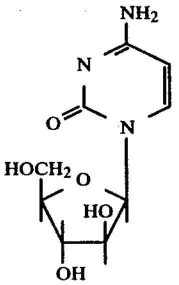 cytosine arabinoside | 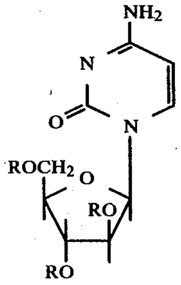 One R is 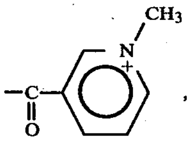, each remaining R is H or 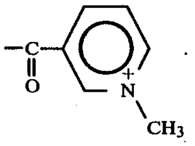. | 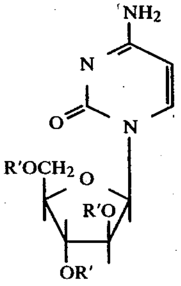 One R' is 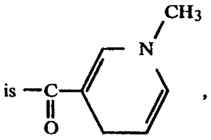, each remaining R' is H or 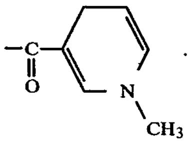. |

-continued
| Starting Material | [D—QC]+ | [D—DHC] |
|---|---|---|
| 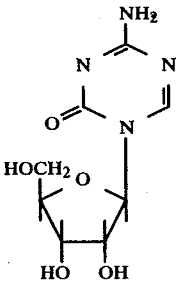 5-azacytidine | 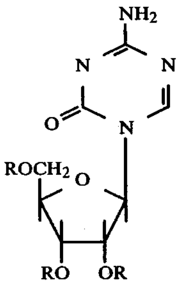 One R is 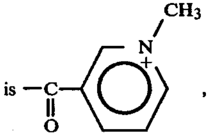 , each remaining R is H or 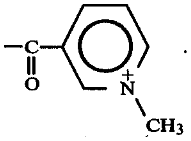 . | 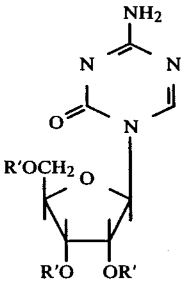 One R' is 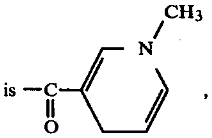 , each remaining R' is H or 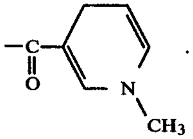 . |
| 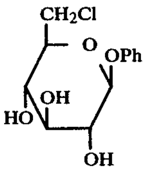 phenyl-6-chloro-6-deoxy-β-D-glucopyranoside | 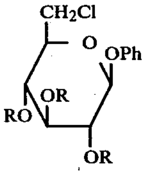 One R is 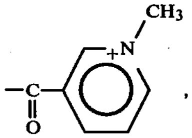 , each remaining R is H or 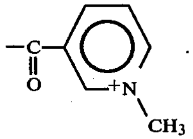 . | 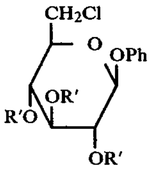 One R' is 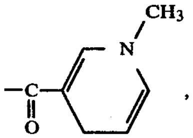 , each remaining R' is H or 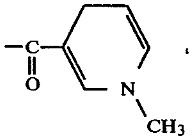 . |

-continued
| Starting Material | [D—QC]⁺ | [D—DHC] |
| --- | --- | --- |
| 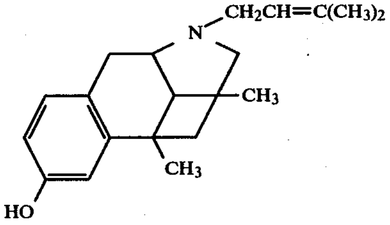 pentazocine | 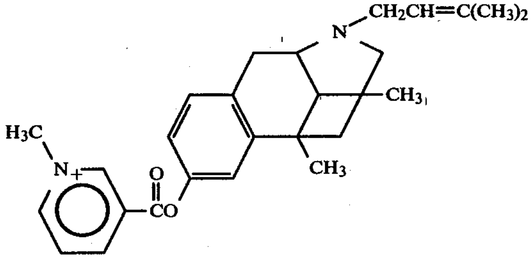 | 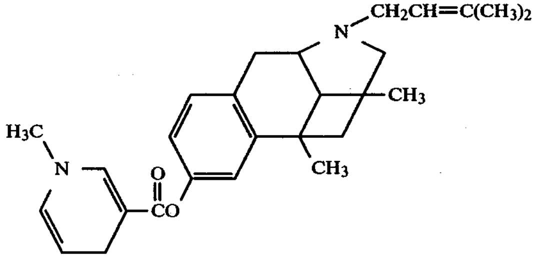 |
| 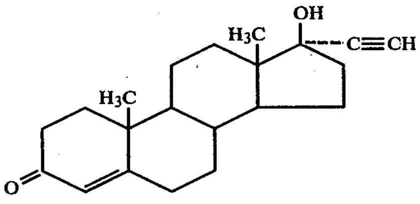 ethisterone | 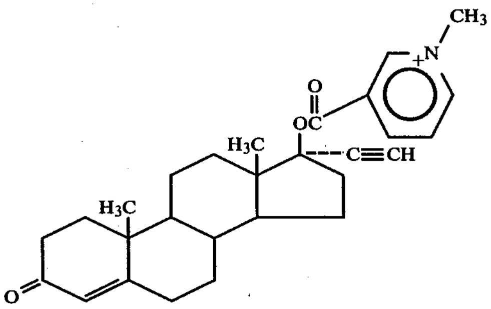 | 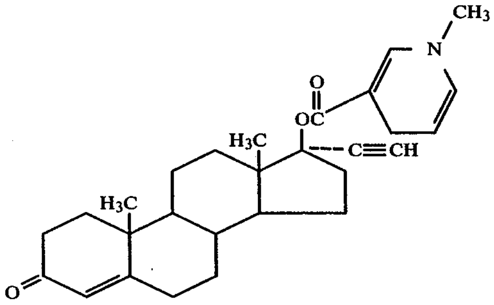 |
| 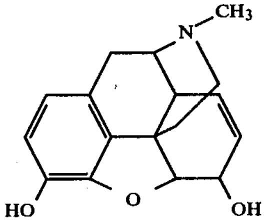 morphine | 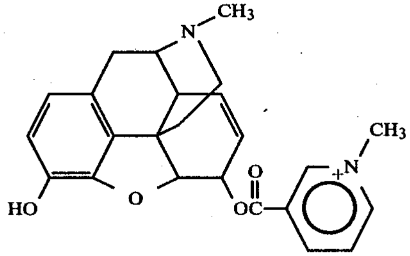 | 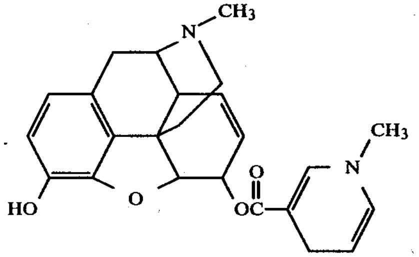 |

-continued
| Starting Material | [D−QC]+ | [D−DHC] |
|---|---|---|
| 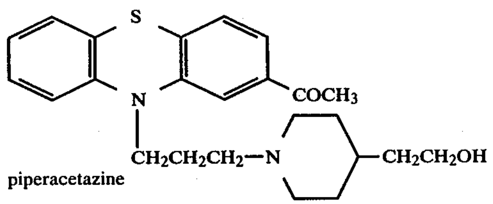 piperacetazine | 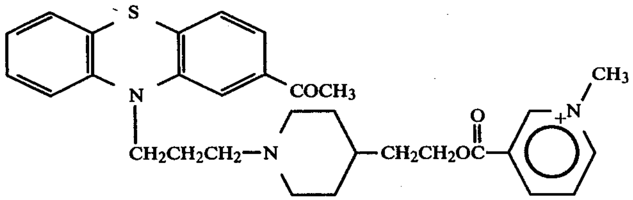 | 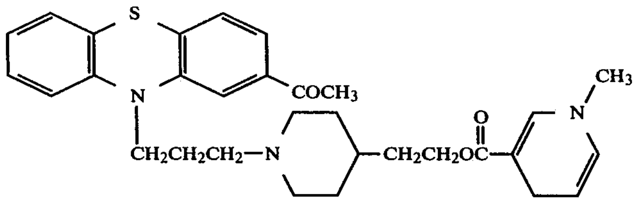 |
| 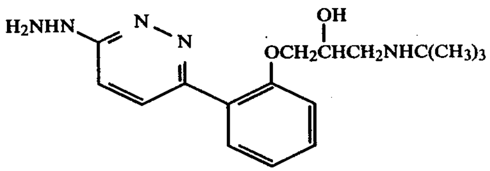 prizidilol | 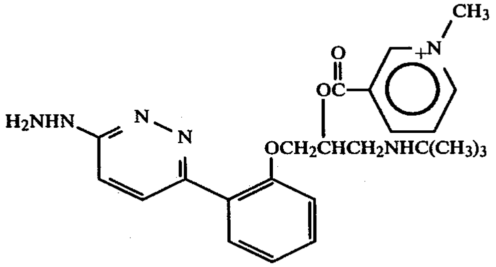 | 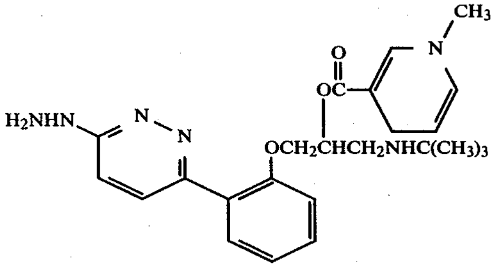 |
| 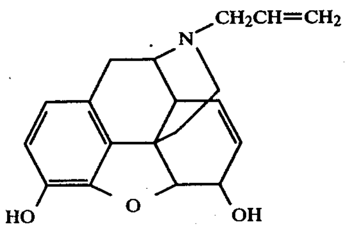 nalorphine | 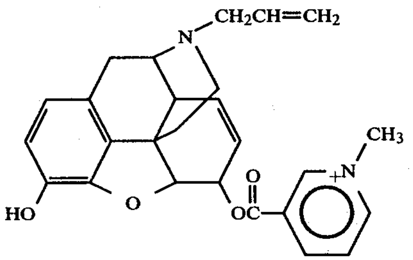 | 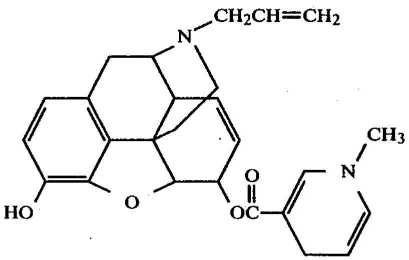 |

-continued
| Starting Material | [D—QC]+ | [D—DHC] |
|---|---|---|
| 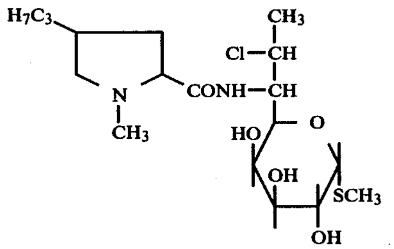 clindomycin | 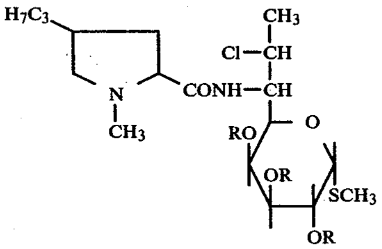 Each R is H or 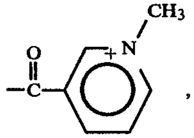, provided at least one R is 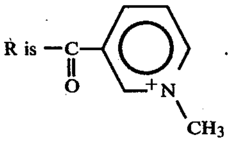. | 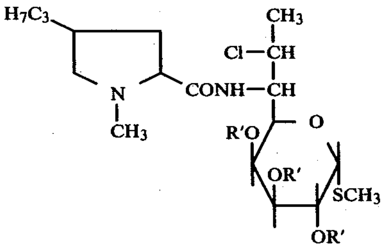 Each R′ is H or 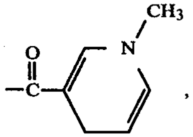, provided at least one R′ is 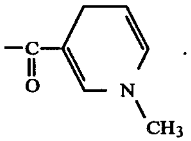. |
| 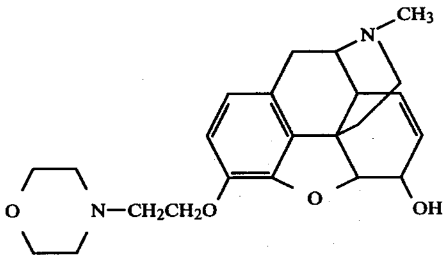 pholcodine | 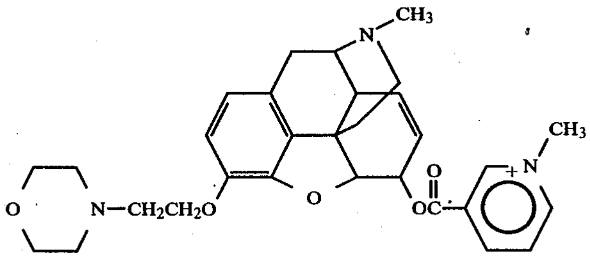 | 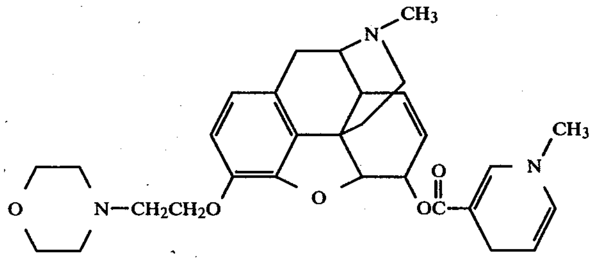 |

-continued
| Starting Material | [D—QC]+ | [D—DHC] |
|---|---|---|
| 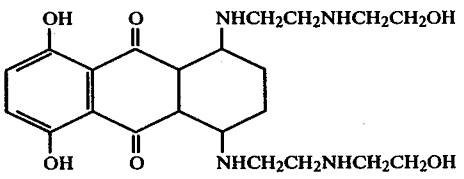 mitoxantrone | 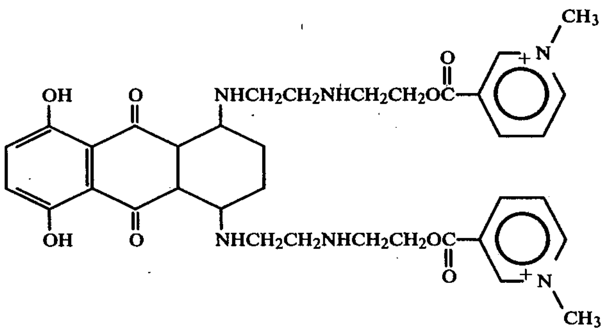 | 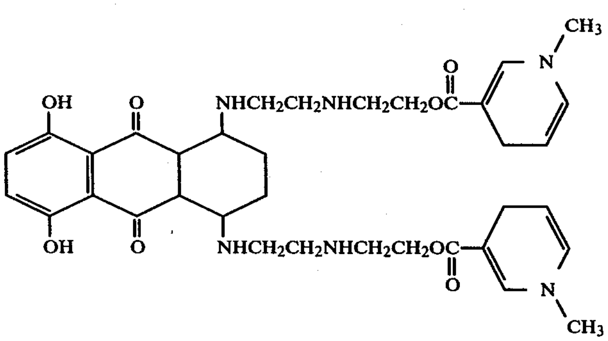 |
| 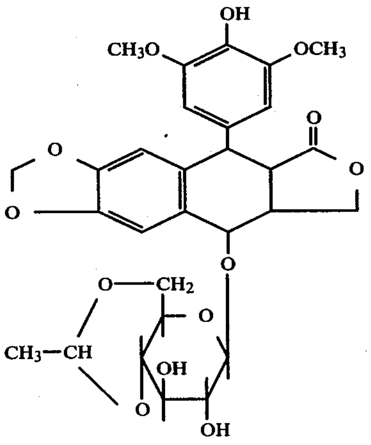 VP-16 (etoposide) | 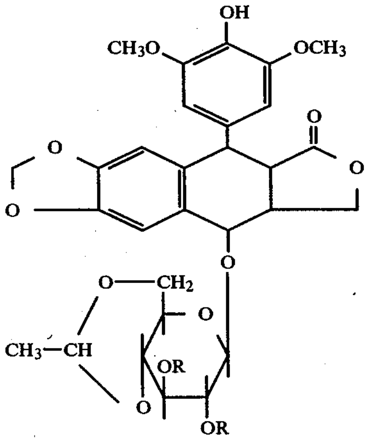 Each R is H or 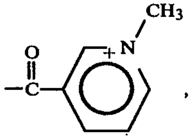, provided at least one R is 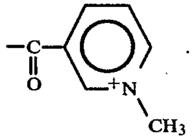 | 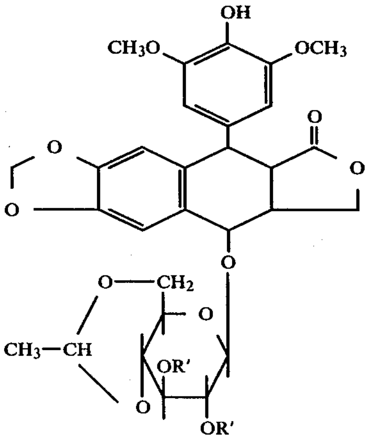 Each R' is H or 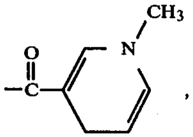, provided at least one R' is 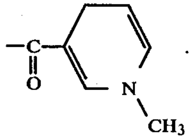 |

-continued
| Starting Material | [D—QC]+ | [D—DHC] |
|---|---|---|
| 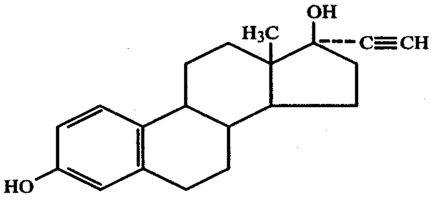 ethinyl estradiol | 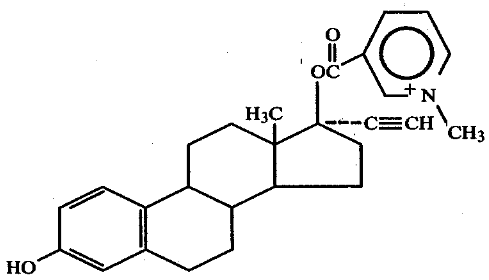 | 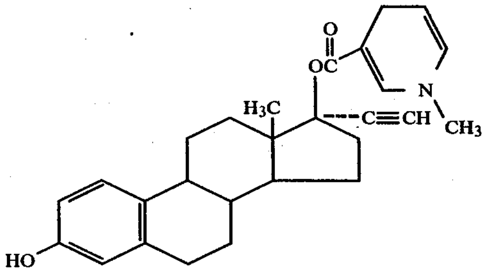 |
| 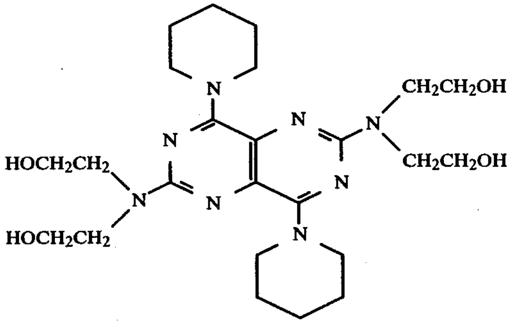 dipyridamole | 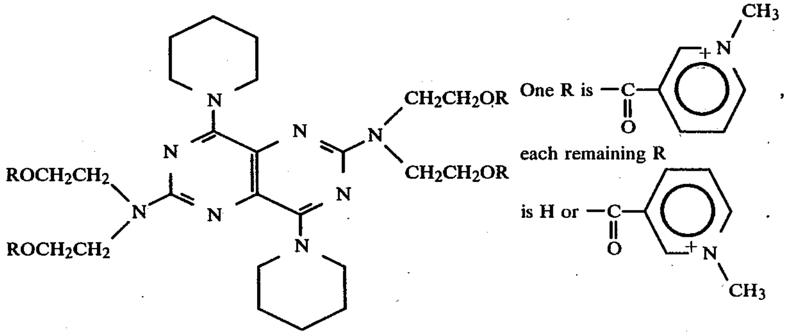 | 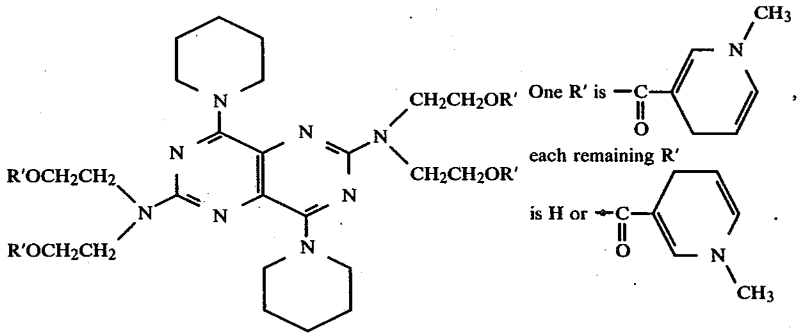 |

-continued
| Starting Material | [D—QC]+ | [D—DHC] |
|---|---|---|
| 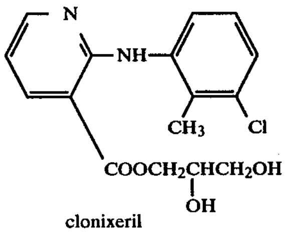 clonixeril | 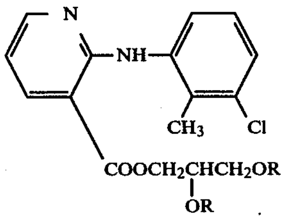 One R is 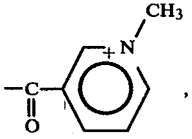, the other R is H or 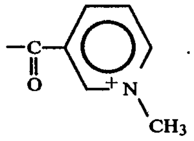. | 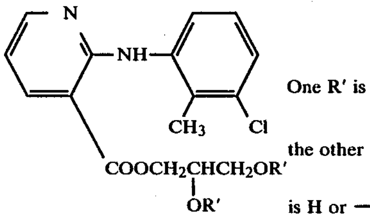 One R' is 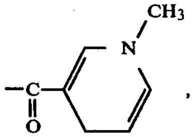, the other R' is H or 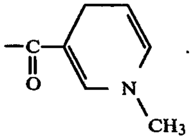. |
| 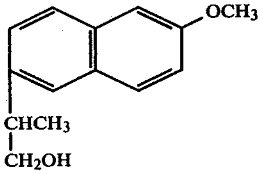 naproxol | 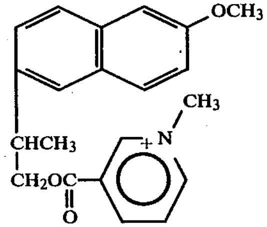 | 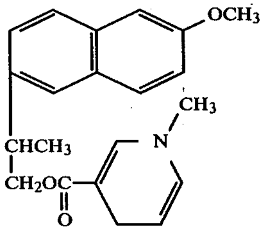 |
| 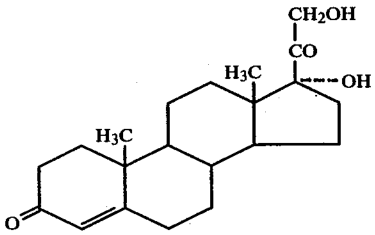 cortodoxone | 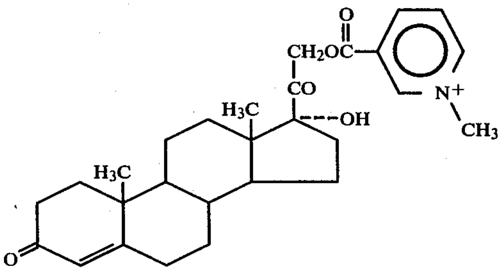 | 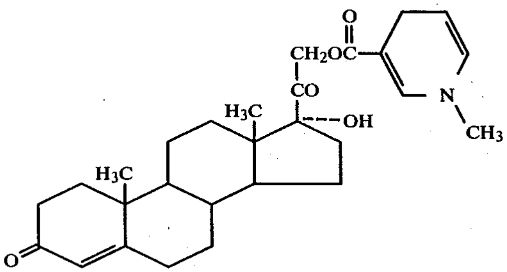 |

-continued
| Starting Material | [D—QC]+ | [D—DHC] |
|---|---|---|
| 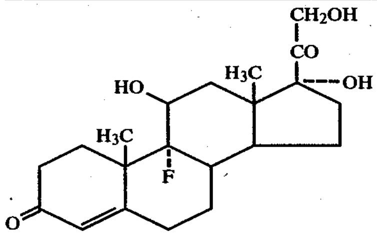 fludrocortisone | 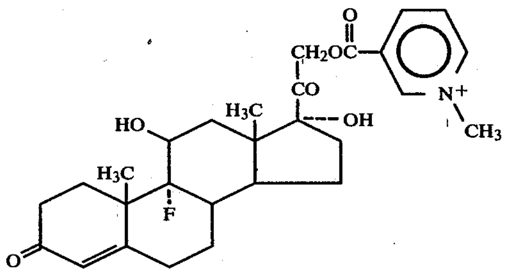 | 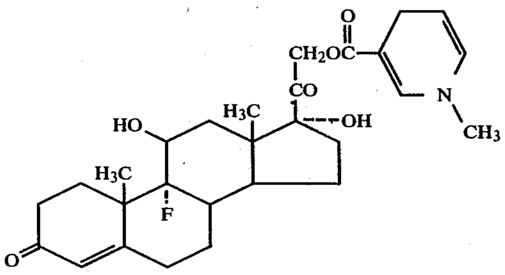 |
| 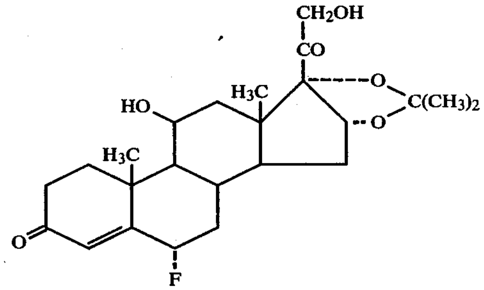 fludrandrenolide | 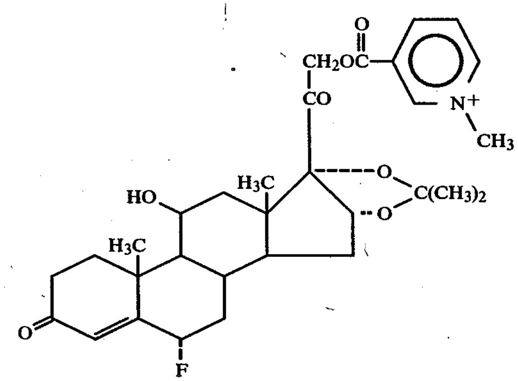 | 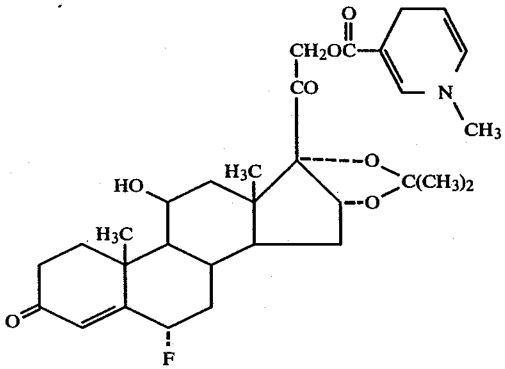 |

| Starting Material | [D—QC]+ | [D—DHC] |
|---|---|---|
| 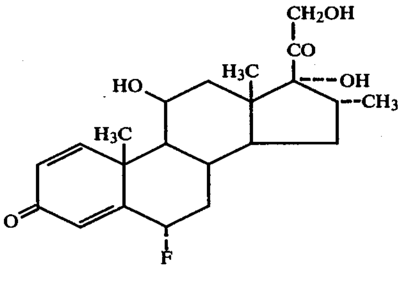 paramethasone | 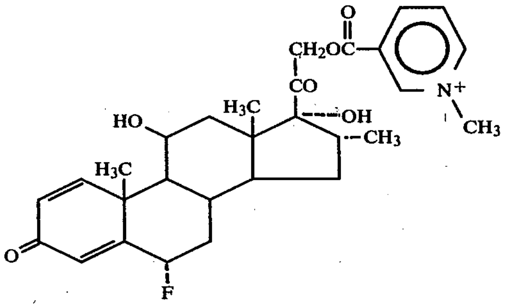 | 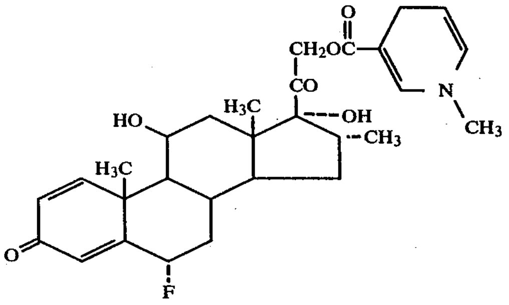 |
| 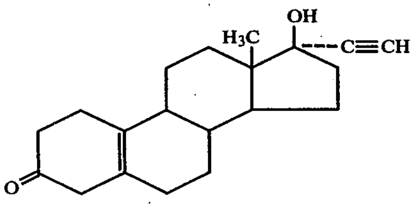 norethylnodrel | 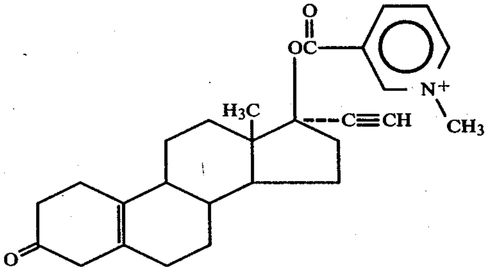 | 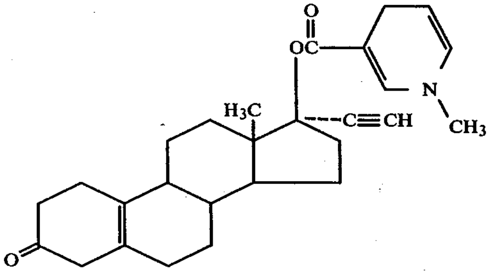 |
| 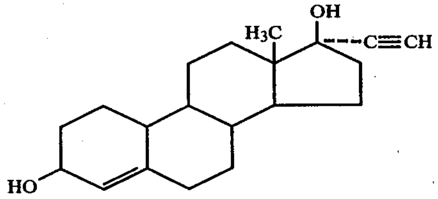 ethynodiol | 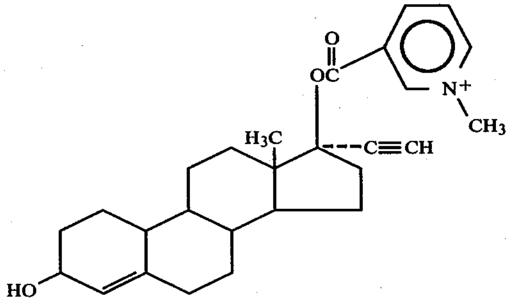 | 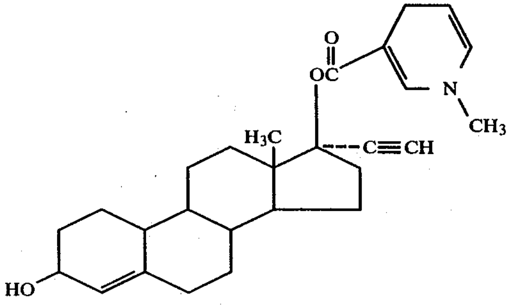 |

-continued
| Starting Material | [D—QC]+ | [D—DHC] |
|---|---|---|
| 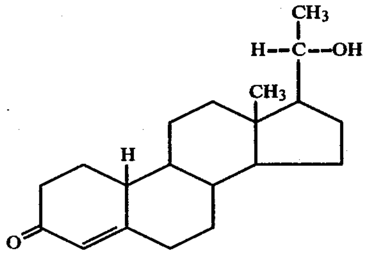 oxogestone | 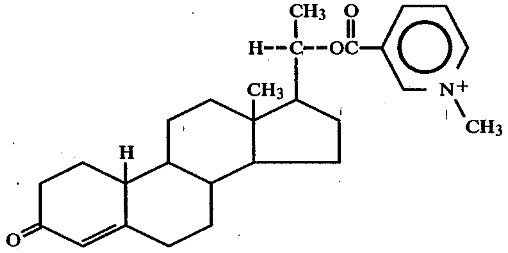 | 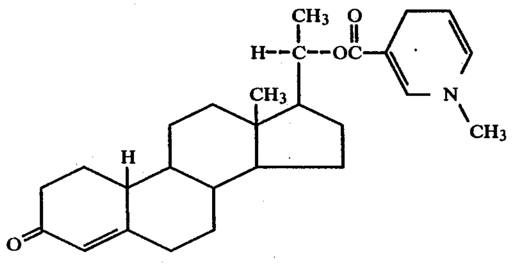 |
| 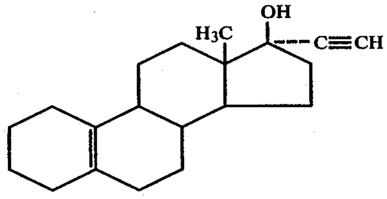 tigestol | 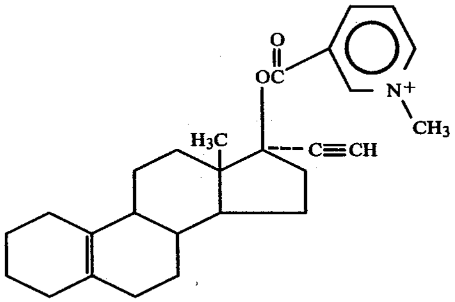 | 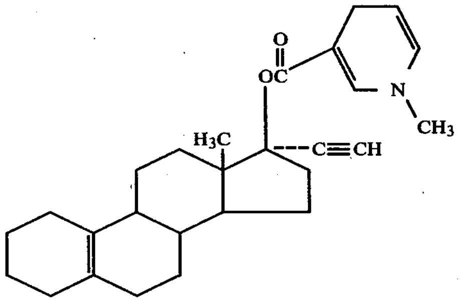 |
| 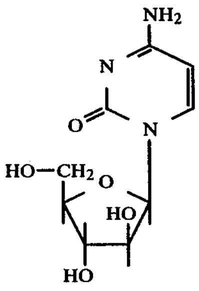 Ara-C (cytarabine) | 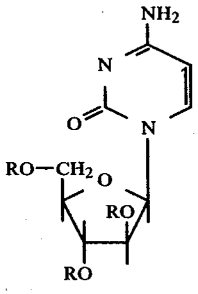 One R is 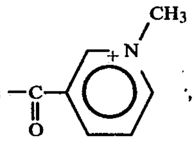 , each remaining R is H or 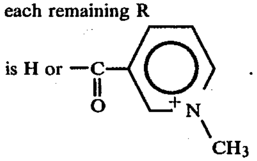 . | 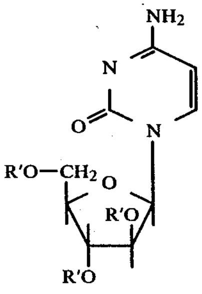 One R′ is 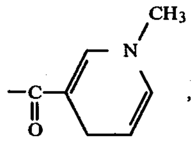 , each remaining R′ is H or 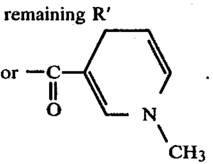 . |

-continued
| Starting Material | [D—QC]+ | [D—DHC] |
|---|---|---|
| 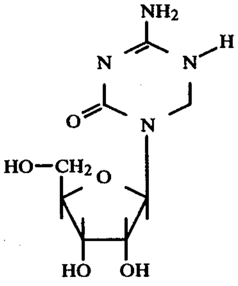<br>dihydro-5-azacytidine | 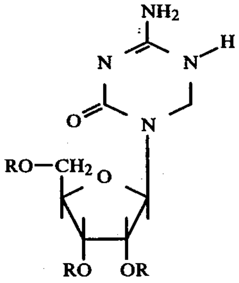 One R is 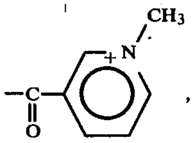,<br>each remaining R<br>is H or 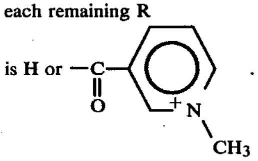. | 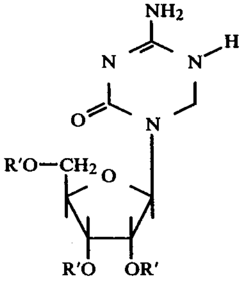 One R' is 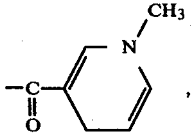,<br>each remaining R'<br>is H or 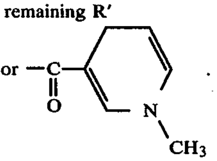. |
| 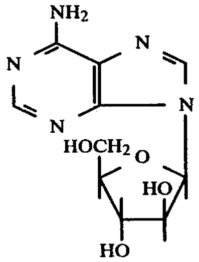<br>Ara-A<br>(vidarabine) | 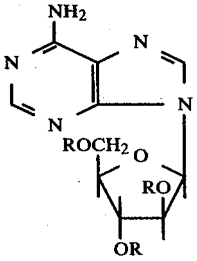 One R is 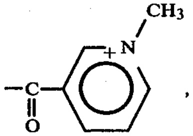,<br>each remaining R<br>is H or 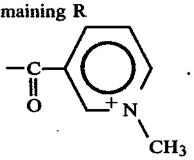. | 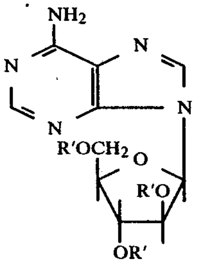 One R' is 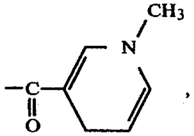,<br>each remaining R'<br>is H or 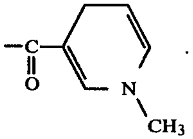. |

-continued
| Starting Material | [D—QC]+ | [D—DHC] |
|---|---|---|
| 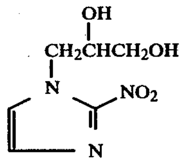 desmethylisonidazole | 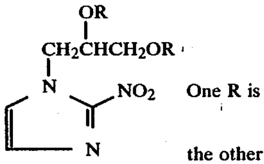 One R is 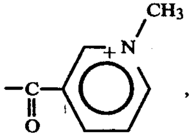 , the other R is H or 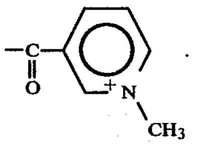 . | 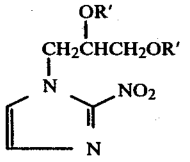 One R' is 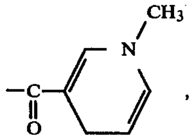 , the other R' is H or 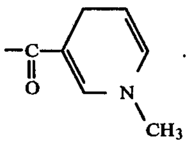 . |
| 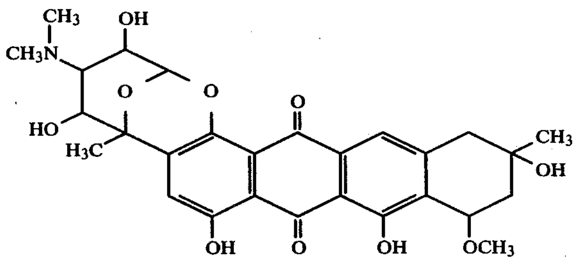 menogarol | 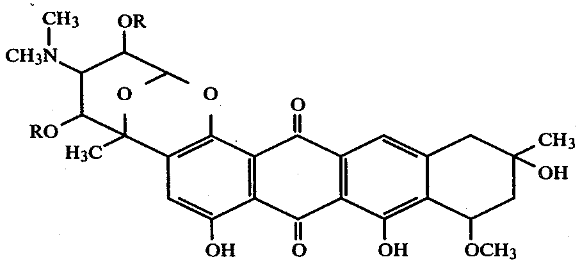 One R is 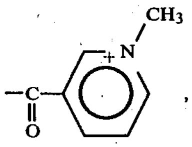 , the other R is H or 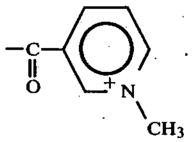 . | 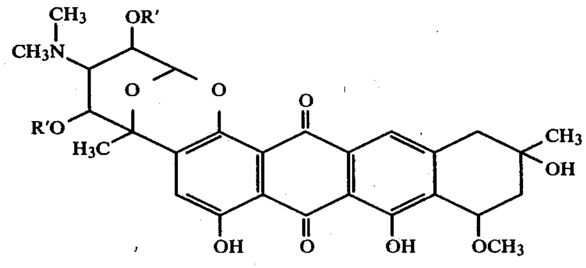 , One R' is 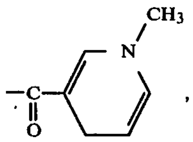 , the other R' is H or 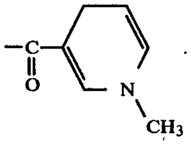 . |

-continued

| Starting Material | [D—QC]+ | [D—DHC] |
| --- | --- | --- |
| 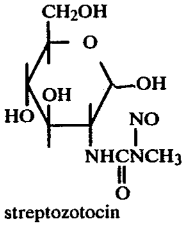<br>streptozotocin | 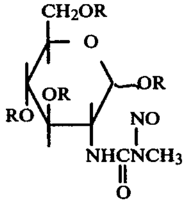 One R is 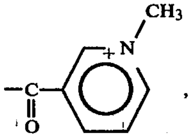 ,<br>each remaining R<br>is H or 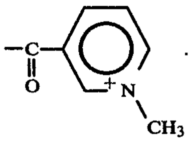 . | 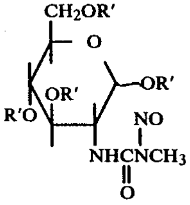 One R′ is 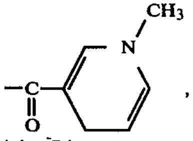 ,<br>each remaining R′<br>is H or 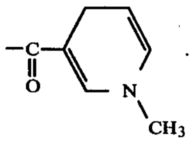 . |
| 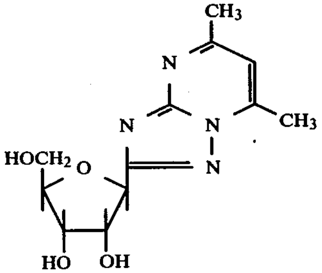<br>5,7-dimethyl-2-β-D-ribofuranosyl-s-triazole (1,5-a)pyrimidine | 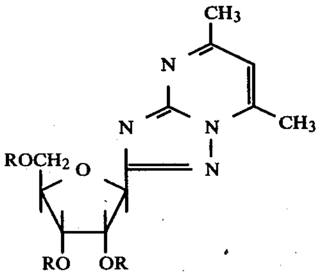 One R is 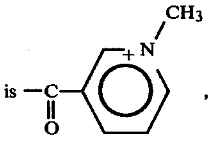 ,<br>each remaining R<br>is H or 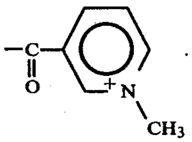 . | 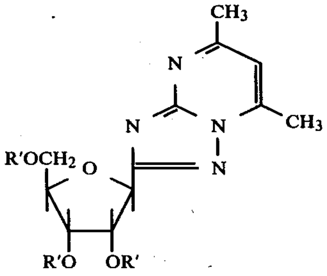 One R′ is 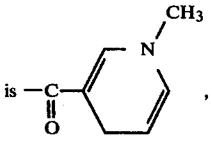 ,<br>each remaining R′<br>is H or 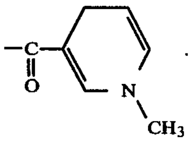 . |
| 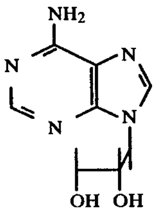<br>(S)—9-(2,3-dihydroxypropyl)-adenine | 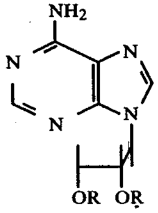 One R is 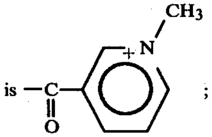 ;<br>the other R<br>is H or 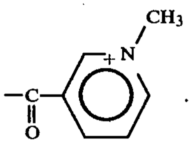 . | 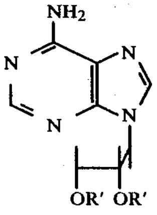 One R′ is 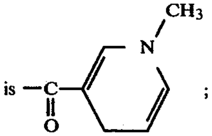 ;<br>the other R′<br>is H or 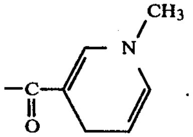 . |

-continued
| Starting Material | [D—QC]+ | [D—DHC] |
| --- | --- | --- |
| 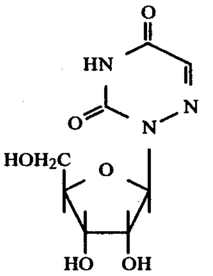 6-azauridine | 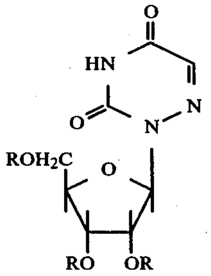 One R is 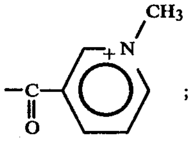 ; each remaining R is H or 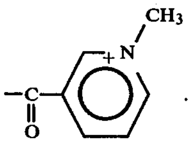 . | 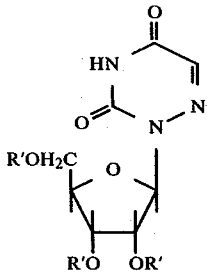 One R′ is 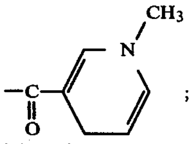 ; each remaining R′ is H or 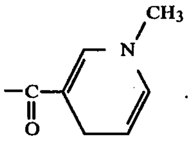 . |
| 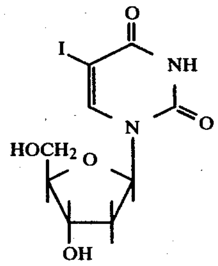 idoxuridine | 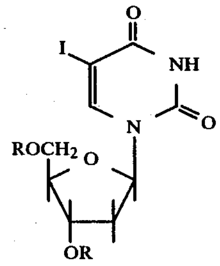 One R is 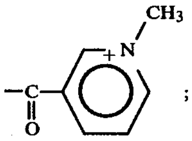 ; the other R is H or 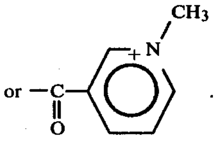 . | 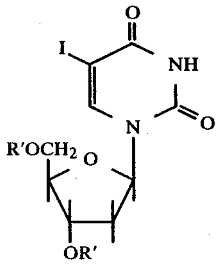 One R′ is 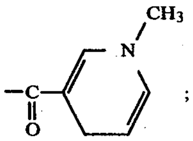 ; the other R′ is H or 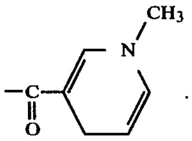 . |

-continued
| Starting Material | [D—QC]$^+$ | [D—DHC] |
| --- | --- | --- |
| 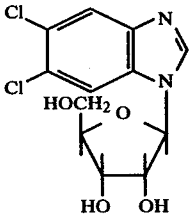 5,6-dichloro-1-β-D-ribofuransylbenzimidaazole | 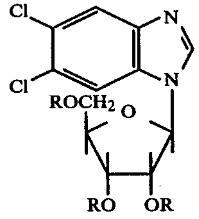 One R is 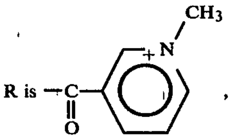, each remaining R is H or 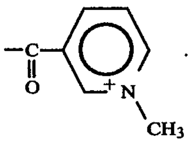. | 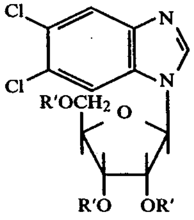 One R' is 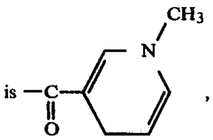, each remaining R' is H or 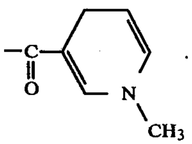. |
| 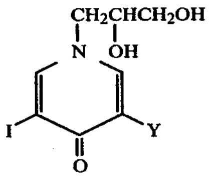 iopydol | 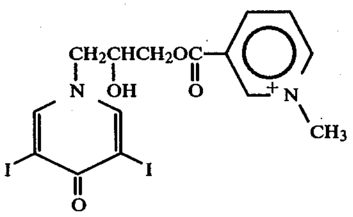 | 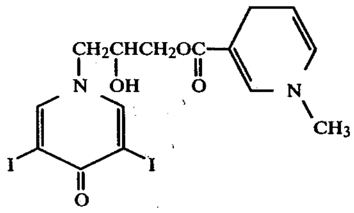 |
| 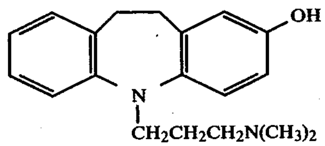 2-hydroxyimipramine | 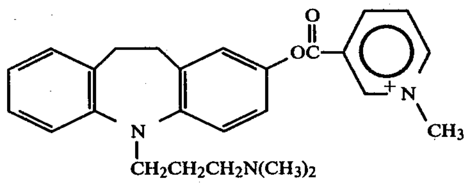 | 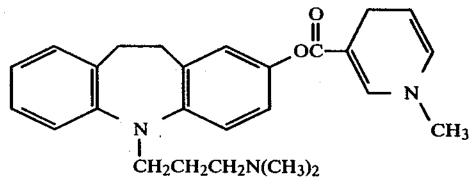 |

-continued
| Starting Material | [D—QC]+ | [D—DHC] |
|---|---|---|
| 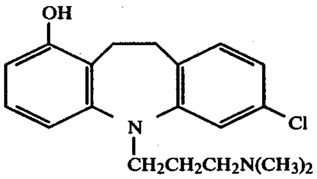<br>8-hydroxychlorimipramine<br>(8-hydroxyclomipamine) | 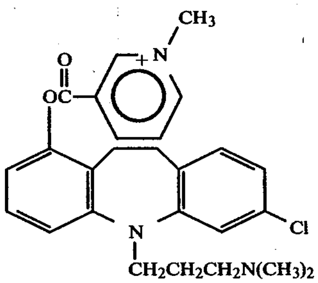 | 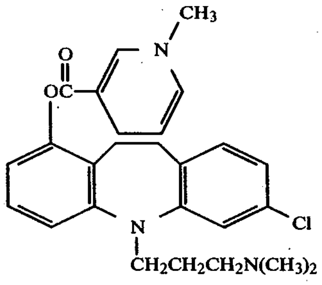 |
| 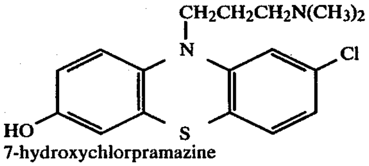<br>7-hydroxychlorpramazine | 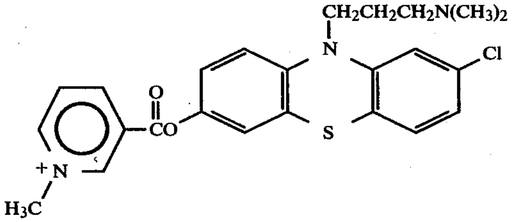 | 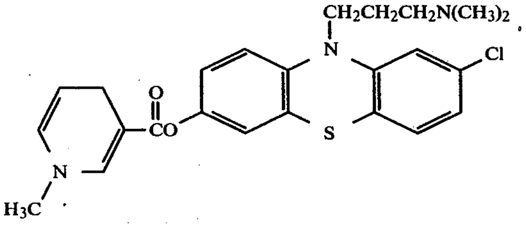 |
| 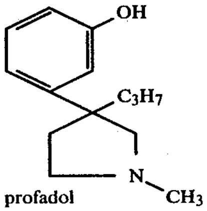<br>profadol | 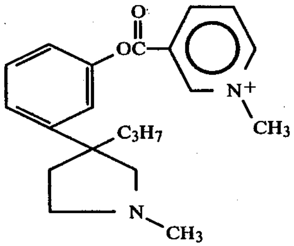 | 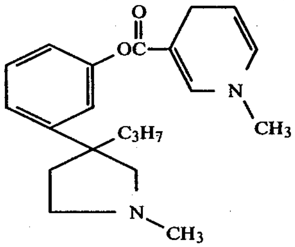 |

-continued
| Starting Material | [D—QC]+ | [D—DHC] |
|---|---|---|
| 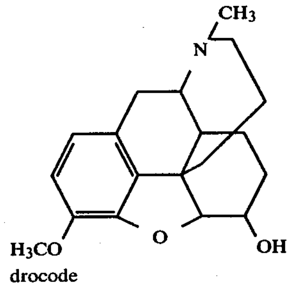 drocode | 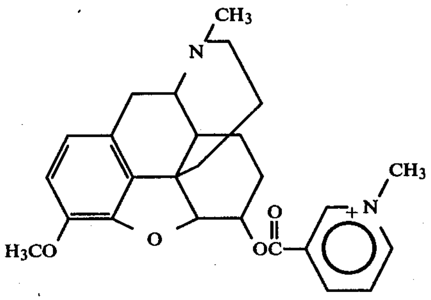 | 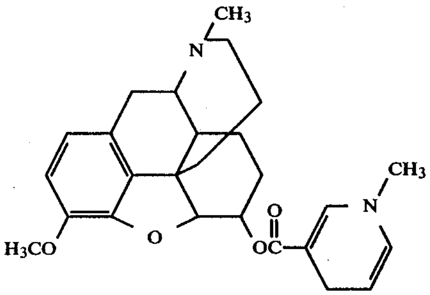 |
| 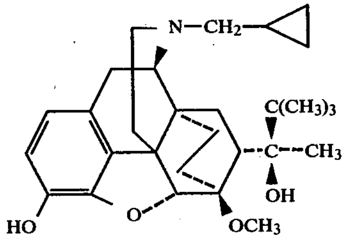 buprenorphine | | 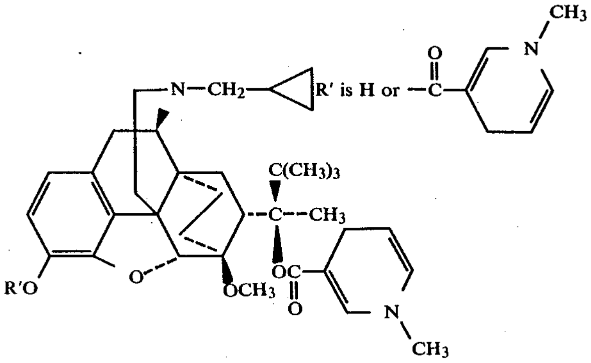  |

-continued
| Starting Material | [D—QC]+ | [D—DHC] |
| --- | --- | --- |
| | 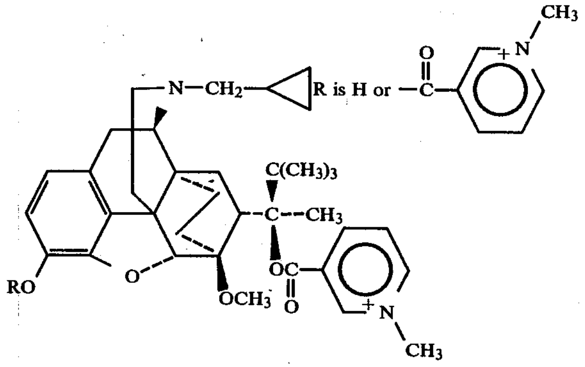 | |
| 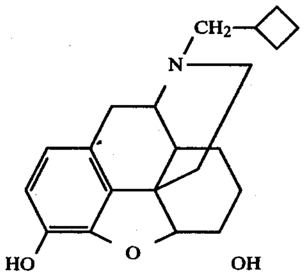<br>nalbuphine | 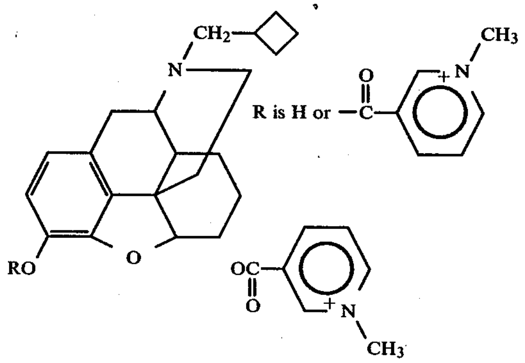 | 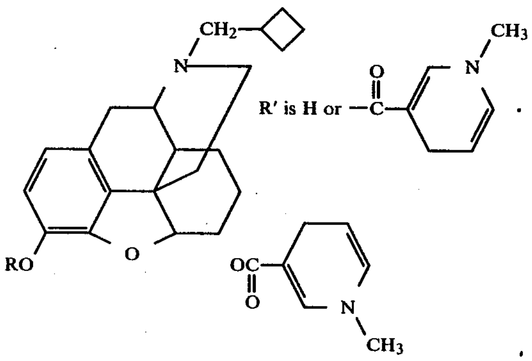 |

-continued
| Starting Material | [D—QC]+ | [D—DHC] |
|---|---|---|
| 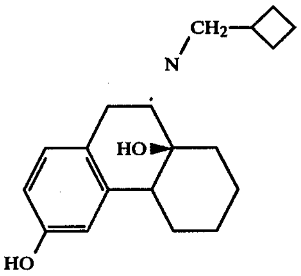 butorphanol | 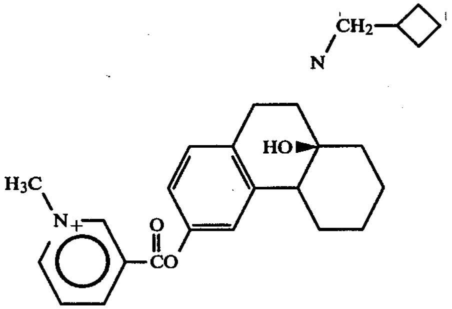 | 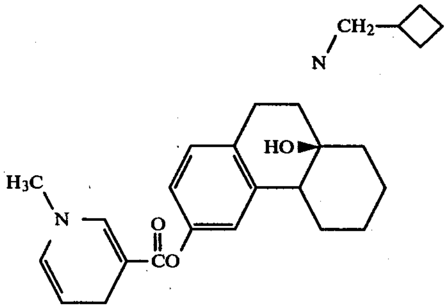 |
| 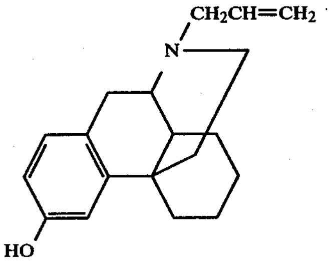 levallorphan | 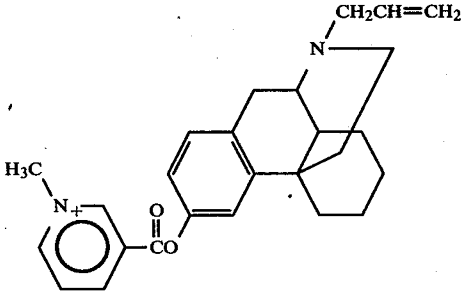 | 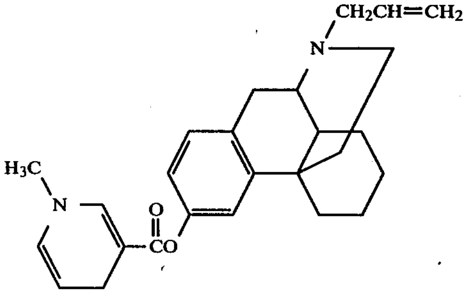 |

-continued
| Starting Material | [D—QC]+ | [D—DHC] |
| --- | --- | --- |
| 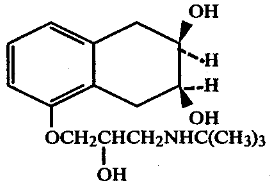 nadolol | 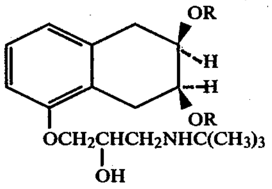 One R is 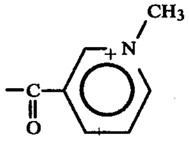 each remaining R is H or 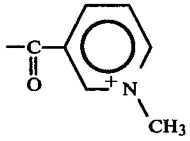 | 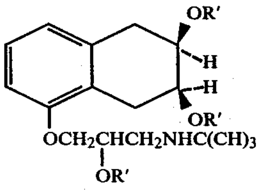 One R′ is 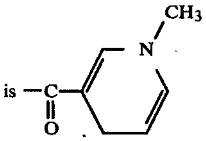 each remaining R′ is H or 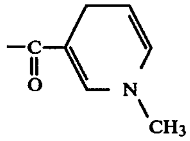 |
| 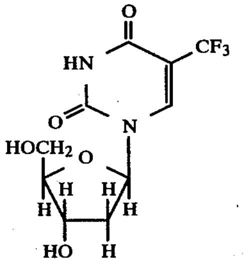 trifluridine | 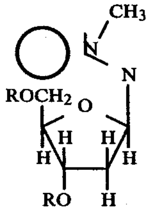 the other R is H or 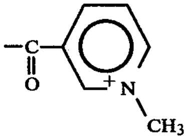 | 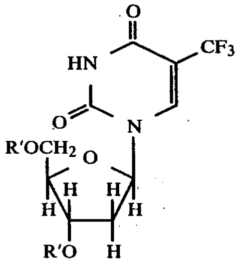 One R′ is 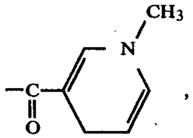, the other R′ is H or 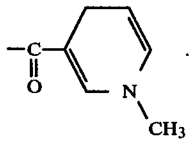 |
| 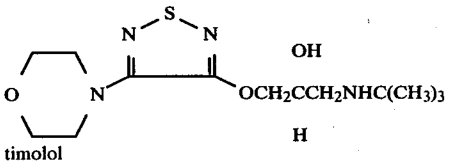 timolol | 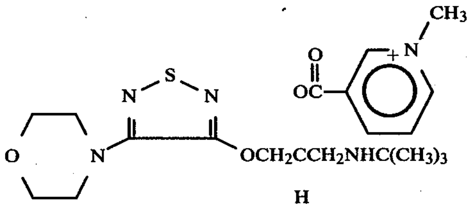 | 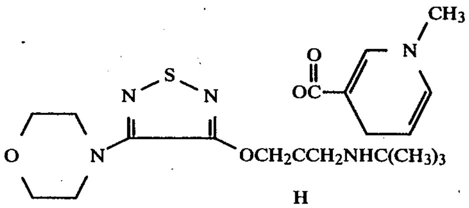 |

-continued
| Starting Material | [D—QC]+ | [D—DHC] |
|---|---|---|
| 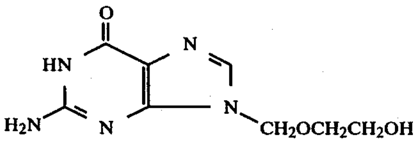 acyclovir | 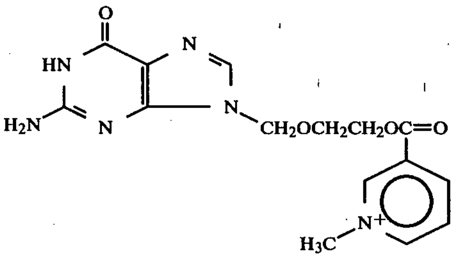 | 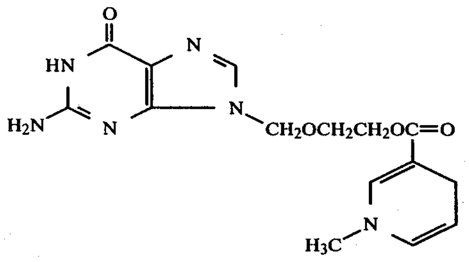 |
| 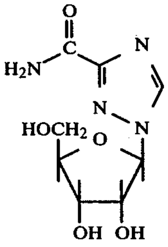 ribavarin | 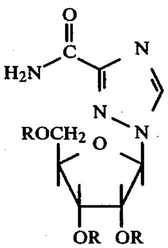 One R is 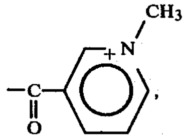, each remaining R is H or 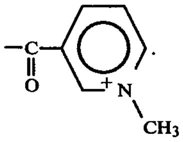. | 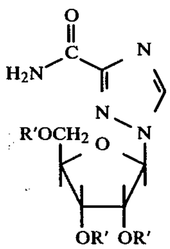 One R' is 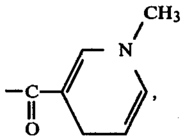, each remaining R' is H or 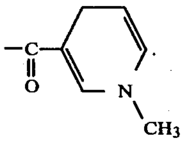. |

Method K′

This is an alternate process for derivatizing drugs containing secondary or tertiary hydroxyl functional groups. According to this process, the drug is reacted with chloral or other aldehyde capable of forming a hemiacetal therewith. In the case of chloral, this converts the —OH function(s) to $$\begin{array}{l} -OCHOH \\ \quad\ \ | \\ \quad CCl_3 \end{array}$$

groupings.

The —OH function(s) of the resultant hemiacetal can then be derivatized by any of the methods for derivatizing —OH groups disclosed hereinabove, e.g. by reaction with nicotinic acid or its acid chloride or anhydride as described in Method K.

This process is of particular value when the —OH group(s) in the drug is/are sterically hindered and/or when it is desired to alter the rate of release of the drug from that obtained when the carrier is hooked directly to the drug's hydroxy function(s).

The representative drugs depicted below may be derivatized in this manner to the corresponding compounds of formulas (II) and (I). Other drugs containing secondary or tertiary —OH groups which are disclosed herein, e.g. in connection with Method K, may be similarly derivatized. This method is of special interest for derivatizing steroids containing secondary or tertiary 17 β-hydroxy substituents, especially steroid sex hormones, and most especially such hormones bearing a bulky 17 α-substituent such as a 17 α-ethynyl grouping.

| STARTING MATERIAL | [D—QC]+ | [D—DHC] |
| --- | --- | --- |
| 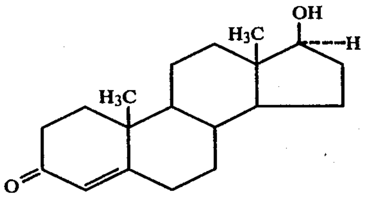<br>testosterone | 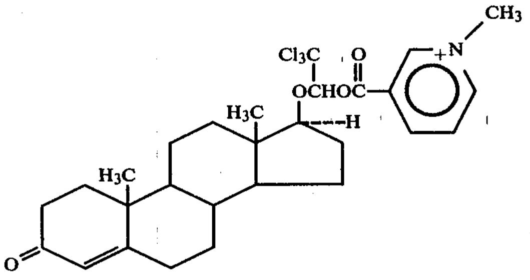 | 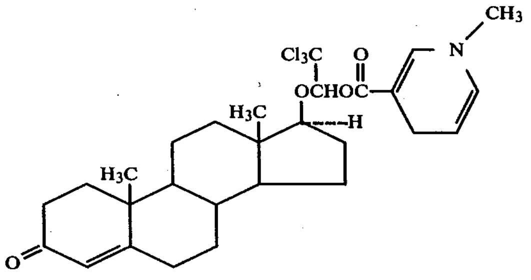 |
| 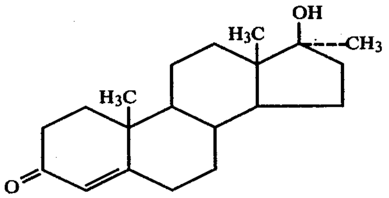<br>methyltestosterone | 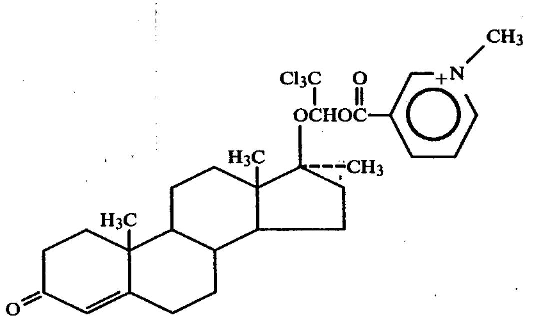 | 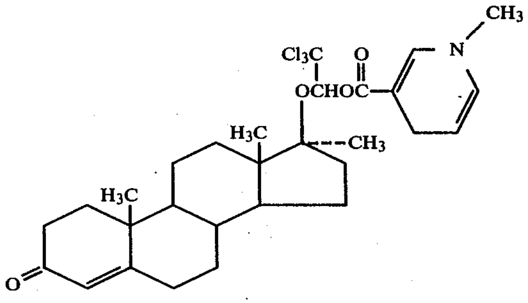 |
| 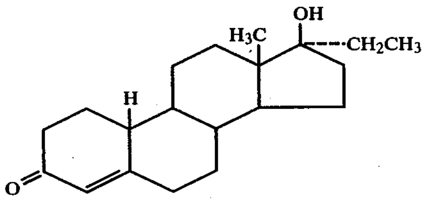<br>norethandrolone | 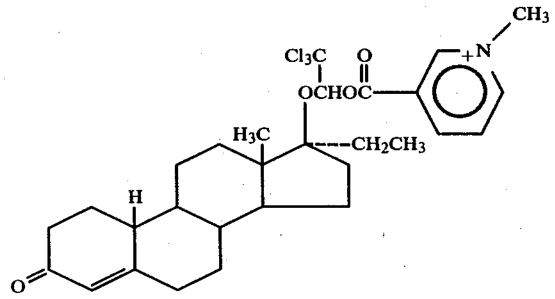 | 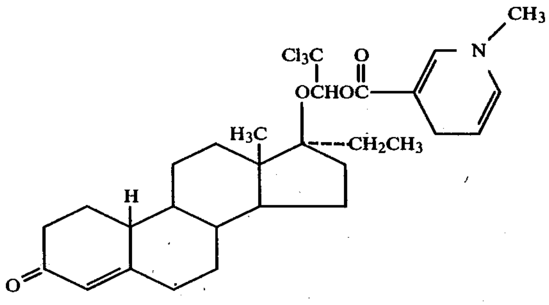 |

-continued
| STARTING MATERIAL | [D—QC]+ | [D—DHC] |
| --- | --- | --- |
| 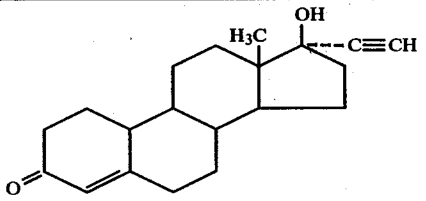 norethindrone | 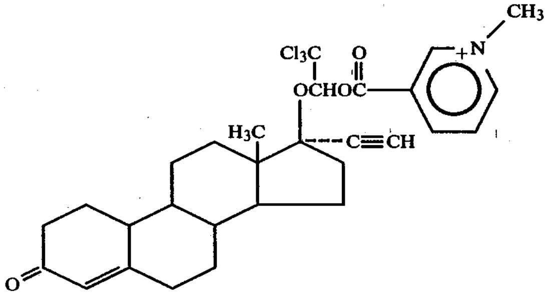 | 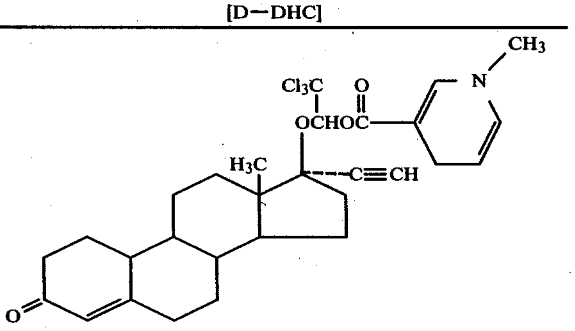 |
| 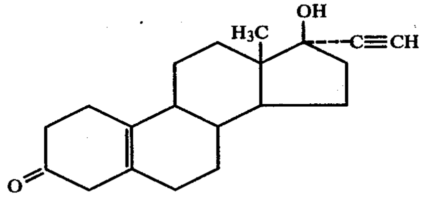 norethynodrel | 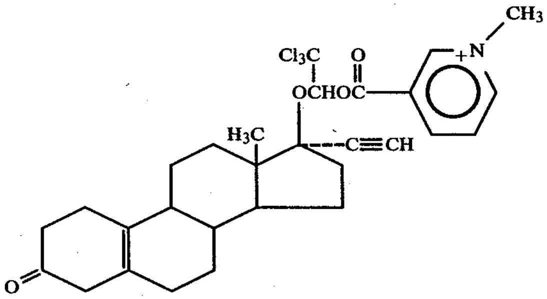 | 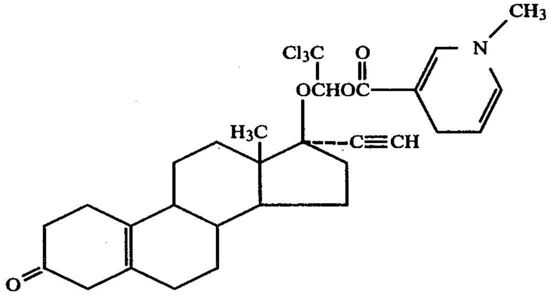 |
| 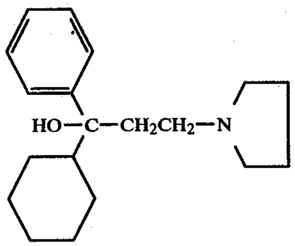 procyclidine | 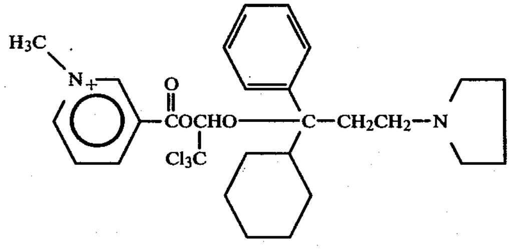 | 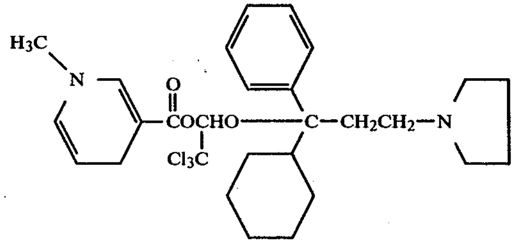 |

Method L

This variation of Method K can be used when the drug contains an amino group which needs to be protected. Generally, the amino group is protected prior to any reaction of the hydroxyl function; typically, a benzyloxycarbonyl group is introduced in conventional manner to protect the amino function and then the process described in Method K is followed. Removal of the protecting group, also in conventional manner, takes place after protection is no longer needed, be it at the end of the synthetic pathway or earlier. Generally, the protecting group is removed before formation of the formula (II) quaternary. Occasionally, an amino protecting group will be utilized which need not be removed, for example, in the case of trifluoroacetyldoxorubicin below.

The representative N- protected drugs depicted below may be derivatized in this manner to the corresponding compounds of formulas (II) and (I). Drugs such as norepinephrine, epinephrine, glucosamine, 6-amino-6-deoxy-D-glucose and pseudoephedrine may be similarly derivatized.

| STARTING MATERIAL | [D—QC]+ | [D—DHC] |
|---|---|---|
| 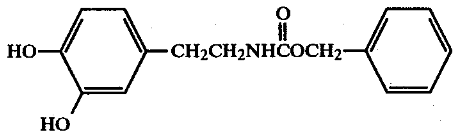 N—benzyloxycarbonyldopamine | 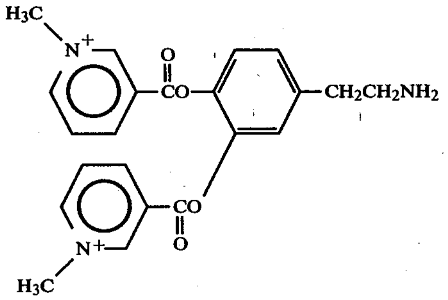 | 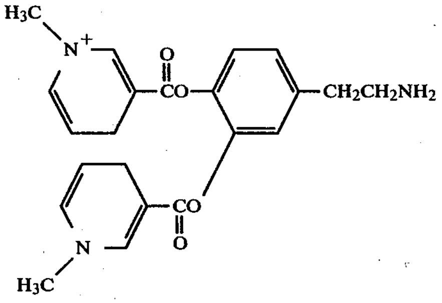 |
| 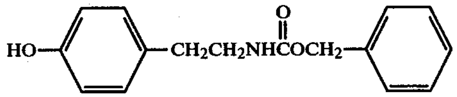 N—benzyloxycarbonyltyramine | 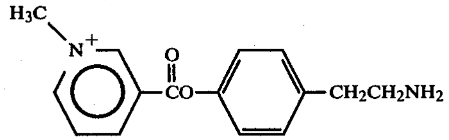 | 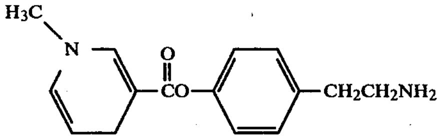 |
| 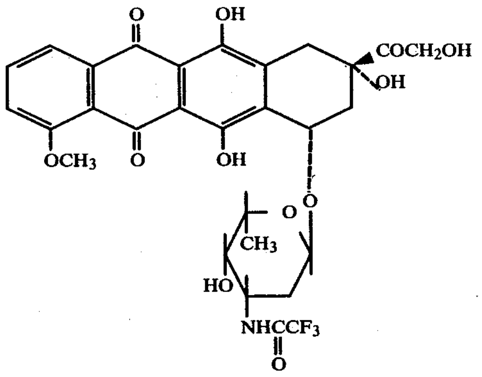 trifluoroacetyldoxorubicin | 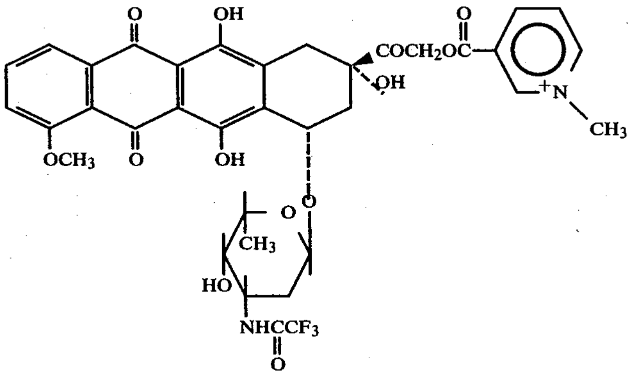 | 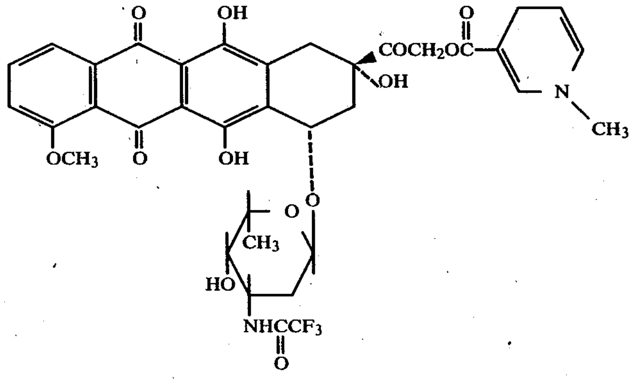 |

-continued
| STARTING MATERIAL | [D—QC]+ | [D—DHC] |
| --- | --- | --- |
| 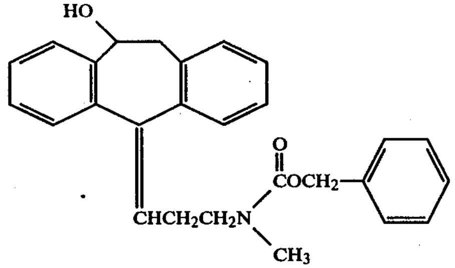<br>N—benzyloxycarbonyl-10-hydroxynortriptyline (E or Z isomer) | 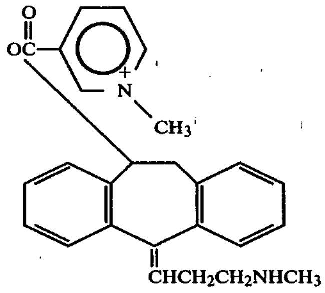 | 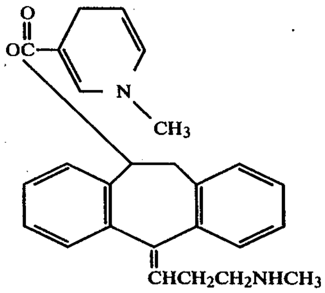 |
| 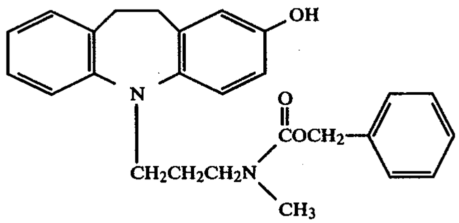<br>N—benzyloxycarbonyl-2-hydroxydesipramine | 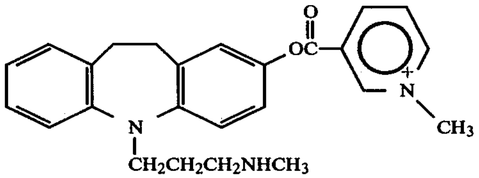 | 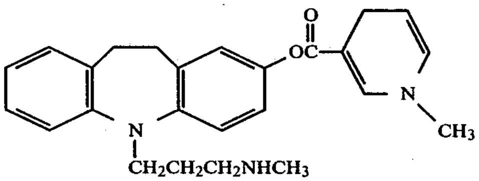 |

Method M

This is a variation of Method K used when the drug contains a —COOH function which is to be protected.

The drug is first converted to the corresponding ethyl or t-butyl ester by conventional esterification techniques. That ester is then used as the starting material and Method K is repeated. The —COOH group may be similarly converted to other ester groups.

The representative drugs depicted below may be derivatized in this manner to the corresponding compounds of formulas (II) and (I). Diflunisal, clorazepate and captopril may be similarly derivatized.

The picolinic acid ester and isonicotinic acid ester quaternary and dihydro derivatives of the drugs specifically mentioned for derivatizing according to this method may be similarly prepared. See Method K.

| Starting Material | [D—QC]+ | [D—DHC] |
|---|---|---|
| 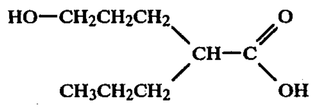 5-hydroxy-2-n-propylpentanoic acid | 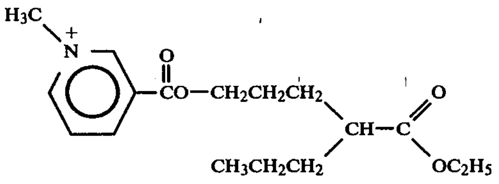 | 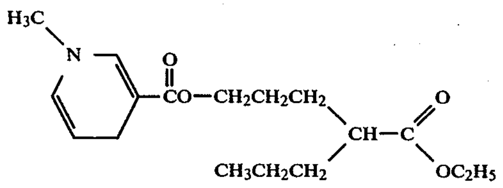 |
| 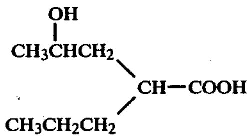 4-hydroxy-2-n-propylpentanoic acid | 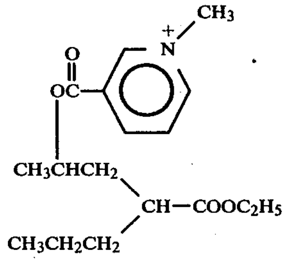 | 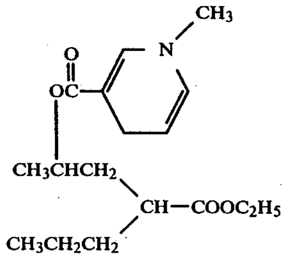 |
| 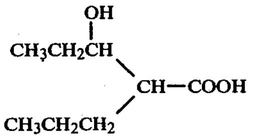 3-hydroxy-2-n-propylpentanoic acid | 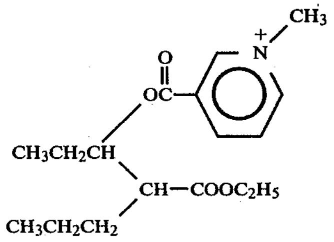 | 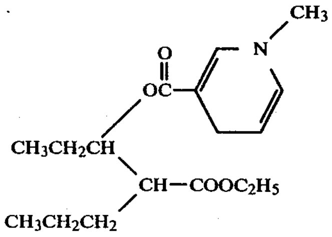 |

-continued
| Starting Material | [D—QC]+ | [D—DHC] |
|---|---|---|
| 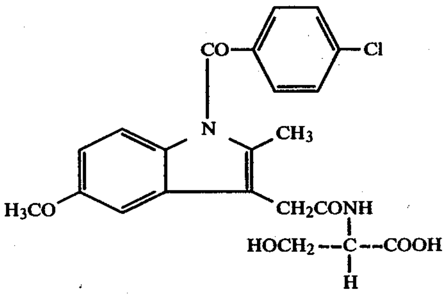 sermatacin | 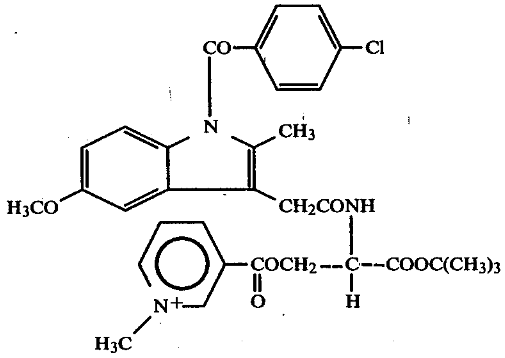 | 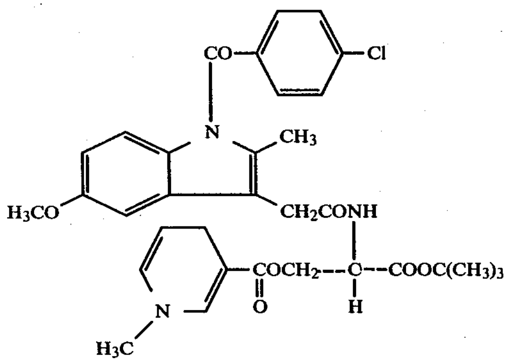 |
| 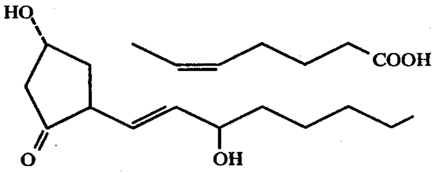 PGD2 | 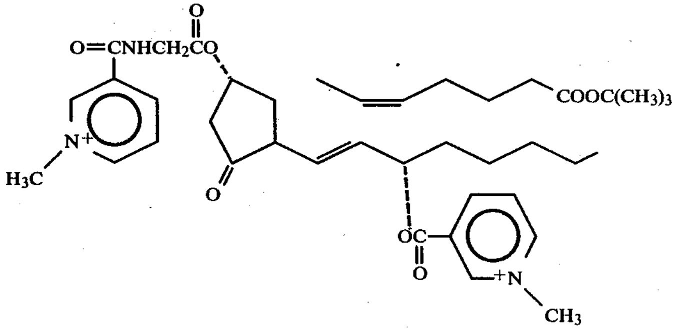 | 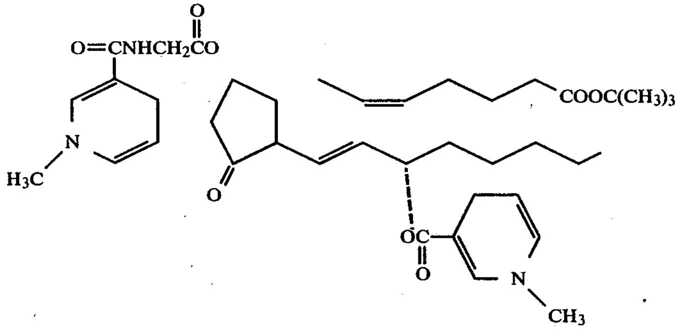 |

Method N

Method K is followed, except that a reactant of the formula

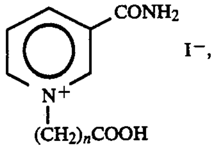

wherein n=1-3, preferably 2, is used in place of nicotinic acid. The quaternary salt of formula (II) thus obtained may then be reduced as described in Method A.

The representative drugs depicted below may be derivatized in this manner to the corresponding compounds of formulas (II) and (I) as may the remaining drugs listed with Method K.

Similarly, Method N may be combined with Method L or M to afford the corresponding derivatives, e.g. of the drugs mentioned with those methods.

A starting material of the formula set forth immediately above can also be substituted for nicotinic acid in Method E, F or G to afford the corresponding derivatives, e.g of the drugs mentioned with those methods.

Method N is of particular use in preparing derivatives of drugs in which the hydroxy function is hindered, e.g., biperiden, cycrimine, procyclidine and trihexyphenidyl.

Alternatively, Method N may follow Method K except that it employs a reactant of the formula

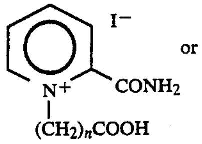

or

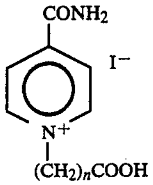

(prepared as described in Method J), to afford derivatives of the drugs indicated with Method K. This altlernative form of Method N may also be combined with Method L or M, to afford the corresponding derivatives of the drugs mentioned with Method L or M, respectively. Also, these alternative Method N starting materials may be substituted for nicotinic acid in Method E, F or G to give the corresponding derivatives of the drugs mentioned with those methods.

| Starting Material | $[D-QC]^+$ | $[D-DHC]$ |
| --- | --- | --- |
| 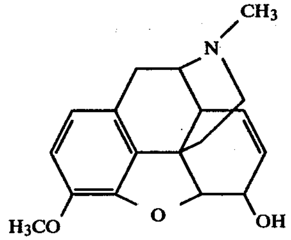 codeine | 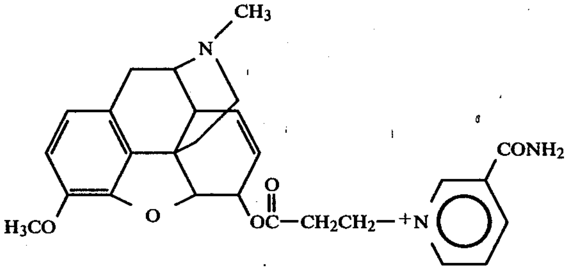 | 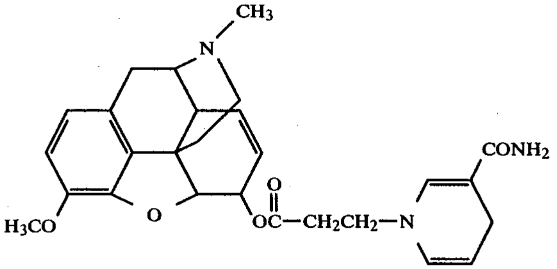 |
| 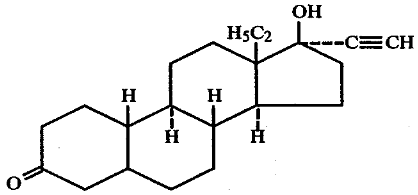 norgestrel | 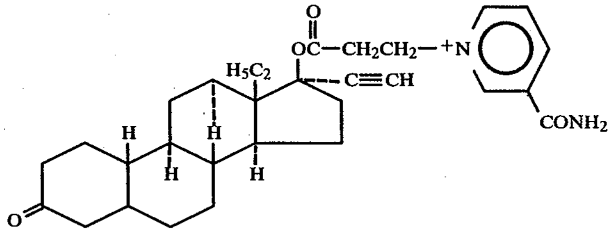 | 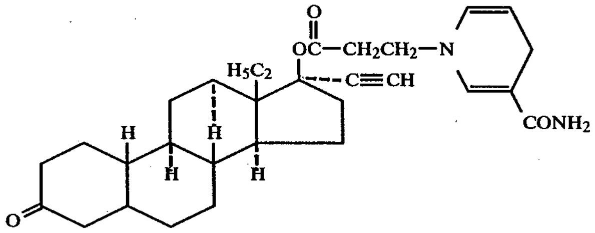 |
| 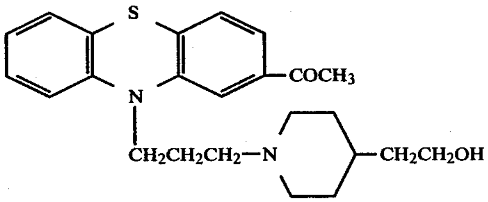 piperacetazine | 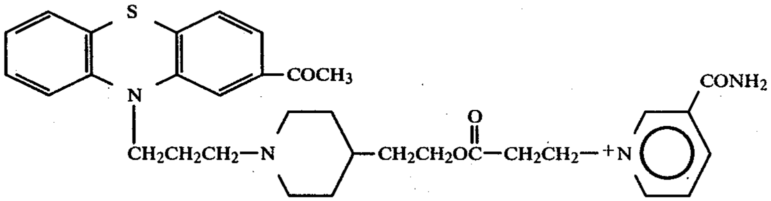 | 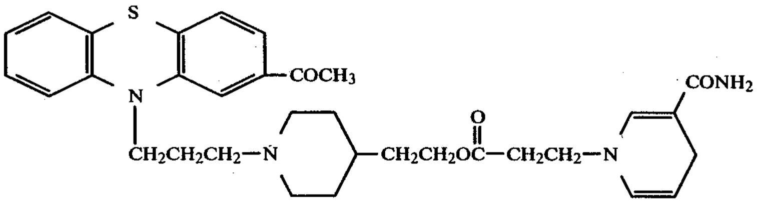 |

-continued
| Starting Material | [D—QC]+ | [D—DHC] |
|---|---|---|
| 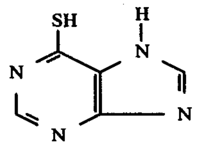 6-mercaptopurine | 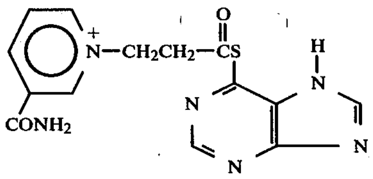 | 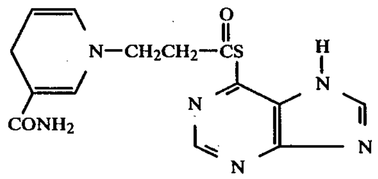 |
| 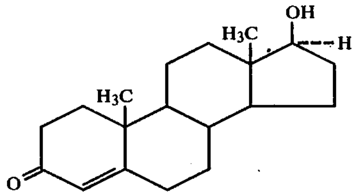 testosterone | 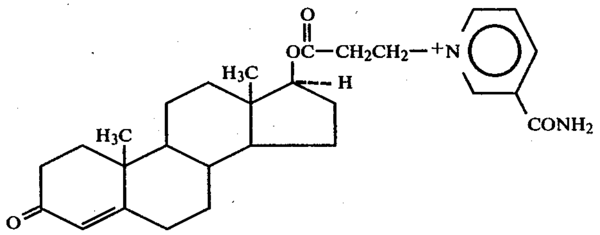 | 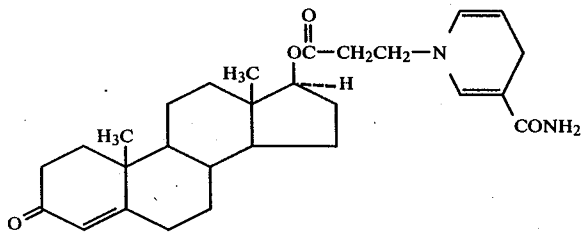 |
| 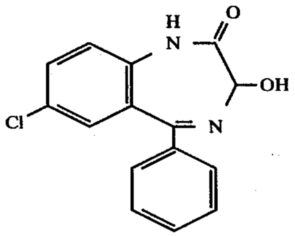 oxazepam | 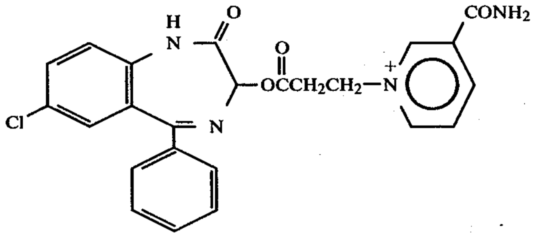 | 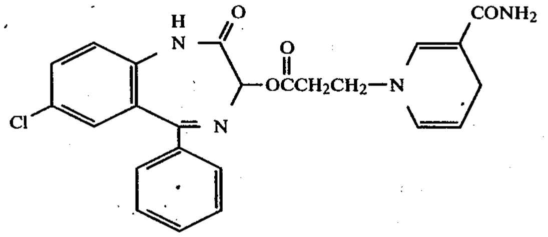 |

-continued
| Starting Material | [D-QC]+ | [D-DHC] |
| --- | --- | --- |
| 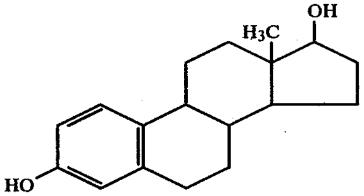 estradiol | 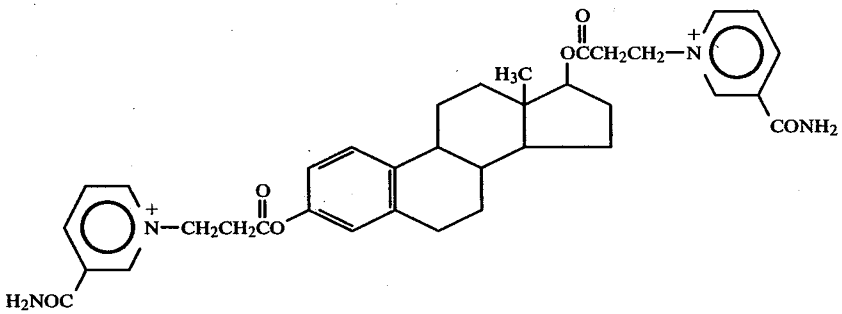 This compound can be subsequently selectively hydrolyzed by known methods to the corresponding 17-monoester of formula (II), which can be reduced to the corresponding preferred 17-monoester of formula (I). | 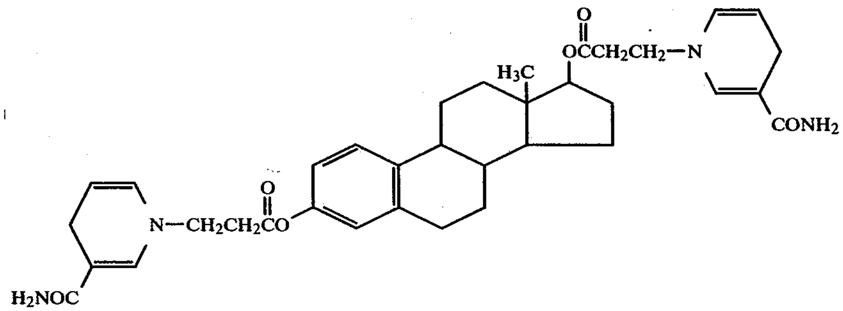 |
| 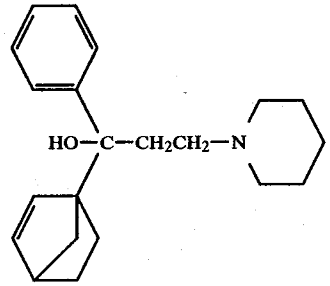 biperiden | 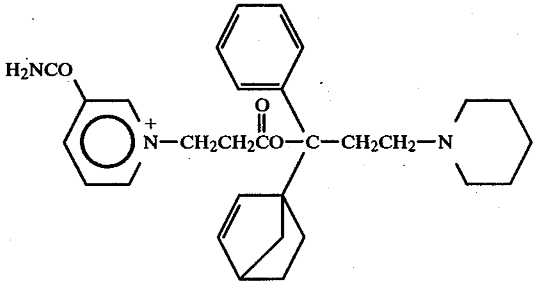 | 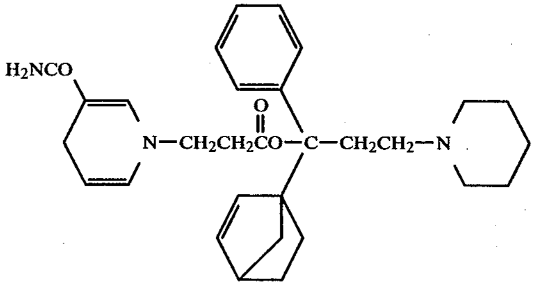 |

-continued
| Starting Material | [Ḋ—QC]+ | [D—DHC] |
|---|---|---|
| 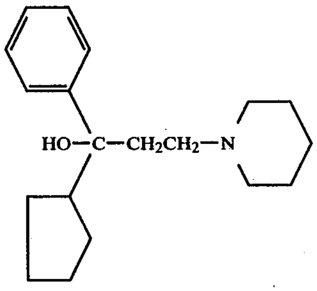 cycrimine | 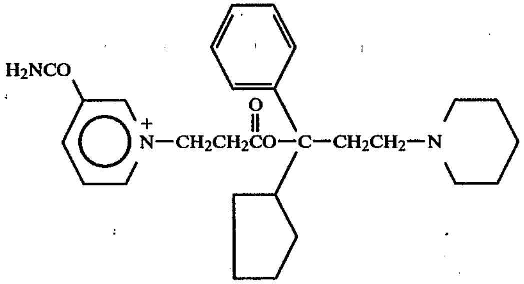 | 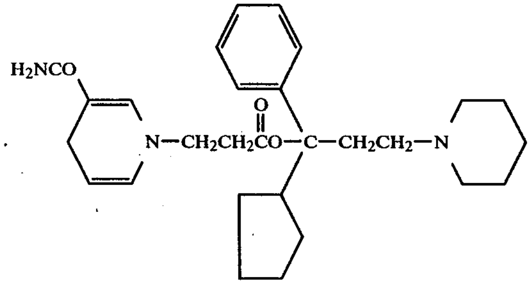 |
| 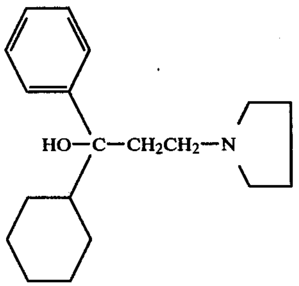 procyclidine | 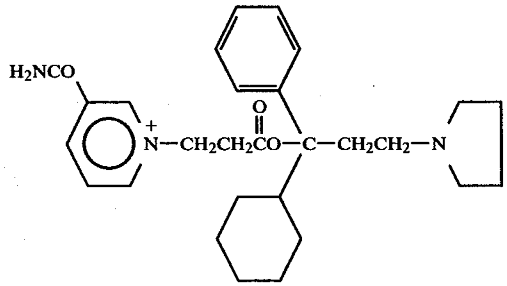 | 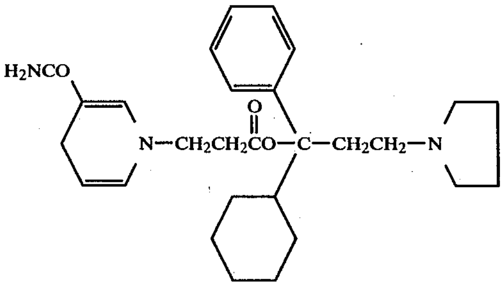 |
| 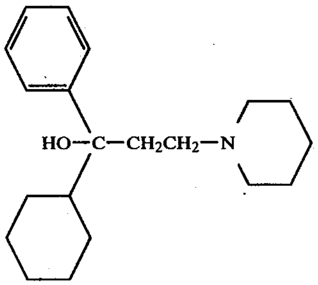 trihexyphenidyl | 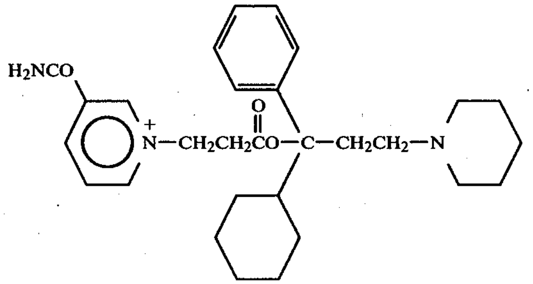 | 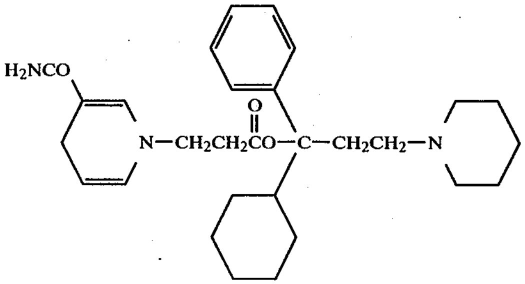 |

Method O

Method K is followed, except that the drug is reacted with 3-quinolinecarboxylic acid or its acid chloride or anhydride or activated ester instead of nicotinic acid or its acid chloride or anhydride or activated ester.

The representative drugs depicted below may be derivatized in this manner to the corresponding compounds of formulas (II) and (I), as may the remaining drugs mentioned with Method K.

Similarly, Method O may be combined with Method L or M to afford the corresponding derivatives, e.g. of the drugs mentioned with those methods.

The procedure of Method O may be repeated using 4-isoquinolinecarboxylic acid or its acid chloride or anhydride or activated ester in place of 3-quinolinecarboxylic acid or its acid chloride or anhydride or activated ester, to afford the corresponding derivatives of drugs such as those indicated with Methods K, L, and M.

3-Quniolinecarboxylic acid or its acid chloride or anhydride or activated ester or 4-isoquinolinecarboxylic acid or its acid chloride or anhydride or activated ester can also be substituted for nicotinic acid or its acid chloride or anhydride or activated ester in Method E, F or G, to afford the corresponding derivatives, e.g., of the drugs mentioned with those methods.

The general procedures described above may be utilized to provide the 1,2-dihydro derivatives as well as the depicted 1,4-dihydros.

| Starting Material | [D—QC]$^+$ | [D—DHC] |
|---|---|---|
| 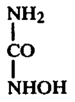 hydroxyurea | 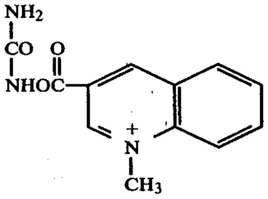 | 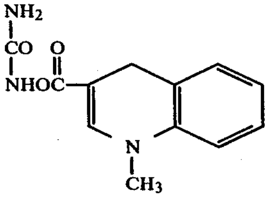 |
| 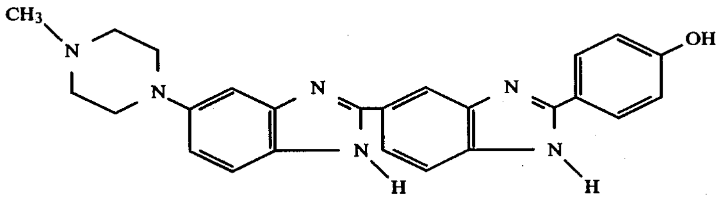 bisbenzimidazole | 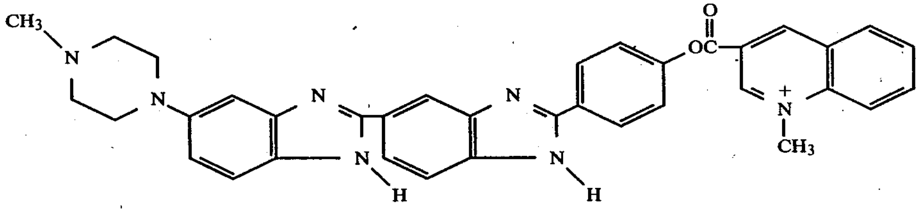 | 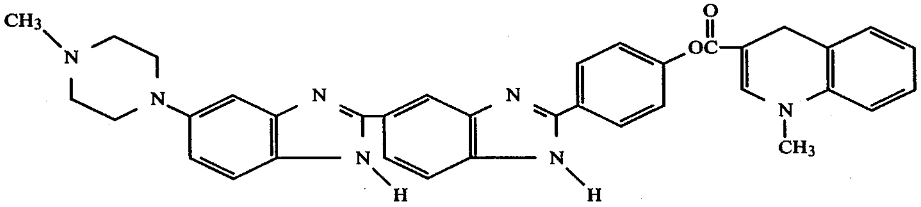 |
| 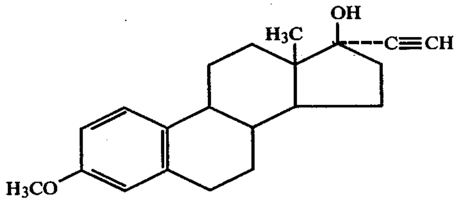 mestranol | 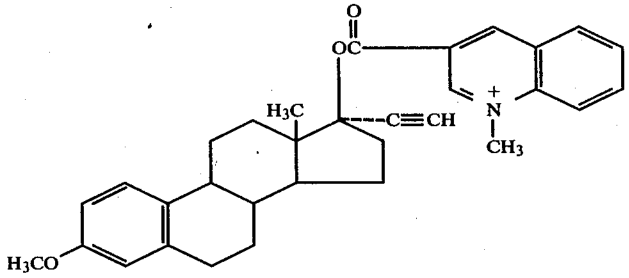 | 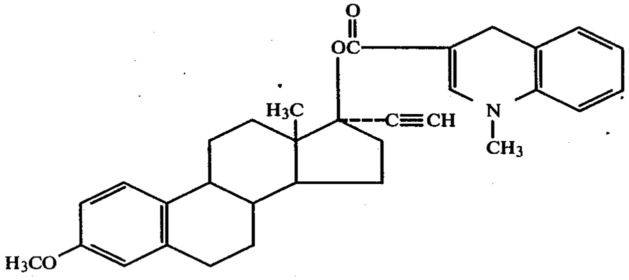 |

-continued
| Starting Material | [D—QC]+ | [D—DHC] |
|---|---|---|
| 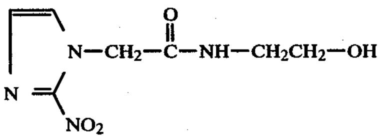 SR-2508 | 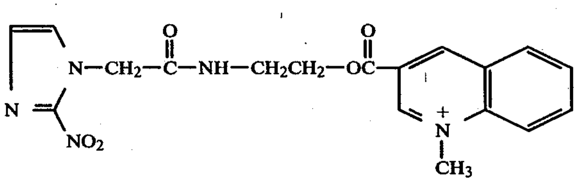 | 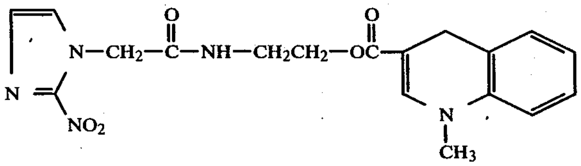 |
| 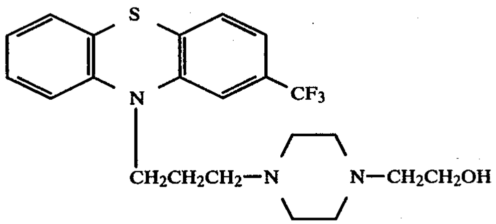 fluphenazine | 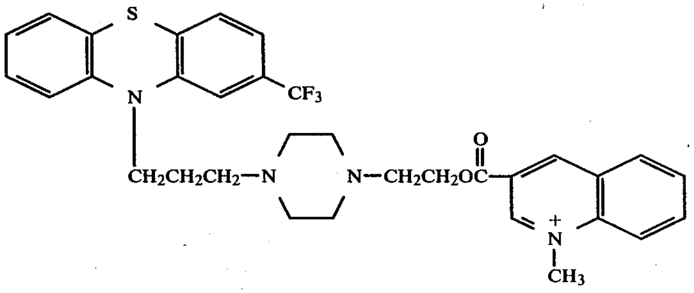 | 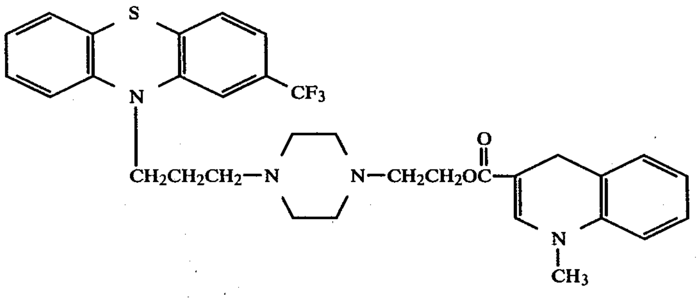 |

-continued
| Starting Material | [D—QC]+ | [D—DHC] |
| --- | --- | --- |
| 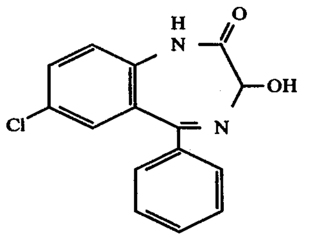 oxazepam | 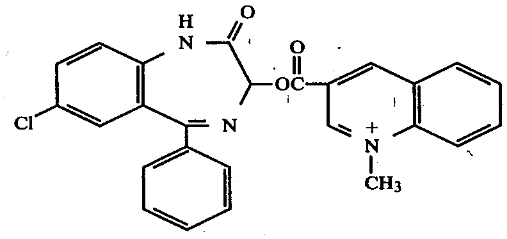 | 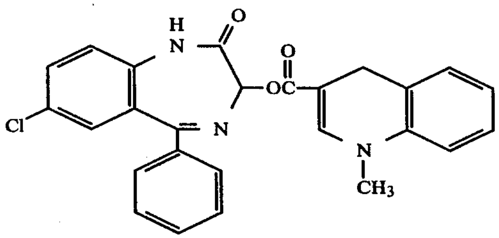 |
| 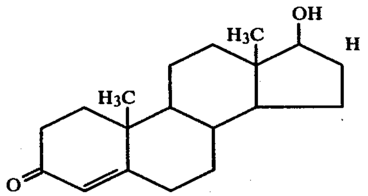 testosterone | 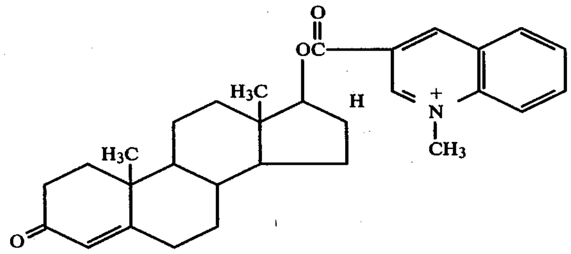 | 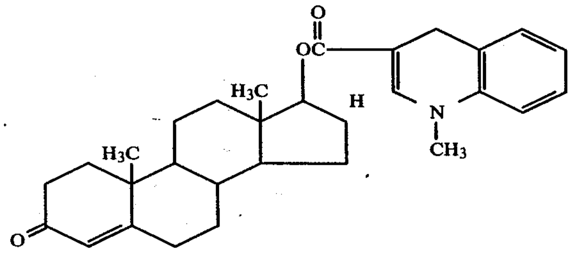 |
| 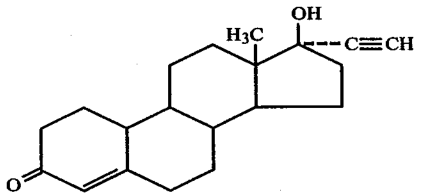 norethindrone | 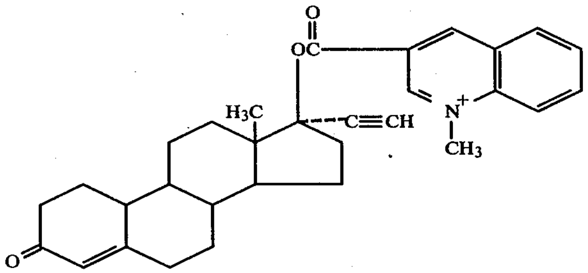 | 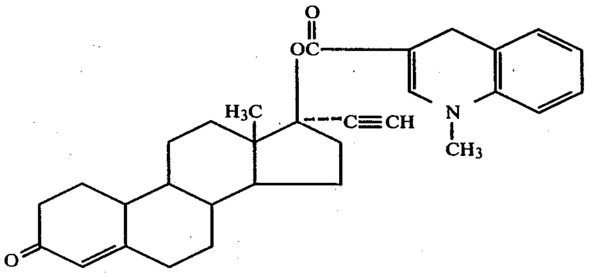 |

-continued
| Starting Material | [D—QC]+ | [D—DHC] |
|---|---|---|
| 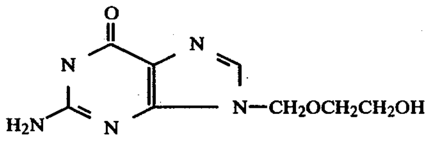 acyclovir | 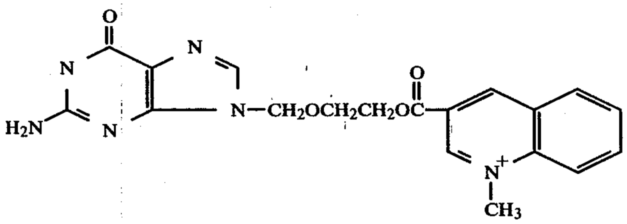 | 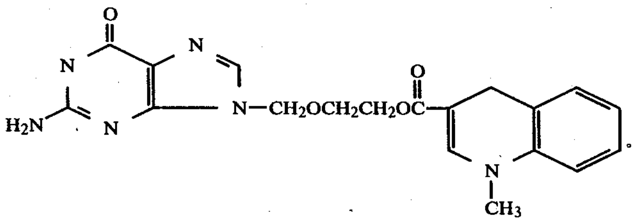 |
| 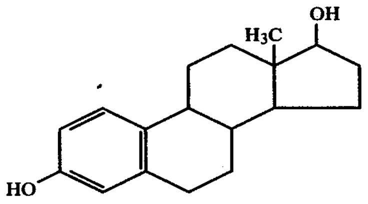 estradiol | 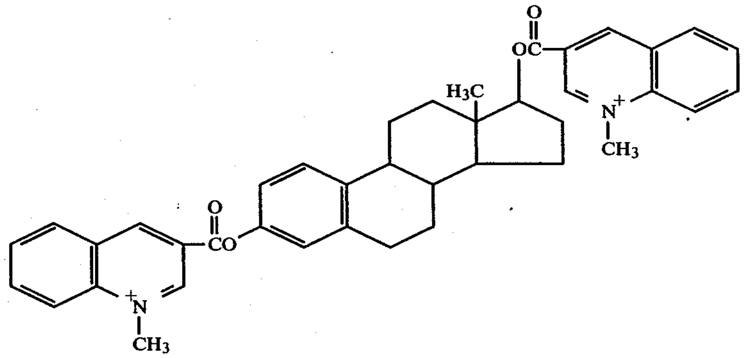 This compound can be subsequently selectively hydrolyzed by known methods to the corresponding 17-monoester of formula (II), which can be reduced to the corresponding preferred 17-monoester of formula (I). | 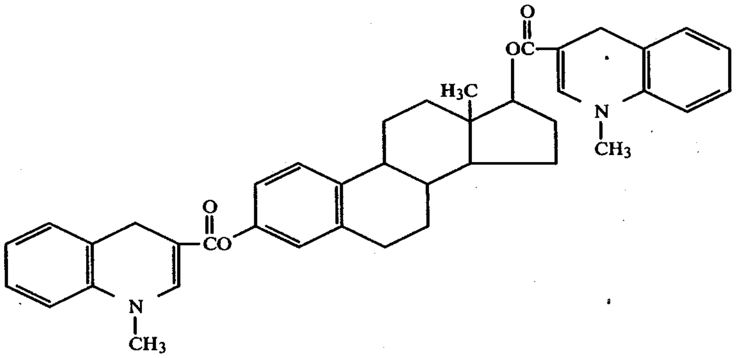 |

-continued
| Starting Material | [D—QC]+ | [D—DHC] |
| --- | --- | --- |
| 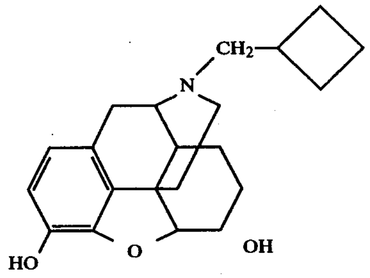 nalbuphine | 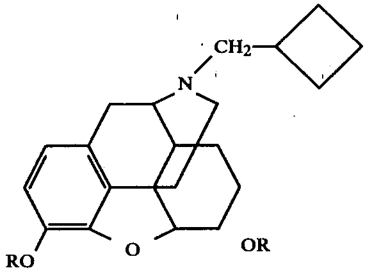 One R is 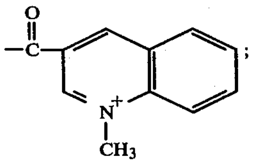 ; the other R is H or 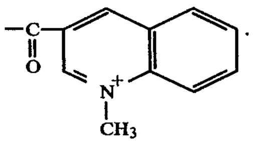 . | 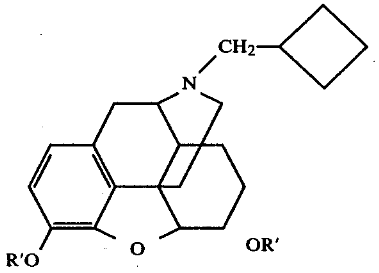 One R' is 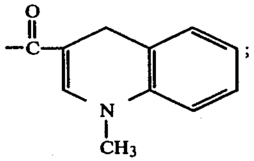 ; the other R' is H or 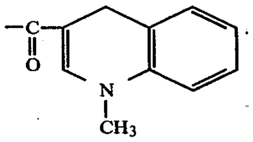 . |
| 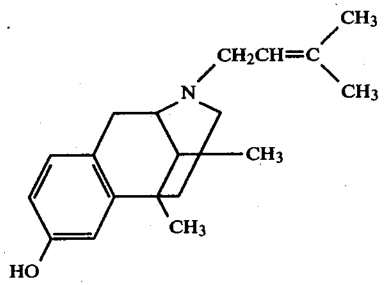 pentazocine | 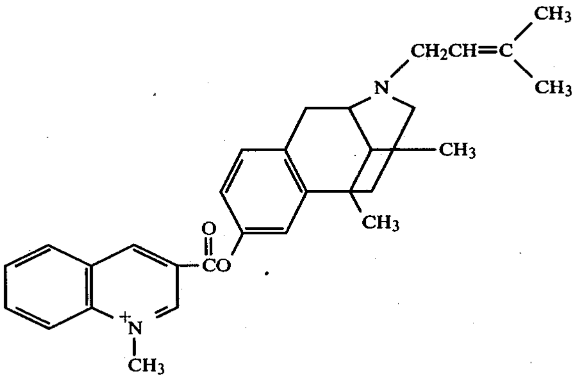 | 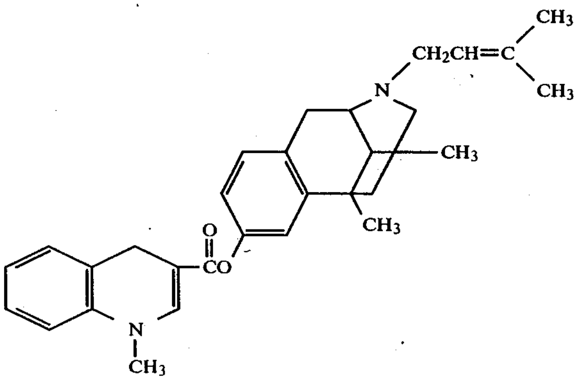 |

Method P

Method K is followed, except that a reactant of the formula

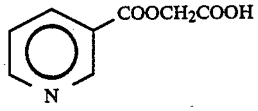

is used in place of nicotinic acid.

The representative drugs mentioned below may be derivatized in this manner to the corresponding compounds of formulas (II) and (I), as may the remaining drugs mentioned with Method K.

Similarly, Method P may be combined with Methods L and M to afford the corresponding derivatives, e.g. of the drugs mentioned with those methods.

A starting material of the formula set forth immediately above can also be substituted for nicotinic acid in Method E, F or G to afford the corresponding derivatives, e.g. of the drugs mentioned with those methods.

Alternatively, Method P may follow Method K except that it employs a reactant of the formula

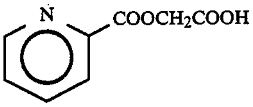

or

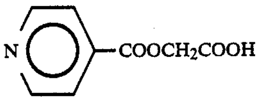

(prepared as described in Method I), to afford derivatives of the drugs indicated with method K. This alternative form of Method P may also be combined with Method L or M, to afford the corresponding derivatives of the drugs mentioned with Method L or M. also, these alternative Method P starting materials may be substituted for nicotinic acid in Method E, F or G to give the corresponding derivatives of the drugs specified wwith those methods.

| STARTING MATERIAL | [D—QC]+ | [D—DHC] |
|---|---|---|
| 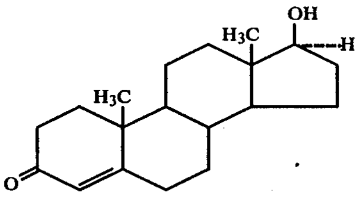 testosterone | 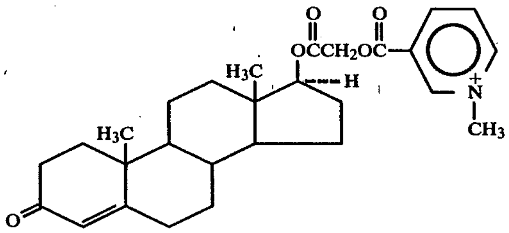 | 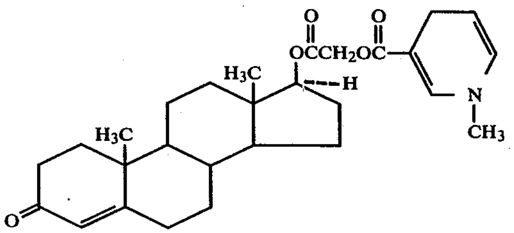 |
| 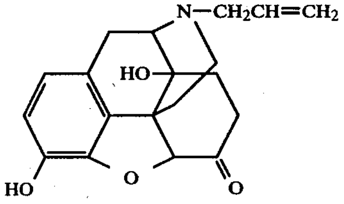 naloxone | 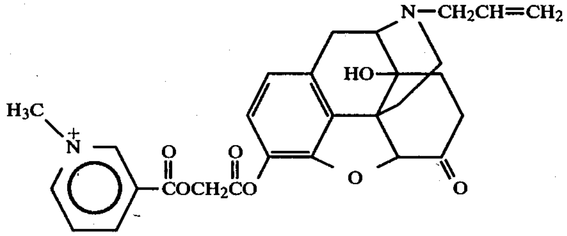 | 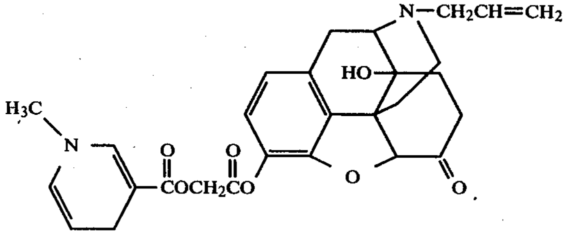 |
| 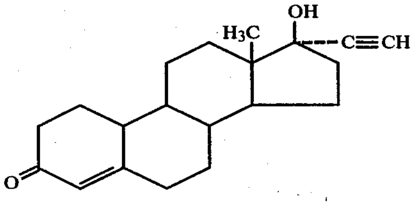 norethindrone | 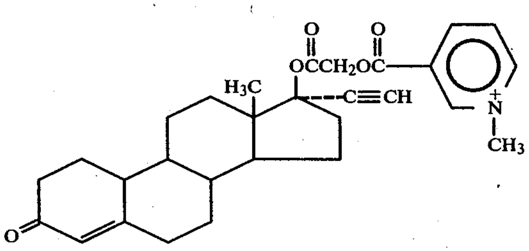 | 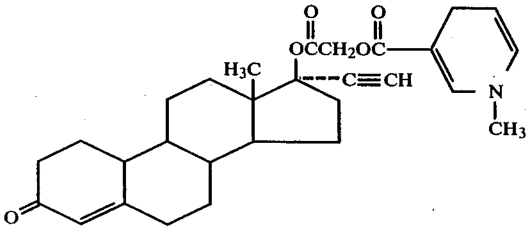 |

-continued
| STARTING MATERIAL | [D—QC]+ | [D—DHC] |
|---|---|---|
| 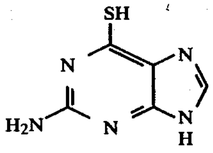 thioguanine | 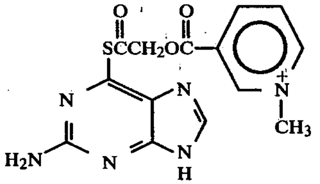 | 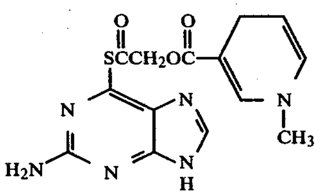 |
| 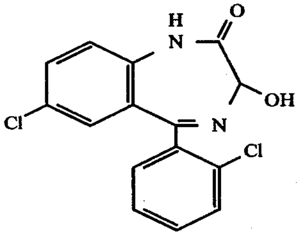 lorazepam | 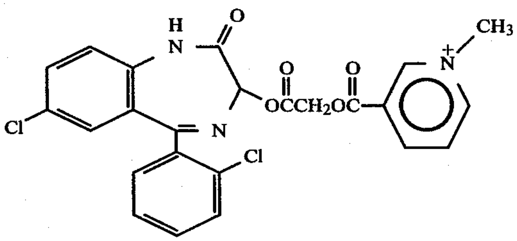 | 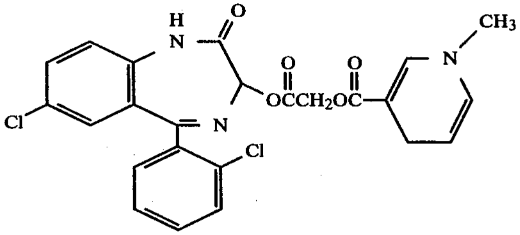 |
| 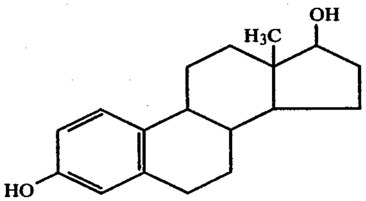 estradiol | | 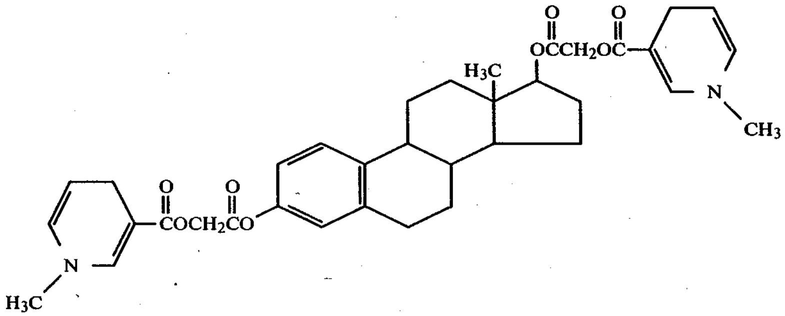 |

-continued
| STARTING MATERIAL | [D—QC]+ | [D—DHC] |
| --- | --- | --- |
| | 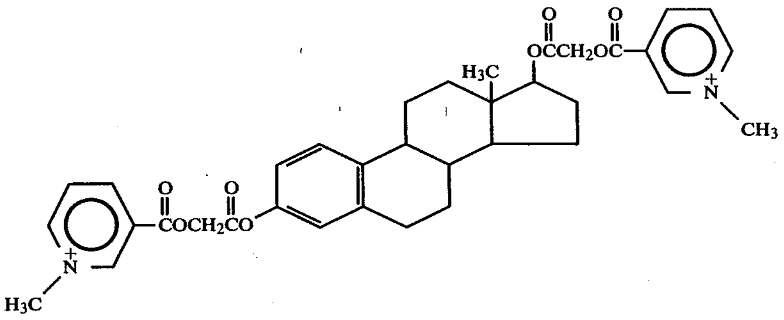 This compound can be subsequently selectively hydrolyzed by known methods to the corresponding 17-monoester of formula (II), which can be reduced to the corresponding preferred 17-monoester of formula (I). | |
| 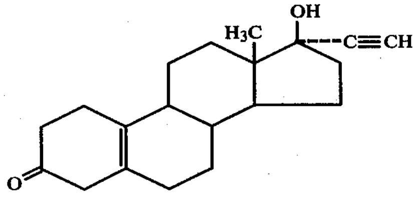 norethynodrel | 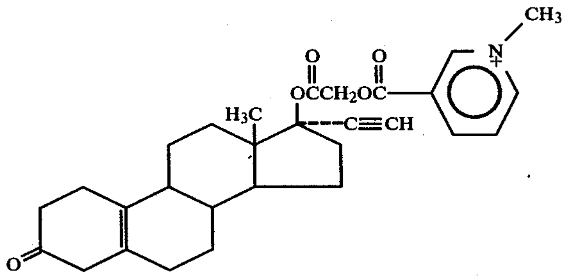 | 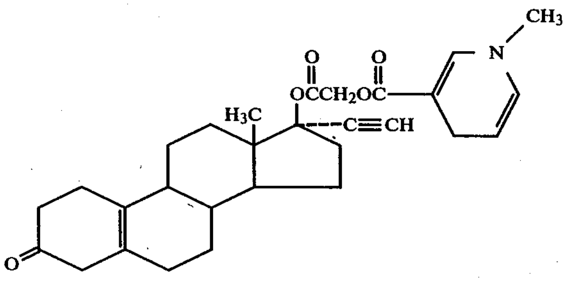 |
| 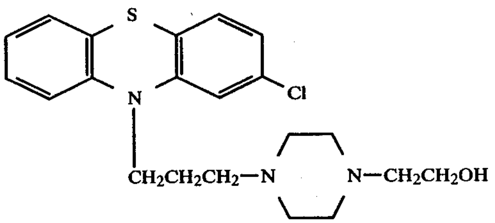 perphenazine | | 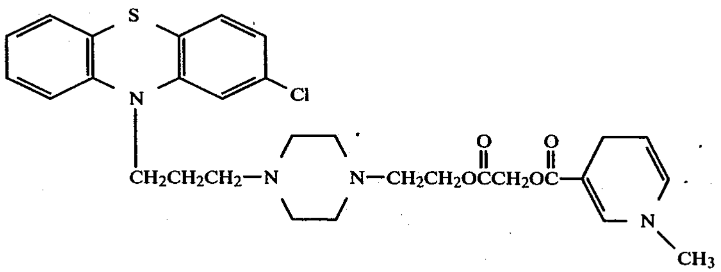 |

-continued
| STARTING MATERIAL | [D—QC]+ | [D—DHC] |
|---|---|---|
| | 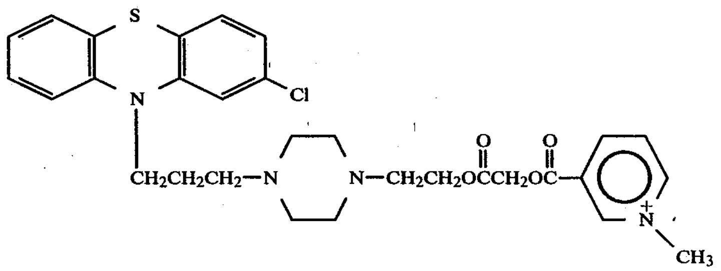 | |

III.

Methods for Derivatizing —COOH Functions in Drugs

Method Q

Nicotinic acid or an activated ester thereof is reacted with an aminoalkanol $H_2N—Z'—OH$ wherein Z' is $C_1$–$C_8$ straight or branched alkylene, e.g. 2-aminoethanol, to afford the corresponding intermediate alcohol, e.g. in the case of 2-aminoethanol, an intermediate of the formula

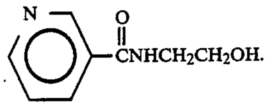

That alcohol is then reacted with a drug containing one or more —COOH functions, in the presence of a suitable coupling agent such as dicyclohexylcarbodiimide. The compound thus obtained is then quaternized and subsequently reduced as described above in Method A.

Analogous starting materials can be readily prepared by reacting the selected aminoalkanol with picolinic acid, isonicotinic acid, 3-quinolinecarboxylic acid, 4-isoquinolinecarboxylic acid or the like to afford the desired intermediate, which can then be quaternized and subsequently reduced as described above.

The representative drugs depicted below may be derivatized in this manner to the corresponding compounds of formulas (II) and (I). Drugs such as methicillin, ticarcillin, oxacillin, dicloxacillin, glyoxylic acid sulfonyl hydrazone, 5-methyltetrahydrohomofolic acid, phenoxymethylpenicillin, fenbufen, fenoprofen, idoprofen, ketoprofen, fluprofen, bucloxic acid, tolmetin, alclofenac, fenclozic acid, ibufenac, meclofenamic acid, flufenamic acid, flufenisal, clonixin, carprofen, etodolac, flutiazin, pirprofen, furosemide, cefoxitin and clorazepate may be similarly derivatized.

| STARTING MATERIAL | [D—QC]+ | [D—DHC] |
|---|---|---|
| 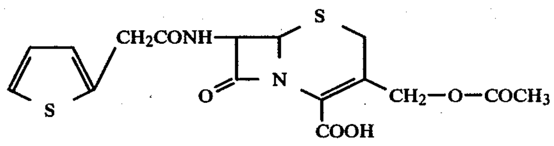 cephalothin | 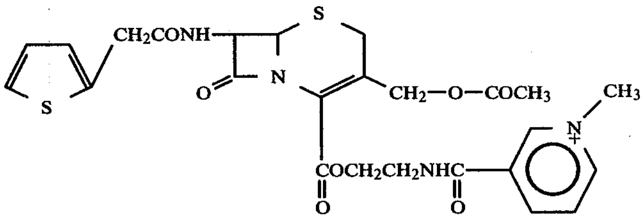 | 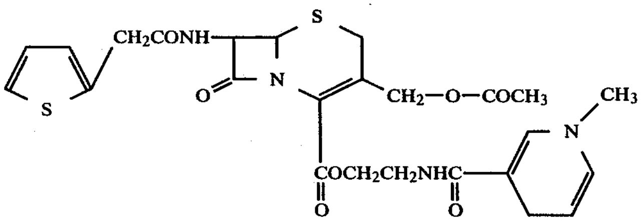 |
| 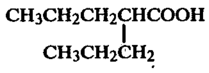 valproic acid | 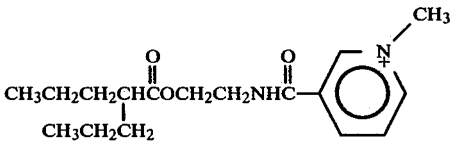 | 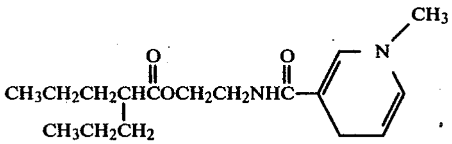 |
| 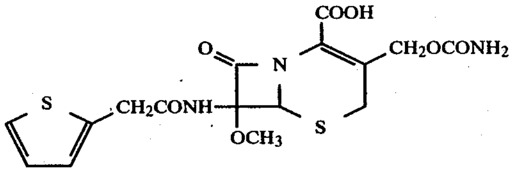 cefoxitin | | 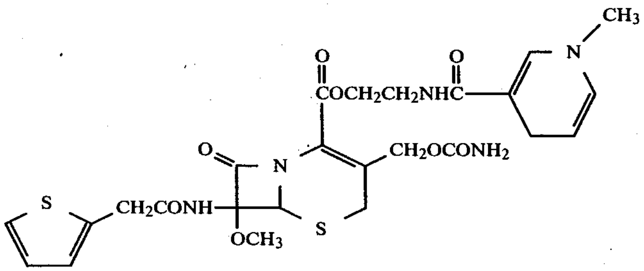 |

-continued
| STARTING MATERIAL | [D—QC]+ | [D—DHC] |
|---|---|---|
| | 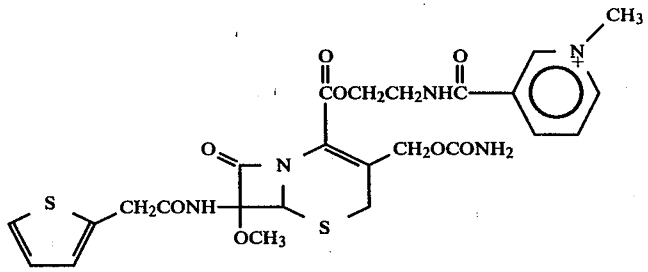 | |
| 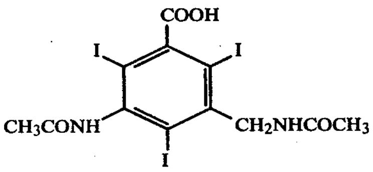 iodomide | 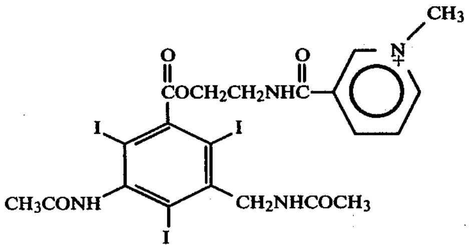 | 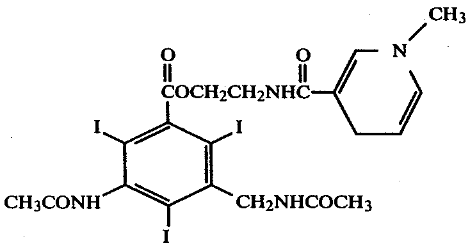 |
| 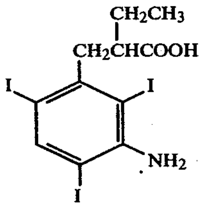 iopanoic acid | 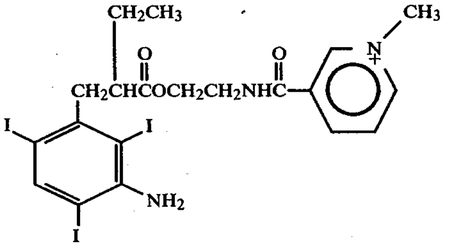 | 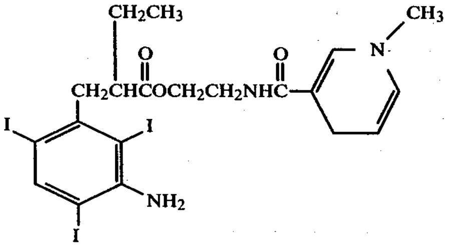 |

-continued
| STARTING MATERIAL | [D—QC]+ | [D—DHC] |
|---|---|---|
| 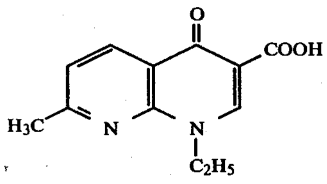 nalidixic acid | 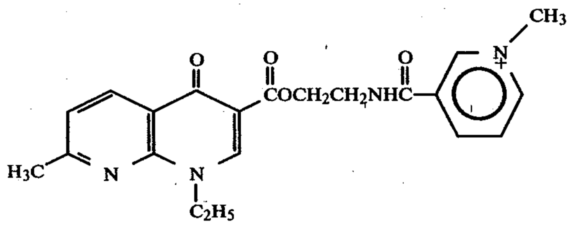 | 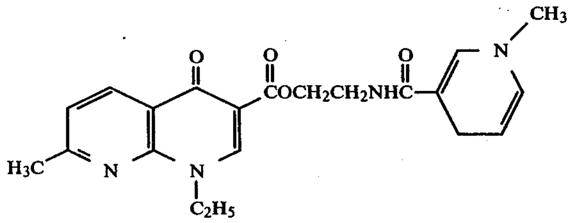 |
| 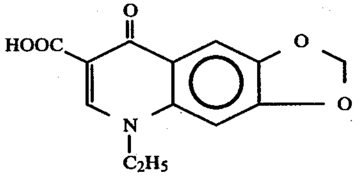 oxolinic acid | 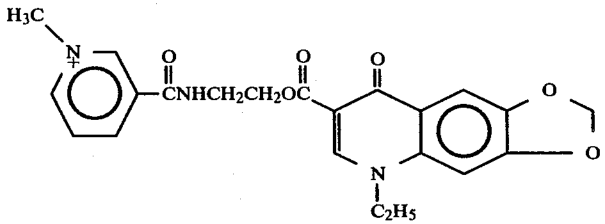 | 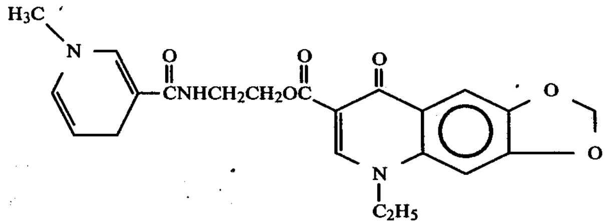 |
| 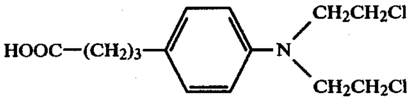 chlorambucil | 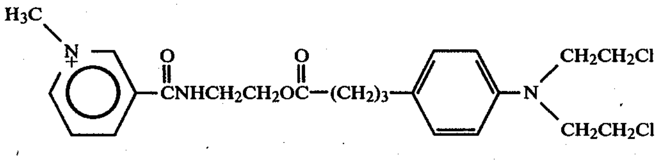 | 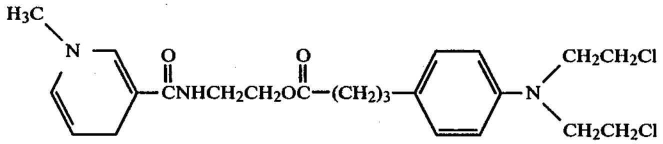 |
| 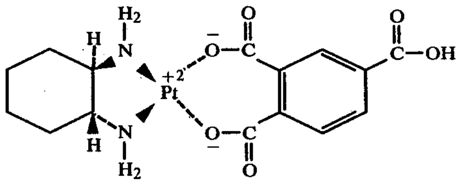 DACH | | 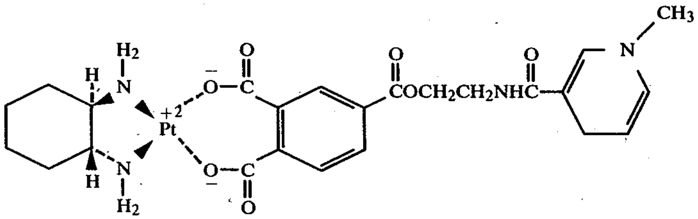 |

-continued
| STARTING MATERIAL | [D—QC]+ | [D—DHC] |
|---|---|---|
| | 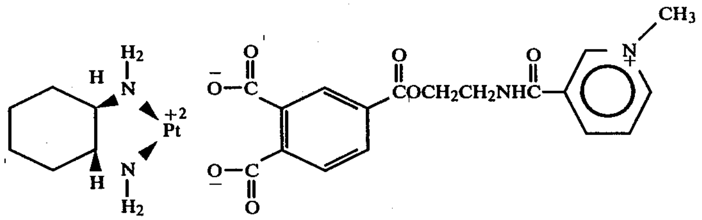 | |
| 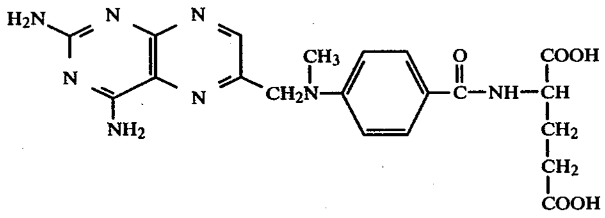 methotrexate | 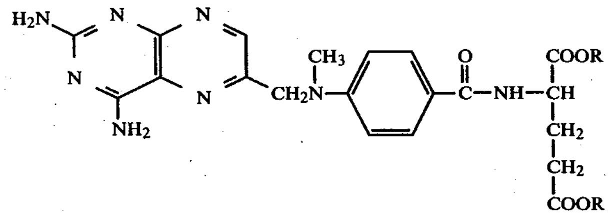 One R is 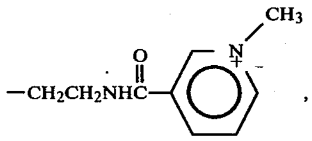, the other R is H or 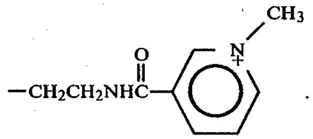. | 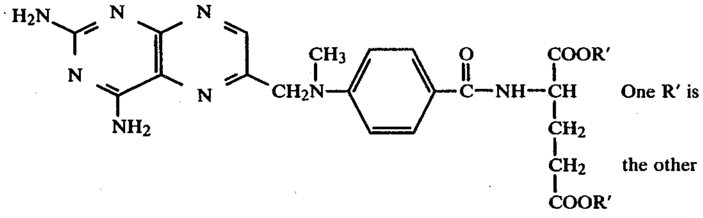 One R' is 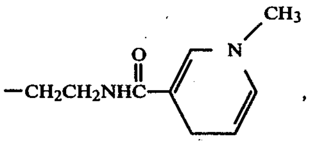, the other R' is H or 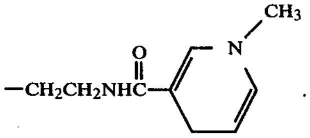. |

-continued
| STARTING MATERIAL | [D—QC]+ | [D—DHC] |
|---|---|---|
| 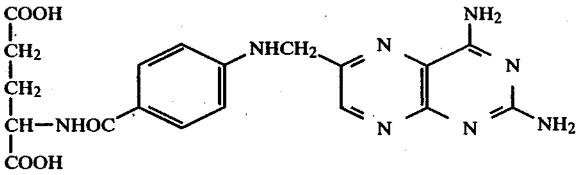<br>aminopterin | 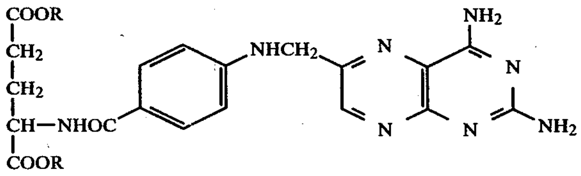 | 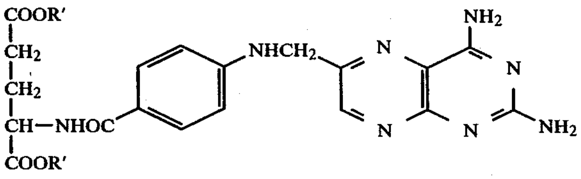 One R' is 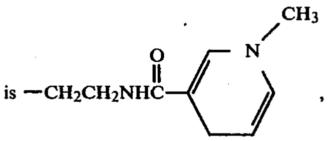,<br>the other R' is H or<br>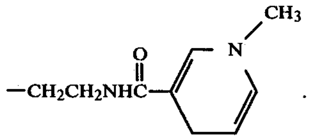. |
| | One R is 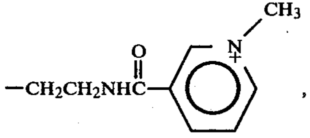,<br>the other R is H or<br>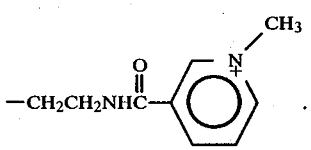. | |
| 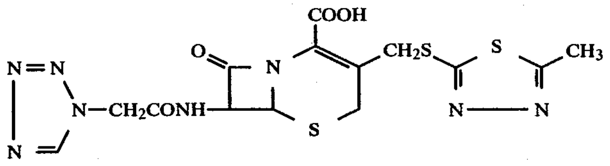<br>cefazolin | | 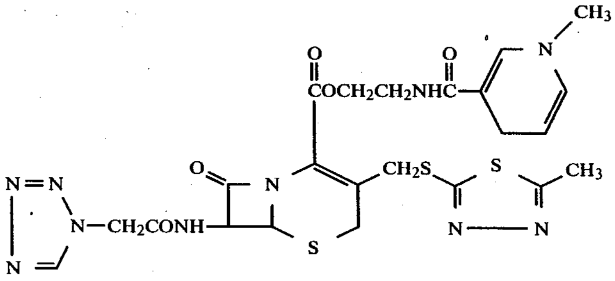 |

-continued
| STARTING MATERIAL | [D−QC]+ | [D−DHC] |
|---|---|---|
| | 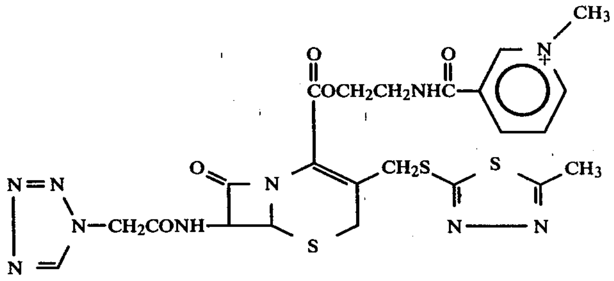 | |
| 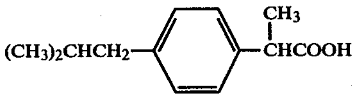 ibuprofen | 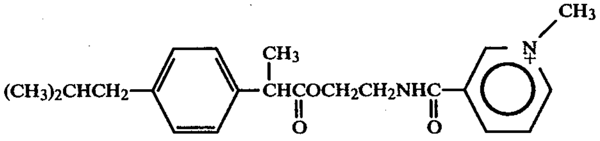 | 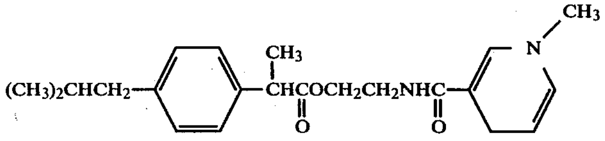 |
| 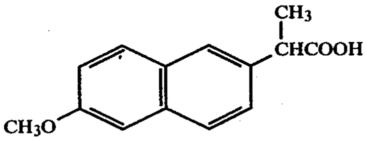 naproxen | 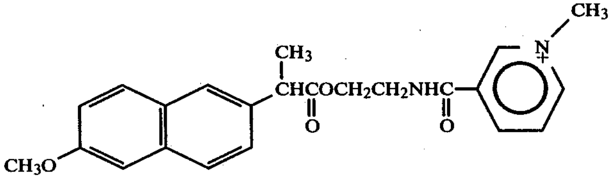 | 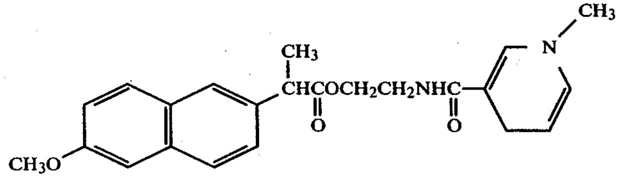 |
| 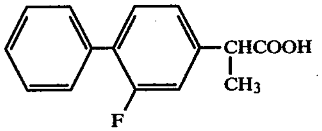 flurbiprofen | 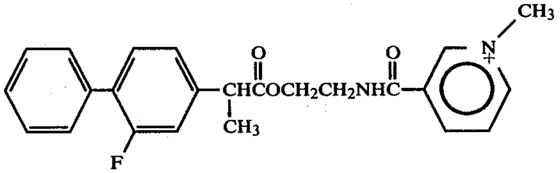 | 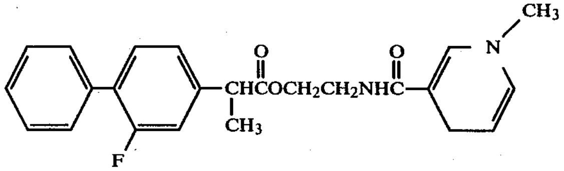 |

-continued
| STARTING MATERIAL | [D—QC]+ | [D—DHC] |
|---|---|---|
| 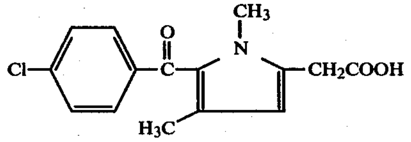<br>zomepirac | 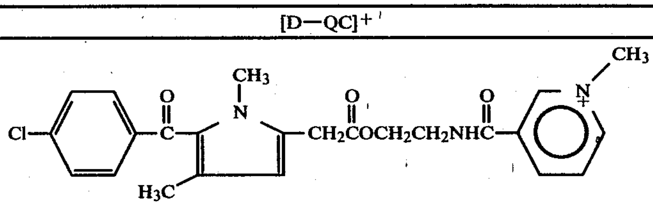 | 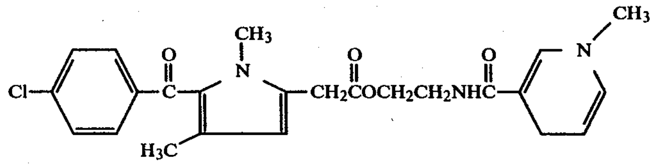 |
| 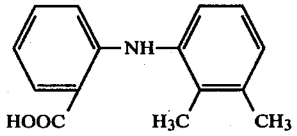<br>mefenamic acid | 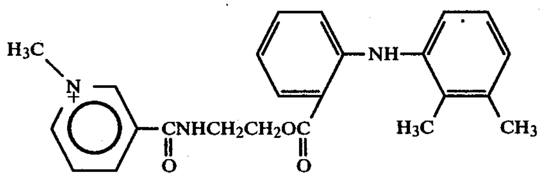 | 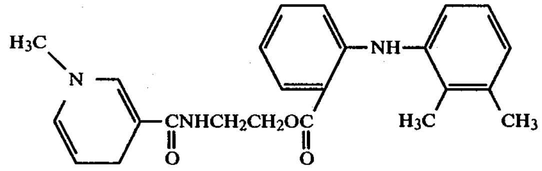 |
| 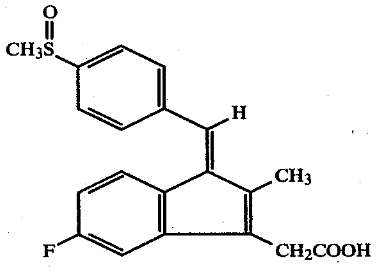<br>sulindac | 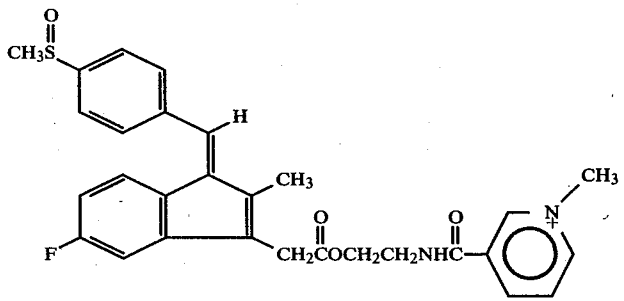 | 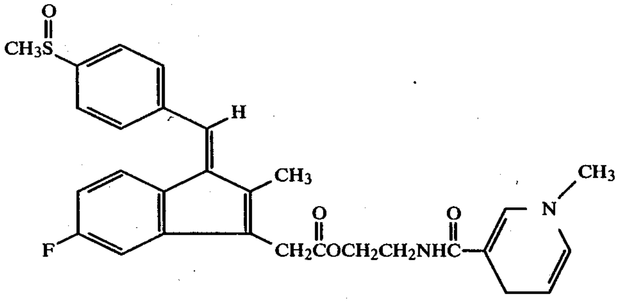 |
| 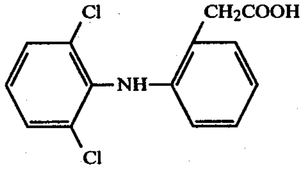<br>diclofenac | 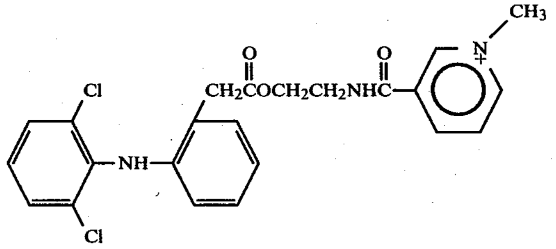 | 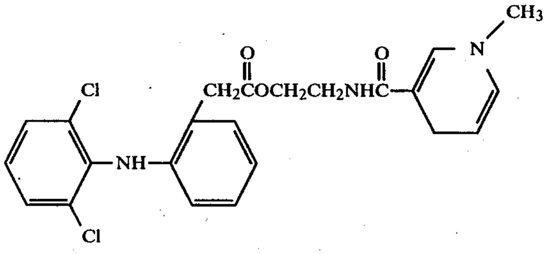 |

-continued
| STARTING MATERIAL | [D—QC]+ | [D—DHC] |
| --- | --- | --- |
| 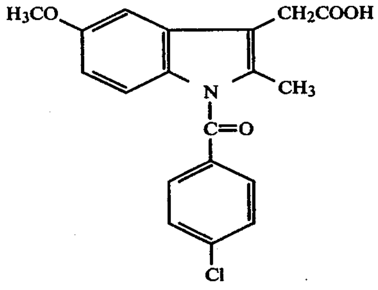 indomethacin | 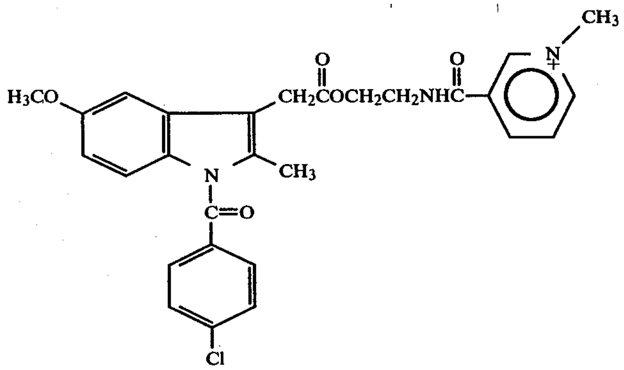 | 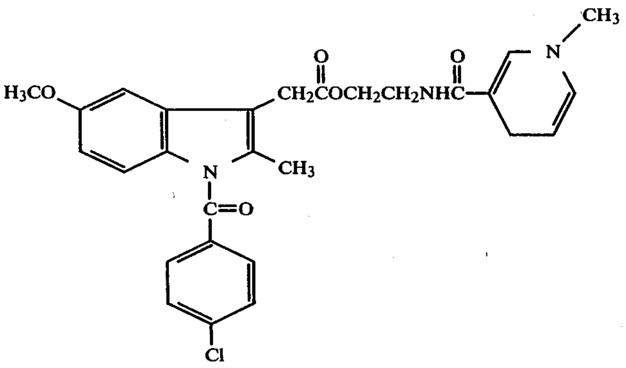 |
| 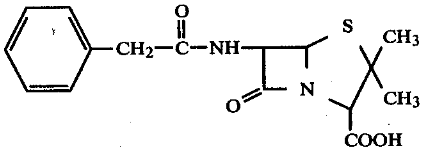 benzylpenicillin | 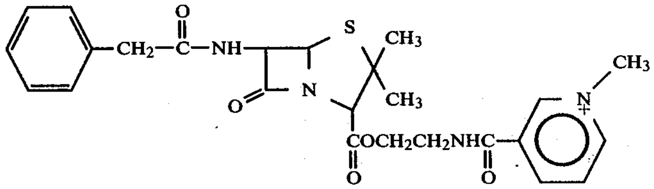 | 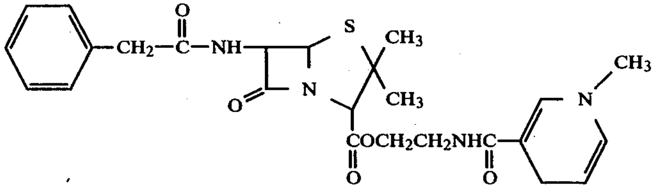 |

-continued
| STARTING MATERIAL | [D—QC]+ | [D—DHC] |
| --- | --- | --- |
| 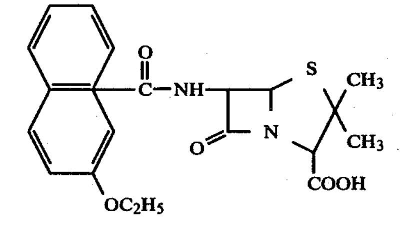 nafcillin | 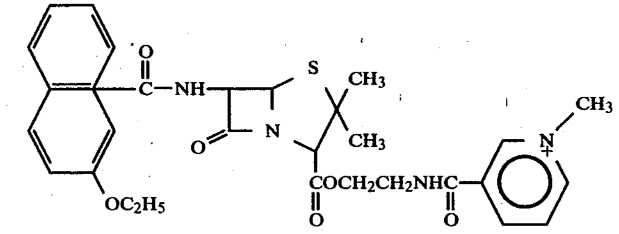 | 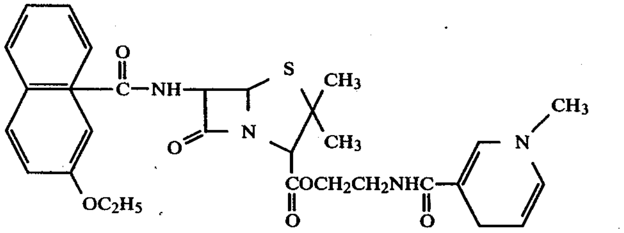 |
| 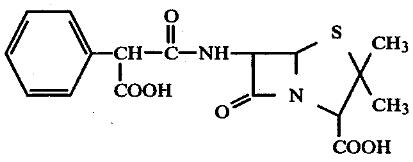 carbenicillin | 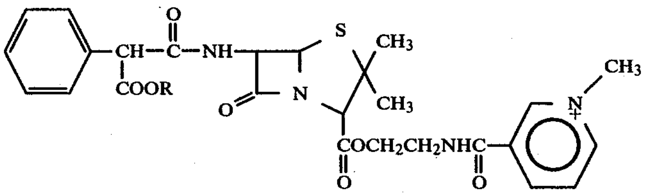 R is H or 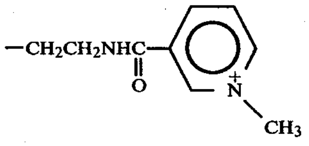 | 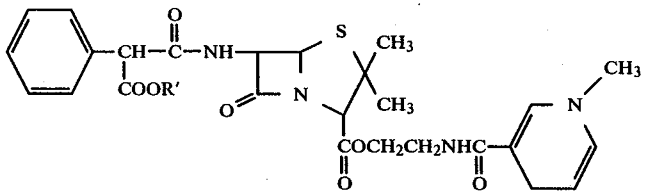 R' is H or 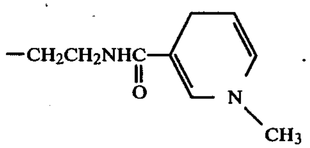 |
| 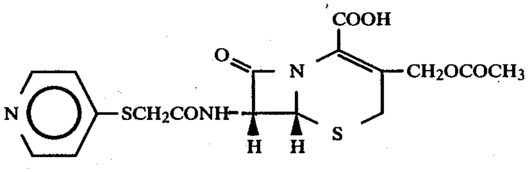 cephapirin | | 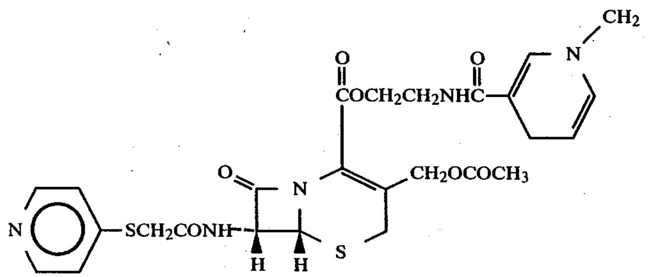 |

-continued
| STARTING MATERIAL | [D—QC]+ | [D—DHC] |
|---|---|---|
| | 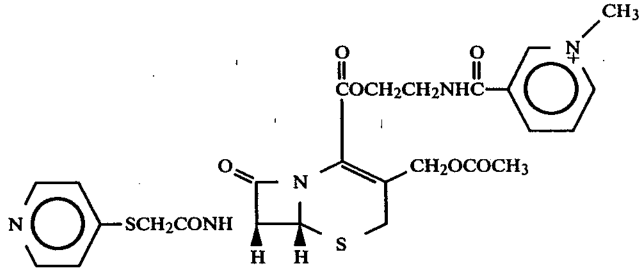 | |
| 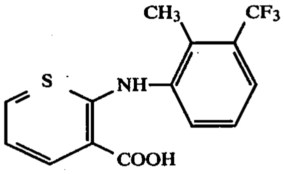 flunixin | 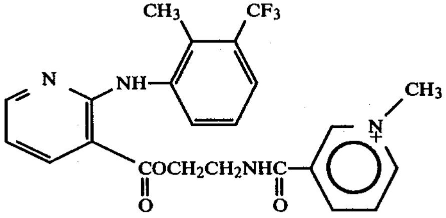 | 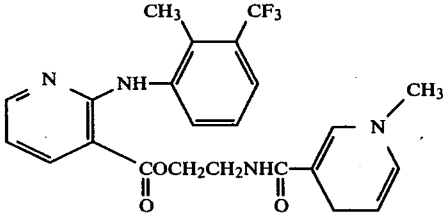 |
| 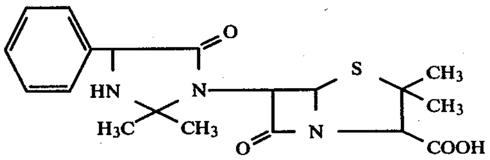 hetocillin | 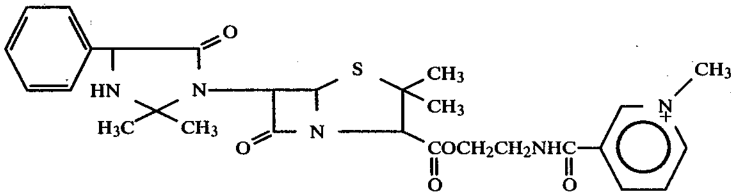 | 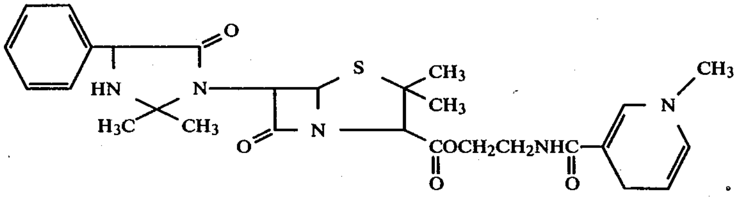 |

-continued
| STARTING MATERIAL | [D—QC]$^+$ | [D—DHC] |
|---|---|---|
| 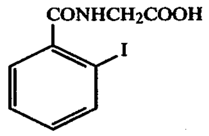 o-iodohippuric acid | 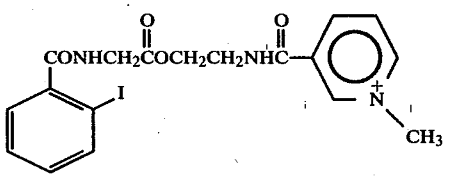 | 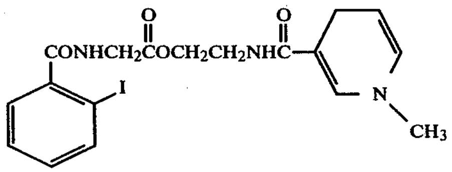 |
| 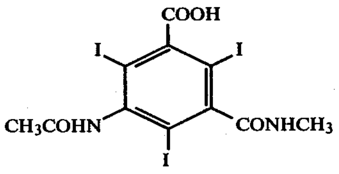 iothalmic acid | 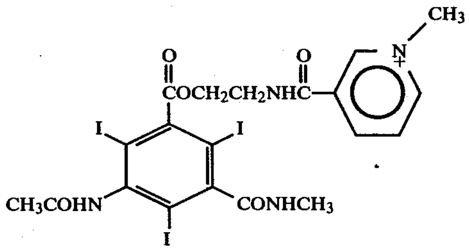 | 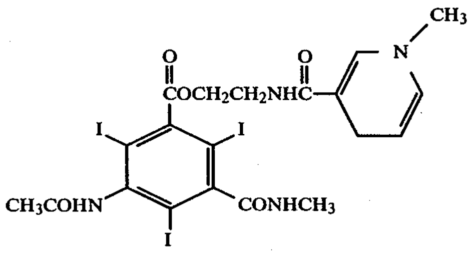 |
| 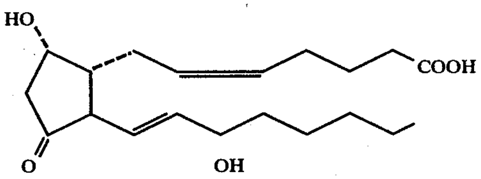 PGD$_2$ | 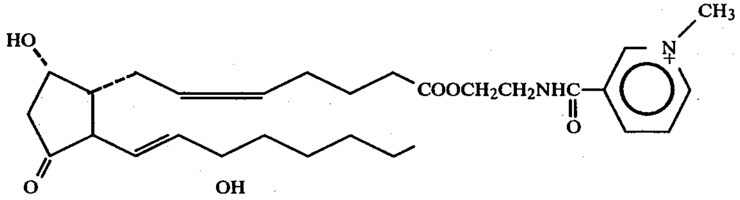 | 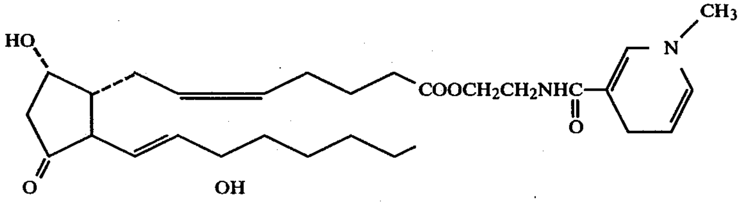 |

-continued
| STARTING MATERIAL | [D—QC]+ | [D—DHC] |
|---|---|---|
| 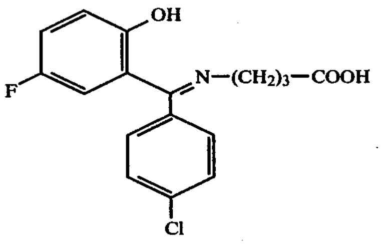 | 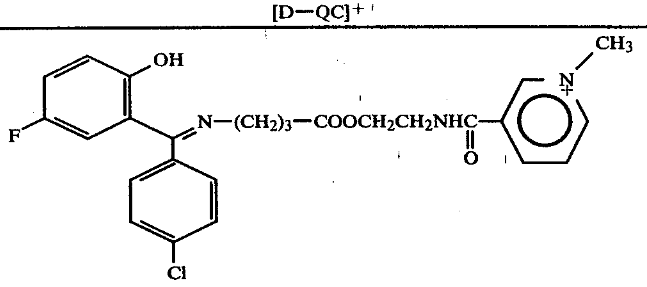 | 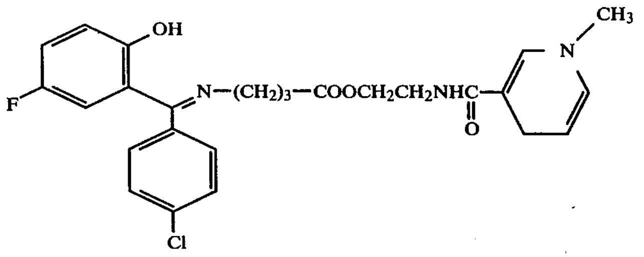 |
| SL 75102 | | |

Method R

This is a variation of Method Q used when the drug contains one or more —OH or —SH functions which are to be protected.

The drug is first reacted with excess trimethylacetyl chloride to convert the hydroxy group(s) to pivalyloxy group(s). (Various other hydroxy protecting groups may be introduced in similar fashion.) The protected drug is then reacted with the intermediate alcohol

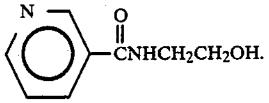

in the presence of dicyclohexylcarbodiimide or other appropriate agent for coupling the —COOH function of the drug to the hydroxy function of the depicted intermediate. (Other intermediate alcohols can be employed, e.g. as described in Method Q.) The resultant compound is then quaternized and the quaternary subsequently reduced as in Method A.

The representative drugs depicted below may be derivatized in this manner to the corresponding compounds of formulas (II) and (I). Drugs such as clorazepate, 4-hydroxy-2-n-propylpentanoic acid, 3-hydroxy-2-n-propylpentanoic acid and captopril may be similarly derivatized.

| STARTING MATERIAL | [D—QC]+ | [D—DHC] |
|---|---|---|
| 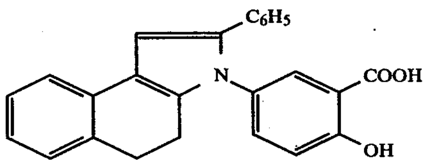 fendosal | 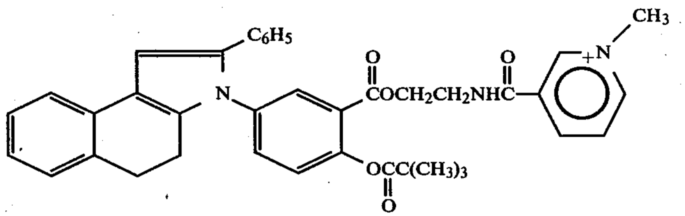 | 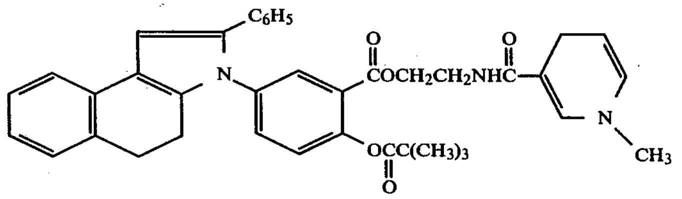 |
| 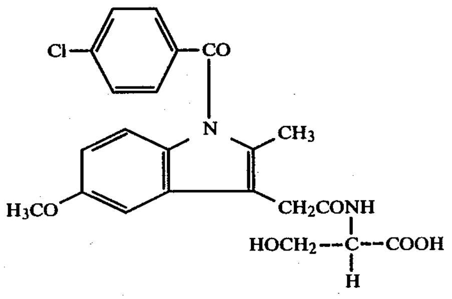 sermetacin | | 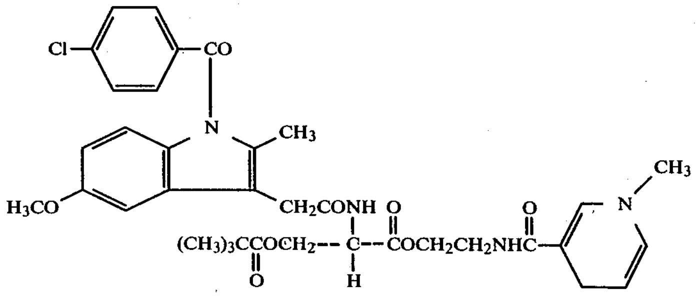 |

-continued
| STARTING MATERIAL | [D—QC]+ | [D—DHC] |
| --- | --- | --- |
| | 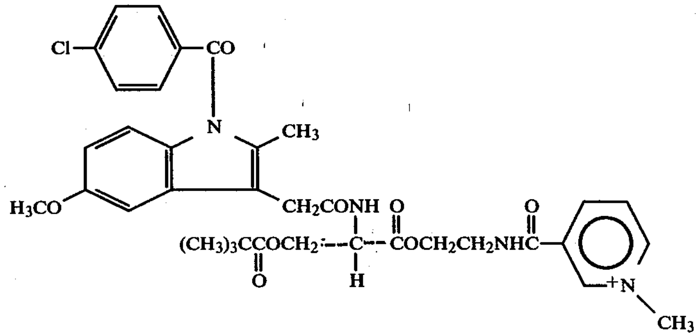 | |
| 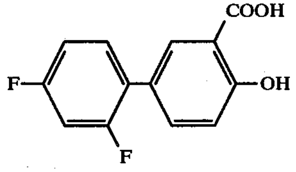 diflunisal | 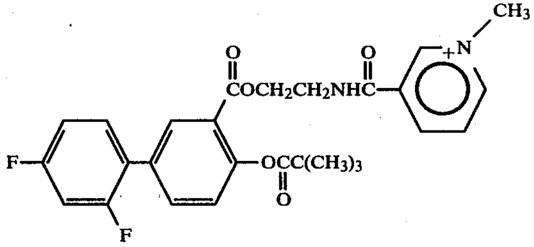 | 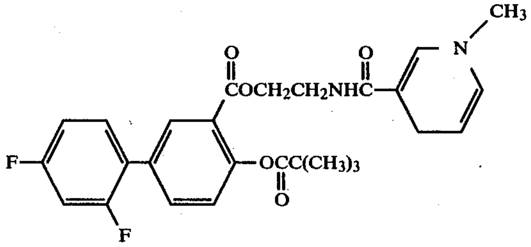 |
| 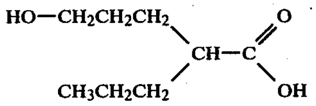 5-hydroxy-2-n-propylpentanoic acid | 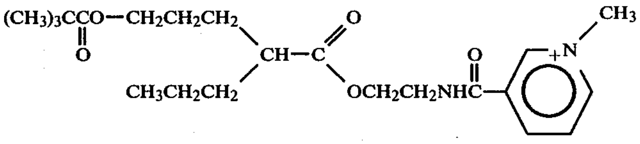 | 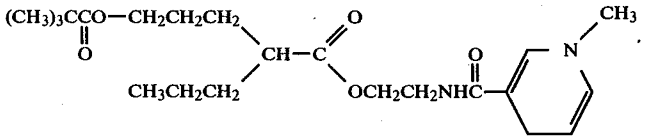 |

-continued
| STARTING MATERIAL | [D—QC]+ | [D—DHC] |
| --- | --- | --- |
| 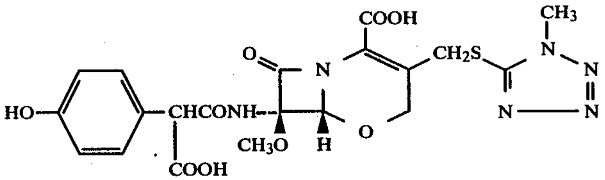 moxalactam | 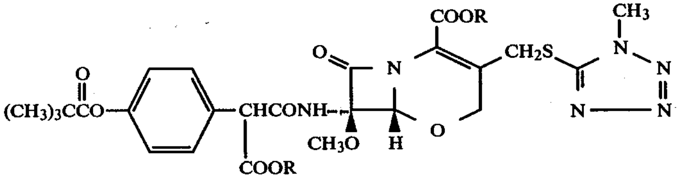 One R is 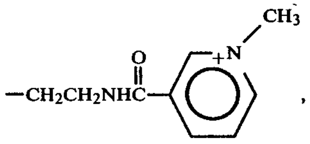 , the other R is H or 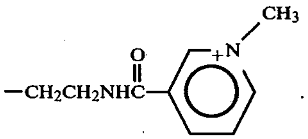 . | 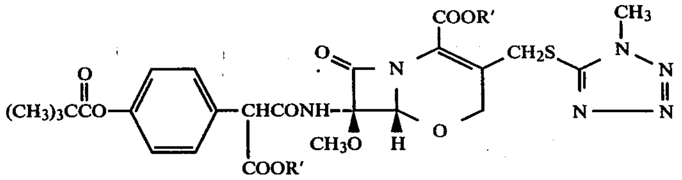 One R' is 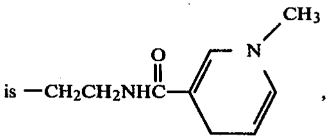 , the other R' is H or 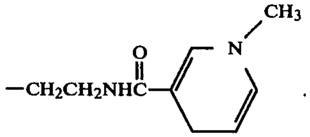 . |
| 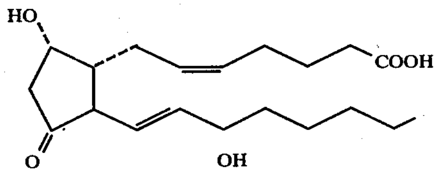 $PGD_2$ | | 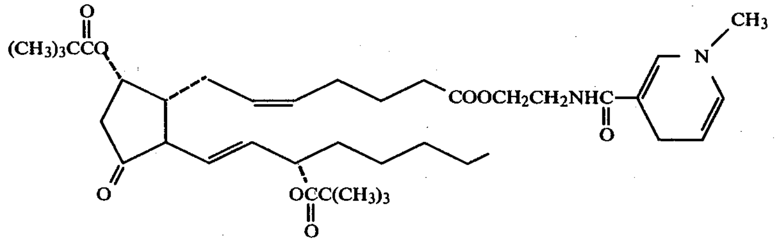 |

-continued
| STARTING MATERIAL | [D—QC]+ | [D—DHC] |
|---|---|---|
| | 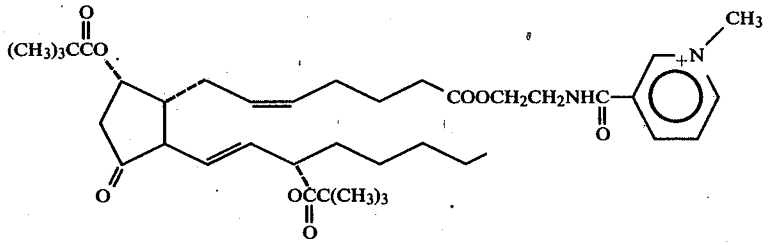 | |

Method S

This is a variation of Method Q used when the drug contains one or more amino functions which are to be protected. Generally, the amino group is protected prior to any reaction of the carboxyl function; typically, a benzyloxycarbonyl group is introduced in conventional manner to protect the amino function and then the N-protected drug is reacted with the intermediate alcohol as is Methods Q and R. Removal of the protecting group, in conventional fashion, takes place when protection is no longer needed, generally before formation of the formula (II) quaternary and subsequent reduction to the compound of formula (I).

The representative drugs depicted below may be derivatized in this manner to the corresponding compounds of formulas (II) and (I). GABA and other omega amino acids, other natural amino acids such as glycine, tyrosine, aspartic acid and glutamic acid, small peptides (e.g. met$^5$-enkephalin and leu$^5$-enkephalin and other 2–20 amino acid unit peptides) and the like may be similarly derivatized.

| STARTING MATERIAL | [D—QC]+ | [D—DHC] |
|---|---|---|
| 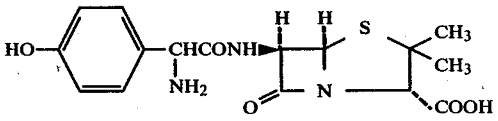 amoxicillin | 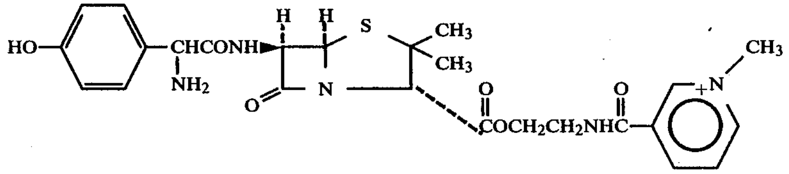 | 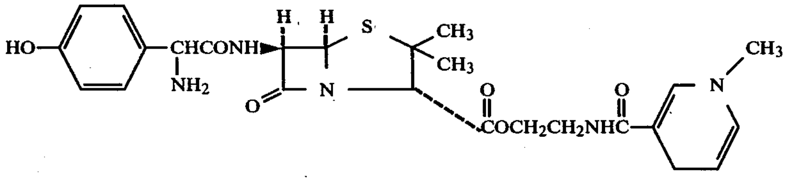 |
| 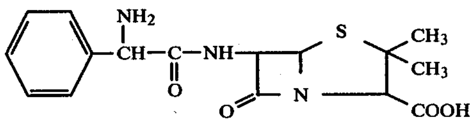 ampicillin | 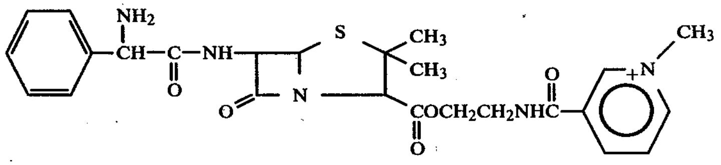 | 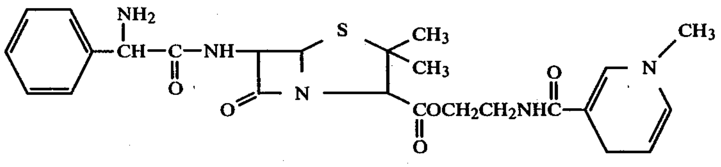 |
| 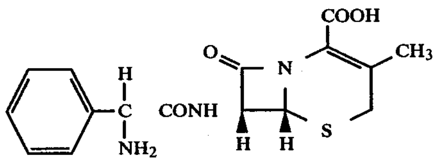 cephalexin | | 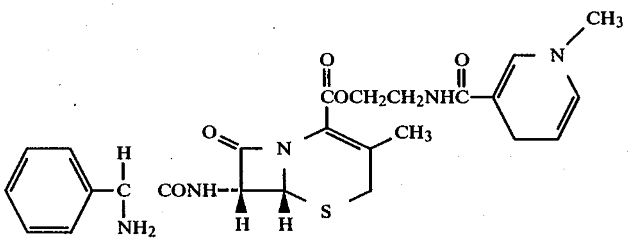 |

-continued
| STARTING MATERIAL | [D—QC]+ | [D—DHC] |
|---|---|---|
| | 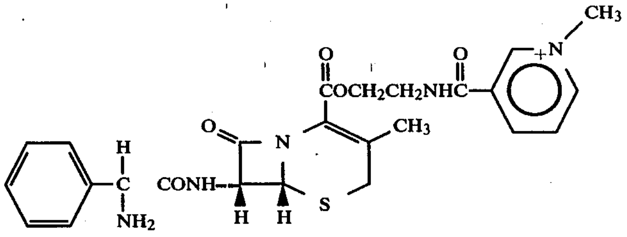 | |
| 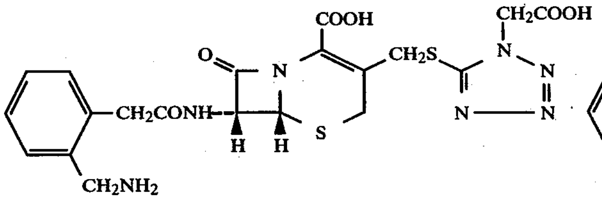 ceforanide | 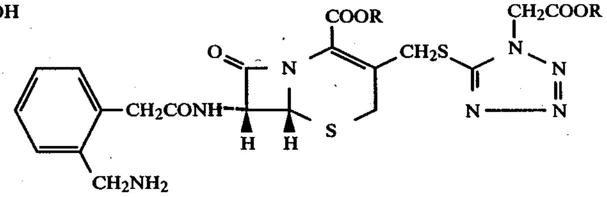 One R is 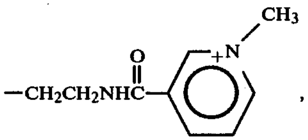 , the other R is H or 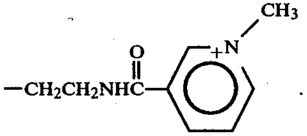 . | 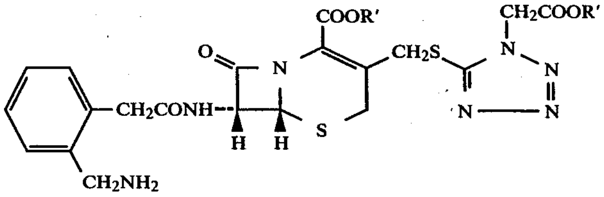 One R' is 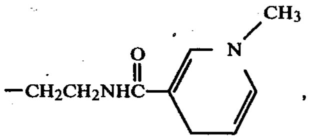 , the other R' is H or 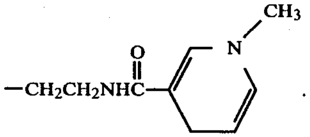 . |

-continued
| STARTING MATERIAL | [D—QC]+ | [D—DHC] |
| --- | --- | --- |
| 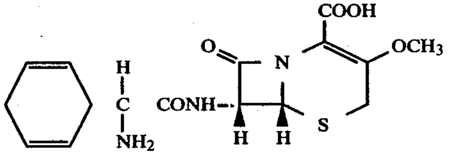 cefroxadine | 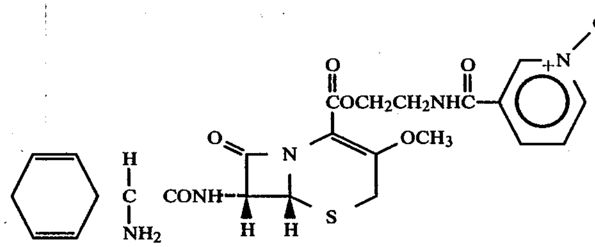 | 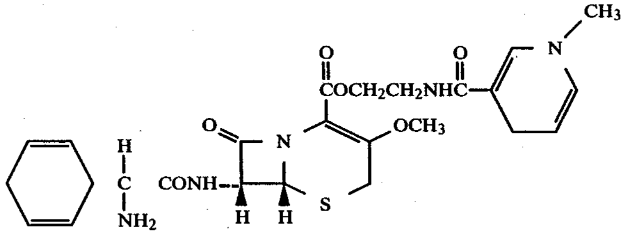 |
| 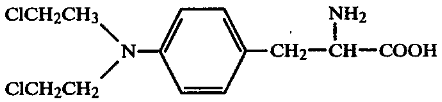 melphalan | 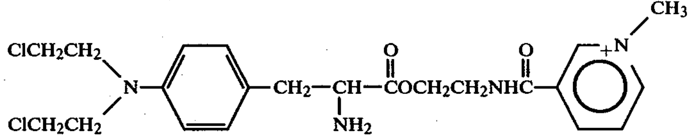 | 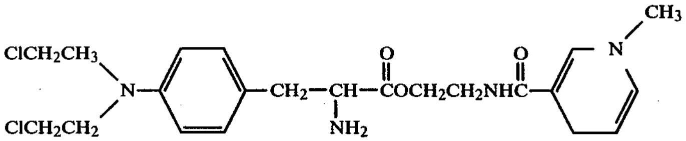 |
| 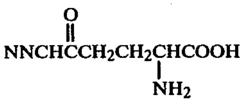 DON | 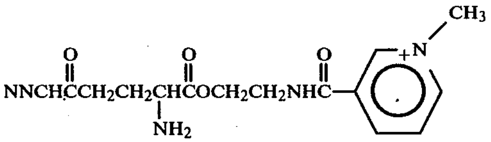 | 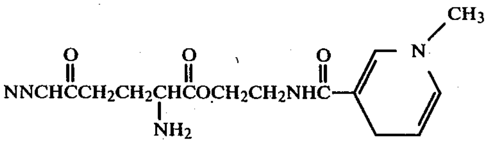 |

-continued
| STARTING MATERIAL | [D—QC]+ | [D—DHC] |
| --- | --- | --- |
| 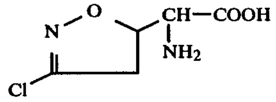 acivicin | 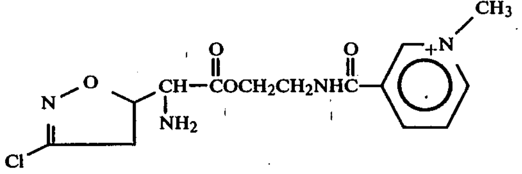 | 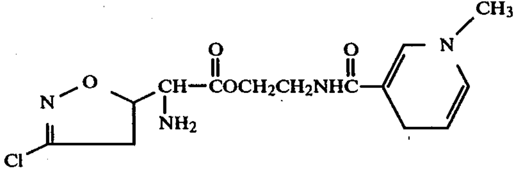 |
| 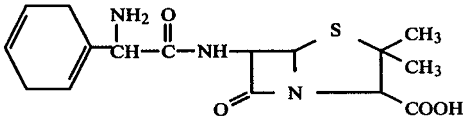 epicillin | 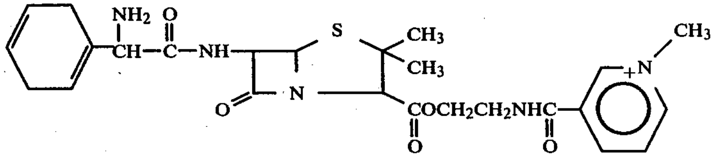 | 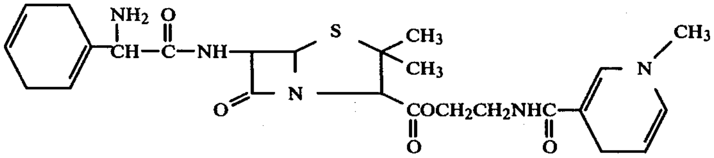 |

Method T

This variation of Method Q can be used when the drug contains one or more $NH_2$ and OH functions which are to be protected. The protecting groups, for example, benzyloxycarbonyl for amino functions and pivalyloxy for hydroxyl functions, are introduced as described in Methods R and S, in the sequence considered most convenient. (Obviously, other protecting groups can be introduced instead.) The carboxyl function(s) are then derivatized according to Method Q. Typically, the hydroxy protecting group(s) are introduced first and are retained throughout the process, while the amino protecting group(s) are generally removed earlier, frequently prior to formation of the quaternary derivative of formula (II).

The representative drugs depicted below may be derivatized in this manner to the corresponding compounds of formulas (II) and (I). Amino acids containing hydroxyl functions (e.g. tyrosine) and small peptides containing such amino acids are also prime candidates for derivation in accord with this method.

| STARTING MATERIAL | [D—QC]+ | [D—DHC] |
| --- | --- | --- |
| 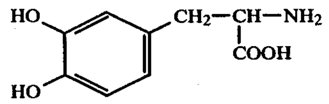 L-DOPA | 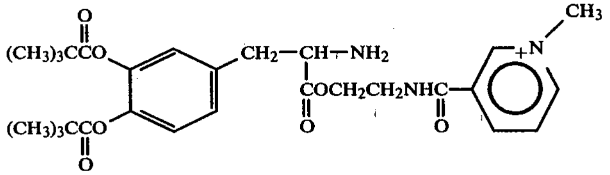 | 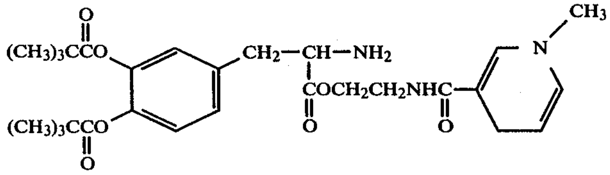 |
| 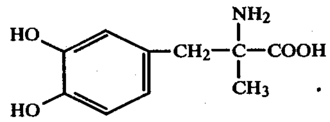 methyldopa | 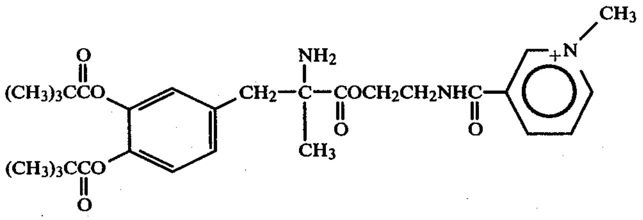 | 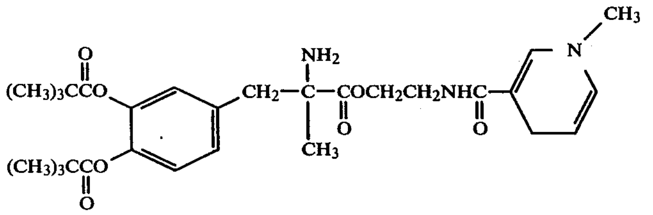 |
| 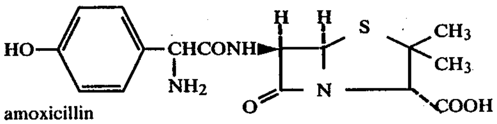 amoxicillin | 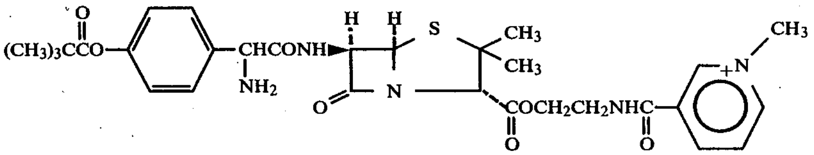 | 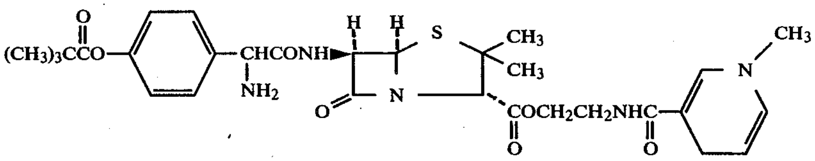 |

Method U

The drug is first reacted with ethylene glycol (or other dihydroxyalkanol having up to 8 carbon atoms), in the presence of a suitable coupling agent such as dicyclohexylcarbodiimide, to convert the —COOH function(s) to the corresponding $-COOCH_2CH_2OH$ (or other

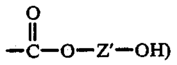

group(s). That intermediate is then reacted with a compound of the formula

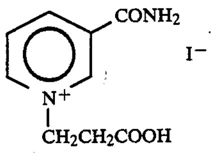

or the like, prepared as described in Method J, in the presence of a coupling agent such as dicyclohexylcarbodiimide, to give the desired quaternary derivative of formula (II). Subsequent reduction to the corresponding dihydro derivative of formula (I) proceeds as described in Method A.

The drugs depicted below may be derivatized in this manner to the corresponding compounds of formulas (II) and (I), as may the remaining drugs mentioned with Method Q.

The procedure described above may be repeated utilizing a reactant of the formula

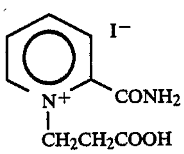

or

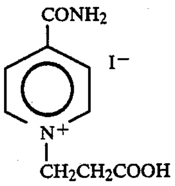

or the like, prepared as described in Method J, in place of the intermediate of the formula

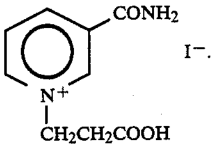

This procedure may also be adapted to preparation of derivatives of the drugs mentioned with Methods R, S and T.

| STARTING MATERIAL | [D—QC]+ | [D—DHC] |
|---|---|---|
| 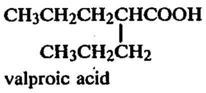 valproic acid | 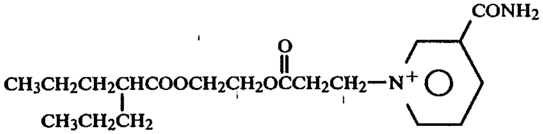 | 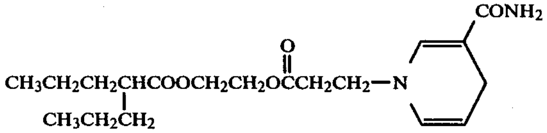 |
| 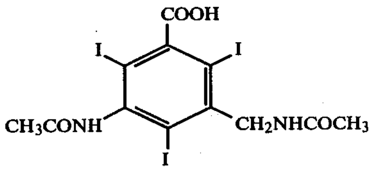 iodamide | 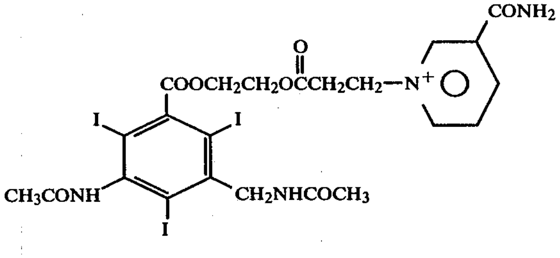 | 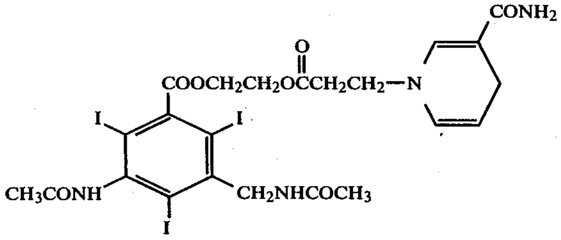 |
| 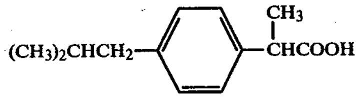 ibuprofen | 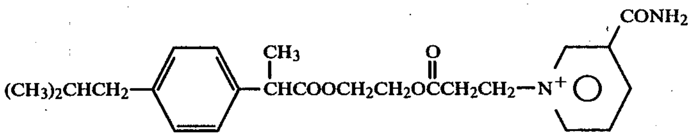 | 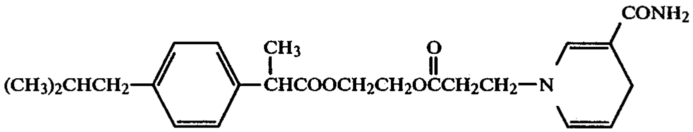 |
| 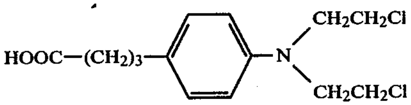 chlorambucil | | 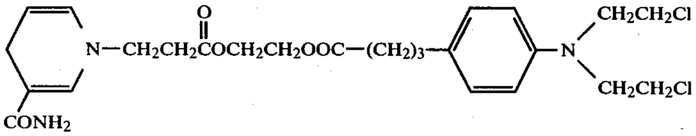 |

-continued
| STARTING MATERIAL | [D—QC]+ | [D—DHC] |
| --- | --- | --- |
| | 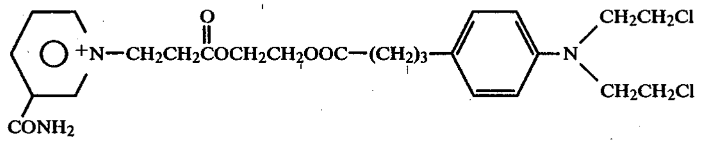 | |
| 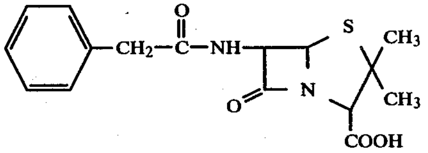 benzylpenicillin | 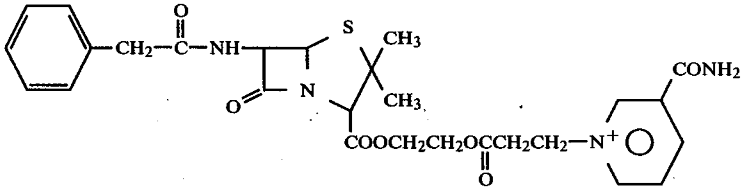 | 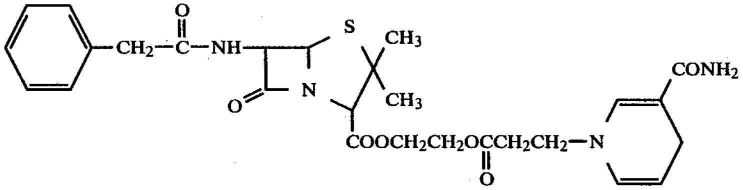 |
| 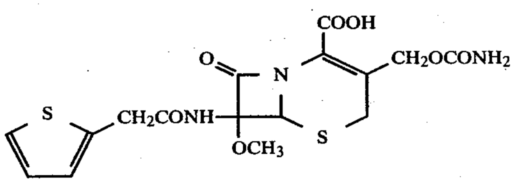 cefoxitin | | 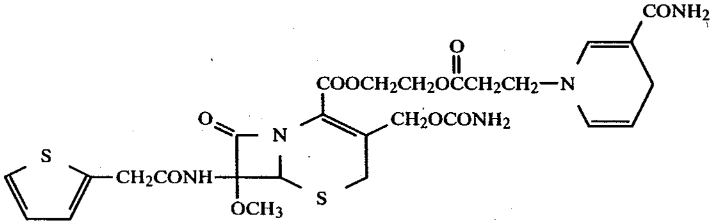 |

-continued
| STARTING MATERIAL | [D—QC]+ | [D—DHC] |
| --- | --- | --- |
| | 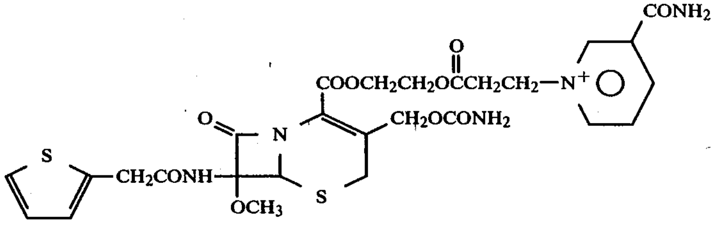 | |
| 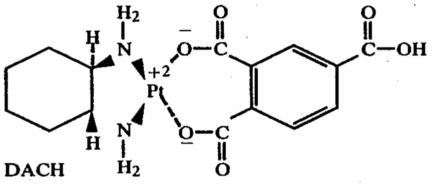 DACH | 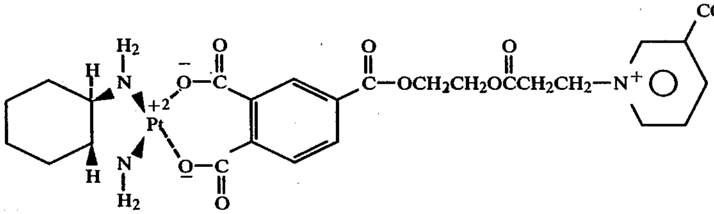 | 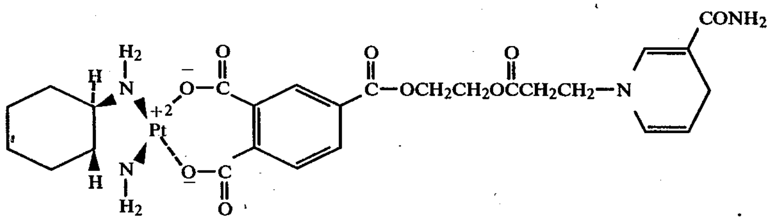 |

Method U'

The drug is reacted with excess alcohol of the formula

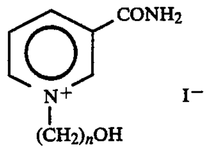

wherein n=1-3, preferably 2, to convert the —COOH function to the corresponding

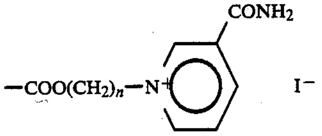

ester grouping. The resultant quaternary of formula (II) is then reduced as described in Method A. when the drug contains more than one reactive carboxyl function, reaction conditions may be varied so that more than one carboxyl function will be converted to ester groupings. (The starting alcohol may be prepared from nicotinamide, e.g. when n=2, by reacting 2-iodoethanol with nicotinamide.)

The representative drugs depicted below may be derivatized in this manner to the corresponding compounds of formulas (II) and (I), as may the remaining compounds mentioned with Method Q.

The procedure described in the first paragraph of this method may utilize a starting alcohol of the formula

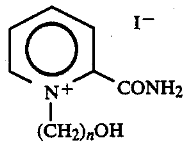

or

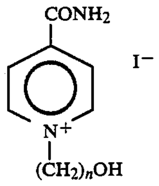

(prepared from picolinamide or isonicotinamide, respectively) in place of the starting alcohol depicted in the first paragraph, to afford the corresponding derivatives of the drugs indicated with this method.

This procedure may also be adapted to preparation of derivatives of the drugs mentioned with Methods R, S and T.

| Starting Material | $[D-QC]^+$ | [D−DHC] |
| --- | --- | --- |
| 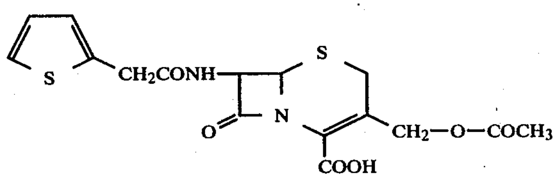 cephalothin | 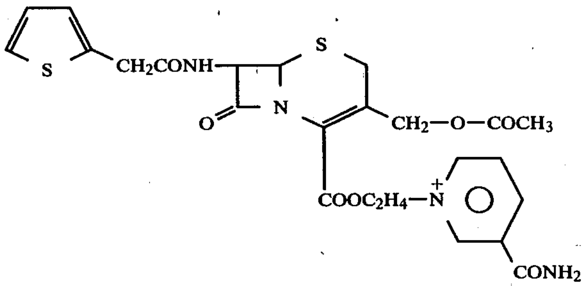 | 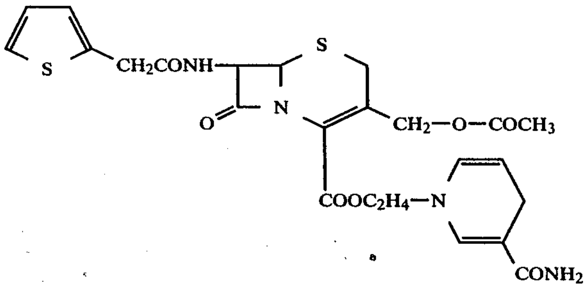 |
| 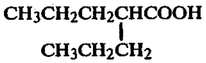 valproic acid | 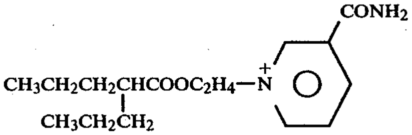 | 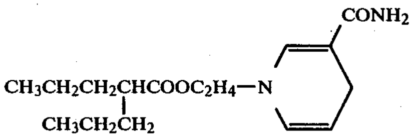 |
| 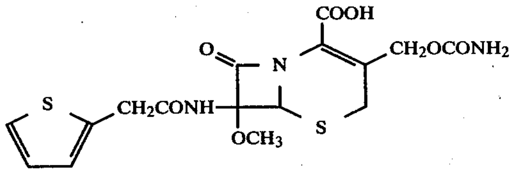 cefoxitin | 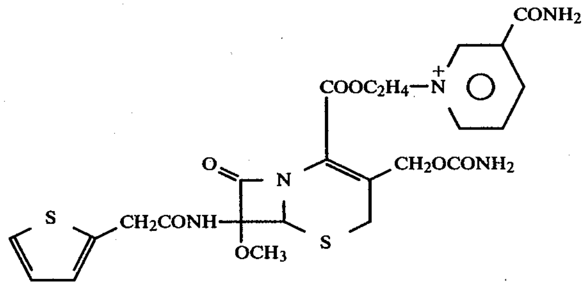 | 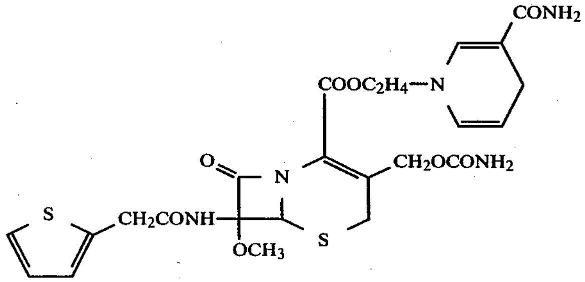 |

-continued
| Starting Material | [D—QC]+ | [D—DHC] |
|---|---|---|
| 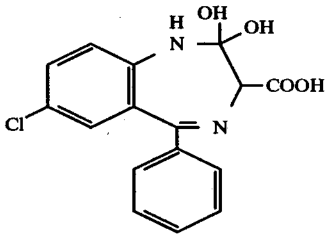 clorazepate | 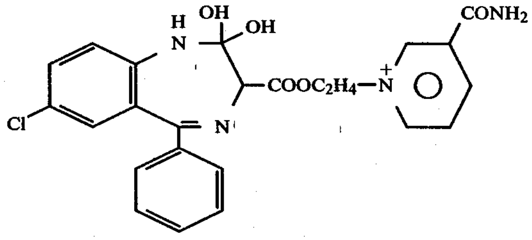 | 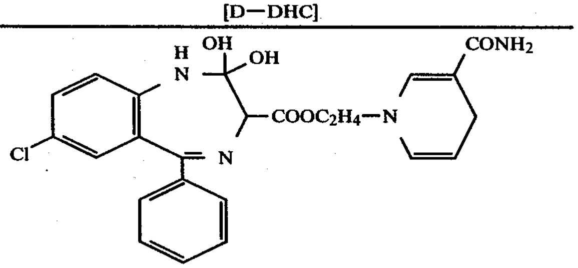 |
| 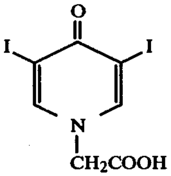 iopyracet | 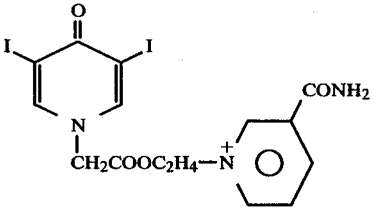 | 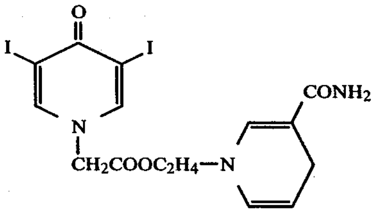 |
| 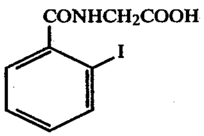 iodouppurate (o-iodohippuric acid) | 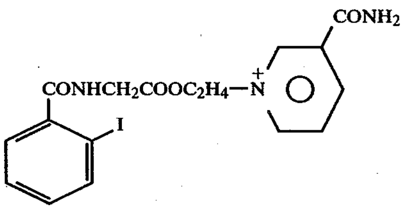 | 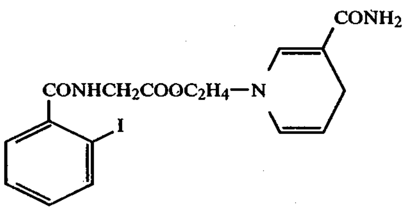 |
| 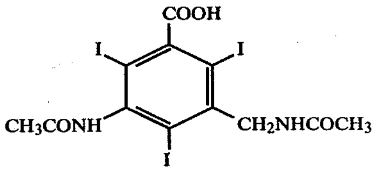 iodamide | 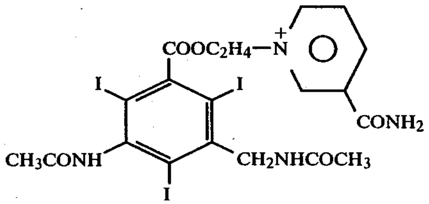 | 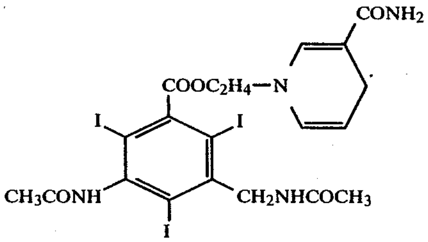 |

-continued
| Starting Material | [D—QC]+ | [D—DHC] |
| --- | --- | --- |
| 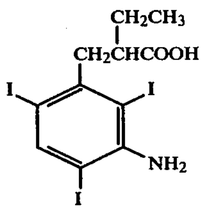 iopanoic acid | 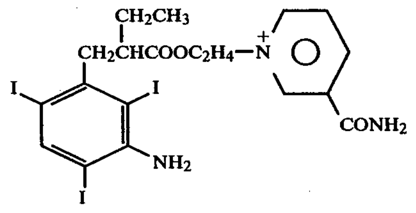 | 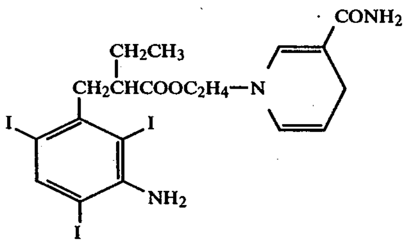 |
| 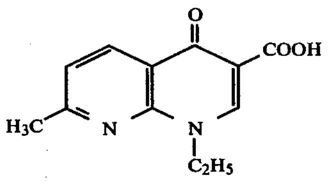 nalidixic acid | 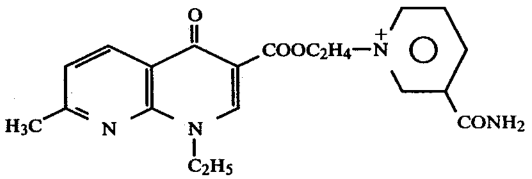 | 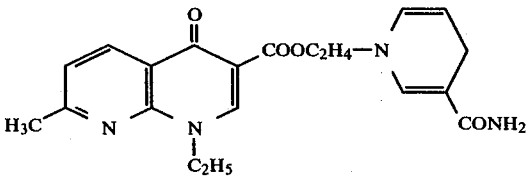 |
| 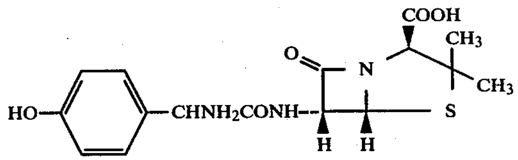 amoxicillin | | 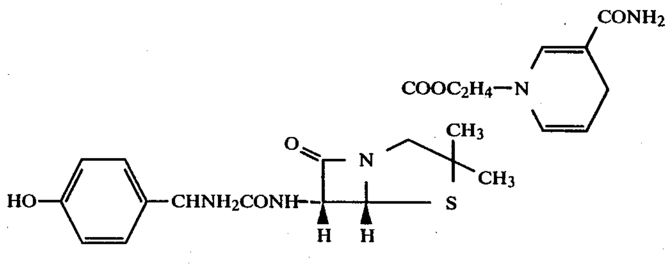 |

-continued
| Starting Material | [D—QC]+ | [D—DHC] |
|---|---|---|
| | 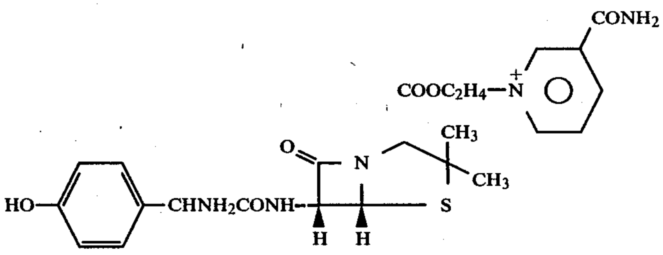 | |
| 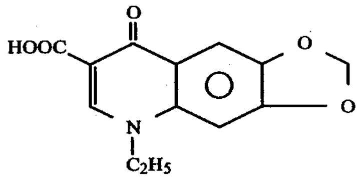 oxolinic acid | 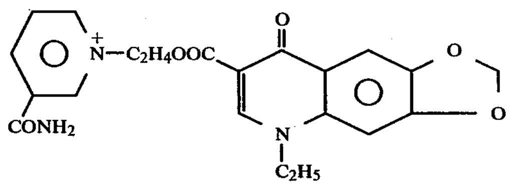 | 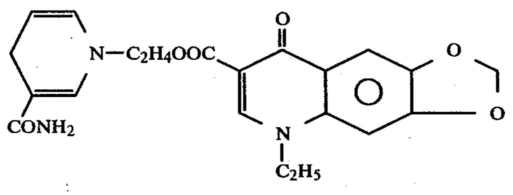 |
| 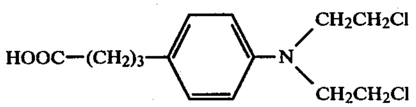 chlorambucil | 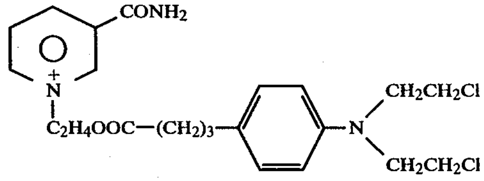 | 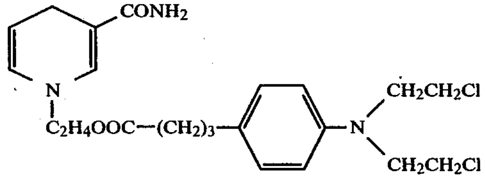 |
| 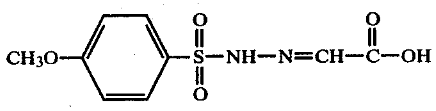 glyoxylic acid sulfonylhydrazone | | 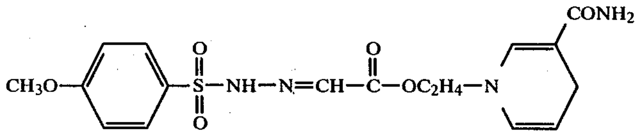 |

-continued
| Starting Material | [D—QC]+ | [D—DHC] |
| --- | --- | --- |
| | 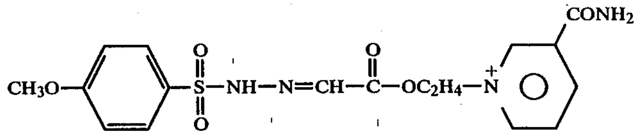 | |
| 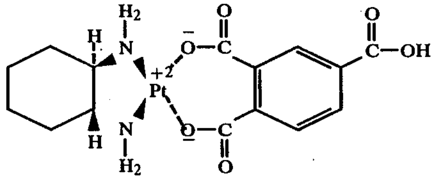 DACH | 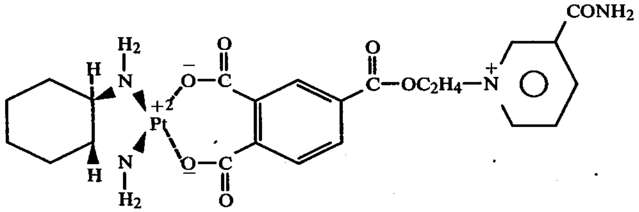 | 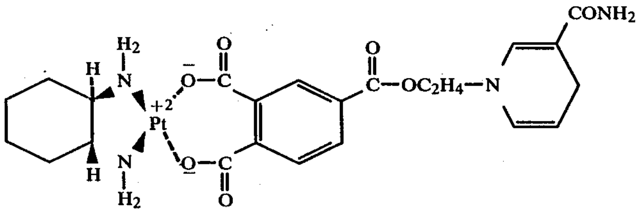 |
| 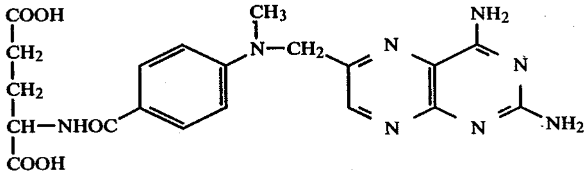 methotrexate | 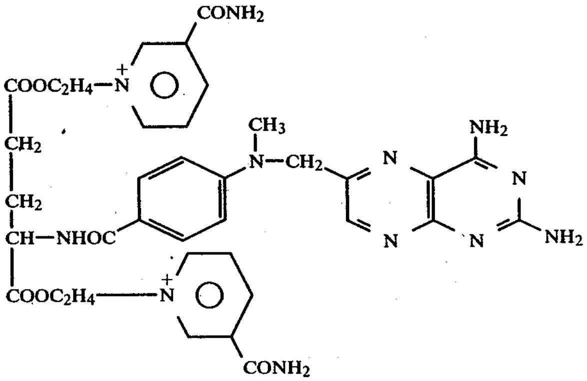 | 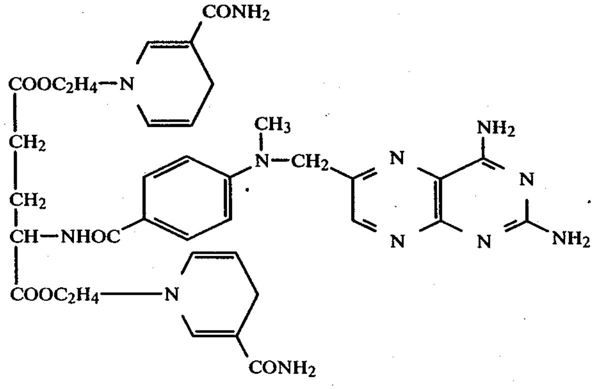 |

-continued
| Starting Material | [D—QC]+ | [D—DHC] |
|---|---|---|
| 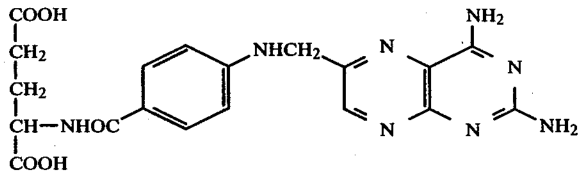 aminopterin | 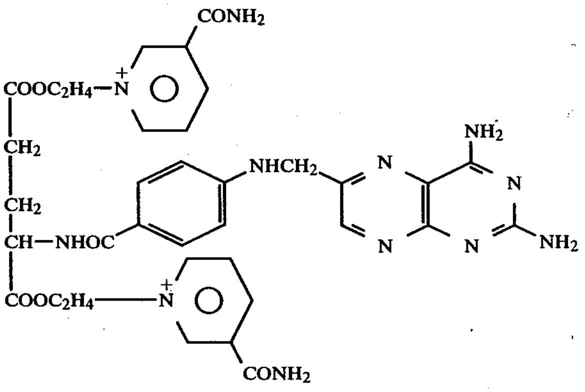 | 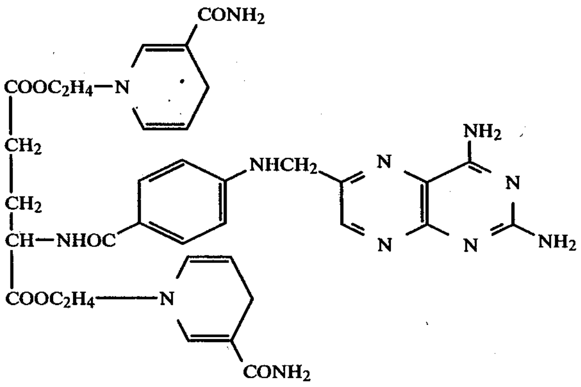 |
| 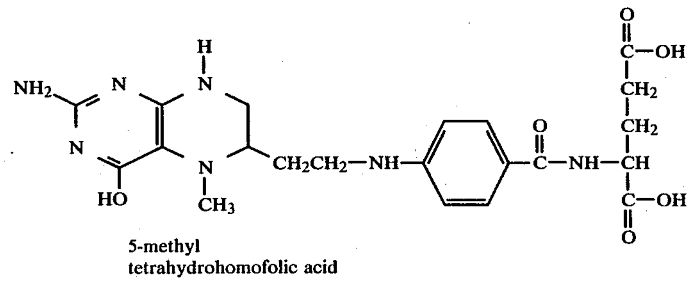 5-methyl tetrahydrohomofolic acid | | 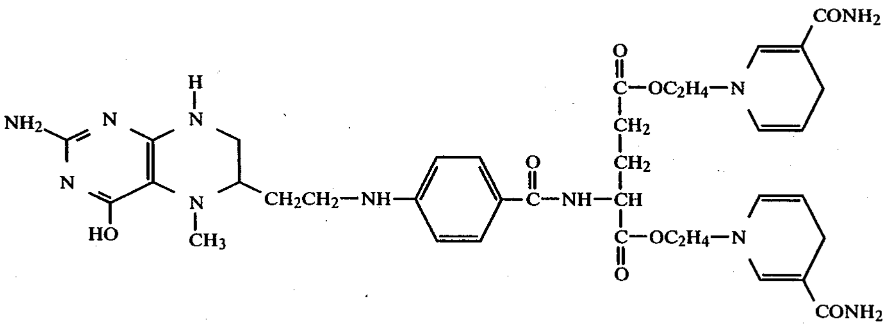 |

-continued
| Starting Material | [D—QC]+ | [D—DHC] |
|---|---|---|
| | 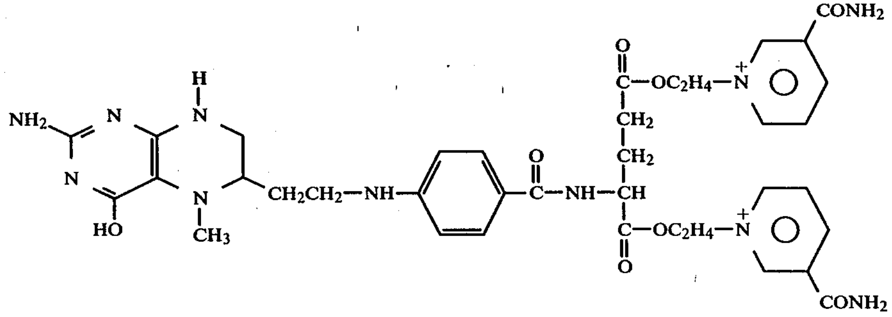 | |
| 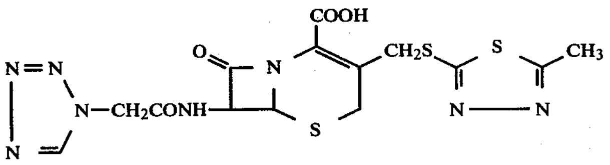<br>cefazolin | 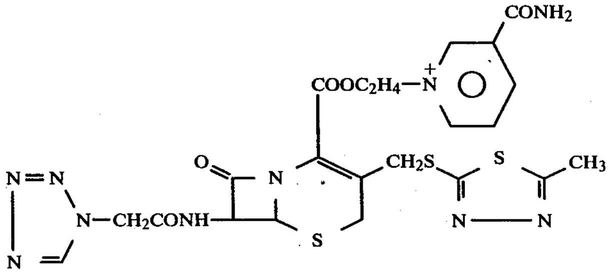 | 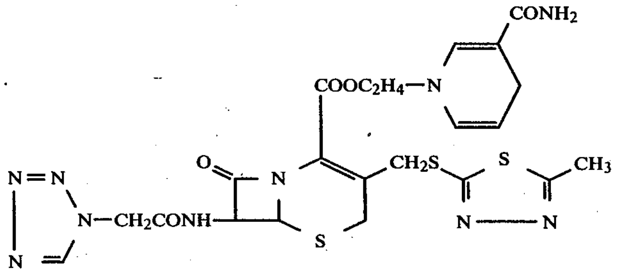 |

-continued
| Starting Material | [D—QC]+ | [D—DHC] |
|---|---|---|
| 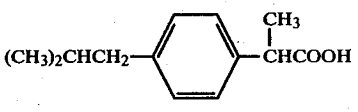 ibuprofen | 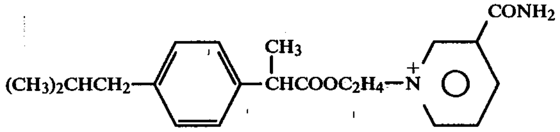 | 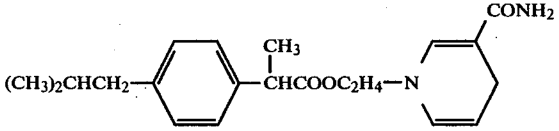 |
| 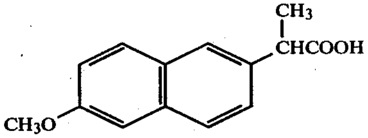 naproxen | 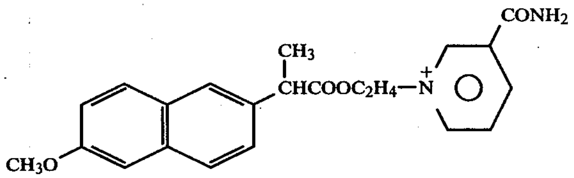 | 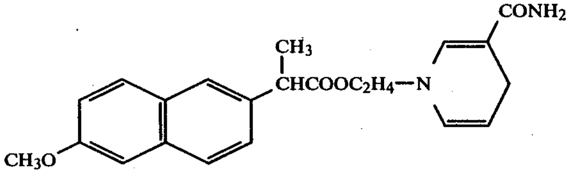 |
| 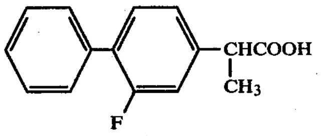 flurbiprofen | 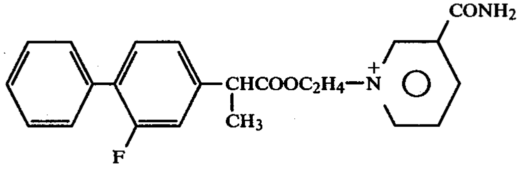 | 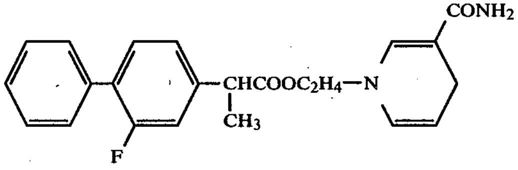 |
| 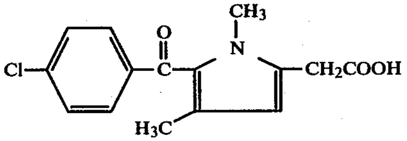 zomepirac | 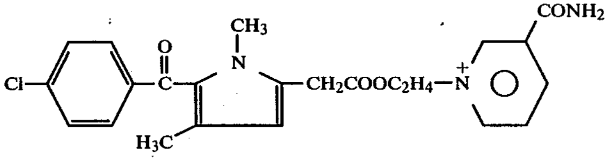 | 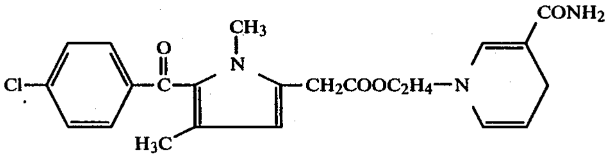 |

-continued
| Starting Material | [D—QC]+ | [D—DHC] |
| --- | --- | --- |
| 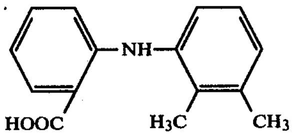 mefenamic acid | 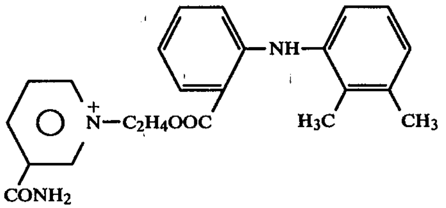 | 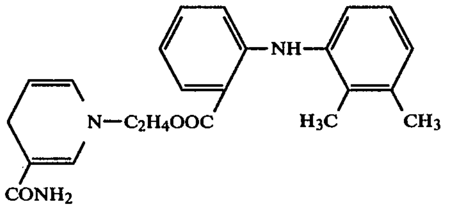 |
| 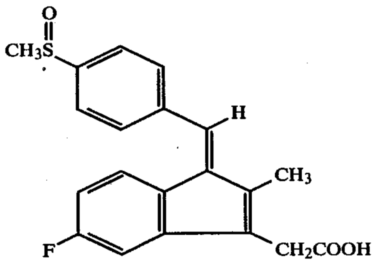 sulindac | 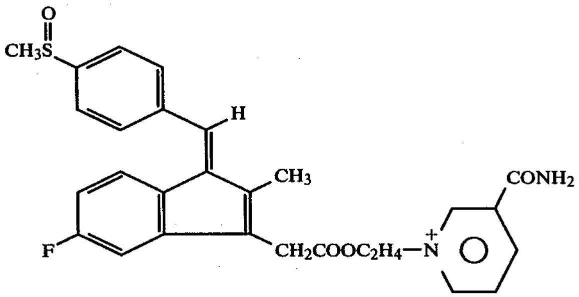 | 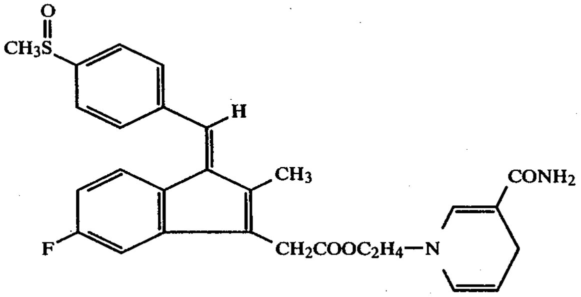 |
| 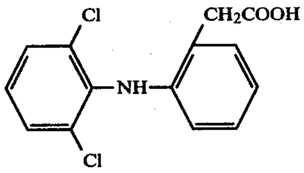 diclofenac | 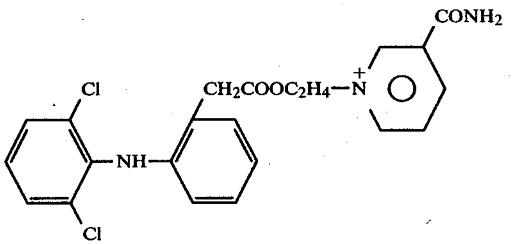 | 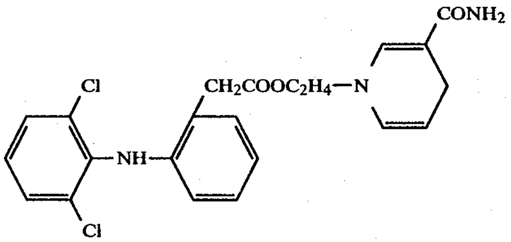 |

-continued
| Starting Material | [D—QC]+ | [D—DHC] |
| --- | --- | --- |
| 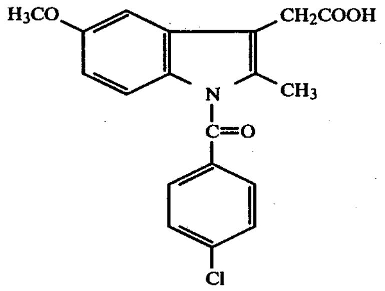 indomethacin | 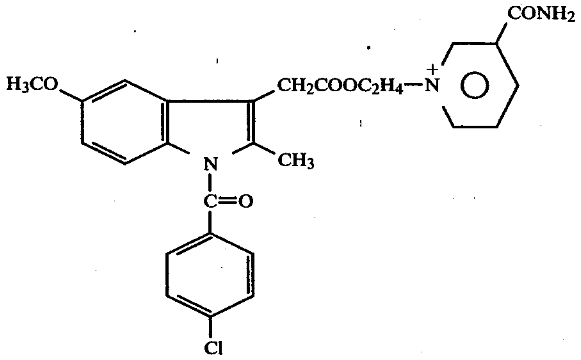 | 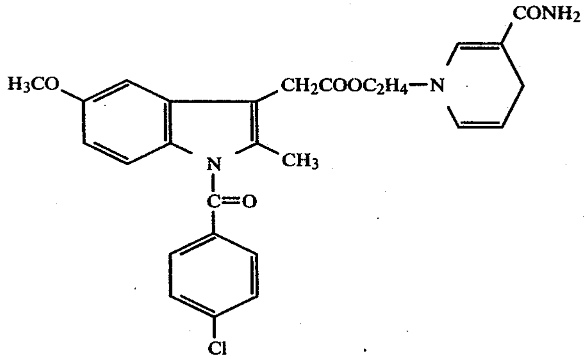 |

Method U″

Method U′ is repeated, except that the starting alcohol employed has the formula

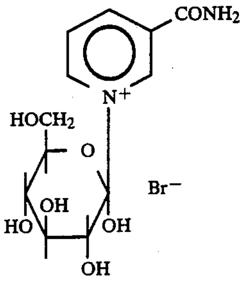

(That starting material may be prepared by reacting bromoglucose with nicotinamide.)

The drugs depicted below may be derivatized in this manner to the corresponding compounds of formulas (II) and (I), as may the remaining drugs mentioned with Method Q.

Alternatively, Method U″ may utilize a starting alcohol of the formula

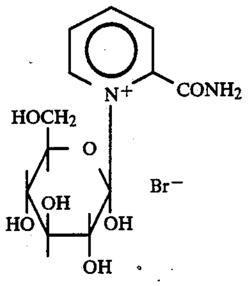

or

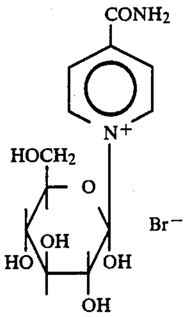

(prepared by reacting bromoglucose with picolinamide or isonicotinamide), to afford the corresponding derivatives of the compounds mentioned with Method Q.

This procedure may also be adapted to preparation of derivatives of the drugs mentioned with Methods R, S and T.

| Starting Material | [D—QC]$^+$ | [D—DHC] |
|---|---|---|
| 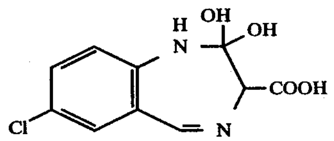 clorazepate | 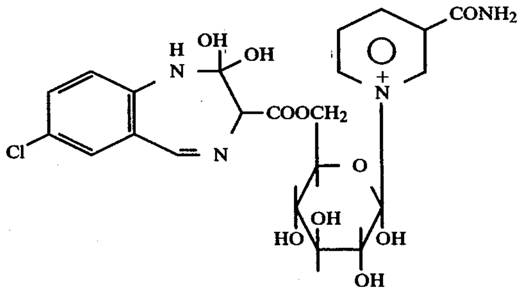 | 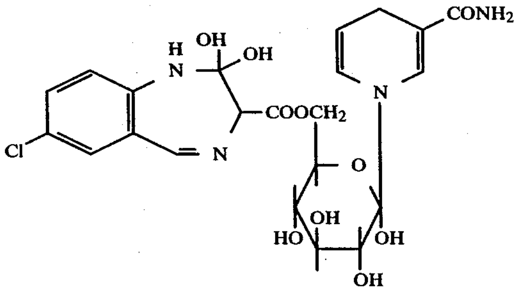 |
| 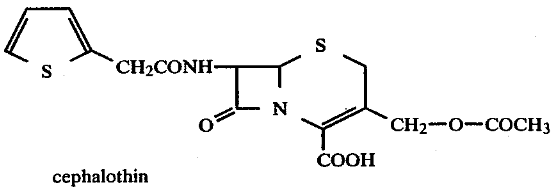 cephalothin | 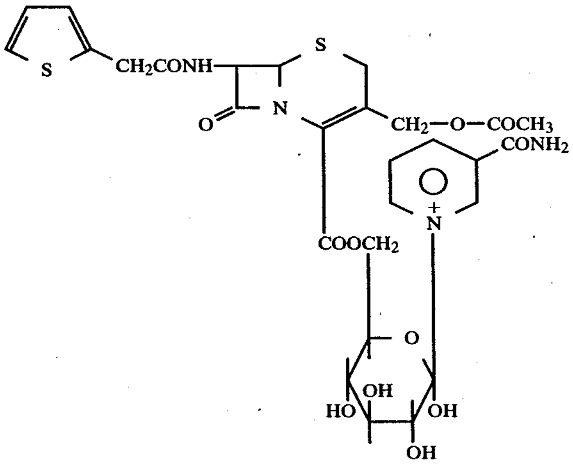 | 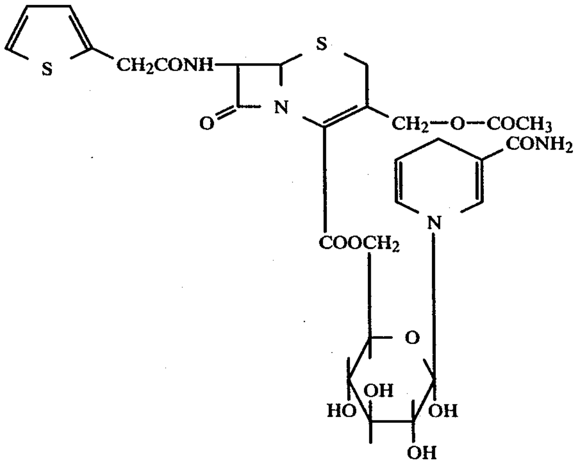 |

-continued
| Starting Material | [D—QC]+ | [D—DHC] |
|---|---|---|
| 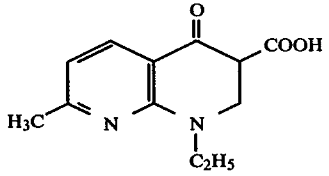 nalidixic acid | 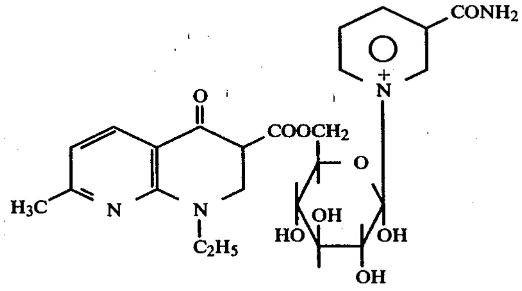 | 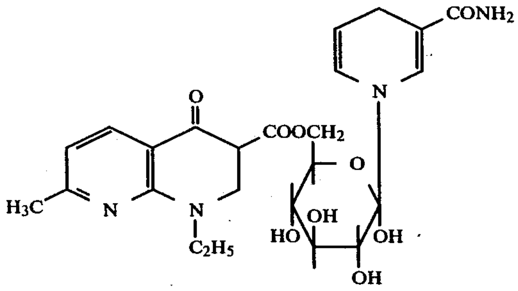 |
| 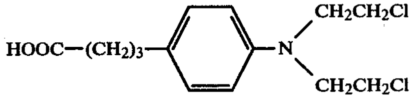 chlorambucil | 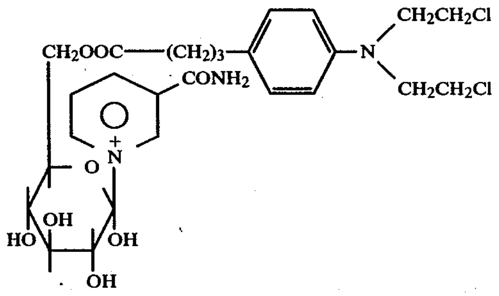 | 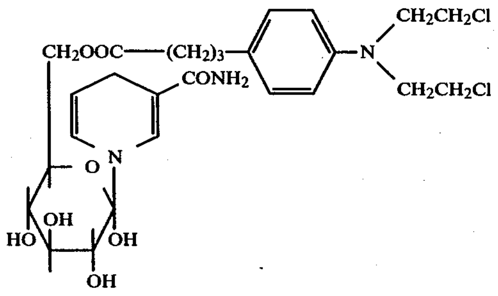 |
| 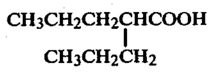 valproic acid | 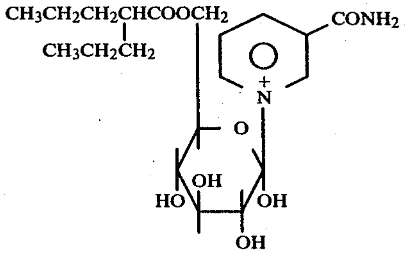 | 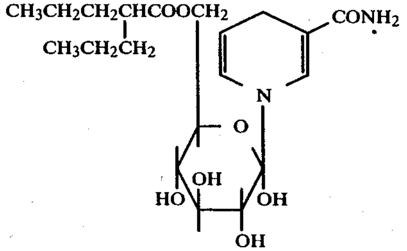 |

-continued
| Starting Material | [D—QC]+ | [D—DHC] |
|---|---|---|
| 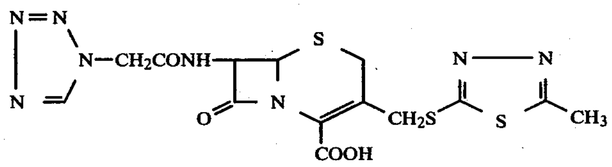<br>cefazolin | 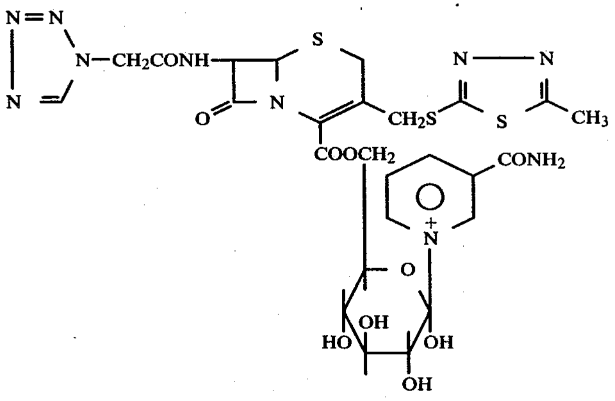 | 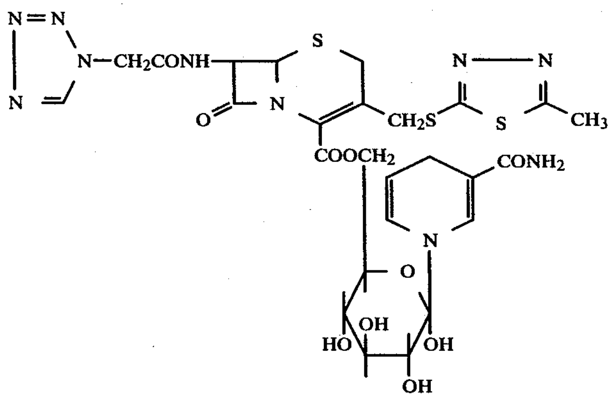 |

-continued
| Starting Material | [D—QC]+ | [D—DHC] |
|---|---|---|
| 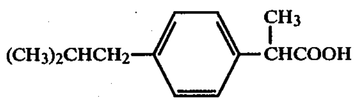 ibuprofen | 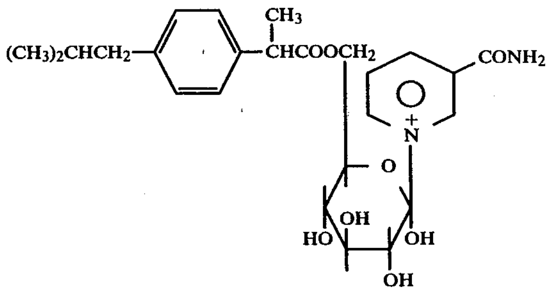 | 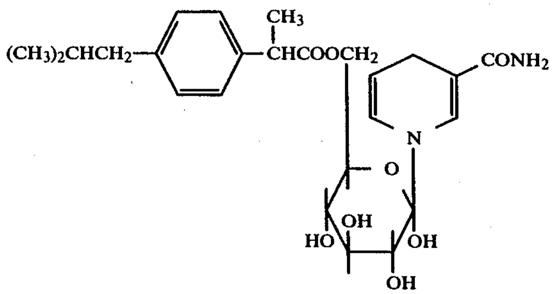 |
| 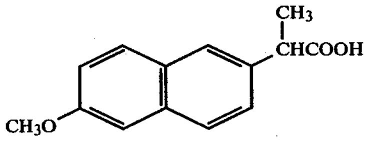 naproxen | 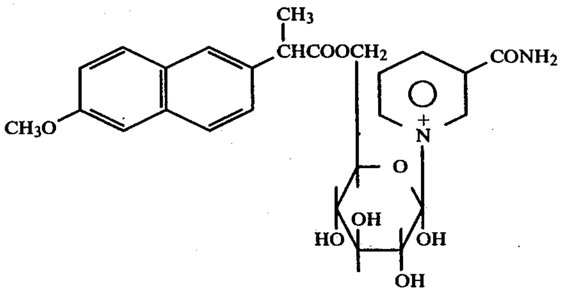 | 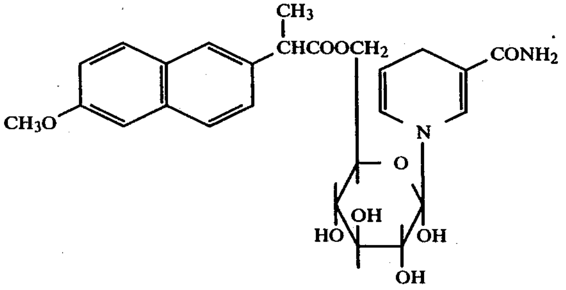 |
| 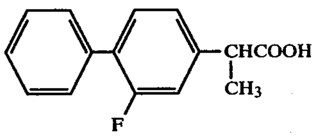 flurbiprofen | 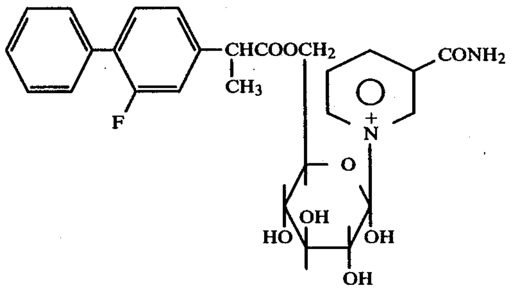 | 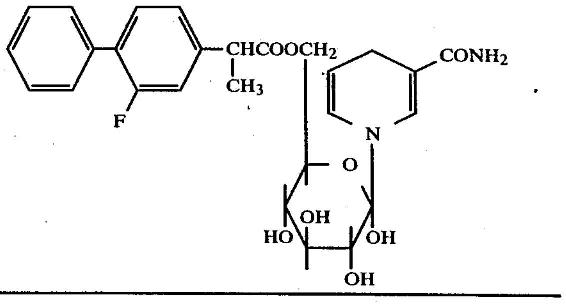 |

Method U'''

Method U' is repeated, except that the starting alcohol employed has the formula

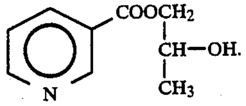

(That starting material may be prepared by reacting nicotinic acid with 1,2-propylene glycol in the presence of dicyclohexylcarbodiimide.)

The representative drugs listed below may be derivatized in this manner to the corresponding compounds of formulas (II) and (I), as may the remaining drugs mentioned with Method Q.

The procedure of Method U''' may be repeated using a starting alcohol of the formula

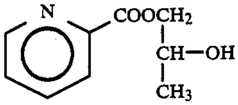
or
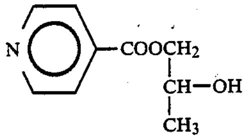

in place of the starting alcohol depicted above (prepared in an analogous manner using picolinic acid or isonicotinic acid in place of nicotinic acid in the reaction with 1,2-propylene glycol), to afford the corresponding derivatives of the drugs indicated in Method Q.

This procedure may also be adapted to preparation of derivatives of the drugs mentioned with Methods R, S

| Starting Material | [D—QC]+ | [D—DHC] |
|---|---|---|
| 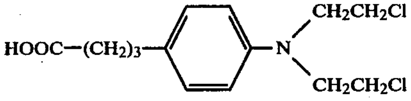 chlorambucil | 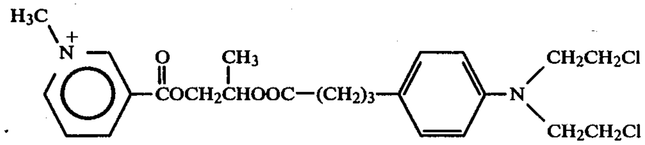 | 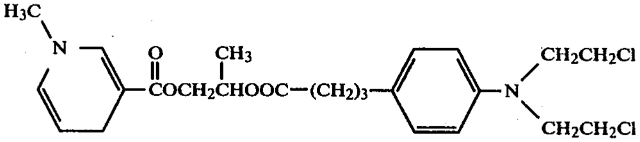 |
| 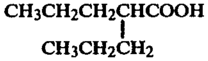 valproic acid | 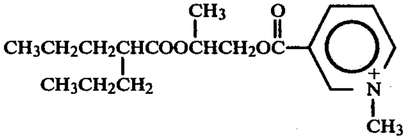 | 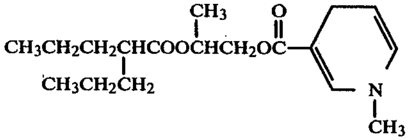 |
| 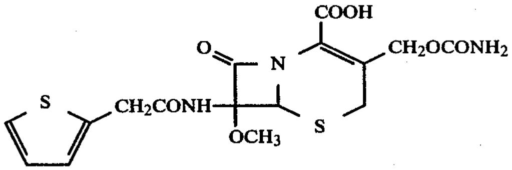 cefoxitin | 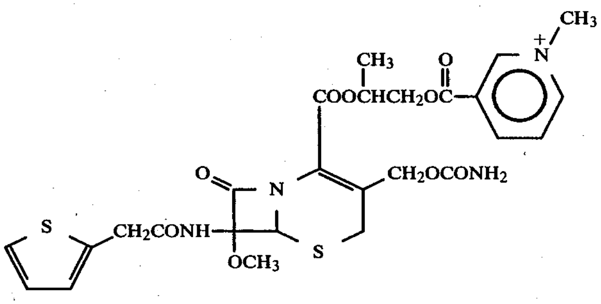 | 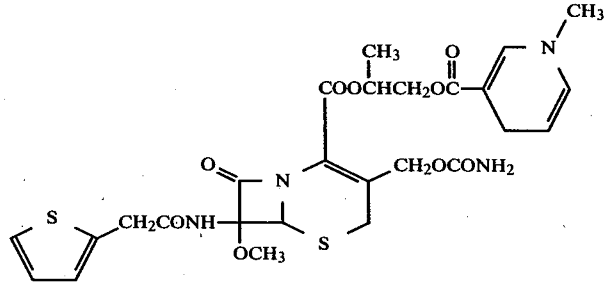 |
| 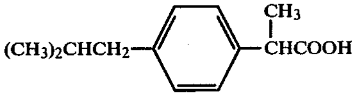 ibuprofen | 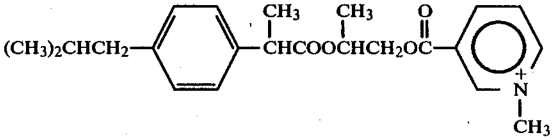 | 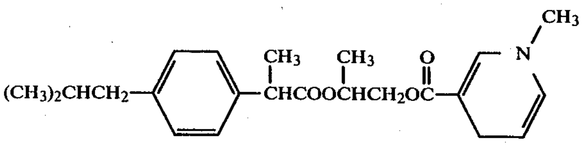 |

-continued
| Starting Material | [D—QC]$^+$ | [D—DHC] |
| --- | --- | --- |
| 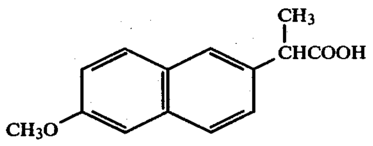 naproxen | 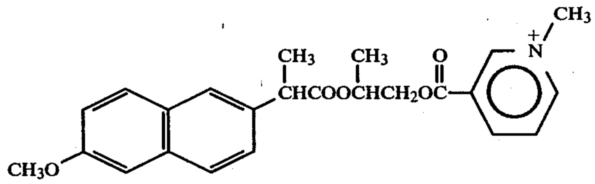 | 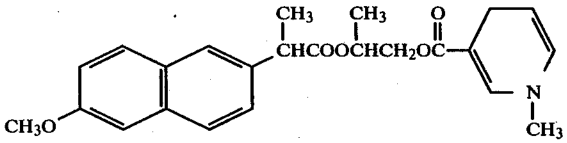 |
| 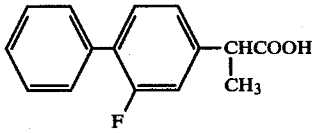 flurbiprofen | 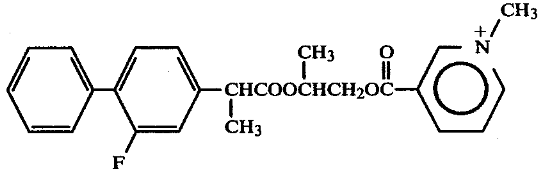 | 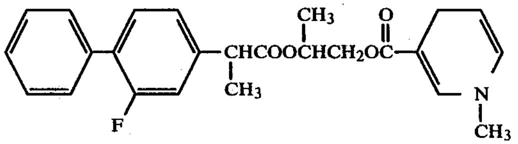 |

Method V

A drug containing one —COOH function is reacted with an equivalent amount of inositol, in the presence of dicyclohexylcarbodiimide or other suitable coupling agent, to convert the —COOH function to a group of the structure

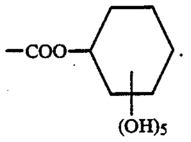

Reaction of that intermediate with nicotinic acid, in the presence of a suitable coupling agent, or with an activated ester of nicotinic acid, affords an intermediate in which the original —COOH has been converted to

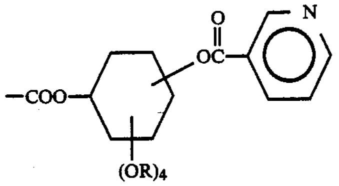

wherein each R is H or

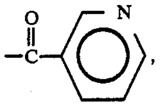

the number of original hydroxy groups esterified varying with the amount of nicotinic acid employed. Subsequent quaternization and reduction are carried out as in Method A.

The drugs depicted below may be derivatized in this manner to the corresponding compounds of formulas (II) and (I), as may the remaining drugs mentioned with Method Q which contain a single —COOH function.

Alternatively, the above procedure may be repeated, replacing nicotinic acid with an analogous starting material, e.g. picolinic acid, isonicotinic acid, 3-quinolinecarboxylic acid, 4-isoquinolinecarboxylic acid or the like.

Repetition of the procedure of the first paragraph of this method utilizing a greater amount of the drug (e.g. 2 to 5 or more moles per mole of inositol) provides an intermediate containing from 2 to 5 acid residues and from 4 to 1 hydroxyl groups. That intermediate is then reacted with nicotinic acid to convert at least one hydroxyl group to the corresponding

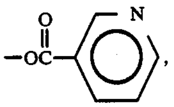

group. Subsequent formation of the quaternary and reduction proceed as in Method A.

This procedure may also be adapted to preparation of derivatives of drugs mentioned with Methods R, S and T.

| STARTING MATERIAL | [D—QC]+ | [D—DHC] |
|---|---|---|
| 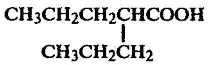 valproic acid | 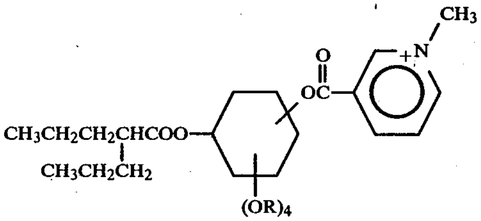 each R is H or 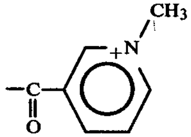 | 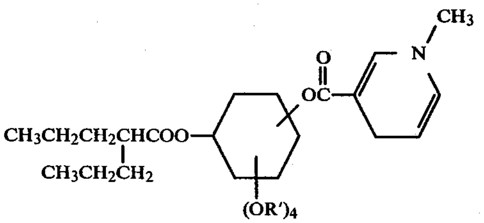 each R′ is H or 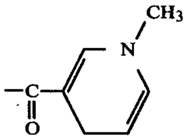 |
| 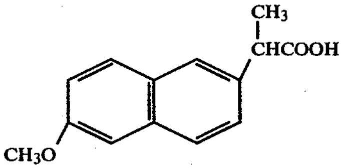 naproxen | 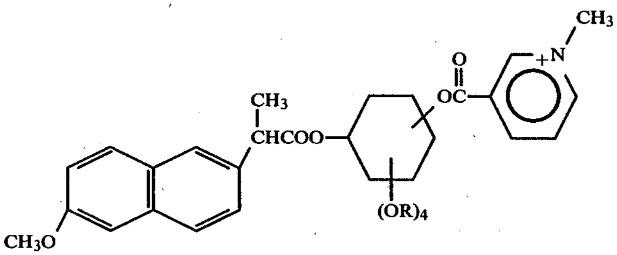 each R is H or 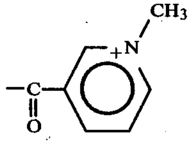 | 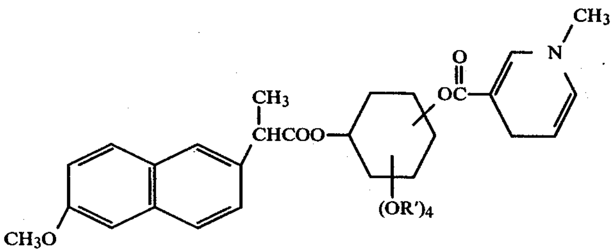 each R′ is H or 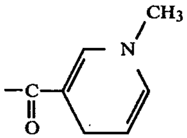 |

-continued
| STARTING MATERIAL | [D—QC]+ | [D—DHC] |
|---|---|---|
| 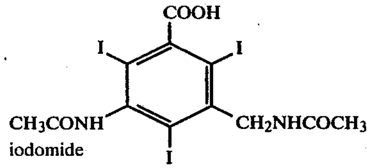 iodomide | 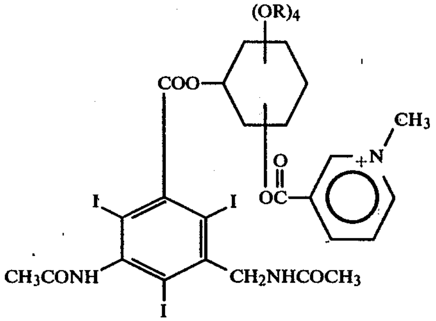 each R is H or 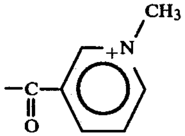 | 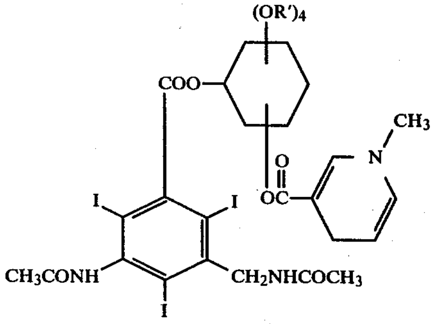 each R′ is H or 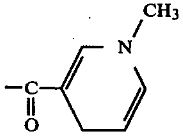 |
| 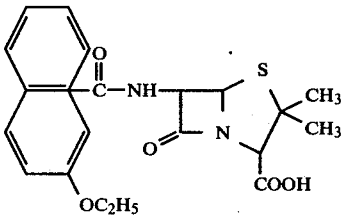 nafcillin | 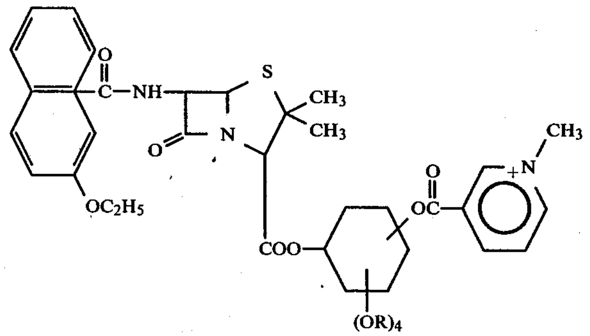 each R is H or 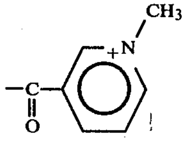 | 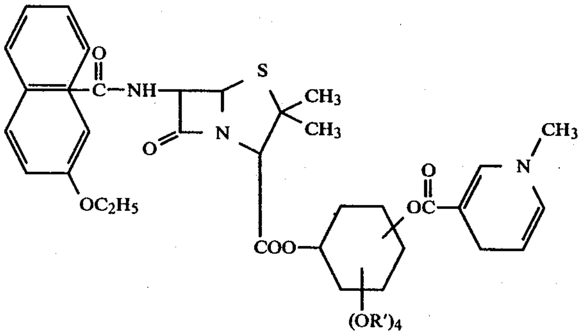 each R′ is H or 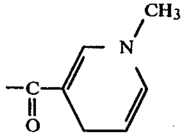 |

-continued
| STARTING MATERIAL | [D—QC]⁺ | [D—DHC] |
|---|---|---|
| 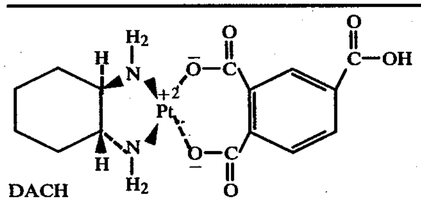 DACH | 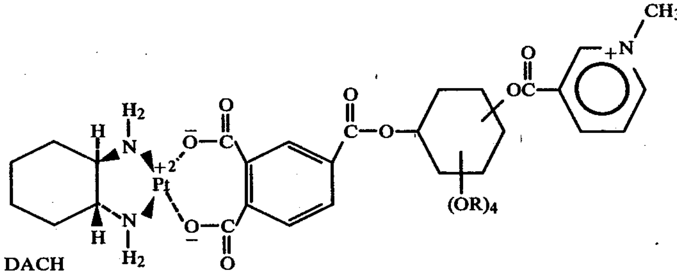 DACH<br>each R is H or 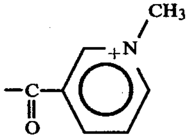 | 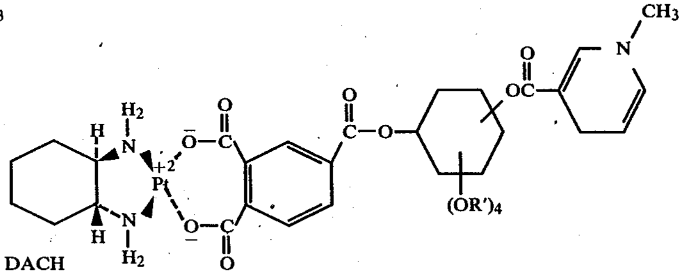 DACH<br>each R′ is H or 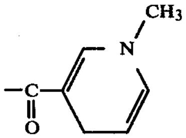 |
| 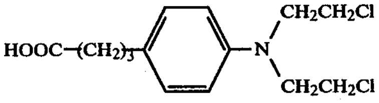 chlorombucil | 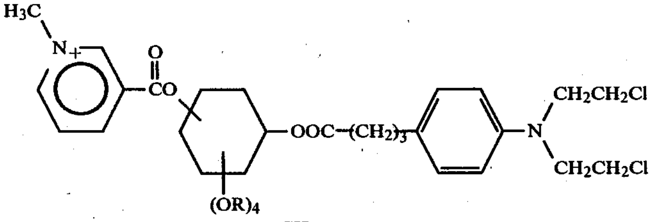<br>each R is H or 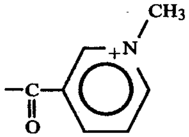 | 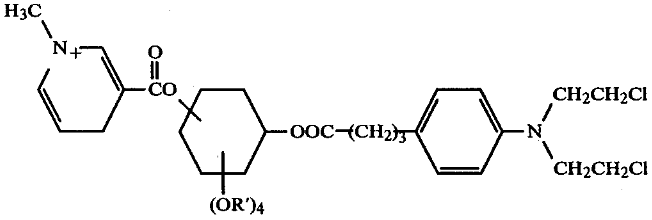<br>each R′ is H or 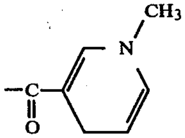 |

Method W

The drug is first reacted with 1,2-propylene glycol (or other dihydroxyalkanol having up to 8 carbon atoms), in the presence of a suitable coupling agent such as dicyclohexylcarbodiimide, to convert the —COOH function(s) to the corresponding

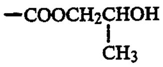

(or other

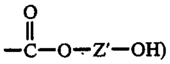

group(s). The resultant intermediate is then reacted with nicotinic acid, in the presence of an appropriate coupling agent, or with an activated ester of nicotinic acid, to give an intermediat of the partial formula

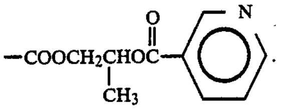

Subsequent quaternization and reduction are carried out as in Method A.

The drugs depicted below may be derivatized in this manner to the corresponding compounds of formulas (II) and (I), as may the remaining drugs mentioned with Method Q.

Alternatively, the above procedure may be repeated, replacing nicotinic acid with an analogous starting material, e.g. picolinic acid, isonicotinic acid, 3-quinolinecarboxylic acid, 4-isoquinolinecarboxylic acid or the like.

This process may of course also be adapted to the preparation of drugs such as those mentioned with Methods R, S and T.

| STARTING MATERIAL | [D—QC]+ | [D—DHC] |
| --- | --- | --- |
| 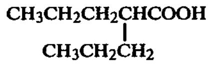<br>valproic acid | 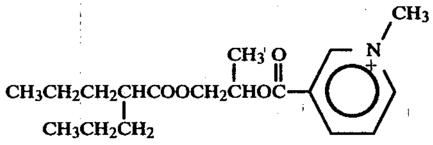 | 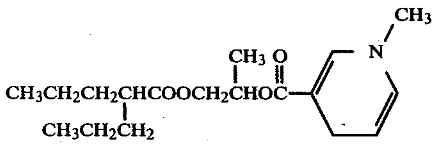 |
| 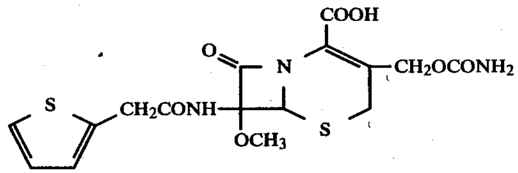<br>cefoxitin | 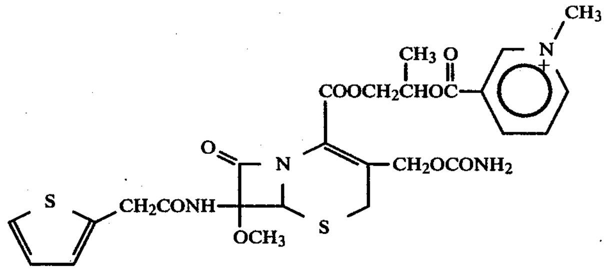 | 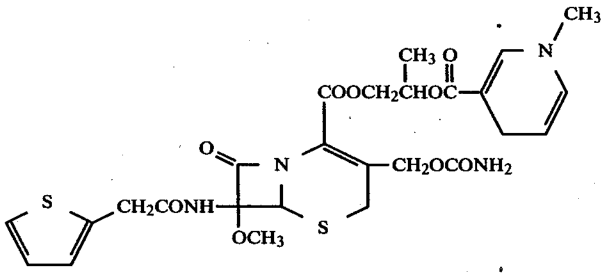 |
| 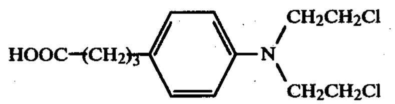<br>chloroambucil | 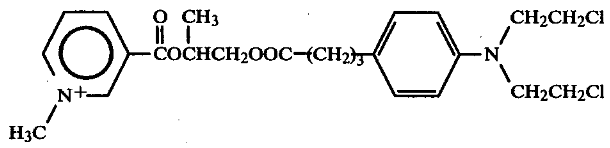 | 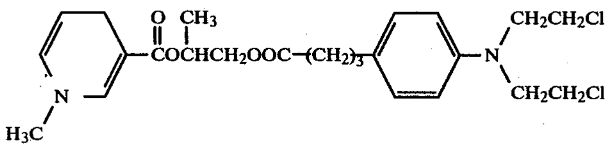 |
| 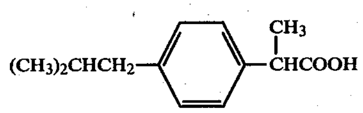<br>ibuprofen | 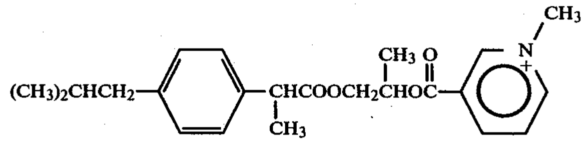 | 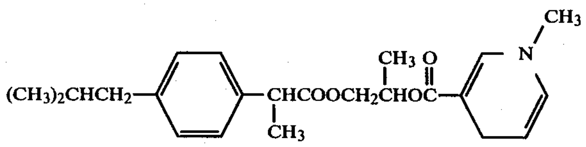 |

-continued
| STARTING MATERIAL | [D—QC]+ | [D—DHC] |
| --- | --- | --- |
| 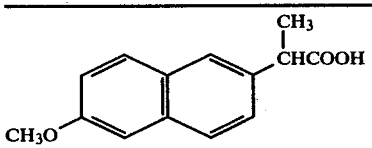 naproxen | 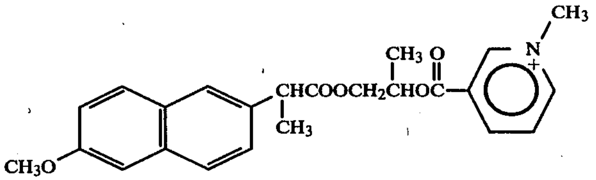 | 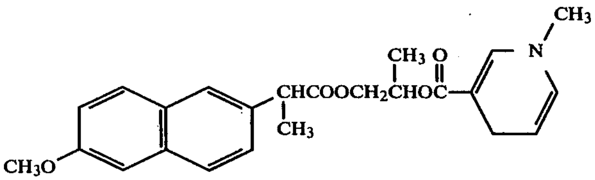 |
| 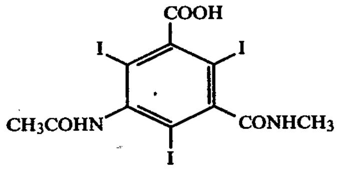 iothalamic acid | 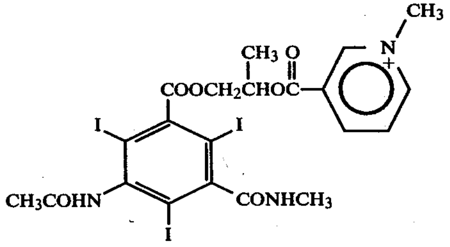 | 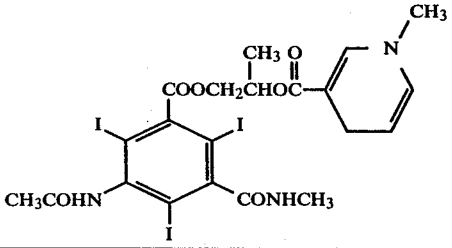 |

Method X

Glucosamine, of the structural formula

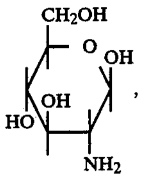

is reacted with nicotinic acid, using equimolar amounts of the reactants, in the presence of a suitable coupling agent such as dicyclohexylcarbodiimide, or with an activated ester of nicotinic acid. The resultant intermediate of the formula

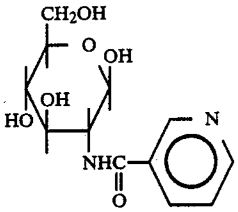

is then reacted with a drug containing one reactive —COOH function, in the presence of dicyclohexylcarbodiimide or other appropriate coupling agent, replacing one or more of the hydroxy groups with acid residue(s), the number of groups replaced varying with the relative amounts of reactants used.

The drugs depicted below may be derivatized in this manner to the corresponding compounds of formulas (II) and (I), as may the remaining drugs mentioned with Method Q which contain a single —COOH group.

Alternatively, the above procedure may be repeated, replacing nicotinic acid with an analogous starting material, e.g. picolinic acid, isonicotinic acid, 3-quinolinecarboxylic acid, 4-isoquinolinecarboxylic acid or the like.

| STARTING MATERIAL | | [D—QC]+ | [D—DHC] |
|---|---|---|---|
| $CH_3CH_2CH_2CHCOOH$ (with $CH_3CH_2CH_2$ on the CH)<br>valproic acid | 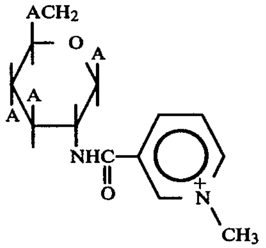 | Each A is —OH or the valproic acid residue, $CH_3CH_2CH_2CHCOO—$ (with $CH_3CH_2CH_2$ on the CH), provided that at least one A is the valproic acid residue. | 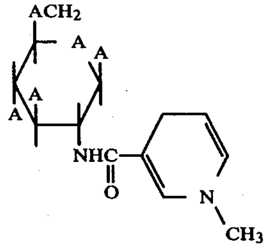 |
| 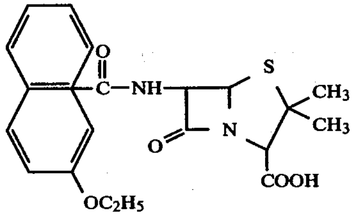<br>nafcillin | 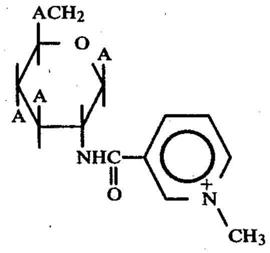 | Each A is —OH or the nafcillin residue,<br>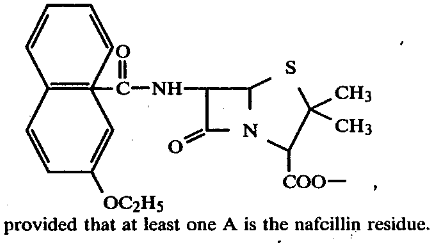 ,<br>provided that at least one A is the nafcillin residue. | 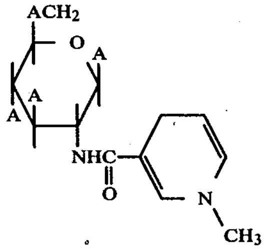 |
| 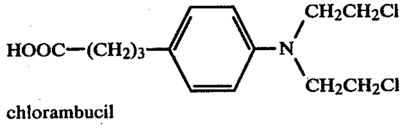<br>chlorambucil | 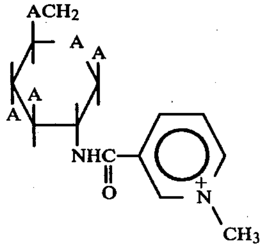 | Each A is —OH or the chlorambucil residue,<br>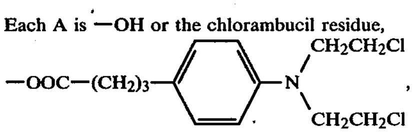 ,<br>provided that at least one A is the chlorambucil residue. | 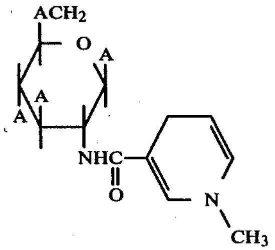 |

-continued
| STARTING MATERIAL | | [D—QC]$^+$ | [D—DHC] |
|---|---|---|---|
| 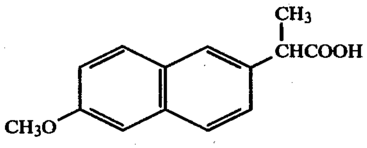 naproxen | 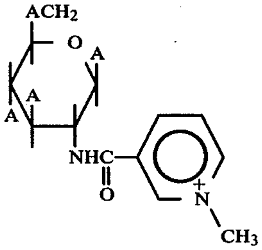 | Each A is —OH or the naproxen residue, 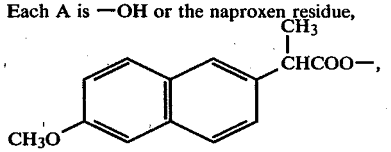 provided that at least one A is the naproxen residue. | 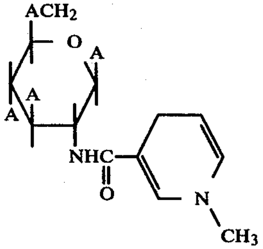 |
| 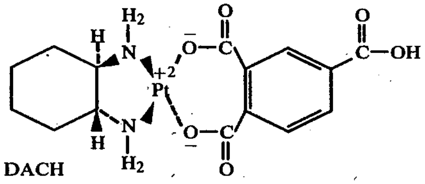 DACH | 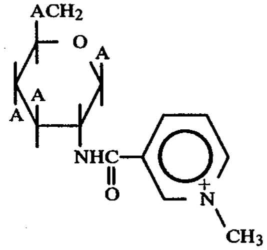 | Each A is —OH or the DACH residue, 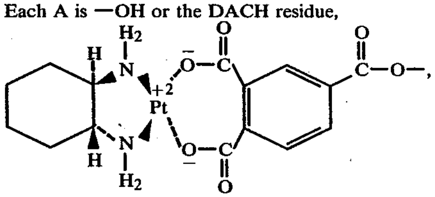 provided that at least one A is the DACH residue. | 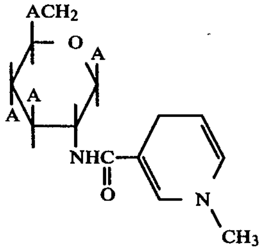 |
| 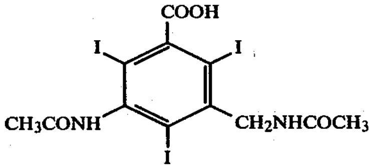 iodamide | 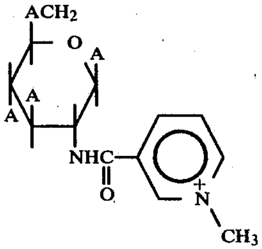 | Each A is —OH or the iodamide residue, 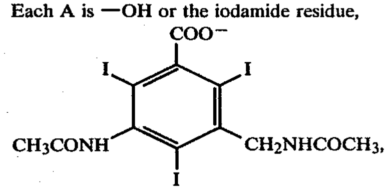 provided that at least one A is the iodamine residue. | 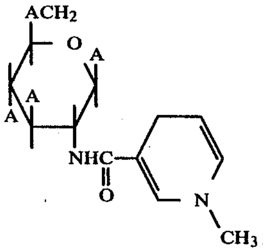 |

Method Y

The procedure of Method W is repeated, using ethylene glycol in place of 1,2-propylene glycol.

The drugs depicted below may be derivatized in this manner to the corresponding compounds of formulas (II) and (I), as may the remaining drugs mentioned with Method Q.

Alternatively, nicotinic acid may be replaced in this process with an analogous starting material, as described in the third paragraph of Method W, and/or adapted to the preparation of derivatives of drugs such as those mentioned with Methods R, S and T.

| STARTING MATERIAL | [D–QC]$^+$ | [D–DHC] |
|---|---|---|
| 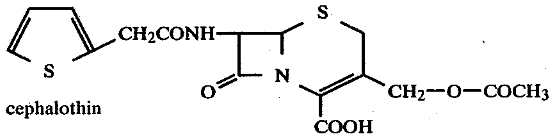 cephalothin | 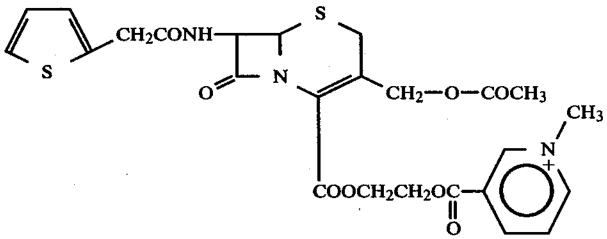 | 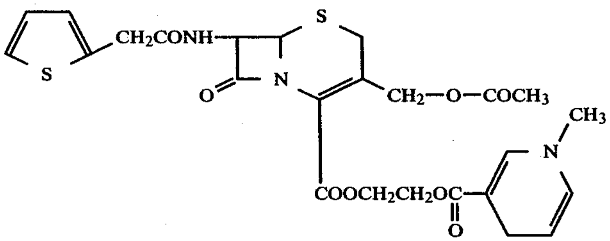 |
| $CH_3CH_2CH_2CHCOOH$ (branch: $CH_3CH_2CH_2$) valproic acid | 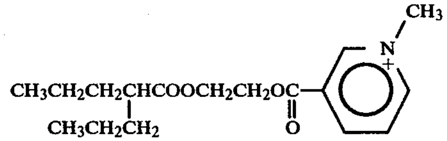 | 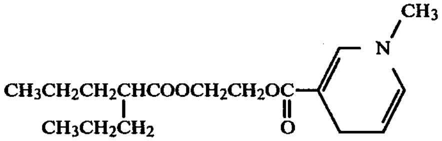 |
| 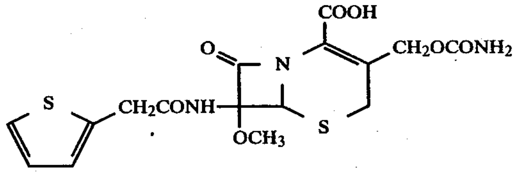 cefoxitin | 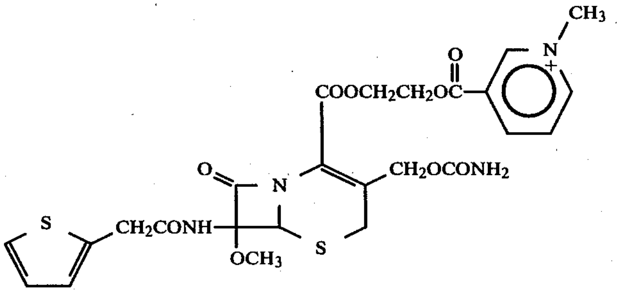 | 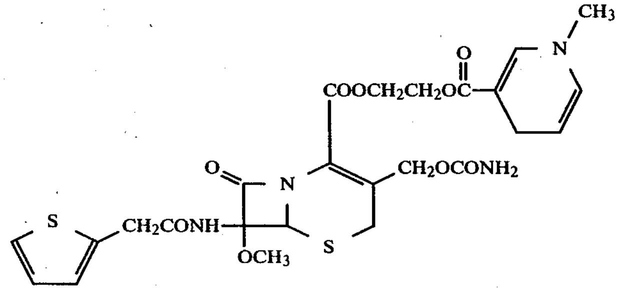 |

-continued
| STARTING MATERIAL | [D—QC]+ | [D—DHC] |
|---|---|---|
| 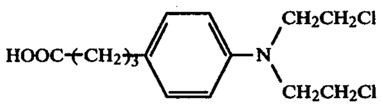 chlorambucil | 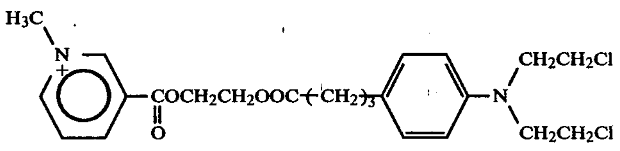 | 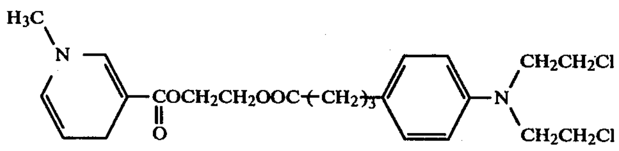 |
| 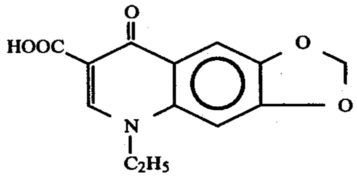 oxolinic acid | 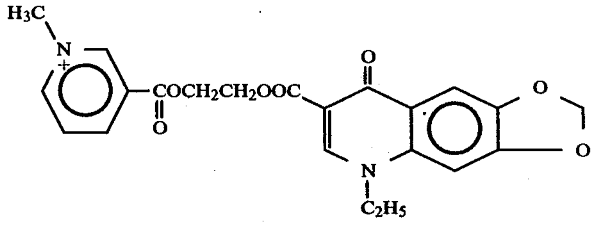 | 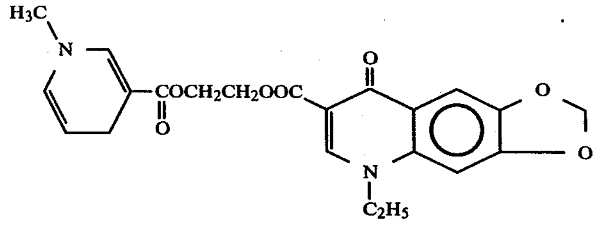 |
| 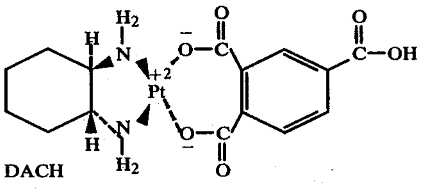 DACH | 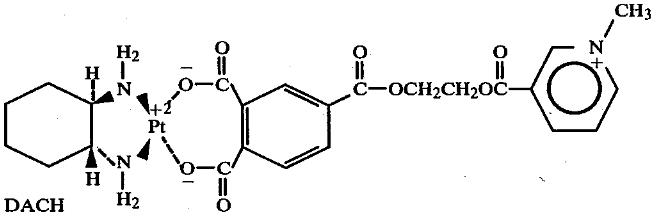 DACH | 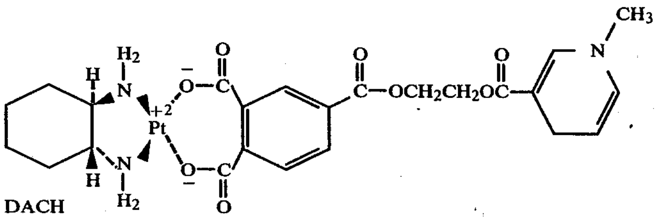 DACH |

-continued
| STARTING MATERIAL | [D—QC]+ | [D—DHC] |
| --- | --- | --- |
| 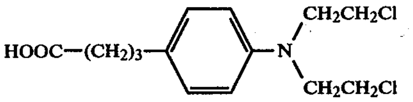<br>chlorambucil | 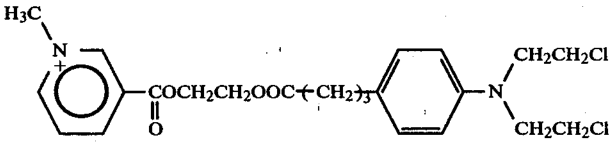 | 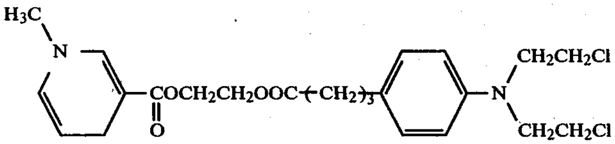 |
| 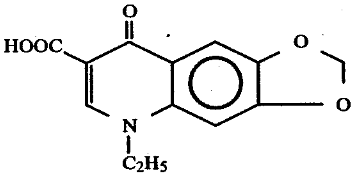<br>oxolinic acid | 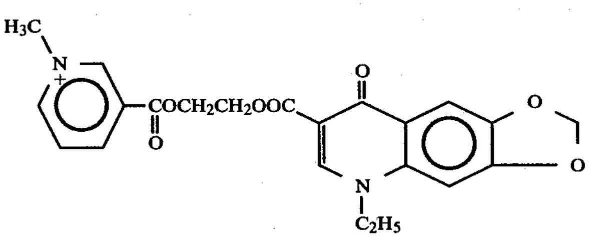 | 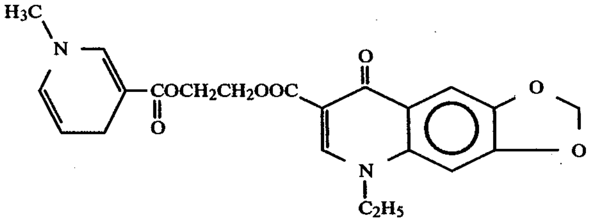 |
| 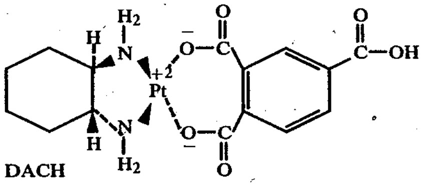<br>DACH | 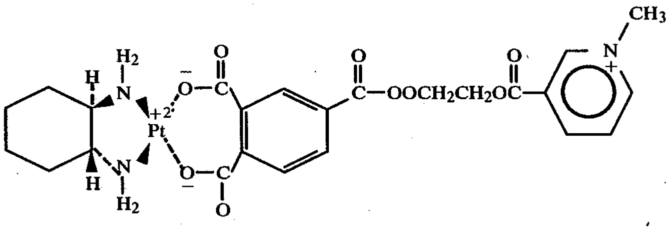 | 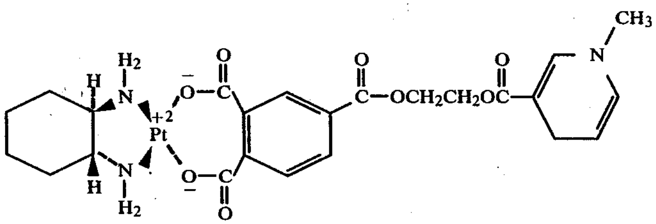 |

-continued
| STARTING MATERIAL | [D-QC]+ | [D-DHC] |
| --- | --- | --- |
| 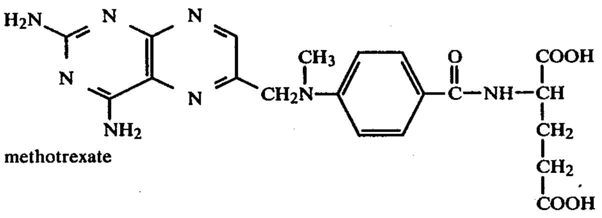 methotrexate | 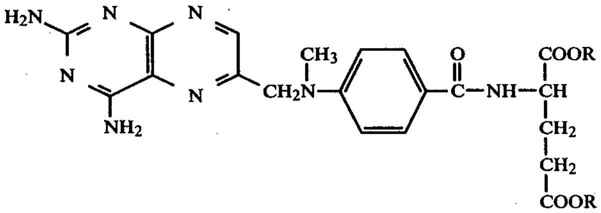 | 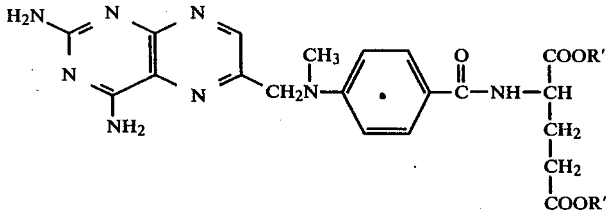 One R' is 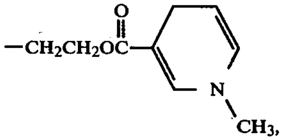 the other R' is H or 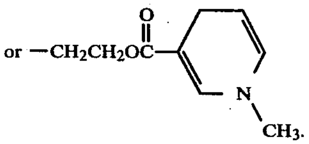 |
| | One R is 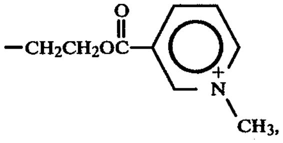 the other R is H or 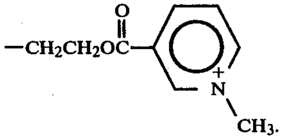 | |
| 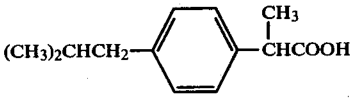 ibuprofen | 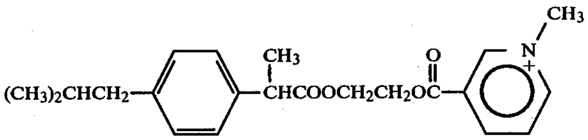 | 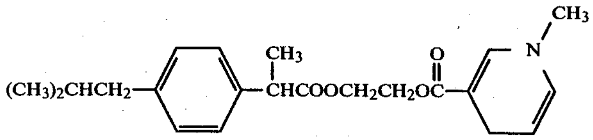 |

-continued
| STARTING MATERIAL | [D—QC]+ | [D—DHC] |
| --- | --- | --- |
| 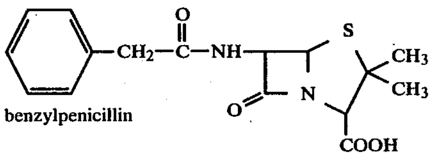 benzylpenicillin | 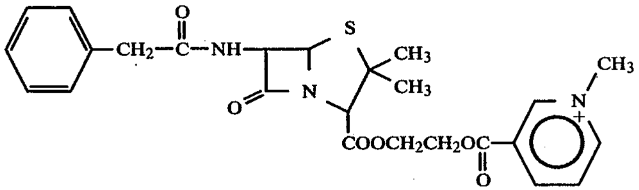 | 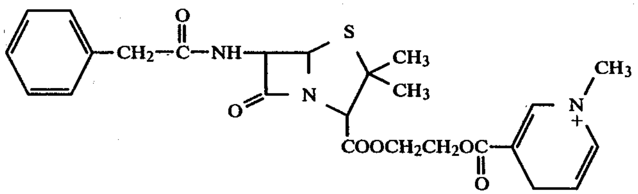 |
| 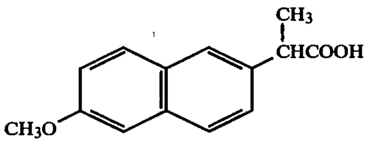 naproxen | 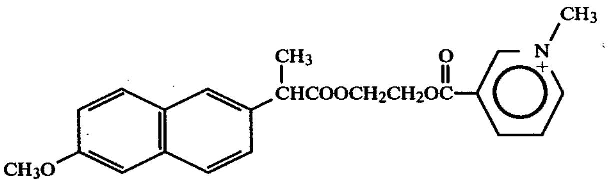 | 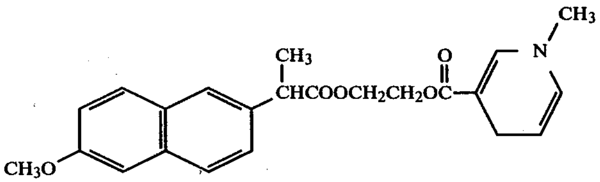 |
| 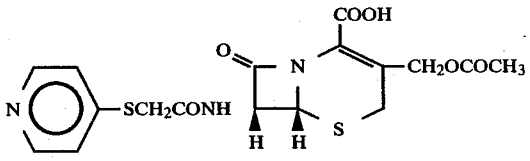 cephapirin | 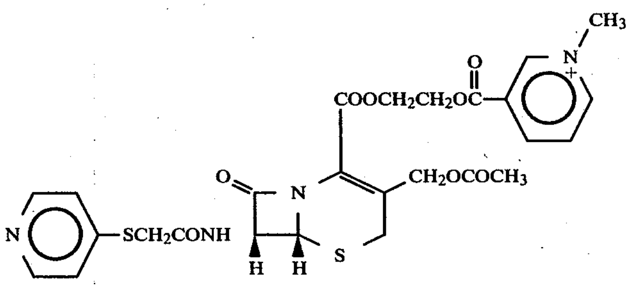 | 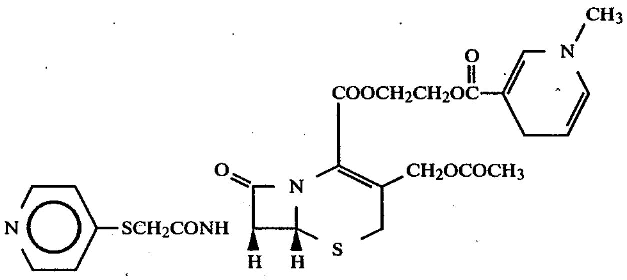 |

-continued
| STARTING MATERIAL | [D—QC]+ | [D—DHC] |
| --- | --- | --- |
| 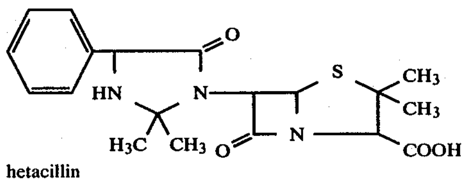<br>hetacillin | 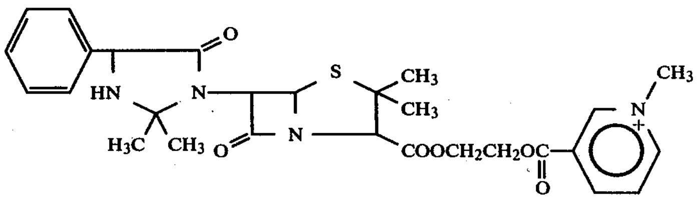 | 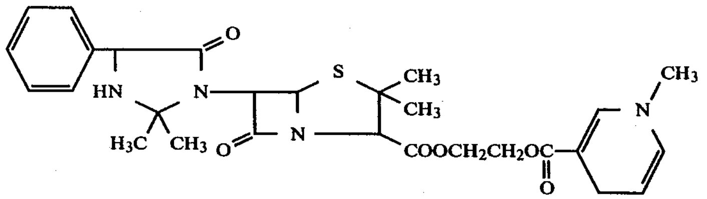 |
| 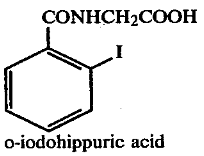<br>o-iodohippuric acid | 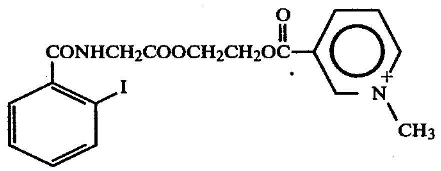 | 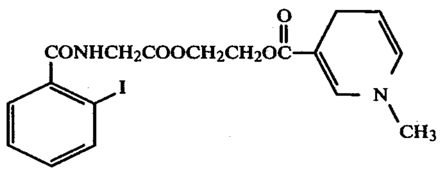 |
| 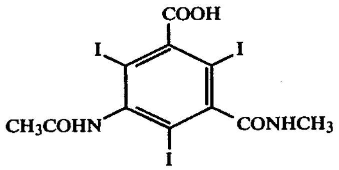<br>iothalamic acid | 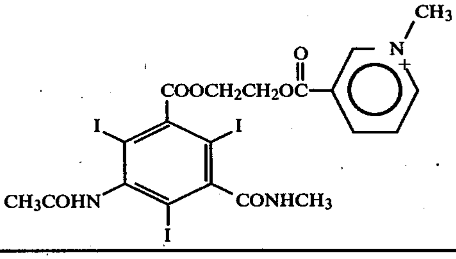 | 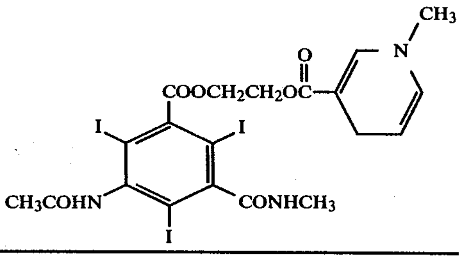 |

Method Z

The process of the first paragraph of Method Q is repeated, using an aminoalkanol of the formula

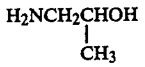

in place of 2-aminoethanol.

The drugs depicted below may be derivatized in this manner to the corresponding compounds of formulas (II) and (I), as may the remaining drugs mentioned with Method Q.

The process variation described in the second paragraph of Method Q may also be applied to Method Z.

This process may of course also be adapted to the preparation of derivatives of drugs such as those mentioned with Methods R, S and T.

| STARTING MATERIAL | [D—QC]$^+$ | [D—DHC] |
|---|---|---|
| 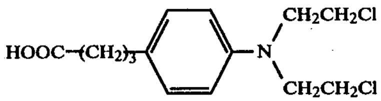 chlorambucil | 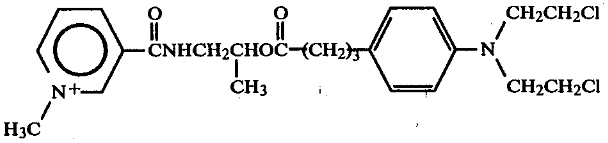 | 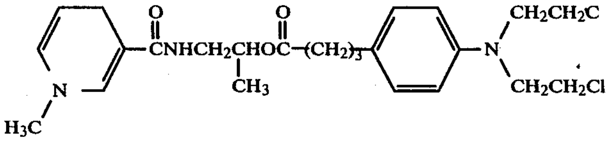 |
| 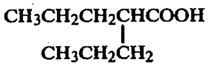 valproic acid | 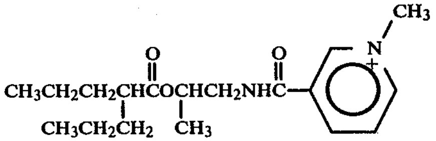 | 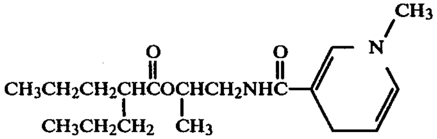 |
| 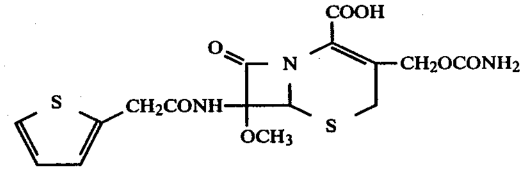 cefoxitin | 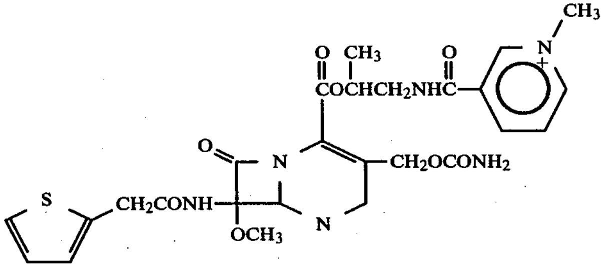 | 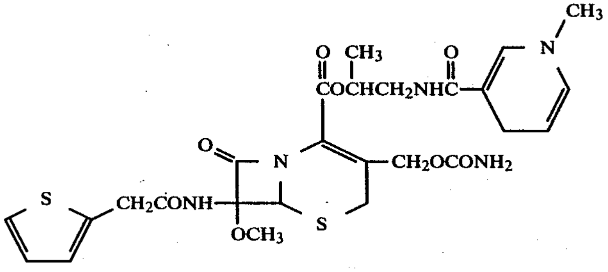 |
| 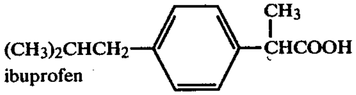 ibuprofen | 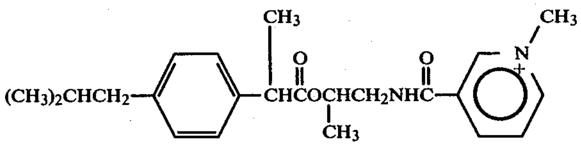 | 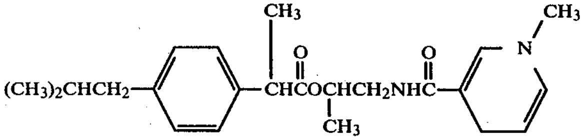 |

-continued
| STARTING MATERIAL | [D—QC]+ | [D—DHC] |
|---|---|---|
| 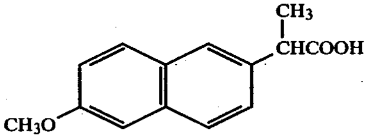 naproxen | 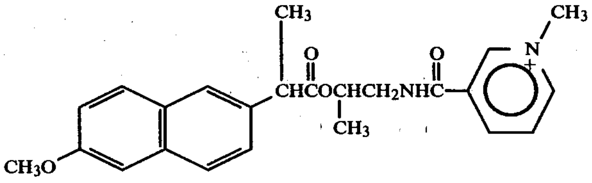 | 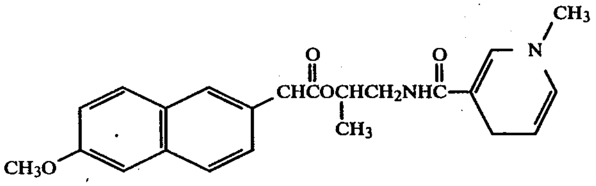 |
| 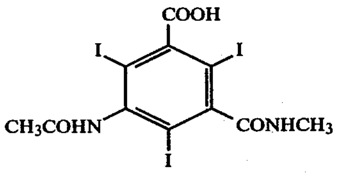 iothalamic acid | 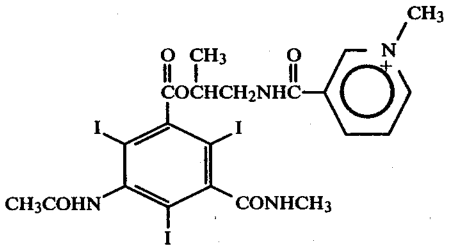 | 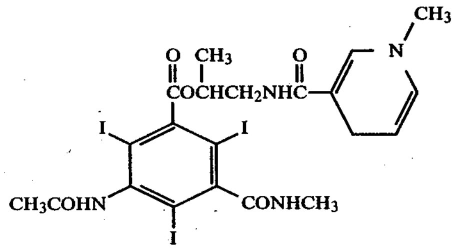 |

IV.

Methods for Salt Formation

An ether solution of a compound of formula (I) is treated with an equivalent amount of anhydrous p-toluenesulfonic acid dissolved in dry ether. Mixing at room temperature is continued until the iminium salt precipitates out of solution. The salt is then removed by filtration.

Imminium salts which may be prepared in this manner include those derived from the following representative compounds of formula (I):

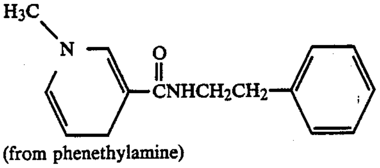

(from phenethylamine)

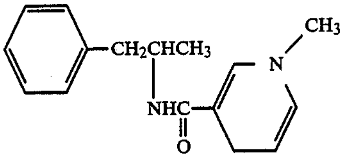

(from amphetamine)

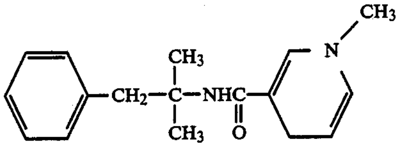

(from phentermine)

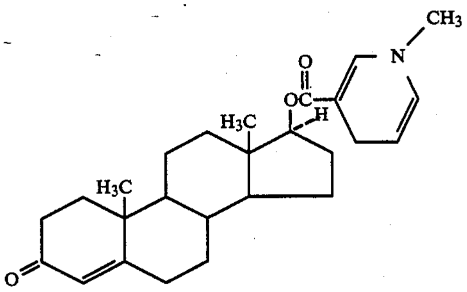

(from testosterone)

In order to further illustrate the present invention and the advantages thereof, the following specific examples are given, it being understood that same are intended only as illustrative and in nowise limitative.

In the examples immediately to follow, all melting points were taken on a Mel-Temp apparatus and are not corrected. Elemental analyses were performed at Atlantic Microlab, Inc., Atlanta, Ga. Infrared spectra were determined using a Beckman Acculab 1 double-beam recording spectrophotometer. NMR spectra were determined by means of a Varian T60A or FX100 spectrometer. All chemical shifts reported are in δ units (parts per million) relative to tetramethylsilane. Ultraviolet absorbance spectra were determined using a Cary Model 219 spectrophotometer. HPLC analysis were performed on Waters Associates Liquid chromatograph with Mode 6000A solvent delivery system, Model U6K injector and Model 440 absorbance detector. And in all cases where Anal. C, H, N is indicated, the elementary analysis of the compound was found within ±0.4 of the calculated value.

EXAMPLE 1

Preparation of N-(β-Phenethyl)nicotinamide

To 10.25 g (0.083 mol) of nicotinic acid, 27.5 ml of thionyl chloride were gradually added. The mixture was stirred at room temperature for 10 min and then refluxed while stirring for 2 hrs. Excess thionyl chloride was then distilled off under reduced pressure. Dry benzene (over sodium, 50 ml) was added and then distilled off under reduced pressure (to remove traces of $SOCl_2$). A white crystalline acid chloride hydrochloride was left, which was used as such for the preparation of amides.

To the solid acid chloride hydrochloride, 150 ml of dry and freshly distilled pyridine were added. To the stirred mixture, 10.45 ml (0.083 mol) of phenethylamine were dropped over 15 min. The mixture was then heated on a water bath while stirring for 2 hrs. Pyridine was distilled off on rotavap. The brown oily residue was poured onto crushed ice. The cream-white solid which separated was filtered by suction, washed with cold water and dried in vacuum; yield 13.3 g (70%), m.p. 79°-80° C.; ir (KBr) 3320 (NH) and 1630 $cm^{-1}$ (C═O), NMR ($CDCl_3$) δ 8.66 (bs, 1H, $C_4$ pyridine proton), 8.46 (bd, 1H, $C_6$ pyridine proton), 8.0-7.6 (m, 1H, $C_4$ pyridine proton), 7.33-6.90 (bs, 6H, $C_6H_5+C_5$ pyridine proton), 7.0-6.57 (hump, 1H, CONH), 3.73 (g, 2H,

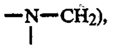

2.97 (t, 2H, $CH_2$—ϕ). Anal. ($C_{14}H_{14}N_2O$) C, H, N.

EXAMPLE 2

Preparation of 1-Benzyl-3-(N-η-phenethyl)carbamoylpyridinium bromide

To a solution of 2.26 g (0.01 mol) of N-(β-phenethyl)-nicotinamide in 5 ml of methanol, 1.4 ml (0.0114 mol) of benzyl bromide were added. The mixture was refluxed for 3 hours. Methanol was distilled off on rotavap. The yellow, oily residue left was scratched when it suddenly solidified into buff, gritty solid. Crystallized from acetone/ether, yield 3.7 g (95%), m.p. 142°-144° C., U.V. max (buffer pH 7.4) 210 and 260 nm; ir (KBr) 3180 (NH) and 1670 $cm^{-1}$ (C═O). NMR ($CDCl_3$/DMSO-$d_6$) δ 10.26 (bs, 1H, $C_2$ pyridine proton), 9.53-8.90 (m, 2H, $C_6$ and $C_4$ pyridine protons), 8.16-7.13 (m, 12H, $2C_6H_5$+CONH+$C_5$ pyridine protons), 6.13 (s, 2H,

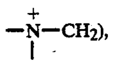

3.96-3.50 (m, 2H, —N—$CH_2$), 3.26-2.83 (m, 2H, $CH_2$—ϕ). Anal. ($C_{21}H_{21}BrN_2O$) C, H, N.

EXAMPLE 3

Preparation of 1-Methyl-3-(N-β-phenethyl)carbamoyl iodide

To a solution of 2.26 g (0.01 mol) of N-(β-phenethyl)-nicotinamide in 5 ml of methanol, 1.3 ml (0.02 mol) in methyl iodide were added. The mixture was refluxed for 3 hrs. Methanol was distilled off on rotavap and the yellow, oily residue was cooled and scratched when a yellow gritty solid was obtained. Crystallized from acetone, yield 3.5 g (95%), m.p. 134°-136° C., U.V. max (buffer pH 7.4) 210, 225 and 226 nm. Ir (KBr) 3240 (NH) and 1665 $cm^{-1}$ (C=O). NMR ($CDCl_3$/DMSO-$d_6$) δ 9.63 (s, 1H, $C_2$ pyridine proton), 9.4–8.9 (m, 2H, $C_4$ and $C_6$ pyridine protons), 8.32–8.06 (m, 1H, $C_5$ pyridine proton), 4.6 (s, 3H, $-\overset{+}{N}-CH_3$), 3.9–3.46 (m, 2H, —N—$CH_2$), 3.2–2.8 (m, 2H, $CH_2$—ϕ). Anal. ($C_{15}H_{17}IN_2O$) C, H, N.

EXAMPLE 4

Preparation of 1-Benzyl-3-(N-β-phenethyl)carbamoyl-1,4-dihydropyridine

To a solution of 3.97 g (0.01 mol) of 1-benzyl-3-(N-β-phenethyl)carbamoylpyridinium bromide in 200 ml of deaerated water, 5.0 g (0.06 mol) of sodium bicarbonate and 200 ml of ether were added. The mixture was stirred in an ice bath and 7.1 g (0.04 mole) of sodium dithionate were added gradually over a period of 5 min. The mixture was stirred for 3 hrs under nitrogen. The ether layer was then separated, washed with water, dried with $Na_2SO_4$ and distilled under vacuo. Yield 2.3 g (72%) of bright yellow, viscous oil was obtained which gave positive test for dihydropyridine with alcoholic silver nitrate solution. U.V. max (buffer pH 7.4) 210 and 355 nm. NMR ($CDCl_3$) δ two overlapping singlets at 7.2 (10H, $2C_6H_5$), 7.1 (bs, 1H, $C_2$ pyridine proton), 5.68 (doublet of doublets, 1H, J=8 and 2 cps, $C_6$ pyridine proton), 6.4–5.0 (hump, 1H, CONH), 4.84–4.60 (m, 1H, $C_5$ pyridine proton), 4.35 (s, 2H, N—$CH_2$), 3.5 (q, 2H, J—7.0, $-N-CH_2$), 3.0 (bs, 2H, $C_4$ pyridine proton) and 2.8 (t, 2H, J=7.0, $CH_2$—ϕ).

EXAMPLE 5

Preparation of 1-Methyl-3-(N-β-phenethyl)carbamoyl-1,4-dihydropyridine

By the similar method described above, 1-methyl-3-(N-β-phenethyl)carbamoyl iodide (3.68 g, 0.01 mol) was reduced using sodium dithionate (7.1 g, 0.04 mol) and sodium bicarbonate (5.0 g, 0.06 mol). Yield 1.8 g (76%) of bright yellow, viscous oil which reduced alcoholic silver nitrate solution. U.V. max (buffer ph 7.4) 210, 290 and 360 nm; NMR ($CDCl_3$) δ 7.2 (s, 5H, $C_6H_5$), 6.9 (bs, 1H, $C_2$ pyridine proton), 5.6 (doublet of doublets, 1H, J=8, 2 cps, $C_6$ pyridine proton), 5.3–5.1 (hump, 1H, CONH), 4.5–4.7 (m, 1H, $C_5$ pyridine protons+N—$CH_3$+$CH_2$—ϕ). Anal. ($C_{15}H_{18}N_2O$) C, H, N.

EXAMPLE 6

Preparation of Diethyl 3,5-pyridinedicarboxylate

To suspension of 8.35 g (0.05 mol) of 3,5-pyridinedicarboxylic acid in 30 ml of absolute ethanol, 10 ml of concentrated sulfuric acid were dropped while stirring. The mixture was then refluxed on a water bath for 5 hrs and poured onto crushed ice. The solution was then made alkaline by the addition of solid $KHCO_3$ in small amounts. A white solid which separated was filtered, washed with water and dried. M.p. 42°-44° C. The mother liquid was extracted with $CH_2Cl_2$ when another crop of the diester was obtained. The overall yield of the crude ester was 9.1 g (82%) of sufficient purity for the examples to follow. NMR ($CDCl_3$) δ 9.62 (d, 2H, J—2 Hz, $C_2$ and $C_6$ pyridine protons), 8.76 (t, 1H, J=2 Hz, $C_4$ pyridine proton), 4.43 (q, 4H, J=7 Hz, 2 $OCH_2$), 1.41 (t, 6H, J=7 Hz, 2 $CH_3$).

EXAMPLE 7

Preparation of 5-Carboethoxy-3-pyridinecarboxylic acid

To a solution of 10 g (0.045 mol) of diethyl 3,5-pyridinedicarboxylate in 75 ml of ethyl alcohol, 25 ml of 2N alcoholic KOH were added while stirring. Stirring was continued for ½ hour at room temperature. To the mixture, 12.5 ml of 4N HCl were added while stirring. The solid which separated was filtered and washed with alcohol. The combined filtrate and washings were distilled on rotovap and the residue was washed with water, filtered and crystallized from ethanol. Yield 7.5 g (86%), m.p. 180°-182° C., NMR ($CDCl_3$/DMSO-$d_6$) δ 10.56 (bs, 1H, COOH), 9.26 (d, 2H, J=2 Hz, $C_2$ and $C_6$ pyridine protons), 8.75 (t, 1H, J=2 Hz, $C_4$ pyridine protons), 4.4 (q, 2H, J=7 Hz, O—$CH_2$), 1.42 (t, 3H, J=7 Hz, $CH_3$).

EXAMPLE 8

Preparation of 5-Carboethoxy-3-(N-β-phenethyl)carbamoylpyridine

To 10 g (0.05 mol) of 5-carboethoxy-3-pyridinecarboxylic acid, 30 ml of thionyl chloride were added and the mixture was warmed on a water bath while stirring until clear (≅3 hrs). Excess thionyl chloride was distilled under vacuum. The residue was cooled to room temperature and 50 ml of sodium-dry benzene was added. The solution was cooled in an ice bath and a solution of 6.2 g (0.051 mol) of phenethylamine and 4 ml of pyridine in 50 ml of dry benzene was dropped while stirring over 1 hr and the mixture was left overnight at room temperature. The mixture was then washed with water until free from $Cl^-$ (tested by $AgNO_3$TS). The organic layer was dried with $Na_2SO_4$ and distilled. The residue was crystallized from ether/pet. ether mixture. Yield 9.0 g (67%), m.p. 159°-161° C.; ir (KBr) 3300 (NH), 1725 (ester CO) and 1650 $cm^{-1}$ (amide CO), NMR ($CDCl_3$) δ 9.13–9.96 (two doublets, 2H, J=2 Hz, $C_2$ and $C_6$ pyridine protons), 8.53 (t, 1H, J=2 Hz, $C_4$ pyridine proton), 7.16 (s, 6H, $C_6H_5$+CONH), 4.36 (q, 2H, J=7 Hz, $OCH_2$), 3.4 (q, 2H, J=7 Hz, N—$CH_2$), 2.9 (5, 2H, J=7 Hz, $CH_2$—ϕ), 1.33 (t, 3H, J=7 Hz, $CH_3$). Anal. ($C_{17}H_{18}N_2O_3$) C, H, N.

EXAMPLE 9

Preparation of 5-Carboethoxy-1-methyl-3-(N-β-phenethyl)carbamoylpyridinium iodide To a solution of 2.9 g (0.01 mol) of 5-carboethoxy-3-(N-β-phenethyl)carbamoylpyridine in 5 ml of acetone, 3 ml of methyl iodide were added. The mixture was refluxed while stirring for 8 hrs and then left overnight. The yellow crystalline solid which precipitated was filtered, washed with acetone, dried and crystallized from acetone. Weight 3.5. g (82%), m.p. 168°-170° C., ir (KBr) 3250 (NH), 1725 (ester CO) and 1670 $cm^{-1}$ (amide CO), U.V. max (buffer pH 7.4) 268 (weak plateau) and 268 nm ($\epsilon$=53, 667), NMR ($DMSO-d_6$) δ 9.53 (bs, 2H, $C_2$ and $C_6$ pyridine protons), 9.33-9.10 (m, 1H, $C_4$ pyridine proton), 7.16 (s, 5H, $C_6H_5$), 4.63-4.26 (complex multiplet, 5H, $-\overset{+}{N}-CH_3 + OCH_2$), 3.56 (q, 2H, J=6 Hz, $-N-CH_2$), 2.90 (t, 2H, J=6, $CH_2$—φ), 1.4 (t, 3H, J=7 Hz, $CH_3$). Anal. ($C_{18}H_{21}IN_2O_3$) C, H, N.

EXAMPLE 10

Preparation of 5-Carboethoxy-1-methyl-3-(N-β-phenethyl)carbamoyl-1,4-dihydropyridine This compound was prepared following the same procedure as in Example 4 using 1.0 g (0.002 mol) of 5-carboethoxy-1-methyl-3-(N-β-phenethyl)carbamoylpyridinium iodide, 1.0 g (0.012 mol) sodium bicarbonate and 1.42 g (0.008 mol) sodium dithionite. Yield, 0.60 g (84%) of orange-yellow viscous oil which reduced alcoholic silver nitrate, but very sowly. U.V. max (buffer pH 7.4) 205 and 390 nm. NMR ($CDCl_3$) 7.33 (s, 5H, $C_6H_5$), 7.0 (s, 2H, $C_2$ and $C_6$ pyridine protons), 5.8-5.3 (hump, 1H, CONH), 4.2 (q, 2H, J=7, O—$CH_2$), 3.66 (q, 2H, J=7 Hz, $-\overset{+}{N}-CH_2$), 3.16 (bs, 2H, $C_4$ pyridine proton), 3.0 (q, 2H, J=7, $CH_2$—φ), 1.4 (t, 3H, J=7, $CH_3$).

EXAMPLE 11

Preparation of 3,5-Di(N-β-phenethyl)carbamoylpyridine

To a solution of 2.53 g (0.01 mol) of diethyl 3,5-pyridinedicarboxylate in 10 ml of methanol, 3.0 g (0.025 mol) of phenethylamine were added. The mixture was refluxed overnight and then distilled. The residue was washed with very dilute HCl solution and water, dried and crystallized form ethanol. Yield 2.9 g (80%), m.p. 189°-190° C. NMR ($CDCl_3$) δ 9.00 (d, J=2 Hz, 2H, 2,6-dipyridyl), 8.33 (5, J=2, 1H, 4-pyridyl), 7.30 (s, 10H, 2 $C_6H_5$), 6.93-6.40 (hump, 2H, 2 COHN), 3.83 (q, J=7, 4H, 2 —N—$CH_2$), 3.00 (t, J=7, 4H, 2 —$CH_2$—φ). Anal. ($C_{23}H_{23}N_3O_2$) C, H, N.

EXAMPLE 12

Preparation of 1-Methyl-3,5-di(N-β-phenethyl)carbamoyl pyridinium iodide

To a solution of 2.0 g (5.3 mmol) of 3,5-di(N-β-phenethyl)carbamoylpyridine in 10 ml of acetone, 2 ml of methyl iodide were added and the mixture was refluxed for 24 hrs. The yellow crystalline solid which separated was filtered, washed with acetone and dried. Weight 1.4 g (51%), m.p. 186°-188° C. U.V. spectrum of a solution in phosphate buffer 7.4 showed a plateau at 275 nm, a shoulder at 225 nm and a sharp peak at 203 nm ($\epsilon$=67,356). Ir (KBr) 3240 (NH), 1665 and 1650 $cm^{-1}$ (twin band, C=O). NMR ($CDCl_3/D_2O$) δ 9.35 (d, 2H, J=2, $C_2$ and $C_6$ pyridine protons), 8.56 (d, 1H, J=2 Hz, $C_4$ pyridine proton), 7.20 (s, 10H, 2 $C_6H_5$), 4.56 (s, 3H, $-\overset{+}{N}-CH_3$), 3.66 (t, 4H, J=7 Hz, 2 —N—$CH_2$), 2.96 (t, 4H, J=7 Hz, 2 $CH_2$—φ). Anal. ($C_{24}H_{26}IN_3O_2$).

EXAMPLE 13

Preparation of 1-Methyl-3,5-di(N-β-phenethyl)carbamoyl-1,4-dihydropyridine

This compound was prepared following the same procedure as in Example 4, using 1 g (0.002 mol) of 1-methyl-3,5-di(N-β-phenethyl)carbamoyl pyridinium iodide, 1.0 g (0.012 mol) sodium bicarbonate and 1.4 g (0.008 mol) sodium dithionite. Yield 0.65 g (86%) of orange-yellow semisolid which could not be crystallized. Its alcoholic solution shows a slow reduction with alcoholic silver nitrate solution. U.V. max (buffer pH 7.4) 388 and 210 nm. NMR ($CDCl_3$) 7.13 (s, 5H, $C_6H_5$), 6.76 (s, 1H, $C_2$ pyridine protons), 3.51 (q, 4H, J=7 Hz, 2

$-N-CH_2$), 3.06-2.60 (m, 9H, O—$CH_2$+$C_4$ pyridine proton +N—$CH_3$).

EXAMPLE 14

Preparation of N-Nicotinoyldopamine (compound 7)

To a pyridine solution containing 11.7 g (0.05 mol) dopamine hydrobromide and 6.15 g (0.05 mol) nicotinic acid at 0° C. were added 10.3 g (0.05 mol) dicyclohexylcarbodiimide (DCC). The reaction mixture was stirred at room temperature for 24 hours and the formed dicyclohexylurea was removed by filtration. The pyridine was removed in vacuo and the residue was crystallized from water at 0° C. The product was isolated by filtration and dried over phosphorous pentoxide. Recrystallization from isopropanol gave 9.0 g (0.035 mol), 70% N-nicotinoyldopamine, m.p. 159°-162° C.; aqueous solution of the compound gave a green color with $Fe^{+3}$ and reduced $AgNO_3$; ir (KBr) 3300, 2960, 1725, 1630, 1590, 1520, 1430, 1290, 1190, 1115, 720 and 710 $cm^{-1}$; NMR ($d_6$-DMSO) β 9.25–6.25 (m, 7H), 3.3 (m, 2H) and 2.65 (m, 2H) ppm. Anal. ($C_{14}H_{14}N_2O_3$) C, H, N.

EXAMPLE 15

Preparation of 3-{N-[β-(3,4-Diacetoxyphenyl)ethyl]}carbamoylpyridine

To an ice cold suspension of 2.06 g (8 mmol) finely powdered nicotinoyldopamine in 50 ml of chloroform, 1.56 g (10 mmol) of acetyl chloride were dropped while stirring. The mixture was refluxed for 3 hrs, then filtered. The filtrate was washed with water until the washing did not give test for chloride ions with $AgNO_3$ T.S. Chloroform was distilled on rotavap and the residue was crystallized from ether/pet. ether. Yield 2.2 g (81%) NMR ($CDCl_3$) 8.90 (bs, 1H, $C_2$ pyridine proton), 8.56 (bd, 1H, $C_6$ pyridine proton), 8.16–7.83 (m, 1H, $C_4$ pyridine proton), 7.36–7.03 (m, 5H, $C_6H_3+C_5$ pyridine proton +NH), 3.60 (q, 2H, J=7 Hz,

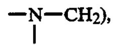

2.90 (t, 2H, J=7 Hz, —$CH_2$).

EXAMPLE 16

Preparation of 3-{N-[β-(3,4-Dipivalyloxyphenyl)ethyl]}carbamoylpyridine (compound 8c)

To a suspension of 5.16 g (0.02 mol) finely powdered nicotinoyldopamine in 100 ml chloroform, 7.23 g (0.06 mol) trimethylacetyl chloride were added under stirring. The mixture was refluxed for 6 hrs and then filtered. The filtrate was washed with water free of chloride ions, then washed once with a 5% solution of $NaHCO_3$, then with water. The chloroform was evaporated and the residue was chromatographed by using a silica gel G column and 2% methanol in chloroform as the eluent. The first fraction was collected and evaporated and the residue was crystallized from ether/petroleum ether. Yield, 6.2 g (73%) of a white crystalline solid, m.p. 112°–114° C., NMR ($CDCl_3$) δ 9.06 (bs, 1H, $C_2$ pyridine proton), 8.73 (bd, 1H, $C_6$ pyridine proton), 8.30–8.13 (m, 1H, $C_4$ pyridine proton), 7.46–7.10 (m, 5H, $C_6H_3+C_5$ pyridine proton+CONH), 3.66 (q, 2H, J=6.25 Hz, —N—$CH_2$), 3.0 (t, 2H, J=6 Hz, —$CH_2$), 1.41 (s, 18H, 2—$C(CH_3)_3$). Anal. Calcd for $C_{24}H_{30}N_2O_5$: C, 67.58; H, 7.09; N, 6.56. Found: C, 67.61; H, 7.10; N, 6.54.

EXAMPLE 17

Preparation of 1-Methyl-3-{N-[β-(3,4-dihydroxyphenyl)ethyl)]}carbamoylpyridinium iodide (compound 6a)

To a solution of 1.26 g (5 mmol) of nicotinoyldopamine (7) in 10 ml of acetone, 1.41 g (10 mmol) of methyl iodide were added and the mixture was refluxed under stirring for 6 hrs. The acetone was removed and the residue was crystallized from methanol/ether. Yield, 1.7 g (87%), m.p. 155°–157° C.(dec). Aqueous solution gave a green color with $Fe^{+3}$, NMR ($D_2O$) δ 9.30–8.28 (ms, 4H, $C_5H_4N^+$), 7.00 (bs, 3H, $C_6H_3$), 4.60 (s, 3H, —$N^+$—$CH_3$), 3.80 (t, 2H, J=7 Hz, —N—$CH_2$), 2.93 (t, 2H, J=7 Hz, $CH_2$). Anal. Calcd for $C_{15}H_{17}IN_2O_3.H_2O$: C, 43.11; H, 4.55; N, 6.70. Found: C, 43.83; H, 4.23; N, 6.81.

EXAMPLE 18

Preparation of 1-Methyl-3-{N-[β-(3,4-diacetoxyphenyl)ethyl]}carbamoylpyridinium iodide (compound 6b)

To a solution of 1.71 g (5 mmol) of 3-{N-[β-(3,4-diacetoxyphenyl)ethyl]}carbamoylpyridine (prepared like compound 8c), 1.41 g (10 mmol) of methyl iodide were added and the mixture was refluxed overnight under stirring. The acetone solution was then decanted from the insoluble oily residue. Ether was added to the acetone solution and the solid which separated was crystallized from acetone/ether. Yield, 1.9 g (78%) of yellow crystalline needles, m.p. 171°–173° C. U.V. (methanol) 215, 265 nm; NMR ($D_2O$) δ 8.86–7.63 (ms, 4H, $C_5H_4N^+$), 6.66 (bs, 3H, $C_6H_3$), 4.4 (s, 3H, —N-+—$CH_3$), 3.50 (t, 2H, —N—$CH_2$), 3.03 (t, 2H, $CH_2$), 2.21 (bs, 6H, 2 $COCH_3$). Anal. Calcd for $C_{19}H_{21}IN_2O_5$: C, 47.12; H, 4.37; N, 5.78. Found: C, 47.23; H, 4.38; N, 5.78.

EXAMPLE 19

Preparation of 1-Methyl-3-{N-[β-(3,4-dipivalyloxyphenyl)ethyl]}carbamoylpyridinium iodide (compound 6c)

To a solution of 5.0 g (11.7 mmol) of compound 8c in 20 ml of acetone, 3.3 g (23.4 mmol) of methyl iodide were added and the mixture was refluxed under stirring for 6 hrs, then cooled. The orange crystalline solid which separated was filtered, washed with ether and crystallized for acetone/ether. Yield, 5.6 g (85%), m.p. 163°–165° C. U.V. (buffer pH 7.4) 270, 215 nm. NMR (DMSO-$d_6$) δ 7.68–7.06 (ms, 7H, $C_5N_4N^++C_6H_3$+NH), 4.56 (s, 3H, —$N^+$—$CH_3$), 3.42 (q, 2H, J=7 Hz, —N—$CH_2$), 3.19 (t, 2H, J=7 Hz, $CH_2$), 1.32 (s, 18H, 2 —$C(CH_3)_3$). Anal. Calcd for $C_{25}H_{33}IN_2O_5$: C, 52.82; H, 5.85; N, 4.92. Found: C, 52.76; H, 5.87; N, 4.90.

EXAMPLE 20

Preparation of 1-Methyl-3-{N-[β-(4-hydroxy-3-methoxyphenyl)ethyl]}carbamoylpyridinium iodide (compound 9)

N-nicotinoyl-3-methoxytyramine was prepared by following the procedure used for the preparation of compound 7. The isolated crude amide was quaternized directly with methyl iodide following the method used for the preparation of compound 6a. Crystallization from methanol gave a yellow crystalline compound, m.p 192°–194° C. with overall yield of 84%, calculated on the basis of 3-methoxytyramine starting material. NMR ($D_2O$) closely similar to that of 6a except for the singlet at δ 3.66 for $OCH_3$.

EXAMPLE 21

Preparation of 1-Methyl-3-{N-[β-(3,4-dihydroxyphenyl)ethyl]}carbamoyl-1,4-dihydropyridine (compound 5a)

To an ice cold solution of 1.0 g (2.5 mmol) of compound 6a in 200 ml of deaerated water, 1.26 g (15 mmol) sodium bicarbonate were added. Nitrogen was bubbled into the mixtue and 1.74 g (10 mmol) of sodium dithionite were added gradually to the mixture under stirring. Stirring was continued for 1 hr and the mixture was then extracted twice with 50 ml of ether. The ether extract was washed with water, dried with anhydrous $Na_2SO_4$ and evaporated to dryness. Yield, 0.36 g (54%) of a yellow solid, m.p. 90°–93° C. (dec.) which gave a green color with ferric chloride test and reduced alcoholic $AgNO_3$ instantly. UV ($CH_3OH$) 220, 350 nm. NMR ($CDCl_3/D_2O$) δ 7.2–6.9 (ms, 4H, $C_6H_3+C_2$ dihydropyridine proton), 5.6 (m, 1H, $C_6$ dihydropyridine proton), 4.6–4.4 (m, 1H, $C_5$ dihydropyridine proton), 3.4 (m, 2H, —N—$CH_2$), 3.1–2.7 (m, 7H, N—$CH_3+C_4$ dihydropyridine protons+$CH_2$). Anal. Calcd for $C_{15}H_{18}N_2O_3.\frac{1}{2}H_2O$: C, 63.59; H, 6.76; N, 9.88. Found: C, 63.56; H, 6.85; N, 9.72.

EXAMPLE 22

Preparation of 1-Methyl-3-{N-[β-(3,4-diacetoxyphenyl)ethyl]}carbamoyl-1,4-dihydropyridine (compound 5b)

To an ice cold solution of 1.4 g (3 mmol) of compound 6b in 200 ml of deaerated water, 1.5 g (18 mmol) of sodium bicarbonate was added. A stream of $N_2$ was bubbled into the mixture and 2.1. g (12 mmol) of sodium dithionite were gradually added under stirring. Stirring was continued for 30 min and then the mixture was extracted with ethyl acetate. The extract was washed with water, dried with anhydrous $Na_2SO_4$ and evaporated to dryness. The yellowish semisolid mass remaining gave a faint green color with ferric chloride test indicating partial hydrolysis of the ester functions. It reduced alcoholic silver nitrate instantly. U.V. ($CH_3OH$) 220, 273 and 355 nm; NMR ($CDCl_3/D_2O$) δ 7.13–6.80 (ms, 4H, $C_6H_3+C_2$ dihydropyridine proton), 5.53 (doublet of doublets, 1H, $C_6$ dihydropyridine proton), 4.63–4.46 (m, 1H, $C_5$ dihydropyridine proton), 3.33 (t, 2H, J=6.5 Hz, —N—$CH_2$), 3.06–2.66 (m, 7H, —N—$CH_3+C_4$ dihydropyridine proton+$CH_2$), 1.8 (s, ≅6H, 2$COCH_3$).

EXAMPLE 23

Preparation of 1-Methyl-3-{N-[β-(3,4-dipivalyloxyphenyl)ethyl]}carbamoyl-1,4-dihydropyridine (compound 5c)

To a cold mixture of 2.0 g (3.5 mmol) of compound 6c, 200 ml of deaerated water and 100 ml of ethyl acetate, 1.14 g (14 mmol) of sodium bicarbonate and 2.43 g (14 mmol) of sodium dithionite were added. The mixture was stirred under $N_2$ for 20 mins. The ethyl acetate layer was separated and the aqueous layer was reextracted with 100 ml of ethyl acetate. The combined ethyl acetate was washed with cold deaerated water, dried over anhydrous $Na_2SO_4$ and distilled on rotovapor. The viscous yellow oily residue was dissolved in 5 ml of acetone, filtered under $N_2$ atmosphere and then evaporated under reduced pressure. The solid residue was dried under vacuum over $P_2O_5$ in $N_2$ atmosphere. It reduced alcoholic $AgNO_3$ instantaneously and gave no color with $DeCl_3$ test. Yield, 1.3 g (83%) m.p. 45°–48° C.; UV ($CH_3OH$) 210 and 355 nm; NMR ($CDCl_3$) δ 7.04–6.92 (m, 4H, $C_6H_3+C_2$ dihydropyridine proton), 5.71–5.61 (doublet of doublets, 1H, $C_6$ dihydropyridine proton), 4.81 (bs, 1H, CONH), 4.60–4.51 (m, 1H, $C_5$ dihydropyridine proton), 3.53 (q, 2H, J=6.3 Hz, —N—$CH_2$), 2.36 (bs, 2H, $C_4$ dihydropyridine proton), 2.91 (s, 3H, N—$CH_3$), 2.79 (t, 2H, J=6.3 Hz, $CH_2$), 1.33 (s, 18H, CO—$C(CH_3)_3$). Anal. Calcd for $C_{25}H_{34}N_2O_5.1\frac{1}{2}H_2O$: C, 63.9; H, 7.93; N, 5.96. Found: C, 63.4; H, 7.81; N, 5.94.

EXAMPLE 24

Preparation of 1-Methyl-3-{N-[β-(4-hydroxy-3-methoxyphenyl)ethyl]}carbamoyl-1,4-dihydropyridine (compound 10)

This compound was prepared following the same method as for the preparation of compound 5c. The crude solid obtained showed the same NMR ($CDCl_3/D_2O$) pattern as compound 5a, except for a peak at δ 3.5 for the $OCH_3$ protons. It was sufficiently pure for the determination of its retention time following the HPLC method of analysis detailed in Example 37 below. No trials were made for its further crystallization or elemental analysis.

EXAMPLE 25

Preparation of N-Nicotinoyltyramine

To an ice cold suspension of 3.69 g (0.03 mol) nicotinic acid in a solution of 5.2 g (0.03 mol) tyramine hydrochloride in 100 ml of pyridine, 6.18 g (0.03 mol) of dicyclohexylcarbodiimide (DCC) were gradually added while stirring. Stirring was continued at room temperature for 24 hrs and the formed dicyclohexylurea was removed by filtration. The pyridine was removed by distillation in vacuo and the residue was triturated with cold water, filtered and crystallized from 50% aqueous methanol. Yield, 6.25 g (86%), m.p. 179°–181° C. PMR (DMSO-$d_6/D_2O$) δ 9.0–8.66 (m, 2H, $C_2$ and $C_6$ pyridine protons), 8.33–8.10 (m, 1H, $C_4$ pyridine proton), 7.66–7.46 (m, 1H, $C_5$ pyridine proton), 7.23–6.70 (m, rH, $C_6H_4$), 3.56 (t, 2H, —$\underset{|}{N}CH_2$), 2.90 (t, 2H, $CH_2$). Anal. ($C_{14}H_{14}N_2O_2$) C, H, N.

EXAMPLE 26

Preparation of 3-{N-[β-(4-pivalyloxyphenyl)ethyl]}carbamoylpyridine

To an ice cold suspension of 4.84 g (0.02 mol) N-nicotinoyltyramine in 100 ml chloroform, 3.6 g (0.03 mol) of trimethylacetyl chloride were dropped while stirring. The mixture was refluxed overnight and the non-reacted nicotinoyltyramine was filtered off. The filtrate was washed with water until free from chloride ions, washed once with 5% solution of $NaHCO_3$ and then with water. Chloroform was evaporated on rotavap and the residue was crystallized from ether/pet. ether. Yield 3.9 g (60%), m.p. 80°–82° C. PMR ($CDCl_3$) δ 8.66–6.93 (m, 8H, $C_5H_4N+C_6H_4$), 3.56 (q, 2H, J=7 Hz, —$\underset{|}{N}$—$CH_2$), 2.86 (5, 2H, J=7 Hz, $CH_2$), 1.33 (s, 9H, C—$(CH_3)_3$).

EXAMPLE 27

Preparation of 1-Methyl-3-{N-[β-(4-hydroxyphenyl)ethyl]}carbamoylpyridinium iodide To a solution of 1.21 g (5 mmol) of nicotinoyltyramine in 10 ml of acetone, 1.41 g (10 mmol) of methyl iodide were added and the mixture was refluxed while stirring for 6 hrs. The fine, yellow solid which separated was filtered and crystallized from methanol ether. Yield 1.78 g (93%), m.p. 208°-210° C. PMR (DMSO-$d_6$/$D_2O$) δ 9.23-8.26 (m, 4H, $C_5H_4N^+$), 7.33-6.83 (m, 4H, $C_6H_4$), 4.50 (s, 3H, $-\overset{+}{N}-CH_3$), 3.70 (t, J=7 Hz, 2H, $N-CH_2$), 2.93 (t, J=7 Hz, 2H, $CH_2$).

EXAMPLE 28

Preparation of 1-Methyl-3-{N-[β-(4-pivalyloxyphenyl)ethyl]}carbamoylpyridinium iodide To a solution of 1.63 g (5 mmol) of the product of Example 26 in 10 ml of acetone, 1.41 g (10 mmol) methyl iodide were added and the mixture was refluxed overnight while stirring. The acetone layer was separated by decantation and the yellowish, oily residue was crystallized from methanol/ether. Yield, 1.94 g (83%), m.p. 155°-157° C. PMR ($D_2O$) δ 9.16-8.00 (m, 4H, $C_5H_4N^+$), 7.33-6.83 (m, 4H, $C_6H_4$), 4.40 (s, 3H, $N^+-CH_3$), 3.5 (t, 2H, J=7 Hz, $-N-CH_2$), 2.90 (t, 2H, J=7 Hz, $CH_2$), 1.30 (s, 9H, $C-(CH_3)_3$). Anal. ($C_{20}H_{25}N_2O_3I$) C, H, N.

EXAMPLE 29

Preparation of 1-Methyl-3-{N-[β-(4-hydroxyphenyl)ethyl]}carbamoyl-1,4-dihydropyridine To an ice cold solution of 1.15 g (3 mmol) of the product of Example 27 in 200 ml of deaerated water, 1.5 g (18 mmol) sodium bicarbonate were added. While the mixture was bubbled with $N_2$ gas, 2.09 g (12 mmol) of sodium dithionite were gradually added to the mixture. The mixture was stirred under $N_2$ for 1 hr and then extracted twice, each with 100 ml of ethyl acetate. The combined extract was washed with water, dried over anhydrous $Na_2SO_4$ and distilled on rotovap. Yield, 0.38 g (50%) of yellowish semisolid which reduced alcoholic $AgNO_3TS$ instantaneously. (PMR as expected.)

EXAMPLE 30

Preparation of 1-Methyl-3-{N-[β-4-pivalyloxyphenyl)]}carbamoyl-1,4-dihydropyridine To an ice cold mixture of 2.34 g (5 mmol) of the product of Example 28, 200 ml of deaerated water and 100 ml of ethyl acetate, 1.63 g (20 mmol) sodium bicarbonate and 3.47 g (20 mmol) sodium dithionite were added while stirring the mixture. Stirring was continued under $N_2$ gas for 30 min. The ethyl acetate layer was separated and the aqueous layer was extracted with 100 ml of ethyl acetate. The combined ethyl acetate extract was washed with 100 ml cold deaerated water, dried over anhydrous $Na_2SO_4$ and evaporated on rotavap. The viscous, yellow residue was dissolved in 5 ml of acetone, filtered under $N_2$ gas through folded filter paper and distilled on rotavap. The solid residue was dried under vacuo over $P_2O_5$ in $N_2$ atmosphere. It reduced alcoholic $AgNO_3$ instantaneously. Yield, 1.06 g (62%). (PMR as expected.)

EXAMPLE 31

Preparation of 3,5-Pyridinedicarboxylic acid didecyl ester hydrochloride 3,5-Pyridinedicarboxylic acid (9.6 g, 0.06 mole) was converted to the diacid chloride by treatment with excess $SOCl_2$. The mixture was refluxed at 100° C. for 6 hrs. Excess $SOCl_2$ was distilled under reduced pressure and 25 ml of decyl alcohol dissolved in benzene were added. The solution was refluxed for 5 hrs after which benzene was distilled and the residue dissolved in ethyl ether. The organic phase was extracted with bicarbonate solution and later dried over $Na_2SO_4$. The ethyl ether solution was acidified with HCl (gas) and 24.2 g of compound (95% yield, m.p. 80°-90° C.) were obtained. 1H (NMR) $CDCl_3$/$d_6DMSO$ δ 9.3 (3H, bs), 8.7 (1H, bs), 4.3 (4H, bT) and 1.4 (38H, bm) ppm.

EXAMPLE 32

Preparation of Didecyl 3,5-dicarboxylate-1-methylpyridinium iodide

The product of Example 31 (10 g, 0.025 mole) was dissolved in an ethyl ether/bicarbonate solution. The organic phase was rinsed with water and dried over $Na_2SO_4$. The solvent was evaporated and the residue was dissolved in acetone and an excess of methyl iodide was added. The solution was refluxed for 8 hrs, after which the solvent was evaporated and ethyl ether was added to the residue. A yellow solid was obtained which was filtered and rinsed with more ethyl ether. The solid was recrystallized from a minimum amount of ethyl acetate to yield 12.5 g (85%) m.p. 104°-105° C. Analytical data: Theory: C, 57.04; H, 8.21. Found: C, 57.18; H, 8.09. Spectrophotometric data in methanol: λ219 $\epsilon=2.7\times10^4$ 1/mol cm; λ277 $\epsilon=3.6\times10^3$ 1/mol cm.

EXAMPLE 33

(i) Oxidation by Hydrogen Peroxide:

To 10 ml of 30% $H_2O_2$ was added 0.2 g of the dihydropyridine derivative (products of Examples 4, 5, 10 or 13). The mixture was stirred and samples were taken to check the UV spectrum. Complete oxidation to the corresponding quaternary salts was observed.

(ii) Oxidation by Silver Nitrate:

To 5 ml of saturated methanolic $AgNO_3$ solution was added 1 ml of 5% methanolic solution of the dihydropyridine derivative. The mixture was shaken and left for 5 min for complete precipitation of silver, centrifuged and an aliquot was taken to check the UV spectrum. Complete oxidation to the quaternary salts was observed.

(iii) Calibration Curves

UV study of the compounds prepared in Examples 2–5, 9, 10, 12 and 13 revealed that they obey Beer's Law with good coefficients and at a wide range of dilution levels. The study was done at 350 nm for the dihydro derivatives and at 262 and 220 nm for all the quaternary and dihydro.

EXAMPLE 34

Kinetics of Oxidation of the Dihydro Derivatives

In Plasma:

0.2 ml of ($6.25\times10^{-4}$M) freshly prepared solution of the dihydro derivative in methyl alcohol was diluted to 10 ml with 20% plasma (diluted whith phosphate buffer pH 7.4). The solution was kept at 37° C. and UV spectrum was scanned from 400 nm to 300 nm every 10 min for 2 hrs against reference made by dilution of 0.2 ml methyl alcohol with 20% plasma to 10 ml.

In Whole Blood:

In each of 5 tubes, 0.1 ml of $10\times10^{-4}$M methanolic solution of the freshly prepared dihydro derivative, was added to 2 ml of fresh heparinized whole human blood and the tubes were kept at 37° C. in a water bath. At the end of the time period to be investigated, 8 ml of acetonitrile was added, and the tubes were shaken vigorously and centrifuged. The extension of the supernatant solution at 350 nm was measured. A reference sample was made by addition of 0.1 ml of methyl alcohol instead of the sample solution following the same procedure.

In Brain Homogenate:

2.0 g of rat brain tissue were homogenized in 10 ml of phosphate buffer, pH 7.4. The homogenate was centrifuged for 15 min at 3000 rpm, decanted, heated in a water bath at 50° C. for 5 min and then centrifuged again. The supernatant solution was diluted to 100 ml with phosphate buffer, pH 7.4.

Reference Sample:

0.2 ml of methyl alcohol was diluted to 10 ml with the brain homogenate solution, and the solution was used to record the base line on a Cary 219 spectrophotometer and as a reference for the dihydro derivative sample solution.

Dihydro Derivative Sample Solutions:

0.2 ml of $6.25\times10^{-4}$M methanolic solution of the freshly prepared dihydro derivative was diluted to 10 ml with the brain homogenate solution. The mixture was scanned at 37° C. from 400 nm to 300 nm every 10 min for 2 hrs on a Cary 219 spectrophotometer.

In Liver Homogenate:

Liver Homogenate Solution:

5.0 g of rat liver tissue were homogenized in 50 ml of phosphate buffer, pH 7.4. The homogenate was centrifuged, decanted, heated in a water bath at 50° C. for 5 min and then centrifuged again. The supernatant homogenate was diluted to 250 ml with phosphate buffer, pH 7.4.

Reference Sample:

0.2 ml of methyl alcohol was diluted to 10 ml with the liver homogenate solution and the solution was used to record the base line on a Cary 219 spectrophotometer and as a reference for the dihydro derivative sample solution.

Dihydro Derivative Sample Solution:

0.2 ml of $6.25\times10^{-4}$M solution of the freshly prepared dihydro derivative in methyl alcohol was diluted to 10 ml with liver homogenate solution. The mixture was scanned at 37° C. from 400 nm to 300 nm every 5 min for 1 hr.

TABLE II

| Medium | Kinetics of Oxidation<br>K $sec^{-1}$ | $t_{\frac{1}{2}}$ m | K $sec^{-1}$ | $t_{\frac{1}{2}}$ m |
|---|---|---|---|---|
| | Comp. | | | |
| | 1-Methyl-3-(N—β-phenethyl)-carbamoyl-1,4-dihydropyridine | | 1-Benzyl-3-(N—β-phenethyl)-carbomyl-1,4-dihydropyridine | |
| Plasma | $1.8\times10^{-4}$<br>n = 13 r = .998 | 64.2 | $7.4\times10^{-5}$<br>n = 12 r = .998 | 156.1 |
| Whole Blood | $8.4\times10^{-4}$<br>n = 5 r = .952 | 13.7 | $4.7\times10^{-4}$<br>n = 5 r = .974 | 24.4 |
| Brain Homogenate | $4.1\times10^{-4}$<br>n = 8 r = .996 | 28.2 | $2.1\times10^{-4}$<br>n = 13 r = .999 | 55 |
| Liver Homogenate | $8.0\times10^{-4}$<br>n = 7 r = .999 | 14.4 | $7.5\times10^{-4}$<br>n = 5 r = .998 | 15.3 |
| | Comp. | | | |
| | 1-Methyl-3,5-di(N—β-phenethyl)-carbamoyl-1,4-dihydropyridine | | 5-Carboethoxy-1-methyl-3-(N—β-phenethyl)carbomyl-1,4-dihydro-pyridine | |
| Brain Homogenate | $8.4\times10^{-6}$<br>n = 6 r = .997 | 22.9 | $1.74\times10^{-5}$<br>n = 6 r = .993 | 11.1 h |
| Whole Blood | $4.9\times10^{-5}$<br>n = 5 r = .949 | 3.9 | $1.13\times10^{-4}$<br>n = 5 r = .972 | 1.7 h |

EXAMPLE 35

In Vivo Study in 1-Methyl-3-(N-β-phenethyl)carbamoyl-1,4-dihydropyridine

A group of rats of average weight (about 350 g) was injected through the jugular with a solution of the freshly prepared dihydro derivative in DMSO (0.05 g/ml solution) in a dose level of 125 mg/kg animal body weight. After the appropriate time period, 1 ml of blood was withdrawn from the heart and the animal was perfused with 20 ml of saline solution. The animal was decapitated. The brains were weighed, kept in the refrigerator overnight and homogenized in 2 ml of water. Acetonitrile, 8 ml, was added and the mixture was homogenized again and then centrifuged. The amount of the quaternary was determined from the HPLC spectrum in relation to a recovery experiment made by adding a specific amount of the quaternary to a blank brain and hybrid in the same manner of homogenization and extraction.

Brain Results:

| t | Normalized value amt in mg/weight lb in grams | t | Normalized value |
|---|---|---|---|
| 5 | .055 | 40 | .1132 |
| 5 | .0423 | 47 | .125 |
| 10 | .099 | 66 | .148 |
| 15 | .0553 | 90 | .1626 |
| 15 | .100 | 90 | .1294 |
| 20 | .0935 | 145 | .0949 |
| 21 | .0743 | 180 | .0838 |
| 25 | .101 | 185 | .1001 |
| 30 | .1242 | 210 | .0707 |
| 32 | .095 | 220 | .0753 |
| 33 | .0778 | | |

Blood Concentration:

The blood withdrawn was left in the refrigerator overnight and 3 ml of saline was added and the mixture shaken, then 17 ml of acetonitrile was added and the mixture was shaken vigorously for 1 min and then centrifuged. The supernatant solution was injected directly into the HPLC.

| Results: | |
|---|---|
| t (m) | mg/ml |
| 25 | .0235 |
| 40 | .0117 |
| 21 | .0205 |
| 33 | .0058 |
| 5 | .0294 |
| 75 | .0058 |
| 40 | .0088 |
| 15 | .0235 |

EXAMPLE 36

Kinetics of Disappearance of the Quaternary from Brain Homogenate

A fresh perfused rat brain was homogenized in 20 ml of phosphate buffer, pH 7.4. A solution of 10.0 mg of 1-methyl-3-(N-β-phenethyl)carbamoylpyridinium iodide in 2 ml aqueous methanol (1:1) was added and the thoroughly mixed mixture was kept at 37° C. in a water-bath. At each time period, 1 ml of the mixture was taken and shaken thoroughly with 8 ml of acetonitrile, centrifuged and injected to HPLC. The amount of the quaternary in the same was determined in comparison with a sample taken at time 0. Linear regression of t against log C shows that $K=4.8\times10^{-5}$ $sec^{-1}$, $t_{1/2}=3.50$ h (in vivo exp.) which was found to be $K=8.45\times10^{-5}$ $sec^{-1}$, $t_{1/2}=2.1$ h, $r=0.957$.

Studies of the Dopamine Derivatives

EXAMPLE 37

Analytical Methods:

A high pressure liquid chromatography (HPLC) method was developed for the studies of the degradation of the dihydropyridine dopamine derivative. The chromatographic analysis was performed on a component system consisting of a Waters Associate Model 6000A solvent delivery system, Model U6K injector and Model 440 dual channel absorbance detector operated at 254 and 280 nm. A 30 cm×3.9 mm (internal diameter) reverse phase μBondapak $C_{18}$ column (Waters Associates), operated at ambient temperature, was used for all separations. The mobile phase used for the separation of the dihydropyridine derivative, its degradation products and oxidation products consisted of 0.005M solution of 1-heptanesulfonic acid sodium salt (PIC B-7 Eastman Kodak) in $CH_3CN$; 0.01M aqueous dibasic ammonium phosphate (2.5:1). At a flow rate of 2.0 ml/min, 6a had a retention time for 5.1 min; 6c, 11.8 min, 5a, 1.7 min; 5c, 3.1 min. A peak was always shown at a retention time of 2.2 min which is believed to be a monodeacylated dihydropyridine derivative, since it eventually did result in 6a.

EXAMPLE 38

Determination of the Enzymatic Hydolytic Cleavage and Rate of Oxidation of Compound 5c In Human Plasma:

The freshly collected plasma used was obtained at the Civitan Regional Blood Center, Inc. (Gainesville, Fla.) and contained about 80% plasma diluted with anticoagulant citrate phosphate dextrose solution U.S.P. The plasma was stored in a refrigerator and used the next day. One hundred μl of a freshly prepared 0.61M solution of compound 5c in methanol was added to 20 ml of plasma, previously equilibrated to 37° C. in a water bath and mixed thoroughly to result in an initial concentration of $3.05\times10^{-3}$ moles/liter. One ml samples of plasma were withdrawn from the test medium, added immediately to 5 ml of ice cold acetonitrile, shaken vigorously and placed in a freezer. When all samples had been collected, they were centrifuged and the supernatants were filtered through Whatman 1 filter papers and analyzed by HPLC.

In Human Blood:

The freshly collected heparinized blood was obtained at the Civitan Regional Blood Center, Inc. (Gainesville, Fla.). The blood was stored in a refrigerator and used the next day. One hundred μl of a freshly prepared 0.19 solution of compound 5c in methanol was added to 20 ml of blood, previously equilibrated to 37° C. in a water bath and mixed thoroughly to result in an initial concentration of $9\times10^{-4}$ moles/liter. One ml samples of blood were withdrawn from the test medium every 5 minutes, added immediately to 5 ml of ice cold acetonitrile, shaken vigorously and placed in a freezer. When all samples had been collected, they were centrifuged and the supernatants were filtered using Whatman 4 filter paper and analyzed by HPLC.

In Rat Brain Homogenate:

The brain homogenate was prepared by the following method. Five Sprague-Dawley rats were killed by decapitation and the brains were removed, weighed (total weight 9.85 g) and homogenized in 49.3 ml of aqueous 0.11M phosphate buffer, pH 7.4. The homogenate was centrifuged and the supernatant was used for the test. 100 μl of 0.18M solution of compound 5c was mixed with 10 ml of homogenate, previously equilibrated to 37° C. in a water bath, to result in an initial concentration of $1.8\times10^{-3}$ moles/liter. Samples of 1.0 ml were withdrawn every 10 minutes from the test medium, added immediately to 5 ml of ice cold acetonitrile and placed in a freezer. When all samples had been collected, they were centrifuged. Each supernatant was filtered through two Whatman 1 filter papers and analyzed by HPLC.

In Rat Liver Homogenate:

The liver homogenate was prepared by the following method. Three Sprague-Dawley rats were killed by decapitation and the livers were removed, weighed and homogenized by tissue homogenizer in 0.11M aqueous phosphate buffer,pH 7.4, to make 20% liver homogenate. The homogenate was centrifuged and the supernatant was used for the test. 100 μl of 0.1M solution of compound 5c in methanol were mixed with 20 ml of the homogenate, previously equilibrated to 37° C. in a water bath, to result in an initial concentration of $9\times10^{-4}$ moles/liter. Samples of 1.0 ml were withdrawn every 5 minutes from the test medium, added immediately to 5 ml of ice cold acetonitrile, shaken vigorously and placed in a freezer. When all samples had been collected, they were centrifuged and each supernatant was filtered through Whatman 1 filter paper and analyzed by HPLC.

Rates of disappearance (overall oxidation and degradation) of compound 5c:

| | | |
|---|---|---|
| (i) | in Plasma: | $R = 2.25 \times 10^{-4}\ sec^{-1}$<br>$t\frac{1}{2} = 51.3$ min<br>$r = 0.998$<br>$n = (3 \times 6)$ |
| (ii) | In 20% Brain Homogenate: | $R = 6.7 \times 10^{-4}\ sec^{-1}$<br>$t\frac{1}{2} = 17.2$ min<br>$r = 0.996$<br>$n = (3 \times 6)$ |
| (iii) | In Blood: | $R = 6.3 \times 10^{-4}$<br>$t\frac{1}{2} = 18.2$ min<br>$r = 0.997$<br>$n = (3 \times 7)$ |
| (iv) | In Liver: | $R = 1.93 \times 10^{-3}$<br>$t\frac{1}{2} = 5.9$ min<br>$r = 0.950$<br>$n = (3 \times 5)$ |

EXAMPLE 39

Determination of Concentration of Compound 6a in Brain and Blood after Parenteral Administration of 5c Male Sprague-Dawley rats of average weight of 150±10 g were used. The rats were anesthetized with IM injection of Inovar and the jugular was exposed. Compound 5c was injected intrajugularly in the form of 10% solution in DMSO at a dose of 64.2 mg/kg (equivalent to 50 mg/kg compound 6a). The injection was given at a rate of 24 μl/min using a calibrated infusion pump. After appropriate time periods, 1 ml of blood was withdrawn from the heart and dropped immediately into a tared tube containing 3 ml acetonitrile, which was afterwards weighed to determine the weight of the blood taken. The animal was then perfused with 20 ml of saline solution, decapitated and the brain was removed. The weighed brain was homogenized with 0.5 ml of distilled water, 3 ml of acetonitrile was added and the mixture was rehomogenized thoroughly, centrifuged, filtered and then analyzed for compound 6a using the HPLC method. The tubes containing the blood were shaken vigorously, centrifuged, decanted and also analyzed for compound 6a using the HPLC method. Quantitation was done by using a recovery standard curve obtained by introducing a known amount of 6a in either brain homogenate or blood and then treated in the same manner. See FIG. 6 and the discussion thereof hereinabove.

EXAMPLE 40

Pharmacological studies:

In vivo effect on pituitary prolactin secretion:

Adult male rats (Charles Rivers, CD-1) weighing 200 to 225 g were provided food and water ad libitum for at least one week period to experimentation. To elevate serum prolactin levels, each rat received a single s.c. implant of a Silastic tube (1.57 mm interior diameter, 5 mm×3.15 mm overall size) packed with crystalline 17-β-estradiol. Two days later the rats were lightly anesthetized with ether and a small incision was made over the right jugular vein for intravenous (I.V.) administration of the test drugs. Compound 6a was injected at a dose of 1 mg/kg body weight/ml saline and groups of six rats were decapitated at 15, 30, 60 and 120 min later to collect blood samples. Control rats (time 0) received an I.V. injection of the saline vehicle and were decapitated 30 min later. Compound 5c was dissolved in 10% ethanol in silane and was injected IV. Rats were decapitated at 15, 30 and 120 min later. Control (time 0) animals received the 10% ethanol vehicle and were sampled 30 min later.

Trunk blood was collected, allowed to clot for 2 h and the serum was separated and stored at −20° C. for subsequent assay for prolactin concentrations. Each serum sample was assayed in duplicate by the double-antibody radioimmunoassay procedure described by the National Pituitary Agency Hormone Distribution Program. Serum prolactin concentrations are expressed in terms of the PRL-RP-2 reference preparation provided. The intraassay coefficient of variation for 10 replicate samples of pooled serum obtained from male rats was 13.8%.

The effects of compounds 5c and 6a on serum prolactin concentrations were evaluated by one-way analysis of variance and Student-Newman Keuls tests. A probability level of less than 0.05 was selected for significance. See FIG. 7 and the discussion thereof hereinabove.

The foregoing procedure was repeated, except for the following changes:

Compound 5c (the dihydropyridine dipivalyl ester derivative of dopamine) was dissolved in 10% dimethylsulfoxide in saline and administered intravenously at a dosage of 1 mg/kg to groups of five or six rats; the rats were decapitated at 1, 2, 4, 8, 12 and 24 hours following administration. Compound 5a (the dihydropyridine dihydroxy derivative) was dissolved in 10% dimethylsulfoxide and administered intravenously at a dosage of 1 mg/kg to groups of six rats; the rats were decapitated at 1, 2 and 4 hours after administration. Control groups of animals received 10% dimethylsulfoxide in saline and were sacrificed 2 hours later. Intravenous administration of 5c was found to maintain a dramatic reduction in serum prolactin concentrations for at least 12 hours following adinistration. Again, the rapid onset and very prolonged inhibitory effects of 5c on prolactin secretion is consistent with the time course of the appearance of 6a in the brain following administration of 5c and the "trapping" of 6a in the brain. Compound 5a did produce a significant reduction in serum prolactin concentration at 2 hours, but by 4 hours the prolactin levels had increased substantially; thus 5a did not show as prolonged an inhibitory effect as that exhibited by 5c.

In vitro evaluation of the prolactin inhibitory effect of 6a:

Adult female rats (Charles Rivers Lab.) weighing 225–250 g were maintained on food and water ad libitum. Animals were sacrificed by decapitation; their pituitary glands were quickly removed from the cranium. The anterior pituitary (AP) of each animal was dissected into two equal halves and placed into incubation media. (Gibco's Minimal Essential Media supplied by Grand Island Biological Co. was used.) The incubation was conducted at 37° C., under continuous aeration (95% $O_2$, 5% $CO_2$); the pH was 7.2. After one hour of preincubation, the media were discarded and replaced with fresh ones containing either DA ($2\times10^{-8}$M), 6a ($2\times10^{-8}$) or ascorbic acid ($10^{-4}$M). In all cases, one-half of AP received the test drug; the other, the ascorbate control. After one hour, samples were taken from the media and the remaining media were discarded. Fresh media containing DA ($2\times10^{-7}$), 6a ($2\times10^{-7}$) and ascorbate, respectively, were then added. One hour later, the second samples were taken. After the 3 h incubation period, each half AP's were weighed.

The samples were diluted 1:50 with phosphate buffered saline and then assayed in triplicate by the radioimmunoassay method described. The data are given as ng prolactin released/mg wet weight/h. Paired Student's T-test was used to evaluate the significance of the inhibitory effects of the test drugs on prolactin secretion. The control AP half and the drug treated half were employed in each pair comparison. See TABLE I and the discussion thereof hereinabove.

Further in vitro evaluation of the prolactin inhibitor effect of 6a vs. dopamine:

Eighteen female rats (Charles River Lab.) weighing 225–250 g were maintained on food and water ad libitum for one week. Animals were sacrificed by decapitation, the pituitary gland was removed from the cranium and the anterior pituitary (AP) was separated from the posterior and intermediate lobes. The AP was discussed into two equal halves and each half was placed in an incubation media consisting of Gibco's Minimal Essential Media containing 25 mM Hepes Buffer (Grand Island Biological Company, Grand Island, N.Y.). The media was maintained at a pH of 7.2 under continuous aeration (95% $O_2$, 5% $CO_2$) at a temperature of 37° C. Following a one hour preincubation period, the media were discarded and replaced with fresh media containing either DA ($10^{-6}$M) or 6a ($10^{-6}$M). The control AP half received media containing $10^{-4}$M ascorbic acid, the vehicle for the drugs. After one hour, the media were sampled and the remaining media were discarded. Fresh media containing DA ($10^{-5}$M) or 6a ($10^{-5}$M) or ascorbic acid ($10^{-4}$M) were then added to the AP halves. One hour later, second samples were taken and the AP halves were weighed to the nearest tenth of a milligram.

Samples of media were diluted 1:50 with phosphate buffered saline and then assayed in triplicate by radioimmunoassay methods. Data are expressed as ng prolactin released/mg net weight/h. Pair student's "t" tests were used to evaluate the significance of the effects of the drugs on the prolactin release rate. The control AP half and its respective drug-treated AP half were employed in each paired comparison. The results are tabulated below:

| Prolactin ng/mg/h | | | | | | | |
|---|---|---|---|---|---|---|---|
| Dopamine (DA) | | | | 6a | | | |
| Control | DA ($10^{-6}$ M) | Control | DA ($10^{-5}$ M) | Control | 6a ($10^{-6}$ M) | Control | 6a ($10^{-5}$ M) |
| 306 ± 50 | 128 ± 22 | 219 ± 26 | 59 ± 20 | 349 ± 49 | 301 ± 51 | 205 ± 25 | 206 ± 28 |

Thus, control AP halves released prolactin at a rate of 300 to 350 ng/mg wet weight/h during the first incubation period and about 200 ng/mg wet weight/h during the second incubation period. Dopamine (DA) concentration of $10^{-6}$ and $10^{-5}$M caused a 58 and 73% decrease in prolactin secretion, respectively. In contrast, N-methylnicotinoyldopamine 6a did not alter the rate of prolactin secretion at concentrations of $10^{-6}$ or $10^{-5}$M. These results confirm the conclusions drawn from the earlier studies which were done at lower concentrations.

In the examples immediately to follow, all melting points were taken on a Mel-Temp apparatus and are not corrected. Elemental analyses were performed at Atlantic Microlab, Inc., Atlanta, Ga. Infrared spectra were determined by using a Beckman Acculab 1 double-beam recording spectrophotometer. NMR spectra were determined by means of Varian T60A or FX100 spectrometers. All chemical shifts reported are in δ units (parts per million) relative to tetramethylsilane. Ultraviolet absorbance spectra were determined using a Cary Model 210 spectrophotometer. HPLC analyses were performed on a Beckman 345 ternary liquid chromatograph with Model 112 solvent delivery system, Model 210 injector, Model 160 absorbance detector and Model 421 controller.

EXAMPLE 41

Preparation of Testosterone nicotinate (compound 41)

Thionyl chloride (2 ml) was added to 0.7 g (5.7 mmol) of nicotinic acid and the mixture was refluxed for 3 hrs. Excess thionyl chloride was removed under reduced pressure. To the cold residue, 10 ml of dry pyridine was added, followed with 1.44 g (5.0 mmol) of testosterone. The mixture was heated with continuous stirring at 100° C. over a watch bath for 4 hrs. Pyridine was removed in vacuo and 5 ml of methanol was added to the oily residue. The mixture was cooled and the solid that crystallized was filtered and recrystallized from methanol/acetone mixture to give 1.4 g of 41 as white crystals (yield 71%), m.p. 187°–188° C. This intermediate was used directly for the synthesis of the chemical delivery system.

EXAMPLE 42

Preparation of 17β-[(1-Methyl-3-pyridiniumcarbonyl)oxy]androst-4-en-3-one iodide (compound 42) (Testosterone-17-nicotinate N-methyl iodide)

To a solution of 1.0 g (2.5 mmol) of testosterone nicotinate 41 in 15 ml of acetone, 1 ml of methyl iodide was added and the mixture was refluxed overnight. The yellow solid that separated was removed by filtration, washed with acetone and crystallized from methanol/ether to yield 1.25 g (92% yield) of pure 42 as yellow crystals, m.p. 215°–220° C. (dec.). U.V. ($CH_3OH$) λ 270 nm (shoulder) ε=4579; 240 (shoulder), ε=19375. NMR ($CDCl_3$) δ10.0–8.3 (ms, 4H, pyridinium protons), 5.73 (s, 1H, $C_4$ testosterone proton), 4.86 (s, 3H, $+N-CH_3$), 2.40–1.06 (ms, 26H, testosterone skeleton protons). Analysis calculated for $C_{26}H_{34}INO_3$: C, 58.32; H, 6.40; N, 2.62. Found: C, 58.17; H, 6.48; N, 2.60.

EXAMPLE 43

Preparation of 17β-[(1,4-Dihydro-1-methyl-3-pyridinylcarbonyl)oxy]androst-4-en-3-one (compound 43)

To an ice cold solution of 1.1 g (2 mmol) of testosterone nicotinate N-methyl iodide 42 in 150 ml of deaerated 10% aqueous methanol, 0.67 g (8 mmol) of sodium bicarbonate and 1.37 g (8 mmol) of sodium dithionite were added. The mixture was stirred for 20 minutes and the pale yellow solid which separated was filtered, washed with water and dried over $P_2O_5$ under vacuum. Wt. 0.82 g (98% yield), m.p. 172°–175° C. UV ($CH_3OH$) λ 356 nm, ε=9511; ir (KBr) 1700, 1660 $cm^{-1}$ (two C=O stretching). NMR ($d_6$-DMSO) δ 6.90 (bs, 1H, $C_2$ dihydropyridine proton), 5.83–5.70 (m, 1H, $C_6$ dihydropyridine proton), 5.56 (s, 1H, $C_4$ testosterone proton), 4.7–4.33 (m, 1H, $C_5$ dihydropyridine proton), 3.26 (bs, 2H, $C_4$ dihydropyridine protons), 2.93 (s, 3H, $N-CH_3$), 2.5–0.83 (m, 26H, testosterone skeleton protons with the angular methyl protons at 1.16 and 0.83). Analysis calculated for $C_{26}H_{35}NO_3$: C, 76.25; H, 8.61; N, 3.42. Found: C, 76.07; H, 8.65; N, 3.38.

EXAMPLE 44

Analytical Methods

A high pressure liquid chromatograph (HPLC) method was developed for the studies of the degradation of the quaternary 42 and dihydropyridine derivative 43. The chromatographic analyses were performed on the Beckman described hereinabove. The absorbance detector was operated at 254 nm. A 15 cm×4.6 mm (internal diameter), 5 μm particle size ultrasphere reverse phase $C_{18}$ column (Altex), operated at ambient temperature, was used for all separations. The mobile phase used for the separation of the dihydropyridine derivative, its degradation products and oxidation products consisted of 0.002M solution of 1-heptanesulfonic acid sodium salt (PIC B-7 Eastman Kodak) in $CH_3CN$, 0.01M aqueous dibasic ammonium phosphate (7:3). At a flow rate of 2.0 ml/min, compound 42 had a retention time of 12 min and compound 43, 5 min. For the analysis of testosterone in the in vivo brain delivery studies, a solvent system consisted of 0.002M solution of PIC B-7 in $CH_3CN$, 0.1M aqueous dibasic ammonium phosphate (1:1). At a flow rate of 2.0 ml/min, testosterone had a retention of 3.3 min and compound 42 had a retention time of 36.5 min (very broad peak).

EXAMPLE 45

Chemical Oxidation Studies (i) By Silver Nitrate: 1 ml of 5% methanolic solution of the dihydropyridine compound 43 was added to 5 ml of saturated methanolic $AgNO_3$ solution. The mixture was shaken, left 10 minutes for complete oxidation, centrifuged and the UV spectrum checked.

(ii) By Hydrogen Peroxide: To a standardized solution of $H_2O_2$ (0.18M) contained in a UV cuvette equilibrated at 37° C., a solution of dihydropyridine compound 43 was added to the sample cuvette to make a concentration of approximately $5\times10^{-6}$M. The mixture was thoroughly mixed and monitored for the disappearance of the dihydropyridine maximum at 356 nm using a Cary 210 interfaced with an Apple II microprocessor and using an enzyme kinetic software package.

(iii) By Diphenylpicrylhydrazyl Free Radical: To 2 ml of $9.3\times10^{-5}$M solution of 2,2-diphenyl-1-picrylhydrazyl free radical in acetonitrile, equilibrated at 26° C., 20 ml of $1.5\times10^{-2}$M solution of the dihydropydine compound 43 in acetonitrile was added to make a final concentration of $1.48\times10^{-4}$M. The mixture was monitored at 515 nm against a reference cuvette containing the same mixture in exactly the same concentrations, but previously prepared and left for at least 10 minutes and used as reference for $A_\infty$. The instrument used was a Cary 210 interfaced with an Apple II microprocessor and using an enzyme kinetic software package.

EXAMPLE 46

Determination of In Vitro Rates of Oxidation of Compound 43 in Biological Media In Human Plasma:

The freshly collected plasma used was obtained at the Civitan Regional Blood Center, Inc. (Gainesville, Fla.) and contained about 80% plasma diluted with anticoagulant citrate phosphate dextrose solution U.S.P. The plasma was stored in a refrigerator and used the next day. 100 μl of a freshly prepared 0.024M solution of compound 43 in DMSO were added to 10 ml plasma, previously equilibrated at 37° C. in a water bath and mixed thoroughly to result in an initial concentration of $2.4\times10^{-4}$ moles/liter. One ml samples of plasma were withdrawn every 20 minutes from the test medium, added immediately to 5 ml of ice cold acetonitrile, shaken vigorously and placed in a freezer. When all samples had been collected, they were centrifuged and the supernatants were filtered through nitrocellulose membrane filters (por 0.45) and analyzed by HPLC, following appearance of 42 (Method A).

In Human Blood:

The freshly collected heparinized blood was obtained at the Civitan Regional Blood Center, Inc. (Gainesville, Fla.). The blood was stored in a refrigerator and used the next day. 100 μl of a freshly prepared 0.048M solution of compound 43 in DMSO were added to 20 ml blood, previously equilibrated to 37° C. in a water bath and mixed thoroughly, to result in an initial concentration of $2.4\times10^{-4}$ moles/liter. One ml samples of blood were withdrawn from the test medium every 10 minutes, added immediately to 5 ml of ice cold acetonitrile, shaken vigorously and placed in a freezer. When all samples had been collected, they were centrifuged and the supernatants were filtered using nitrocellulose membrane filters (por 0.45) and analyzed by HPLC, following appearance of 42 and disappearance of 43.

In Rat Brain Homogenate:

The brain homogenate was prepared by the following method. Five female Sprague-Dawley rats were killed by decapitation and the brains were removed, pooled, weighed (total weight 9.2 g) and homgenized in 36.8 ml of aqueous 0.11M phosphate buffer, pH 7.4. 100 μl of 0.024M solution of compound 43 in DMSO were mixed with 20 ml of the homogenate, previously equilibrated to 37° C. in a water bath, to result in an initial concentration of $2.4\times10^{-4}$ moles/liter. Samples of 1.0 ml were withdrawn every 10 minutes from the test medium, added immediately to 5 ml of ice cold acetonitrile, shaken vigorously and placed in a freezer. When all samples had been collected, they were centrifuged and the supernatants were filtered through nitrocellulose membrane filter (por 0.45) and analyzed by HPLC (Method A).

EXAMPLE 47

In Vitro Determination of the Site-Specific Conversion of the Prodrug 42 to Testosterone A fresh brain homogenate was prepared as above described. 100 μl of 0.017M solution of the quaternary compound 42 in methanol were mixed with 10 ml of the brain homogenate, previously equilibrated to 37° C. to result in an initial concentration of $1.7\times10^{-4}$M. Samples of 1.0 ml were withdrawn every 20 minutes from the test medium, added immediately to 5 ml of ice cold acetonitrile and placed in a freezer. When all the samples had been collected they were centrifuged and the supernatant was filtered through nitrocellulose membrane filter (por 0.45) and analyzed for the quaternary compound 42.

EXAMPLE 48

In Vivo Brain Delivery of Testosterone Following Administration of the Dihydro Compound 43

Female Sprague-Dawley rats of average weight of 225±10 g were used. The rats were anesthetized with IM injection of Innovar[R] (0.13 ml/kg) and the external jugular was exposed. Compound 43 was injected intrajugularly in the form of 2.5% solution in DMSO at a dose of 40 mg/kg (equivalent to 52.3 mg quaternary 42 or 28.2 mg testosterone). The injection was given at a rate of 44.4 μl/minute using a calibrated infusion pump. After appropriate time periods, 1 ml of blood was withdrawn from the heart and dropped immediately into a tared tube containing 5 ml acetonitrile which was later weighed to determine the weight of the blood taken. The animal was then perfused with 20 ml of saline solution, decapitated and the brain was removed. The weighed brain was homogenized with 1 ml of distilled water, 5 ml of acetonitrile was added and the mixture was rehomogenized thoroughly, centrifuged, filtered and then analyzed using the HPLC method. The tubes containing the blood were shaken vigorously, centrifuged, filtered and also analyzed using the HPLC method described at 0.05 sensitivity limit for determination of the quaternary 42 and at 0.001 sensitivity limit for determination of liberated testosterone. Quantitation was done using a recovery standard curve obtained by introducing a known amount of either compound 42 or testosterone in either brain homogenate or blood and then treating in the same manner of extraction and analysis.

EXAMPLE 49

In Vivo Brain Delivery of Testosterone Following its Administration

Female Sprague-Dawley rats with an average weight of 225±10 g were injected with testosterone at a dose level of 28.2 mg/kg following the same procedure previously described. Samples of brain and blood collected were analyzed for testosterone using HPLC.

EXAMPLE 50

In Vivo Brain Delivery of Quaternary 42 Following its Administration

Following the same procedure, female Sprague-Dawley rats were injected I.V. with the quaternary solution (0.18%) in DMSO at a dose level of 13.0 mg/kg (it was found to be toxic at higher doses). The brain samples collected were analyzed for presence of the quaternary 42 using HPLC.

EXAMPLE 51

Results of Experiments of Examples 45–50

The rates of oxidation of the dihydro derivative 43 with silver nitrate, hydrogen peroxide and diphenylpicrylhydrazyl free radical (DPP.) were determined. The reactions were carried out under pseudo first order conditions, either with higher concentrations of the oxidant in the case of hydrogen peroxide or higher concentrations of 43 in the case of the picryl reagent. With DPP., a reference sample was made using the same amounts as the test sample, but prepared 10 minutes before mixing and monitoring the test sample. This reference is used as a measure of $A_\infty$ and these were the data used to calculate the kinetic parameters. The in vitro rates of oxidation of the dihydro derivative were also determined in biological fluids, e.g. 80% plasma, whole blood, 20% brain homogenate and 20% liver homogenate. The rate of disappearance of the ester 42 and appearance of testosterone in the medium was also determined. Finally, the in vivo brain delivery and blood concentration profile of the quaternary derivative and testosterone released, against time, was determined following a single injection of the dihydropyridine derivative 43 to female rats. These results were compared to blood and brain kinetics of testosterone following administration of such.

Chemical Oxidation of the Dihydropyridine Derivative 43

(i) By Silver Nitrate:

It was observed that this dihydro derivative 43 is more stable towards oxidation than the monophenethylamine type derivatives reported hereinabove; it takes a few minutes' standing for the silver to form. The product is exclusively the quaternary salt 42, as verified by the change in the UV and NMR spectra.

(ii) By Hydrogen Peroxide:

At low concentrations of the dihydro compound 43 ($5\times10^{-6}$M), compared to the high concentration of the peroxide (0.18M), the oxidation proceeds according to a first order kinetics. $k=2.7\pm0.3\times10^{-3}$ $sec^{-1}$ $t_{1/2}=3.98\pm0.7$ min r=0.995 At higher concentrations, the dihydro compound is insoluble in $H_2O_2$.

(iii) By Diphenylpicrylhydrazyl (DPP.) Free Radical:

The reaction was carried out under pseudo first order conditions using excess of the dihydropyridine derivative. With the concentrations used, all runs gave good first order plots over 3 half lives, with correlation coefficient better than 0.9998. $k=4.87\pm31\times10^{-2}$ $sec^{-1}$ $t_{1/2}=14.1\pm0.6$ seconds Trials to determine the second order rate constant using different concentrations of DPP. were unsuccessful.

(iv) In Vitro Oxidation and Hydrolysis in Biological Media:

Table III shows the rates, half-lives and correlation coefficient for the process of oxidation of the 1,4-dihydropyridine derivative 43 in different biological media.

The rate of hydrolysis of the quaternary 42 in 20% brain homogenate was also determined and it was found to be $3.6\times10^{-5}$ $sec^{-1}$, corresponding to a half-life, $t_{1/2}$, of 5:16 h.

TABLE III

Kinetics of in vitro oxidation of the dihydropyridine ester 43 to the quaternary derivative 42 in biological fluids.[a]

| Medium | k(sec$^{-1}$) | $t_{1/2}$ (min.) | r | Method[b] |
|---|---|---|---|---|
| 80% Plasma | $8.12 \times 10^{-5}$ | 142 | .959 | A |
| 20% Brain Homogenate | $1.72 \times 10^{-4}$ | 67 | .997 | A |
| Whole Blood | $1.74 \times 10^{-4}$ | 66 | .997 | A,B |

[a]At 37° C., initial concentration of [43] = $2.4 \times 10^{-4}$ M
[b]Method A: Following appearance of [42]
Method B: Following disappearance of [43]

Figure 8:
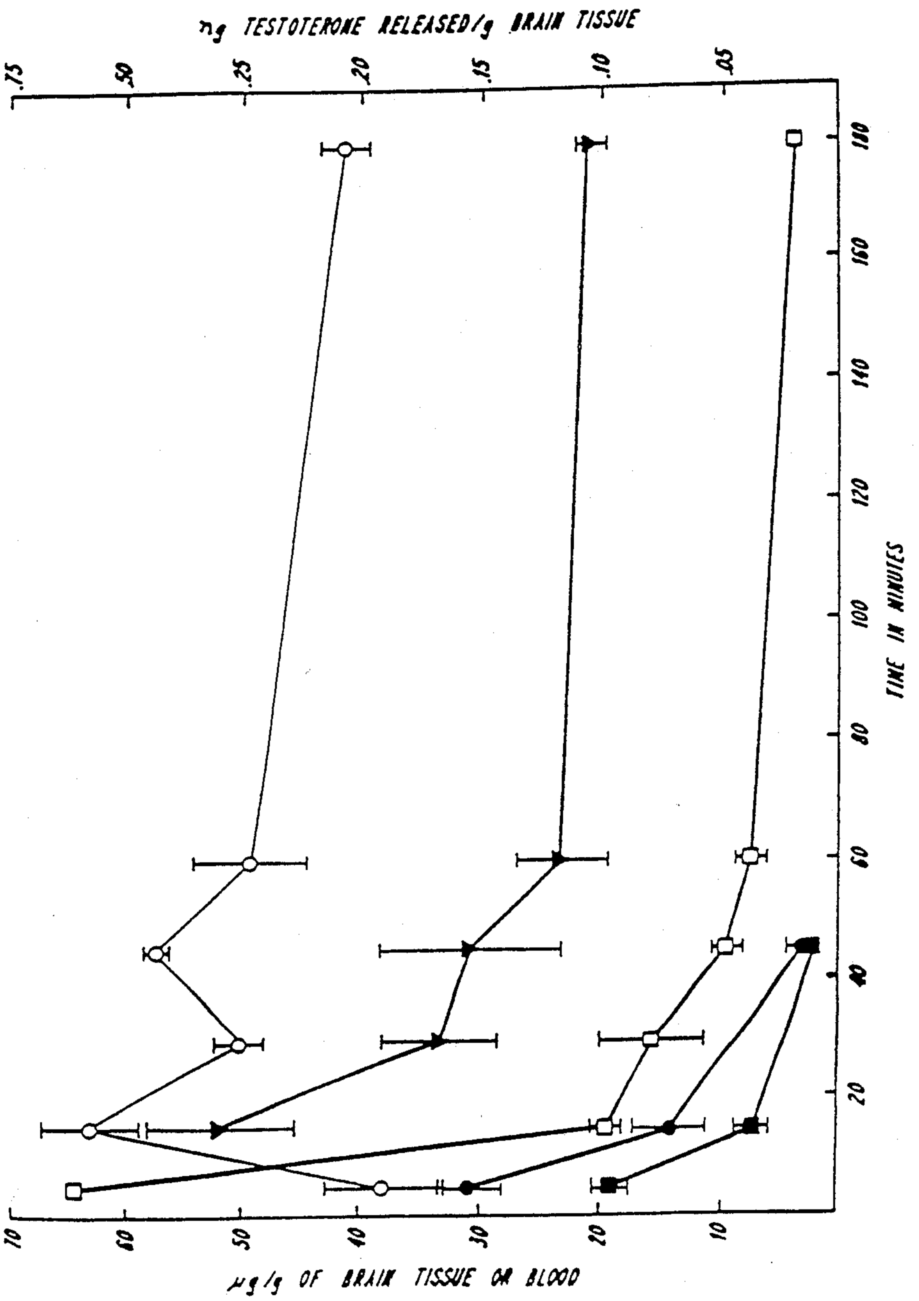
FIG. 8 is a graph plotting concentrations with standard errors against time for testosterone-17-nicotinate-N-methyl cation, calculated as iodide, in brain (O) and in blood (□) and concentration of released testosterone (ng/g) in brain (▼), all following administration of the corresponding dihydropyridine compound. Also plotted are concentrations of testosterone in brain (●) and blood (■) following administration of testosterone, per se.

(v) In Vivo Administration of Compound 43 and Testosterone:

FIG. 8 illustrates the concentration of the quaternary derivative 42 in brain and blood and concentration of testosterone released in the brain, following intravenous administration of the 1,4-dihydropyridine derivative 43. Also, FIG. 8 shows the concentration of testosterone in brain and blood following administration of testosterone. Statistical analysis of the descending portions of the curves shown in FIG. 8 provides the following results:

| | | |
|---|---|---|
| (1) Rates of disappearance of the quaternary compound 42: | | |
| from brain = $2 \times 10^{-3}$ min$^{-1}$ | $t_{1/2}$ = 5.7 hr | r = .833 |
| from blood = $1.27 \times 10^{-2}$ min$^{-1}$ | $t_{1/2}$ = 54 min | r = .833 |
| (2) Rate of disappearance of released testosterone following administration of dihydro compound 43 = | | |
| $2.65 \times 10^{-3}$ min$^{-1}$ | $t_{1/2}$ = 4.4 h | r = .768 |
| (Results analyzed for up to 5 hrs, the data shown in FIG. 8 are for 3 hrs) | | |
| (3) Rate of disappearance of testosterone following administration of testosterone: | | |
| from brain = $5.5 \times 10^{-2}$ min$^{-1}$ | $t_{1/2}$ = 12.6 min | r = .994 |
| from blood = $4.74 \times 10^{-2}$ min$^{-1}$ | $t_{1/2}$ = 14.5 min | r = .959 |

Thus, 17β-[(1,4-dihydro-1-methyl-3-pyridinylcarbonyl)oxy]androst-4-en-3-one 43 could be obtained in a high yield (more than 90%) from testosterone 17β-nicotinate by simple chemical procedures. The dihydro product obtained directly from the reduction reaction medium was found by HPLC to be quite pure and a single crystallization from hot methanol afforded an analytically pure product. No signs of oxidation were observed during crystallization, even from hot methanol, filtration or drying. The crystalline solid dihydro compound did not show signs of oxidation, decomposition or polymerization when tested by HPLC, during the 2-month shelf storage at ambient temperature under nitrogen. This compound 43 was found to be quantitatively oxidizable to the corresponding quaternary derivative 42, as identified by UV spectroscopy, whether by silver nitrate or hydrogen peroxide. The process of oxidation with silver nitrate is slower than that with the dihydropyridine derivative of phenethylamine reported hereinbelow. Oxidation with hydrogen peroxide or DPP., at pseudo first order conditions, was found to take place at measurable rates ($t_{1/2}$=3.98±0.7 min and 14.1±0.6 seconds, respectively) compared to the rates of oxidation of the corresponding phenethylamine and dopamine derivatives which were found to be too fast to be monitored using the same procedure. The in vitro investigation in biological fluids indicated a facile oxidative conversion of the dihydro form 43 to the corresponding quaternary 42, but at a slower rate than that of the analogous amides of phenethylamine or dopamine.

Insofar as concerns the in vivo studies of compound 43, the results shown in FIG. 8 indicate that the dihydro derivative penetrates the BBB and is readily oxidized in the brain to the quaternary precursor 42. The in vivo rate of oxidation of the dihydro seems faster than that obtained from the in vitro experiment. No dihydro derivative could be detected in the brain without the sensitivity limits of the procedure. After 42 reaches its maximum concentration, within about 15 minutes, its concentration starts a decline phase corresponding to overall excretion and/or metabolismhydrolysis. The overall rate of this phase was calculated to be $2\times10^{-3}$ min$^{-1}$ ($t_{1/2}$=5.7 h). In the same time, the concentration of 42 in blood was decreasing progressively from the beginning at a rate $1.27\times10^{-2}$ min$^{-1}$ or with a half life of 54 min. Equimolar administration of testosterone using the same solvent (DMSO) and the same route of administration showed a rapid absorption of testosterone into the brain, reaching a maximum concentration within 5 minutes, followed by fast clearance from both brain and blood ($t_{1/2}$=12.6 min and 14.5 min respectively). The ratio of brain/blood concentration for testosterone was found to be 1.6 at 5 minutes and 1.8 at 15 minutes from administration. The ratio of brain/blood concentration of the quaternary 42 was found to increase progressively with time (3.23 at 15 min, 6.33 at 45 min and 12 at 3 hrs from administration). This indicates the predicted "lock in" property for the quaternary 42. Testosterone was found to be released from the quaternary ester 42 and could be detected in the brain following administration of the dihydro derivative 42. Analysis of the time concentration curve for release of testosterone indicated two phase kinetics for disappearance from the brain. The first phase is a fast descending one at a rate of $1.2\times10^{-2}$ min$^{-1}$ followed by a slow clearance phase with a rate of $5.8\times10^{-4}$ min$^{-1}$ and a half life of about 20 hrs which corresponds to about 130 hrs for complete clearance from the brain. This result, if compared to that obtained by H. Frey, A. Aadvaag, D. Saahum and J. Falch, *Eur. J. Clin. Pharmacol.,* 16, 345 (1979), for the clearance of testosterone from plasma after oral administration (about 6 hrs), is very promising. Although the concentrations of testosterone in the brain following administration of compound 43 are low compared to that following administration of testosterone, this is by no means a disadvantage because such high concentration of testosterone may not be needed for receptor saturation. By dose manipulation of the dihydro derivative, a concentration of testosterone just sufficient for receptor saturation for a delayed period could be attained.

In the examples immediately to follow, all melting points were taken on a Mel-Temp apparatus and are not corrected. Elemental analyses were performed at Atlantic Microlabs, Inc., Atlanta, Ga. Infrared spectra were determined by means of a Beckman Acculab 1 double-beam recording spectrophotometer. NMR spectra were determined by means of a Varian T60A spectrometer. All chemical shifts reported are in δ (parts per million) relative to tetramethylsilane. Ultraviolet absorbance spectra were determined using a Carey Model 219 spectrophotometer. HPLC analyses were performed on a Waters Associates Liquid chromatograph with Model 6000A solvent delivery system, Model U6K injector and Model 440 absorbance detector.

EXAMPLE 52

Preparation of the 1-Methyl-3-carbamoylpyridinium derivative of Tyr-Gly-Gly-Phe-Leu-$OC_2H_5$ (1-Methyl-3-carbamoylpyridinium derivative of leu[5]-enkephalin ethyl ester)

N-α-t-Butoxycarbonyl-O-benzyl-L-tyrosine (7 g, 0.019 mol) was dissolved in tetrahydrofuran in a three-neck round bottom flask which was cooled to approximately −10° C. in an ice/acetone bath under a nitrogen atmosphere. N-methylmorpholine (6.3 ml, 0.06 mol) was added to the stirred solution, followed by 2.5 ml (0.019 mol) of isobutyl chloroformate. Immediately after the addition of isobutyl chloroformate, N-methyl morpholine hydrochloride precipitated. After 5 min, 3.7 g (0.019 mol) of L-leucine ethyl ester hydrochloride, dissolved in dimethylformamide, were added. The reaction mixture was stirred at this temperature for an hour, after which the solvent was evaporated. The residue obtained was dissolved in ethyl acetate/water and the organic layer was extracted with sodium bicarbonate solution, water, 0.01N HCl and water. The organic layer was dried over $Na_2SO_4$ and after evaporation of the solvent an oil was obtained. Crystallization from $CHCl_3$/petroleum ether yielded 7.4 g (0.014 mol, 76%) m.p. 104°-107° C., of N-α-t-butoxycarbonyl-O-benzyl-L-tyrosylglycylglycine ethyl ester. $^1H$ NMR ($CDCl_3$) δ 7.2 (5H, s), 6.9 (4H, doublet of doublets), 5.0 (2H, s), 1.1 (12H, m). The ethyl ester was cleaved by treating 6.2 g (0.012 mol) of it with an equivalent amount of 2N NaOH in methanol. The solution was stirred at room temperature for half an hour after which the solvent was evaporated. An equivalent amount of 2N HCl was added to the cooled residue and the solid obtained was filtered and dried to yield 3.5 g (96%), m.p. 118°-122° C., of the free (t-butoxycarbonyl-O-benzyl)tyrosylglycylglycine. t-Butoxycarbonylphenylalanylleucine ethyl ester was prepared starting with 6 g (0.019 mol) of t-butoxycarbonyl-L-phenylalanine, and 3.7 g (0.019 mol) of leucine ethyl ester hydrochloride. Work up and crystallization from $CHCl_3$/petroleum ether yielded 6.5 g (84%), m.p. 109°-112° C., of the desired compound. $^1H$ NMR ($CDCl_3$) δ 7.2 (5H, s), 6.4 (1H bm), 5.1 (1H, bm), 4.3 (4H, bm), 3.1 (2H, bm), 1.3 (20H, m).

The t-butoxycarbonyl protecting group was cleaved by treatment of 4.9 g (0.012 mol) of t-butoxycarbonylphenylalanylleucine ethyl ester with 60 ml of 33% trifluoroacetic acid/$CH_2Cl_2$. The solution was stirred at room temperature for half an hour, after which the solvent was evaporated and the residue was treated with a bicarbonate solution which resulted in the formation of a solid. The solid, phenylalanylleucine ethyl ester, was filtered, rinsed with water and dried to yield 5.6 g (97%), m.p. 150°-154° C.

t-Butoxycarbonyl-O-benzyltyrosylglycylglycylphenylalanylleucine ethyl ester was prepared by the same method using 0.1 mol of starting materials, (t-butoxycarbonyl-O-benzyl)tyrosylglycylglycine and phenylalanylleucine ethyl ester. A white solid was obtained which was recrystallized from methyl alcohol/water to yield 4.9 g (63%), m.p. 149°-152° C.

The t-butoxycarbonyl group of t-butoxycarbonyl-O-benzyltyrosylglycylglycylphenylalanylleucine ethyl ester was cleaved as previously described to give O-benzyl-tyr-gly-gly-phe-leu-OEt.TFA (trifluoroacetic acid) salt. Anal. calc. of $C_{39}H_{48}O_9N_5F_3.H_2O$: C, 58.13; H, 6.25; N, 8.69. Found: C, 58.06; H, 6.26; N, 8.69).

Nicotinic acid (160 mg, 1.3 mmole) and O-benzyl-tyr-gly-gly-phe-leu-OEt.TFA salt (1 g, 1.3 mmole) were dissolved in pyridine and 268 mg (1.3 mmole) of dicyclohexylcarbodiimide were added. The mixture was stirred at room temperature for 24 hrs, after which the dicyclohexylurea was filtered and the pyridine distilled in vacuo. Water was added to the residue and the solid obtained was filtered and washed with more water. The solid N-nicotinoyl-O-benzylpentapeptide ethyl ester was recrystallized by methanol/water. $^1H$ NMR gave the expected pattern.

The N-nicotinoyl pentapeptide derivative (500 mg, 0.64 mmol) obtained above was dissolved in 10% formic acid/methanol, followed by addition of 500 mg of palladium black. The mixture was stirred overnight at room temperature, after which the solvent was evaporated. The residue was neutralized with a saturated $NaHCO_3$ solution and extracted with ethyl acetate. The solvent was evaporated and the residue recrystallized from ethyl acetate/ethyl ether to yield 370 mg (0.54 mmol), 84% of product. $^1H$ NMR gave the expected pattern, corresponding to

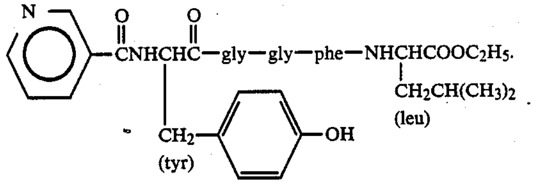

Anal. calc. for $C_{36}H_{44}O_8N_6.4H_2O$: C, 56.83; H, 6.89; N, 11.04. Found: C, 56.88; H, 6.56; N, 10.48. That product (30 mg, 0.44 mmol) was dissolved in acetone and an excess of methyl iodide was added. The solution was refluxed for 8 hrs, after which the solvent was evaporated and the residue was filtered from ethyl ether. A yellowish (260 mg, 0.31 mm), 71%, product was obtained, corresponding to the 1-methyl-3-carbamoylpyridinium derivative of leu[5]-enkephalin ethyl ester. Anal. calc. for $C_{37}H_{47}O_8N_6I$: C, 53.50; H, 5.70; N, 10.12. Found: C, 53.44; H, 4.77; N, 10.07.

EXAMPLE 53

Preparation of N[2-(3-Indolyl)ethyl]nicotinamide

To a solution of 1.97 g (10 mmol) of tryptamine hydrochloride and 1.23 g (10 mmol) of nicotinic acid in 10 ml of dry pyridine at 0° C. were added 2.20 g (10.7 mmol) of dicyclohexylcarbodiimide. The reaction mixture was stirred at room temperature for 24 hrs, and the formed dicyclohexylurea was removed by filtration (2.34 g). The pyridine was removed in vacuo, and 10 ml of methanol were added to the residue. Insoluble dicyclohexylurea in methanol was removed by filtration (0.05 g). The methanol was removed in vacuo and 10 ml of methylene chloride was added to the residue. Insoluble compound in methylene chloride was removed by filtration (0.04 g). The methylene chloride was removed in vacuo and the residue was crystallized from isopropanol. Recrystallization from methanol/isopropanol gave 1.92 g (72.5%) of N-[2-(3-indolyl)ethyl]nicotinamide as pale brown plates, m.p. 150°-152° C. IR (KBr) 3280, 3050, 2940, 1646, 1526, 1412, 1302, 1102, 740, 697 $cm^{-1}$. Anal. calc. for $C_{16}H_{15}N_3O$: C, 72.42; H, 5.91; N, 15.84. Found: C, 72.51; H, 5.74; N, 15.77.

EXAMPLE 54

Preparation of 1-Methyl-3-{[N-2-(3-indolyl)ethyl]}carbamoyl-pyridinium iodide

To a solution of 1.06 g (4 mmol) of N-[2-(3-indolyl)ethyl]nicotinamide in 5 ml of methanol, 1 ml (16 mmol) of methyl iodide was added. The mixture was refluxed for 5 hrs. The methanol and excess methyl iodide were removed in vacuo. The residue was recrystallized from methanol/isopropanol to yield 1.42 g (87.4%) of 1-methyl-3{[N-2-(3-indolyl)ethyl]}carbamoyl pyridinium iodide as yellow needles, m.p. 215°-217° C. IR (KBr): 3280, 3000, 2940, 1660, 1540, 1500, 1316, 1220, 735 $cm^{-1}$. Anal. calc. for $C_{17}H_{18}N_3OI$: C, 50.13; H, 4.46; N, 10.32; I, 31.16. Found: C, 50.22; H, 4.49; N, 10.27; I, 31.06. The product has the structural formula:

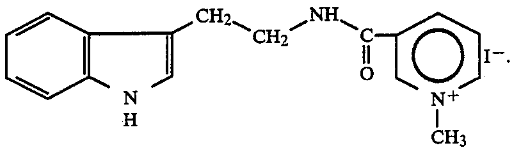

EXAMPLE 55

Preparation of 1-Methyl-3-{N-[2-(3-indolyl)ethyl]}carbamoyl-1,4-dihydropyridine

To a solution of 0.61 g (1.5 mmol) of 1-methyl-3{[N-2-(3-indolyl)ethyl]}carbamoylpyridinium iodide in 50 ml of deaerated water and 50 ml of ethyl acetate, 1.00 g (12 mmol) of sodium bicarbonate was added. The mixture was stirred in an ice bath and 1.65 g (8 mmol) of sodium dithionite was added gradually under nitrogen. The mixture was stirred for 6 hrs, the ethyl acetate layer was decanted and the water layer was extracted with ethyl acetate. The combined solution was washed with water, dried with anhydrous sodium sulfate and the solvent removed in vacuo. A yield of 1-methyl-3{N-[2-(3-indolyl)ethyl]}carbamoyl-1,4-dihydropyridine of 0.29 g (69%) was obtained as a yellow semisolid, m.p. 40°-70° C. IR (KBr) 3250, 2900, 1670 $cm^{-1}$. Anal. calc. for $C_{17}H_{19}N_3O.\frac{1}{4}H_2O$: C, 70.32; H, 6.94; N, 14.47. Found: C, 70.47; H, 6.76; N, 14.52. The product has the structural formula:

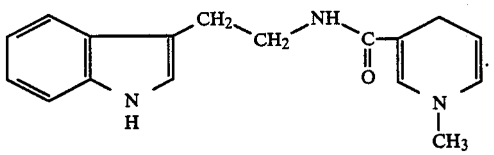

EXAMPLE 56

Preparation of 5-Benzyloxygramine

A solution of 8.90 g (0.04 mol) of 5-benzyloxyindole in 40 ml of dioxane was added dropwise, over the course of 30 mins, to an ice-cooled, stirred mixture of 40 ml of dioxane, 40 ml of acetic acid, 3.2 ml of 37% aqueous formaldehyde (0.04 mol) and 8.8 ml of 25% aqueous dimethylamine (0.05 mol). The solution was stirred and cooled for two hrs and then allowed to warm to room temperature overnight. The next day, 500 ml of water were added, and the turbid mixture which resulted was filtered after the addition of charcoal. The filtrate was made alkaline (to pH 8-9) with 400 ml of 10% sodium hydroxide solution. The gramine quickly solidified and was filtered off after cooling in the refrigerator overnight. Washing with water, and drying gave 9.20 g (82.0%) of coarse powder, m.p. 125°-128° C. Recrystallization from ethyl acetate gave slightly green glittering cubes, m.p. 136°-137° C., of the desired 5-benzyloxygramine. IR (KBr) 3110, 3020, 2920, 2840, 2800, 2755, 1610, 1575, 1470, 1455, 1480, 1210, 1190, 1000 and 780 $cm^{-1}$.

EXAMPLE 57

Preparation of 5-Benzyloxyindole-3-acetamide

A solution of 8.41 g (0.03 mol) of 5-benzyloxygramine, 7.5 g (0.15 mol) of sodium cyanide, 120 ml of ethanol and 30 ml of water was refluxed for 90 hours. The solution, which contained some precipitate, was diluted with 200 ml of water and cooled in the refrigerator. The crystalline material which separated was washed thoroughly with water and dried, giving 4.40 g (52.3%) of a slightly brown sticky tan powder, m.p. 137°-140° C. Recrystallization from methanol/benzene gave small needles, m.p. 156°-158° C., of 5-benzyloxyindole-3-acetamide. IR (KB) 3400, 3290, 3180, 1645, 1610, 1580, 1485, 1450, 1275, 1210, 1200 and 795 $cm^{-1}$.

EXAMPLE 58

Preparation of 5-Benzyloxytryptamine hydrochloride 4.21 (0.015 mol) of 5-benzyloxyindole-3-acetamide which were dissolved in 200 ml of tetrahydrofuran were added gradually to a solution of 3.80 g (0.1 mol) of lithium aluminum hydride in 200 ml of ether over a 30 minute period and under a nitrogen atmosphere. The solution was refluxed for 24 hrs. The excess hydride was decomposed with ethanol and then water was added to ensure complete decomposition of the precipitated complex. The ether layer was decanted and the residue was washed with fresh ether. The combined solution was washed with water and dried over solid potassium hydroxide. The solvent was evaporated in vacuo and the oily residue was taken up in ether and precipitated with hydrogen chloride gas. The pale purple 5-benzyloxytryptamine hydrochloride was recrystallized from ethanol/ether, yield 3.00 g (66.0%), m.p. 263°-265° C. IR (KBr) 3290, 3010, 2910, 1600, 1580, 1480, 1200, 1100 and 1000 $cm^{-1}$.

EXAMPLE 59

Preparation of N-{2-[3-(5-benzyloxy)indolyl]ethyl}nicotinamide

To a solution of 303 mg (1 mmol) of 5-benzyloxytryptamine hydrochloride and 123 mg (1 mmol) of nicotinic acid in 5 ml of pyridine at 0° C. was added 220 mg (1.07 mmol) of dicyclohexylcarbodiimide. The reaction mixture was stirred at room temperature for 24 hrs and the formed dicyclohexylurea was removed by filtration. The pyridine was removed in vacuo, and the residue was recrystallized from methanol/isopropanol. Yield 218 mg (58.9%), m.p. 192°-194° C. of N-{2-[3-(5-benzyloxy)indolyl]ethyl}nicotinamide. IR (KBr) 3280, 3050, 2900, 1655, 1590, 1535, 1480, 1310, 1220, 1200, 1185, 1020, and 710 $cm^{-1}$.

EXAMPLE 60

Preparation of 1-Methyl-3-N-{2-[3-(5benzyloxy)indolyl]ethyl}carbamoylpyridinium iodide To a solution of 185 mg (0.5 mmol) of N-{2-[3-(5-benzyloxy)indolyl]ethyl}nicotinamide in 2 ml of methanol there was added 0.2 ml (3.2 mmol) of methyl iodide. The mixture was refluxed for 3 hrs. The methanol and excess methyl iodode were removed in vacuo. The residue of yellow solid gradually turned purplish. Yield 128 mg (50.0%), m.p. 228°-230° C., IR (KBr) 3210, 3020, 1670, 1495, 1480, 1190, 1025, 1000, 770 $cm^{-1}$. The product has the formula

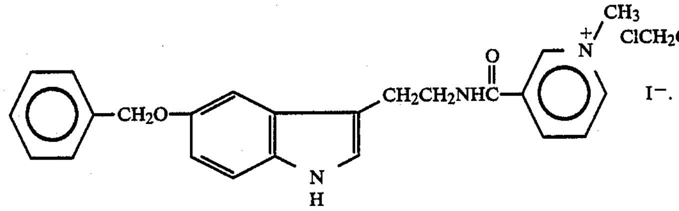

Catatylic hydrogenolysis, using palladium-on-charcoal catalyst, of 1-methyl-3-N-{2-[3-(5-benzyloxy)indolyl]ethyl}carbamoylpyridinium iodide affords 1-methyl-3-N-{2-[3-(5-hydroxy)indolyl]ethyl}carbamoylpyridinium iodide. Subsequent esterification with trimethylacetyl chloride affords the corresponding pivalyl ester of the formula

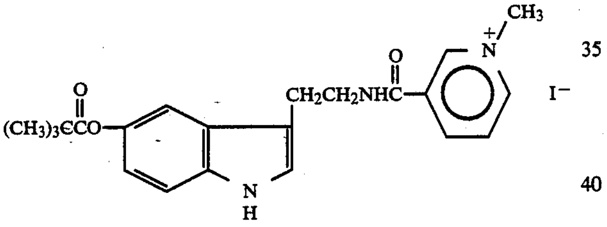

which can then be reduced as described hereinabove to the corresponding dihydro derivative of the formula

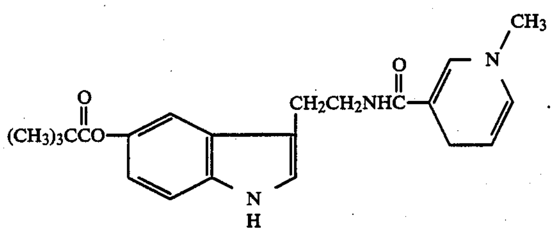

EXAMPLE 61

Peparation of 1-Methyl-3-{{N-{1-ethoxycarbonyl-2-[4-bis(2-chloroethyl)aminophenyl]}ethyl}}carbamoylpyridine Melphalan ethyl ester hydrochloride (153 mg, 0.41 mmol) was dissolved in acetonitrile (5 ml). A mixture of dicyclohexylcarbodiimide (89 mg, 0.43 mmol) and nicotinic acid (50.9 mg, 0.41 mmol) in acetonitrile (1 ml) and pyridine (1 ml) was added to the stirred solution of hydrochloride at 0° C. After approximately 5 minutes, the clear mixture became cloudy. The mixture was allowed to warm to room temperature and stirred for 44 hr, after which time the precipitate was removed by filtration. Solvents were removed at reduced pressure to give an orange oil which was taken into chloroform (15 ml) and washed with cold water (5 ml). Removal of solvent in vacuo gave 90 mg of a soft yellow solid (50% yield) which was used without further purification in the following step. δ($CDCl_3$): 9.3 (bs, 1H, pyridine H-2); 8.9–9.2 (m, 1H, pyridine H-4); 7.9–8.2 (m, 1H, pyridine H-6); 7.5 (m, 1H, pyridine H-5); 6.95 ($AB_q$, 4-H); 4.9–5.3 (m, 1H, C—H; 4.3 (q, 2H, $OCH_2$); 3.5–3.9 [bs, 8H, $(CH_2CH_2)_2$]; 3.2 (dist. d, 2H, $ArCH_2$); 1.3 (t, 3H, $CH_3$). The product has the formula:

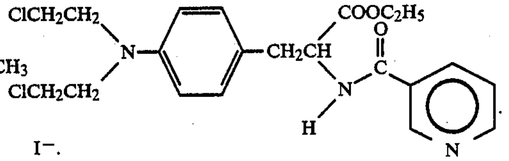

EXAMPLE 62

Preparation of 1-Methyl-3-{{N-{1-ethoxycarbonyl-2-[4-bis(2-chloroethyl)aminophenyl]}ethyl}}carbamoylpyridinium iodide The product of Example 61 (76.5 mg, 0.173 mmol) in acetone (10 ml) was treated with methyl iodide (0.1 ml, 1 mmol) and the mixture was heated at gentle reflux; further methyl iodide (0.1 ml) was added after 4 hours. Thin layer chromatography ($CHCl_3$:methanol, 10:1) showed several spots, including a quaternary compound at the origin. No further change in TLC was apparent after 6 hours, at which time heat was removed and solvents were evaporated in vacuo to leave a red-orange oil (118 mg). The oil was dissolved in $d_6$ acetone and insoluble particles were removed by filtration through a cotton plug. δ[$(CD_3)_2CO$] 9.7 (bs, 1H, pyridine H-2); 8.9–9.5 (m, 2-H, pyridine H-4, H-6); 8.1–8.4 (m, 1H, pyridine H-5); 4.8–5.1 (m, 1H, CH); 4.7 (s, 3H, $N^+CH_3$); 4.2 (q, 2H, $OCH_2$); 3.75 [bs, 8H, $(CH_2CH_2)_2$]; 3.2 (s, HOD+$ArCH_2$); 1.25 (5, 3H, $CH_3$). The product is further characterized by the structural formula:

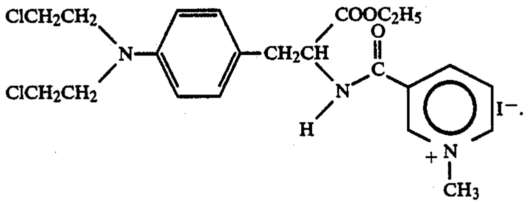

EXAMPLE 63

Preparation of 1-Methyl-3-{{N-{1-ethoxycarbonyl-2-[4-bis(2-chloroethyl)aminophenyl]}ethyl}}carbamoyl-1,4-dihydropyridine The product of Example 62 (101 mg, 0.174 mol) and sodium bicarbonate (5.8 mg, 6.8 mmol), as a suspension in ice cold $N_2$ deaerated water (15 ml) and methanol (2 ml), were treated with sodium dithionite (91 mg, 5.2 mmol) and ethyl acetate (20 ml). The original pale yellow suspension became yellow instantly, and after 2 hours the mixture was clear. Aqueous and organic layers were separated and the aqueous layer was extracted with ethyl acetate (4×20 ml). The combined organic layers were dried over sodium sulfate at 0° C. in the dark. Removal of solvent in vacuo gave a yellow-orange oil which reduced methanolic $AgNO_3$: yield 77 mg, 97%, δ($CDCl_3$) 6.5–5.9 (bd, 1H, pyridine H-6); 4.5–5.1 (m, 2H, pyridine 4–5+C—H); 4.2 (q, 2H, $OCH_2$); 3.75 [bs, 8H, $(CH_2CH_2)_2$]; 3.05–3.3 [m, 4H, $CH_2Ar$+pyridine H-4 ($CH_2$)]; 3.0 (s, 3H, $NCH_3$); 1.3 (t, 3H, $CH_3$). λmax (methanol) 356.5 nm. The product has the formula:

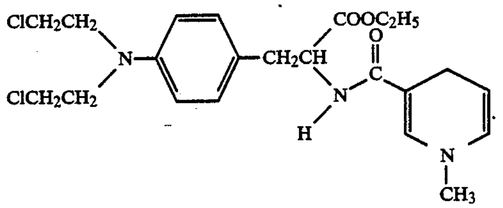

EXAMPLE 64

Preparation of 3-Nicotinoyloxyestra-1,3,5(10)-trien-17-one (Estrone Nicotinate)

To nicotinic acid (41 g, 0.333 mol) at 0° C. was added thionyl chloride (115 ml, 1.58 mol) with stirring. The mixture was refluxed for one hour, and the white crystalline product was filtered and washed sparingly with dry benzene. Excess thionyl chloride was azeotroped off with dry benzene immediately before use. Yield 90% (53.97 g) of nicotinoyl chloride hydrochloride; NMR, IR identical with literature values.

To nicotinoyl chloride hydrochloride (2.65 g, 0.015 mol) in pyridine (20 ml) at 0° C. was added estrone (2 g, 0.0074 mol). The mixture was refluxed for one hour and then poured over 100 ml of ice cold water, filtered, and dried over $P_2O_5$ under vacuum. Yield 72% (2.0076 g), m.p. 207°–210° C. NMR ($CDCl_3$) δ9.3–9.1 (br s, 1H, $C_2$ pyridinium proton), 8.8–8.6 (br d, 1H, $C_6$ pyridinium proton, 8.4–8.2 (br d, 1H, $C_4$ pyridinium proton), 7.5–7.1 (m, 2-H, $C_5$ pyridinium proton+$C_1$ estrone proton), 7.0–6.7 (m, 2H, $C_{2,4}$ estrone protons), 3.2–1.3 (estrone skeletal protons, 15), 1.0–0.9 (s, 3H, $C_{18}$ estrone protons). IR (KBr) 1750–1730 $cm^{-1}$ (broad C═O stretching). Anal. calculated for $C_{24}H_{25}NO_3$; C, 76.76; H, 6.72; N, 3.73. Found: C, 76.37; H, 6.96; N, 3.67. The product is further characterized by the structural formula:

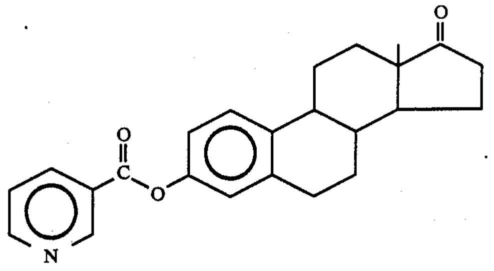

EXAMPLE 65

Preparation of 3-[(1-Methyl-3-pyridiniumcarbonyl)oxy]estra-1,3,5(10)-trien-17-one iodide To estrone nicotinate (0.5 g, 0.0013 mol) in acetone (20 ml) was added methyl iodide (1 ml, 0.016 mol) and the mixture was refluxed overnight. The deep yellow precipitate was filtered, washed with acetone, and dried. Yield 90% (0.6226 g); m.p. 245°–248° C. (dec.). NMR ($d_5$-DMSO) δ9.8–9.7 (br s, 1H, $C_2$ pyridinium proton), 9.4–9.0 (m, 2H, $C_4$, $C_6$ pyridinium protons), 8.4–8.0 (m, 1H, $C_5$ pyridinium proton), 7.4–7.2 (m, 1H, $C_1$ estrone proton), 7.1–6.9 (m, 2H, $C_{2,4}$ estrone protons), 3.2–1.3 (estrone skeletal protons, 15), 1.0–0.9 (s, 3H, $C_{18}$ estrone protons). IR (KBr) 1755–1740 (broad C═O stretching). Anal. calculated for $C_{25}H_{28}NO_3I$: C, 58.03; H, 5.47; N, 2.71. Found: C, 58.16; H, 5.51; N, 2.67. The product has the formula:

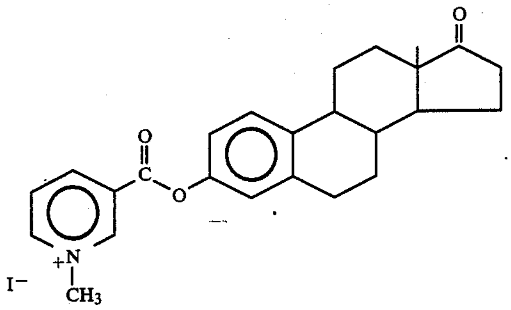

EXAMPLE 66

Preparation of 3-[(1-Methyl-1,4-dihydro-3-pyridinylcarbonyl)oxy]estra-1,3,5(10)-trien-17-one To 3-[(1-methyl-3-pyridiniumcarbonyl)oxy]estra-1,3,5(10)-trien-17-one iodide (0.600 g, 1.16 mmol) in a 50:50 mixture of methanol and deaerated water (80 ml) were added $NaHCO_3$ (0.58 g, 7.0 mmol) and $Na_2S_2O_4$ (0.81 g, 4.6 mmol). The mixture was stirred under $N_2$ for 2 hours. The precipitate was filtered, dissolved in methanol at room temperature, filtered, and then re-precipitated with deaerated water. This precipitate was then filtered and dried over $P_2O_5$ under vacuum. Yield 67% (0.3029 g). The product decomposes over the range 130°–180° C. NMR (CDCl) δ7.2–7.0 (m, 2H, $C_1$ estrone protons+$C_2$ dihydro proton), 6.8–6.6 (m, 2H, $C_{2,4}$ estrone protons), 5.8–5.3 (m, 1H, $C_6$ dihydro proton), 5.0–4.6 (m, 1H, $C_5$ dihydro proton), 3.2–3.0 (m, 2H, $C_4$ dihydro protons), 3.0–2.8 (s, 3H, N—$CH_3$), 2.5–1.2 (estrone skeletal protons, 15), 1.0–0.9 (s, 3H, $C_{18}$ estrone protons). IR (KBr) 1745–1740 (C═O stretching). Anal. calculated for $C_{25}H_{29}NO_3$ ($+\frac{1}{2}H_2O$): C, 74.96; H, 7.56; , N 3.50. Found: C, 75.44; H, 7.27; N, 3.38. The product is further characterized by the structural formula:

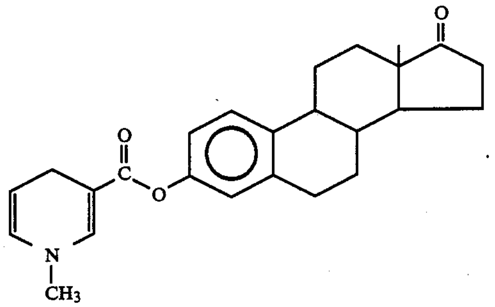

EXAMPLE 67

Preparation of 17β-Nicotinoyloxyestra-1,3,5(10)-trien-3-ol 3-methyl ether

To nicotinoyl chloride hydrochloride (3.15 g, 0.017 mol) in pyridine (20 ml) at 0° C. was added estradiol 3-methyl ether (2 g, 0.0070 mol). After refluxing one hour, the mixture was poured over 100 ml of ice water, filtered and dried over $P_2O_5$ under vacuum. Yield 76% (2.0674 g), m.p. 140°-142° C. NMR ($CDCl_3$) δ9.3-9.0 (br s, 1H, $C_2$ pyridinium proton, 8.8-8.6 (m, 1H, $C_6$ pyridinium proton), 8.4-8.1 (br d, 1H, $C_4$ pyridinium proton), 7.5-7.0 (m, 2H, $C_5$ pyridinium proton+$C_1$ estradiol proton), 6.8-6.5 (m, 2H, $C_{2,4}$ estradiol protons), 5.1-4.7 (m, 1H, $C_{17\alpha}$ estradiol proton), 3.8-3.6 (s, 3H, O—$CH_3$), 3.0-1.2 (15H, estradiol skeletal protons), 1.0-0.9 (s, 3H, $C_{18}$ estradiol protons). IR (KBr) 1725 (C=O stretching). Anal. calculated for $C_{25}H_{29}NO_3$: C, 76.68; H, 7.48; N, 3.58. Found: C, 76.49; H, 7.50; N, 3.55. The product has the formula:

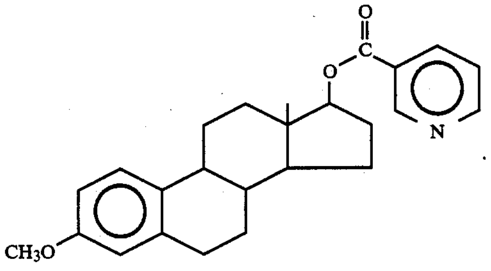

EXAMPLE 68

Preparation of 17β-[(1-Methyl-3-pyridiniumcarbonyl)oxy]estra-1,3,5(10)-trien-3-ol 3-methyl ether iodide To 17β-nicotinoyloxyestra-1,3,5(10)-trien-3-ol 3-methyl ether (1.5 g, 0.0038 mol) in acetone (20 ml) was added methyl iodide (1 ml, 0.016 mol) and the mixture was refluxed overnight. The pale yellow precipitate was filtered, washed with acetone, and dried. Yield 76% (1.5595 g), m.p. 230°-234° C. (dec.). NMR ($d_6$-DMSO) δ9.5-9.3 (br s, 1H, $C_2$ pyridinium proton), 9.2-8.8 (m, 2H, $C_{4,6}$ pyridinium protons), 8.3-8.0 (m, 1H, $C_5$ pyridinium proton), 7.2-7.0 (m, 1H, $C_1$ estradiol proton), 6.8-6.5 (m, 2H, $C_{2,4}$ estradiol protons); 5.2-4.8 (m, 1H, $C_{17\alpha}$ estradiol proton), 4.6-4.4 (s, 3H, N—$CH_3$), 3.8-3.6 (s, 3H,O—$CH_3$), 3.0-1.2 (15H, estradiol skeletal protons), 1.0-0.9 (s, 3H, $C_{18}$ estradiol protons). IR (KBr) 1745 (C=O stretching). Anal. calculated for $C_{26}H_{32}NO_3I$: C, 58.53; H, 6.06; N, 2.63. Found: C, 58.25; H, 6.07; N, 2.59. The title compound has the formula:

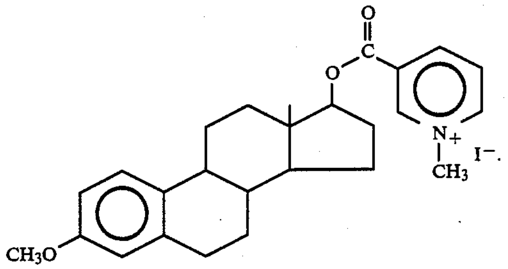

EXAMPLE 69

Preparation of 17β-[(1-Methyl-1,4-dihydro-3-pyridinylcarbonyl)oxy]estra-1,3,5(10)-trien-3-ol 3-methyl ether To 17β-[(1-methyl-3-pyridiniumcarbonyl)oxy]estra-1,3,5(10)-trien-3-ol 3methyl ether (0.600 g, 1.12 mmol) in a 50:50 mixture of methanol and deaerated water (80 ml) were added $NaHCO_3$ (0.57 g, 6.7 mmol) and $Na_2S_2O_4$ (0.78 g, 4.5 mmol). The mixture was stirred under $N_2$ for 2 hours. The precipitate was filtered, dissolved in methanol at room temperature, filtered, and then reprecipitated with deaerated water. This precipitate was then filtered and dried over $P_2O_5$ under vacuum. Yield 74% (0.3383 g). The product decomposes over the range 120°-170° C. NMR ($CDCl_3$) δ7.3-7.2 (m, 1H, $C_1$ estradiol proton), 7.0-6.9 (s, 1H, $C_2$ dihydro proton), 6.8-6.6 (m, 2H, $C_{2,4}$ estradiol protons), 5.8-5.6 (m, 1H, $C_6$ dihydro proton), 5.0-4.6 (m, 2H, $C_5$ dihydro proton+$C_{17\alpha}$ estradiol proton), 3.9-3.7 (s, 3H, O—$CH_3$), 3.2-3.0 (m, 2H, $C_4$ dihydro protons), 3.0-2.8 (s, 3H, N—$CH_3$), 2.4-1.2 (15H, estradiol skeletal protons), 1.0-0.9 (s, 3H, $C_{18}$ estradiol protons). IR (KBr) 1705 (C=O stretching). Anal. calculated for $C_{26}H_{33}NO_3$: C, 76.61; H, 8.18; N, 3.44. Found: C, 76.75; H, 8.43; N, 3.37. The product is further characterized by the structural formula:

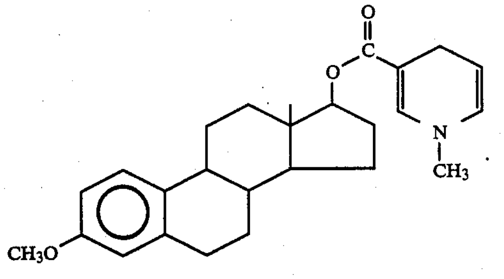

EXAMPLE 70

Preparation of Estra-1,3,5(10-triene-3,17β-diol 3,17-dinicotinate (Estradio 3,17β-dinicotinate)

Estradiol (2 g, 0.0073 mol) was added to nicotinoyl chloride hydrochloride (5.3 g, 0.029 mol) in dry pyridine (30 ml) at 0° C. The mixture was refluxed for 1 hour and then poured over 100 ml of ice water, filtered and dried over $P_2O_5$ under vacuum. Yield 90% (3.18 g), m.p. 148°-150° C. NMR ($CDCl_3$) δ9.2-9.0 (br s, 2H, $C_2$ pyridinium protons), 8.7–8.3 (m, 2H, $C_6$ pyridinium protons), 8.4–8.0 (m, 2H, $C_4$ pyridinium protons), 7.5–7.1 (m, 3H, $C_5$ pyridinium protons+$C_1$ estradiol proton), 6.9–6.7 (m, 2H, $C_{2,4}$ estradiol protons), 5.0–4.7 (m, 1H, $C_{17\alpha}$ estradiol proton), 3.2–1.3 (estradiol skeletal protons, 15), 1.0–0.9 (s, 3H, $C_{18}$ estradiol protons). Ir (KBr) 1750, 1725 $cm^{-1}$ (2 C═O stretching). Anal. calculated for $C_{30}H_{31}N_2O_4$: C, 74.50; H, 6.47; N, 5.79. Found: C, 74.40; H 6.32; N, 5.75. The product has the formula:

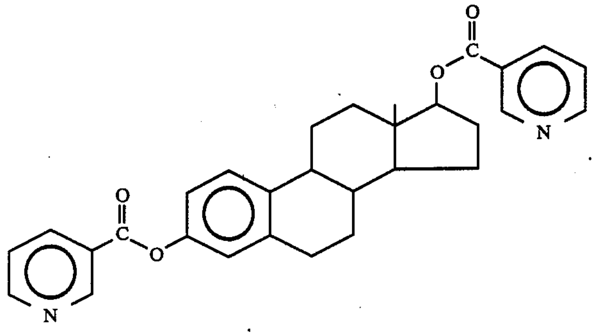

EXAMPLE 71

Preparation of 3,17β-Bis[(1-methyl-3-pyridiniumcarbonyl)oxy]estra-1,3,5(10)-triene diiodide Methyl iodide (1 ml, 0.016 mol) was added to estradiol 3,17β-dinicotinate (1 g, 0.0021 mol) in acetone (20 ml) and the mixture was refluxed overnight. The deep yellow precipitate which formed was filtered, washed with acetone, and dried. Yield 72% (1.262 g), m.p. 256°–258° C. (dec.). NMR ($d_6$-DMSO) δ9.6–9.2 (br s, 2H, $C_2$ pyridinium protons), 9.2–8.7 (m, 4H, $C_4$+$C_6$ pyridinium protons), 8.4–8.0 (m, 2H, $C_5$ pyridinium protons), 7.3–7.1 (m, 1H, $C_1$ estradiol proton), 7.1–6.9 (m, $C_{2,4}$ estradiol protons), 5.0–4.7 (m, 1H, $C_{17\alpha}$ estradiol proton), 4.5–4.3 (s, 6H, N—$CH_3$), 3.2–1.3 (estradiol skeletal protons, 15), 1.0–0.9 (s, 3H, $C_{18}$ estradiol protons). IR (KBr) 1750–1735 $cm^{-1}$ (broad C═O stretching). Anal. Calculated for $C_{32}H_{36}N_2O_4I_2$: (+1 $H_2O$): C, 48.99; H, 4.89; N, 3.57. Found: C, 48.78; H, 4.66; N, 3.63. The product is further characterized by the structural formula:

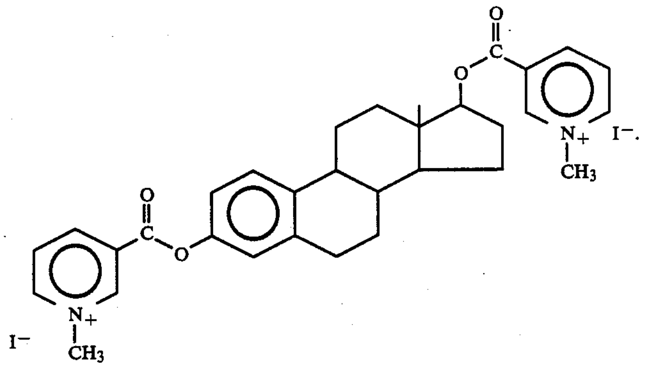

That compound was converted to the corresponding 3-hydroxy steroid of the formula

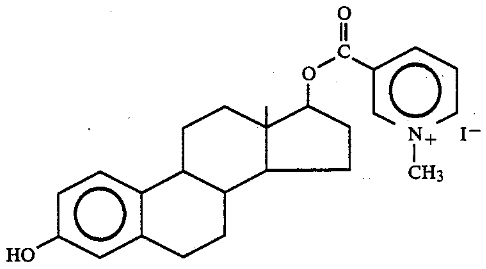

by partial hydrolysis; the resultant 3-hydroxy compound was then reduced, as generally described hereinabove, to afford the corresponding dihydro derivative of the formula

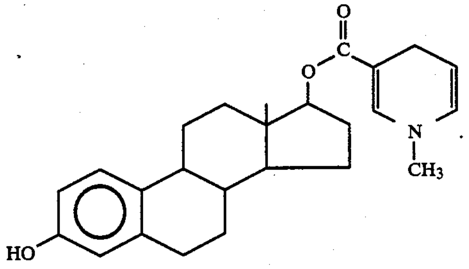

When that dihydro derivative was administered to male rats, the corresponding 3-hydroxy-17-quaternary derivative was found in the brain.

EXAMPLE 72

In Vitro Testing of Estrogenic Steroid Derivatives

The products of Examples 66 and 69 both reduce methanolic silver nitrate. The product of Example 66 requires more time and some warming.

The two above-mentioned dihydro derivatives show disappearance of UV absorption at 359 and 358 nm, respectively, upon addition of $H_2O_2$. Diphenylpicrazyl radical absorption at 516 nm can also be shown to decrease upon addition of ether of these compounds.

Disappearance of the product of Example 66 in brain and plasma homogenates was studied using the Cary 210 and Apple II microprocessor.

| | Brain Homogenate | | |
|---|---|---|---|
| Concentration | $t_{\frac{1}{2}}$ (min.) | k ($sec^{-1}$) | r |
| $2.68 \times 10^{-4}$ M | 11.2 | $1.03 \times 10^{-3}$ | 0.9998 |
| $1.18 \times 10^{-4}$ M | 8.7 | $1.33 \times 10^{-3}$ | 0.9998 |
| $4.07 \times 10^{-5}$ M | 7.5 | $1.53 \times 10^{-3}$ | 0.9989 |

| | Plasma Homogenate | | |
|---|---|---|---|
| Concentration | $t_{\frac{1}{2}}$ (min.) | k ($sec^{-1}$) | r |
| $1.43 \times 10^{-4}$ M | 39.7 | $2.97 \times 10^{-4}$ | 0.992 |
| $7.04 \times 10^{-5}$ M | 52.7 | $2.19 \times 10^{-4}$ | 0.969 |
| $2.75 \times 10^{-5}$ M | 66.2 | $1.75 \times 10^{-4}$ | 0.953 |

EXAMPLE 73

Preparation of Estra-1,3,5(10)-triene-3,17β-diol 17-nicotinate (Estradiol 17β-nicotinate)

0.5% Potassium bicarbonate in 95% methanol (60 ml) was added to estradiol 3,17β-dinicotinate (0.5 g, 0.0010 mol) and the slurry was stirred overnight at room temperature. Water (60 ml) was added and repeated extractions into chloroform were made, combined and dried over anhydrous sodium sulfate. The chloroform was removed in vacuo and the resulting pinkish-white solid was suspended in methanol at room temperature. The white powder thus obtained was separated by filtration and dried. Yield 94% (0.3663 g), m.p. 221°-222° C. Anal. calc. for $C_{24}H_{27}NO_3$: C, 76.36; H, 7.22; N, 3.71. Found: C, 76.20; H, 7.25; N, 3.70. The product has the formula:

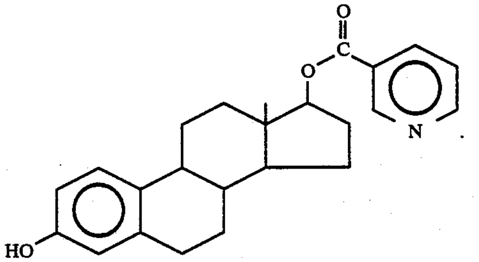

EXAMPLE 74

Preparation of 17β-[(1-Methyl-3-pyridinium)carbonyloxy]estra-1,3,5(10)-trien-3-ol iodide Methyl iodide (2 ml, 0.032 mol) was added to estra-1,3,5(10)-triene-3,17β-diol 17-nicotinate (2.0953 g, 0.0056 mol) in acetone (200 ml) and the mixture was refluxed overnight. The pale yellow precipitate which formed was removed by filtration, washed with acetone and dried. Yield 83% (2.4203 g), m.p. 268°-272° C. (dec). Anal. calc. for $C_{25}H_{29}NO_3I$: C, 57.92; H, 5.65; N, 2.70. Found: C, 57.70; H, 5.73; N, 2.68. The product has the formula:

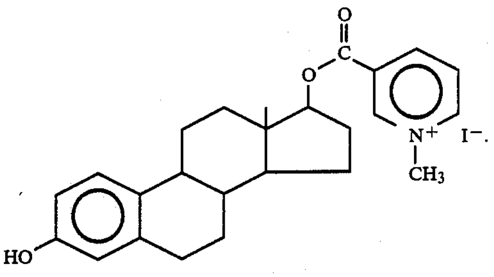

EXAMPLE 75

Preparation of 17β-[(1-Methyl-1,4-dihydro-3-pyridinyl)carbonyloxy]estra-1,3,5(10)-trien-3-ol To 17β-[(1-methyl-3-pyridinium)carbonyloxy]estra-1,3,5(10)-trien-3-ol iodide (1.09 g, 0.0021 mol) in 50:50 t-butanol/deaerated water (150 ml) was added $NaHCO_3$ (1.06 g, 0.0126 mol) and $Na_2S_2O_4$ (1.46 g, 0.0084 mol). The mixture was stirred under $N_2$ for one hour.

The precipitate which formed was removed by filtration, dissolved in ether and dried over anhydrous $Na_2SO_4$. The ether was removed in vacuo. Yield 64% (0.2416 g). The product decomposes over the range 115°-130° C. Anal. calc. for $C_{25}H_{31}NO_3$ ($+\frac{1}{2}H_2O$): C, 74.59; H, 8.03; N, 3.48. Found: C, 74.57; H, 8.04; N, 3.40. The product is characterized by the structural formula:

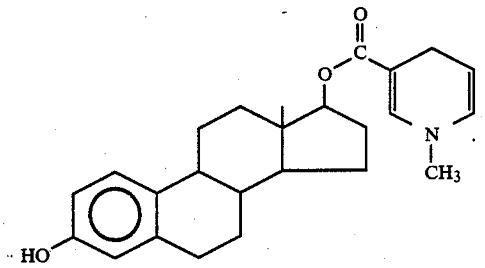

EXAMPLE 76

Preparation of 17α-Ethynylandrost-4-en-17β-ol-3-one 17-nicotinate (Ethisterone nicotinate)

Ethisterone (2.5 g, 8.0 mmol) was dissolved in 100 ml of dry pyridine. Excess nicotinoyl anhydride (2.5 g, 11.0 mmol) and a catalytic amount of DMAP were added. The solution was stirred for 5 days, then poured into ice water. The resulting white powder was removed by filtration and washed. Yield 85%, 2.84 g, m.p. 203°-204° C. The product has the formula:

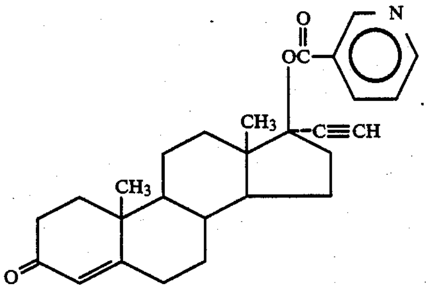

EXAMPLE 77

Preparation of 17α-Ethynyl-17β-[(1-methyl-3-pyridinium)carbonyloxy]androst-4-en-3-one iodide Ethisterone nicotinate (1 g, 1.79 mmol) was dissolved in 50 ml of acetonitrile. Methyl iodide (0.76 g, 5.3 mmol) was added and the solution was refluxed overnight. The yellow solid thus obtained was removed by filtration and washed. Yield 95%, 1.27 g. UV($CH_3OH$) $\lambda_{max}$=224 nm. The product has the formula:

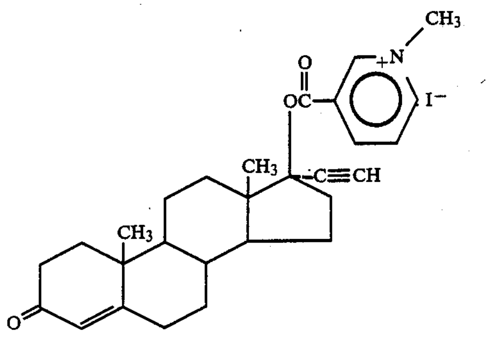

EXAMPLE 78

Preparation of 17α-Ethynyl-17β-[(1-methyl-1,4-dihydro-3-pyridinyl)-carbonyloxy]androst-4-en-3-one The product of Example 77 (300 mg) was added to 100 ml of cold degassed water. Then, 0.135 g of $NaHCO_3$ and 0.281 g of $Na_2S_2O_4$ were added and the solution was stirred for 30 minutes, then repeatedly extracted with chloroform. The chloroform layers were combined and dried over $MgSO_4$. The solvent was removed under reduced pressure, yielding a yellow, high melting foam. Yield 0.11 g or 47%. UV($CH_3OH$) $\nu_{max}$=240 nm, others 208 nm, 362 nm. The compound has the structural formula:

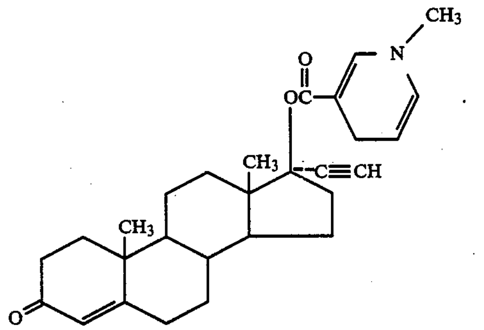

EXAMPLE 79

Preparation of N-Nicotinoyltyrosine ethyl ester

Nicotinic acid (12.3 g, 0.1 mol) was dissolved in dry pyridine (300 ml). The solution was cooled and dicyclohexylcarbodiimide (20.6 g, 0.1 mol) was added. After dissolution, tyrosine ethyl ester hydrochloride (24.6 g, 0.1 mol) was added and the solution was stirred overnight. The precipitated dicyclohexylurea (DCU) was removed by filtration. Additional DCU was removed by triturating the oil with hot water. The product was purified with acetone. Calculated for $C_{17}H_{18}N_2O_4\cdot\frac{1}{2}H_2O$: C, 63.16; H, 5.88; N, 8.66. Found; C, 63.10; H, 5.96; N, 8.59. The product can also be named N-[1-ethoxycarbonyl-2-(4'-hydroxyphenyl)ethyl]nicotinamide.

EXAMPLE 80

Preparation of N-[(1-Methyl-3-pyridinium)carbonyl]tyrosine ethyl ester iodide

N-Nicotinoyltyrosine ethyl ester (20 g, 0.06 mol) was dissolved in 200 ml of acetone. A two molar excess of methyl iodine (25.6 g, 0.18 mol) was added and the mixture was refluxed for 6 hours. The solvent was removed under reduced pressure to yield the desired product as a solid foam. NMR analysis confirmed the identity of the product, which has the structural formula

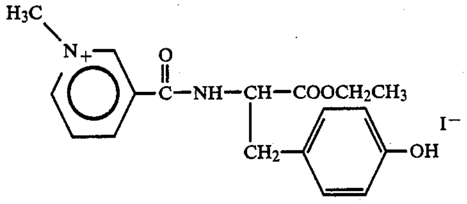

and can also be named 1-methyl-3-{N-[(1'-ethoxycarbonyl)-2'-(4"-hydroxyphenyl)ethyl}carbamoylpyridinium iodide.

EXAMPLE 81

Preparation of 1-Methyl-3{N-[(1'-ethoxycarbonyl)-2'-(4"-pivaloyloxyphenyl)ethyl]}carbamoylpyridinium trifluoroacetate The product of Example 80 (6 g, 0.013 mol) was dissolved in 50 ml of cold trifluoroacetic acid at 0° C. in an ice bath. Pivaloyl chloride (3.14 g, 0.026 mol) was slowly added and the solution was warmed to room temperature. After 24 hours, the solvent was removed under reduced pressure. The resulting dark oil was triturated with petroleum ether but no solidification occurred. Identity of the product was confirmed by NMR analysis. The product was dissolved in aqueous methanol (10%) and extracted with ethyl ether to remove a highly colored contaminate before using as the starting material in Example 83 below.

EXAMPLE 82

Preparation of 1-methyl-3-{N-[(1'-ethoxycarbonyl)-2'-(4"-isobutyryloxyphenyl)ethyl]}carbamoylpyridinium trifluoroacetate The product of Example 80 (6 g, 0.013 mol) was dissolved in 50 ml of trifluoroacetic acid cooled to 0° C. in an ice bath. To that solution with stirring, was slowly added isobutyryl chloride (2.77 g, 2.76 ml). The solution was stirred overnight at ambient temperature and the solvent was removed under reduced pressure. The oil was stirred overnight with petroleum ether and then dried in vacuo, but no solidification occurred. Identity of the product was confirmed by NMR analysis. The product was dissolved in aqueous methanol (10%) and extracted with ethyl ether to remove a highly colored contaminant before using in Example 84 below.

EXAMPLE 83

Preparation of 1-Methyl-3-{N-[(1'-ethoxycarbonyl)-2'-(4''-pivaloyloxyphenyl)ethyl]}carbamoyl-1,4-dihydropyridine The product of Example 81 (4.07 g, 0.0079 mol) was dissolved in 100 ml of 25% aqueous methanol. Nitrogen gas was bubbled through the solution. To the solution, stirring in an ice bath, was then added $NaHCO_3$ (2.02 g, 0.024 mol). Ethyl ether (100 ml) was added, followed by the addition of $Na_2S_2O_4$ (4.12 g, 0.024 mol). The yellow biphasic solution was stirred for 30 minutes, then the layers were separated and the aqueous layer was extracted twice with 75 ml portions of ethyl ether. The combined organic fractions were dried over $Na_2SO_4$ and the solvent was removed under reduced pressure to afford a solid foam which oxidized ethanolic silver nitrate. Anal. Calc. for $C_{23}H_{20}N_2O_5 \cdot \frac{1}{2}H_2O$: C, 65.23; H, 7.33. Found: C, 65.76; H, 7.28; N, 6.95.

EXAMPLE 84

Preparation of 1-Methyl-3-{N-[(1'-ethoxycarbonyl)-2'-(4''-isobutyryloxyphenyl)ethyl]}carbamoyl-1,4-dihydropyridine The product of Example 82 (2.20 g, 0.0044 mol) was dissolved in 100 ml of aqueous methanol. The solution was cooled in an ice bath with a stream of $N_2$ passing through it. To this solution, $NaHCO_3$ (1.11 g, 0.0132 mol) and ether (100 ml) were added. Then, sodium dithionite (2.30 g, 0.0132 mol) was added and the solution was stirred for 30 minutes. The layers were separated and the aqueous phase was washed with ethyl ether. The combined organic layers were dried over anhydrous $Na_2SO_4$ and reduced in volume. The resultant orange oil oxidized ethanolic silver nitrate. Identity of the product was confirmed by NMR analysis.

EXAMPLE 85

Preparation of 1-Methyl-3-{N-[(1'-ethoxycarbonyl)-2'-4''-acetoxyphenyl)ethyl]}carbamoylpyridinium trifluoroacetate The product of Example 80 (4.70 g, 0.01 mol) was dissolved in 30 ml of trifluoroacetic acid cooled in a water bath. Acetyl chloride (1.56 g, 0.02 mol) was added, with stirring. The solution was then stirred overnight. The solvent was removed under reduced pressure and the resulting oil was dissolved in aqueous methanol and extracted with ethyl ether. The product was obtained as a pale yellow oil. Its identity was confirmed by NMR analysis.

EXAMPLE 86

Preparation of 1-Methyl-3-{N-[(1'-ethoxycarbonyl)-2'-(4''-acetoxyphenyl)ethyl]}carbamoyl-1,4-dihydropyridine The product of Example 85 (2.76 g, 5.7 mmol) was dissolved in 25% aqueous methanol. The solution was stirred at 0° C. while adding $NaHCO_3$ (1.44 g, 0.017 mol). A layer of 100 ml of ethyl ether was added, followed by the addition of $Na_2S_2O_4$ (2.98 g, 0.017 mol). The system was stirred for 30 minutes, then the layers were separated. The aqueous layer was extracted with ether (2×50 ml), then the combined organic layers were extracted with cold degassed water. The ether layer was dried over $Na_2SO_4$ and the solvent was removed under reduced pressure to given an orange oil. UV ($CH_3OH$) 214 nm, 358 nm. Anal. calc. for $C_{20}H_{24}N_2O_5O$: C, 64.52; H, 6.45; N, 7.53. Found: C, 63.90; H, 6.72; N, 7.70: I, 0.0.

EXAMPLE 87

Preparation of Valproic acid chloride (2-Propylpentanoyl chloride)

To 4.32 g (30 mmol) of valproic acid in an ice bath, thionyl chloride (3.60 g, 30 mmol) was slowly added, with stirring. The neat mixture was allowed to come to room temperature and then heated in a water bath at 50° C. for 30 minutes. 50 Ml portions of dry benzene were twice added and removed under reduced pressure. The resultant product was used in subsequent reactions without further purification.

EXAMPLE 88

Preparation of Valproic acid 2-iodoethyl ester (2'-Iodoethyl 2-propylpentanoate)

To the product of Example 87 (4.87 g, 30 mmol), 2-iodoethanol (5.16 g, 30 mmol) was added with stirring and cooling in an ice bath. The neat mixture was then heated to 100° C. in a water bath for 10 minutes, then removed from the heat and stirred for an additional 10 minutes. The reaction mixture was then dissolved in 50 ml of ether, washed with water (1×30 ml), 5% NaOH (2×30 ml), and again with water (2×30 ml). The ether layer was dried over anhydrous sodium sulfate and the solvent was removed under reduced pressure. A light yellow liquid product was obtained in 67% yield from valproic acid (6.0 g). Silver nitrate gave a bright yellow precipitate. NMR analysis confirmed the identity of the product.

EXAMPLE 89

Preparation of 1-[2'-(2''-Propyl)pentanoyloxy]ethyl-3-carbamoylpyridinium iodide The product of Example 88 (3.28 g, 11 mmol) and 50 ml of dimethylformamide were added to nicotinamide (1.22 g, 10 mmol). The mixture was heated to reflux for 3 hours, then was cooled. Removal of solvent under reduced pressure afforded a brown oily residue, which was stirred with ether (60 ml) for 30 minutes, giving a yellow powder. The ether was decanted and a fresh portion of ether (50 ml) was added. The crude product was vacuum filtered under $N_2$, then was recrystallized from isopropanol/ether to give 3.5 g of the desired product (84% yield), m.p. 111°-112° C. The product has the formula:

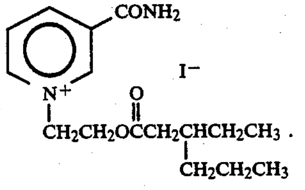

EXAMPLE 90

Preparation of
1-[2'-(2"-Propyl)pentanoyloxy]ethyl-3-carbamoyl-1,4-dihydropyridine To 50 ml of ice-cold degassed deionized water, the product of Example 89 (420 mg, 1 mmol) was added. To that solution, $NaHCO_3$ (366 mg, 4 mmol) and $Na_2S_2O_4$ (696 mg, 4 mmol) were added, with stirring. Nitrogen gas was bubbled through the solution for 30 minutes. The aqueous solution was then extracted with ether (6×25 ml) until the ether layer was no longer yellow. The combined ether extracts were washed with water (1×50 ml) and dried over $MgSO_4$. The ether layer was decanted from the drying agent and the solvent was removed under reduced pressure. To the oil residue, ether was added and then removed (10×5 ml) on a vacuum pump. A foam was formed, which returned to an oil upon exposure to the atmosphere. Structure was confirmed by NMR analysis.

EXAMPLE 91

Preparation of
2-(3-Pyridyl)carbonylamino-3-(3,4-dihydroxy)phenylpropanoic acid ethyl ester L-DOPA ethyl ester (5 g, 17.8 mmol) in dry pyridine (20 ml) was treated with a solution containing dicyclohexylcarbodiimide (4 g, 10% excess) and nicotinic acid (2.21 g, 17.8 mmol) in dry pyridine (50 ml) at room temperature. The mixture was stirred for 24 hours, after which time the urea which formed was removed by filtration and washed with $CH_3CN$. Solvents were removed in vacuo to give an orange, highly hygroscopic foam. The crude product was taken up in $CHCl_3$ (100 ml) containing 1 drop of methanol and washed with cold water (50 ml). Drying over $MgSO_4$ and removal of solvent in vacuo left an orange foam, which was taken up in $CH_3CN$ (15 ml). Insoluble material was removed by filtration through a glass wool plug. The filtrate was evaporated to dryness to give a hygroscopic yellow-orange foam which collapsed on exposure to the atmosphere. The product was taken up in $CHCl_3$ (60 ml) and washed, first with 0.5% and then with 0.25% aqueous sodium bicarbonate. Drying over $MgSO_4$ and evaporation to dryness left an orange foam which did not collapse on atmospheric exposure. NMR analysis confirmed that the product has the structure:

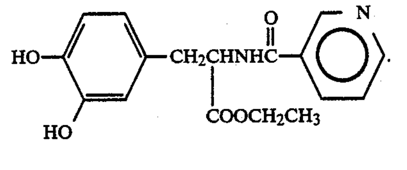

EXAMPLE 92

Preparation of
2-(3-Pyridyl)carbonylamino-3-(3,4-dipivaloyloxy)-phenylpropanoic acid ethyl ester The product of Example 91 (250 mg, ~0.76 mmol) was taken up in $CHCl_3$ (15 ml) and allowed to react with pivaloyl chloride (200 mg, 10% excess) at gentle reflux overnight. Removal of volatiles in vacuo yielded a yellow foam, which was again treated with $CHCl_3$. Triethylamine was added until complete solution was obtained, at which point pivaloyl chloride (200 mg, 10% excess) was added and the solution was heated at reflux for 4 hours, then allowed to cool overnight. Washing with water (50 ml), drying over $MgSO_4$ and removal of solvent in vacuo gave an off-white foam which gave a negative $FeCl_3$ test, indicating no free phenolic groups remained. The material was highly hydroscopic. NMR analysis confirmed the identity of the product.

EXAMPLE 93

Preparation of
1-Methyl-3-{N-[1-ethoxycarbonyl-2-(3,4-dihydroxy)-phenyl]}carbamoylpyridinium iodide The product of Example 91 (250 mg, 0.76 mmol) in $CH_3CN$ (10 ml) was treated with methyl iodide (100 mg, 2-fold excess) at room temperature. The solution was stirred overnight, after which time the solvent was removed in vacuo to give a yellow foam, m.p. 75°-82° C. NMR analysis confirmed the identity of the quaternary salt.

EXAMPLE 94

Preparation of
1-Methyl-3-{N-[1-ethoxycarbonyl-2-(3,4-dipivaloyloxy)phenyl]}carbamoylpyridinium iodide The product of Example 92 (190 mg, 0.38 mmol) in $CH_3CN$ (10 ml) was treated with $CH_3I$ (250 mg, 5 equivalents) and the mixture was heated at gentle reflux, using an ice-cooled condenser. After 4 hours, heating was discontinued and volatiles were removed in vacuo to leave a yellow foam (200 mg, 82%). The material is hygroscopic and melts over a broad range. Testing with methanolic $FeCl_3$ indicates that no free phenolic OH's remain. Identity of the product was confirmed by NMR analysis.

EXAMPLE 95

Preparation of
1-Methyl-3-{N-[1-ethoxycarbonyl-2-(3,4-dipivaloyloxy)phenyl]}carbamoyl-1,4-dihydropyridine The product of Example 94 (180 mg, 0.28 mmol) in distilled water (20 ml) and ethanol (1.0 ml) at 0° C. was treated with $NaHCO_3$ (95 mg, 4 equivalents) and $Na_2S_2O_4$ (146 mg, 3 equivalents) under nitrogen. Ethyl ether (40 ml) was added and the mixture was stirred for 40 minutes. Then the organic and aqueous layers were separated and the aqueous layer was reextracted with ethyl ether (3×20 ml). The combined organic layers were dried ($MgSO_4$) and the solvent was removed in vacuo to leave an oily foam. The product was taken up in a minimum of $CHCl_3$ and passed down a short neutral alumina column, using $CHCl_3$ as eluant. The isolated material showed NMR and UV spectral properties in accord with the assigned structure:

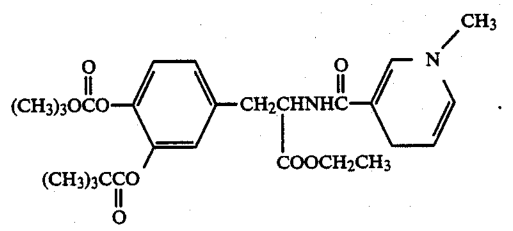

EXAMPLE 96

Preparation of 4-Aminobutanoic acid benzyl ester hydrochloride

GABA (4 g, 38.8 mmol) was suspended in 50 ml (0.48 mol) of benzyl alcohol. The reaction mixture was stirred, with cooling on an ice bath, while 20 ml $SOCl_2$ was added dropwise over a 30 minute period. The mixture was slowly brought to the reflux temperature and refluxed for 4 hours. The resultant pink viscous solution was cooled to room temperature. Addition of 50 ml of ethyl ether and refrigeration overnight produced white crystals which were collected by filtration, recrystallized from a mixture of ethyl ether and ethanol and dried, m.p. 115°-116° C.

EXAMPLE 97

Preparation of 3-{N-[(3'-benzyloxycarbonyl)propyl]carbamoyl}pyridine

Nicotinic acid (1.07 g, 8.7 mmol) was dissolved in a minimum amount of dry pyridine. Dicyclohexylcarbodiimide (1.97 g, 9.6 mmol) was dissolved in the mixture, with stirring. The solution was cooled to 0° C. and 4-aminobutanoic acid benzyl ester hydrochloride (2 g, 8.7 mmol) was added. After 30 minutes, the solution turned yellow and a precipitate was observed. Stirring was continued for 48 hours, after which time 1.8 g of dicyclohexylurea was removed from the yellow solution by filtration. The solution was evaporated to dryness and the residue was washed with 40 ml of ice cold water, extracted into ethyl acetate and dried over $Na_2SO_4$. Evaporation of solvent left the desired product as a sticky yellow oil. Identity of the product, which has the structural formula

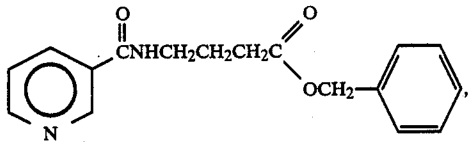

was confirmed by NMR analysis.

EXAMPLE 98

Preparation of 1-Methyl-3-{N-[(3'-benzyloxycarbonyl)propyl]}carbamoylpyridinium iodide The product of Example 97 (0.92 g, 3.09 mmol) was dissolved in a minimum amount of acetone and cooled to 0° C. Methyl iodide (0.40 ml, 6.4 mmol) was added in one portion and the solution was slowly brought to the reflux temperature. The mixture was refluxed for 3 hours, then stirred overnight. Evaporation of solvent left a yellow oil which crystallized and which was recrystallized from acetone/ethyl ether. The light yellow crystals thus obtained were collected by filtration and dried. Anal. calc. for $C_{18}H_{21}N_2O_3I.\frac{1}{8}H_2O$: C, 48.86; H, 4.84; N, 6.33; I, 28.72. Found: C, 48.84; H, 4.81; N, 6.33; I, 28.94. UV ($\lambda_{max}$)=264, 236 nm. NMR and IR analysis also confirmed the identity of the product.

EXAMPLE 99

Preparation of 1-Methyl-3-{N-[(3'-benzyloxycarbonyl)propyl]}carbamoyl-1,4-dihydropyridine The product of Example 98 (200 mg, 0.45 mmol) was dissolved in 20 ml deaerated water. Sodium bicarbonate (0.23 g, 6-fold excess) was added to the solution, with stirring. Sodium dithonite (0.31 g) was added and a yellow color was observed. Ethyl acetate (30 ml) was added and the mixture was stirred for 1$\frac{1}{2}$ hours. The organic layer, containing the yellow dihydro compound, was separated from the aqueous layer and dried over $Na_2SO_4$. Evaporation of ethyl aetate left a yellow oil which reduced methanolic silver nitrate immediately. UV and NMR analysis confirmed the identity of the product, which has the formula

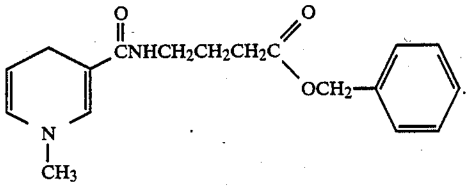

EXAMPLE 100

Preparation of 4-Aminobutanoic acid cyclohexyl ester hydrochloride

GABA (8 g, 77.6 mmol) was suspended in 100 ml (0.96 mol) of cyclohexanol. Thionyl chloride (40 ml) was added dropwise to the mixture at 0° C. The mixture was then refluxed for 4 hours, cooled and crystallized from ethyl ether. The white crystals obtained in this manner were filtered and dried. NMR analysis confirmed the identity of the product.

EXAMPLE 101

Preparation of 3-{N-[(3'-Cyclohexyloxycarbonyl)propyl]}carbamoylpyridine

Nicotinic acid (2.2 g, 18 mmol) was suspended in 50 ml of dry pyridine. Dicyclohexylcarbodiimide (3.68 g, 17.9 mmol) was dissolved in the solution, with stirring. 4-Aminobutanoic acid cyclohexyl ester hydrochloride (4 g, 18 mmol) was added and the mixture was stirred for 48 hours. Precipitated dicyclohexylurea was removed by filtration and the filtrate was evaporated to dryness. The residue was washed with 25 ml of ice cold water and extracted into ethyl acetate. The layers were separated and the organic layer was evaporated to dryness. NMR analysis confirmed the structure of the product.

EXAMPLE 102

Preparation of 1-Methyl-3-{N'-[(3'-Cyclohexyloxycarbonyl)propyl]}carbamoylpyridinium iodide The product of Example 102 (1.74 g, 6 mmol) was dissolved in a minimum amount of acetone and the resulting white precipitate was filtered. Methyl iodide (1.5 ml, 24 mmol) was added in one portion to the solution, with stirring, at 0° C. The mixture was allowed to gently reflux overnight. Filtration of a white precipitate and evaporation of the yellow filtrate produced a reddish oil, which was dissolved in acetone, filtered and evaporated to dryness. Anal. calc. for $C_{22}H_{23}O_3N_2I$: C, 47.26; H, 5.79; N, 6.48; I, 29.38. Found: C, 47.03, H, 5.85; N, 6.44; I, 29.26.

EXAMPLE 103

Preparation of 1-Methyl-3-{N-[(3'-cyclohexylcarbonyl)propyl]}carbamoyl-1,4-dihydropyridine The product of Example 102 (0.11 g, 0.26 mmol) was dissolved in 25 ml of ice cold deaerated water. $NaHCO_3$ (0.09 g, 4-fold excess) was added, followed by $Na_2S_2O_4$ (0.14 g, 3-fold excess). Ethyl acetate (25 ml) was added and the mixture was stirred under nitrogen for 30 minutes. The organic layer was extracted and dried to give an orange oil that reduced methanolic silver nitrate immediately. NMR analysis confirmed that the product has the structure:

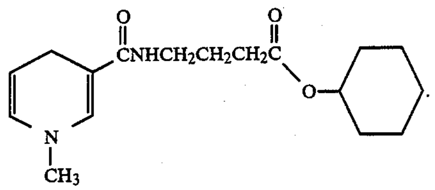

EXAMPLE 104

Preparation of 3-{N-[(3'-Benzyloxycarbonyl)propyl]}carbamoylquinoline

3-Quinolinecarboxylic acid (1.55 g, 9 mmol) was dissolved in 25 ml of dry pyridine. Dicyclohexylcarbodiimide (1.97 g, 9.6 mmol) was added and dissolved, with stirring. 4-Aminobutanoic acid benzyl ester hydrochloride (2.06 g, 9 mmol) was added and the mixture was stirred for 48 hours at room temperature. The precipitated urea was removed by filtration, the filtrate was evaporated to dryness and the residue was washed with 10 ml of ice cold water and extracted into ethyl acetate. That solution was dried over sodium sulfate. The solvent was evaporated, the remaining residue was dissolved in acetone, filtered and evaporated to dryness to give 2.2 g (70%) of the desired product. NMR analysis confirmed the structure of the product.

EXAMPLE 105

Preparation of 1-Methyl-3-{N-[(3'-benzyloxycarbonyl)propyl]}carbamoylquinolinium iodide The product of Example 104 (1 g) was suspended in 25 ml of acetonitrile, the mixture was cooled on ice and 0.6 ml of $CH_3I$ was added in one portion. Using an ice-water cooled condenser, the mixture was brought to a gentle reflux and refluxing was continued overnight on an oil bath. Thin layer chromatography confirmed that the resulting dark orange solution was the desired product. Addition of $CH_3CN$ and evaporation on a rotovap produced a dark orange foam. Crystallization and recrystallization with acetone/ethyl ether gave the desired product as an orange powder, m.p. 104°-105° C. Anal. calc. for $C_{22}H_{23}N_2O_3I.\frac{1}{2}H_2O$: C, 52.91; H, 4.81; N, 5.61. Found: C, 52.92; H, 4.84; N, 5.60. The product has the structure:

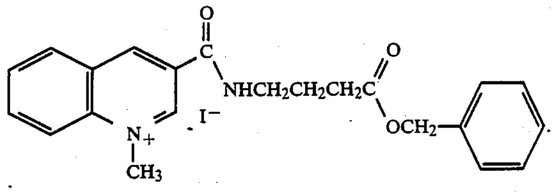

EXAMPLE 106

Preparation of 1-Methyl-3-{N-[(3'-benzyloxycarbonyl)propyl]}carbamoyl-1,4-dihydroquinoline The quaternary salt produced in Example 105 (200 mg, 0.41 mmol) was suspended in 10 ml deaerated water. Sodium bicarbonate (0.42 g) was added to the solution, with stirring, followed by 0.58 g of $Na_2S_2O_4$. A yellow color appeared immediately and the quaternary derivative dissolved. Ethyl acetate (20 ml) was added and the solution was stirred under nitrogen for 4 hours. The layers were separated and the yellow organic layer was dried over sodium sulfate and evaporated to dryness. The resulting yellow oil reduced methanolic silver nitrate immediately. The structure of the product was confirmed by NMR analysis to be:

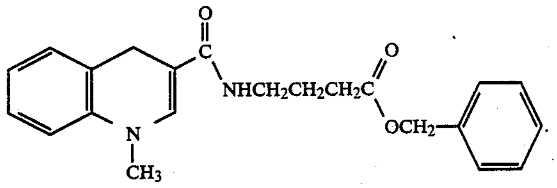

EXAMPLE 107

Preparation of 3-{N-[(3'-Cyclohexylcarbonyl)propyl]}carbamoylquinoline

3-Quinolinecarboxylic acid (1.55 g, 9 mmol) was dissolved in a minimum amount of dry pyridine. Dicyclohexylcarbodiimide (2.1 g, 10 mmol) was added and the solution turned yellow. 4-Aminobutanoic acid cyclohexyl ester hydrochloride (2 g, 9 mmol) was added and the mixture was stirred for 2 days. The precipitated urea was removed by filtration, the filtrate was evaporated to dryness and the residue was washed with 10 ml of ice cold water. Extraction into ethyl acetate, subsequent drying with $Na_2SO_4$ and evaporation produced a yellow solid, which was dissolved in acetone, filtered and evaporated to dryness. NMR was in good agreement with the expected spectrum.

EXAMPLE 108

Preparation of 1-Methyl-3-{N-[(3'-cyclohexylcarbonyl)propyl]}carbamoylquinolinium iodide The product of Example 107 (1.95 g, 5.7 mmol) was dissolved in acetone and 2 ml of methyl iodide was added in one portion, with cooling on ice. The mixture was brought to reflux slowly and allowed to reflux overnight. The dark orange reaction mixture was subsequently crystallized from acetone and ether to give a dark orange powder. The structure of the product was confirmed by NMR and UV analyses.

EXAMPLE 109

Preparation of 1-Methyl-3-{N-[(3'-cyclohexylcarbonyl)propyl]}carbamoyl-1,4-dihydropyridine The product of Example 108 (300 mg, 0.88 mmol) was suspended in 10 ml of deaerated water. $NaHCO_3$ (1.22 g) was added, followed by $Na_2S_2O_4$ (0.09 g). The mixture turned yellow immediately. Ethyl acetate (20 ml) was added and the solution was stirred for 4 hours. The organic layer was dried and evaporated to dryness, leaving a yellow oil which reduced methanolic silver nitrate immediately. The product has the formula:

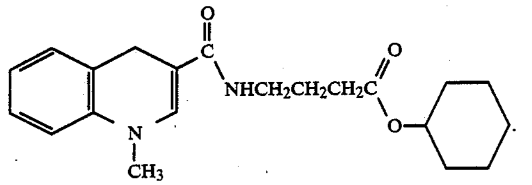

EXAMPLE 110

Preparation of L-Tryptophan ethyl ester hydrochloride

A mixture of L-tryptophan (14.3 g, 0.07 mol) in 200 ml of ethanol containing ~7 g of anhydrous HCl was refluxed for 5 hours. The mixture was cooled and the solid which separated was recrystallized from ethanol/ether. Yield 17.4 g (92.5%), m.p. 226°-228° C. The product has the formula:

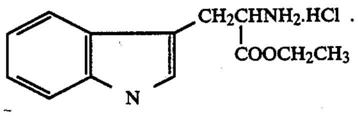

The product may also be named ethyl L-2-amino-3-indolepropionate.

EXAMPLE 111

Preparation of N-[1-Ethoxycarbonyl-2-(3'-indolyl)ethyl]nicotinamide

To a solution of L-tryptophan ethyl ester hydrochloride (5.4 g, 0.02 mol) and nicotinic acid (2.5 g, 0.02 mol) in 30 ml of dry pyridine was added dicyclohexylcarbodiimide (4.5 g, 0.022 mol). The mixture was stirred for 24 hours at room temperature, then the urea formed was removed by filtration. Pyridine was evaporated under vacuum and the residue was dissolved in 200 ml of methylene chloride. The solution was washed with 10% $NaHCO_3$ and water and methylene chloride was removed under vacuum. Yield 5.1 g (76%). NMR analysis confirmed the identity of the product. Anal. calc. for $C_{19}H_{19}N_3O_3.\frac{1}{4}H_2O$: C, 66.75; H, 5.75; N, 12.29. Found: C, 66.59; H, 5.92; N, 12.25.

EXAMPLE 112

Preparation of 1-Methyl-3-{N-[1'-ethoxycarbonyl-2'-(3"-indolyl)ethyl]}carbamoylpyridinium iodide The product of Example 111 (5 g, 0.015 mmol) was dissolved in 20 ml of methanol and methyl iodide (5 ml, 0.08 mol) was added. The mixture was refluxed for 5 hours, then methanol and excess methyl iodide were removed under vacuum. Yield 6.9 g (96%). Anal. calc. for $C_{20}H_{22}N_3O_3I.3/2H_2O$: C, 47.44; H, 4.98; N, 8.30; I, 25.06. Found: C, 47.44; H, 4.91; N, 8.29; I, 25.10.

EXAMPLE 113

Preparation of 1-Methyl-3-{N-[1'-ethoxycarbonyl-2'-(3"-indolyl)ethyl]}carbamoyl-1,4-dihydropyridine To a solution of 0.96 g (2 mmol) of the product of Example 112 in 5 ml of methanol, 50 ml of deaerated water and 50 ml of ethyl acette was added 1 g (12 mmol of $NaHCO_3$. To this ice-cold mixture kept under nitrogen was added 1.65 g (8 mmol) of sodium dithionite. The mixture was stirred for 3 hours, then the ethyl acetate layer was separated and the aqueous layer was extracted with ethyl acetate. The combined ethyl acetate extracts were washed with water and dried over sodium sulfate. Ethyl acetate was removed under vacuum. Yield 0.52 g (73.6%). Anal. calc. for $C_{20}H_{23}N_3O_3$: C, 67.97; H, 6.56; N, 11.89. Found: C, 67.67; H, 6.63; N, 11.79. The product has the structural formula:

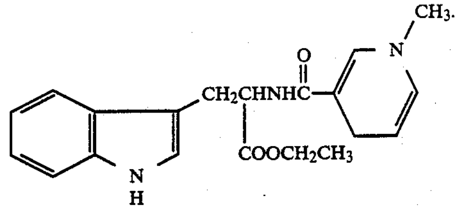

EXAMPLE 114

Prepared of 1-Methyl-3-{N-[β-(3,4-dihydroxyphenyl)ethyl]carbamoyl}pyridinium iodide To a solution of 2 g (7.7 mmol) of nicotinoyldopamine in 40 ml of dry methanol was added 2.5 g (17.6 mmol) of methyl iodide. The reaction mixture was refluxed with stirring, for 6 hours. Methyl iodide (1.5 g, 1.05 mmol) was added and refluxing was continued overnight. Methanol was removed and ethyl acetate was added, affording yellowish crystals of the desired product. Yield 2.4 g (77%), m.p. 173°-174° C.

EXAMPLE 115

Preparation of 1-methyl-3-{N-[[β-[3,4-bis(isobutyryloxy)phenyl]ethyl]]carbamoyl}pyridinium trifluoroacetate To an ice-cold solution of the product of Example 114 (3 g, 7.5 mmol) in 30 ml of trifluoroacetic acid, isobutyryl chloride (2.4 g, 22.5 mmol) was added slowly, with stirring. Stirring was continued overnight at room temperature. Trifluroracetic acid was evaporated under vacuum and the residue was crystallized from ethyl ether:hexane (3:1). Yield 1.2 g (30.4%), m.p. 87°-91° C.

Substantial repetition of the procedure of the preceding paragraph, substituting trimethylacetyl chloride for the isobutyryl chloride used above, affords after appropriate purification, 1-methyl-3-{N-[β-(3,4-dipivalyloxyphenyl)ethyl]carbamoyl}pyridinium trifluoroacetate in 72% yield (4.0 g), m.p. 158°-160° C.

EXAMPLE 116

Preparation of
1-Methyl-3-{N-[[β-[3,4-bis(isobutyryloxy)phenyl]ethyl]]carbamoyl}-1,4-dihydropyridine A solution of 0.55 g (1 mmol) of 1-methyl-3-{N-[[β-[3,4-bis(isobutyryloxy)phenyl]ethyl]]carbamoyl} pyridinium trifluoroacetate in 50 ml of deaerated water containing 10 ml of methanol was extracted three times with 30 ml portions of ether. To the resultant aqueous solution was added $NaHCO_3$ (0.25 g, 3 mmol) and 50 ml of ethyl ether and the mixture was kept under nitrogen. To this ice-cold mixture was added sodium dithionite (0.52 g, 3 mmol) and the mixture was stirred vigorously for 30 minutes. The ether layer was separated and the aqueous layer was extracted twice with ether. The combined ether extracts were washed with water and dried over sodium sulfate. Ether was removed under vacuum, leaving an oily product. NMR analysis confirmed that the product has the structural formula:

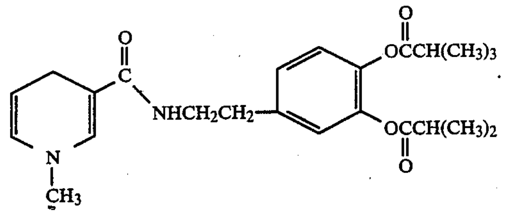

EXAMPLE 117

Preparation of
5-[(3-Pyridyl)carbonyloxy]-3-{β-ethoxycarbonyl-β-[N-(3-pyridyl)carbonylamino]ethyl}indole The ethyl ester hydrochloride of 5-hydroxytryptophan, i.e. ethyl L-2-amino-3-(5-hydroxyindolyl)propionate hydrochloride, was prepared by reacting 5-hydroxy-L-tryptophan with ethanol in the presence of HCl. To a solution of the ethyl ester hydrochloride (285 mg, 1 mmol) and nicotinic acid (246 mg, 2 mmol) in 3 ml of dry pyridine was added dicyclohexylcarbodiimide (430 mg, 2.1 mmol). The reaction mixture was stirred at room temperature for 24 hours and the urea formed was removed by filtration. Pyridine was removed in vacuo and the residue was dissolved in 1 ml of methanol and 20 ml of ethyl acetate. The ethyl acetate solution was washed with 10% $NaHCO_3$ solution and then with water. Ethyl acetate was removed in vacuo and the residue was chromatographed on a silica gel column using 5% methanol in chloroform as the eluent. Chloroform was removed in vacuo to yield 270 mg (58.9%) of the desired product of the formula:

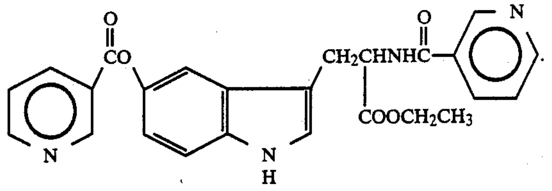

EXAMPLE 118

Preparation of
5-[(1-Methyl-3-pyridinium)carbonyloxy]-3-{β-ethoxycarbonyl-β-[N-(1-methyl-3-pyridinium)carbonylamino]ethyl}indole diiodide The product of Example 117 (150 mg, 0.33 mmol) was dissolved in 20 ml of methanol and excess methyl iodide was added. The mixture was refluxed for 4 hours and the methanol and excess methyl iodide were removed in vacuo to yield 230 mg (93.9%) of the desired product. Anal. calc. for $C_{27}H_{28}N_4O_5I_2$: C, 43.68; H, 3.80; N, 7.55; I, 34.19. Found: C, 43.47; H, 3.86; N, 7.52; I, 34.08. NMR analysis confirmed that the product has the structure:

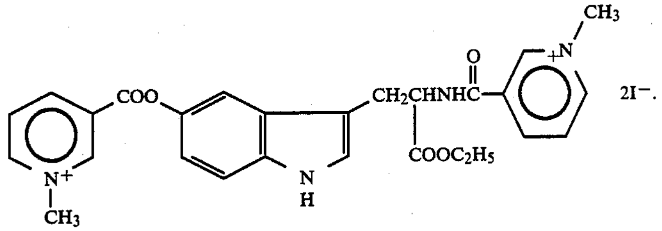

EXAMPLE 119

Preparation of
5-[(1-Methyl-1,4-dihydropyridin-3-yl)carbonyloxy]-3-{β-ethoxycarbonyl-β[N-(1-methyl-1,4-dihydropyridin-3-yl]carbonylamino]ethyl}indole To a solution of the product of Example 118 (200 mg, 0.27 mmol) in 2 ml of methanol, 20 ml of deaerated water and 20 ml of ethyl acetate, 500 mg of sodium bicarbonate was added. The mixture was stirred in an ice bath under nitrogen and 0.7 g of sodium dithionite was added. The mixture was stirred for 5 hours. The ethyl acetate layer was decanted and the water layer was extracted with ethyl acetate. The combined ethyl acetate solution was washed with water, dried over amhydrous sodium sulfate and the solvent removed in vacuo to yield 110 mg (83.0%) of the desired product. NMR analysis confirmed that the product has the structural formula:

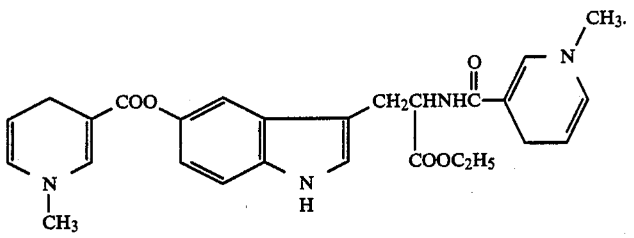

EXAMPLE 120

Preparation of N-[β-Phenethyl) 2-bromoacetamide

To a stirred solution of 2.263 g (0.0187 mol) of phenethylamine in 10 ml of 8% sodium hydroxide solution, cooled to −10° C., were introduced dropwise 3.14 g (0.02 mol) of bromoacetyl chloride. The reaction mixture was stirred at below −10° C. for one hour. The precipitate produced was filtered, washed thoroughly with cold water, dried and recrystallized from chloroform, m.p. 60°-61° C., yield 3.2 g (71%); IR (KBr) 3280 (NH), 1675 (CO) $cm^{-1}$. PMR further confirmed that the product has the structural formula:

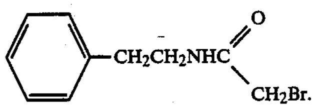

EXAMPLE 121

Preparation of N-(β-Phenethyl) 3-bromopropionamide

The title compound was prepared similarly to the product of Example 120, but using 3-bromopropionyl chloride instead of bromoacetyl chloride. Yield 85%, rrecrystallized from aqueous ethanol, m.p. 69°-70° C.; IR (KBr) 3315 (NH), 1640 (CO) $cm^{-1}$. PMR further confirmed that the product has the structural formula:

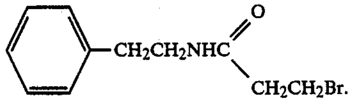

EXAMPLE 122

Preparation of N-(β-Phenethyl) 4-bromobutyramide

The title compound was prepared similarly to the product of Example 120, but using 4-bromobutyryl chloride. Yield 80%, recrystallized from aqueous ethanol, m.p. 62°-63° C.; IR (KBr) 3100 (NH), 1635 (CO) $cm^{-1}$. PMR further confirmed that the product has the structural formula:

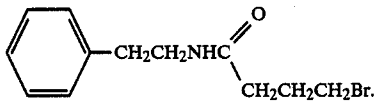

EXAMPLE 123

Preparation of 3-Carbamoyl-1-[N-(β-phenylethyl)carbamoylmethyl]-pyridinium bromide To a solution of 2.419 g (0.01 mol) of N-(β-phenethyl) 2-bromoacetamide in 20 ml dry acetonitrile were added 1.2 g (0.01 mol) of nicotinamide. The mixture was refluxed until disappearance on thin layer chromatography of the reactants (3 to 4 days). Plates of Silica Gel G and a chloroform:methanol (9:1) sys-tem were used. The acetonitrile was evaporated in vacuo and the residue was recrystallized from methanol/chloroform to yield the title compound (2.8 g, 77%), m.p. 178°-180° C. UV max (methanol) 265 nm; IR (KBr) 3380 (NH), 3250 (NH), 1690 (CO), 1655 (CO) $cm^{-1}$. Anal. calc. for $C_{16}H_{18}BrN_3O_2.H_2O$: C, 50.27; H, 5.23; N, 10.98. Found: C, 50.25; H, 4.77; N, 10.62. PMR analysis further confirmed that the product has the structural formula:

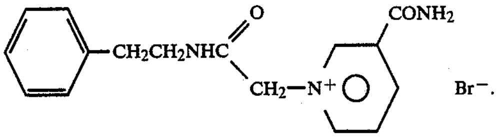

EXAMPLE 124

Preparation of 3-Carbamoyl-1-{2'-[N-(β-phenylethyl)carbamoyl]ethyl}pyridinium bromide The title compound was prepared according to the procedure of Example 123, using N-(β-phenethyl) 3-bromopropionamide and nicotinamide. Yield 66%, recrystallized from ethanol/benzene, m.p. 120°-122° C. UV max (methanol) 266 nm; IR (KBr) 3280 (NH), 1695 (CO), 1640 (CO) $cm^{-1}$. Anal. calc. for $C_{17}H_{20}BrN_3O_2$: C, 53.98; H, 5.33; N, 11.11. Found: C, 53.87; H, 5.35; N, 11.10. PMR further confirmed that the product has the structure:

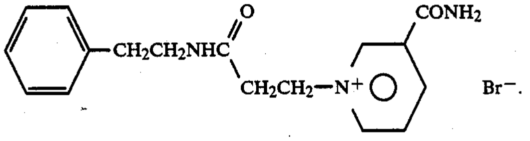

EXAMPLE 125

Preparation of 3-Carbamoyl-1-{3'-[N-(β-phenylethylcarbamoyl]-propyl}pyridinium bromide The title compound was prepared according to the procedure of Example 123, using N-(β-phenethyl) 4-bromobutyramide and nicotinamide. Yield 83%, recrystallized from ethanol/acetone, m.p. 112°-114° C. UV max (methanol) 265 nm; IR (KBr) 3350 (NH), 3320 (NH), 1692 (CO), 1642 (CO) $cm^{-1}$. Anal. calc. for $C_{18}H_{22}BrN_3O_2$: C, 55.11; H, 5.65; N, 10.71. Found: C, 54.93; H, 5.67; N, 10.70. PMR further confirmed the structure of the product to be:

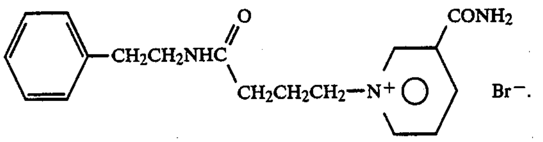

EXAMPLE 126

Preparation of 3-Carbamoyl-1-[N-(β-phenylethyl)carbamoylmethyl]-1,4-dihydropyridine To a solution of 3.64 g (0.01 mol) of the product of Example 123 in 150 ml of deareated 15% aqueous methanol were added 5.04 g (0.06 mol) of sodium bicarbonate. The mixture was stirred in an ice bath, and 6.96 g (0.04 mol) of slodium dithionite were added over a period of 5 minutes. The reaction mixture was stirred for one hour under nitrogen and a pale yellow crystalline precipitate was formed. The precipitate was filtered, washed with water, and recrystallized from aqueous methanol, m.p. 126°-128° C., yield 2.4 g (84%). UV max (methanol) 348 nm; IR (KBr) 3280 (NH), 1680 (CO), 1645 (CO) $cm^{-1}$. Anal. calc. for $C_{16}H_{19}N_3O_2 \cdot \frac{3}{4} H_2O$: C, 64.30; H, 6.91; N, 14.06. Found: C, 64.32; H, 6.91; N, 14.06. The structure of the product was further confirmed by PMR to be:

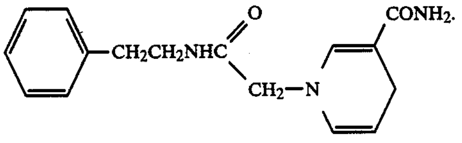

EXAMPLE 127

Preparation of 3-Carbamoyl-1-{2'-[N-(β-phenylethyl)carbamoyl]ethyl}-1,4-dihydropyridine The product of Example 124 (3.78 g, 0.01 mol) was reduced according to the procedure described in Example 126 with sodium dithionite (6.96 g, 0.04 mol). After completion of the reaction, the product was extracted with ethyl acetate, washed with water, dried over anhydrous sodium sulfate, and the solvent was evaporated in vacuo. A yield of 2.4 g (80%) of the title compound was obtained as a yellowish amorphous powder, m.p. 121°-123° C. UV max (methanol) 350 nm; IR (KBr) 3430 (NH), 3260 (NH), 1670 (CO), 1630 (CO) $cm^{-1}$. Anal. calc. for $C_{17}H_{21}N_3O_2 \cdot \frac{3}{4} H_2O$: C, 65.26; H, 7.24; N, 13.43. Found: C, 65.19; H, 6.87; N, 13.61. The structure of the product was further confirmed by PMR to be:

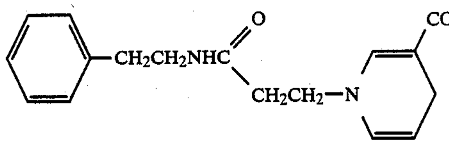

EXAMPLE 128

Preparation of 3-Carbamoyl-1-{3'-[N-(β-phenylethyl)carbamoyl]-propyl}-1,4-dihydropyridine The product of Example 125 (3.92 g, 0.01 mol) was reduced with sodium dithionite (6.96 g, 0.04 mol) according to the procedure of Example 126. A yield of 2.2 g (65%) of the title compound was obtained as an orange-yellow amorphous powder, m.p. 55°-60° C. UV max (methanol) 358 nm; IR ($CHCl_3$) 3325 (NH), 1682 (CO), 1645 (CO) $cm^{-1}$. Anal. calc. for $C_{18}H_{23}N_3O_2 \cdot \frac{3}{4} H_2O$: C, 66.07; H, 7.49; N, 12.85. Found: C, 66.05; H, 7.56; N, 12.84. The structure of the product was further confirmed by PMR to be:

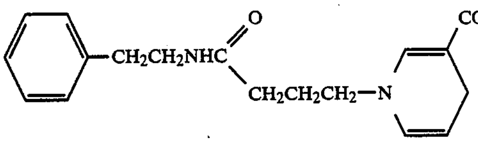

EXAMPLE 129

Preparation of 17β-[(Bromoacetyl)oxy]androst-4-en-3-one (Testerosterone bromoacetate)

To a solution of 2.884 g (0.01 mol) of testosterone in 30 ml of dry benzene was added 1.008 g (0.012 mol) of sodium bicarbonate; then, while stirring, there were introduced dropwise 1.888 g (0.012 mol) of bromoacetyl chloride over a 5 minute period. The reaction mixture was then stirred under reflux for 6 hours until no testosterone could be traced by TLC. (Plates of Silica Gel G and a $CHCH_3/CH_3OH$ system were used.) The inorganic residue was filtered while hot, the filtrate was evaporated in vacuo and the residue was recrystallized from methanol, m.p. 144°-145° C., yield 3.2 g (78%). IR (KBr) 1735 (C=O), 1660 (C=O) $cm^{-1}$. PMR as expected. The product has the formula:

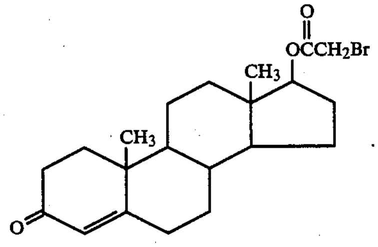

EXAMPLE 130

Preparation of 17β-[(3'-Bromopropionyl)oxy]androst-4-en-3-one (Testosterone β-bromopropionate)

The title compound was prepared according to the method of Example 129, but using 3-bromopropionyl-chloride. Yield 80%, recrystallized from methanol, m.p. 153°-154° C. IR (KBr) 1740 (C=O), 1667 (C=O) $cm^{-1}$. PMR as expected. The product has the structural formula:

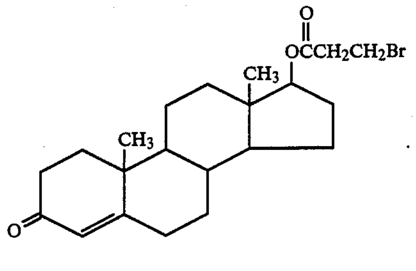

EXAMPLE 131

Preparation of 17β-{(±)[2'-Bromopropionyl]oxy}androst-4-en-3-one (Testosterone α-bromopropionate)

The title compound was made according to Example 129, but using (±) 2-bromopropionyl chloride. Yield 80%, recrystallized from methanol, m.p. 187°-188° C. IR (KBr) 1732 (C=O), 1658 (C=O) $cm^{-1}$. PMR as expected. The product has the formula:

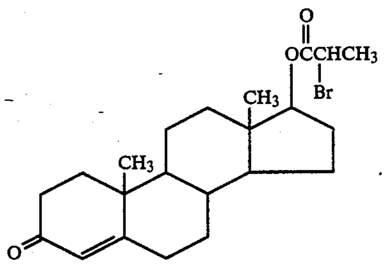

Similarly prepared using 4-bromobutyryl chloride was 17β-[(4'-bromobutyryl)oxy]androst-4-en-3-one, having the formula:

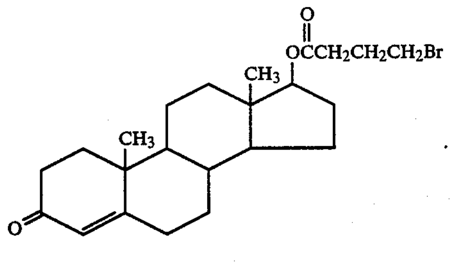

EXAMPLE 132

Preparation of 17β-{[(3"-Carbamoyl-1"-pyridinium)acetyl]oxy}androst-4-en-3-one bromide To a solution of 4.09 g (0.01 mol) of testosterone bromoacetate in 30 ml of dry acetonitrile was added 1.22 g (0.01 mol) of nicotinamide. The mixture was refluxed until complete disappearance of the reactants (2 to 3 days) as detected by TLC (Plates and solvents as in Example 129). On cooling, a white crystalline precipitate was produced, which was filtered, washed with aetonitrile and recrystallized from acetonitrile. Yield 3.62 g (68%), m.p. 237°-238° C. UV max (methanol) 236.5 nm; IR (KBr) 3130 (NH), 1745 (C=O), 1680 (C=O) $cm^{-1}$; PMR as expected. Anal. calc. for $C_{27}H_{35}BrN_2O_4.\frac{1}{2}H_2O$: C, 60.00; H, 6.66; N, 5.18. Found: C, 59.87; H, 6.70; N, 5.17. The product has the formula:

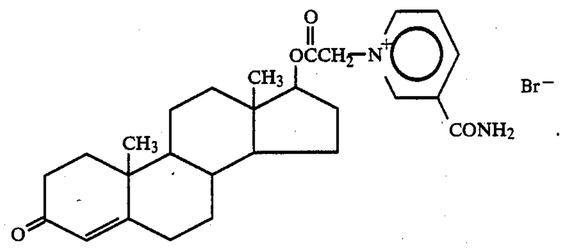

EXAMPLE 133

Preparation of 17β-{[3'-(3"-Carbamoyl-1"-pyridinium)propionyl]oxy}androst-4-en-3-one bromide The title compound was prepared as the product of Example 132 using equimolar amounts of testosterone β-bromopropionate and nicotinamide. Yield 60%, recrystallized from methanol/acetonitrile, m.p. 215°-216° C. UV max (methanol) 238 nm; IR (KBr) 3150 (NH), 1720 (C=O), 1670 (C=O) $cm^{-1}$; PMR as expected. Anal. calc. for $C_{28}H_{37}BrN_2O_4$: C, 61.65; H, 6.79; N, 5.14. Found: C, 61.39; N, 6.89; N, 5.07. The product has the formula:

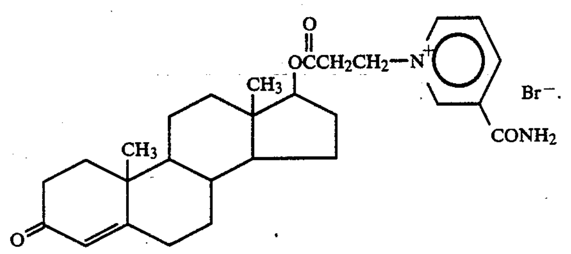

EXAMPLE 134

Preparation of 17β-{[(±)2'-(3"-Carbamoyl-1"-pyridinium)propionyl]oxy}androst-4-en-3-one bromide The title compound was prepared as in Example 132 using equimolar amounts of testosterone α-bromopropionate and nicotinamide. Yield 60%, recrystallized from acetonitrile, m.p. 236°-237° C. UV max (methanol) 237 nm. IR (KBr) 3080 (NH), 1740 (C=O), 1670 (C=O) $cm^{-1}$. PMR as expected. Anal. calc. for $C_{28}H_{37}BrN_2O_4$: C, 61.65; H, 6.79; N, 5.14. Found: C, 61.52; H, 6.81; N, 5.12. The product has the formula:

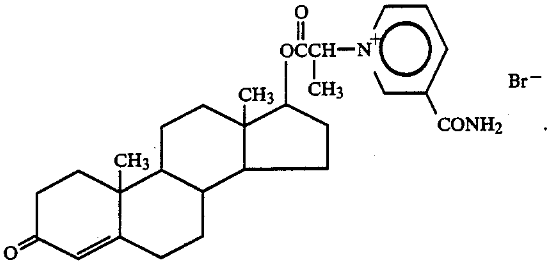

Similarly prepared using 17β-[(4'-bromobutyryl)oxy]androst-4-en-3-one and nicotinamide was 17β-{[4'-(3"-carbamoyl-1"-pyridinium)butyryl]oxy}androst-4-en-3-one bromide, having the formula:

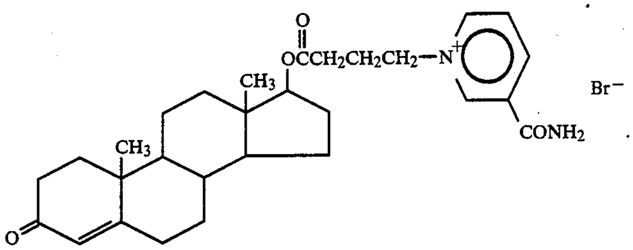

EXAMPLE 135

Preparation of 17β-{[(3"-Carbamoyl-1",4"-dihydropyridinyl)acetyl-]oxy}androst-4-en-3-one To an ice-cold solution of 1.593 g (0.003 mol) of the product of Example 132 in 150 ml of deaerated 25% aqueous methanol were added 1.512 g (0.018 mol) of sodium carbonate and 2.088 g (0.012 mol) of sodium dithionite. The mixture was stirred for 30 minutes at 0° C. under nitrogen. The dihydro product formed was extracted with dichloromethane, washed with water and dried over anhydrous slodium sulfate. The filtrate was flushed with dry nitrogen, and the solvent was evaporated in vacuo at ambient temperature. The residue was dried over $P_2O_5$ under vacuum to yield 0.98 g (72%) of the title compound, m.p. 160°-165° C. Alcoholic solution shows immediate reduction to alcoholic solution of silver nitrate. UV max (methanol) 342 nm; IR (KBr) 3160 (NH), 1730 (C═O), 1655 (C═O) $cm^{-1}$. PMR as expected. Anal. calc. for $C_{27}H_{36}N_2O_4.3H_2O$: C, 64.03; H, 8.30; N, 5.53. Found: C, 63.54; H, 7.94; N, 5.59. The product has the formula:

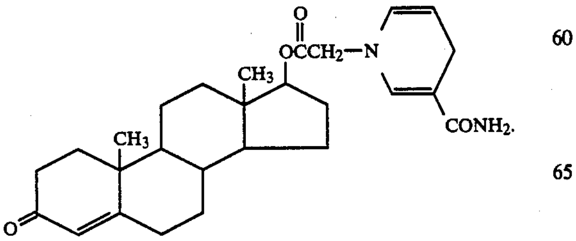

EXAMPLE 136

Preparation of 17β-{[3'-(3"-Carbamoyl-1",4"-dihydropyridinyl)propionyl]oxy}androst-4-en-3-one The title compound was prepared according to the method of Example 135, utilizing the product of Example 133 as starting material, in a 56% yield as a yellowish amorphous powder, m.p. 75°-77° C. The product's alcoholic solution shows immediate reduction to alcoholic solution of silver nitrate. UV max (methanol) 346 nm; IR (KBr) 3200 (NH), 1725 (C═O), 1665 (C═O) $cm^{-1}$; PMR as expected. Anal. calc. for $C_{28}H_{38}N_2O_4.3H_2O$: C, 64.62; H, 8.46; N, 5.38. Found: C, 64.59; H, 7.78; N, 5.19. The product has the formula:

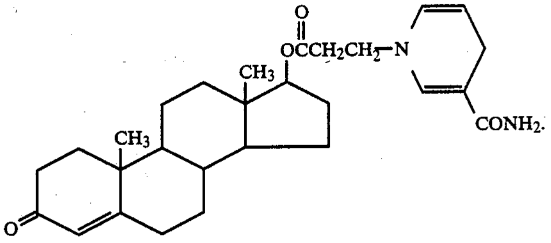

EXAMPLE 137

Preparation of 17β-{[(±)2'-(3"-Carbamoyl-1",4"-dihydropyridinyl)-propionyl]oxy}androst-4-en-3-one The title compound was prepared by the method of Example 135, using the product of Example 134, first paragraph, as starting material, in a 78% yield as a yellowish amorphous powder, m.p. 145°-150° C. Its alcoholic solution shows immediate reduction to alcoholic solution of silver nitrate. UV max (methanol) 344 nm; IR (KBr) 3160 (NH), 1725 (C═O), 1655 (C═O) $cm^{-1}$; PMR as expected. Anal. calc. for $C_{28}H_{38}N_2O_4.2H_2O$: C, 66.93; H, 8.36; N, 5.57. Found: C, 66.79; H, 7.69; N, 5.43. The product has the formula:

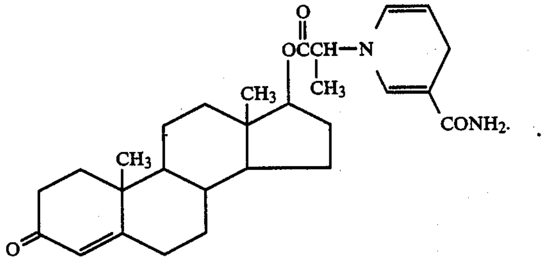

Similarly prepared from 17β-{[4'-(3''-carbamoyl-1''-pyridinium)butyryl]oxy}androst-4-en-3-one bromide was 17β-{[4'-(3''-carbamoyl-1'',4''-dihydropyridinyl)-butyryl]oxy}androst-4-en-3-one, having the structural formula:

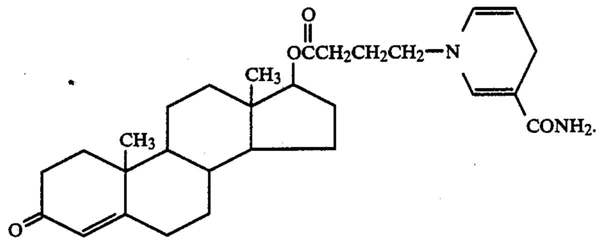

EXAMPLE 138

Preparation of 5,5-Diphenyl-3-hydroxymethyl-2,4-imidazolidinedione

Phenytoin (5 g, 0.02 mol) was suspended in 180 ml of water; 20 ml of formaldehyde (37% solution) and 0.25 g $K_2CO_3$ were added and the mixture was stirred at 25°-30° C. for 24 hours. The white solid which formed was removed by filtration and washed repeatedly with a 3% solution of formaldehyde, then air dried for 3 to 4 hours and over $P_2O_5$ in a vacuum dessicator. Yield 91-93%, m.p. 185°-189° C. Anal. calc. for $C_{16}H_{14}N_2O_3$: C, 68.07; H, 5.00; N, 9.93. Found: C, 67.97; H, 5.05; N, 9.93. The product has the formula:

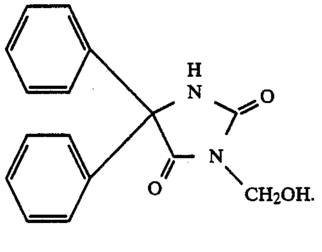

EXAMPLE 139

Preparation of 5,5-Diphenyl-3-[(3'-pyridyl)carbonyloxymethyl]-2,4-imidazolidinedione The product of Example 138 (3.00 g, 0.011 mol) was dissolved in 150 ml of dry pyridine, then nicotinic anhydride (4.25 g, 0.019 mol) was added. The resultant solution was stirred at room temperature (25°-30° C.), under dry conditions, for 40 hours. The solution was poured into 2.5 l of water and the resultant white solid was removed by filtration, washed well with water and dried over $P_2O_5$ in a vacuum dessicator. 95% yield, m.p. 178°-182° C. Anal. calc. for $C_{22}H_{17}N_3O_4$: C, 68.21; H, 4.42; N, 10.85. Found: C, 68.12; H, 4.43; N, 10.83. The product has the formula:

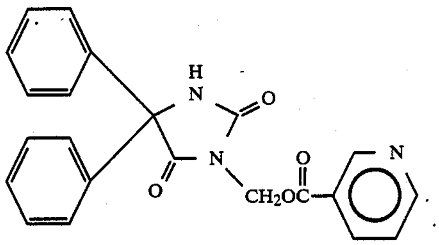

EXAMPLE 140

Preparation of 5,5-Diphenyl-3-[(1'-methyl-3'-pyridinium)carbonyloxymethyl]-2,4-imidazolidinedione iodide The product of Example 139 (0.5 g, 0.0013 mol) was dissolved in 50 ml of acetonitrile, then 0.3 ml of methyl iodide was added and the reaction mixture was maintained at room temperature for 6 days. The solvent was removed by vacuum distillation and ethyl ether was added to the residue. The ether solution was refrigerated for 2 hours, then the yellow, hygroscopic crystals which formed were dried over $P_2O_5$ in a vacuum dessicator, giving the desired product in 85% yield. UV and $H^1NMR$ spectra confirmed that the product has the structure:

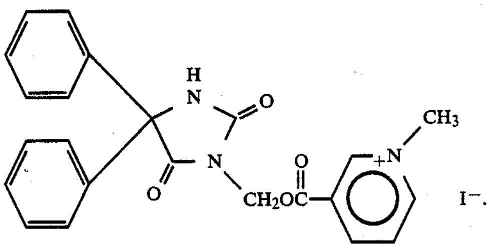

Repeating the above procedure in nitromethane at a 50°-70° C. bath temperature using excess methyl iodide, added gradually, for 5 to 6 hours, afforded the same product in nearly quantitative yield.

EXAMPLE 141

Preparation of 5,5-Diphenyl-3-[(1'-methyl-1',4'-dihydropyridin-3'-yl)carbonyloxymethyl]-2,4-imidazolidinedione:

The quaternary salt obtained in Example 140 (0.4 g, 0.0008 mol) was dissolved in 40 ml of water, 3 ml of methanol and 15 ml of ethyl acetate. The reaction mixture was cooled to 0° to 5° C. and deaerated, then sodium bicarbonate (0.39 g, 0.0046 mol) and sodium dithionite (0.54 g, 0.0032 mol) were added. The mixture was stirred under nitrogen at 0°-5° C. for 35 minutes. The organic layer was removed and the aqueous layer was extracted twice with 15 ml portions of ethyl acetate and the organic solutions were extracted with 10 ml of cold deaerated water. After drying over $Na_2SO_4$, the solvent was removed by vacuum distillation and the oily yellow solid was crystallized by addition of ether. Yield 70%. UV and $H^1$-NMR analyses confirmed that the product has the formula

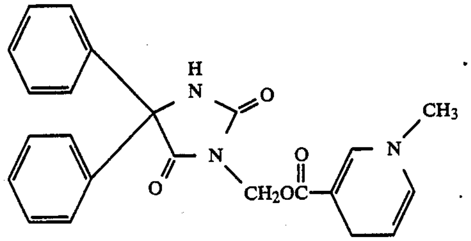

EXAMPLE 142

Preparation of 3-Bromoacetyloxymethyl-5,5-diphenyl-2,4-imidazolidinedione 5,5-Diphenyl-3-hydroxymethyl-2,4-imidazolidinedione (2 g, 0.0071 mol) was dissolved in bromoacetylchloride (15 g, 8 ml, 0.096 mol) by heating in an oil bath (70°-80° C. bath temperature) for about 15 minutes, until the formation of HCl ceased. The mixture was cooled and 30 ml of ethyl ether were added. White crystals formed. The mixture was cooled to 0° C., then the crystals were removed by filtration and dried over $P_2O_5$. Yield: 2.15 g (75%), m.p. 179°-183° C. Anal. calc. for $C_{18}H_{15}N_2O_4Br$: C, 53.61; H, 3.75; N, 6.95; Br, 19.82. Found: C, 53.60; H, 3.79; N, 6.92; Br, 19.90. The product has the formula:

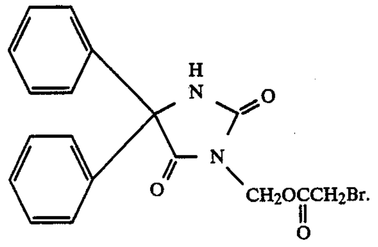

EXAMPLE 143

Preparation of 3-(3'-Bromopropionyl)oxymethyl-5,5-diphenyl-2,4-imidazolidinedione 5,5-Diphenyl-3-hydroxymethyl-2,4-imidazolidinedione (5 g, 0.018 mol) was reacted according to the procedure of Example 142 with 3-bromopropionyl chloride (6.8 g, 0.04 mol, 4 ml), using a bath temperature of 100° C. A white crystalline product was obtained in 65% yield (4.9 g), m.p. 133°-134° C. Anal. calc. for $C_{19}H_{17}N_2O_4Br$: C, 54.69; H, 4.11; N, 6.72; Br, 19.15. Found: C, 54.79; H, 4.12; N, 6.69; Br, 19.25. The product has the formula:

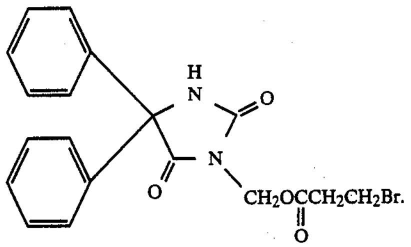

EXAMPLE 144

Preparation of 3-(2'-Bromopropionyl)oxymethyl-5,5-diphenyl-2,4-imidazolidinedione:

5,5-Diphenyl-3-hydroxymethyl-2,4-imidazolidinedione (2 g, 0.0071 mol) was dissolved in 2-bromopropionyl chloride (8.5 g, 5 ml, 0.05 mol) by heating for 30 minutes on a 100°-110° C. oil bath. The reaction mixture was cooled, 20 ml of ethyl ether were added, and the resultant solution was extracted with aqueous potassium carbonate, dried and then crystallized. The product was obtained as a solid white substance (1 g, 34%), m.p. 112°-115° C. Anal. calc. for $C_{19}H_{17}N_2O_4Br$: C, 54.69; H, 4.11; N, 6.72; Br, 19.15. Found: C, 54.77; H, 4.15; N, 6.69; Br, 19.25. The product has the formula:

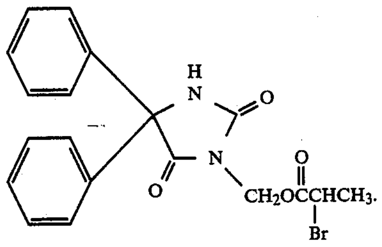

EXAMPLE 145

Preparation of 3-(3'-Carbamoyl-1'-pyridinium)acetyloxymethyl-5,5-diphenyl-2,4-imidazolidinedione bromide:

The product of Example 142 (2.02 g, 0.005 mol) dissolved in 15 ml of nitromethane was mixed with nicotinamide (0.61 g, 0.005 mol). The solution was stirred on a 90°-100° c. temperature oil bath for 2 hours. The mixture was cooled to 60°-70° C. and the white crystals which had formed were removed by filtration and washed with nitromethane. Yield 61% (1.65 g), m.p. 193°-197° C. (dec). Anal. calc. for $C_{24}H_{21}N_4O_5Br$: C, 54.87; H, 4.03; N, 10.67; Br, 15.21. Found: C, 54.70; H, 4.05; N, 10.64; Br, 15.25. The product has the formula:

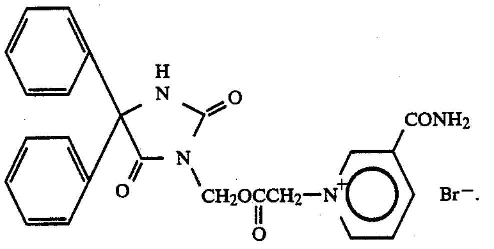

EXAMPLE 146

Preparation of 3-[3'-(3''-Carbamoyl-1''-pyridinium)propionyloxymethyl]-5,5-diphenyl-2,4-imidazolidinedione bromide The product of Example 143 (2.09 g, 0.005 mol) was dissolved in 15 ml acetonitrile, then nicotinamide (0.61 g, 0.005 mol) was added. The solution was refluxed for 6 days, then the solvent was removed. To the gum-like residue, 30 ml of ethyl ether was added and the mixture was stirred for 2 hours. The white substance which formed was removed by filtration ad washed with ether. Yield 78% (2.1 g); m.p. 98°-100° C. (dec.); UV and $H^1NMR$ as expected. The product has the formula:

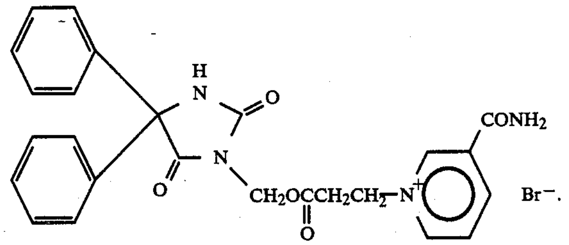

EXAMPLE 147

Preparation of 3-[2'-(3''-Carbamoyl-1''-pyridinium)propionyloxymethyl]-5,5-diphenyl-2,4-imidazolidinedione bromide The product of Example 144 (0.69 g, 0.00165 mol) was dissolved in 8 ml of acetonitrile, then nicotinamide (0.2 g, 0.00165 mol) was added and the solution was refluxed for 22 hours. The silvent was removed from the resultant brown noncrystalline substance at 50° C., then ethyl ether (15 ml) was added and the mixture was stirred for 2 hours. The light brown substance was removed by filtration and washed with ether. Yield 56% (0.5 g), m.p. 158° C. (dec.). The product has the formula:

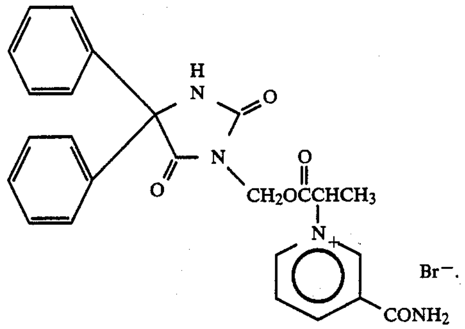

EXAMPLE 148

Preparation of 3-[(3'-Carbamoyl-1',4'-dihydropyridin-1'-yl)acetyloxymethyl]-5,5-diphenyl-2,4-imidazolidinedione The product of Example 145 (0.52 g, 0.001 mol) was dissolved in a mixture of 60 ml of water and 30 ml of ethyl acetate. The mixture was cooled at 5° C. and deaerated, then sodium bicarbonate (0.5 g, 0.006 mol) and sodium dithionite (0.7 g, 0.004 mol) were added and the resultant mixture was stirred, with deaeration and cooling, for 30 minutes. The layers were separated and the aqueous layer was extracted with 30 ml of ethyl acetate. The organic solution was extracted with 20 ml of cooled, deaerated water. After drying over sodium sulfate, the solvent was removed. Yield 55% (0.25 g) of yellow crystals, melting at 155°-160° C. (dec.). The product reduced alcoholic silver nitrate solution and has the formula:

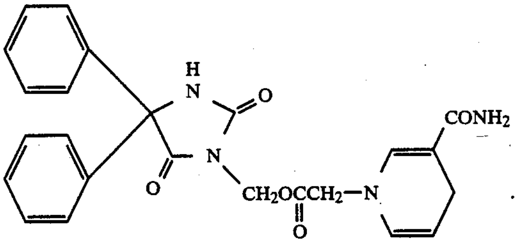

The products of Examples 146 and 47 can be similarly reduced to the corresponding dihydro derivatives.

EXAMPLE 149

Preparation of 3-(3'-Pyridyl)acetyloxymethyl-5,5-diphenyl-2,4-imidazolidinedione 3-Pyridylacetic acid hydrochloride (0.87 g, 0.005 mol) and 5,5-diphenyl-3-hydroxymethyl-2,4-imidazolidinedione (1.41 g, 0.005 mol) were dissolved in 14 ml of dry pyridine, then dicyclohexylcarbodiimide (1.03 g, 0.005 mol) in 2 ml of pyridine was added. The reaction mixture turned yellow. The mixture was stirred at room temperature for 24 hours, then the urea which formed was removed by filtration and the solvent was removed by vacuum distillation. Methylene chloride (10 ml) was added to the residue and, after 10 minutes, a small amount of urea was removee by filtration. The organic solution was extracted with potassium carbonate (1 g) dissolved in 25 ml of water, then dried and concentrated. Ethyl ether was added to the oily residue, and white crystals formed. After cooling, the product was removed by filtration, washed with ether and dried. Yield 65% (1.3 g), m.p. 157°-161° C. Anal. calc. for $C_{23}H_{19}N_3O_4$: C, 68.82; H, 4.77; N, 10.49. Found: C, 68.49; H, 5.28; N, 10.39. The product has the structure:

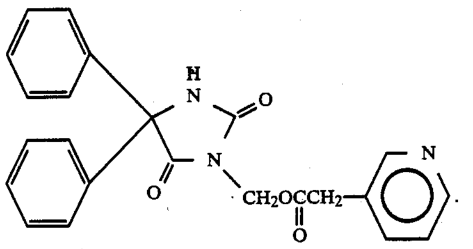

EXAMPLE 150

Preparation of 3-(1'-Methyl-3'-pyridinium)acetyloxymethyl-5,5-diphenyl-2,4-imidazolidinedione iodide The product of Example 149 (0.4 g, 0.001 mol) was dissolved in 20 ml of nitromethane, methyl iodide (0.9 g, 0.4 ml, 0.006 mol) was added and the mixture was warmed for 2 hours at 70° C. on an oil bath. Removal of solvent by vacuum distillation afforded a yelllow crystalline product melting at 110°-115° C. Yield 100% (0.54 g). The product has the structure:

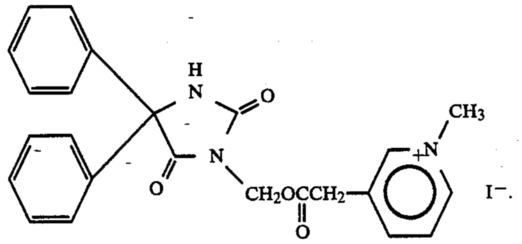

That material can then be reduced using sodium dithionite as generally described hereinabove, to afford the corresponding dihydro derivative of the formula:

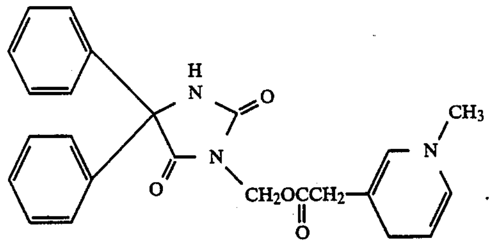

EXAMPLE 151

Preparation of 10,11-Dihydro-N-methyl-N-(3-pyridyl)carbonyl-5H-dibenz(b,f)azepine-5-propanamine Freshly prepared nicotinoyl chloride hydrochloride (0.55 g, 0.003 mol) was suspended in methylene chloride (12 ml) cooled to 5° C. and sodium bicarbonate (0.053 g, 0.0063 mol) was added. After 5 minutes, desipramine hydrochloride (0.75 g, 0.0025 mol) was added and the mixture was stirred for 3 hours at 5° C. The sodium chloride was removed by filtration and the organic solution was extracted with aqueous sodium bicarbonate, dried over sodium sulfate, filtered through Celite™ and concentrated. Ethyl ether (5 ml) was added to the oily residue and white crystals formed. Yield 62% (0.58 g), m.p. 84°-86° C. The product has the formula:

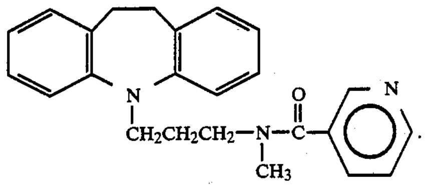

EXAMPLE 152

Preparation of 10,11-Dihydro-N-methyl-N-(1-methyl-3-pyridinium)-carbonyl-5H-dibenz(b,f)azepine-5-propanamine iodide The product of Example 151 (0.3 g, 0.0008 mol) was dissolved in 10 ml of nitromethane, methyl iodide (0.7 g, 0.3 ml, 0.005 mol) was added and the mixture was maintained at 24 hours at room temperature. The solvent was removed by vacuum distillation, ethyl ether was added to the residue and hygroscopic crystals of the desired product were obtained. Yield 90% (0.37 g), m.p. 110° C. (dec.). The product has the formula

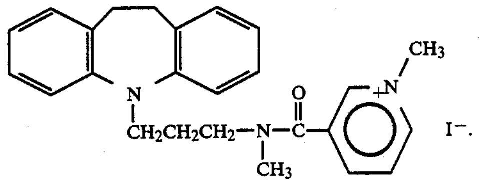

The material can then be reduced as generally described hereinabove, to afford the corresponding dihydro derivative, 10,11-dihydro-N-methyl-N-(1-methyl-1,4-dihydropyridin-3-yl)carbonyl-5H-dibenz(b,f)-azepine-5-propanamine, having the formula:

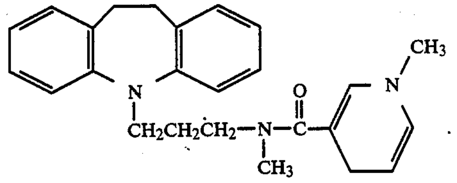

EXAMPLE 153

Preparation of N-Nicotinoyloxysuccinimide

Nicotinic acid (4.025 g, 0.0327 mol) and N-hydroxysuccinimide (3.763 g, 0.0327 mol) were dissolved in 130 ml of dioxane. Dicyclohexylcarbodiimide (6.75 g, 0.032 mol in 20 ml of dioxane was added. The reaction mixture was then stirred at room temperature for 3 hours. The dicyclohexylurea which precipitated was removed by filtration and the solvent was removed by rotary evaporation. The crude product was recrystallized from ethyl acetate to give light yellow crystals which are then washed with anhydrous ether. The product, obtained in 72% yield (5.2 g) and melting at 129°-131° C., has the formula:

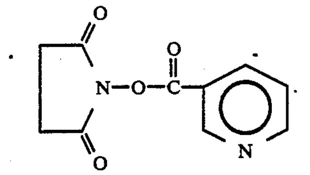

EXAMPLE 154

Preparation of N-[(1-methyl-3-pyridinium)carbonyloxy]succinimide iodide

N-Nicotinoyloxysuccinimide (5.0 g, 0.0227 mol) was dissolved in 80 ml of dioxane and methyl iodide (4.24 ml, 0.0683 mol) was added. The reaction mixture was refluxed at 70° C. overnight. The solution changed to a red color while a yellow precipitate formed. The precipitate was removed by filtration, washed thoroughly with anhydrous ether and dried. Yield 87% (7.134 g) of the quaternized product of the formula:

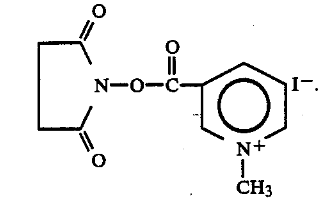

EXAMPLE 155

Preparation of 2-Amino-1,9-dihydro-9-{[2-(1′-methyl-3′-pyridinium)-carbonyloxyethoxy]methyl}-6H-purin-6-one iodide Acyclovir sodium salt was converted to the free acid by first dissolving it in water (10 ml) and then adding a few drops of 0.01M HCl, until some precipitation was observed. The precipitate was centrifuged and to the supernatant was added a few more drops of 0.01M HCl to ensure complete precipitation of the free acid. Complete precipitation was achieved with the pH at 11.00. The percipitate thus obtained was washed well with small amounts of ice-cold water and then with anhydrous ether and allowed to dry.

The quaternized activated ester obtained in Example 154 (0.72 g, 0.002 mol) was dissolved in 50 ml of dimethylformamide and acyclovir (0.450 g, 0.002 mol) in 50 ml of dimethylformamide was added. The reaction mixture was stirred at room temperature for 7 days, then one additional equivalent of the activated ester was added and the reaction mixture was stirred at 50° C. for 3 days. The volume of solvent was reduced by rotary evaporation and the residue was allowed to stand overnight. The light yellow crystals thus obtained were separated and dried. The product melted at 220°-224° C. and was assigned the structure depicted below:

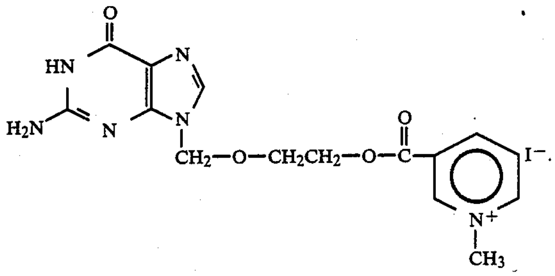

That product can then be reduced with sodium dithionite as generally described hereinabove, to afford the corresponding dihydro derivative, 2-amino-1,9-dihydro-9-{[2-(1′-methyl-1′,4′-dihydropyridin-3′-yl)carbonyloxyethoxy]methyl}-6H-purin-6-one, having the formula:

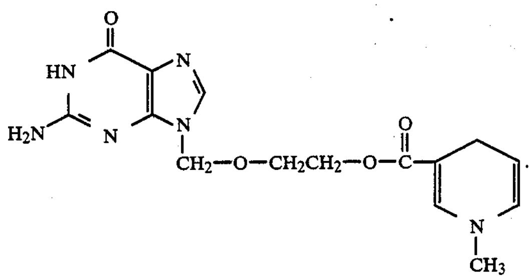

In the discussion to follow, the expression "at least one reactive functional group selected from the group consisting of amino, hydroxyl, mercapto, carboxyl, amide and imide" and portions of that expression are used. The functional groups designated in that expression have the following meanings:

The word "amino" means a primary or secondary amino function, i.e. $-NH_2$ or $-NHR$. The secondary amino function is also represented herein as $-NH-$, particularly since the exact identity of the R portion of $-NHR$ is immaterial, R being a part of the drug residue D itself which is left unchanged by this invention.

The word "hydroxyl" means an $-OH$ function.

The word "carboxyl" means a $-COOH$ function.

The word "mercapto" means an $-SH$ function.

The word "amide" means a carbamoyl ($-CONH_2$) or substituted carbamoyl ($-CONHR$) or a sulfamoyl ($-SO_2NH_2$) or substituted sulfamoyl ($-SO_2NHR$) functional group. The $-CONHR$ and $-SO_2NHR$ groups may also be represented herein as $-CONH-$ and $-SO_2NH-$, respectively, since the identity of R is immaterial, R being a part of the drug residue D is itself which is left unchanged by this invention.

The word "imide" means a functional group having the structure

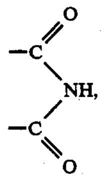

that is, the structure which characterizes imides (i.e. compounds having a succinimide-type or phthalimide-type structure).

The many different dihydropyridine⇄pyridinium salt redox carrier moieties illustrated for use hereinabove are merely exemplary of the many classes of carriers contemplated by this invention. While the following list of carrier classes is not meant to be exhaustive (and, indeed, yet other carrier classes are illustrated both hereinabove and hereinbelow), the following major classes of quaternaries and the corresponding dihydro forms are prime examples of the moieties encompassed hereby:

(1) For linkage to a drug having at least one hydroxyl or mercapto or primary or secondary amino functional grouping, replacing a hydrogen atom from at least one of said functional groupings with one of the following [QC+] groupings:

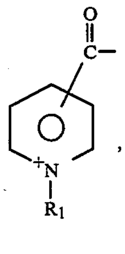
,
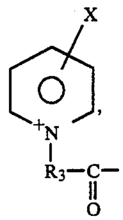
,
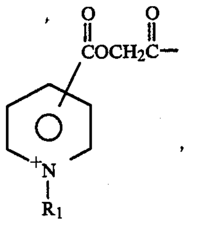
, (a) (b) (c)

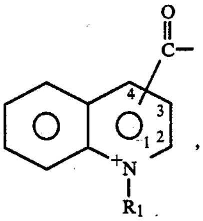
,
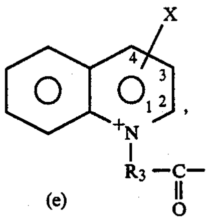
, (d) (e)

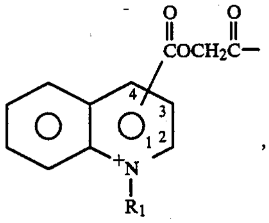
,
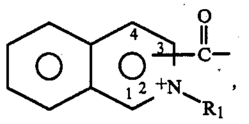
, (f) (g)

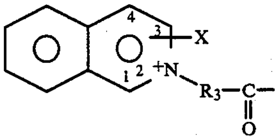
or (h)

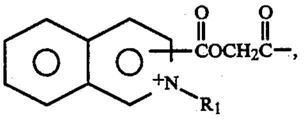

(j)

wherein $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H of $C_1$-$C_7$ alkyl, or X is —CH—NOR'" wherein R'" is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring;

(2) For linkage to a drug having at least one carboxyl functional grouping, replacing a hydrogen atom from at least one of said carboxyl groupings with one of the following [QC+] groupings:

(a) When there are one or more —COOH groups to be derivatized:

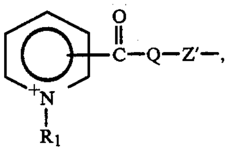
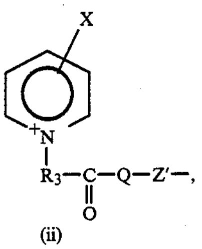

(i) (ii)

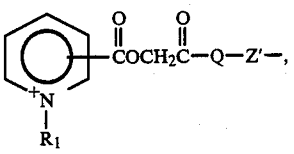

(iii)

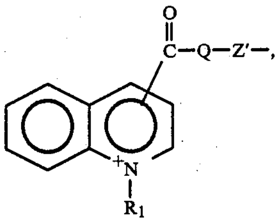

(iv)

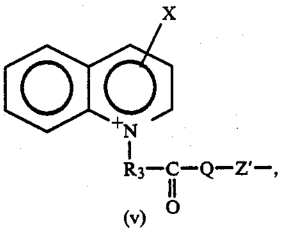

(v)

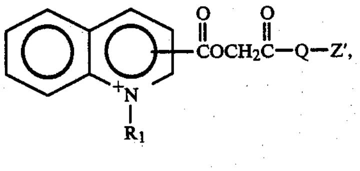

(vi)

-continued

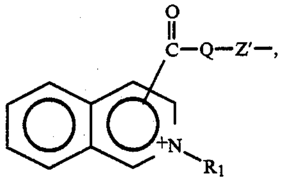

(vii)

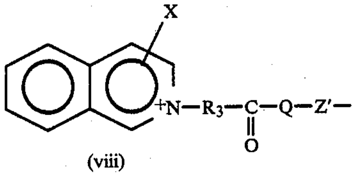 or (viii)

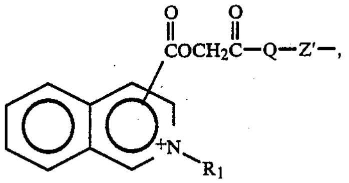

(ix)

wherein Z' is $C_1$–$C_8$ straight or branched alkylene, preferably $C_1$–$C_3$ straight or branched alkylene; Q is —O— or —NH—; $R_1$ is $C_1$–$C_7$ alkyl, $C_1$–$C_7$ haloalkyl or $C_7$–$C_{10}$ aralkyl; $R_3$ is $C_1$–$C_3$ alkylene, X is —CONR'R" wherein R' and R", which can be the same or different, are each H or $C_1$–$C_7$ alkyl, or X is —CH═NOR'" wherein R'" is H or $C_1$–$C_7$ alkyl; the X substituent in formula (ii) and the carbonyl-containing groupings in formulas (i) and (iii) can each be attached at the 2, 3 or 4 position of the pyridinium ring; the x substituent in formula (v) and the carbonyl-containing groupings in formulas (iv) and (vi) can each be attached at the 2, 3 or 4 position of the quinolinium ring; and the X substituent in formula (viii) and carbonyl-containing groupings in formulasd (vii) and (ix) can each be attached at the 1, 3 or 4 position of the isoquinolinium ring;

(b) Alternatively, when there is only one —COOH group to be derivatived:

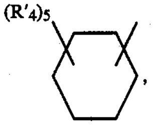, 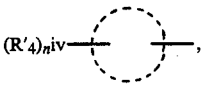, (x) (xi)

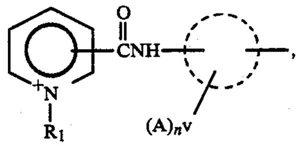, (xii)

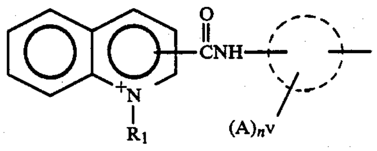 or (xiii)

-continued

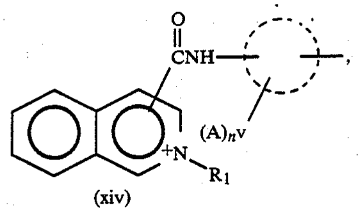, (xiv)

wherein 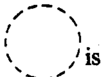 is the skeleton of a sugar molecule; $n^{iv}$ is a positive integer equal to the total number of —OH functions in the sugar molecule from which said skeleton is derived; $n^{v}$ is a positive integer one less than the total number of —OH functions in the sugar molecule from which said skeleton is derived; each A in each of structures (xii), (xiii) and (xiv) can independently be hydroxy or D', D' being the residue of a centrally acting drug containing one reactive carboxyl functional group, said residue being characterized by the absence of a hydrogen atom from said carboxyl functional group in said drug; and each $R'_4$ in each of structures (x) and (xi) can independently be hydroxy,

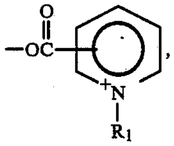,

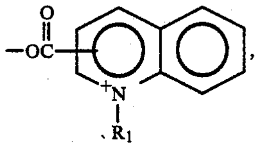,

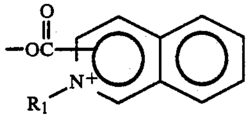 or D', wherein D' is defined as with structures (xii), (xiii) and (xiv); $R_1$ is $C_1$–$C_7$ alkyl, $C_1$–$C_7$ haloalkyl or $C_7$–$C_{10}$ aralkyl; and the depicted carbonyl-containing groupings can be attached at the 2, 3 or 4 position of the pyridinium or quinolinium ring, or at the 1, 3 or 4 position of the isoquinolinium ring; with the proviso that at least one $R'_4$ in each of structures (x) and (xi) is

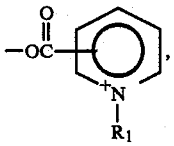,

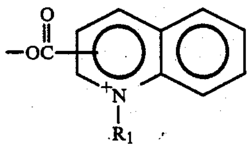 or

-continued

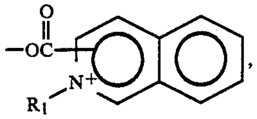

wherein $R_1$ and the position of the carbonyl-containing groupings are defined as above; and with the further proviso that when more than one of the $R'_4$ radicals in a given compound are the aforesaid carbonyl-containing groupings, then all such carbonyl-containing groupings in said compound are identical.

(3) For linkage to a drug having at least one —NH— functional group which is part of an amide or imide structure or at least one low pKa primary or secondary amine functional group, replacing a hydrogen atom from at least one of said functional groupings with one of the following [QC+] groupings:

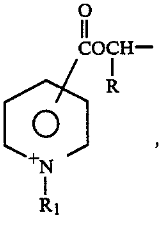

,

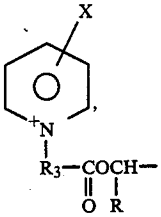

, (k) (l)

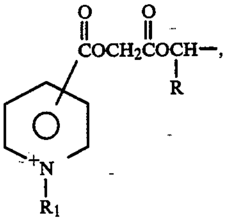

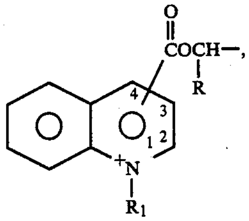

(m) (n)

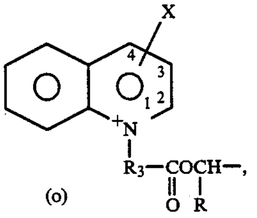

(o)

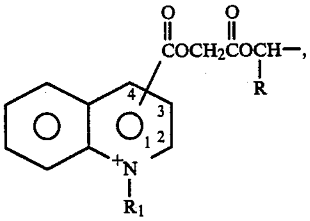

(p)

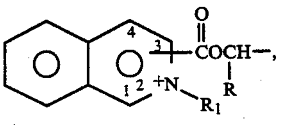

(q)

-continued

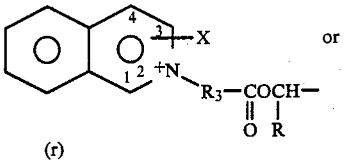

or (r)

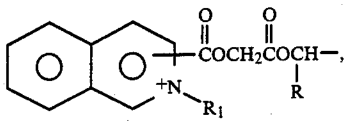

(s)

wherein $R_1$ is $C_1$–$C_7$ alkyl, $C_1$–$C_7$ haloalkyl or $C_7$–$C_{10}$ aralkyl; R is hydrogen, $C_1$–$C_7$ alkyl, $C_3$–$C_8$ cycloalkyl, $C_1$–$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; $R_3$ is $C_1$ to $C_3$ alkylene; X is —CONR'R" wherein R' and R", which can be the same or different, are each H or $C_1$–$C_7$ alkyl, or X is —CH=NOR'" wherein R'" is H or $C_1$–$C_7$ alkyl; the carbonyl-containing groupings in formulas (k) and (m) and the X substituent in formula (l) can each be attached at the 2, 3 or 4 position of the pyridinium ring; the carbonyl-containing groupings in formulas (n) and (p) and the X substituent in formula (o) can each be attached at the 2, 3 or 4 position of the quinolinium ring; and the carbonyl-containing groupings in formulas (q) and (s) and the X substituent in formula (r) can each be attached at the 1, 3 or 4 position of the isoquinolinium ring. Here and throughout this application, the expression "$C_1$–$C_7$ haloalkyl" means $C_1$–$C_7$ alkyl substituted by one or more halogen atoms. Also here and throughout this application, the alkyl radicals, including alkyl and alkylene portions of other radicals, can be straight or branched unless otherwise specified.

Drugs containing secondary or tertiary hydroxyl functional groups can be linked to any of the [QC+] groupings (k) through (s) above in which the

portion is derived from an aldehyde $RCH_2O$ capable of reacting with said drug to form the corresponding hemiacetal, as discussed in more detail in Method K' hereinabove.

The dihydro forms [DHC] corresponding to the aforementioned quaternaries are as follows:

(1') For Group (1) above:

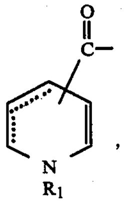

,

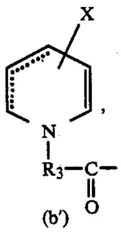

,

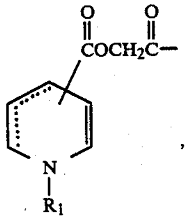

, (a') (b') (c')

-continued

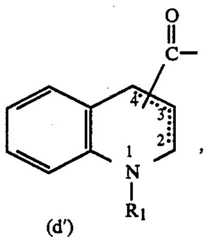

(d')

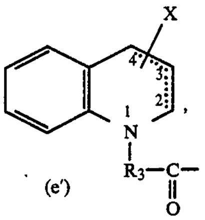

(e')

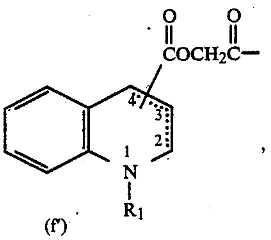

(f')

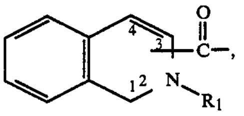

(g')

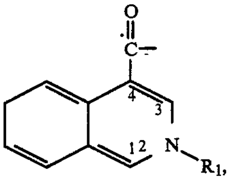

(g'')

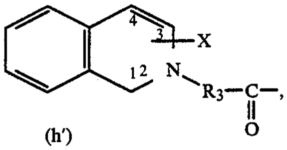

(h')

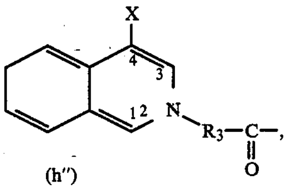

(h'')

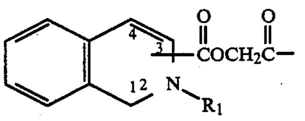

or (j')

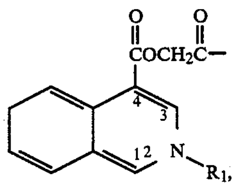

(j'')

wherein the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$-$C_7$ alkyl, $C_1$-$C_7$ haloalkyl or $C_7$-$CH_{10}$ aralkyl; $R_3$ is $C_1$ to $C_3$ alkylene; X is —CONR'R'', wherein R' and R'', which can be the same or different, are each H or $C_1$-$C_7$ alkyl, or X is —CH=NOR''' wherein R''' is H or $C_1$-$C_7$ alky; the carbonyl-containing groupings in formulas (a') and (c') and the X substituent in formula (b') can each be attached at the 2, 3 or 4 position of the dihydropyridine ring; the carbonyl-containing groupings in formulas (d')

and (f') and the X substituent in formula (e') can each be attached at the 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring;

(2') For Group (2) (a) above:

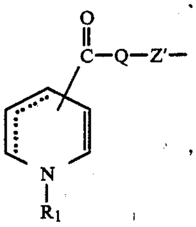

(i')

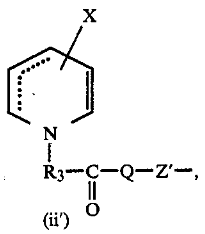

(ii')

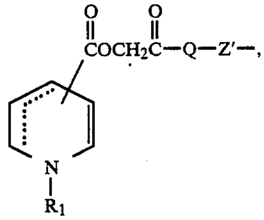

(iii')

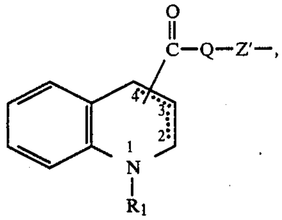

(iv')

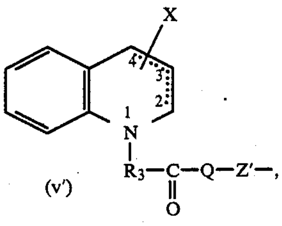

(v')

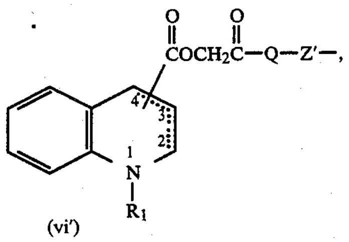

(vi')

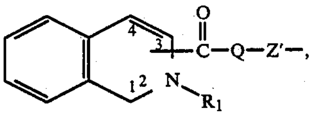

(vii')

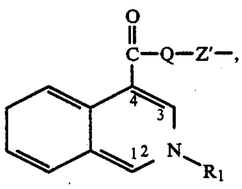

(vii'')

-continued

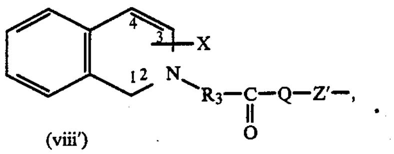

(viii')

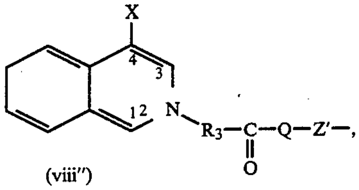

(viii'')

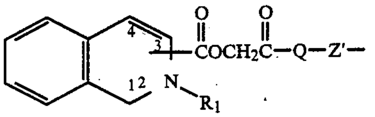

or (ix')

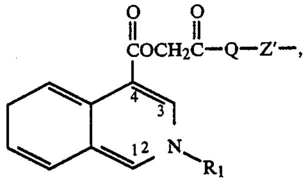

(ix'')

wherein the dotted line in formulas (i'), (ii') and (iii') indicates the presence of a double bond in either the 4 or 5 position of the dihydropyridine ring; the dotted line in formulas (iv'), (v') and (vi') indicates the presence of a double bond in either the 2 or 3 position of the dihydroquinoline ring; Z' is $C_1$–$C_8$ straight or branched alkylene, preferably $C_1$–$C_3$ straight or branched alkylene; Q is —O— or —NH—; $R_1$ is $C_1$–$C_7$ alkyl, $C_1$–$C_7$ haloalkyl or $C_7$–$C_{10}$ aralkyl; $R_3$ is $C_1$–$C_3$ alkylene; X is —CONR'R'' wherein R' and R'', which can be the same or different, are each H or $C_1$–$C_7$ alkyl, or X is —CH=NOR''' wherein R''' is H or $C_1$–$C_7$ alkyl; the X substituent in formula (ii') and the carbonyl-containing grouping in formulas (i') and (iii') can each be attached at the 2, 3 or 4 position of the dihydropyridine ring; the X substituent in formula (v') and the carbonyl-containing groupings in formulas (iv') and (vi') can each be attached at the 2, 3 or 4 position of the dihydroquinoline ring; and the X substituent in formula (viii') and the carbonyl-containing groupings in formulas (vii') and (ix') can each be attached at the 1, 3 or 4 position of the dihydroquinoline ring.

(3') For Group (2) (b) above:

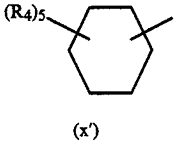

,

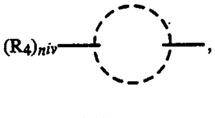

, (x') (xi')

-continued

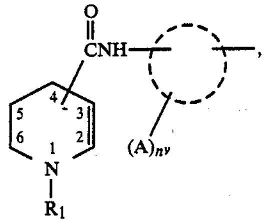

(xii')

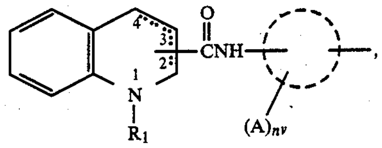

(xiii')

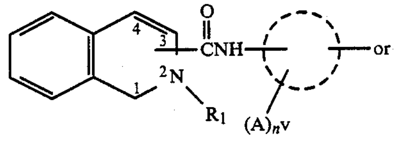

or (xiv')

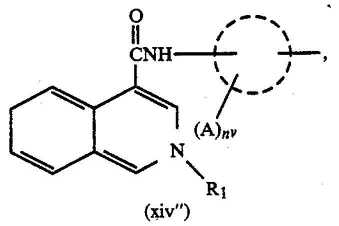

(xiv'')

wherein the dotted line in formula (xii') indicates the presence of a double bond in either the 4 or 5 position of the dihydropyridine ring; the dotted line in formula (xiii') indicates the presence of a double bond in either the 2 or 3 position of the dihydroquinoline ring; is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii'), (xiii'), (xiv') and (xiv'') can independently be hydroxy or D', D' being the residue of a centrally acting drug containing one reactive carboxyl functional group, said residue being characterized by the absence of a hydrogen atom from said carboxyl functional group in said drug; and ech $R_4$ in each of structures (x') and (xi') can independently be hydroxy,

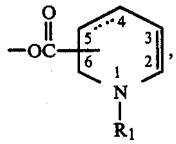

,

-continued

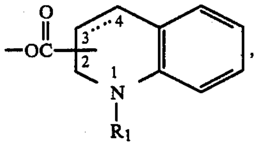

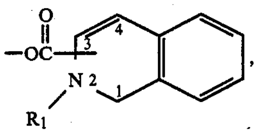

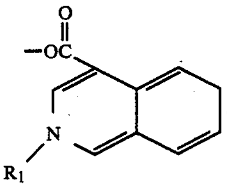

or D', wherein the dotted line is defined as with structures (xii') and (xiii'); D' is defined as with structures (xii'), (xiii'), (xiv') and (xiv''); $R_1$ is $C_1$–$C_7$ alkyl, $C_1$–$C_7$ haloalkyl or $C_7$–$C_{10}$ aralkyl; and the depicted carbonyl groupings can be attached at the 2, 3 or 4 position of the pyridinium or quinolinium ring or, except where otherwise specified, at the 1, 3 or 4 position of the isoquinolinium ring; with the proviso that at least one $R_4$ in each of structures (x') and (xi') is

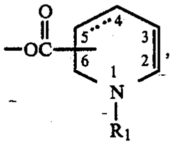

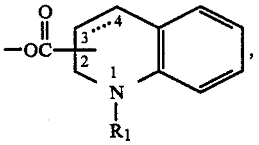

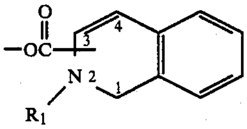

or

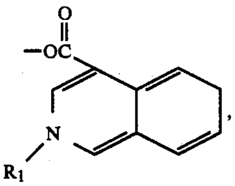

wherein $R_1$, the dotted lines and the position of the carbonyl-containing groupings are defined as above; and with the further proviso that when more than one of the $R_4$ radicals in a given compound are the aforesaid carbonyl-containing groupings, then all such carbonyl-containing groupings in said compound are identical.

(4') For Group (3) above:

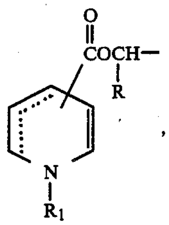

(k')

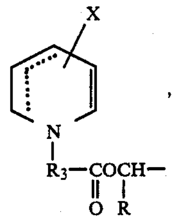

(l')

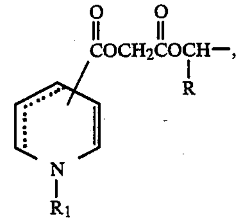

(m')

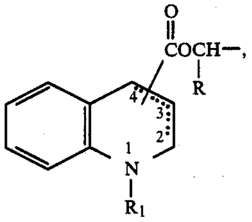

(n')

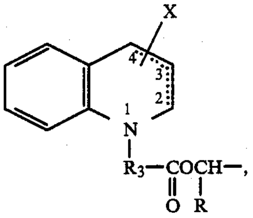

(o')

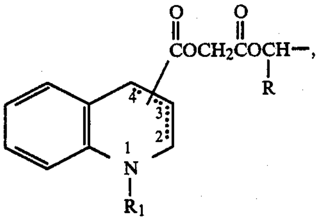

(p')

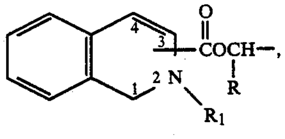

(q')

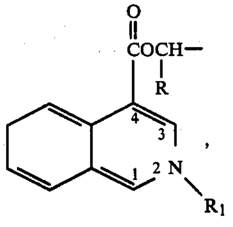

(q'')

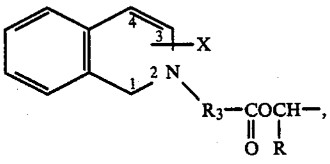

(r')

-continued

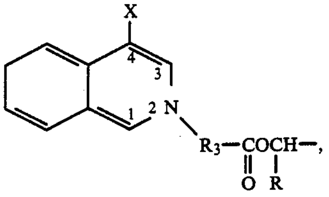

(r'')

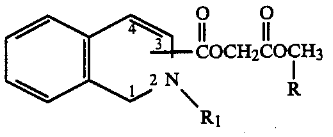

or (s')

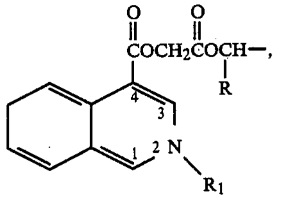

(s'')

wherein R is hydrogen, $C_1$–$C_7$ alkyl, $C_3$–$C_8$ cycloalkyl, $C_1$–$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; the dotted line in formulas (k'), (l') and (m') indicates the presence of a double bond in either the 4 or 5 position of the dihydropyridine ring; the dotted line in formulas (n'), (o') and (p') indicates the presence of a double bond in either the 2 or 3 position of the dihydroquinoline ring; $R_1$ is $C_1$–$C_7$ alkyl, $C_1$–$C_7$ haloalkyl or $C_7$–$CH_{10}$ aralkyl; $R_3$ is $C_1$ to $C_3$ alkylene; X is —CONR'R'', wherein R' and R'', which can be the same or different, are each H or $C_1$–$C_7$ alkyl, or X is —CH=NOR''' wherein R''' is H or $C_1$–$C_7$ alkyl; the carbonyl-containing groupings in formulas (k') and (m') and the X substituent in formula (l') can each be attached at the 2, 3 or 4 position of the dihydropyridine ring; the carbonyl-containing groupings in formulas (n') and (p') and the X substituent in formula (o') can each be attached at the 2, 3 or 4 position of the dihydroquinoline ring; and the carbonyl-containing groupings in formulas (q') and (s') and the X substituent in formula (r') can each be attached at the 1, 3 or 4 position of the dihydroisoquinoline ring.

The presently preferred dihydropyridine⇄pyridinium salt redox carrier moieties of this invention are those wherein $R_1$, when present, is $C_3$; $R_3$, when present, is —$CH_2CH_2$—; X, when present, is —$CONH_2$; the depicted carbonyl-containing groupings in formulas (a) and (c) and the X substituent in formula (b) are attached at the 3-position; the depicted carbonyl-containing groupings in formulas (d) and (f) and the X substituent in formula (e) are attached at the 3-position; the depicted carbonyl-containing groupings in formulas (g) and (j) and the X substituent in formula (h) are attached at the 4-position; Z', when present, is $C_2$ or $C_3$ straight or branched alkylene; Q, when present, is —NH—; the X substituent in formulas (ii) and (v) and the depicted carbonyl-containing groupings in formulas (i), (iii), (iv) and (vi) are attached at the 3-position; the X substituent in formula (viii) and the depicted carbonyl-containing groupings encompassed by formulas (x), (xi), (xii), (xiii) and (xiv) are in the 3-position of the pyridinium or quinolinium ring and in the 4-position of the isoquinolinium ring; all $R'_4$'s in structures (x) and (xi) are —OH except for the one $R_4$ in each structure which must be the carrier moiety; all A's in structures (xii), (xiii) and (xiv) are —OH; 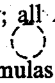 is the skeleton of a glucose molecule; R in formulas (k), (l) and (m) is hydrogen, methyl or $CCl_3$; and the depicted carbonyl-containing groupings in formulas (k) through (s) are in the 3-position of the pyridinium or quinolinium ring and in the 4-position of the isoquinolinium ring; and the corresponding dihydro moieties.

Especially preferred dihydropyridine⇄pyridinium salt redox carrier moieties are the quaternaries of Group (1), structures (a), (b), (d), (e), (g) and (h); those of Group (2), structures (i), (ii), (iv), (v), (vii) (viii), (x) and (xii); and those of Group 3, structures (k), (l), (n), (o), (q) and (r); and the corresponding dihydro forms, most especially when they contain the preferred structural variables identified in the preceding paragraph.

From the foregoing, it is apparent that the present invention provides two major classes of novel chemical compounds, i.e. the compounds of general formula (I) above, including their salts, and the compounds of general formula (II) above. Preferably, these two major clases consist of:

Compounds of the formula $$D\text{-}[DHC]_n \qquad (Ia)$$

and the nontoxic pharmaceutically acceptable salts thereof, wherein D is the residue of a centrally acting drug containing at least one reactive functional group consisting of amino, hydroxyl, mercapto, carboxyl, amide and imide, said residue being characterized by the absence of a hydrogen atom from at least one of said reactive functional groups in said drug; n is a positive integer equal to the number of said functional groups from which a hydrogen atom is absent; and [DHC] is the reduced, biooxidizable, blood-brain barrier penetrating lipoidal form of a dihydropyridine⇄pyridinium salt redox carrier;

with the proviso that when the compound is other than a salt of a compound of formula (Ia), when n is 1, when [DHC] is

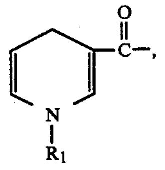

wherein $R_1$ is $C_1$–$C_7$ alkyl or $C_7$–$C_{10}$ aralkyl, and when the centrally acting drug of which D is the residue contains only one primary or secondary —OH functional group, no other —OH functional groups and no —$NH_2$, —NH—, —SH or —COOH functional groups, then D must be the residue of a centrally acting drug other than a steroid sex hormone or long chain alkanol;

and with the further proviso that when the compound is other than a salt of a compound of formula (Ia), when n is 1, when [DHC] is

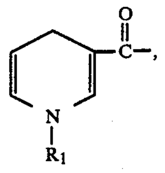

wherein $R_1$ is $C_1$–$C_7$ alkyl or $C_7$–$C_{10}$ aralkyl, and when the centrally acting drug of which D is the residue contains only one —$NH_2$ functional group and no other functional groups, then D must be the residue of a centrally acting drug other than a sympathetic stimulant; and Quaternary salts of the formula $$D\{QC^+]_n qX^{-t} \quad \text{(IIa)}$$

wherein D and n are as defined with formula (Ia); [QC+] is the hydrophilic, ionic pyridinium salt form of a dihydropyridine⇄pyridinium salt redox carrier; $X^-$ is the anion of a pharmaceutically acceptable organic or inorganic acid; t is the valence of the acid anion; and q is the number which when multiplied by t is equal to n; with the proviso that when n is 1, when [QC+] is

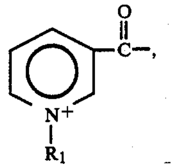

wherein $R_1$ is $C_1$–$C_7$ alkyl or $C_7$–$C_{10}$ aralkyl, and when the centrally acting drug of which D is the residue contains only one primary or secondary —OH functional group, no other —OH functional groups and no —$NH_2$, —NH—, —SH or —COOH functional groups, then D must be the residue of a centrally acting drug other than a steroid sex hormone or long chain alkanol;

and with the further proviso that when n is 1, when [QC+] is

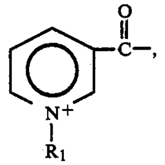

wherein $R_1$ is $C_1$–$C_7$ alkyl or $C_7$–$C_{10}$ aralkyl, and when the centrally acting drug of which D is a residue contains only one —$NH_2$ functional group and no other functional groups, then D must be the residue of a centrally acting drug other than a sympathetic stimulant.

Within each of the classes (Ia) and (IIa), the following subclasses are particularly noteworthy:

(A) Compounds of formulas (Ia) and (IIa) wherein the D portion of the compound of formula (Ia) or (IIa) is identical to the corresponding portion of the centrally acting drug from which D can be considered to be derived, and the carrier is attached through an amino functional group in the drug. Preferred groups of compounds in this subclass include the following:

(1) Cerebral stimulants, including sympathomimetic amine-type cerebral stimulants, such as amphetamine, dextroamphetamine, levamphetamine, aletamine, cypenamine, tyramine, phentermine, methamphetamine, fencamfamin, zylofuramine, phenethylamine, etryptamine and tranylcypromine; tricyclic antidepressant-type cerebral stimulants, especially dibenzazepines and their analogues, e.g. desipramine, nortriptyline, protriptyline, maprotiline, octriptyline, and many other cerebral stimulants, alerting agents and antidepressants of various types, as exemplified by amiphenazole, amedalin, cartazolate, daledalin, fluoxetine, nisoxetine, bupropion, difluamine and methylphenidate.

(2) Neurotransmitters, such as dopamine, histamine, tryptamine and serotonin.

(3) Narcotic analgesics, such as anileridine, noracymethadol and piminodine.

(4) Hypotensives, such as clonidine, hydralazine, bethanidine, guanethidine, debrisoquin, propanolol and prizidilol.

(5) Sympathomimetic amines, such as ephedrine, oxymetazoline and pseudoephedrine.

(6) Anticancer and antitumor agents, such as doxorubicin and daunomycin.

(7) Antiviral agents, such as amantadine, 2-guanidino-4,5-di-n-propyloxazole, 2-guanidino-4,5-diphenyloxazole, glucosamine and 6-amino-6-deoxy-D-glucose.

(8) Antibiotic and antibacterial agents, such as phenazopyridine, bacampicillin and pivampicillin.

(9) Sedatives, muscle relaxants, anticonvulsants, tranquilizers (including benzodiazepine tranquilizers) e.g. benzoctamine, tracazolate, chlordiazepoxide, tiletamine and aminoglutethimide.

(10) Diagnostics, including radiolabeled diagnostics, e.g., iodometaraminol.

(B) Compounds of formulas (Ia) and (IIa) wherein the drug from which D can be considered to be derived contains an amino function through which the carrier is attached and also contains at least one —OH functional group, and D in formula (Ia) or (IIa) contains, in place of the hydrogen atom of at least one of the —OH groups in the drug, at least one hydrolytically or metabolically cleavable hydroxyl protective group. Within subclass (B), preferred compounds are those in which D is a protected residue of a neurotransmitter, such as dopamine or serotonin; a cerebral stimulant, such as tyramine; a sympathomimetic amine, such as ephedrine, phenylephrine or pseudoephedrine; an adrenergic agent, such as norepinephrine or epinephrine; an anticancer or antitumor agent, such as pentostatin; an antiviral, such as glucosamine or 6-amino-6-deoxy-D-glucose; or a hypotensive, such as atenolol or metoprolol.

(C) Compounds of formulas (Ia) and (IIa) wherein the drug from which D can be considered to be derived contains an amino function through which the carrier is attached and also contains at least one —COOH functional group, and D in formula (Ia) or (IIa) contains, in place of the hydrogen atom of at least one of the —COOH groups, at least one hydrolytically or metabolically cleavable carboxyl protective group. Preferred compounds within this subclass are those in which D is a protected residue of anticancer and antitumor agents, e.g. melphalan, DON, L-alanosine and acivicin; antibiotics, especially penicillins such as amoxacillin and ampicillin and cephalosporins such as cephalexin, cefroxadine and ceforanide; hypotensives such as methyldopa and furosemide; dopaminergic agents such as L-DOPA; and amino acids and small peptides containing 2-20 amino acid units, e.g. GABA, tyrosine and other natural amino acids, met[5]-enkephalin, leu[5]-enkephalin and the like.

(D) Compounds of formulas (Ia) and (IIa) wherein the drug from which D can be considered to be derived contains an amino function through which the carrier is attached and also contains at least one —OH functional group and at least one —COOH functional group, and D in formula (Ia) or (IIa) contains, in place of the hydrogen atom of at least one of the —OH functional groups and at least one of the —COOH functional groups in said drug, respectively, at least one hydrolytically or metabolically cleavable hydroxyl protective group and at least one hydrolytically or metabolically cleavable carboxyl protective group. Of particular interest are the compounds in which D is a protected residue of a hypotensive, e.g. methyldopa; or a sympathetic stimulant/dopaminergic agent, e.g. levodopa.

(E) Compounds of formulas (Ia) and (IIa) wherein the D portion of the compound of formula (Ia) or (IIa) is identical to the corresponding portion of the drug from which D can be considered to be derived and the carrier is attached through a hydroxyl or mercapto functional group in the drug. Preferred groups of compounds in this subclass include the following:

(1) Tranquilizers, including benzodiazepines, such as oxazepam, temazepam and lorazepam; phenothiazines, such as carphenazine, fluphenazine, acetophenazine and the like; and other tranquilizers such as haloperidol, clopenthixol and hydroxyzine.

(2) Steroids, including androgens, e.g. testosterone; progestins, e.g. norgestrel and norethynodrel; estrogens, e.g. natural estrogens such as estradiol and semisynthetic estrogens such as mestranol; and antiinflammatory steroids such as cortisone, hydrocortisone, triamcinolone and the like.

(3) Narcotic analgesics, such as codeine, pentazocine and morphine.

(4) Narcotic antagonists and mixed agonists/antagonists, e.g. nalorphine, naloxone, buprenorphine, nalbuphine and butorphanol.

(5) Cerebral stimulants, including tricyclic antidepressants such as opipramol and centrally active hydroxylated metabolites of tricyclic antidepressants, e.g. 2-hydroxyimipramine.

(6) Anticancer and antitumor agents, e.g. mitoxantrone, etoposide, hydroxyurea and Ara-AC.

(7) Antivirals, e.g. ribavarin, acyclovir and trifluridine.

(8) Non-steroidal antiinflammatory agents, clonixeril and naproxol.

(9) Hypotensives, e.g. prizidilol and nadolol.

(10) Diagnostics, e.g. iopydol.

(F) Compounds of formulas (Ia) and (IIa) wherein the drug from which D can be considered to be derived contains a hydroxyl or mercapto function through which the carrier is attached and also contains at least one amino functional group, and D in the formula (Ia) or (IIa) contains, in place of a hydrogen atom of at least one of the amino groups in the drug, at least one amino protective group. Of particular interest are derivatives of neurotransmitters, stimulants, sympathetic amines, anticancer or antitumor agents, adrenergic agents and antiviral agents. The stimulants include centrally active metabolites of tricyclic antidepressants (e.g. 2-hydroxydesipramine).

(G) Compounds of formulas (Ia) and (IIa) wherein the drug from which D can be considered to be derived contains a hydroxyl or mercapto function through which the carrier is attached and also contains at least one carboxyl group, and D in formula (Ia) or (IIa) contains, in place of the hydrogen atom of at least one of the carboxyl groups in the drug, at least one hydrolytically or metabolically cleavable carboxyl protective group. Of particular interest here are the derivatives of valproic acid metabolite anticonvulsants and CNS prostaglandins.

(H) Compounds of formulas (Ia) and (IIa) wherein the drug from which D can be considered to be derived contains an amide or imide or low pKa primary or secondary amine function through which the carrier is attached and the D portion of the compound of formula (Ia) or (IIa) is identical to the corresponding portion of the drug from which D can be considered to be derived. Especially significant members of this group are the hydantoin anticonvulsants, e.g. phenytoin, ethotoin and mephenytoin, as well as other anti-convulsants, e.g. phenobarbital, aminoglutethimide, progabide and valpromide; tranquilizers, e.g. benzodiazepine-type tranquilizers such as bromazepam and oxazepam, and centrally active N-desmethyl metabolites of N-methylated benzodiazepine tranquilizers; hypnotics; nonsteroidal antiinflammatory agents; anticancer agents such as cyclophosphamide; anti-depressants, such as sulpiride; antibiotics, especially tetracyclines; and antivirals, such as trifluridine.

(I) Compounds of formulas (Ia) and (IIa) wherein the drug from which D can be considered to be derived contains an amide or imide or low pKa primary or secondary amine function through which the carrier is attached and the drug also contains at least one hydroxyl group, D in formula (Ia) or (IIa) containing, in place of the hydrogen atom of at least one hydroxyl group in the drug, at least one hydrolytically or metabolically cleavable hydroxyl protective group. Significant members of this group include antivirals such as trifluridine and benzodiazepine tranquilizers such as oxazepam.

(J) Compounds of formulas (Ia) and (IIa) wherein the drug from which D can be considered to be derived contains an amide or imide or low pKa primary or secondary amine function through which the carrier is attached and the drug also contains at least one carboxyl functional group, D in formula (Ia) or (IIa) containing, in place of the hydrogen atom of at least one —COOH in the drug, at least one hydrolytically or metabolically cleavable carboxyl protective group. Especially significant members of this group include anticancer and antitumor agents, antibiotics (particularly penicillins and cephalosporins) and CNS anticholinergics.

(K) Compounds of formulas (Ia) and (IIa) wherein the drug from which D can be considered to be derived contains a —COOH function through which the carrier is attached, and the D portion of the compound of formula (Ia) or (IIa) is identical to the corresponding portion of the drug from which D can be considered to be derived. Especially significant members of this group include nonsteroidal antiinflammatory agents such as naproxen, ibuprofen and the like; diagnostics, including radiolabeled ones such as o-iodohippuric acid and iothalamic acid, as well as the corresponding "cold" compounds; CNS prostaglandins, such as $PGD_2$; antibiotics, especially cephalosporins and pencillins; anticonvulsants, e.g., valproic acid and SL 75102; anticancer and antitumor agents, e.g. chlorambucil, DACH and methotrexate.

(L) Compounds of formulas (Ia) and (IIa) wherein the drug from which D can be considered to be derived contains a —COOH function through which the carrier is attached and the drug also contains at least one hydroxyl function, D in formula (Ia) or (IIa) containing, in place of the hydrogen atom of at least one —OH in the drug, at least one hydrolytically or metabolically cleavable hydroxyl protective group. Within this class, derivatives of valproic acid metabolite-type anticonvulsants and NSAID's are especially noteworthy.

(M) Compounds of formulas (Ia) and (IIa) wherein the drug from which D can be considered to be derived contains a —COOH function which the carrier is attached and the drug also contains at least one amino function, D in formula (Ia) or (IIa) containing, in place of a hydrogen atom of at least one of the amino functions in the drug, at least one amino protective group. Significant members of this group include penicillin antibiotics, cephalosporin antibiotics, anticancer and antitumor agents, amino acids and small peptides.

(N) Compounds of formulas (Ia) and (IIa) wherein the drug from which D can be considered to be derived contains a —COOH function through which the carrier is attached and the drug also contains at least one amino function and at least one hydroxyl function, D in formula (Ia) or (IIa) containing, in place of a hydrogen atom of at least one amino function and in place of the hydrogen atom of at least one hydroxyl function, respectively, at least one amino protective group and at least one hydrolytically or metabolically cleavable hydroxyl protective group. Particularly significant members of this class include dopaminergic agents, hypotensive agents, antibiotics, hydroxyl-containing amino acids (e.g. tyrosine) and small peptides containing same.

It is apparent from the foregoing that the present invention provides a wide variety of carrier moieties and compounds containing those carriers which are adapted for the site-specific and sustained delivery of centrally acting drugs to the brain. Many of the dihydro moieties which are depicted as structures (a') through (j''), (k') through (s''), (i') through (ix'') and (x') through (xiv') hereinabove, and the corresponding quaternary forms, as well as compounds containing those carriers, are specifically contemplated by applicant's earlier copending applications, e.g. by Ser. No. 516,382. Moreover, applicant's earlier applications, and particularly Ser. No. 516,382, specifically contemplate some additional carrier moieties and derivatives containing same, and those additional carriers and derivatives are likewise within the ambit of this application. Among the classes of compounds specifically provided by both Ser. No. 516,382 and the present application, the following are particularly noteworthy:

(A*) Compounds adapted for the side-specific/sustained delivery of a centrally acting drug species to the brain, said compounds being:

(i) compounds of the formula $$D^*(-Q^*)_{n^*} \qquad (I')$$

wherein $D^*$ is the residue of a centrally acting drug containing at least one $-NH_2$ or —NH— functional group, said residue being formed by removal of a hydrogen atom from at least one of the $-NH_2$ or —NH— functional groups in said drug; $n^*$ is a positive integer equal to the number of said $-NH_2$ or —NH— functional groups from which a hydrogen atom has been removed; and $-Q^*$ is a radical of the formula

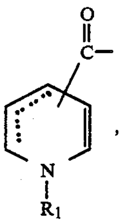,
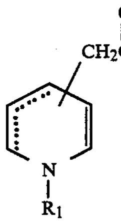,
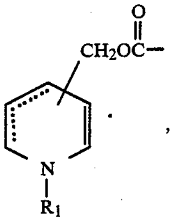, (a*) (b*) (c*)

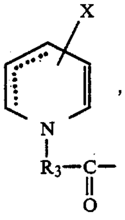,
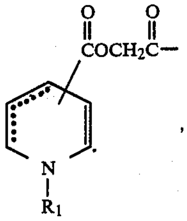, (d*) (e*)

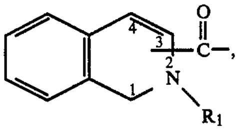,
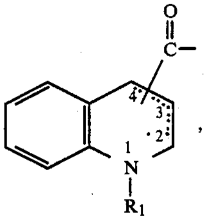, (f*) (g*)

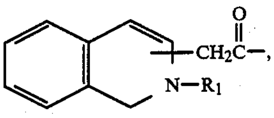,
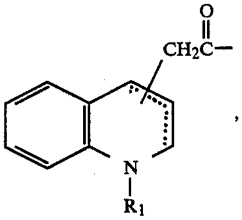, (h*) (i*)

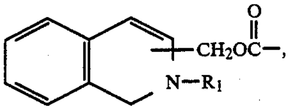,
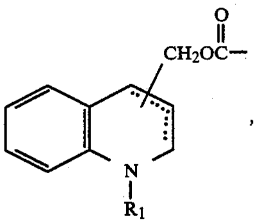, (j*) (k*)

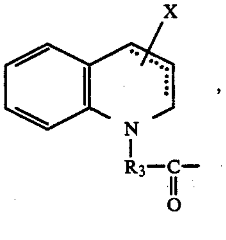,
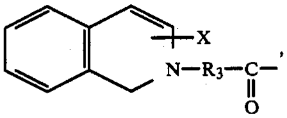, (l*) (m*)

-continued

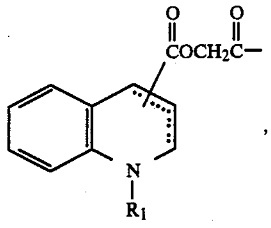

(n*)

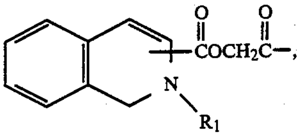

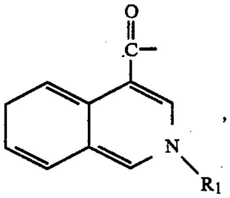

(o*) (p*)

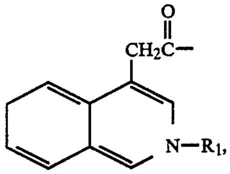

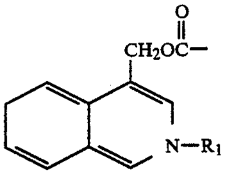

(q*) (r*)

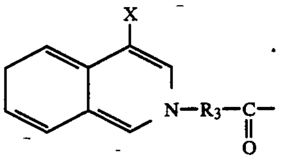

or

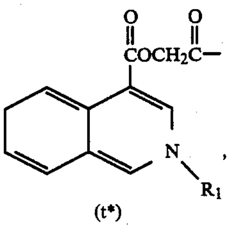

(s*) (t*)

wherein the dotted line in formulas (a*), (b*), (c*), (d*) and (e*) indicates the presence of a double bond in either the 4 or 5 position of the dihydropyridine ring; the dotted line in formulas (g*), (i*), (k*), (l*) and (n*) indicates the presence of a double bond in either the 2 or 3 position of the dihydroquinoline ring; $R_1$ is $C_1$-$C_7$ alkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the

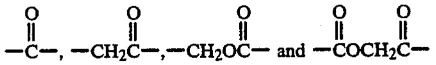

groupings in formulas (a*), (b*), (c*) and (e*) and the X substituent in formula (d*) can each be attached at the 2, 3 or 4 position of the dihydropuyridine ring; the

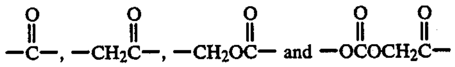

groupings in formulas (g*), (i*), (k*) and (n*) and the X substituent in formula (l*) can each be attached at the 2, 3 or 4 position of the dihydroquinoline ring; and the

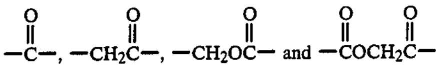

groupings in formulas (f*), (h*), (j*) and (o*) and the X substituent in formula (m*) can each be attached at the 1, 3 or 4 position of the dihydroisoquinoline ring; and (ii) non-toxic pharmaceutically acceptable salts of compounds of formula (I');

with the proviso that when the compound is other than a salt as defined in (ii) above, when n* is 1, when —Q* is

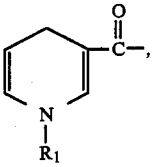

wherein $R_1$ is $C_1$-$C_7$ alkyl or $C_7$-$C_{20}$ aralkyl, and when the centrally acting drug from which D* is derived contains only one —$NH_2$ functional group and no other functional groups, then D* must be the residue of a centrally acting drug other than a sympathetic stimulant. The corresponding compounds in which —Q* is (a*), (b*), (c*), (e*), (f*), (g*), (h*), (i*), (j*), (k*), (n*), (o*), (p*), (q*), (r*) or (t*) wherein $R_1$ is $C_1$-$C_7$ haloalkyl are also within the scope of class (A*) as defined herein. Within class (A*), preferred compounds are those wherein —Q* is a radical of the formula:

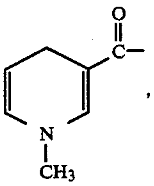

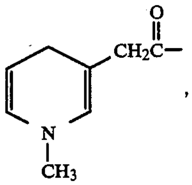

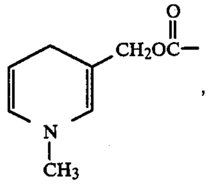

(a*') (b*') (c*')

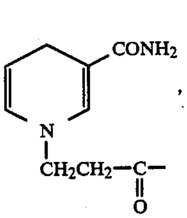

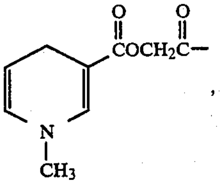

(d*') (e*')

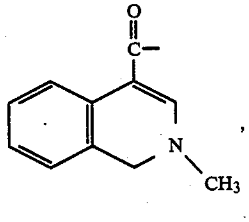

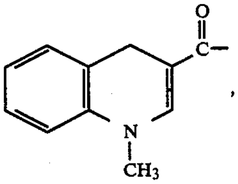

(f*') (g*')

-continued

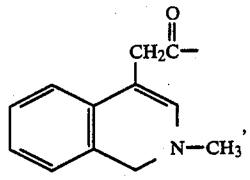,
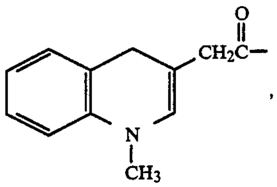, (h*') (i*')

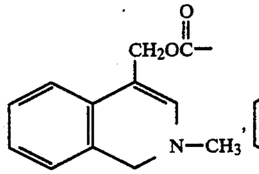,
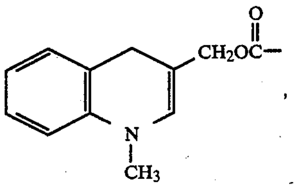, (j*') (k*')

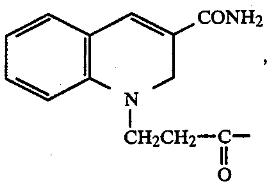, (l*')

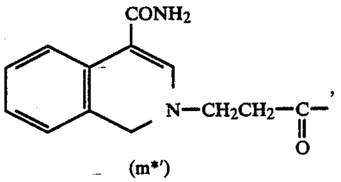, (m*')

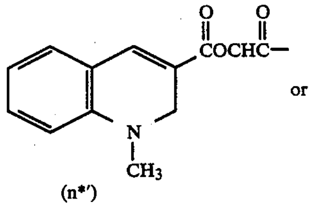
or
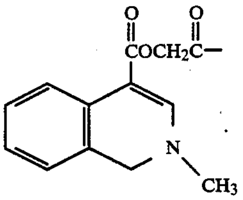

(n*') (o*')

Also preferred are those compounds of class (A*) wherein D* is the residue of hydralazine, bactobolin, clonidine, bethanidine, tranylcypromine, chlordiazepoxide, methamphetamine, phentermine, phenmetrazine, anileridine, protriptyline, daunamycin, dextroamphetamine, levamphetamine, amphetamine, phenylethylamine, doxorubicin, amantadine, mitoxantrone, tryptamine, desipramine or nortriptyline.

(B*) Compounds of Class (A*) as defined above, wherein the centrally acting drug from which D* is derived also contains at least one —COOH functional group, and D* contains, in place of at least one of the —COOH functional groups in said drug, at least one —COOY' group wherein Y' is a hydrolytically or metabolically cleavable carboxyl protective group. Within Class (B*), preferred compounds are those in which Y' is $C_1$-$C_7$ alkyl and/or wherein D* is the residue of an amino acid or of a peptide containing 2 to 20 amino acid segments (especially an enkephalin or an endorphin). Also preferred are the compounds of Class (B*) wherein D* is the residue of tryptophan, ampicillin, cephalexin, melphalen, L-alanosine, DON, acivicin, GABA, γ-vinyl GABA, or γ-acetylenic GABA, met[5]-enkephalin, leu[5]-enkephalin, γ-endorphin, α-endorphin, β-endorphin, LH-RH, neurotensin, oxytocin M or vasopressin.

(C*) Compounds of Class (A*) as defined above, wherein the centrally acting drug from which D* is derived also contains at least one —OH functional group, and D* contains, in place of at least one of the —OH functional groups in said drug, at least one —OY group wherein Y is a hydrolytically or metabolically cleavable hydroxyl protective group. Within Class (C*) preferred compounds are those wherein Y is an acyl group or a carbonate group and/or wherein D* is the residue of a neurotransmitter, especially a catecholamine. At the present time, preferred compounds in this general class include those in which D* is the residue of serotonin, norepinephrine, epinephrine, dopamine, tyramine or phenylephrine.

(D*) Compounds of Class (A*) as defined above, wherein the centrally acting drug from which D* is derived also contains at least one —OH functional group and at least one —COOH functional group, and D* contains, in place of at least one of the —OH functional groups and at least one of the —COOH functional groups in said drug, at least one —OY group and at least one —COOY' group, respectively, wherein Y is a hydrolytically or metabolically cleavable hydroxyl protective group and Y' is a hydrolytically or metabolically cleavable carboxyl protective group. Within Class (D*) preferred compounds are those wherein Y is an acyl group or a carbonate group and/or Y' is $C_1$-$C_7$ alkyl. Of particular interest are the compounds in which D* is the residue of methyldopa or levodopa.

(E*) Compounds adapted for the site-specific/sustained delivery of a centrally acting drug species to the brain, said compounds being:

(i) compounds of the formula $$D''(-Q')_{n'} \qquad (I'')$$

wherein D'' is the residue of a centrally acting drug containing at least one —NH— functional group which is part of an amide or imide structure or at least one low pKa primary or secondary amine functional group, said residue being formed by removal of a hydrogen atom from at least one of said functional groups in said drug; n' is a positive integer equal to the number of said functional groups from which a hydrogen atom has been removed; and —Q' is a radical of the formula

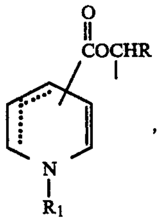,
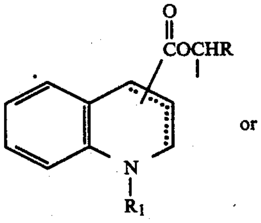
or
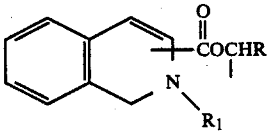

wherein the dotted lines indicate the presence of a double bond in either the 4 or 5 position of the dihydropyridine ring and in either the 2 or 3 position of the dihydroquinoline ring; $R_1$ is $C_1$–$C_7$ alkyl or $C_7$–$C_{10}$ aralkyl; R is hydrogen, $C_1$–$C_7$ alkyl, $C_3$–$C_8$ cycloalkyl, $C_1$–$C_7$ alkyl substituted by one or more halogen atoms, pyridyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio lower alkylsulfinyl or lower alkylsulfonyl; and the

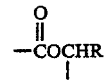

grouping can be in the 2, 3 or 4 position of the dihydropyridine ring, in the 2, 3 or 4 position of the dihydroquinoline ring and in the 1, 3 or 4 position of the dihydroisoquinoline ring; and (ii) non-toxic pharmaceutically acceptable salts of compounds of formula (I''). Within Class (E*), preferred compounds are those wherein —Q is a radical of the formula

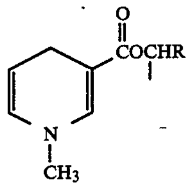

wherein R is as defined above, especially when R is hydrogen, methyl, phenyl or trichloromethyl, and/or when D'' is the residue of a tetracycline antibiotic containing a $—CONH_2$ function. Of particular interest in this general class are those compounds wherein D'' is the residue of cyclophosphamide, ethotoin, phenobarbital, chlortetracycline, glutethimide, uracil mustard, bemegride, aminoglutethimide, phenytoin, butalbital, demeclocycline, minocycline, doxycycline, oxytetracycline, ethyl β-carboline 3-carboxylate, nifedipine, methylphenidate, 3-deazaguanine, PCNU, spiromustine or L-ICRF.

(F*) Compounds adapted for the site-specific/sustained delivery of a centrally acting drug species to the brain, said compounds being:

(i) compounds of the formula $$(D'''(—Q'')_{n''} \qquad (I''')$$

wherein D''' is the residue of a centrally acting drug containing at least one —OH— or —SH functional group, said residue being formed by removal of a hydrogen atom from at least one of the —OH or —SH functional groups in said drug; n'' is a positive integer equal to the number of said —OH or —SH functional groups from which a hydrogen atom has been removed; and —Q'' is a radical of any one of formulas (a*) through (t*) inclusive as set forth in the definition of Class (A*) above, the structural variables in those formulas also being defined as in (A*) above; and (ii) non-toxic pharmaceutically acceptable salts of compounds of formula (I''');

with the proviso that when the compound is other than a salt as defined in (ii) above, when n'' is 1, when —Q'' is

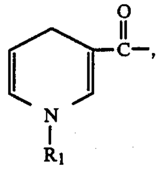

wherein $R_1$ is $C_1$–$C_7$ alkyl or $C_7$–$C_{10}$ aralkyl, and when the centrally acting drug from which D''' is derived contains only one primary or secondary —OH functional group, no other —OH functional groups and no $—NH_2$, —NH—, —SH or —COOH functional groups, then D''' must be the residue of a centrally acting drug other than a steriod sex hormone or long chain alkanol. The corresponding compounds in which —Q'' is (a*), (b*), (c*), (e*), (f*), (g*), (h*), (i*), (j*), (k*), (n*), (o*), (p*), (q*), (r*) or (t*) wherein $R_1$ is $C_1$–$C_7$ haloalkyl are also within the scope of class (F*) as defined herein. Within Class (F*), preferred compounds are those in which —Q'' is a radical of any one of formulas (a*') through (o*') set forth in connection with Class (A*) hereinabove. Also preferred are those compounds wherein D''' is a steroid sex hormone, i.e., an androgen, estrogen or progestin. When D''' is the residue of an androgen, it is preferable the residue of testosterone or methyl testosterone or other known 17β-hydroxy-containing analogue of testosterone. When D''' is the residue of an estrogen, it is preferably the residue of a natural estrogen (estradiol, estrone or estriol) or of a known semi-synthetic estrogen having a 17β-hydroxy substituent, such as ethinyl estradiol, mestranol or quinestrol. When D''' is the residue of a progestin, it is preferably the residue of a known semi-synthetic progestin having a 17β-hydroxy substituent, such as norethindrone, norgestrel, ethisterone, dimethisterone, allylestrenol, cingestol, ethynerone, lynestrenol, norgesterone, norvinisterone, ethynodiol, oxogestone, tigestol or norethynodrel. Within Class (F*), another preferred group of compounds consists of the compounds in which D''' is the residue of an anti-inflammatory steroid, especially a known anti-inflammatory steroid having a 21-hydroxy substituent, such as cortisone, hydrocortisone, betamethasone, dexamethasone, flumethasone, fluprednisolone, methyl prednisolone, meprednisone, prednisolone, prednisone, cortodoxone, fludrocortisone, paramethasone or triamcinolone. Yet another preferred group of Class (F*) compounds is the group in which D''' is the residue of a narcotic analgesic, narcotic antagonist or narcotic agonist-antagonist, especially when it is the residue of a known compound of this type bearing at least one hydroxy substituent, such as codeine, pentazocine, naloxone, oxycodone, hydromorphone, oxymorphone, nalorphine, morphine, levorphanol, meptazinol, cyclazocine, phenazocine, profadol, metopon, drocode, myfadol, buprenorphine, nalbuphine, butorphanol, levallorphan, naltrexone, alazocine, oxilorphan or nalmexone. Still another preferred group of Class (F*) compounds consist of compounds in which D''' is the residue of an anticancer or antitumor agent; preferably D''' is the residue of a podophyllotoxin derivative (especially etoposide or teniposide) or of Ara-AC, pentostatin, thioguanine, hydroxyurea, dihydro-5-azacytidine, tiazofurin, sangivamycin, Ara-A, 6-MMPR, trimethyl TMM, SR-2555, bisbenzimidazole, SR-2508, aclacinomycin A, phyllanthoside, 6-mercaptopurine, desmethylisonidazole, menogarol, aphidicolin, 5-FUDR, trifluoroacetyl doxorubicin, cytosine arabinoside, 5-azacytidine, Ara-C or streptozotocin. Yet another preferred group of compounds within this general class consists of compounds in which D''' is the residue of an antiviral agent such as ribavarin, acyclovir, syn or anti-6-[[(hydroxyimino)phenyl]methyl]-1-[(1-methylethyl)-sulfonyl]-1H-benzimidazol-2-amine, 5,7-dimethyl-2-β-D-ribofuranosyl-s-triazole(1,5-a)pyrimidine, 2-deoxy-D-glucose, 2-deoxy-2-fluoro-D-mannose, phenyl-6-chloro-6-deoxy-β-D-glucopyranoside, (S)-9-(2,3-dihydroxypropyl)adenine, idoxuridine, 5,6-dichloro-1-β-D-ribofuranosylbenzimidazole or bisihydroxyvinyluridine. Another preferred group of compounds in Class (F*) consists of compounds in which D''' is the residue of a benzodiazepine or phenothiazine tranquilizer, especially those in which D''' is the residue of a known benzodiazepine such oxazepam, lorazepam or temazepam, or of a known phenothiazine such as acetophenazine, carphenazine, fluphenazine, perphenazine or piperacetazine. Other Class (F*) compounds of interest are those in which D''' is the residue of thiopental, haloperidol, opipramol, clopenthixol, ethamivan, hydroxyzine, apomorphine, iopydol, clindamycin, lincomycin, benzestrol, diethylstilbestrol, pholcodeine or dipyridamole.

(G*) Compounds of Class (F*) as defined above, wherein the centrally acting drug from which D''' is derived also contains at least one —COOH functional group, and D''' contains, in place of at least one of the —COOH functional groups in said drug, at least one —COOY' group wherein Y' is a hydrolytically or metabolically cleavable carboxyl protective group. Within Class (G*), preferred compounds include those in which D''' is the residue of a valproic acid metabolite (such as 5-hydroxy-2-n-propylpentanoic acid, 4-hydroxy-2-n-propylpentanoic acid or 3-hydroxy-2-n-propylpentanoic acid), clorazepate or diflunisal.

(H*) Compounds of Class (F*) as defined above, wherein —Q'' is a radical of the formula

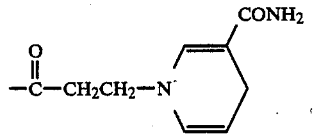

and D''' is the residue of a centrally acting drug containing a hindered tertiary —OH functional group; especially when D''' is the residue of biperiden, cycrimine, procyclidine or trihexylphenidyl.

(I*) Compounds adapted for the site-specific/sustained delivery of a centrally acting drug species to the brain, said compounds being:

(i) compounds of the formula $$D^{iv}(-Q''')_{n'''} \qquad (I^{iv})$$

wherein $D^{iv}$ is the residue of a centrally acting drug species containing at least one —COOH functional group, said residue being formed by removal of an —OH from at least one of the —COOH functional groups in said drug; n''' is a positive integer equal to the number of said —COOH functional groups from which an —OH has been removed; and —Q''' is a radical of the formula

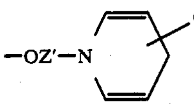

,

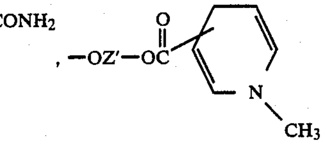

or

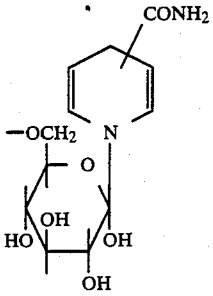

wherein Z' is $C_1$–$C_8$ straight or branched alkylene;

(ii) compounds of the formula

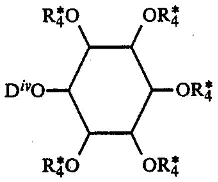

(I$^v$)

wherein $D^{iv}$ is defined as above and each $R_4$* can independently be hydrogen, $D^{iv}$ or a radical of the formula

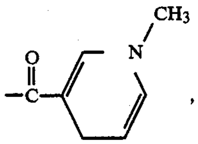

, with the proviso that at least one $R_4$* is a radical of the formula

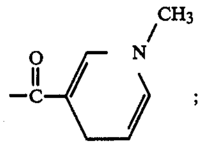

;

(iii) compounds of the formula

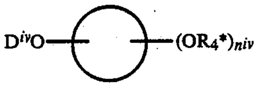

(I$^{vi}$)

wherein $D^{iv}$ is defined as above,  is the skeleton of a sugar molecule, $n^{iv}$ is a positive integer equal to the total number of —OH functions in the sugar molecule from which said skeleton is derived, and $R_4$* can independently be hydrogen, $D^{iv}$ or a radical of the formula

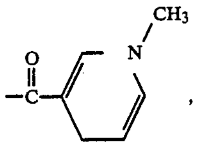

with the proviso that at least one $R_4^*$ is a radical of the formula

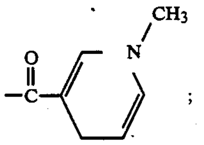

and (iv) non-toxic pharmaceutically acceptable salts of compounds of formula ($I^{iv}$), ($I^{v}$) and ($I^{vi}$). Within this class, preferred compounds are those in which z' is

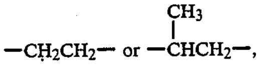

and/or in which ◯ is the skeleton of a pentose or hexose, especially when ◯ is

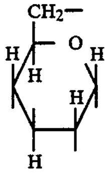

or

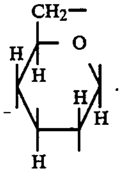

Also preferred Class (I*) compounds are those in which $D^{iv}$ is the residue of an antibiotic, a radiodiagnostic, a non-steroidal anti-inflammatory agent or an anticancer or antitumor agent. At the present time, compounds of particular interest within this class are those in which $D^{iv}$ is the residue of cephalothin, valproic acid, cefoxitin, clorazepate, iodopyracet, iodouppurate, iodamide, iopanoic acid, nalidixic acid, amoxicillin, oxolinic acid, chlorambucil, glyoxylic acid sulfonylhydrazone, DACH, methotrexate, aminopterin, 5-methyltetrahydrohomofolic acid, cefazolin, ibuprofen, naproxen, flurbiprofen, zomepirac, mefenamic acid, sulindac, diclofenac, indomethacin, benzylpenicillin, phenoxymethylpenicillin, methicillin, nafcillin, ticarcillin, furosemide, oxacillin, carbenicillin, dicloxacillin, fenbufen, fenoprofen, indoprofen, ketoprofen, fluprofen, bucloxic acid, tolmetin, alclofenac, fenclozic acid, ibufenac, meclofenamic acid, flufenamic acid or flufenisal.

(J*) Compounds adapted for the site-specific/sustained delivery of an benzodiazepine tranquilizer to the brain, said compounds having the formula

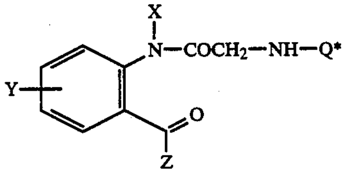

and the nontoxic pharmaceutically acceptable salts thereof, wherein —Q* is as defined in connection with Class (A*) above and X, Y and Z are identical to the corresponding groupings in a known benzodiazepine tranquilizer having the formula

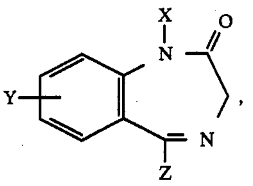

especially when —Q* is a radical of any one of formulas (a*') through (o*') set forth in connection with Class (A*) hereinabove. Presently preferred compounds in this class are those having the formula

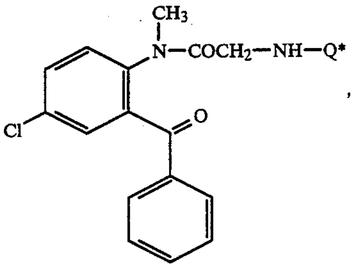

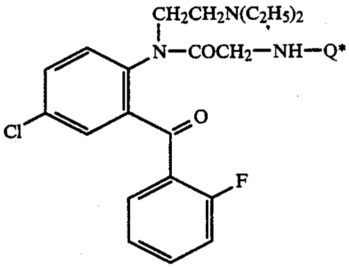

or

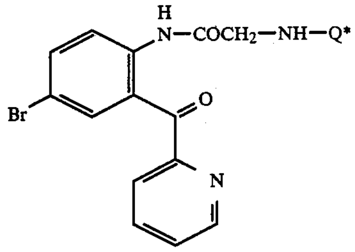

(K*) Non-toxic pharmaceutically acceptable quaternary salts having the formula $$D^*(-Q^{*\oplus})_{n^*}\ Y_{n^*}^{\ominus} \qquad (II')$$

wherein D* and n* are as defined in connection with Class (A*), Y⊖ is the anion of a non-toxic pharmaceutically acceptable acid and —Q*⊕ has the formula (aa*)

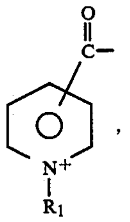

-continued (bb*)

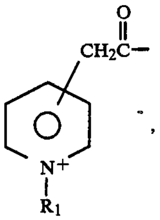

(cc*)

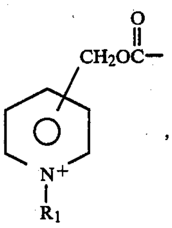

(dd*)

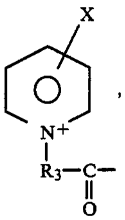

(ee*)

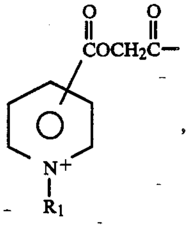

(ff*)

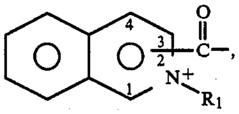

(gg*)

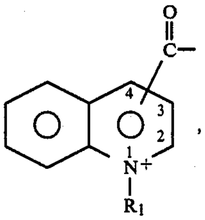

(hh*)

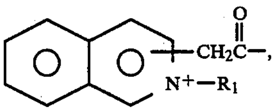

(ii*)

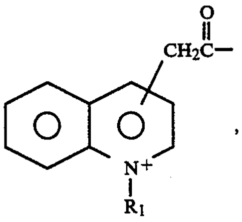

-continued (jj*)

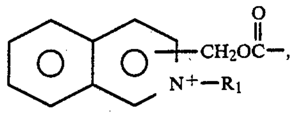

(kk*)

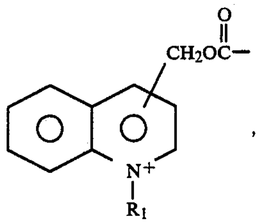

(ll*)

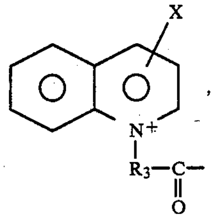

(mm*)

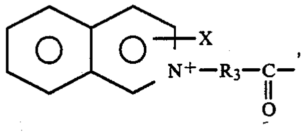

(nn*)

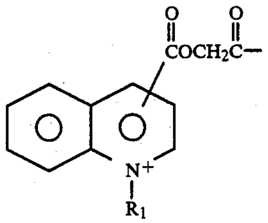

or (oo*)

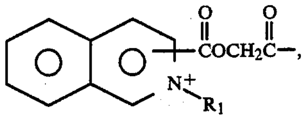

wherein $R_1$ is $C_1$–$C_7$ alkyl or $C_7$–$C_{10}$ aralkyl; $R_3$ is $C_1$ to $C_3$ alkylene; X is —CONR'R'' wherein R' and R'', which can be the same or different, are each H or $C_1$–$C_7$ alkyl, or X is —CH═NOR''' wherein R''' is H or $C_1$–$C_7$ alkyl; the

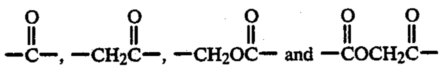

groupings in formulas (aa*), (bb*), (cc*) and (ee*) and the X substituent in formula (dd*) can each be attached at the 2, 3 or 4 position of the pyridinium ring; the

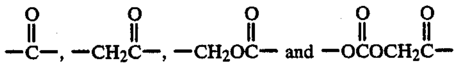

groupings in formulas (gg*), (ii*), (kk*) and (nn*) and the X substituent in formula (ll*) can each be attached at the 2, 3 or 4 position of the quinolinium ring; and the

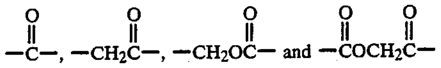

groupings in formulas (ff*) (hh*), (jj*) and (oo*) and the X substituent in formula (mm*) can each be attached at the 1 3 or 4 position of the isoquinolinium ring; with the proviso that when n* is 1, when —Q*⊕ is

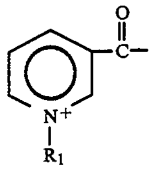

wherein $R_1$ is $C_1$–$C_7$ alkyl or $C_7$–$C_{10}$ aralkyl, and when the centrally acting drug from which D* is derived contains only one —$NH_2$ functional group and no other functional groups, then D* must be the residue of a centrally acting drug other than a sympathetic stimulant. The corresponding compounds in which —Q*⊕ is (aa*), (bb*), (cc*), (ee*), (ff*), (gg*), (hh*), (ii*), (jj*), (kk*), (nn*), (oo*), (pp*), (qq*), (rr*) or (tt*) wherein $R_1$ is $C_1$–$C_7$ haloalkyl are also within the scope of class (K*) as defined herein. Within this class of compounds, preferred compounds are those wherein —Q*⊕ has the formula:

(aa')

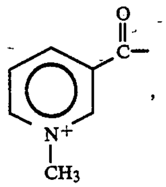

(bb')

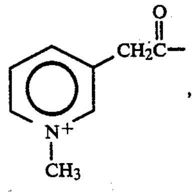

(cc')

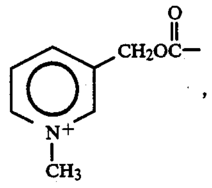

(dd')

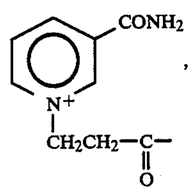

-continued (ee')

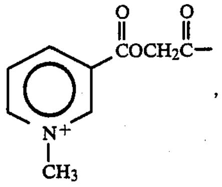

(ff')

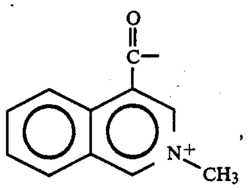

(gg')

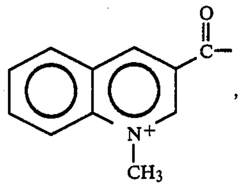

(hh')

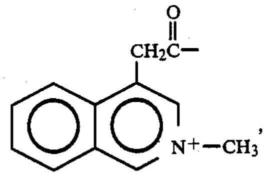

(ii')

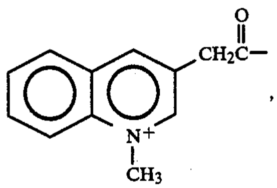

(jj')

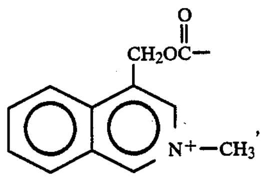

(kk')

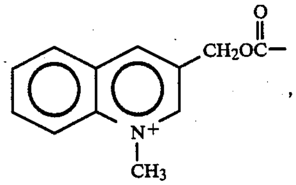

(ll')

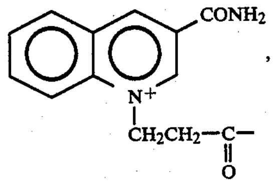

(mm')

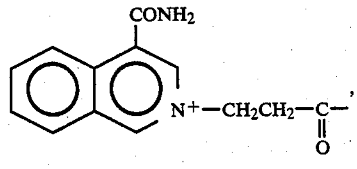

-continued (nn')

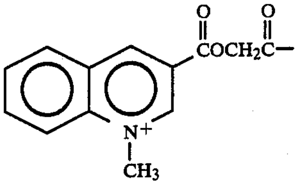

or (oo')

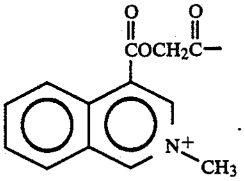

(L*) Non-toxic pharmaceutically acceptable quaternary salts having the formula $D''(-Q'^{\oplus})_{n'}\ Y_{n'}^{\ominus}$ (II'')

wherein D'' and n' are as defined in connection with Class (E*) above, $Y^{\ominus}$ is the anion of a non-toxic pharmaceutically acceptable acid and $-Q'^{\oplus}$ has the formula

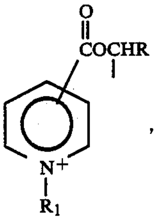

,

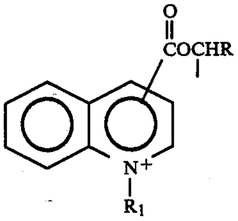

or

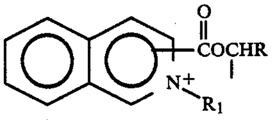

wherein $R_1$ is $C_1$–$C_7$ alkyl or $C_7$–$C_{10}$ aralkyl; R is hydrogen, $C_1$–$C_7$ alkyl, $C_3$–$C_8$ cycloalkyl, $C_1$–$C_7$ alkyl substituted by one or more halogen atoms, pyridyl, furyl, phenyl, or phenyl substituted by one or more halo, lower alkyl, lower alkoxy, carbamouyl, lower alkoxycarbonyl, lower alkanoyloxy, lower haloalkyl, mono (lower alkyl)carbamoyl, di(lower alkyl)carbamoyl, lower alkylthio, lower alkylsulfinyl and lower alkylsulfonyl; and the

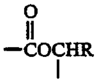

grouping can be in the 2, 3 or 4 position of the pyridinium ring, in the 2, 3 or 4 position of the quinolinium ring and in the 1, 3 or 4 position of the isoquinolinium ring.

(M*) Non-toxic pharmaceutically acceptable quaternary salts having the formula $D'''(-Q''^{\oplus})_{n''}\ Y_{n''}^{\ominus}$ (II''')

wherein D''' and n'' are as defined in connection with Class (F*) above, $Y^{\ominus}$ is the anion of a non-toxic pharmaceutically acceptable acid and $-Q''^{\oplus}$ has any one of formulas (aa*) through (oo*) set forth in connection with Class (K*) above, wherein the various substituents are defined as in (K*) above; with the proviso that when n'' is 1, when $-Q''^{\oplus}$ is

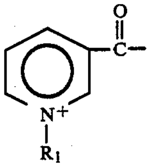

where $R_1$ is $C_1$–$C_7$ alkyl or $C_7$–$C_{10}$ aralkyl, and when the centrally acting drug from which D''' is derived contains only one primary or secondary —OH functional group, no other —OH functional groups and no $-NH_2$, —NH—, —SH or —COOH functional groups, then D''' must be the residue of a centrally acting drug other than a steroid sex hormone or long chain alkanol. The corresponding compounds in which $-Q''^{\oplus}$ is (aa*), (bb*), (cc*), (ee*), (ff*), (gg*), (hh*), (ii*), (jj*), (kk*), (nn*), (oo*) (pp*) (qq*) (rr*) or (tt*) wherein $R_1$ is $C_1$–$C_7$ haloalkyl are also within the scope of class (M*) as defined herein. Within Class (M*), preferred compounds are those in which $-Q''^{\oplus}$ has any one of formulas (aa') through (oo') set forth in connection with Class (K*) above.

(N*) Non-toxic pharmaceutically acceptable quaternary salts having the formula:

(i) $D^{iv}(-Q'''^{\oplus})_{n'''}\ Y_{n'''}^{\ominus}$ (II$^{iv}$)

wherein $D^{iv}$ an n''' are as defined in connection with Class (I*) above, $Y^{\ominus}$ is the anin of a non-toxic pharmaceutically acceptable acid and $-Q'''^{\oplus}$ has the formula

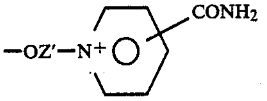

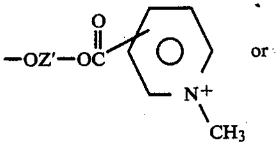

or

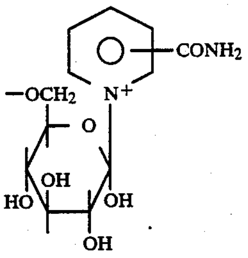

wherein Z' is $C_1$–$C_8$ straight or branched alkylene;

(ii) 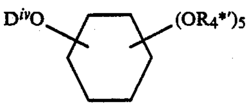 (II$^v$)

wherein $D^{iv}$ is as defined in connection with Class (I*) above and each $R_4{}^{*\prime}$ can independently be hydrogen, $D^{iv}$ or

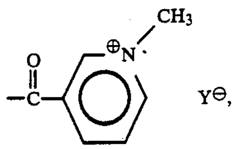

wherein Y⊖ is defined as above, with the proviso that at least one $R_4{}^{*\prime}$ is (iii)

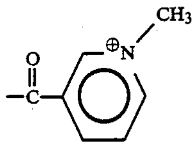

; and $D^{iv}O$—— ——$(OR_4^{*\prime})_n iv$ (Ivi)

wherein $D^{iv}$ and are as defined in connection with Class (I*) above, and each $R_4{}^{*\prime}$ can independently be hydrogen, $D^{iv}$ or

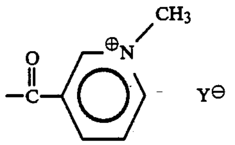

wherein Y⊖ is defined as above, with the proviso that at least one $R_4{}^{*\prime}$ is

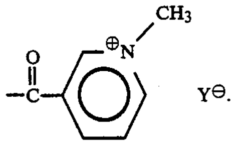

Accordingly, provided hereby are not only a generic method and novel class of pro-prodrugs for the specific and/or target enhanced delivery to the brain of a wide variety of drug species via the bidirectional transport of the drug species into and out of the brain employing dihydropyridine ⇄pyridinium salt carrier redox systems, but also a system providing insight into the basic transport processes (both active and passive) of, and enzymatic activities in, the blood-brain barrier, as well as into the various processes specific to the function of the brain. Again, another very significant aspect of the bioreversible redox delivery system according to this invention is the toxicity implication, for significantly reduced is systemic toxicity by accelerating the elimination of the drug/quaternary carrier system. And even central toxicity is reduced by providing for low level, sustained release of the active drug species in the brain. Low toxicity is provided both as regards the quaternary carrier and in combination with the drug. Again, the present invention is not bases on a simple prodrug concept, as was the case with the earlier work done with 2-PAM In that case, a hydrophilic compound (2-PAM) was made lipoidal by making its dihydropyridine form (Pro-2-PAM) to enable its peenetration through lipoidal barriers. This allowed the compound to get into the brain as well as other organs, but this prodrug manipulation did not and could not result in any brain specificity. And while the possibility of carrying drugs to the brain was also hypothesized earlier, all the experimental evidence reported in the literature negates any possible specificity, for the only compound delivered to the brain (2-PAM via Pro-2-PAM) showed similar efflux properties from the brain as from the other organs. There is no suggestion in the art of the brain-specific delivery which has now been achieved and which is a result of a surprisingly slow in vivo oxidation of the dihydro carrier system compared to the one reported in the earlier 2-PAM⇄Pro-2-PAM system. Indeed, a most surprising and unexpected feature of the present delivery system is that it will result in a build-up of the concentration of the intermediate charged species (quarternary form) in the brain even after one single bolus injection of the starting lipophilic chemical delivery system (dihydro form). There is a first portion of the brain level versus time curve which shows a significant increase in the brain (up to doubling or even more) from the starting overall concentration, and this process takes place against the concentration gradient; see, for examle, FIG. 6 (dopamine) and FIG. 8 (testosterone). The blood levels do simultaneously fall, and ater some time (for example, for 1 to 1½ hours) significantly higher concentrations of the precursor, now in its hydrophilic carrier (quaternary) form, will be found in the brain as compared to the rest of the body. This is brain-specific delivery; it is not simply delivery of something which otherwise cannot get to the brain, but is delivery of a given agent in an inactive form specifically to the brain, which then will subsequently lead to a sustained brain-specific delivery of the active specie itself. In the case of testosterone and dopamine, for example, slow enzymatic cleavage of the quaternary form "locked in" the brain provides sustained release of the drug itself.

While the invention has been described in terms of various preferred embodiments, the skilled artisan will appreciate that various modifications, substitutions,omissions, and changes may be made without departing from the spirit thereof. Accordingly, it is intended that the scope of the present invention be limited solely by the scope of the following claims.

What is claimed is:

1. A compound of the formula

D-[DHC]$_n$ (Ia)

or a non-toxic pharmaceutically acceptable salt thereof, wherein D is the residue of a steroidal female sex hormone having one or two reactive hydroxyl functional groups, one such hydroxyl group being a 17β-hydroxy substituent, said residue having a hydrogen atom absent from at least one of said reactive hydroxyl functional groups in said drug, said steroidal female sex hormone being selected from the group consisting of estradiol, ethisterone, ethinyl estradiol, mestranol, norgestrel, norethindrone, norethynodrel, norgensterone, norvinisterone and ethynodiol; n is a positive integer equal to the number of said functional groups from which a hydrogen atom is absent; and [DHC] is a radical of the formula

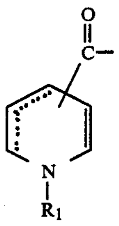

wherein the dotted line indicates the presence of a double bond in either the 4 and 5 position of the dihydropyridine ring; $R_1$ is $C_1$-$C_7$ alkyl, $C_1$-$C_7$ haloalkyl or $C_7$-$C_{10}$ aralkyl; and the carbonyl grouping is attached at the 2, 3 or 4 position of the dihydropyridine ring.

2. A compound according to claim 1 wherein [DHC] is a radical of the formula

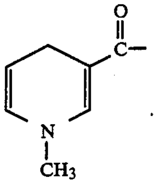

3. A compound according to claim 1 wherein D is a residue of estradiol.

4. A compound according to claim 1 wherein D is the residue of ethisterone.

5. A compound according to claim 1 wherein D is a residue of ethinyl estradiol.

6. A compound according to claim 1 wherein D is the residue of mestranol.

7. A compound according to claim 1 wherein D is the residue of methyl testosterone.

8. A compound according to claim 1 wherein D is the residue of norgestrel.

9. A compound according to claim 1 wherein D is the residue of norethindrone.

10. A compound according to claim 1 wherein D is the residue of norethynodrel.

11. A compound according to claim 1 wherein D is the residue of norgesterone.

12. A compound according to claim 1 wherein D is the residue of norvinisterone.

13. A compound according to claim 1 wherein D is a residue of ethynodiol.

14. A compound according to claim 1, having the structural formula

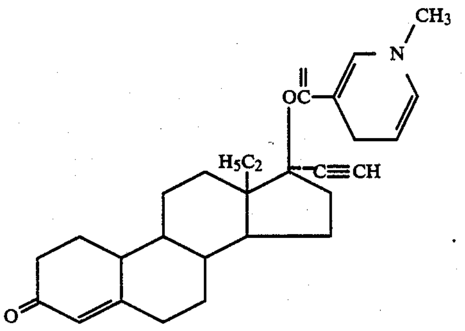

15. A compound according to claim 1, having the structural formula

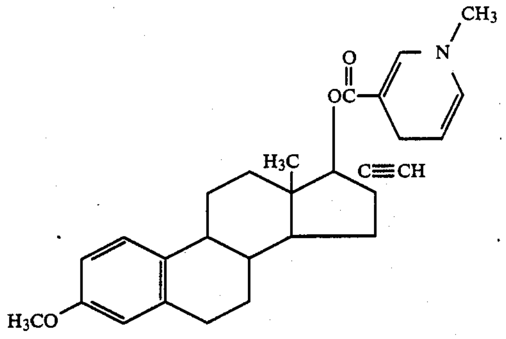

16. A compound according to claim 1, having the structural formula

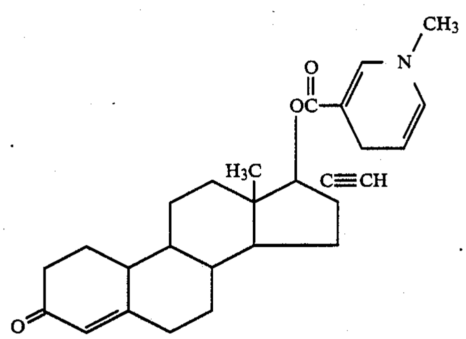

17. A compound according to claim 1, having the structural formula

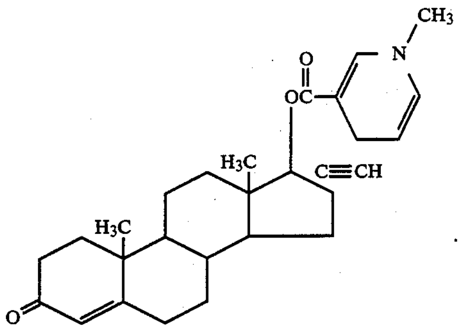

18. A compound according to claim 1, having the structural formula

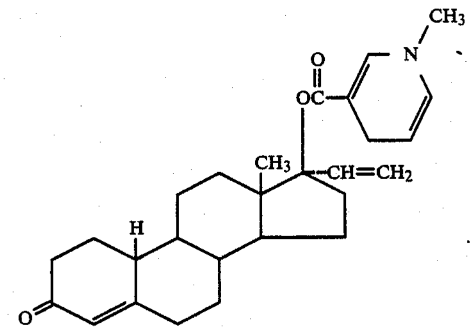

19. A compound according to claim 1, having the structural formula

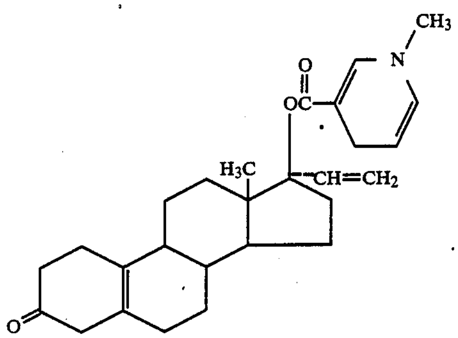

20. A compound according to claim 1, having the structural formula

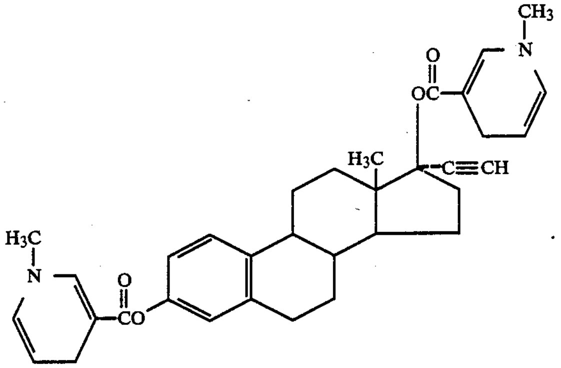

21. A compound according to claim 1, having the structural formula

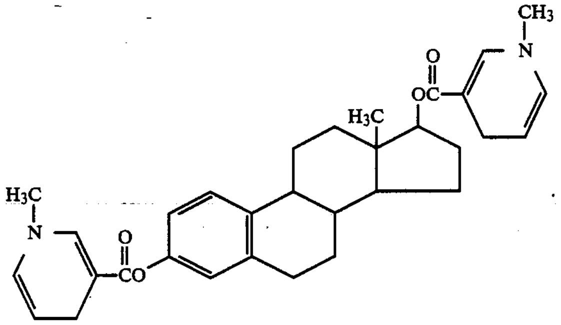

22. A compound according to claim 1, having the structural formula

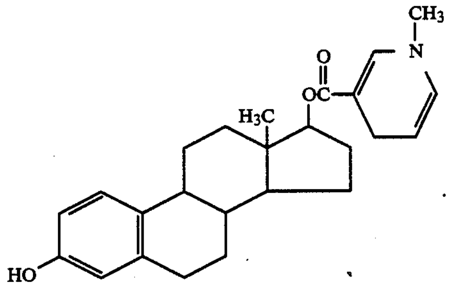

23. A compound according to claim 1, having the structural formula

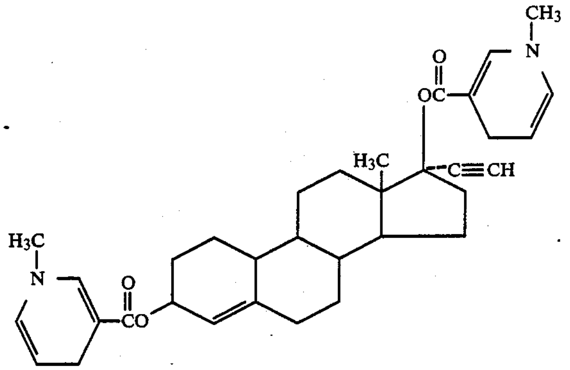

24. A compound according to claim 1, having the structural formula

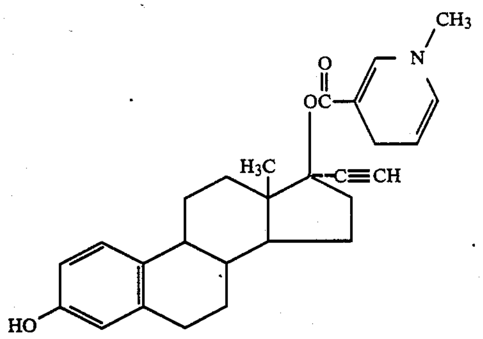

25. A compound according to claim 1, having the structural formula

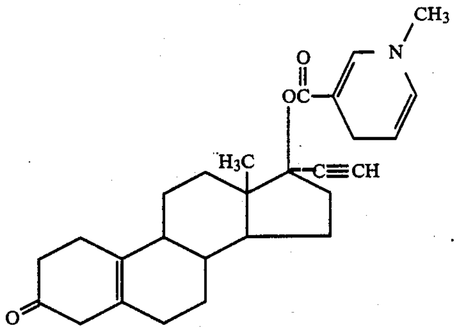

26. A compound according to claim 1, having the structural formula

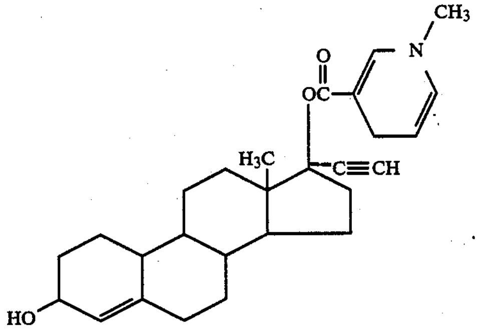

27. A quaternary salt of the formula $D—OC^{+}]_{n}\,qX^{-t}$ (IIa)

wherein D is the residue of a steroidal female sex hormone having one or two reactive hydroxyl functional groups, one such hydroxyl group being a 17β-hydroxy substituent, said residue having a hydrogen atom absent from at least one of said reactive hydroxyl functional groups in said drug, said steroidal female sex hormone being selected from the group consisting of estradiol, ethisterone, ethinyl estradiol, mestranol, norgestrel, norethindrone, norethynodrel, norgesterone, norvinisterone and ethynodiol; n is a positive integer equal to the number of said functional groups from which a hydrogen atom is absent; $X^-$ is the anion of a pharmaceutically acceptable organic or inorganic acid; t is the valence of the acid anion; q is the number which when multiplied by t is equal to n; and $[QC^+]$ is a radical of the formula

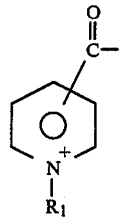

wherein $R_1$ is $C_1$–$C_7$ alkyl, $C_1$–$C_7$ haloalkyl or $C_7$–$C_{10}$ aralkyl; and the carbonyl grouping is attached at the 2, 3 or 4 position of the pyridinium ring.

28. A quaternary salt according to claim 27 wherein $[QC^+]$ is a radical of the formula

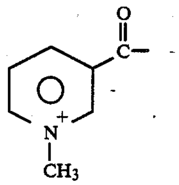

29. A quaternary salt according to claim 27 wherein D is a residue of estradiol.

30. A quaternary salt according to claim 27 wherein D is the residue of ethisterone.

31. A quaternary salt according to claim 27 wherein D is a residue of ethinyl estradiol.

32. A quaternary salt according to claim 27 wherein D is the residue of mestranol.

33. A quaternary salt according to claim 27 wherein D is the residue of methyl testosterone.

34. A quaternary salt according to claim 27 wherein D is the residue of norgestrel.

35. A quaternary salt according to claim 27 wherein D is the residue of norethindrone.

36. A quaternary salt according to claim 27 wherein D is the residue of norethynodrel.

37. A quaternary salt according to claim 27 wherein D is the residue of norgesterone.

38. A quaternary salt according to claim 27 wherein D is the residue of norvinisterone.

39. A quaternary salt according to claim 27 wherein D is a residue of ethynodiol.

40. A quaternary salt according to claim 27 having the structural formula

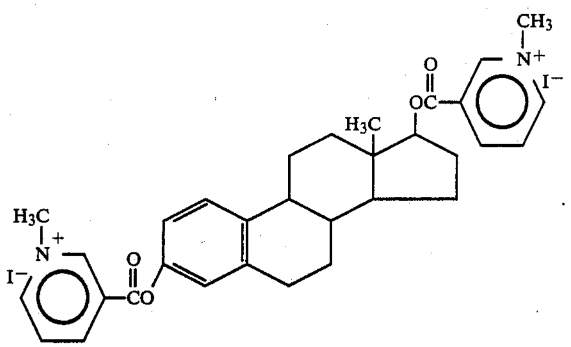

41. A quaternary salt according to claim 27, having the structural formula

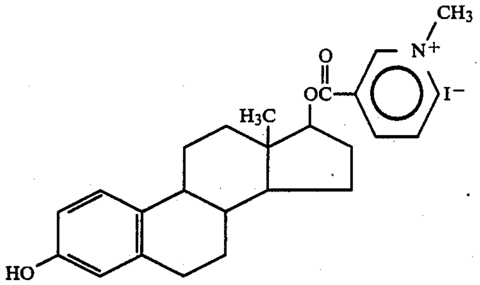

* * * * *

UNITED STATES PATENT AND TRADEMARK OFFICE
CERTIFICATE OF CORRECTION

PATENT NO. : 4,900,837

DATED : February 13, 1990

INVENTOR(S) : Nicholas S. BODOR

It is certified that error appears in the above-identified patent and that said Letters Patent is hereby corrected as shown below:

In item [57]:

In the Abstract, on page 2, in the line bridging columns 1 and 2, substitute -- functional -- for "function"; and in the last line on page 2, substitute -- entities -- for "entitles"

In Claim 1, second line in column 555, substitute -- or -- for "and"

In Claim 27, column 559, lines 1-2, substitute the following for formula (IIa):

-- $D \text{-}[QC^{+}]_{n}qX^{-t}$ --

Signed and Sealed this

Twenty-ninth Day of October, 1991

*Attest:*

HARRY F. MANBECK, JR.

*Attesting Officer*

*Commissioner of Patents and Trademarks*